US006274339B1

(12) United States Patent
Moore et al.

(10) Patent No.: US 6,274,339 B1
(45) **Date of Patent: *Aug. 14, 2001**

(54) METHODS AND COMPOSITIONS FOR THE DIAGNOSIS AND TREATMENT OF BODY WEIGHT DISORDERS, INCLUDING OBESITY

(75) Inventors: Karen Moore, Maynard; Deborah Lynn Nagle, Watertown, both of MA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/245,041

(22) Filed: Feb. 5, 1999

(51) Int. Cl.$^{7}$ ........................ A01K 67/027; A61K 38/22; C07K 14/59; C07K 16/26; C12N 15/16

(52) U.S. Cl. .................... 435/69.1; 435/69.1; 435/252.3; 435/320.1; 435/325; 435/471; 435/70.1; 435/71.1; 435/71.2; 536/23.5

(58) Field of Search ................................ 435/69.1, 320.1, 435/252, 254.2, 348, 325; 436/94; 536/23.1, 23.4

(56) References Cited

U.S. PATENT DOCUMENTS 4,190,496 2/1980 Rubenstein ................................ 435/7
5,075,217 12/1991 Weber ...................................... 435/6
5,364,759 11/1994 Caskey ..................................... 435/6

FOREIGN PATENT DOCUMENTS

WO 00/15651 3/2000 (WO) .

OTHER PUBLICATIONS www.ncbi.nlm.nih.gov (National Center for Biotechnology Information) GenBank Accession No. AA062169. Mj85g11.r1 Soares mouse p3NMF19.5 Mus musculus cDNA clone Image:482948 5' similar to WP:F33C8.1 CE05796 Perlecan–Like Glycoprotein; mRNA sequence (Marra, M. et al.). Database [Online]. Last update: Sep. 23, 1996. Accessed on: Jun. 14, 2000. Released from GenBank on Sep. 23, 1996.

www.ncbi.nlm.nih.gov (National Center for Biotechnology Information) GenBank Accession No. AA350292. EST57511 Infant brain *Homo sapiens* cDNA 3' end, mRNA sequence (Adams, M.D. et al.). Database [Online]. Last update: Apr. 21, 1997. Accessed on: Jun. 14, 2000. Released from GenBank on Apr. 21, 1997.

www.ncbi.nlm.nih.gov (National Center for Biotechnology Information) GenBank Accession No. R87660. Yp89g01.s1 Soares fetal liver spleen 1NFLS *Homo sapiens* cDNA clone Image:194640 3', mRNA sequence (Hillier, L. et al.). Database [Online]. Last update: Aug. 16, 1995. Accessed on: Jun. 14, 2000. Released from GenBank on Aug. 16, 1995.

www.ncbi.nlm.nih.gov (National Center for Biotechnology Information) GenBank Accession No. T69367. Yc37g02.r1 Stratagene liver (#937224) *Homo sapiens* cDNA clone Image:82898 5', mRNA sequence (Hillier, L. et al.). Database [Online]. Last update: Feb. 23, 1995. Accessed on: Jun. 14, 2000. Released from GenBank on Feb. 23, 1995.

www.ncbi.nlm.nih.gov (National Center for Biotechnology Information) GenBank Accession No. T92696. Ye26f05.r1 Stratagene lung (#937210) *Homo sapiens* cDNA clone Image:118881 5', mRNA sequence (Hillier, L. et al.). Database [Online]. Last update: Mar. 22, 1995. Accessed on: Jun. 14, 2000. Released from GenBank on Mar. 22, 1995.

www.ncbi.nlm.nih.gov (National Center for Biotechnology Information) GenBank Accession No. H11351. Ym13b02.r1 Soares infant brain 1NIB *Homo sapiens* cDNA clone Image:47626 5', mRNA sequence. (Hillier, L. et al.). Database [Online]. Last update: Jun. 26, 1995. Accessed on: Jun. 14, 2000. Released from GenBank on Jun. 26, 1995.

www.ncbi.nlm.nih.gov (National Center for Biotechnology Information) GenBank Accession No. AA350293. EST57512 Infant brain *Homo sapiens* cDNA 5' end, mRNA sequence (Adams, M.D. et al.). Database [Online]. Last update: Apr. 21, 1997. Accessed on: Jun. 14, 2000. Released from GenBank on Apr. 21, 1997.

www.ncbi.nlm.nih.gov (National Center for Biotechnology Information) GenBank Accession No. AA297697. EST113254 Fetal heart II *Homo sapiens* cDNA 5' end, mRNA sequence (Adams, M.D. et al.). Database [Online]. Last update: Apr. 18, 1997. Accessed on: Jun. 14, 2000. Released from GenBank on Apr. 18, 1997.

(List continued on next page.)

*Primary Examiner*—Karen Cochrane Carlson
*Assistant Examiner*—Patti Robinson
(74) *Attorney, Agent, or Firm*—Pennie & Edmonds LLP

(57) ABSTRACT

The present invention relates to mammalian mahogany genes, including the human mahogany gene, which are novel genes involved in the control of mammalian body weight. The invention encompasses nucleotide sequences of the mahogany gene, host cell expression systems of the mahogany gene, and hosts which have been transformed by these expression systems, including transgenic animals. The invention also encompasses novel mahogany gene products, including mahogany proteins, polypeptides and peptides containing amino acid sequences mahogany proteins, fusion proteins of mahogany proteins polypeptides and peptides, and antibodies directed against such mahogany gene products. The present invention also relates to methods and compositions for the diagnosis and treatment of mammalian body weight disorders, including obesity, cachexia, and anorexia, and for the identification of subjects susceptible to such disorders. Further, the invention relates to methods of using the mahogany gene and gene products of the invention for the identification of compounds which modulate the expression of the mahogany gene and/or the activity of the mahogany gene product. Such compounds can be useful as therapeutic agents in the treatment of mammalian body weight disorders, including obesity, cachexia, and anorexia.

19 Claims, 173 Drawing Sheets

Figure 1:
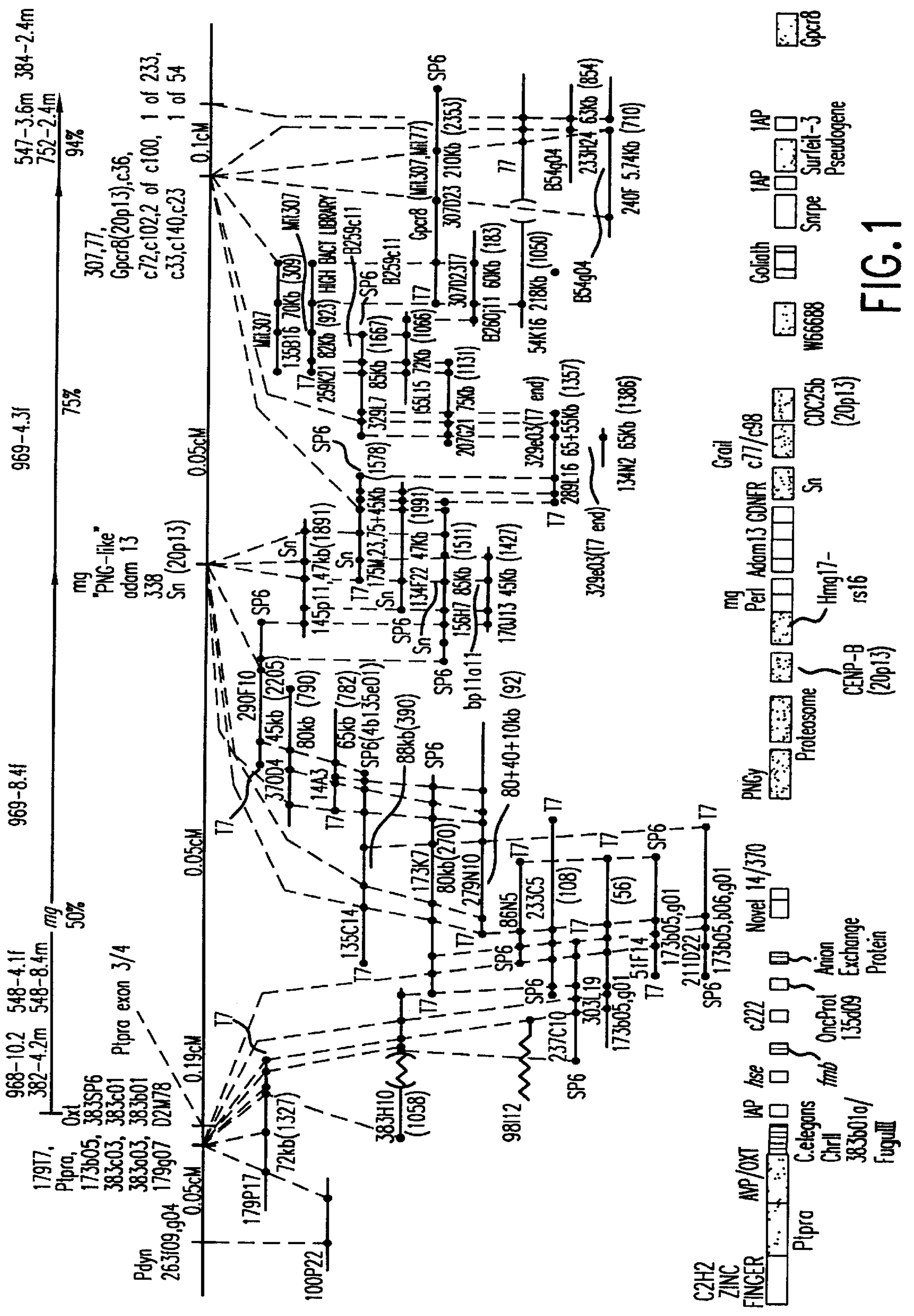

OTHER PUBLICATIONS www.ncbi.nlm.nih.gov (National Center for Biotechnology Information) GenBank Accession No. AB011120. *Homo sapiens* mRNA for KIAA0548 protein, partial cds (Nagase, T. et al.). Database [Online]. Last Update: Apr. 10, 1998. Accessed on: Jun. 14, 2000. Released from the DNA Data Bank of Japan (DDBJ) on Apr. 10, 1998.

www.ncbi.nlm.nih.gov (National Center for Biotechnology Information) GenBank Accession No. AA297214. EST112757 Embryo, 12 week *Homo sapiens* cDNA 5' end, mRNA sequence (Adams, M.D. et al.). Database [Online]. Last update: Apr. 18, 1997. Accessed on: Jun. 14, 2000. Released from GenBank on Apr. 18, 1997.

www.ncbi.nlm.nih.gov (National Center for Biotechnology Information) GenBank Accession No. AA298732. EST114356 Supt cells *Homo sapiens* cDNA 5' end similar to laminin, B1 chain, mRNA sequence (Adams, M.D. et al.). Database [Online]. Last update: Apr. 18, 1997. Accessed on: Jun. 14, 2000. Released from GenBank on Apr. 18, 1997.

www.ncbi.nlm.nih.gov (National Center for Biotechnology Information) GenBank Accession No. AI076479. Oz28b04.x1 Soares_total_fetus_Nb2HF8_9w *Homo sapiens* cDNA clone Image:1676623 3' similar to contains L1.b1 L1 repetitive element ;, mRNA sequence (NCI–C-GAP http://www.ncbi.nlm.nih.gov/ncicgap). Database [Online]. Last update: Oct. 1, 1998. Accessed on: Jun. 14, 2000. Released from GenBank on Aug. 7, 1998.

www.ncbi.nlm.nih.gov (National Center for Biotechnology Information) GenBank Accession No. AA771958 ai37e06.s1 Soares_parathyroid_tumor_NbHPA *Homo sapiens* cDNA clone 1359202 3' similar to contains L1.t3 L1 repetitive element ;, mRNA sequence (NCI–CGAP http://www.ncbi.nlm.nih.gov/ncicgap). Database [Online]. Last update: Dec. 31, 1998. Accessed on: Jun. 14, 2000. Released from GenBank on Jan. 29, 1998.

www.ncbi.nlm.nih.gov (National Center for Biotechnology Information) GenBank Accession No. R84298. Yp89g01.r1 Soares fetal liver spleen 1NFLS *Homo sapiens* cDNA clone Image:194640 5' similar to contains L1 repetitive element ;, mRNA sequence (Hillier, L. et al.). Database [Online]. Last update: Aug. 14, 1995. Accessed on: Jun. 14, 2000. Released from GenBank on Aug. 14, 1995.

www.ncbi.nlm.nih.gov (National Center for Biotechnology Information) GenBank Accession No. D81046. HUM126G05B Human fetal brain (TFujiwara) *Homo sapiens* cDNA clone GEN–126G05 5', mRNA sequence (Fujiwara, T. et al.). Database [Online]. Last update: Feb. 9, 1996. Accessed on: Jun. 14, 2000. Released from the DNA Data Bank of Japan (DDBJ) on Feb. 6, 1996.

www.ncbi.nlm.nih.gov (National Center for Biotechnology Information) GenBank Accession No. AA378603. EST91322 Synovial sarcoma *Homo sapiens* cDNA 5' end, mRNA sequence (Adams, M.D. et al.). Database [Online]. Last update: Apr. 21, 1997. Accessed on: Jun. 14, 2000. Released from GenBank on Apr. 21, 1997.

www.ncbi.nlm.nih.gov (National Center for Biotechnology Information) GenBank Accession No. D60710. HUM126G05A Clontech human fetal brain polyA+ mRNA (#6535) *Homo sapiens* cDNA clone GEN–126G05 3', mRNA sequence (Fujiwara, T. et al.). Database [Online]. Last update: Aug. 28, 1995. Accessed on: Jun. 14, 2000. Released from the DNA Data Bank of Japan (DDBJ) on Aug. 27, 1995.

www.ncbi.nlm.nih.gov (National Center for Biotechnology Information) GenBank Accession No. D20236. HUMGS01210 Human promyelocyte *Homo sapiens* cDNA clone pm1235 3', mRNA sequence (Murakawa, K. et al.). Database [Online]. Last update: Oct. 7, 1996. Accessed on: Jun. 14, 2000. Released from the DNA Data Bank of Japan (DDBJ) on Jun. 18, 1994.

www.ncbi.nlm.nih.gov (National Center for Biotechnology Information) GenBank Accession No. AA345684. EST51733 Gall bladder I *Homo sapiens* cDNA 5' end, mRNA sequence (Adams, M.D. et al.). Database [Online]. Last update: Apr. 21, 1997. Accessed on: Jun. 14, 2000. Released from GenBank on Apr. 21, 1997.

www.ncbi.nlm.nih.gov (National Center for Biotechnology Information) GenBank Accession No. H45413. Yo66a08.s1 Soares breast 3NbHBst *Homo sapiens* cDNA clone Image:182870 3', mRNA sequence (Hillier, L. et al.). Database [Online]. Last update: Jul. 31, 1995. Accessed on: Jun. 14, 2000. Released from GenBank on Jul. 31, 1995.

www.ncbi.nlm.nih.gov (National Center for Biotechnology Information) GenBank Accession No. AA044305. Zk51d07.s1 Soares_pregnant_uterus_NbHPU *Homo sapiens* cDNA clone Image:486349 3', mRNA sequence (Hillier, L. et al.). Database [Online]. Last update: May 10, 1997. Accessed on: Jun. 14, 2000. Released from GenBank on Sep. 4, 1996.

Duke–Cohan et al., 1995, "A Novel Form of Dipeptidylpeptidase IV Found in Human Serum", J. Biol. Chem. 270:14107–14114.

Nagase et al., 1998, "Prediction of the Coding Sequences of Unidentified Human Genes. IX. The Complete Sequences of 100 New cDNA Clones from Brain Which Can Code for Large Proteins in vitro", DNA Research 5:31–39.

Altschul, 1990, "Basic Local Alignment Search Tool", J. Mol. Biol. 215:403–410.

Börjeson, 1976, "The Aetiology of Obesity in Children", Acta Paediatr. Scand. 65:279–287.

Bork and Doolittle, 1994, "*Drosophila kelch* Motif is Derived from a Common Enzyme Fold", J. Mol. Biol. 236:1277–1282.

Bork and Beckmann, 1993, "The CUB Domain—A Widespread Module in Developmentally Regulated Proteins", J. Mol. Biol. 231:539–545.

Bray, 1992, "Genetic, Hypothalamic and Endocrine Features of Clinical and Experimental Obesity", Prog. Brain Res. 93:333–341.

Bray, 1989, "1989 McCollum Award Lecture. Genetic and Hypothalamic Mechanisms for Obesity—Finding the Needle in the Haystack", Am. J. Clin. Nutr. 50:891–902.

Coleman, 1978, "Obese and Diabetes: Two Mutant Genes Causing Diabetes—Obesity Syndromes in Mice", Diabetologia 14:141–148.

Dietrich et al., 1996, "A Comprehensive Genetic Map of the Mouse Genome", Nature 380:149–152.

Dinulescu et al., 1998, "Mahogany (mg) Stimulates Feeding and Increases Basal Metabolic Rate Independent of Its Suppression of Agouti", Proc. Natl. Acad. Sci. USA 95:12707–12712.

Drickamer, 1995, "Multiplicity of Lectin–Carbohydrate Interactions", Struct. Biol. 2:437–439.

Duke–Cohan et al., 1998, "Attractin (DPPT–L), a Member of the CUB Family of Cell Adhesion and Guidance Proteins, is Secreted by Activated Human T Lymphocytes and Modulates Immune Cell Interactions", Proc. Natl. Acad. Sci. USA 95:11336–11341.

Ewing and Green, 1998, "Base–Calling of Automated Sequencer Traces Using Phred. I. Accuracy Assessment", Genome Res. 8:175–185.

Ewing and Green, 1998, "Base–Calling of Automated Sequencer Traces Using Phred. II. Error Probabilities", Genome Res. 8:186–194.

Friedman and Liebel, 1992, "Tackling a Weighty Problem", Cell 69:217–220.

Friedman et al., 1991, "Molecular Mapping of Obesity Genes", Mammalian Genome 1:130–144.

Gordon et al., 1998, "Consed: A Graphical Tool for Sequence Finishing", Genome Res. 8:195–202.

Grundy and Barnett, 1990, "Metabolic and Health Complications for Obesity", Disease–a–Month 36:641–731.

Guan et al., 1991, "Grail: An Integrated Artificial Intelligence System for Gen eRecognition and Interpretation", Proc. $8^{th}$ IEEE Conf. on Artificial Intelligence for Applications pp. 1–3.

Herberg and Coleman, 1977, "Laboratory Animals Exhibiting Obesity and Diabetes Syndromes", Metabolism 26:59–99.

Houghton et al., 1991, "Generation and Use of Synthetic Peptide Combinatorial Libraries for Basic Research and Drug Discovery", Nature 354:84–86.

Knoll et al., 1993, "Cytogenetic and Molecular Studies in the Prader–Willi and Angelman Syndromes: An Overview", Am. J. Med. Genet. 46:2–6.

Lam et al., 1991, "A New Type of Synthetic Peptide Library for Identifying Ligand–Binding Activity", Nature 354:82–84.

Lane and Green, 1960, "Mahogany, a Recessive Color Mutation in Linkage Group V of the Mouse", J. Hered. 51:228–230.

Lu et al., 1994, "Agouti Protein is an Antagonist of the Melanocyte–Stimulating–Hormone Receptor", Nature 371:799–802.

Maestrini et al., 1996, "A Family of Transmembrane Proteins with Homology to the MET–Hepatocyte Growth Factor Receptor", Proc. Natl. Acad. Sci. USA 93:674–678.

Michaud et al., 1994, "Differential Expression of a New Dominant Agouti Allele ($A^{iapy}$) is Correlated with Methylation State and is Influenced by Parental Lineage", Genes & Dev. 8:1463–1472.

Miller et al., 1997, "Genetic Studies of the Mouse Mutations mahogany and mahoganoid", Genetics 146:1407–1415.

Moll et al., 1991, "The Genetic and Environmental Sources of Body Mass Index Variability: The Muscatine Ponderosity Family Study", Am. J. Hum. Gen. 49:1243–1255.

Nakayama et al., 1998, "Identification of High–Molecular–Weight Proteins with Multiple EGF–Like Motifs by Motif–Trap Screening", Genomics 51:27–34.

Nishina et al., 1994, "Atherosclerosis in Genetically Obese Mice: The Mutants Obese, Diabetes, Fat, Tubby, and Lethal Yellow", Metab. 43:554–558.

Robbins et al., 1993, "Pigmentation Phenotypes of Variant Extension Locus Alleles Result from Point Mutations that Alter MSH Receptor Function", Cell 72:827–834.

Schultz et al., 1998, "Smart, A Simple Modular Architecture Research Tool: Identification of Signaling Domains", Proc. Natl. Acad. Sci. USA 95:5857–5864.

Songyang et al., 1993, "SH2 Domains Recognize Specific Phosphopeptide Sequences", Cell 72:767–778.

Stunkard et al., 1990, "The Body–Mass Index of Twins Who Have Been Raised Apart", N. Eng. J. Med. 322:1483–1487.

Weis and Drickamer, 1996, "Structural Basis of Lectin–Carbohydrate Recognition", Ann. Rev. Biochem. 65:441–473.

GAATTCCGGGCGAAGGGGAGCCGGCGTGCGGGGTGTGTATGTGTTCGCTGGGCGCCGGCTCAGCCCCAGGAAGATGGTG

GCGGTGGCGGCGGCGGCGGCGACTGAGGCGCGGCTGAGGGGGAGCACGAGGACGACAGCAGCGCCTGCGGGCAGGAAGG

GCAGGCAGCACCGACCCTGCACCGCGACAGGGGCCTGGAGGCCGGGACCGCGCGCCCGGCTGTGTCTCCCGCGGGTGCT

GTCGCGGGCGCTGCCCCCGCCGCCGCTGCTGCCGCTGCTCTTTTCGCTGCTGCTGCTGCCGCTGCCCCGGGAGGCCGAG

GCCGCTGCGGTGGCGGCGGCGGTGTCCGGCTCGGCCGCAGCCGAGGCCAAGGAATGTGACCGGCCGTGTGTCAACGGCG

GCCGCTGCAACCCTGGCACCGGCCAGTGCGTCTGCCCCACGGGCTGGGTGGGCGAGCAATGCCAGCACTGCGGGGGCCG

CTTCAGGACATCTGTCTCACGCCTATAATCACAGCTGTTCGGAAGGTGAGGCTGGAGGAACAGTTCGAGGCAAGCTTCG

GCTACAGAATAAGTTCAAGAGTAACCTGGGGCAACTTGGGCTTGTCTCCAAAACCAAAATGAGCGAAAAGGAGCAAGCT

AGAGTCTTTTGGGAAAATTTTAGCTGACTAATTTTTCACCGAGAACTAACTGGCTCTTCTGGATTTGTAACAGATGGAC

CTGGGAATTATAAATATAAGACGAAGTGCACATGGCTCATTGAAGGACAGCCAAATAGAATAATGAGACTTCGCTTCAA

CCATTTTGCTACAGAATGTAGCTGGGACCATTTATATGTTTATGATGGGGACTCAATCTACGCACCTCTGATTGCTGCC

TTTAGTGGCCTCATTGTTCCTGAAAGAGATGGCAATGAGACGGCTCCTGAGGTCACTGTCACTTCAGGTTATGCACTGC

TGCATTTTTTCAGTGATGCTGCTTATAATCTGACTGGATTTAATATCACTTACAATTTTGACATGTGTCCGAATAATTG

FIG.2A(1)

CTCAGGCCGAGGAGAGTGTAAGAGCAGTAACAGCAGCAGCGCTGTTGAGTGTGAATGTTCTGAAAACTGGAAAGGGGAG

TCGTGTGACATTCCTCACTGTACAGACAACTGTGGCTTTCCTCACCGAGGCATCTGTAATGCAAGCGATACCAGAGGGT

GCTCCTGCTTTCCTCACTGGCAGGGTCCTGGATGTTCAATTCCTGTGCCAGCTAACCAGTCTTTTTGGACTCGAGAAGA

ATATTCTGATTTAAAGCTTCCCAGAGCCTCTCATAAAGCTGTGGTCAATGGAAATATAATGTGGGTTGTTGGCGGATAT

ATGTTCAACCATTCAGATTACAGCATGGTTTTAGCGTATGACCTGACTTCTAGGGAATGGCTTCCACTAAACCATTCTG

TGAACAGTGTGGTTGTAAGATATGGTCATTCTTTGGCATTACATAAGGATAAAATCTACATGTATGGAGGAAAAATTGA

TTCAACAGGGAACGTGACCAATGAGCTGAGAGTATTTCATATTCATAATGAATCATGGGTATTGTTAACTCCGAAAGCT

AAGGATCAGTATGCAGTGGTTGGACACTCAGCACACATTGTTACACTGGCATCTGGCCGTGTGGTCATGTTGGTCATCT

TCGGTCATTGCCCACTCTATGGATATATAAGCGTTGTGCAGGAATATGACTTGGAAAAGAACACATGGAGTATATTACA

TACTCAGGGTGCTCTTGTGCAAGGGGGTTATGGCCACAGTAGTGTTTATGATGACAGGACCAAGGCTCTGTACGTTCAT

GGTGGCTACAAGGCTTTCAGCGCCAACAAATACCGGCTTGCAGATGACCTCTACAGATACGATGTGGATACTCAGATGT

GGACCATTCTTAAGGACAGCCGATTTTTCCGTTACTTGCATACAGCTGTGATAGTGAGTGGAACCATGCTGGTGTTTGG

AGGGAACACACACAATGACACTTCCATGAGCCACGGTGCCAAATGCTTCTCCTCGGACTTCATGGCTTATGACATTGCT

FIG.2A(2)

TGTGACCGATGGTCAGTGCTTCCCAGACCTGAGCTCCATCATGATGTCAACAGATTTGGCCATTCAGCAGTCTTGTACA

ACAGCACCATGTATGTGTTCGGCGGCTTCAACAGCCTCCTCCTCAGTGACGTCTTGGTCTTTACCTCGGAGCAGTGCGA

TGCACACCGCAGTGAAGCTGCTTGTGTGGCAGCAGGACCTGGTATCCGGTGTCTGTGGGACACACAGTCGTCTCGATGT

ACCTCCTGGGAGTTGGCAACTGAAGAACAAGCAGAAAAGTTAAAATCAGAGTGTTTTTCTAAAAGAACCCTTGACCATG

ACAGATGTGACCAGCACACAGATTGTTACAGCTGCACAGCCAATACCAATGACTGCCACTGGTGCAATGATCACTGTGT

CCCTGTGAACCACAGCTGCACAGAAGGCCAGATCTCCATTGCCAAGTATGAGAGTTGCCCCAAGGATAACCCCATGTAC

TACTGCAATAAGAAAACCAGCTGCAGGAGCTGTGCCCTAGACCAGAACTGCCAGTGGGAGCCCCGGAATCAAGAGTGCA

TCGCCCTGCCGGAAAATATCTGTGGCAATGGCTGGCATTTGGTTGGAAACTCGTGTCTGAAAATCACTACTGCTAAGGA

GAATTATGACAATGCTAAATTGTCCTGTAGGAACCACAATGCCTTTTTGGCTTCCCTCACATCCCAGAAGAAGGTGGAG

TTTGTCCTTAAGCAGCTTCGATTAATGCAATCATCTCAAAGTATGTCCAAGCTCACTCTGACTCCATGGGTTGGTCTTC

GGAAGATCAATGTGTCTTACTGGTGCTGGGAGGATATGTCTCCATTCACAAATAGTTTGCTGCAGTGGATGCCATCTGA

GCCCAGTGATGCTGGCTTCTGTGGGATCTTGTCAGAGCCTAGTACTCGGGGATTAAAGGCTGCAACCTGCATCAACCCT

CTCAATGGCAGCGTCTGTGAAAGGCCTGCAAACCACAGTGCCAAGCAGTGCCGGACACCATGTGCCCTGCGGACAGCGT

FIG.2A(3)

GTGGCGAGTGCACTAGCAGCAGCTCGGAGTGCATGTGGTGCAGTAACATGAAGCAGTGTGTGGACTCCAATGCCTACGT

GGCCTCCTTCCCTTTTGGCCAGTGTATGGAATGGTATACGATGAGCAGCTGCCCACCTGAAAATTGCTCTGGCTACTGT

ACCTGCAGCCATTGCTTGGAGCAGCCAGGCTGTGGTTGGTGTACTGATCCTAGCAATACTGGGAAAGGAAAATGTATTG

AGGGCAGCTATAAAGGACCTGTGAAGATGCCGTCACAGGCCTCTGCAGGAAATGTGTATCCACAGCCCCTTCTGAACTC

CAGCATGTGTCTAGAGGACAGCAGATACAACTGGTCTTTCATTCACTGTCCAGCTTGCCAGTGCAACGGACACAGCAAA

TGCATCAACCAGAGTATCTGTGAGAAGTGTGAGGACCTGACCACGGGCAAGCACTGCGAGACCTGCATATCTGGCTTCT

ATGGTGACCCGACTAATGGAGGCAAATGTCAGCCATGCAAGTGCAATGGGCACGCATCACTGTGCAACACCAACACCGG

CAAGTGCTTCTGTACCACCAAAGGTGTCAAGGGGGACGAGTGCCAGCTATGTGAGGTAGAAAATCGATACCAAGGAAAC

CCTCTCAAAGGAACATGCTACTATACCCTTCTCATTGACTATCAGTTCACCTTTAGCCTGTCCCAGGAAGACGACCGCT

ACTACACAGCCATCAACTTTGTGGCTACTCCTGATGAACAAAACAGGGATTTGGACATGTTCATCAATGCCTCCAAAAA

CTTCAACCTCAACATCACCTGGGCCACCAGCTTCCCAGCCGGAACCCAGACTGGAGAAGAGGTGCCTGTTGTTTCAAAA

ACCAACATCAAGGAATACAAAGATAGCTTCTCTAATGAGAAATTTGATTTTCGCAACGATCCAAACATCACTTTCTTTG

TTTATGTCAGTAATTTCACTTGGCCCATCAAAATTCAGATTGCCTTCTCCCAGCACAGCAACTTCATGGACCTGGTACA

FIG.2A(4)

GTTCTTCGTGACTTTCTTCAGTTGTTTCCTCTCGCTGCTTCTGGTGGCTGCAGTGGTCTGGAAGATCAAGCAGAGCTGT

TGGGCATCCAGGCGGAGAGAGCAACTTCTTCGGGAGATGCAACAGATGGCCAGCCGCCCCTTTGCTTCTGTAAACGTTG

CCTTGGAAACAGATGAGGAGCCTCCTGATCTTATTGGGGGGAGTATAAAGACTGTTCCCAAACCCATTGCACTGGAGCC

GTGTTTTGGCAACAAAGCCGCTGTCCTCTCTGTGTTTGTGAGGCTCCCTCGAGGCCTGGGTGGCATCCCTCCTCCTGGG

CAGTCAGGTCTTGCTGTGGCCAGCGCCCTGGTGGACATTTCTCAGCAGATGCCGATAGTGTACAAGGAGAAGTCAGGAG

CCGTGAGAAACCGGAAGCAGCAGCCCCCTGCACAGCCTGGGACCTGCATCTGATGCTGGGGCCAGGGACTCTCCCACGC

ACGAGCTAGTGAGTGGCACACCAGAGCCATCTGCAGGGAAGGGCGTGGCGGGGAAATGGCTGTGCGGTGCGGGACGGAA

GACTGGAAACCCTCAAAGCATCTGACTCACCTGCATGATCACAAGCTTTCTTTGACGGTTTCTCCCATCCGTGTTCCAG

CATCTAACCTTTTACTTTTGCATAGGAAATACTTGATTTAATTACAGGTCCAGGGATGAGCTGATGGTTGCTGGAGGAG

GCCAGTGTAGAGCCAGTGAGAGAACTAGGAATGACACTCAGGTTCACTGTGGAAAACTGTTCTTGGGACTGTCTCAACT

GTGCAAAAAACAAAAGATGGAGTGTTTACAAGTAGACATTCGTCATCAGTTGTTCTTGAACATGGTCTTTTAAAAACTA

GTCAGATGAATTAACTTGTTTTCATCTGAAGCCTGCTATCTTTTTTAAAAGATGTGCTATTTATTCTTGCACGATTTAG

GCAATTATCTCTCTTCCAGGGAGTACCTTTTTTTCTAGTTGAGAATTAATAATGGTCCATCTCTTTTGATCATATCAAG

FIG.2A(5)

CTAGGATAGAAGGGGGGCTATTTTAAATGTCAAGGTCAGCAGTGTTACTTTGAATGTAAACTGGTATAATAGGTAGTTT

TCTATAGTAACTTGATTAATTTAGTCTTAATCCATTTGAAACTCTCTCTTCCTTTCTCTCTGCCTGTCCCTCTCCTTCT

CCATCTCACCCTCCCTCTCTCACACATACACACACAAACACATACACACAACACTAAGTGCCTAGACTTTAAATAGATC

TAGCAATTGGAAAGTTAGTAAGCCTAAGTTTTTACATAATTGCATTCCTACATTCTTGTAAAATTTAAATAGCTACCAT

TGGCAATCTGCTTTTTTTCTAAAATCTGATTTGCAGCCAGGAAAGAATTTTCTCACCCAAGGAACATTTGATCTAGCAG

CAGGGATGAGAGGAAAGCAGAAATGAATGAACTGTGAAAGCTCCTGTTTTTATTATCAAAAAGGACACTGTCAAGAAGG

CGCCCCCTGCCCCCACCCCCGTGTCACCCTAGGCCTGATAAGCGATCAGAGGAAAGGACTCATTCATGTCACGCTTCCT

TGAGCAGAAAAGAGCACTGAGAGCACTTGGGACCCCTGGATCAGAGAGCATCTGTGTGTCCTGCAGCCTCCTCTGAACT

TGTGGTTCATTCTCAGGCTGGGGTGGACTCAGATGCCAGGAAAGGGACAGCCTCCCATTGTCAGGCAGAAGCTGCCCAA

AGCCTGGAGAAGGACTTGTTTGCCCTCTTTCCCCCAGGAGGGGCTCGACCCACCCACCCTCCCTCTCAGACCAAGGTGG

TGGCTGTGAGGAGGGCAGCAAATGCTGACAAGGATGAAAAGCACATGGAAAAAAATGGACGAGGAGGGAAAACTCTGCC

AAATGGAAAATGACCAAATTTAAGAGGGTGGGACAGTCCCCTGCTCCTCTCCCAGAGGGCACTGCTTGGAAATTGTGTT

TTCCCCATTTATGGTGCTCTGTATTCTGGCATTATGCAGCAGCCTCCCAGAAGCTCTCTTCTGCTTCAAAACCTGGGAT

FIG.2A(6)

CTCTGGCATTACCCTATTGGGATGGACCGCTGGACAGCAATGCTCGAGTTTGTGAATTTGGAGAGATACTCAAAAGAGC

TAAAACTGCAGCATTTTACCTTTAAATGCAGTGCCTAGAGAGAGAGTATTGTCTCTTCCCCAACACTAACCCCACTCCC

ATGAAGAATTGCCTGGAAAGATGTTTTCAAGGAATTTGAACCATAAAACACTATCTGATGCACAGAACACCTCTACTTT

GAGACTCACCTCTCATAAAGCTTCTTTTTCACATTACTGTTAAAGACCAGACGTTCTAGAAAAGACCCCTCCTCTCATG

AGCTCCCCCATCCCTGCTACAGAACACAGCACCCATGGCGCCTGCAGTGGACTGGCCCCTTAATTCCCACAGGCCCCCC

CAGCAAGGCCAAAGGGAGGCCCCTGGGTATTGTCCTCCTACAAGGAAGATCCTCTTTGTTTGTTCAAAGGACCAGTTTT

CCTAGGCCAAAGAAGTCTCTTCCCCATGTTAGTCCTATGCCTTGAAATATCATGCACCATGACCCACAGCCATCTGGTT

ATGTCTTATTTTTTTCCTAAAAGATAATGTTTATTTTTAAAAAGGAAGGAAGAAGCAAGTGAAGTTTCATTCTGCTCCA

GCGGTGGGGAAGCCGCTGAATCCACCTGCTTCTCCTTTGCAACCGACAGCAAACAGCTTTCTCCGGCCTCAGGGCAGAA

AAAGGGAATGGCAGGGAGTAAGAGGCGCTGGGCTCGGAGCCTGTTTCCAAGAAGGAATTGGTTGTCATCTGGCAGTGTT

GCGCGTCACAAGAGAGCCTGTATATAAATTAAAATAGTCAAGACAACACTGACCTTGCACTTGTACATAACTATACAGT

AGTGTCCAGAATGTTCAGACATTCGGAGTGTACATAAAACAGAAAAAATCTTCATGTATTTTTATTAAATATAACAATG

TCTGAGTTTCACCTAAGATGTTTTTGTGCCATATGCTGGATATCCAGGTTCTCGCCAGGCCCCGATACATGAATAACAA

FIG.2A(7)

ACCCAAGAAACGCATCCCCATTGTGTGATGTGTTCAGATGCATCTGGCACCAATTAGGTATTTCTTAAAACAGGACTCA

TCTGTCAGAGTGCACATGAAAAATCAGGCAGGGAATCGAAACGACAGCGCTGGAGGAGACTCAGGAAGCAGAGGCGTCC

CTGCCGCTGCCCTTGGCCCTGCAAGCACATCATGACCCTTTCTGGCAGCCTCTTGGTGCTCTGGGTAGTGAGGGATGAC

CAGTCTTGTCCTGAGAAATGTTTCTCTTAGTCTTTAAGTTCAAAGACTAACCTGTAGCAATCAGACTTTCCAAAAGGGG

GTTCTCCATTTTTTGTAGTTTTGTCTAAATTTTTAATGACCATTTCCTGGAATCAGTTTATTATACTGAAAACTGGGGG

TGGGAGTAGGGAGCTAGTTTGTTGATAAATAGTTCCCATTTCCCCGTGGAGAATTTGACATACCCTGGACTCCTGTGTG

CCTCCTGCCATCCCTGCACACAGCCTGGGGAGAAGCCTGTGCCTCCCCGTGTGGAGAGAAGGCAACCCCAGATCCCCTG

AGCTAACCCGGAGGAAAGGCAGTCCTGGACAGAAGACTGTCAGCAGAAGGAAAGTACTGGACTACCCGTGGGTAAGTCC

TGCCATTCAAGACTGGAGACACCTGGGAAATAAAAAGAGCAGGGCACTGCTGGTGGGAAGAGGCATTTTACCTTCCAGT

GCAAATCCTGCTCCTTTGATTTAATGGGGTGTACTGGGGCCAGGGGCTGATTCACTTCCTTGGGAGATGGTGGTGTTTT

CATGAACATCTTTGATCCTTCCATTTCATTTATTCATCCATCCATTCAACAAGTATTTGCTAAACACTAACTTAAGCTA

ATGCTAGGGTAGTGACTGAGATGTAAAAATAGATTTTAGAATTAAAACAAAATCCAAGTCCTCACACCCCTGTCATCCC

AGGAGATCTTTCCTTGTGGTGGTTTCTGTGAGAATTGGCCATCCTGAGGACACAGCCAGGACGGCAGAGGCCTCCTGGC

FIG.2A(8)

CTCAGGGCATGCCCTGCCTACCTTCTGAAATGTTTACCCCATTGACCAAACTTGGCTCCAGCCATTGCGGTGGTTTCTA

GATAGCCAGGCCCACCAAGAGATATTGCCCCTTGATGAGAGTCAAACACCCTGCCTACAAGGAGATGTTTTGAAATGGA

GAGGAAAATTGGCACCTCATCTTTTAAAGGCAGTAATGGAATTGATTTTCAGTAACTGAATTTGTGCACAAAACATTCT

AAACACTAGTGAAGCCTGTTTCGTTGAACTAATTCTGGCTCTGGAAATGTTTTTGTTTTATAGTTATTTACGATTTCGT

TTGTTTGGATTCAAGCTTAGTTTGTTAATATGTATAATTTAGCATCTATTACACTCATGTAAATATGGAGTAAGTATTG

TAAACTATTTCATTGCGGGGATTGTGGGTGTTATACATACATTTAGGACTGCAATTTTTTGGTATTTTTTGTATTGTAA

AATAACAGCTAATTTAAGCAGGAACAAGAGAACTAAGGGAGGTCTGTGCATTTTAAACACAAATGTGAAGAACTTGTAT

ATAAACAAAAGTAAATACTATAATACAAACTTCCTTCTGAAATAAAAGTAGATCTGGT

FIG.2A(9)

MRLRFNHFATECSWDHLYVYDGDSIYAPLIAAFSGLIVPERDGNETAPEVTVTSGYALLHFFSDAAYNLTGFNITYNFD
MCPNNCSGRGECKSSNSSSAVECECSENWKGESCDIPHCTDNCGFPHRGICNASDTRGCSCFPHWQGPGCSIPVPANQS
FWTREEYSDLKLPRASHKAVVNGNIMWVVGGYMFNHSDYSMVLAYDLTSREWLPLNHSVNSVVVRYGHSLALHKDKIYM
YGGKIDSTGNVTNELRVFHIHNESWVLLTPKAKDQYAVVGHSAHIVTLASGRVVMLVIFGHCPLYGYISVVQEYDLEKN
TWSILHTQGALVQGGYGHSSVYDDRTKALYVHGGYKAFSANKYRLADDLYRYDVDTQMWTILKDSRFFRYLHTAVIVSG
TMLVFGGNTHNDTSMSHGAKCFSSDFMAYDIACDRWSVLPRPELHHDVNRFGHSAVLYNSTMYVFGGFNSLLLSDVLVF
TSEQCDAHRSEAACVAAGPGIRCLWDTQSSRCTSWELATEEQAEKLKSECFSKRTLDHDRCDQHTDCYSCTANTNDCHW
CNDHCVPVNHSCTEGQISIAKYESCPKDNPMYYCNKKTSCRSCALDQNCQWEPRNQECIALPENICGNGWHLVGNSCLK
ITTAKENYDNAKLSCRNHNAFLASLTSQKKVEFVLKQLRLMQSSQSMSKLTLTPWVGLRKINVSYWCWEDMSPFTNSLL
QWMPSEPSDAGFCGILSEPSTRGLKAATCINPLNGSVCERPANHSAKQCRTPCALRTACGECTSSSSECMWCSNMKQCV
DSNAYVASFPFGQCMEWYTMSSCPPENCSGYCTCSHCLEQPGCGWCTDPSNTGKGKCIEGSYKGPVKMPSQASAGNVYP
QPLLNSSMCLEDSRYNWSFIHCPACQCNGHSKCINQSICEKCEDLTTGKHCETCISGFYGDPTNGGKCQPCKCNGHASL
CNTNTGKCFCTTKGVKGDECQLCEVENRYQGNPLKGTCYYTLLIDYQFTFSLSQEDDRYYTAINFVATPDEQNRDLDMF
INASKNFNLNITWATSFPAGTQTGEEVPVVSKTNIKEYKDSFSNEKFDFRNHPNITFFVYVSNFTWPIKIQIAFSQHSN
FMDLVQFFVTFFSCFLSLLLVAAVVWKIKQSCWASRRREQLLREMQQMASRPFASVNVALETDEEPPDLIGGSIKTVPK
PIALEPCFGNKAAVLSVFVRLPRGLGGIPPPGQSGLAVASALVDISQQMPIVYKEKSGAVRNRKQQPPAQPGTCI

FIG.2B

AGATTTTATGCCTTCGTACACGCCTCCCATAAGATGGACAAGGTGTACTA

ATTACTGCCATTACTGTTGCTGACCCCAGAGGTCAATGTCCTCACATGGC

CTCTACTGGCACTGTCTGGGCAGAAACTGTATATCCAACTGGTGAACCTG

AAAGCCCTATGACTACTTGGTGTCTCTGGTGCTAACCCTAGTCGTTGGGG

CATCTTACTGTATCCTGGTAAGGAAAGACATCCAGGCTCCCCACTTAYMK

WWACYRGYWMRGMYCAKGSYMGRGCYAAWKTKCTGTRRMRTCTGGCTGGC

ATAGAGACATTACTATTGAAAGTTTTGTCTTTCTAAATCCTTGGACTAAA

GAGAGCACAAGATTTTCTGGAAGATCTTGCTTTAAATTTTTTTTTTATTC

TTTTGAGATGCTACATATAATTAGAGGCCCTGCACATGGAGGCGAGAACC

CCACCTCTGGGCTACATCCTACGTCTTTTCCTTAGGGTATTTTTTTTTCT

TTCTTGTACCTATCAGTATTACTAAGTTGCAAATGTGCTCAGCAGTAAAT

TTAACATACATAGGCAAAAAGAAAAGTCTCAGGACACCCTGCCTCACACT

GTTTACTGTGCTCAGGAGTACTGAGCCATACTGTTTTCTTGCTGCTGCTT

TTTTTCTCTTGGTTGTTTACACACAGTGTTCAAGGTGTGTTAATCATAGT

TAGTATTTCAATTTTTTCTTAGGTCAGCAAGAAAGCTCACAGAGGAAGAG

TGCTTTGCTGCCAGCCTGATGACCTGGGTGACCCAAGTGATCTCACCTAC

AGGGTGGGAGCACAGCACAGCATTCCAAGTCTTTTTCTGACCACACAGGC

ACTATGGCACACAAACACACAGGATACATAAATGTTAAAAAAAAAAAAAG

ACTTTTATATTTTTCTCCATATAATTTAAAAGATTCCTCTTTCAACATTC

CTTTTGCAAAGCAGTATCATTGTGTTTGTATATGTGTGTCCTTCCACATT

TTGTCTTCAATTCTAAATTTTTAGAATTGTTAGCCTGGTCCTCTCATTTC

FIG.3B(1)

TACTACTTTCTCTAGTAAACTGTCCTTTCATATTACACATCGCTCTCCTG

TCACCTGTTTTAGAGCTGTCATCCATTTTATAAGGTTACTTCACTGTTCT

ACACTACTTTGTGTCTTTTAATTACTATGCCTGGGGTGATTCAAAAACTG

TCTGTGATGGGTTGGTTGAGGATGGCTCCAATAGGTTCAACACTTGGTCC

TGATTGGTGGAACTGTTTTGGGAAGGATTAGGAGGTGTGACCTTGTGGGG

GAGTGTGTCACTGGGAGTGAGTGACCTTTGAGGTTTCAAAAGCCCATGCT

AGGCCCAGTGTCTGTCTGCCTGTCTGTCTGTCTCCTCCCTTTGCTCTTTC

TTCCCTCCCACTTGCTTGCAGATCAGATTCGAGCTCTTAGCTACTGCTCC

CGTGCTGTGCCTTGCTGCTACCATGCTTCTTGCCATGATGTTCATAGACT

TACTCTCTGAAACTGTAAATAAGCCCCCTAATAAAATGCTTTCTTTTAAA

ACTGCCTTGATCATGGTGTCTCTTCAAAGAAATAGAACATTAACAAAAAC

ACTATACCAAACTGCCTAATAGTCCTACTAATTTTATGATGAGTGCTAGT

GCTTTATAATCACTAGAAGAAAAAATTTCCAGGCCATAAAATTAACATGG

TTTTAAGTATGTATAAATCTTGTCTTGAAATCTGTTTTCTATAACTAACT

CTAATATGATAATGTATATTCTACCTTCAAAAAAGCACAAATAAGACTTC

AAACCCTGGGAATTGTTAGACAAAGGCCATTTAATACTAATAAGCTATAA

ACTGAAACCATCTGATATATGAAAACTATTAATAAAATCAAGATAAAATA

ACCCCTATTTATATAACTTACTATATACCTAAAGCAAAATATCAAAGAAA

GTACCTTAAAAAGATAAATTATTCTTATTTTGACAATGAATTCTTTGGGG

CGTTAAATTGTAGAATATCAACACATATCAAGAAAGTTTAGAAGAAAACT

ACCAAAGTTTAAACAGACTTTCCTCGGTAATTACTGGTGATTTCTTGGCT

FIG.3B(2)

TTTTTTTTTTACACTGCAGTTTTTCAGGGTGGAAACTTAAGCTTTGTACA

GAAGCACTTACCACCACTCTCAGAGCTGGAAATGGCTCAAAGGGCAAAGC

ATTACAAGCCTGGCAACCTGAACCAAATACCCAAAACACTTGCAAAGGTG

AAAGGAGAAAACTAACTCCAGGAAGTTGTCCTTCGAGCTCCTCTTGCACA

CCACTGTATACACCCCCTTATATACACTCAGTTACCATAAATAAAATGTT

TCATTATAAAGACACTTACGCTAAAACCATGCTGTAATCTGAATGGTTGA

ACATATATCCGCCAACAACCCACATTATATTTCCATTGACCACAGCTTTA

TGAGAGGCTCTGGGAAGCTTTAAATCAGAATATTCTTCTCGAGTCCAAAA

AGACTGGTTAGCTGGCACAGGAATTGAGCATCCAGGACCTAATAAAAAAA

AAAAAAACAACAACAACAACAAATAGCTTCACAAAATGCAGCCTGAAAGT

TTATAGTATTCCAAGTTCCAATCTAAGTGCAAAGAATATTTAAAGACTTG

TGGGGCTAGAGAGATGGCTCAGTGGTTAAGAAAACTGACTGCTCTTCTTG

GAGGTCCTGAGTTCAAATCCCAGCAACTACATGGTGGCTCACAACCATAT

GTAATGGGGATCTGATGCCCTCTTCTGGTGTGTCTGAAGACAGCAACAAT

GTACTCACATGAAATAAATAAATTAATTTTTTTAAAAAACAGACCAGAAAA

AAAAAAAAAAAAAAGACTTGTGTTTCCTTTAGCACTTAAGCGCAAACATC

TTTAACTTGTGGGGTTTTAAAGGTTTTTACATGTACAGGTATTTTGTTTA

CATGTATGCCTATATACCACTTGCTTGCTTGGTACCCAATGATGTCAGGA

AAAGGCATTGAATCCCCTGGAACTAGAGTTACAGATCTTATGAGCTACTT

TGTGGATGCTAGGATCAAACCTGAGTCCTCTGGAAGAGCAACCAGTACTC

TTAACCAAGAAGCCATCTGCTTAGCACCTAACATGAGTTTTTAACTTACT

FIG.3B(3)

CAAGATACAGACCAAAACCAATCACTCCCTTATAAAATTTAATACTACAC

ACTTTCTGATAATTTGGCAATTTCTGATAATCAGGTTAAACTTTTTTAGA

GGTAAAAATCTTGCTGAAGCAACATTTAGTAGAAAGGGTAGACCAAGGGG

TTATTATATTAACTCATGTGGAAAAGGCATTAGGGTTGAAATATAATGAC

AGATCAAAATCGATCTTCTGGCAAGTCCAGGCGCTGAATAGATGAAAGAG

ACAAAGGGAGAATTGGACAAACTAAAAACATTTACATGAACACTTACTTT

CTGAGGACCTAAGCATAGAAGGAAAATCACTAAACCAACGATGACTGCTT

CCTCAATACCCCAGGGAATTCCCTACAGTACCTTAGTACCCGGTTGTGTT

GGGTAATGGCACTAGATGACAGCACTGAGACTCTAAGGAACGCTTGTCCT

CCTCTCAGCTTGAGTCTCTGCTTCTCTATCACCAGACCATGTTCCCTAAT

TCCCACGAATGAGTTGCAAAGGATTTGTCAAACCTTTCCACAATTCTAAG

CACATAGATAACAACCACATATATGTAAATTCAAAGAATCTGAATAAATG

GAGATGAATGCTTAAATGCCACCTGATACATGATTAACATAAGGCGTATG

GCTGCTAAAATAAACTCCCTACAGTTCACTAACTCAGAACTTTCTGTGAG

GGAAAGGACTTTGAAGGGCAGCTCCTACCCTGCCAGTGAGGAAAGCAGGA

GCACCCTCTGGTATCGCTTGCATTACAGATGCCTCGGTGAGGAAAGCCAC

AGTTGTCTGTACAGTGAGGAATGTCACACGACTCCCCTTTCCAGTTTTCA

GAACATTCACACTCAACAGCGCTGCTGCTGTTACTGCTCTTACACTCTCC

TCGGCCTGAGCAATTATTCGGACACATGTCAAAACTACAAAGACAGGAGA

AAACGAAGTCAACAATTTCAACTAAGCAACATTGCAACTAATGCAGACCT

TCCTCCTTCAGTTTAAGTTCAGTTCATTTGCAAGTGTGACTGCAGGACTT

FIG.3B(4)

ACCAGTTAGCCCAAGTGTGCTCACAGAGCTCTGTGTAGCTAGAGCCCCAG

GCTCAAGTAATGAAATCAAATCAACCTTGCTGCATTCACATATGAAGAAG

GAAGAATAAATAACTCACAAAGTTAGAGAAATTACAAAACAATAGACATT

TGTGCAAAATCACTTAGACTTAGCTCAAGACTGGCAACCAGGATCCTACT

CTTTCTGGTAGCTCATTAGTAAAGAGTTCTACAAAAGCAGCAAGGTCATG

CTAGGAAGTGGAGGAAGGAGAGGAAGCCAATGAGCTGCCAACATTCACGG

TATACATTTCTCTGTAAAGATTCTGAGAATTAACAGAATTTAAGATTATT

TTCCAGTGATGTAGTTAAAGGTCTTTAGTAACTTTTATCAGCTTAGAAGG

AGAAGAGCAGTTAACTTCATGTATGAGTTTAAGTGTCTCATGACTTAAGA

TAACAGTTTTGCTACAATTTGAAATGCCATACTTCAGACTTTTTAAAGGG

GTGCATTAGTGGACTATTACAATAGCTTAAAAATATAGATTTCTCCTACT

GATGATTATTACTGAGACACTACTAGTCTTTATTAAATTCACTTAGCAAA

ACTCCTGACATTTTCTTCCAGCAGCGGAAGAATGTCTCTCTCTTCTAGGA

GATCCTCAGTGACAAGATCTAGAAAGACCAAGAACTGTGGTCCCAACCAG

TGGGGCTGATATTTGTTTAACCTTTTAGCTCCTGTTTCTTCAATTATGAA

AAAAAAAAAAAAGAAGAAGAAGAAAATCCATGTTAAAATTTAGCAAGGAG

CCTGACTAGCTAGAAGCCTCCCTCCAATATATTAGTGTTATTAAGTCATT

TGAGTAGTATCACAAATATTAAATCTAAATATCTTACTTGTAAGTGATAT

TAAATCCAGTCAGATTATAAGCAGCATCACTGAAAAAATGCAGCAGTGCA

TAACCTGAAGTGACAGTGACCTCAGGAGCCGTCTCATTGCCATCTCTTTC

AGGAACAATGAGGCCACTGAAATGTAAACACAGACCAGATTACAGCAACT

FIG.3B(5)

TCAACAGAAACTGTCTATATGTTACTATTTGATCCTGCTGCTCCTGTTCC

AACACACACTGTAAATGTGACTCTAGCTGGCCTCAAATTCACAGACCCAC

CTGCTTCCACCTCCTGGGTTATAGGCATGCGCTACTATGCCCAACATCTA

AAAGGATTTGAAATCTATGACTTTGATTGAATTTTTGGTTTTTTGTTTTT

GCTATAAACTTTTTATTATAATACTCTCAAGTCTCTACAATAACATTATT

AACAAACTTTATGAATTGACAACTGTCAAATATATACTGTTGAAAGAAAA

TACTTTACATATTTTTGTAATATGTATCATATAATCTTTTTAATGTATTT

TATAGATGTCTTATATAAGTAAAAATAGAAAAGTTTACTGATTTATAATC

CTTATACTATTAGCTTTCAGACGTATTTTTGTTGTTAAACTGGTAACACA

TTTTATGTTTATAATTCACAATAAGCACTGCCACTGAAGGTGCCAAAGGC

TCCCTAGAATCTCAGTAAGAACCTAGTGGGTAATATTTGAAGTTTTGGAT

GCCAGTAAATTCATGTGTAAAGATTTATTGAGTAAGTGACTACCAGCGGG

ACAGTGGTGGTGCACGCCTTTAGTCCCAGCACTTGGGAGGCAGAGGCAGG

CGAATTTCTGAGTTCGAGGCCAGCCTGGTCTACAGAGTGAGTTCCCAGGA

TAACCAGGGCTACACAGAGAAACCCTGTCACCCTGTCTCAAAAAAAAAAA

AAAAAAAAAAAAGAATATACCATTTTTAAGGCATTTGATCCACAAAATCA

TACCACCTTGTTTTACAAAAGATATATATTAACTTGAAGGCTGGAAATGG

TGGCACATGTCTTTAGTCCCAGTATTGGGAAGACAGACCCAGATGGATCT

CTGAGTTCAAGACCAGCATGGTCTACATAGTGAATTCCATGTAAGTTTGT

CCGTGTGTGTAACTTGAAACCTCATTATAGAATGGAAGTGTCTACCCCAC

CCCACTTACCAACAGTAAGGAATATTATGTTGGTCCCGCTCATTTAATAC

FIG.3B(6)

ATGGTGTACTCCCAAGGTAAATCATTTTCATGTTTAGTCGCTCCTATTAT

TTTTTCCATTATCAATTCACTACAACTACTACCACCAATCACATTTAGCC

ACTAGAAAAGCCATGTGATTTGCTCCACACATACAACTTCACTCAATAAA

TAAACATCTTATCAGTACTACTCTCTCTTTCACTCACTCAATCCCTAGTC

CCCTAAGTTTTTGGACGATTACACCAGGTAAATTCCTACTTCAGGGTTAT

GACCATCTTAAAAACTACGACCTAGCAATTCTCTTTGTATAAGAAATACT

TCCCCGTATATACACAGAAAAACAAAGAACACTACTACAGCACTATTCAG

ATGACAACTGACTAAAAGTCACCTAATTGCTTATTTATGGGAGTTGATTA

AATTAGTCATTACAAATCTGTAGGTCTGCAAGACTAACCAAGAGCTTCGT

GAGGACAATAGGTAGGGCTACCCAGAGAAACCCTGTCACCCTGTCTCGAA

AAAAAAAAAAAAAAAGGGAGGCACAGAGAAAAAACAACAGGCCCGGGGTA

CCTGTACATCTATGTAAGCGTAGGTACATGCACATAAAAGTGACTACAAG

AGAACATAAACAGAGAGCGCCGATGAGAAGAGGATGGGATTTTTCATTTA

ATTTGCGTGTATGAGAGCACCTATATGTGCATGTTATCCGCACCAAAGTG

TGTAGGGTACATTATGTGAGTGTGCCTGCAGACGTCACTGTCAGGTGTCT

TCAATCACTCCCCTCCTTTTTCTTCTGGAGATAAGAGTTTCATGAAGTAG

TACTGGCTGGACTAGAACTCACTATGCAAACCAGGCTGGCCTTGAATTCT

CAGAGAGCCTCTTGAGTGCTGGAATTATATGCATGTGCCGCAACACAGCC

CACCTCATTTTGGGGGGTAGGATCTTTCACTGAACCTGAGCTCACTGATT

GGTTAGACCGGACTGGCCAGTAAGTTCCAGGACCTCTCTTGTCTCCGCCT

CTTCAGCACTGTGATCACAGGCTCACAACCACACCTGGACTTTTACTTGA

FIG.3B(7)

GTCCTGGAGATCTAAACTCAGCTCTCCATGCCTGTGCAGAAGGAATTAAA

CTGAGCCAGCTGTCTCAGTATCAAGAGAGAACATAGGAACTGTAAGATTC

TGACAGTACTCTAGGGCTTACAGAACACCGACACATTTTCTACTATGTAT

TCAGTTAATAAAAGAATAAATACAAACAAAAAAACATGAGAAACATATAG

AGGCAGAGACAGACAGACACACACACACACACACACACACACGCACACAC

ACACACACACACACACGCACTTAGACGGGTGTGGGGGAAGAAAGAGCAAG

GCCACCTAGAAACAGGTACGTTCCATGCAAATGATCACAGGAAAGGATTG

GGGATTTTTAACCACTTGTGGGAAATGCTGTACTCTCCTATTCTAGCACA

GATTTGAGGAAAAAGTAGACCAGAGAGTCTGTCCTTCCACATATCCTGGA

AAGTCACTGACATGTCCAAGTTTTGATTTCTTCATAGGGACAATGAGAGA

AACCCAGACTATCTCACAGCAGCACAGCAAGGACCAACCAGCAGAGCAGG

AGAAGTGCTTACAGCAGTGTGCTGCTAGAAGGTGCAACAGTCTTCTTACA

GAGGGCATTTAAATATGCAGGATGGATAAGTTTGCCAACTACAACTACAG

AGGCTGGACAAGGTAGGACAGCTTCTTCACTGTCAAAGACGTTTGGGCAG

TTGCTTCTATTTACCTTAAAATCAAACTGTGACAGCTGTGGCATATATAG

ATTTCTCCCAGAATGAAAACACATTAACTCACTTATGTCAATAATATGGA

GTAAACACAAACATAGTCTATCTAGCTCAGCATGCAAGACATGTGAGGAA

GAGGAGCTACTGTGAGTCCCTATCCCTGTCCCTAAGGAAACCAATATATG

TAAATGTAGTCTAAGCTGCAGGCAGTTCTTCAACTGCCTACCCCAGGCTG

CTCACCACTTCACATTCTAAGCACAGACTAGAAAGTATGATCAACCTCTG

AACACTGTGCTATAATGTTACCATCAATCTCACACACAAATTTCATAACA

FIG.3B(8)

TTTTAAGTAAGTCTATGATGATTCTATGTTGTGTCCCAGTTATATAAGAT

CCATAGGTCACAGGGTAGACATTCAAGGACACCAACATTTGGAATTTTGG

GTTTTTTTGGTGTACTGTATATACTTGCTAGTGCAGGTACCCATGCTCAT

GTGTGTAGAAGTTGGGCGTCTTTCTTCTATCACTGTCTACTTTATATTTT

CTTTATTGTTTCATTTGATATGTATAGGTGTTTTGCCTGCATATATGTGT

ATGTTTGTTGCCAGAAGAGGGTATTGAATTCCCTGGGACTAGAGTTACAG

GTGGTTGTGAGGCACCATTATGGGTACTGGGACTCAATCCTGGGTTCTCT

GGAAGGGCAGCCAGTACTTTTAATCACTGAGCCATCTCTTTAGCTTCCTT

CGTTCATTCGTTCGTTCATTCCTTCATTCCTTCATTCCTTCATTCAGAGG

ATTGAGATACCTTCCTCAGTTAGGCTGGCTAGCCAATGGACTCTGGGAAT

CTATCTGTTCAGCTATTCTCTCCTTCCCCATCCAAGTGCTGGGGATACAG

GCAGGTCCTACTGGGTTCATTTTGAAAAATTACAGAACTATGTATTTTCT

TCATAAATCTGAAACTCAGCATAACTGTCTCAGGCTAACATGGAATCCCT

AAATATATATGAGGCACAACCTGACTTTACCAACTGTACTATGTAAATTT

GCTAGTATATTAGTCAACACTTAATGGAAAAACATCTGATAAAAACAACT

TACAGGCCAATAGGCAAGGAGACACTTGGGGAGGTGGATTCAAGGCAGTC

ACTGGATTCTTGAATTTAAGTCCAGCCTAGGCTACATGAGATTCTGCTTC

AAAAAATAAACAATTAAATTTATGGGGGAAAGAATGATGTATTTTGGTTT

CAGAAATTCCATCCTATCATCCAAGGGAGATATTGTATAACAGCGAAGTT

CCTCAGCTCACAGCAGTCAGTAGCATATAGACAATCCTGGCTCCAAGCCT

ATGAAAACACAGCCTGTACTAAAGGTGTGTTCCTGTGTTTTGAGTGAGAT

FIG.3B(9)

GTGCCCCCTAAGTCTTGTGTATTTGAATACTTGGCACTCACTTGGTGGCG

ATTTGGGAGGAATTAGGAGGTGTGGCCTTGGTGGAAAAGGAGCATCACTA

GGGTCAAGGTTTCAAAATCCTCCTGCCATCATCCCCAATATGTCCTCTCT

GCCTCCTGCTTGCAGTTCAAGCTATGAGCTCTTAGTTACTACTTCCACCA

CCTACCCCTGCTATCTCTGCTCCATCATCATGGACTCCTATTCTGGTGGA

ACTGTTAGTCCAAAAAAGTCCTTTCTTCTACAACTTGATTTGATGCCAGA

TCTAGCCCCCCAGCCTAGCTAGCAATATACCAAGGTATACCATCTTGAAC

TCTAGGTGTCTCTCAATCCAATCAAGCTACATAAGATTAACCATCATACC

TAGTCATCCCCAAATCAGTGTATCTCTCTCCTCCCAAGACTATAAGCTCC

TCAAGGGTCAAAATATGTAGAAAGGAAGAAAGATTCTCAAAGGTCAAGGA

TCAGACCTTGGTGAGGATTGAGCACTGTCTACACTTTGCCTGGTAAAGAA

GGGTCCACAATGTAAAAGAGAACTGACCTGAACAGTTTTCAATTAGGTGC

TAACAAATGTCTCATACGTATTGAGTTTCTTATAAATAAATAAATAAATA

AATAAATAAATAAGCAAGCAAGCAAGCAAGCACTTAAGAGCACTAGCTGC

TTTCTTCCTGAAGACCTGGTTTCAATTACCCAGCACTTATACAGAGGCTC

ATACCAATTGTAACTCCAGTTTGATGATATCCAACATCTTCTTCTAGCCT

TCAGACACCAAGCACCAAGCATGTAATGGTATAACACATGTATACCAAAC

ACCCATACAAACCAATTTTTAAAAAAATATTCGAGCCGGCGTGGTGGCGC

ACGCCTTTAATCCCAGCACTCGGGAGACAGAGGCAGGTGGATTTCTGAGT

TCGAGGCCAGCGTGGTCTACAGAGTGAGTTCCAGGACAGCCAGGGCTGCA

CAGAGAAACCCTGTCTCGAAAAACCAAAAAAAAAAAAAAAAAAAAAAAAT

FIG.3B(10)

AGTCATTTTAGGGCTGGAGAGATGGCTCAGGGGTTAAGAGCACTGACTGT

TCTTCCAGAGGTCCTTAGTTCAATATCCAGCAACCACATGGTGGCTCACA

GCCATTTGTAATGGGGATCCAATATCCCATTCTGGTGTGTCTGAAGACAG

CTATAGTGTAAATAAAATAAAGAAATCATATAAATAAAATAAATAAATCT

TTTTAAAAATATTAATTAACCCAGGCTGAACCTAAACTTACAAACTTCCC

ACATTAGGCTCTTTAATGCGGGTGTTATAGGTCTGAATACCAGCTTAAGA

ATAATATTCTTCTGAAGAATGTGCCCTGGTCAATCACCATGACCACACCT

GCCAACAGGTCCTTCATAAAATACTTGGTATATGTTGAATGTTCCATAAA

ATTATGGAGCTAGAAAAGGTAGTGAGCTAGAAGGATATTAAAGATATAAA

CCATTGCCCCAGTGGTCCTCACATTTGTCTAGTAATAGAACGTTGTTAAA

CTGTTTTTATTTAGAATTTCAATATATAAAAGACAAATATGAAATAGTCC

GGAAGCAAATTAAGCTACAGCTTGCAGCAAAGCCAGATAGAATGCAGATT

AAACTAACACAGTACCTTTGTCTTATGTTTTAGATGCTAAAGTCTAGTCT

ACAACCCCAGCTGCCCTTGAACTCTTAGCAGTCCTCTTGCTTCAGCCTCT

CATGCTGCTAGGGTTAAAAGTATGTGCGACCACACACAGTTTTGAAGTTT

AGAGCACTTAAATGATCTATTCAGCAACTCAGGCAGGATTTACACTGAAA

GTAAATTATCTTATGAATCCTTTTTGGTTTTCCTTTTATTCATTTCATTC

ATGCACCTTACATGAACTATCTATTGCTAGGCTGTCTCTATACTGGATGC

TCAGCACATCACCAACATGCCGATTCTTCTACTGGTACAATGGCAATGCT

GAGAAAACCACACAACCTAAGACAGTAGGGAGGTGGTGCTCTGATTGTTG

GTGTTGTTGTTGTTGTTGTTTTGGTTTTTCGAGACAGGGTTTCTCTGTGT

FIG.3B(11)

AGCCCTGGCTGTCCTAGAACTCACTCTGTAGACCGGGCTGGCCTCAAACT

CAGAAATCCGCCTGCCTCTGCCTCCCAAGTGCTGGGATTAAAGGCGTGTG

CCACCACGCCGGGCTCTGGTGCTCTGATTTTTAAATACAACAATTTTCAG

CTAGCAATGTAACTCAGTAGTAAAATGCCTGCCCAGCATGCACAAGGCTC

CAGACTGGACCCTGAGCACCACAACACTTTTTAAAAGATGTGTTTATTTT

ATTTTATGTGCATGAGTGTTTTGCTTACATGAATGTCTGCACTGTGTTTA

CCTGGTGCCTGTGAAGGTTAGAAGGCAATGGAGCTATGGAGAGTTGTAAA

CTACCATGTGGAAATGGAGCTATGGAGAGTTGTAAACTACCATGTGGGTA

CTAGGAATTGAATCAGGGCACTCCTCTGCAAGAACAACAAAGGCTCTTAA

CAGCTAAAATATTACTACAAACCCACACCACAAAATTTTAAATTGATAGA

CATTATCACCTTAGTTCTAGATAGAGAATGTGCTTGGCATTGTAAGTACT

AAAAAGGTTTTGGGGTGGATCTTTTATATTATCTCACTATAATTTTATAA

AATTAATACTCAAATATGTTATAAGTTAAGGTTTTTATTTTTGTTTTTCA

TTTCTGTATTTTGTCTATGTAGCTCTGCCTGGCCTGAAACTCATGGGAAC

TTGACTGGCCTCAAACTCAGAGAGACCTGAACGGCCCTGCCTCCAAAGAG

CTGGGACTAACCATGCCCAACAGTAGGTAGCTTTAATACCTAACCAGTGT

ATTAGTTCATGCTCTCAATTAACCAACATTCTCTACATACAGAAATTTTT

ATGCCTATTTAATCAAATACACAGTCTAAGTAAACTCTAAGTACAACTGC

TTGGCTCATATTCTTACAATGGCTATGGCTAGCTAATTCAAAGGCCAGTC

ACATAAAAGGGTCTCTATGAATTCTGATTAACAAATGCAGTTAAATAGAT

GAATTCCTAAAAAGTAGTATCATAATAATATCATATTTAGTTTTTGTGCT

FIG.3B(12)

TCCATTATAGTTTGAGGTGCCTCCTCCCATAATGCAAGGTATATTTCAAA

TAATAGATATATACATGGTTAACACATGGCAAATGCCATTTTAAATGCTT

AGCACAGCCTGCTCTTTGGCTCCATTAAGTGAAACTCTTAAGTTCTCAGT

TAAAATAATTGTTGGAGAGCTATAGGAGCAATGGGTGGAGAACTAGTCTT

CTAATTTGTCCTTTGCCTCCTTGCGTACTAAGTAGTCCCTCCCTCACTAT

GTGGCATTCCAGCAGACTACCACCAAGAGAAGAACAGAAAAGTGTTGATT

TCTTTCTAAAGTAAAGAAATAAGGGGCCAGTGAGATACCTCAGCAGGTCA

AAGCCATTTGCCTAGAAACCAAAGTTCAATCCTTGGAAGCCCTGTAAAGG

TGGAATTAGAAAACAGACTCCACAAAACTGTCCTCTAACCTCCACTCGGG

CACACATGTGCCAACCCCTCCATTCTCCCTCCCCCACATACAAAGTAACA

ATAAACTTTCAGAAAATTTAAGTTGCTACGCATGGTGATTGATGAATGTC

TTTAATTCTAGCTCTTGGGAAGCAGAAGTGGGTGGATCTCTGTCAGTTCA

AGACCAACCTGGTCTATATAGTGTGTTCCAGGCATCCAGGACTACACACA

CACACACAAAATTACGTGAAGGAAGTAGAATGTTTGAAGGAAAGAAGTCT

GGAAATGGGGATGGAGAGAGACCTCAGCAATTAAGAAAAGGTCTTGCACC

GGACGTGGTGGTGCATGCCTTTAATCCCAGCACTCGGGAGGCAGAGGCAG

GCGGATTTCTGAGTTCGAGGCCAGCCTGGTCTACAAAGTGAGTTCCAGGA

CAGCCAGGGCTACACAGAGAAACCCAGTCTCGAAAAAACCAAAACCAAAA

ACAGAAAACCAGTATGATAGGTCAGGCAATTGGATCGAGACAGGACACTC

AAGATAGCTAGCCTGTGCAATATAGAAAGAAGTCTCATGGAAGAGAGAGG

GAAGGGAAGGAGGGGGGAGAGAGAGAGAGAGAGAGAGAGAGAGAGAGAGA

FIG.3B(13)

GAGAGAGAGAGAGAATGAGAGCGAGAGAGCGAGCGCACCTCAGTTGATAC

AAGATTGGGGCCCTGAGTTCCATCCCCAGCATCCCATAAATTGGGTGTAG

CAGCACACACCTGTATCCCAGCAGAGAGGCAAAAGACAAGTTCAAAGTCC

TATATGGAAAAAGTGTGAGATCAGCCTGGAGACCTGGTGTGTGGCAGTGG

GGTGAGGGGTGTCATCAAGGAGAAGGCTTAGTAAGTAAAGGACCTGCGTT

GGTTCTTGAGTTCAAGTCTCCAGCAATCAGAGAAAGCCAGAACCATTGCA

CAAACTTGTAAGCCAAGTGTTGGACTGGACAGAGACAGGCAAATGTTTGA

GGTCCAGGTTCAGTAAGAGACCCTATCTCAAAAAATCTGATGGAGAGTAA

CACTGGAAGAACTCAGAGTGAGTCACACATGCACACACAGGTGAATGTGT

ATACAAAGGGGGCAGGGAGGGAGAATGAGAGGAGACTGGGAGATATCTGT

AGTTCATGTCTGTAATTCTAGCACTTCAGAGGCAGCTGGAGCTACACAGC

AAGACCCCGTCTCAAAAACAAACCCAAGCCTGACAGTGGTGAGGTACACC

TTTAAGCCCAGAGGCAGGAGAATCTCTGAGTTCAAGGGCAGCCTGAGTGA

GTTCCAGGACAACCAGGGCTCCACAAAGAAACACTGTCTTGAAAAAAACC

AAAACCAACCAAACAAAAAAGAATCAAAAACAACCACCACCACTACAACA

AAGCAAACAAGGGAGAAGGTATAAAATGCTTAGGAGAGTCTTCCTTTAGT

CTCCATCCTTTGGGTACTCCTTCCCCACAGAAAGCCACTACTACCAATTT

CTTACATAAGCTGCTGTTTTAGACACAGGTTTTTTTTTTTTTTAAATATA

GTAACATATTCATGTGTAGCTCATTTTTCTAGTGAGTGGTTGGTCCTTCT

TTTAACAGTTTAAAGGACCTCTATGTTTAAAGGCGATTGGCCCTTGTCTG

GAGTATGGGTTGTATTTTCCCAATTTGTGAGTTTTACCCAACCTATTGCC

FIG.3B(14)

TATTACCTATGGCCATTTATTCTTGTCGATAAGTAGTTTCCAATTGTATG

ACTATGGTCACAGTGTTCCATGGACTCTTCTGCCGCTAGACAGCCCCTGG

GTCTGAATTTGAGATGGTTACAAGGGTGATTGGCTCTGCTCCCTGGGTGC

TGGGATTAAAGGCGTGCACCTCCACACCCAATTTGTTCTGTTTTGTAAGA

AATGAGGTTTTATTGTGTTGCTCAGGCTGATCTCAGTCTCCTGGCCTCAA

GGTATCCTCCCATGTCGATACACAGCACAAGGCGTAGGAAAAGTGGCAGA

TTTTTTTAAATTAAGTTTTCTTTCCAAAATATAGATTCAGAAATGTGAGA

TTTTCACAAAGTGAACCTGCTCACTTCCCTGGCTCTMGAATCTCCATTGT

GGCTCCCGCCCATCCCTTTTGCCCACCAGTGGCTGTTGTATTGACTTCTA

TCCCATTCCTTAACTATACCTGTCCTTGGTCTTCGCTGTGAACTTGCTTG

GGCTGAGAATCACCTTGTTCCGGGCACATCAGGTCAGTGAGGGTGTTTCC

AGAGAGTTTTAACAGAGACCAGAAGACCCACTCCAAATGTGGGTGGCAAT

ACCTGATGTTCTGTCATCCTGGACTGGGTAGGAAGAGGAAAGTAAGAAGC

AAACGGCACCCCCACCTCTCTGTCTGCTTCCTCGCCGACACAAAGTGACC

AGGGCCTCCCACTCCTGCCCCCTCAGCTAGAGACACTTGCTGCCATCTTT

CCAACCACTCTGAGACTGTGCCTACTAACCGTGACCCAAAATAAATGTTT

CCTTCCTTAAGGTTGCCTTTGTTAGCTCCTTTAATAGAGCGGTAGGACAT

GTAACTGCCACAGGCAGCCATCGCTGCCAGCCCCTCCCACTGACCGTCTG

AGAACCACACTCAGCTGTAGGCACAGCTCTCATAGCTGTGTGGGCGTAGC

TCTGTCTACTCGGTCATTCCCCTGCTGCCGAGCATTTATTGTTTTCAGTT

CCTGGCTGATGGGTAGCACTGTTATGAACATCCTAGTACAAATCTCAGGG

FIG.3B(15)

TGACACGCGCCTTCATTTTTCCTGAGAAAATGCCCAAGGATAAAATGCTA

GGGCCAAGGGAAGAATATTTCACCATTAAGAGACACTGGTCAGGACTGGA

AAGATGGCCCAGTGGTTAAGAGCACTGACTACTCTTCCAGAGGTCCTGAG

TTCAATTCTCAGCAACCACATGGTGGCTCACAACCATCTGTAATGGGATC

CAATGTCCTCTTCTGGTGTGTCTGAAGACAGTGACAGTGTACCTACATAC

ATGAAATAAATAAATAAATATCTGAGAGAGACAGACAGACAGACACTGGC

TAGTCATCTCACAATGTTCTCATGTTTAAAATATGATACCATTTGTATAA

AGCAGAAACACAGGAAAAATAAAATCTGTGGTATTATATTTGATTTTTAA

ATTAACTTGATTAGTGAAGTTAGCAGCTACACTGGGCAGGGGTTGGGAGT

GGGGTACTCTGAAGTGCTGGTATTTCTGGTTTTGTTTTTTGTTTGTTTGT

TTTTTTATCTTATTTATATTACATAGAAAGCCATTTTGCTAATACACTTA

CCATGTGTATATATTGTGCTTGAATTACAGCTAAGTAATTATTTCTGAGG

GGCTTTAGACTACTGAAGATTGGGCCCAATGAGCCCCACCCCAAGTAGTC

TCCAACATCCCTCTTGGAAGTACTTGAGAGCAAAGATTCAAGTCACATGT

CCCCAAACCCTCAGCAGCCACCACCCTTTAGGTGTGGCTTTTGCTCTCGG

TCATCCTGGAACATCTTGCCATCTTTGGTTTGTTCTCTCCCTGTCTTGCC

TCTGGTAGAGCTGGGTTTCTGTGCTTCTATTCAACCATGTACAAGAACCA

TGTGCCACCTGCCATGTGCCAAGCCTGTGCCAGTCCCTGTGAGCGAGCAG

CCCACCCCGTGAGTTATCATGTGAGGAGCTATGAGGAGCAGGAAGGGGCC

CGGATGACTTCAGCAGACAGTATGAAGCAAGCACTGTGCGATTTATGCTC

CCTGGCCACATGCCCACAGATGGTGTCTGAGACACTAGCGTTTAATATTT

FIG.3B(16)

GAATTCTCCACATTCTAGCCTAGACATTTTGGTTGCAAGAAGAAAATTGA

CTCCAGTTGTATCCTGGAATGAAATTTATTGGAGGAAAATACTGGACAGG

CTCCCAGAGAAAATACGATATTCAGGCACAAAAAGAAATGGGGACTGAGG

ATCTGAAGTTCAAGGTCATCTGTAATGAGATTGAAGTCAGTTTGGGCTAC

ATGGGACCTGGTCTAGGGGGAATGGGGAAGAGAAGGGAAGGGATCGAGAT

AGGGAT

FIG.3B(17)

CAATGTGCTCTGACGATTAATGGGCTAGAAATGTGTGGCTGTTGATTAGT

GAAAAGATGTCATGGTTCAGGAGATTGGTAGTCTCTGTGGGAAGACAACT

CACTGAAAGGGAGGAAATAGCCTGGAAGAGATAAAGAGACAGTGATCAGC

TAGGAAGCTTAAAATTTAAATTTTGTTGGAAGTACTGTTAGGAATACTAG

CAGAGGCCAGATGAATGTATGGTTAAGTTATAGCAAAGGAAAAGATTGTT

AATGGTGAGGTTAGGAATGCAGGGTGACACCAACCTGTAATGTCAGCATT

AGCGAGATAGAAGCAGGTGTTTAAGGCCATTCTCTGCTACTTAGCAAGTT

GAGGCCAATCTGGACCACATGAGACCTTTTTTCAAAAATAAATCTCCTTA

AACAAAAGAGGCTGGGTTTTTTGATAGATTCTTCAAGATGTTAATGTAAA

TAAATGGAAGACCAAGGATGGCATGCTAATATCCTCAGTGTCTGAAGAAG

GACTATGTAGTGTTGGCTGCTGACTCTGAAGTAAGTGCTCATTACTGACA

GATAGTGTATCTTAGAGCCTGGCAGATGGGATGGAAGTGAGGAAGCAAGT

AGCACCTTTGTATATTATGTTCTAAGTAGCCAGAGATACTTGACACAAAA

CAAAGTTGAGAAAATGTATCTTCTAGAAAATACAGACATGGAAAGGTGTC

CTTTCTATAAAAGAGGTATTAAACATTAACCTGAAAAAAAAGTTAGCAAA

TTGGGCTTTGGCAAATGAATATAGTCAAGTTTCATTTTTATTTTGTTTTT

TGTATATGACTGTTTGGCTTGTTGTACCATGTGTGTTCCTGGTGCCTAGG

AAGTCAGCTGGAGTTACAGATGGTGTGAGTTGCCATGTGGGTGCTGAGAG

ATGAACCTAGGTCCTCTGGAAGAGCAGTTAGTGCTCTTAACCACTGAGCC

ATCTCTCTAGTTCCTTCTGTAGAATTTTCATTAATTTACAAAGGAGAAAG

TATAAATGATAAAACCATGAGAAGATAGACCGGCACTAGAATTAGTGGAG

FIG.3C(1)

TCAAAATGTTAATGATATGTCAGATACGCCTTATATGAGGAAGTTGCAAA

ATTATGAAAATCCAGGCACTCCACTGAGTTAGAAATCTAGGCTCTGATGC

ATACTGCTATGGTAAGGTAGCAAGTGGCCATTGAGTGCAGAAGTGAGTCT

GGATGGGTCTTCTGGTGTTGTGGAGCACACAGACTGCTGTCTTCTGCATT

GCAGTTTCACCTGTATTTCCTTGGAACTACTTAGCTTTGCAACTAGGCGT

TAAAAAAAACTTTATATTTATGGTTTTAAGTTATTTATTTGTTTTATTTT

ATTTTATGAGACATAGTCTCACTCTCTAACCTAGGCTGGCCTGGAACTGC

CTAGGTAACTTGAGCTGGTGATTCTCTTGCCATAGCCTTCTAAAATTTTA

GATTGCAGGCATAAGCCAGACCACTCCTGACTTTTGTAGCCATTTTTCTG

ACATGAAGTGTAACTTTGCTTTCATAACTAAAATGATTTAGTTGTTTTGT

TATTGTTTAATCCCTTTTGCTTTGAATGTATCCTTTTGTGTGGGTGGCAG

ATATATAACCACAGACTTTTCCACAGGCATCCTACCCTAGGTCCAGAAAT

GACTCTGAGACGTCTTATATATGAATGAATGCCTAGGCCAATAGCTTTGG

CTGATTTCCACGGGTTCATAGCTCAGTTATCCCATTTAAACTAGTCTAAG

TCATGCCATGAGGCTACATACCCCTCCTTCAGTTTCAGGCGACTGTCTTC

TCAGTTGTGTAATGTCCTATCCTCTGTTGCTGCTCCCCAACCCCCATCCT

TGCGTCATAGTCCGTCTGTCCTCGTCTCCCCCCATTTACTTGCACAACGG

ACTCTACTCTAGAAGTCCTCTCTGTGCTGGAGCTTGCACCTCCGCTCTCC

CCGTCTAAGCTAATAGGCAACAGCATTGTACAGACAGGTGATGCTTCCAT

ACATCGCACAGGAGATTCTCCCTACACAGATACTTATTCATCCAGCGTGA

ATGCAACCGTCCAGGCGTGTTCTCCTAGTTGTAGTACATGCTGTTGTATC

FIG.3C(2)

AGTCTGATGAATTTCTTTGTCTTTACAACCAAGAAAGATAATACTGTAAG

AAATTTTGACTAACATTTTTTCTTTATTTAAATTACAGACTAACTGGCTC

TTCTGGATTTGTAACAGATGGACCTGGGAATTATAAATATAAGACGAAGT

GCACATGGCTCATTGAAGGACAGTAAGTTATAATGGCTGACTTTATTTTA

ATTTATTATAAGAGCACAGTATAGCACAAAATACTTCCATGTGTGTTATT

GCTATTTCTTGAGACAGGACCTTTCTGACTGAGTAACTCAGGCTGACCTT

GAATTTTGCTATGCTACCTCTGCTTCCCAAGTGCTAGGGTGGTAGGTGTG

GACCACCATGCCCTGCTGCTAAAATACCGTTCATTGATGCTTTTCATTTG

GATAGTGTTCTTGCTTTTTAAAATTTACTTTTTGGGGGACCAGAGAGATG

GCTCAGTGGGTAAAGTGCTTGCTGAACAAGTCTGGTTATGTGAGTTAATC

CCTGGCTCCCACAGTGGAAGAGTGACTCCTGAAAGTTGTCTTCTGACTCC

CACGCTTGTGCATGCACGCACACACACAAATAATAAAATAAAAAATTAAA

AGGAAAATTTTCTTTTTTGGGTGATAGGGATTGAACCTATGACTTCACTAA

GCAAGTGCTCTATTGTTAAATAATTCCTTTAATTTGTGGGTTTTTTTTTT

TTAGGTTCCAAGTTGACTTAATGTTATAAATGAAAGATACATACCAGAAA

TTTGCATATTTCTAATAGTTTAAAAAACTTAGTTAAAATCTTTTTAATAG

TTTGCTTAAATCTTTATATAATAATGCTATTATATCATTTTTCTAAATAT

TGATTTTATTATCAGCAAAACAGTAAATGAGCCATCAGAATAACCACTGT

AGCCTGTTTCCCTGGCCCTCTGTCCTTCCATCTGTCTATCTTCTCTTTTT

TTTCCTTTTTTGTGCCTGTCATTTAGGGCAAAGCATTTTAGTCTCTGAAC

AAAACTTTGAAATTTCCAAGTAACTCTTGTTTATTTGTTGTGTCTCATAT

FIG.3C(3)

TCAACCCAAGAAATATTATTTACTAACTCATTTAAAAGCAACAATTATAA

CCCACTACATGTTAGCAGAAAAACCTATTTGTTTTTATTGAGACGGGATC

ACACTAGTAAGCACTACATGGCATGGCGTTCACTGTGTAGATCAGGCAGG

CTGGCTTCGTGCTCTTGACAGTCCTCCTGTGTTTGTCTCTCACTTCTGAG

TGCTGGGATTATAGACATTACCAACACACCGATTTGGGGGGTTGGGGTAC

TGGGATCAGTCCAGAGTTGCATGGATGCTAGGCAAGCACTCCACCAACTT

AGCTATATCCCTGGTCATAAATGTCATAAGGAAAAAAATTCCTTATATTT

AAAGAAATTTTAAGAATTGCATTGTTTAAGATTTCACAGATCTCTTTGCT

ATCTGGCAATCTTTTTTGATATTTTGTTTTGTTTTTAAAAATATGTGGTA

TGTAAACAAACTTAAATATGAATGGGACAGTTCCAGATGAGAGTGAAAAG

TTAAATATTTGGGAGAAAAATTGATAGGTTTATCTATTATGGAAAATTTC

AGAGATTTTAGTAAAATTTGAAAATGGAGCTGGGAGGTCTGAGGTAGTCA

TCTAAAGCTGCCAGTTGTAGAGCGTGTTGGAGTGTGGAGTCAGAGGGAGT

TACTGATACACTTGTTGAAATTGCCCAGGCTTCATGGGAAGTGATGAGGG

GCTGTTACTGTGACTCTGGGCAGGGCTTGTTAGTTTCCTTTGGATTTAGT

CTCAGTCAGAGTTGATACATAGTTTCCTGAGGACGTGGCTTTTTGGTACA

GTGCTGTGAAAAGGCAGAGAAGCAGGTAAACTTAGAAAATGTGTGTTTTT

AAAGTGATGTGTTATGAAATCTTACGTAAGATGAATAAAGAAAGAAGTGG

GGACACTGAGGGCTCCTGTTTCTAAATGTTAAAAGCAAGGCTGGAAACAT

TCTTTGAAGGCCCCTGAAGTCAGAGCCCGTGTCTCTTTTGGTTCCCAGGA

CATTTTTGATATTCCCTTACACATAGCAAATACTAACTAGATCTCTGACA

FIG.3C(4)

AATGCAGGAAAGCTGTTTATATTTATATATATTTATATTGTATATTTTTC

TCCTTATAAATTCTTTAAAAGTCTGTTTTAGTAGTTAATGTTATGATTAT

TATAAATTACTTAATTATTTTTCTAGGCCAAATAGAATAATGAGACTTCG

CTTCAACCATTTTGCTACAGAATGTAGCTGGGACCATTTATATGTTTATG

ATGGGGACTCAATCTACGCACCTCTGATTGCTGCCTTTAGGTAAGCCCTG

CTGCATTTCATCTCAGGAAGTAAGTGTGTCTCCAGGATGGAGTCCGTGCT

GCATTTACTTTATTCTGCAGTCACACTCATCTCATGGAATTAGTTCTGTT

CTGGTGAGCTACAGTTCACTTGGTTTTTATGTACTGGGTCGTTTTCCATG

TATACTAGTATGTAGCCACGGTTAGTCTTGAACTTCTGGTTCTCCTGCCT

CCACCTTCCAAGTGCTAGGAGTATAGGCTTGTGCCACTGTGCCTGACTCA

TTTCACATTCTTGAACTGTGAAGTTTTGATAACACTATTAAATTTACCTG

CTATTTGTGATTTTGTTAAAGTTTGCATTAAAAAGTTTTTGACTATATTG

ATAATATTTTTGTGACAAATTTAAATCAGAAACCATACCTTTCTTGTTCT

TGTATGTATTTCATTCCATAGGCCCTTAGGAATAACTTTTTTCAATAGTA

TATAGTTCTCTCAGTTTGTATATATGTATTATTAGGGATAGGAGGAGCTT

TCTGGAAGACTATTTATAAATTGGACAATGGCTAGCTGTTGAGAGTGAGG

AATTTGCTAGTTTTGTTTTGTAAATCCCTCCCCAATGCATCTGTATTAGT

GATTTAATAAAATAATGCAATTTTGTCAGTTATATGGGTTGCACTGAATT

TTTGCTATTTTATTTTAAGAAAGATTTTTGTGTGTCTACAGTGTATATGA

GTGTATGATATGTGTGCGTGTGCATGTGTGTGTGTACTTCTATGCAGGTA

CTCACATGCTATGGTGTGCACGTAAGGTTGGAGTGCAGCCTCACATGTTG

FIG.3C(5)

```
ATCATTATATTCCACCTTGTTAGAGATAGGTTGTCTTTGTTGTTTGCTGC

GGCCTGGAGCTGGAGCTGGAGCTAACGAGTCTCAGCCACCTGACATGGGT

ACTGGGAACCAAGAGCAGCAAGACCTCTTCTTCTTCTTCTTCTTTTTTCA

TTTTCGGTTTTTCAAGACAGGGTTTCTCTGTATAGCCCTGGCTGTCCTGG

AACTCACTCTGTAGACCAGGCTGGCCTCGAACTCAGAAATCTGCCTGCCT

CTGCCTCCCAAATGCTGGGATTAAAGGTGTGTGCCACCACCACCCAGCCT

AAAAGATTTTCTTACTAAAATATATTTCTAAATTAATTAGTTGGAATCTG

GTTCATACTTCTTTTTGAAACAAAACCAGCATTTTTTTTCATTCTACATA

CAGAGACATTGACACTAGACACTGGTTATGAGTAGTTACTATAAGAATGG

GAAATTATTCCACCCTTGTAAAACTTAATACAACTCCTTATCAGGCTCTG

AAGACTTTTTAAAAGCAAGAATTGTATATAACACACAGAAATGATTTAGA

CTATTTAGATCTTTATTGCATGGGATTTTAAAATTATTATTGTATTTCGT

GGGCATGTTTTGTCTATGTAGCATATGTGCCTGTAGAGGCAACCACCAAG

TAGGTCCTGGGAATCAAACCTGGTACCCCTGCTCTTAGGTGTTCTTAACT

GCTGAGCCATCTCTCCAGTCCTC
```

FIG. 3C(6)

AGGCAAGAAAGAGCCAGCGAGCCTCCAGACAGACCATTAGAAATTCCACA

GTCAGCACAATAGGGAGAACAGTAAATCTTACATTAAAAGAAGGCCAGGG

CCTGGTAGCAAAAGGTTTTAATTTAAGCACTTGAGAGGGAGAGGAGGCAA

ATCTCTCTGATTGGGGGTTGGGGTTAATGGTGAATGCCATGACACCCTGC

TCAGAGTTAGCCTTCTCCCCTAAAAAAATTTTAAATTCATTTTCAATGCT

GACACAGTTAATCATAGACATTGTATCTCAGACACCTCAACATACTCCAG

ACTGCAGCACCAGCCCACTGCTGAGGCTGTCGTTCAGTTGGTAGAAGGCA

TGCTCAGCATTCGCGAAGCACCAGACTTCATCCTTAGCACTACATAAAAC

TGGGTGTGGTCATGCACACTTATAACTTCAGCACCATGGAGGCAGAGGCA

GGATGATGAGAACTTGAGGATCATTCTCAGTTACATAGGGAGTTTGAGGT

TAAGCAGGGGTACAGGAGGCCTGTCTCAAACAAACAGACAAACAGACAAA

CAAACAAACTTCAAAAAACTCTTGAAGTACTAGGCCTAGTACGTGCTGAG

ATTGTAGGTATATGTCATCATGCCTGTTGTAGAATGAGTGAGAGCGGACT

CCATAGGCTTATAGATTTGAATCTTGGTGTCTGTCTATGTCATGTCATCC

CTGCACAAAAGCCCACACTAGGCCCACACATTCTCTCTGTCTGCTGCATG

TGGGTTAGATGTGAGCTCTCAGCTGCTGCTCCAGTGCCATGCCTGCCTGC

TGCCAGGCTCCAGCCATGACGGTCAGGGACTAACTCTCTGAAACTGTAAC

CAAGTTCCCAATGAAATGCTTTCTTTCATAAGTTGCCTTGGTCATGGTGT

CTGCTTCACAGCAATAACACGGTGACTAAGATACCTGGCTCCTCCCCTCC

CCACCCCACCATTATTTACCATAAAGTAAACAATACACAGTTGGATAACA

TGATACTGAAGTTATTTTCCTGTTTCCTGATGTAACCCAATTTTGGACAA

FIG.3D(1)

GATTAAGCCTTAAATAGCAAGCTGTGAGGCAGGATAAAGAAAAAGCTCGC

AGGCCAATGTCTGCTTTACCAAATTCTGTTCAGCAGTCTAAAGCTGCCGT

CACCTCGACTCCTGTGATGGCATTTCCATCACTATCTTAGATATTCCCTG

GGTCACAACCTTTTAGTACACAGATTGCAACTCTGATGGAATGGCTGACT

GCTTGGCTAATTAAAGCAAGCTAGAGTTTGTCTGGCTTCCTTGTCTGAAT

GGGGAGGTGGTATTTACAAAATTTTGTAAATAAACTACTATATTTGCATG

ATGTATATAAATTTGATGTGGCTGCTTTTAAATCATTTAACCTAAACTGT

CCCACAGAATCATCTGTTTGATTGGAAAGATTGTAGCTTCAAGAGAATTT

CTGCTGAACCTGAAATGATTCATAATGATGTGTCTGAAGAATGTGTGCTA

TCACCTACGGTTTTTGTTTTAGTTGATATTTGTACTTTAAGATTTCCTTT

ATGTATGTGTGTGTGTGTGTATTTATGTGAATGTATACCTCATGTATGTG

GTGCTCAAGGACACCTGAAGAAGGGCTCTGGAGCTGGAGTTACAGGGAGT

TGTGAGTGCTAGGAAAGAAAGCTGGGTACACTGGGAAATCAAAAGGTGCT

TCTAACCACTGAGAAATCCTGCCAGCCCCTTGGTTTATTAAAAATATCAA

ACAAAACCAACACTAGTTACATAAGTATCTCTCTCTCTTTCTTTCTCTCT

TTCTTTCTCTCTCTCTTTCTCTCTCTCTCTCTGTCACACACACACACA

CACACACACACACACACACACACACAAAGGATCCATAATAGTTCTTCTGT

ATCCCGGTTAAATATAAGTTCTTAGGGGCTAGAGAGATGGCTCAGCAGTT

AAGAGTGCTTGTTGTTCTTCCAGAGGACCCAAGTTCAGATCCTAGTACAC

ACATCAGGCAGCTCACAGCTACCCATATCTCCAGCTCCAGGAAGAACCAA

TCAATGCCTATGGCCCATGCAAGCACCAGCACACATATGCTCCACAAACA

FIG.3D(2)

TCCATATATATAGCTAAAAGTAATAAAAATAAATCTTCAAAAAATTAATT

CTGGTTGAACTGAAAAAGATCACCTAACATTTAGAAAAAGCAGTTTACTA

GTGAATAGGACATAAATCATGGTATCAAATATTCTGTTGTTAAAGGAAGC

AACTAGAAAAAGCATGTGTTTGAAATAACCAATGGATACAAAACAAATGA

GGCAACCCCAACATCTGTCAGTACCTTGCAAACCAACACAATAAATTTGA

TTTTATTTAAATCGTAGTTATTTTTCATGCTAGTAGTTTTGAAACACAAT

AAATTTGATTTTATTTAAATCGTAGTTATTTTTCATGCTAGTAGTTTTGA

AACCAAGATCTAGATTTTGTATAGCCACATAAATACACATTAGAATTGCA

AACTGATACGAGCTTCATCTTCATCAGTCTCTCTTCATGAAAAGCAGTTA

CAGGGACTGAGACATGACTCAGCAGTTACGGCATGGGCTGTTCTTCCATA

CGACATGGATTCAATTCTCAGTGCCCAAATGTTGGCTCACAACCATTTGT

AACTCTGGTCCCAGGGGATCTGACACTCTTCTTGGCTTCTATGGCCACTG

TATTCATACGGTACACAGACACATATGCAGGCAAAACTCAACAAAAAAAA

TAAGGTTTAAAAAAAAGAATTAGAACTTAAAGGCACTTCATTCCGTCAGC

ACTAAATCAGCCTCTCTGGAGTCTTCCCACTTCATGAGAAAATCGTCAGC

TCTCCACTGCTGTCTGTGGCTGAGGAGCAGGACCTGGACAACGTTCAGAG

ATTGTCAGTGCATCTCTTTTCTTCTTTGGTTTGCTGTCATCAGGTTCACT

GTCACATTCCCTTTGTACCATCCTTCCTTTAACAGCCTTTTGAAAATGCA

GAAATGTTGGATGCTGCCTTCAGTTCACACAGGCTGTCTTTTTAGCTCCT

CATCTATCTATGCTTAATTTGTTAGTGGTGCTCACCCATGTATGTGTTTA

TGTCATGAAGCCACAAGATGAGCCTTGATTGAGTCTTGCTGTCAGTGTGG

FIG.3D(3)

ATCACAGAAATGACACCCTATCATCTTTGCTTCCTGCTTGTTAGAAGTCA

TTGATTCTGCTTATACTCAAGGCCCACAGTATTATACTTGGGTGTGAACC

CCAGGAAGCAGGGAGGTGGGGGGTGTCATGGATACTACTCAGATATCTGA

CTGTTGTGATATTTCATCAGTTCTCATTGGTCCTATCTTTAAAATCTGCC

CTACATCTAGAGCTGGCTGTGGTGGTGTGTGTGGTGGCATCAGTATCAGA

ACTTGGATTACAGAGGCAGGAAGATTGTGATTTTTGAGGCCAGAATAGGT

GCATACAAAGATCCTGTCTGCAAAAGAAACAAATGTGCAAATAATTATAA

CTACTTTACTAATAGCCTAACTAATAACCACTGCTAGTGCTGTGTCCACG

AAAAGGTGAAGTAAACTGTGAAAATGACTTCCCCTTCTGTGTGACACACG

CCGTCATGTGATTTTACTTGTGTCTCATCATTGTTTTTCCTTCTGTTTGC

ATGTGTGAATGTTCACATGTGGAAGCCAGAAGTCAGTGTTGAGTGTCTTC

ATAATTGATCTCTATTCTCTTTGTTTTGAGACAGGGTTTTGAGACTAAGC

CCAGTGCTCAGTGATTCATCCAGTAAACTGTAGGGAGCTTCCTGTCTCTG

CCTCCACAGTGTTGGGATTACAAGCATGATCCAAATTATGTGACAAGCGC

TTTACTAACTTAGCCATGTCCTCAGCTCCCCACTCCCCTTTTCTTTTCTT

CTTCTTTTTTTTAGACTTACTTGTTTATTTTTATGAATGTCTTGCCTGCA

TGCATACACACACACACACACACACACACACACACACACACCCCACATGC

AAGCAATTCCAGAAGAGGGCATTGAATCCCTGAAACTGGAGTTCCAGTTA

ACTGTGAGCCTGTCATGTGCGTACTGGGAGCTAAATCCGGGTTCTCTGGA

AGGTCAGCAAGGTCTTACCTGGGAGCCGTCTCTTTAGCTCATGTGTTTCT

CTCTTGAAGCAAGAAACCTAGGAATCATTTTGAAACTTCCTTCACAGCCT

FIG.3D(4)

TTATCATAACTTCACGTCAATTTTTACCTACTCTTTCAACAAATACATGT

TATATTTACTTATTTTTATGTTTAGCCTGCTATTGGTTTCTACTTAGCCT

CTTGCAGTAGAGTTCTGTCAGATTTATGTTTCTATTGCTTTTAATTTATT

TGTAAAGGTGAATGGGAAAATATTTAAAAATTACAGATCCCATCATTTAC

TATATTCTTAAAAGCCATGGCTAGCCAGGCTTGGTTGTGCATGCTTGTAC

TCCCAGGACTCTGACAACTCAGTAAGGAGGAGAGTGAATCAGAAAATAGC

GCCAGCCTGTGCTGCTTAGCAAGAAACAGAAACAAGTACAATCACACACA

TAGAAAATCCCCCATTAATACCATCCCATTAGATATAATGGTCCTGTATG

ACCATTCAACCACTGTTTGTCCTCTGTACTGCAGTAACAGTCTTCTGCCC

TTGCCCGTGAAGCACGTGCGCACCCCGCCTCCAAGTGCTTTTGCACTGGT

GTCCTCCGTCTAGATGTCCTGTTACTATATGTAAGGACTGGTTTCTCCTC

CTCTTTACAGTTCAATCTAATTGTCTCATGAAAAGATCTTTCCTGACCAT

CTGGTTCAGACAGGTTCTCCCTGTTGTTGTTTTGTTTTTTGTTTTATAGT

TCTAAATTCCTTTCAGGAACTTTTGCTTATTTTAAATTCCCTGAGTGCAT

ACGTGTGCTTGTTGTTGCTCATGCTCGTTGTTTGGGCTTACTTTACTATC

AGCTCTGGATGTGGTTCACAGAAGGTGCTCAGGGGAGCACTCTCAGCCAC

TCATCTCACACGGGTTATAGATATATGTATTGATGCTACGTTTGCTTGTG

AGCCATGTTTTAAAGATTAGAATATCTTTTCTATGTGTACTCTATCAAAA

CACATGTTAGGGCTTTATCTATTTTATACAGATATTGGTGTTCTTGCTTT

ACTAATTTTCATGGAATTTCGGTGAATATTAGTATTTTAGATAGGAAGAC

TTGTCTCAAAATGTAGCTCAGCTGGTTGAGTGCCTGCCTGCATGTAGAAA

FIG.3D(5)

GCCCTGTATTCACTCTCCAGCACCTCAGAAGTGGGCCATGGTGCATATGC

TGTCATCTCAGCACTCCGGAGGGAGAGAAAAGAGAATCTGGAGTTCAAGG

TTATCCTTGGCTATATAACAAGTCCAAGATCAGCCTGGGCTACATGGCAT

CCTGCCTCAAAATCAAACACCAAATCAAAAAGCTCACATCTTGATCCAAA

AGAAGGTAGAGAGAATACACTGGGAAAGTCTTTGAAACCTCAAAGCTAAC

TCCAAGTGACAGTGACACCTCCTTAGCAGGGCCATAAATTCTAATCCTTC

CCCAAAGCCCACCAACTGGAGACCAAGTATTCAAAGATAAGAATCTATGC

AGTCCATTCTCCTTCAAACTACCACAGTAGGTTTTCTTAAAAAAAGAAAA

AAGAATATTTTAATTGATTGTGATTATTCAGTATTATTCATGAATAATCA

TGAACTACATGGCAGGACTATAAACTATTATTTTTTTTAAAGATTTATTT

ATTTATTTTATGTATGTGAGTACACTGTAGCTGTCTTCAGACACACCAGA

AGAGAGCATCAAATCCCATTACAGATGGTTGTGAGCCACCAAGTGGTTGC

TGGGAATTGAACTCAGGACCTCTGGAAGAACAGTCAGTTCTCTTAACCAC

TAAGCCATCTCTCCAGCCCCTATAAACTATTATTATATTTATAAAATATA

AATCCGTGAGTCTGTGCACCCCTGTGTGCACATGGATGGGACATCTTTGA

ACTGGATTATATCATACTTAGAAGAATACAAGATACTCTGTTTTGTCATT

TGGGTGAAAATATGGTCTGTTTATTTTGCAGGTATGACCTGACTTCTAGG

GAATGGCTTCCACTAAACCATTCTGTGAACAGTGTGGTTGTAAGATATGG

TCATTCTTTGGCATTACATAAGGTAAACTATCTCAACTCTTCACCAAGCA

AGAAGTTCAACTCTTCCTGTTGCTTTATGTCATTGAATACTATCGAGCTT

TGGTTTTAGTTGGTATAAGCTTTGTTTTGATGTCATGGAGGTATATAATT

FIG.3D(6)

CACCAAGTTGTCACCAAGTTGTAATTGGAAATTGAAGTTAGAACGATTTT

AATCCATGGTGTCTTGCATTTGGATACTCTGATCACAGTTAACAATGAAG

ATTAAATAGTGTCAGCAAGCCTATGCCCATTATCAAGTCTAGCATACTGC

ATGCGTGTGACTGAGTAGCCATTGTTATCTCCTTGTTTTGAGCGTATATT

GTAGAATGAGGCAACTGTATTTTCCACACCATTTTCGTTCTGTAACACGT

TTCATGTAGAGAAGGTGATTTAGAGAGGGGAAGAATGTGATTGTATTGGT

TGGTTCTTTCTCTATGCTATTCCTAGCAAGTCACCGAAGAGCTCATGTTA

CTCACACTTCTTAAGCTGGGATCACAATGAGATTGTGAACCACTCATTGT

TGTTTTCCAATATAATTTTTAAAAAGATGTATTTATTTTTATTTTATGTG

TGTGGGTGTTTTGCCTGCATGTATGCCTGTGTATACTGTTCCTCCAGAGG

TCAGAAGAGGATGGCATCAGAACTGGTGGCTGTTAGCTGCCATGTGGGTA

CTAGGAACTAAACCCGGGTCCTCTGCAAGAGCAGCAAGTGTTCATAAACT

CTCTCTCCAGCCCTAGAGTTGATTTCTTAATGGTTTTAAAAATCCTGTTT

ACATCTTTCTTATAGGATAAAATCTACATGTATGGAGGAAAAATTGATTC

AACAGGGAACGTGACCAATGAGCTGAGAGTATTTCATATTCATAATGAAT

CATGGGTATTGTTAACTCCGAAAGCTAAGGATCAGTATGCAGTGGTTGGA

CACTCAGCACACATTGTTACACTGGCATCTGGCCGTGTGGTCATGTTGGT

CATCTTCGGTCATTGCCCACTCTATGGATATATAAGCGTTGTGCAGGAAT

ATGACTTGGGTATGTATTTTTTCCAGTGGAGGCATCTTGAATATCATACT

GAGAACCCCTGCCCTTATTATTAGGACACCGTAACAAAATTCAGCATGAT

CTTGATCCAGTACCTTGTCTTGAAATAGTATCAGTAGATAACTGGTGAGA

FIG.3D(7)

TTGAGGTTGTTGAAGTCCCTGTGCAACAGCTGTTTCTTACTTGTCAAGGT

CTAGTCTTGGCTTGGGAGGGGTTCTGAGGAAAGGGGTGTCAAAAAACCCA

AAAAGTCCAATTGTAGGTCCAAGCTGGCAGCTGTATATTGCATTAAGGAA

AGCTGAGGGAAATTTGGGATATTTATTTCATCTATTAGTCTACATCAAGC

AAGTCAAGCGCTCACAGTCAACGTTTGCACCCTCAAATTAGTAACAAAAG

AGGGGGAACTGAGGAGTCCAGCATGGTCCTGGTTGGGACAGAATGACATG

GTTCCAGCCCTGAGACAGGGGCAGCAGGTCCGGGCCTCCATGGATGTCAC

ACTATGGACATAAACCTGTTTGTATAATAATGTACATATTTCATGCTCCT

CTTCTGAGTAATGTCCTTCTGTTAATGTGAATGACTTCATGATAATCAGA

GCCAGTGTGAGTCTGGGAAGTAAATGGTGGGACCTTCAGGACAGCTCTTA

AGGCTGTGGAAAAGAACATGAGTTCAAAACCATATACTTCCTCAACTATA

CAAAAATAGAAGGATGCAATATGAATTGTATGAGGGGCTTCACAGATCTA

AAGGAACAAAAGCAGCTTCGCTGTGAGCCAACTTGTCAGAAAGATATTGA

GTAAGCAGTTAAAGAGATTTAGGGAGTGCTGATTGCTAGAGGAGGCCACC

CAGCTAAGTTTGTGCTTACAAAGGCAGACAAAGTCCTGAGTTCAGGGTGG

GCCTGGAACAGAGCAAGGTTAGTTAGACCTTGGTGTGGTAGAAATGGTAA

TTTCCAGACAGGATACCCAACTAGTTTTTGTGCTTAACAGAGGCAGGTAG

ATCTCTGAATTCTTTTGTAATGTTAAAAGGAAATGTGTGCTTGTTGTCTC

CCAAGGGGCCTGAGTCCCAGGATGCTGATTTATAGGAAACCTGGAGTAAC

TGGGTTTATGACCTGCAGGAGACGAGCTATCCAGAATGTTTTTTGCAATA

GCAAGAGAGAACTGCCTGGAGAACTGCCTTCAGCAAAGAATAGCAAGAGA

FIG.3D(8)

AAGCTGTCTAGAGAGAGAGCTGTCTGTAGAGAAAGCCGGTCAGAGAGAAA

GTAGACTGGAAAACTGTCTCCAGCTTGGACCCACAATTTGACTTTTTGTT

TTTGTTGACAAGTTGCCCTCCCCCAGAAACACCTTCCTCAGGACCCCTCC

CAAGCCAAGGCAGGGCCTTGGCCCTTCTTGTCAGCTTGCAAGGAGCCAAA

GATAGCATTAAATGCTTTGGATATCAAAATAAGCAAAATGCAAAACAGTA

AACACTCTAAAATAATTCTGGCTAGTCCTTTAAATATTAGGCCAGTGCAC

TGTTATTTTACCTTAATGTATAATCTTGTGTTACATTTTATTGTTTTTAT

TGTATAATAGGAATGTCAGAATTATAATTTTGTAACATTTGTTTGACATT

CCTGTGAAAATGCATCTAAAGATCATTAAAGTGCATCTGAAGATCATAAG

GACTCACTGAGGAGCACAGGGAATTAAGTGTCTGCTTAAGAGAACTTTGA

ATCTTTAATCTTTAGAATTTGTTTTAAAAATTTGAATCTTGCCAGTGTGG

TGGCGCATCCCTTTGGTCCCAGCACTCAAGGGGCAGAGGCAGGTGTATCT

CCATTAGTGTGAGGCCAGCCTGGTCTACAGAGCAAGTTCCAGGCCAGGCA

GGGTACACAGAGAAACCCTAGCTTAACAAAACAAAACAAAATATGAATCT

TTAAAAACTTGTTCTGTGAAAATTTCATACATGTATACAATATAGCTTGT

TCATATCCACCGCCATTCCTTCCAGCTCCTCTAGGCTTTCCCAGTGCATC

TCCTTCCTAGCCTTATGGCCTCCCTTTCAGGGTGAAGGTTAGCACACTGA

GTCCAGTTAGTGCTGATCCGATGCAGTCTTGTCTAGATGGTCTTCTTTAT

AATAAGGTGAAAGTATATCCTAAACTTCCGTCTTTTGCTCTAAGGTGTTT

AGACTTTAAACTAATGTTTAAATCGTTTAAATAATTTATTATTTCATAAG

AAGAGGAGCCTGCAACATTGACTTTAACTATTGTCTCTTATCCAGAAAAG

FIG.3D(9)

AACACATGGAGTATATTACATACTCAGGGTGCTCTTGTGCAAGGGGGTTA

TGGCCACAGTAGTGTTTATGATGACAGGACCAAGGCTCTGTACGTTCATG

GTGGCTACAAGGCTTTCAGCGCCAACAAATACCGGCTTGCAGATGACCTC

TACAGATACGATGTGGATACTCAGATGTGGTGGGTGTTTTCCTAGAGCTT

TCCCTTGGTAGTCTAGAATCTGCAGAGGCAATTGATTAAAAATACTGTGC

TATGGTTTGACTTTTGTTCAGCATTGTATGTAACAAAGTTAGGAGATCAA

TACAGTAATAGAGTTAAGGTACTAATGGTGCTGTTGCTGTCTGTTAGTGC

TTAGTGCTTTAGACCTGATTCACTGAACTCTAGCAAGGTTTCCTCTCTTC

AGAATTCTCAGCAATAAAAGCTGTGCTGATTTTATCCATACTTAAAAAGC

ATATCCTTCCTTTTCTCTTTTTGGTGTTGGGGATCAAACCTTGTACATGA

ATAGGCTATACCATCTTTATCCATTTACATCACCAAACAGGATGCTCTCG

TGCCTATTTGATAGGGTTTTCACTCACTTCGAACTGAAACTTGGGTTGTA

AGAGTATGGTACTTTTAGCAAATGGAAATAAATTTGAGTTATGATGCAAT

TATAAAGCACTGGTCTCTCTGTATTTCCCTCCTCCTTCTACTCCCTCCCT

CTTCCTTTCTGACCCCCTCTCTCAACATACATTAGAGACCATGCTTTGAC

TGTCAATTTATGCTGTGCTGAAGATCAGGTCTTTAGTGGCTGTGAACCAC

GGAGCCTATGCAGTGGAAGTTCTGGTCTCTGGCTTTTGCCTTACTAATAA

AACACTGAGCATAAATTTTGATTTGTATTTCACAATTCTTACCTGGAATT

CTTAAGTGGAATTATGGAGCCATAGAGAATGAACATTTTAGGGCTTTTAA

TATAGTTTCCCGAAATTTTAACAGATTTTCATGATTGTTAAAGGAAGTGG

CTTACGTATAGGGGGAAATCAAGTATTGCACATTTGAATCTAAAGTTATA

FIG.3D(10)

AAGTAATTACATTTAAATTGGCAAATAAGTATTCTTTTAAAACTAACCTT

ATATTTATTATTTCTAAATAAACTCAAAAGGACCATTCTTAAGGACAGCC

GATTTTTCCGTTACTTGCATACAGCTGTGATAGTGAGTGGAACCATGCTG

GTGTTTGGAGGGAACACACACAATGACACTTCCATGAGCCACGGTGCCAA

ATGCTTCTCCTCAGACTTCATGGCTTATGACATTGGTAAGCTTTCCAAAG

ATGTTTTAGCTTCAGGAATATTTTCTTTGCTGATGGAAAGATCACTATGT

TAAAATAATTGCACCATTTAAAAGAAGTCCAGGTGGTAGAATTTGCATTT

AATTTGAGTAGGGTTACACATCTATTGAAAAGCATTATTTTGGATTAAAC

TACATTAAATTCTTTGTGAAATCACTCTTCTTAATTGCTTTAATTCTTTT

TTTAGGTTGAGTTAATTGGTATCTTCTTTCTTATAAGTGCCTTACATAGT

AGTGGTGGTAGTTGTAACCACCAGTGTTATGTTAAGTTTGATGGGATATG

CTGTTTCCTAGAAACCTGGTTTTACACATGCTGTTGATGTCAATATACAT

GTGGCCAGAAGAGGGCAGTGTCTGTTTATTCCTGGAAAATAAACATCAGC

TGCTCTGTTGTGTAAATATCACCCATGTGATGTTCTTTCTGTTTATTTGT

CTTTGCATTTTGAGACAGCCTCACTATGTAGTCTAATTGGCTGAAGCTCA

GTATATAGATCAAGGTGACCTTGAACTTAGAGAAATCCTCCTGCCTCTTC

TGAGTGCTAAGATTAAAGATGTGTACTACGAATGAAAAAAAAAAATGTGT

ACTACCACACCTGACTAGAGATTCATTTTAAAAATTATTCTTATTGTGAT

AAAATGCTCAGAATAACACTCACCATCTTAATGTTTTAAGTAGTTTAGAT

TTAAATATATTCCTAGTGTTATTCATGTTATAATACCATCTGCTTGCCGA

CTTCTTGTAAAACTGAAACTCTGCCCTTAAACAATAGTTCCTCTCTTCAT

FIG.3D(11)

CCCTCACTCCAGCCTCTTGAAATCATTTTCTATATCTCTATGATTTTGAC

TAGTCTAAATTAGGCATTTTTTAAAAAAAATATTTTGTTTACTTGTATGT

GTATGAGTGTTTTGCATGCATGTATGTTAAGCACACCATGTATATTCAGT

GCCCATAGAAGCCAAAAGTAGGCATAGATTCCCCAGAGCTGGAATTACAG

ACTTTTGTGAGCCACCATGTGGGTGCTGGATACTGTGCCCAAATCCTTTG

GAGGAATAGTGAGTCTTCTTAGCTGTTGAGCCATCTTGTCAGCCCTAGAT

GTTTGTTTTTAACAAACGTGTTTTTGCCAGCCATTGAGTTTTTAAATTGA

GAATGGGGGGTACACTATAGTTAGTCCTTAGCTTCAAGCTTGTGGAAGCA

GAAATGAGAAGACAATATAATCTTAACTCAGGAGGATTCTTGCTGGCTGA

AACAAAGATGTGAAATTACCTCCGAGCACTCCTAAGCCACTGGGGTGAGC

AGGGTGGTCTGGAGAGGCCTTGAAGAGAAGCTGTCTGAGCTTGTTCCTGG

GGACACTGGGAGTCAAATAGACCTCCTGGGCAGGGGGATTTAGTGCAGAC

AAGAGGCAGGAAAGTACATGTCAAATATTTAGGACTTTTGAACCGCTACC

TTTCTTTTGTCATGGTAACACAGAAGGTAGCAGGTGACTGTTAGACTAGA

ATGTTCAGATCTGATTCAGAGTGCCAGGGATCGTTGGTTGGTCTTGTGTA

AAGTCTCACAAGTGATAGAATCATATGTGTGTCTTAGACTTTTTTTGTTG

TAGGTATTTTAGATTTTTCTTGTTTTTCCTTTTTGTAAGTCTGGCCCTCA

CACTATGGTCCAGGCAGGCTTAAGACTTATGGTAACCATCCTACTCTGCC

TTTATGGGCCACCATGACCAATTTAAGAAGCTCTCTTGGGTGGCATTGTG

ATAAGTGATCTGGAAGGGGCATATTGACAGTTAGCAGGCTGCTACTGCAG

AAGTCCTAATTAGGTTTGTATCAAGGCCATGGAAGGAGCAGTGACTTCTA

FIG.3D(12)

GTACCTGGCTGTTGTGTGTCTTGACAAAAATATAACTGCCCTTTCTTCCC

AAGTGTCTACTATGGACCACCTTTGCCAAAACTAAAAGCAGATTCAGAGA

AAAACATATCATGATTGCACATGGCTATAATCCCTGAACTTAGGAGGATG

AGAAATATGGCAAGATTGAGACCAGTCTGAACTATCTAGTAAGACCGTGT

CTTTAATAAAAATAGTAAAAATTATAAAATCAGGGAGTAGGATCTGGGAA

GAAGAGAATGAAGTAAGTGTGGGGCATATCCAATTGGAGATGTCTTTAGG

ACAGAGCTGATTGCTGAGAGGTGGTTGTAGGAGAGGTGAGTTATTGTGGG

GCATAAAAGATGAGCAAGAGTCAGAGACAGTTGGAGAACAGAGTCTGAAC

AAGAGTAGAGACTAAAGAGAGTGTCAGAGAAGCAGGGAGAAAATAGGTGA

GATTGATGACCTGTGAGATATGTTAATGGCCAGAAGAGTGGCTAAAAATG

ACTGGAGAATCCTTCAGACTTGTCAACAAAGAAATCCTTTAGCCTAATTT

AGGGTGCAGGCGGCTGAGGAAGGACATAGGTGAAATATGTGCTCTGTGTG

TTCATTTTTATTAAAGCTTATCTGCAAAGGCCTCAGATTTGCTGTGTACT

TGTAGCTGAGGCTCTTTTGAACTCCTGGTTCTCCTGGCTCCACCTTCCCA

AGTGCTAGGATTACAGATGTGTGCCCTAGTTAAAATAGCTGTATACCTAG

CATTAAAAATTTTAAGTTAGAAAATACTGTGGTGCTCCGGGGATGCATCT

CAGCAGTAGAGTGCTTGCCTGCTATACACAAGGCCCTGGGACTGATCCCT

AGCACCACAAATACTAAAGCAGACATTCTGGTAGGGAAAACTGGTAGACA

GCAGAGTGGTGACCATCAGGAGGGGGGTTGTGGGTGATGAATGACTACAT

TAATTAGAAGTTCTGTGCAGTATATTTATTTCATGCCCTGAAACATTGCT

GCTGCTGTTGCTGCTTTCCTTTACACATAATAACATAACTAAAAGACAGA

FIG.3D(13)

CAAGCATGTGGTATGAGGCTGTGGATGAGGCATTCTTTGTTTTCCTTTTT

TTTTTTTTTTTGAGACAGGGTTTCTCTGACCTGGCTGTCTGAAACTCAGT

AGGTAGAACAGGCTGGCCTTGAATGCACAGAGACCCTCCTGCTTCTGCCT

TCTGAGTGCTGGGTTCAAAATTTATGTTTTTTTCTATAAAGACTGAGAGT

TCACATGGACTATATATGACAACCTACTCTGAAATGTGTTTTTCTCCCCC

TTAGCTTGTGACCGATGGTCAGTGCTTCCCAGACCTGAGCTCCATCATGA

TGTCAACAGATTTGGCCATTCAGCAGTCTTGTACAACAGGTAATTGGAAA

GCAAAGGCTCTATTACTGTCTTACATCTTATATTCATTTTTAATATCAAC

TTCCTAACAGTTGTATCTGAATGGTAAGAGGTTTGGGGAGAAAAAAGGAG

AGAAGGCAGTTCTAAGTGCACGATAAGGTAAGGGGAATAGGACTGGGAGG

TTATGGGGTCAAAGAGCAAGTCTGAAGTCTGCACTATATCCAGGTGTGTG

CTCAGGAATACTTTTCTGACCAGCAGAGCTCTTTTTCCATTTGCTCCAGG

AACCTTAGTCCTGTAAAGGACATGCAAAGGACTAGGGTTGTGGGCCAGCA

ATAGAGTGTTTATCTAGCTTGCACAAGATCCTGAGTTCTGACCTCAGCAT

TTTGCCTTCTGCAAACACAGCATTTGCCATAAGGGACATGCAGAATGGCC

ATTTTACCTAGTCACTTGAAAGTGTGCTTTAAGATTGAGAAACTTAACAG

CCTGCTGATGCTGACTTTTCTTATTTTGCTTCTGTTACTGCTTTCTGCTT

CTTTCTTTAATACTCTAATGCTTACATTATATAGTCCTACAGGTATTCAA

ATTTTCTGTTGGAGTTTCCTAATACAAGTAATTTAACTTGCATTAGGAAA

AGGATAAAAGTGCCATTCTGGAGTTGTGAAGAATGACCGTTTAGAAGCTA

GATAGTGGGGAAAGATGATATCTTTAATCATGTGATTATTTAGTGTTTTA

FIG.3D(14)

CAAGTATATAGGGGATTGTGGCAAGACCATTGTATGATTAGAGACTAAAG
TGGAAAGATTTTTTAAATATCTTGTTAACTTGAGTGTTATCTTAAATTAC
AATCTGATGCTTTCCTTCAGAAAAAGCCCTAAATGCCTCTTGAGGTTTTC
ATCTGGCAAGTATCATGTCACCTGGCCTTGCTGGTGGAATCTGCCCCAGC
TCATGTGTGTTCTTAGTGTTCTCCTAGCACAGAGTTAGGCACGTGTGGGC
ATTTGCATACTAATGTATAGTAATAGTAACAATTGAATGAATTGTCTATT
AAAACATTCTTAAGTTTTACCCAAACACAGAGAGGTCGACAATTTGTCAT
AAAATGTAGTTTATCCATGAATCAAAATCAGGAATGACTGTCTGAACAGT
GTTTTTATTTTTTATTTTATTTTATTTTGTGTAATTTCTGTGATGTGTTT
GAATATCTCAGTTTTAGGCAGGATTGGAAATGTTAGAGGTTGGTAAGAGG
TCATGGTTGCAGTTTGATCATGAGAGAAATCGATGGCTCTCCCTTCATTG
CAGTGTTGTCAGTCAGCAGTGTGGGATCACCTATGTCTAACAGTTGTTCT
AATTGAGAGAGGATTACAGGAGGGAAAGCAGTGAGATTGTGAGGTGCTAG
ATGAGGAGATGGCATTTACCTAGCAGCCTTCTCTCCCGCCCTCCCATCAT
GTGACCTGAGAGATTCACAATTTCTGAAGATATCAGCTGTGCTTAGTTTA
AGCAATAGTTTTATTAACTAAATCCAACTTGATTCATGTTATTCCCAGGG
AACCAGTGGTAGGATTAAAAATGAATCCTAGTGTTCTTTTTGGTTATTGG
AATGTCAAGTTTTCAGACACTGTAACGAATACAGAGCCATACAATCACTA
TATTTATTTGGTCCTTTGTTGACTTAGAAAAATTGAAGCCCAGTTTAGGT
GAGCTACCAAATTTCTCATTGTGGATTAGTATTAAACTTGCGTGGAGTTG
TGGGATCTTGGAAGTGGGGGCTAAGCATCCGTGTTTGTCACAGCCCAGAA

FIG.3D(15)

GGAACAGATGAGGTTCCTTTTGAGGAGTCTTATGTCTTTATGAACTTGGA

CTTAGAAATATTTGATGTGTTTAATTCTGCTGTAGTTTTTTAAACTCTAG

CTAGTGAGCATCTTTTCACAGGAGCGCTTGAGTCTGACCTACAGCCATTG

TCTGTCTCTGGTGTGCATATTACAAATGCACTGGGAGCGTTTCTTGACCC

AAACATATAATTAGATTTTTCTTCTAAAAAGGTCTAGTTTGGGAAGGAAT

GAAAGGGATTAGAGAAATGTTGTGGGTTTGGTATTTATTTATTTATTTAT

TTATTTATTTAATGTATATGAATGATCTATCTTCATGTATACCTGCATGC

CAAAAGAGGACATCAGACTCATGATGGTGATGAACCATCATGTGGTTGCT

GGGAATTGAACTCAAGACCTCTGGAAAAACAGCTGGTGATCTTAACTGCT

GAGGCATCTCTCCAGCCCAATTGTTCTGTTTTAGTTTGAGGATGAACATC

TAATTTAGAGATGCCCTGCTTTTCCAAAAGTGAGTTTTAAACACTAATTT

CCATTGTCAGTGGATTGGTCTTTTAAGAATATAGGTAGTGGTGGCACACG

CCTTTAATCCCAGCACTTGGGAGGCAGAGGCAGGTGGATTTCTGAGTTCG

AGACCAGCCTGGTTTACAGAGTGAGTTCCAGGACAGCCAGGGATACACAG

AGAAACCCTGTCTCGAAAAGCAAACAAACAAAAACAAAACAAACAAACAA

AAACAAACAAAAAGAATATAGGTTGGAATAGGTTGGAAGCAGCCAATGAT

AGTGCATACCTTTAATCCCAGCACTTGAGAAGCAGAGGCAGGTGGAACTC

TGAGTTTGAGGCCAGCCTAGTTAGTCTACAGAGTATTTTCCTGGAGAGCC

AAGGCTATATATAGAAACCCTATCTTGAAAGGCCAAAAAAGGAGGAAAAA

AAAAAAAAAGAAAAGAAAAAAGAAAAAAAGAATGCAGGTTGGGCAGTCAG

GGTAAGTGTCTAAGGTAAGAGGAATTCTTCAAGGTGGAAAGTCATGAGTT

FIG.3D(16)

CTGCGCCAGCCTAGGCTACAGAGTACTGAAAGGGGAAGAGACTGTCCATG

TGTCAGACCCTCATTTCTCCAAAAGTCACATGACTATATTTTTTCTGTAT

TGCCCACTCTTCCATACATGCACCTAACAATAAATATTGAAGTTCACTCT

GTGGCACTATATCTATGTGATAGACTTCTAGAAAAGTGATTTAAAGTTCA

AAAGGTAAATACGTAGTTTTGTTTCAAGTTGCCAAAATCCCTTTAGTAGA

CTCCTACAATCTTACATGCCCAGTAGCAGTATAGAAGCTTGCTTGTTGCC

TTGAAGCCTCACCAATTCAAATATTAGGTAACATTTGTTACATTTTTCTT

TGTCAGCTGGATAGGTAATGAATGACACAACAATGTGTTCCCATTTTCTC

TGCATTACTAATTGAAGTCCTATCACCCACAGCAGACTGAAGAGTTCCTT

TAATATTTTATGGACTTTGACAAACCTAGGATTCATAGCTTCCATACAGA

GAGGAATTTCACAAATAGCAAAGTTGGGCTGTTAGAAGAATAAAAAGAGA

ATTCTGAGTACAGCTTCTCAAAGAAGAGTCCCACGTAGGTGTCCTCTGGG

ATGTGCCTAGATGCAGGGTTATTGTACAGGAGCTCTTCTGTCTGCTCTCT

GATACTTGAGATTATAGGGTTGCAGGGAAATGCATTAGATGGCATTACAA

ACTGATAAGATAAAGTTAGGAGCTATCAGAGATTTAGGACATGGTTTTTC

TCTGTAAATGGGGCTTCTGGTGAGATTCCTAGAAAATGCTGTTTATAGCT

AGGAATGGGGTTATAGCTAGGAATGGGGAAAGACCTTAAGCAGTTGTGAG

CTGTGGTGGAATGCATGTGTTTTCAGTTTGCTAAGGCTTCCGGGAATACT

TTTCCTGTCGATAATTTTCTTTCACTCTCTTTGTAGCCTTCTTTGTATTA

AAATCCTCTCTGCTTGCTTTTGTGTGTGAATGTGTGTATGTGTGTGTTTG

TGTATGTGTGTGTATGCATGTGCATGTAGGTCCCTACATAGGACAGAACA

FIG.3D(17)

TATTTCCTGGAGTTATAGGTGCTTGTGAGCAGCCTTTTAGGGAACCAAAC

TCTGTCCTCTGGAAGAGTAGCCCCTTTAACTGCTGAGTCATTTCAGCCTC

AAGAATCTTCTCTTTTCCCTATTAGTAGAAGATGTCATCTTAGCTCTAGG

AACTACACCACCTCTGGCCTCAGTGGACACCCATTTACATATGCACATAC

AGCAGACAGACATATAACTAAAGATAAAATAAATCTTTTTAAAATGTCAT

TTCCCTGTGTACTAATTTTCCATGTACACACTCACAGGTAGATTTTTAAA

CTATTCTGAGTGATCACAAAGCAGAGCAGAAGGTGAAATTTGAGAGAATA

GATGATATTAGTGGATTTTGAGACCTTGAAAATAATGTCTCAGAGCATTA

AATTAATCACTCATGTATGTATGTATGTATATAAGTATGTATGCATGTAT

TATGTGGATGGGGGTGCTGTAGCACATGTGTGGAAGTCAGAGGACAACTT

TGTGAAGTCATGTTTCTCCTTCCATCTTTATATGGTTCCAGTGATTGAGC

TCAGATTGTCTACCTGTGTAGCAAGTGCCTTACCTGCTGACCTGTCGCAC

TAGCCCTCTCAGAGGACTTTTAATATTTGGAATATTTCTAACGATTGACA

GTCAAAAGTTTATTGTGAGCCAGGCACTTAAAATCCTAGCACTTGTGAGA

CACAAGATGGAGGTCAGTCCAGTCTACTGAGTTCTAGACCAGCAAGGGCT

ACACAGTGAAACCTGTCTCAAAAATTTCAAAAGCGGAGCTAGAGAAATTA

CCCAAGGAGCTAAAGGGAACTGCAACCCTATAGGTGGAACAACAATATGA

ACTAACCAGTACCTGGGAGCTCTTGTCTTTAGCTGCATATGTATCAAAAG

ATGGCCTAGTCGGCCATCACTGCAAAGAGAGGCCCATTGGACTTGCAAAC

TTTATATGCCCCAGTACAGGGGAACGCCAGGGCCAAAAAGGGGGAGTGGG

TGGGTAGGGGATTGGGGGGGTGGGTATGGGGAACCTTTGGGATAGCATTG

FIG.3D(18)

AAAATGTAAACGAGGAAAATACCTAATAATAAAAAAAAGAAATGATATCA

GAAAAAAATAAAAAAATAAAAAATAAAATAAAATAAAATTTCAAAAGCAA

CAACTCAAACCAGCCCTACGTCGTGCCTCTGAGTTCTCAGTAAATTCCTT

CTCTCTCTCCTCTCAGCACCATGTATGTGTTCGGCGGCTTCAACAGCCTC

CTCCTCAGTGACGTCTTGGTCTTTACCTCGGAGCAGTGCGATGCACACCG

CAGTGAAGCTGCTTGTGTGGCAGCAGGACCTGGTATCCGGTGTCTGTGGG

ACACACAGTCGTCTCGATGTACCTCCTGGGAGTTGGCAACTGAAGAACAA

GCAGAAAAGTTAAAATCAGAGTGTTTTTCTAAAAGAAGTATGTTTTTTCT

CTACTTAGAATTTAAAAATCTAATTTTATCTGAATTGTGAAGGAACCTAG

TCTCTGTACTTTCCTGTTCACCTTACTCTCTAGTTATTTCTTAATAAAAA

AATACACAAGATCTTTGGATGGGAGGAAGCATGTGGCTCCTGGAAGCTGT

TAGCAGGTAATAAGTTGTCTTTGAATTACACAGGCTTTGTGTACCAACTC

CTGGTCTGGCTGCAGGTGATCTGAAGCCATAGCACAATGAAATTTGTTTT

CATTTTGGTTTTATGAGACAGGGTCTTGCTCTATAGCTCATACTGGTCAA

GCTCCTTGTCAGCCTCCTCCTTCAGCCTCTTGAATGCTGGGGTTATAGGC

ATGCATCACTGGCCCTACTTGGGAAATATTTTGATGACAGACATGCTATA

TATTTCTTTGTTCAGTTTAGTAGCCACTAGCAATCTGTTATTATTAGATA

TTTGAAATGTGGCTATGTAACTAAGGGGCTAACTGTTTTCTTTTCTTTAG

TGTATGTAGTGAGGCAGATGTAGTAGCACACGCCTGCAATCCAGACACTC

ACGAGGCTGAGGCAAGAGGCAGTTCTAGGCCAGCCTGGGCTGTGTAATGA

GACCTTGTCTCAAGAGCCAAAACATCAACAATAAAAGAACAGTATGTGGC

FIG.3D(19)

TATTGGCTGTTATGTTGATGATGAAGGTCTAGTGTTAAGGATAAGAGCCT

CTAATGGTATGATCACATATAGCAAATTGCTCTGGTAGACAGCAGAGAGC

TGCTGTTCTTGAAAAGTATTTCCAGCCCCCTTTAGCTGTATATAGCAAGC

AGTACAGCATAACAGACAAACTATGGTCCCTTCTTCTAGAGCCCCTGGCG

TGCTCTTGTTATTTTTCTCTCCTTTGCTACTTGCTTAGTGGTTGCTCTGA

GCACCACTTCACCAACTCAGCGAAGTAACGTGCAAAAATGTTTGGAAAAT

AAGAATGCCTCCAAGATATTTGTCCATATCAATCTTTAAAGTATGAAACT

ACTTCCTTATCTAGTTGTTGCAGTTACATGAGAGTTATATTAGGCAGAGA

CTACTTCTGTTTTTCTGGTATGTGTTAAATAAAGTTGTGCAGGGACATAA

AGCTCCTGAGGCTGTGCTGTTGATTAGAATTTTGGTTCATTTATGGAAAA

CAGCTTACCAGAACCTGGTAGGATTCATAATTCTCCCGAAACAGTTAGAA

TTGGTAGAATAACCAAAATTTAAAGTTAAGCTTAAATATACAGTGCATTG

GAAATAATATTATCTTCTGAGGTTCAGTATGAGCCCATTAGTTTACCTCA

CTTTCTGGGTAGACCTAATCCTGTCAGAGTAAACTTGGCAAGAAAAGCAG

CCTACATGAAAACTGATCAGGCAGGGAAGTTTCTGTGGCCTCTCTTCCTG

CTTGTGTATGTCATATTCATGAAATGATTTATAGATGGCAACATGGCTTT

TAGCTTCTTGTTTGGGGATTTAATGAGAATTATGTTAGGTCTACAAAGAG

TGGAAGTTGTGAAATCCACAGGTTTGGAGTCACATGAGTATATAGAGTTC

GAGTTAGCAAGTGCCTCCTGTGGGGTTGTGGGTCACTGGGTATACCTGCA

CCCAGGTAGGCCTTGCATTTGTAACAAGGACAAATGTATTGGTCTCTCAT

ATTGCTTTCTTAGGCTTCTGCACAGCTTCTGGTGTTAATTCTGTTGCTAG

FIG.3D(20)

TTGATGTTTGTCGTGGGAAGAAAAGCATCCATTACTTCTTAGAAGCTATA

AAATTAACAGACCTTTGCTTTTCACTTTCTGGACACTATGGGAGGACAGT

TATAAAACAGTGTTTCTCGGATTGTCTGCTTATATCTGTTTTATTTTAAC

CTAAACATGGCACTGCTTTTTTCCTTTCAGTTTGACTATACACTTTGCTT

CCTGACTATTGTTAGGAGCTTTCCTACCTCAGATTATACATAAGAGAGGC

TGCCGCATAGTTGATGGGTTTGTCTTCTCTCTGTAGCCCTTGACCATGAC

AGATGTGACCAGCACACAGATTGTTACAGCTGCACAGCCAATACCAATGA

CTGCCACTGGTGCAATGATCACTGTGTCCCTGTGAACCACAGCTGCACAG

AAGGCCAGGTCAGATGCTGTTTTTCACGGATTTTAGGGAATAGAAAAATG

CTAGATGAGTGTGAGTGTAGGGCAAATAATGAGTAGAGTTCTTTTTAAAA

TGGGATATCGATTTGAATTCTACTGTTGCTCAGGTTTTCTCTTAGGAAGG

GATGCTATATACATCCTGATTCCAAGGATCGCTCCTGCTGCTGAGGTCTT

TGTGCAGTGTTTCCGAAAGCATGTTTTACAGAATGCCCTTGGCCCATATC

TGACTCAGCATGACATCTGGGCTAATCATGTATGATTTGTTATAGGTGAT

AATAGGCTATGAGTAAGGTGATCCAGCTTTTGCTGTCTTTGATGGCTTAT

GACATTTTTTTCTCAAAGTTTAATGCATTTCATAAGAAATAAGACTTGAG

ATTGCTATGGTGGGCACGGGCTGGGAGGAGCTCTGGAAAAGCAGCAGGTT

CAGCTTTCACGTTTTACAGATAAGCATTGGCTGAGGCTTGGTGGTGCCAG

TGGTTCCGTTGGGCTGCTAGCTTGCCAGCTAAAAGCATGTTAGTGAGAAT

ACACACTGTGGTATTCACATTGCAGTGCTGCTTCCTGTTCATTCTAATTC

TATCATTCATCCATCTACCTATCTCTATCTATCTATCTATCTATCTATCT

FIG.3D(21)

ATCTACCTACCTACCTACCTACCTACCTACCTACCTACCTACCTACCACT

TATCTAATTCTATCTGTCTGTCTGTCTGTCTTTCTGTCTATCTATCCTCC

ATCTAATTCTATCTATCTGTCCACCTATCTATCATCTAATTTTATACATC

CATCCATCTATCCATCTATCTGTCTGTCTATCATATATGTAATTCTAACC

ATTCATCTATCTATCCACTTATCTGTCTGTCATCTAATTCCATCCATTTA

TGTATCTATCTATATATCTAATTCTATCTATTCAATTCTTTTCTTTTTTT

CTATCTTTCTTTCTGCAGTTACCATTCTCAGTTAATTCTCACTGAGTTAT

TTGTGTGAATAACAAAACACTTCTCCCCTGTGTTCCAGATCTCCATTGCC

AAGTATGAGAGTTGCCCCAAGGATAACCCCATGTACTACTGCAATAAGAA

AACCAGCTGCAGGAGCTGTGCCCTAGACCAGAACTGCCAGTGGGAGCCCC

GGAATCAAGAGTGCATCGCCCTGCCGGGTAGGCCTTGCACAGGGATGTCC

TCTATAAGGTCCAAGCTTGGTCCTCCCTCCTCAGATCAAGGTGGACCTAG

GAACAAGATTGCTTATTCTGTCTATTTAGCCCTCTCACTATTGGGGGGGG

GGGGGGGCGATATTTTGTATGTTTTTAACTTAAATGTGGTTTTTATGTAT

GTATTTACTAGCCTTTGAAAGAAAGTGAAGTGTCAGCTCATGTTCTGGAG

AATTGGGGGGTAGCTTAGATCCATGTTACAAACTGTGTCCCACTGTCCTT

CCTTCTGCTGTGAAGGAGAACCTGGCACTAGAGCTCTGTGGTCTCAGCAG

CAGTCAGGAACCTGCAGGAAGCACTTACTGACAGTTGTGTGAGAAGAGAT

TTCTGTACCAGCATCATCTCCCATGTGACCTTCCTTCCCGACTATTTCAG

CAGAGGTTGTTCAGGGTATTAACTTAGGTCCTGAGGCCAGCTAGCCCTGA

CTAAATCTCTATGATGTATTTGCTTGATCAGGATATCCAGGAAGGGGAGC

FIG.3D(22)

TTCTGTGCTCTCCAACATCGAGGTTTGAGGGGAAGTTGGTCTGACTCTTT

TGAAAGCATTTTATTTAGTTTGCTGAATGGGCTTTAGTTTAGCCAGTGTT

CTATTGCTGTGAAGAGATACCATTTCCAACGTGTAACTTTTATGAAAGGA

AACATTTAAGTGGGGGCTTGCAGTCTCAGAAGCTATTATCATCATGACAG

GGAGCATAGAGGCACAAAGGCAGGCATTAGAGTGGTAGCTGAGAGCTACA

TCCTCATCTGTGAGCAGAGGCAGACAAGGTGTGAAAAAGACAGAACCTGG

CCTGGGCTTTTGAGACCTCAAAGTCTACCACCCCCAGTGAGACACTTCCT

CCAACAGCTCCTGCAACAAAGCTCCATCCCCCGATCCTTCTCCAGTCCTG

CCACTCCCTGGTGAATGAGCACTCACATATATGAGCCTATGGGGGTCATT

CTTACTCAAGCCACTACAGGCTTTGTTTTGTGTCTCAGACTTTATGTCAA

TAGAATACCTAGACACCTTGTTACAAGACAGGCCTGGAAAGCCTGCAGTG

CTGACTCCCTGCCAGTAGCACATTCTGAGGAGCAAGTCCCTTAAGTCGCT

TACCTGCTCTTACATTACGCCTTTCCCTGACCATTTAGTGAGCACTGTTG

GTGTCCCCAACCTGAACCTGGTTCTGGGGAAACACTTGCTTATTCACTTC

CGTGCTAATGGCCAGGGAGCAAGCATGCTTTCATGCAACACTGTGAGTTC

AGTACAACCACAGGAGGAGATTGCAGACTTCCTTCGTGTACTGTATCACT

ATGAGGTTTTCCAAACCAGTCTCCCTTTCACCTCATTTTTTGGCATGCCT

TATGTACTTGCTTATACTTTCTATCTTATGACATGAAAACAGAGTGGCAT

TTGGAGGCTTAAATTTATCACATTCCCAATTCAATTCCATTTTCAGTTTA

CTCTTTCTGTATATACATCAGTGTGCAGATAAATATCTCTTTGTGTGAGC

ATTGGAGGCCAGAGGTTAACCTCTGGTATATTCTTCCTCTATCACTCTTC

FIG.3D(23)

ACAGGGTCCTTTGATGAATGTGGAGCTCACTGATTACATAGACTAGCTGA

CTCAACCCTCAGGCCTCATAACCCTGCCTCTAGCCCTCAGATGAGATTAC

AAGCAAGCAAAACTACGCCTGGCCTTTTATGTGGGTGCTTGGAATTTGAA

CTGGGTACTTATGCTTGACACAAGTATTTTATCCACTGAACCATCTCCCA

AGCCTCCATTTGCAGTTTTTTACCTCACCCTTCCAATATATATATTTATT

TGTATGCCCTTTGTTCAAGATTTTAGTCACCTTTTACATTTTTCTTCAAA

AATAATTGCACCAATTTCTTAATAATGGCACCCAAAAGTAGGAACATTAG

CCTAGAGTATACCCTGTGAGCCAGGAAATGTGACTGGTGAGACTTGTAAA

AGGGTCTTTTTATTCTGGCCCTCAGCGGAGGCTCAGCAGTGGAGCATGCA

TGCTGTTCCTCTGGAGGACCCGAGGTCCCCAGGGGCCAGGTCACAACCAC

TTGTAACTTTAACTCTGATCTAATGCCCTCTATGGCTTTTGTGCTATAGT

CTCTTGCACTAACCCACACTCAAGGCACACATACACACATTCTTTAAAAG

ATAAATTATTTTATTTTCAAAGGTTTTTTTCTGCATATAGAAGTTAATAA

TTTGTCTGTTATGCTCACCAGATCCTAACAAAGCACCTGAAATTCAAATC

AGGATGAGTTCAGATGTTCAGTATTTTGAACTAGTAAACCGAACTGCATA

ATTCCTAAAACTTTGTTTTCTTTCCTCTTCCCCTTTAAAAAAGAAAATAT

CTGTGGCAATGGCTGGCATTTGGTTGGAAACTCGTGTCTGAAAATCACTA

CTGCTAAGGAGAATTATGACAATGCTAAATTGTCCTGTAGGAACCACAAT

GCCTTTTTGGCTTCCCTCACATCCCAGAAGAAGGTGGAGTTTGTCCTTAA

GCAGCTTCGATTAATGCAATCATCTCAAAGTATGGTGAGTTAATGTGTTC

AGAACTTTGGTTTCTAGGGCACAACAGCAGCTCTTATGTAGAAGGCCACA

FIG.3D(24)

GTTGTATGTTATTTGCCTGGTAAGAGAAAGAATTACAATAAATGATTAAT

AATATACTGTGGGCCTCTATTTCAGAGGCTCTTCTTTTGATACCTTTCTT

CTTGTCTTAAAAAGTTCAGTACTTTGCATATTTTATTAGTTGTTATTATT

AAGTAAATTATAAGGTATGAACATATGGAATGAATGGTAATATGTGTACA

TATTCTGGTGACATCAGATTATTTTGTACTTGATTTATATCTAGATTCTG

CTTGGGAAAAGGGAGAGTAAAATGTTAGTTACCTAGGTGTCATTAAAGCC

ATCTACAGCCCCTGGAGGTATTATTATAGCACATAGTGTAATCGTCAGTA

AGAAATGTAAAATCTGCCCAGGTTTTATAGCCTTCTTCCTAAGGCTTCTG

AACTCAGAAAGTTCTCTTACTCTAGAGCCAAACTCTCAAATGGCTTGTAG

TTACTATATAGTCTCATTTGGTATTTTTCTTGGTAAGTCTAATTCTAAGA

CTTGTGATTTGACTGTGATGCTTCAGTCAATTAGATATTCACAGAGCAGC

TTTTCTGTCTATGCTGGCTGTGGTACAGAGAGATGTGAGGGACATGTTTT

TGTCTAGCCAGGAGAAGACAGAATGCAGCTCAGCATCTCTCATTTGGCAC

CACCTTCATGTGATGGGATGCCGGTATGGTGTGGGTCCTGGTTGTTAAAT

CTCAGGAAGTCCATATATCCAGAAATGACCTCAACTATAGGTGGATTTCT

GGCAATTAGGTAAAAGTCAGCATTCCTTGGGCACTTGGGAAACTGGTTAC

CATCTGCATAAAGGAGTCATTTCCCTTCTATCTGGCAGAAGGGACATATG

GCTATCTATTGTGCCTGTCAGCATGGAAGCACATGCTAGTCTCCAGGTCC

CCCCAATATCACAAGTACCTATAGCAGTGAATTAGTTAAACTGATTTGGC

TCCCAATGGGTCAAGTACAGCTGCACCTGCCCAAGAGCTCTTTGGGTTTG

CAAATGAGAGACACATAGTTAATTTTTATATGCTTTGACTAGTTCAGTTG

FIG.3D(25)

CTGGACATTTCTAATCCTCCCTGCAGTAGCATACATTAACCCCTCCAACT

TTCCTGAGTCAACTTACTAACTCAACATTTCATCTCTGACACCCCAGACC

TAATGGCAGAGTGGCCCTTAGAGCCACTTTCCCAATTTTTTTTTTATCAG

ATATTTTCTTTATTTTCATTTCCAATGTCCCCTTTCCTAGTTTCCCTGTC

CTCTCCCCCTGCTCCCCAACCCACCCACTCCCTCTTCCTGGCCTTGGCAT

TCCCCTATACTGGGGCATAGAGCCTTCACAGGACCAAGGACCTCTCCTCC

CATTGATGACCGACTAGGCCATCCTCTGCTGAATATACAGCTAGCACCAC

GAGTCCCACCATGTGTTTTCTTTGATTGGTGGTTTAGTCTCAGGGAGCTC

TGGGGTACTGGTTAGTTCATATTGGTGTTCACTTTCCCAAATTCTTACAT

GGCTGGTTTAGTTCTTTCCTGCAGCTCTTAGGTCTAATCCCTTTCCTTCC

TCTGTCATGGTGATTGCCTTCCTCTCCTATCTCAGTTCCTTGCCTGCTCA

ATCTAAAAGTCCCACCTCCATCTTTCTGCCCAGCCACTGGCTGTATGCAG

TTCTTTATTATCAGTTGAAGCCAGCTAGGGGCAGAGACCTTCAGGTCTGT

AAGTGCTTTGGGGAGCAGAATTAAGACAAAGCATTAGAACCAATTCCCAA

CAAGTACCTGCTATACATTTCAAAGTCCATATTAGTCTCCTGGGTCTTCC

CTTCCCCAGCTACTTGTCCTCCTTGTAATCCAAATGACAAGCTTTTTCAC

ACATCTCTTTATCTCACATTTCCCTAGCCCTGGCCATGTCCACTTGTTCT

TTTACTCTCTGCTCTGCTCTCTTTCCAATGCCTCTGGATATTTTCTCTCT

CTTATTCACAATAAAAACCAAACCAAACCAAACAAAAAACCTTACCCTAA

TAATGGAGTGGTCACGCCTGAGGTTTCCTTACTGCTCCCCCTTGCACACG

TCTTGTGTCTGACACACTGGCAGGCTTTTATTAGCAGCAGGCTCTAGGAG

FIG.3D(26)

CTGAGAGAAGCAGCAGGCACCTCTGAGGTGGTAGTTACTAGAGTGATTAG

AACAGACAGTGGAGACGTGGCTGGAAATATGGACTCTGGTGTTTGGAGCC

AAGTATGGTAGGCGGCAGAAGCCAGCAGAAGCATGATCCACACCTTCACC

AGGTTGCTTCCATTGGGAAAGGCTGGACCCCTTGGGAAGGGGTCCCTTTG

TGCCTTCCTAGGTGTTCGGAGCCAGGTGTGTGAGGGATACAGTAAAGGGA

CTGACTGCATGACTGCTCCATTAGGGTGAAGGGTTTTGTTGTGAATAGGA

GAAACAAAATGTGCAGAGGCATCTGGGAGAGAGCAGAGCAGAGTGAAAAG

GAAGCAGTGTAGGCATGGTCAGGGCTAGGGACAGCGGAGACAGCAAGATA

GCGAGTGGGTGATAAGGTGAGAGAGAGTGTGTGTGTGCGGTGCACACATC

ACGTGCATTATAAGGAGGCTGAGTAGCTAGCTGGGGGGAGGGAAGGGCCA

GAAAACTAGCATGCACTCTGAAACGGGTACTTGTGATGCTGAGGGAGCTT

GGGGGAGAAGGGCATGCCTCAAGACCAGAAGAGGGAGTTGGAGTTACAGT

TTGTAAGATGCCTAATTTGAATGCTGAGATCCAAACTCTGATCCTTTGGC

TGAACATCATATCTGCTGAGCCATCTCTCCAGCCCCTAGAAAGGTGGTGA

TGGTGGTTGTTCTTGTTTTGTTTTATTTTGTTTAAATGGGGAGCCAGGTA

CAGTACATCATGCCTTTAATCCCAGCAGGAGATTCAGGAGATAGAGACAG

GTAGATCTCTTTGAGTTCAAGGGCACCTTGGTGTGTATAGGAAATTCCAT

CCACCCAGGGCTACAGAAGGGTACCTTGTCTTTAAAAAAAAAAAAAAGAA

AGAAAGAAAGAAAAAGAAAAAAAAAAGAGAATGAAATTTCAGAGTTATGC

AAGATAGGAGCTCAGTGGTAGAGTGTGTGCCCAGGAAGTGCTGGGTTTGA

CTCCTCAGAACAACAGCAGGGGCAGAAACTAGTCTACAGGTTCATGAGTG

FIG.3D(27)

GTGTTTTGTTTTGTTTTACATAAAATGTGTTGAATTAGATAAGTAGATAA

AATGTGACTCATACACAGATAAATAGATAAAATGTGATACATGTACCTGT

ACATAGAAGATTATGATCTCACCTTTAAAAAGGAGGAAATAGAGAGTTTT

GGTAGTTACACCACAGGAAAACTGGAAAAGAAAATGTATATATGAGGCTG

TGCCCCATGGCTAAAGGAACATGTTTTTAAGTCATTTGAATTCACCAAAC

AGTTTTAGGTAATGATATATGGTTTTGCATACAACCAGTATTTTATAAAT

ATTAGCAAGGTCACATCATTTATGAACCAACATTTAAACTAAATTTGTAA

ATCATCATTTCTTTATAGCACTTGTCATAGAACATAAGTAGTTTAAAATG

TGATTATTGCTTTGCTCTTGATGTCTGAAAATCTTCATGTATTCTCTTCT

TTGAGCCATTTTTATGCTTTGCAGTACTGGATGCATATTGAAGTGATCAC

TTATTTTAATCTACCTTGCCTGAGTTTGGGGAATAGATGGTTTCCACATG

TCTGTGGGTTATGCCTAAGCTAGTGGTTTTTATGTTAGAGCTTGTTTTGG

GGAAGGCACTGGTTGCATTCATAGCTGTGTTTCTTTTGCCTGTAGTCCAA

GCTCACTCTGACTCCATGGGTTGGTCTTCGGAAGATCAATGTGTCTTACT

GGTGCTGGGAGGATATGTCTCCATTCACAAATAGTTTGCTGCAGTGGATG

CCATCTGAGCCCAGTGATGCTGGCTTCTGTGGGATCTTGTCAGAGCCTAG

TACTCGGGGATTAAAGGCTGCAACCTGCATCAACCCTCTCAATGGCAGCG

TCTGTGAAAGGCCTGGTAAGGACATGGGTGCATATAGTGCTCCAGGAGGA

GCCAAGACAGCAAAGGAGGCACAGCTGAATGAGCGCTGAGGTGATGAAGT

ACTTATGGCAGCAGGGAGAGGAGCACCAATTTAGGCATATGTATTTCAAA

CAGAACCCGATTCCAGATAGTCTTTCTTGGCCTCTGACTGCTTTAAGCCA

FIG.3D(28)

TACTGAAAACCAAAAATAAAATTGCTGAAAGAACCCAGTTTATATTGAGC

TGCACTGTTTCGTTGGTCTCAAAGTGTTGAGAATTGTTCTAGAAGATTAT

TTCCTTGGTGTTGGCAGAGAAGTGCTATGGAGGAAACAACAACCTGAAAC

CAAAGAAACATTTAGAAAAGCAGCAAGTCAGGACACTATTCAGACACTGC

TGGGGTGGGGGGAGAGGGGCATGGCCAAAGAAGCCGACAGAGCCAACACC

AGGCTGTGGCAATGTCCTGCGCTGAGGTTAAGGTTAGACTCCATGAGGCC

AGGCCCAGAACAGCCATACACAAATGAGGACTCCAAAACAAGAGGTGCAA

GTGTAGTGGAGACTCCATCCCTGCAGGTCCTGTTTCAGGAAATGATTGTA

CTTTGCCTGAGTAATACAGCCTAGGAGCTACTTTCTGATAGGGTTTTTTA

AATACTTACAAAGAATTATTTATCTTTAATCATGTGGTTTTGTATGTGTG

TGCTTGCACATGCAGTGCTTGTGAGAGAGAGTATGTGTGAGAGCATGCAT

GTATGAGAGTGTGAGAATATATGTGAGAGAGTGTGAGTGCATGTGTGCGT

GTGTGCATCTGTGTGTACAGGTGTGTGTACATGCATGTGTGTATAAGAGT

ATGTGAGAGTGTGGGTGTGTGTGTGAGAGTATGTGAGAATATATGTATGA

GTGTGTGTGAGTATGAGTGTATGTGCGTGCCTGCATGTGTGTGTGTGTGT

GTGTGTGTGTGTGTGTGTGTGTGTGTGTGTAGAAGTGGCCTTGGAAAACA

GAGTTGTCAGATCTCTTAGAGATATAGTTGCAGTTGGTTGTGAGCCATCT

CATATGAGCGCTGGAAGTTGAAATTGGGTTCTCTGGAATCCTCTGGGTTC

CTTGTTGAAGCCTGAATATTTTGATAAATATTTATGTCATTATCCCTCAA

AATTGTAAATGTAGAATTTAACAAACTCAGGTCTTGAGTCATCTTTGTCC

CAAGGTTTGTTTGTTTGGTTTTTTGTTCCCCCACCTTTTCTTCAGTGCTT

FIG.3D(29)

TTAAAAAAGAGAGTCCATTTTTTCCTAAATGTTTAAATACAGTTGAGGAA

TAGAACATCTGACTCCAATTTCCTGGGTTTCCCTCCATGTAGTGTAGTGC

TGACCTGATTTCAGTGTGCATTGAAAACTTTGATCACTTGGAAGGCAGCT

ATGCTCACCACTATACTACCAATGTCTGCAATCCTATAGGAGAAACAACA

ATATGAACTAACTAGTACCCCCCAGAGCTGTGTCTCTAGTTGCATATGTA

GCAGAGGATGGCCTAGTCAGCCATCATTGGGAGGAGAGGCCCTTGGTATT

GCGAAGATCATATGCCCCAGTACAGGGGAATGCCAGGACCAGGAAGCAAG

AGTGGGTGGGTTGGGGAGCAGTGCGGGGGGGGGGGGTATAGGGGGTTTTG

GGGATAGCATTTGAAATGTAAATGAAGAAAATAACTAATAAAAATTGCCT

TAAAAAAAAACAAAAAAGAAAAGTTTTTGATCTTAGCTGACCAGTGTCTC

TTTGGGTCTTAATTTCCAGCAAACCACAGTGCCAAGCAGTGCCGGACACC

ATGTGCCCTGCGGACAGCGTGTGGCGAGTGCACTAGCAGCAGCTCGGAGT

GCATGTGGTGCAGTAACATGAAGCAGTGTGTGGACTCCAATGCCTACGTG

GCCTCCTTCCCTTTTGGCCAGTGTATGGAATGGTATACGATGAGCAGCTG

CCCACGTAAGTGGAAGGAGCTTTTGAACATTTGCAGGCAAGTTGGGCTTG

ACTTTCTGCTCAAGTCCATGCAGAAGCTGGTCGGGCCGGCCCTTCCAGAT

TAACATGTATGTATAGAATGCAGCACAGTGTTCCATGCAGTAAATCAGTT

ACATCAAGGAGAAGGCACAGGGTACAGAAATACCTTTTCTTCTTCAGGGT

AATATTATAATTCAATCTGTATAATGTTTCTACATCTTAATCTACCAGTA

TGTAAAGTGCTTTCTAGTAGAGGCCTCCCCAGCTCCCTTTTTCATCCAAC

ATCCTGATATTAAAAGGTTGGAAAAGTCCCTGTTATATATTATGTAAAAT

FIG.3D(30)

GTGGGGCCCTTTAAATTATTTCAGTTCAATAATCACTATAGGGTACTATT

TTTAATTCATGGAAGTTAAATCATCTGTTAAAAGAAAAGGTAATAACAGT

AAATTCAAATCTTGTGATAGTGAATTACAAGTTGGATTGTTTTGCCTTGT

TTTTTAATAGCTGAAAATTGCTCTGGCTACTGTACCTGCAGCCATTGCTT

GGAGCAGCCAGGCTGTGGTTGGTGTACTGATCCTAGCAATACTGGGAAAG

GAAAATGTATTGAGGGCAGCTATAAAGGACCTGTGAAGATGCCGTCACAG

GCCTCTGCAGGAAATGTGTATCCACAGCCCCTTCTGAACTCCAGCATGTG

TCTAGAGGACAGCAGATACAACTGGTCTTTCATTCACTGTCCAGGTAAGA

TGCCTGTGTATCCTAGTTCAAATCTCGTACATAAACTAGACGCCCAGATC

CCTTGGCTCACTTGTTTTCTTGACTGTGTTTGAGTTCTTTCTGTGTTCTG

CATCACCTTGTTGGATCATAGCTGGCAAAGGTGCTCTCCTTTCTGTGGGC

TTTTTCTTTACTTGATTGATTGTTTCTTTGGTTGCACAGAAGCTTTTTAG

CTTTCTGAAGTCCCATTTGCCAGTTGTCCTTAATTCCTGGGCGAGTAGAA

GCCTCATAAAAAAAAGTTCCTTCCTACACATGTATCATGTAGGGCACTGC

CTATGTTTTATTCCAGAAGTTTCAGAGGTTCGGGTTATGTCTTTGATCCA

TTTAGGGTTACTTTTTGTGAAAGGTAATGGACACAGTTCTGTTTCATTCA

TTATTCTACATGTGGACATCTACTTTTCCCAGCACCAGTTTTGAAGATGT

TATCTTTTCTGCAGGTTGTTTGTTTGCTTGTTTTGTCTCTTCAGAAAATC

CCAGATGGCGGTAGCTGTGAGTGCTTAGGCTTGGCCTACCTGTTTCATTA

TGTTGGCTTGCATGTCTGTTTTGTGCAGTGCCACCATATTGTCTTAATTG

CTATAGCTCTGCAATCTATCTTGACATCTGTGTTGGCAATCCTGCAGTTT

FIG.3D(31)

CGACCCTTCTGCTCAGCAGTGCTTTGGCCATCTGGGGTCTTTTCTGGGTT

CATAATGAATTTTAGGATTTTTTTTTCTATTTCTGAGAAAGTATTGTTGA

TATTTTGATTGCGATTGAATTGAATCTGTAAATTGCTTTTGGTAGAATGG

TCATTTTCACAATATTAATTTTACTGATCCATGAACATAGGATGACTCCA

GTCTCTCATGTCTCCCTATAGCCCTGTCTTAAGAGATTTGGAGTCTTCAT

TGTAGAAGTCCTTCACCTCCTTGGTTAAGTTTATTTCTAGATATTGTATT

GTCTTTGGTATTATAAATGGTAGTATGTCCATGATCTTGTTCTCAGTGTT

TTTTTAGTTTAGTTTTTTTTAATTTATGTGTATGAGTGTTTGTTTTATAT

ATGTGTATATGTGCATTCATGTCCTCTGGGCATCAGATCCCCTGGGACTG

GATTTACAGACAGCTTTGAGCTGCCTGTAGGTGCTGAGAATTGAACCCAG

GTCCTCTGCAAGAACAGCCAGTGCTCCTACTCCCCAGCCCCAGAAGTACT

AATTTTTAAGAGCTGATTTTCTACCTTTGCTGACATTGTTGATTGTTTCT

AGAAGTTTAGTGATAGAGTTTTTGAGATTTCTTATATATCTTATGTTATC

TGTAAAAAGGGATAATTTGACTCCTTTTCCTATTTATATCCTTTTATTTC

TTTCATTTGCCATATTGTTCTAGCTAGTGCTTCCCGCTCAGTATTGAAAA

GAGTGGTGATTGTGAACAGCTTTTCTTATTTCTTATTTTAATGGGATTAT

TCACCCATTTAAGATAATGTTGGTTATGGGTTTGTCATACACAGCCCTTC

TTATATTGAGGTATGTTCCTTCCAGTCCTGTTCTCTCTAGGACTTTTTTT

TTTTTAATCAAGAAAGCATATTGGGTTTTTTGTTGTTGTTATTTTGTTTT

GTTTTTCTAGACAAGGTTTCTCTGTGCAGCCCTGGCTGTCCTGGAATTCA

CTCTGTAGACCAGGCTGGCCTTGAACTCAGAAATCCACCTGCCTCTGCCT

FIG.3D(32)

CCCGAGTGCTGGGATTAAAGGCGTGCACCACCACTGCCTGGCACATGTTG

GTTATTTTGCAAGCCCTTTCTACATCTACTAAGATGAGCATGTGGTTTCA

TCTTTGTCTGTTTATATTGTCTGTTGTATTTATTGACTTATGTGTGTTGA

GCCAACCTGAAGTTCTGGGATAAAACCCACATGCTTTGGATGATTTTTGT

GCTATGTGCTTATATTGTGTTTGTTAGTGCTTTATTGAGGACGTCTGCAT

CCGTGTTCATCTGGGGTACTGTCTGTAGTTTGCTTATTTTGTTGTCTTTA

CCTGCTCTGCATTTTAGAGTAATCCTGGATTTATAGAAAGCATTTGGGAG

TAGTCCTTCTGTTTATTAAAAAAAAAAATTAAGAATGATTGGTTGTTGTG

TGGTGGAATTCTGCTGTGAACCCATCTGGTTCTGGACTCTATTCGGAAGG

CTTTTTATTACTGTTTCAGTCTCCTTGTTTGCAGTGATCTATTTAGGTTG

CTAATCTCCTTATGATTCATTTGGATGAATCAAGAAATTAATCCATCTCT

TTAGATTTCCAGCTTAATGGAATATGAGTGTTAAAGTATTTCTTTATAGC

ATTCTGTATTTTTTGGCATCTGTTGTAATATTTCCCTGTTCTTTCTGTTA

ATCTCTTTCTTTCTTGTGGTTAGTTGGGCTAAGAGGCTCTTGGTTTTTTT

TTTTTTTTTTTATCTTTTTAAAGGACCAGCTCTTAGATTCATTAATTCTT

TGTATTATTTTCCTTGTTTCTTTTTCACTGATTTCATTTTAGATTTTATT

ATTTCTTGCCATCTACTGCGTTTGGGTTGGTTTTAGTTATTTTTCCAAGA

TTTTCAGTTTCATCACTAAGTCATTCATTTGGGCTCTTTTGGGTTTCTTC

ACGAGAACCCACTTGGGACTGTTACCTTCCCTTTTAGACCTGCTTTTAAT

GTGCCCCAGAGATTTGTTACATTGTCTTTTCGATTTAACTTAGTTTCAGG

AATATTTTGATTTCTTCTTTGACCCATTCATCATTCGGTAATGAGTTGTT

FIG.3D(33)

TAATCTCTAGTGAGTTTATACATTTATTAGAATTTTGTTTACTGATGATT

TTAAGGTGTTTGGCTTTGTTTGTTTGTTTGTTTGTTTGTTTTTCGAGACA

GGGTTTCTCTGTTGTAGCTCTGGCTTTCTCTATGTAGAACAGTCTGACCT

CAAATTCACAGAGATCCACCTGCCTCTGCCACTGAAGTTCTGGGATTAAA

GGTGTGTGCCACCACTACCTGGCTGATTTTAAGTTTTATTACATAATAGA

CAGGTAGGGTACATAGATTTTCTACATTTGTGAAGGTTTGCGTTGTTTGT

CAGCATGTAATTCTGTGTGCTGCTGAGGGAATGTATGTTGTTTTGACAGT

TAGGTGGAAAAGTCTGTAGACATCTGTTAGATCCATTTTACATTTCAAGA

AGCCATTTAATTCTGAAGTTTCTCTGCTTATTTTTTCCCAGGTGACTTAC

CTATTGGAGAAAATAGGGTGCTAAAATCATTTACTATTATTGTTTTTTTT

AAGAAGAAAATAATTAATTTAAAAAACCCTGGAAAGAAAGATACCAAATG

TGAATCATGTTTCCTGGATAGTGGGGTTATATTTGATCATTTATTTTTCC

TCTCAAATACTGTGAGTTTTTACAATGAATAACAACATAAATATTTTTAT

GTTGCTGTGGACTTTAACTTTGCTTTGATAATATATTTGGTTTTTTGAGA

CTAATTTCTTTTTGATATTTTATTTTCTCATACTAGTTTTTAGTAAACTT

TGGTTTTGTTTTGTTTGTATTTTTTAGACTGGCCACCAACTTGCTATGTT

GTCAAGGGTGGCCTTAAAATCCACACCCAATACTTTGTCCTCTCTTTCTT

TCTTTCTTTTTTTTTTTTATTGGAACAAAATTTCTAGGTGGGAATCTCAC

TATGTTACCCAGGCTGACCTGAAACTTCTGGGCTTAAGCAAGATGGGTGC

ACATGATCAGAGACGCTGCGCTGCCCGCCTCAGCCCCTGCTAGTTGGAAC

TATAGGCACAGACAGCTGTACTTCACTCATTTCAATGATTTAACATTTAG

FIG.3D(34)

ACTATATGCAAATAAATATGAAATGTATTCACCAAGTTCTCCTATGGGAG

AAACAGAGCCCTTAAGATTTTTTCCTTTCAGCTTGCCAGTGCAACGGACA

CAGCAAATGCATCAACCAGAGTATCTGTGAGAAGTGTGAGGACCTGACCA

CGGGCAAGCACTGCGAGACCTGCATATCTGGCTTCTATGGTGACCCGACT

AATGGAGGCAAATGTCAGCGTAAGTCACACAGGTCAAGTTAGTCACAAGT

CAGGTACAATAGTACAGTACCTGCAGTTGACTTAAATATCTTAAAGGGAA

AAGGCCTCTTGGTTTGGGATATTGCCTTTCTTAATTATGTTAAATTGTTA

AAAGTTTAACTGAGGGGCTAGAAATGTGGCTCAGTTGGCTAAGAACACTG

ACTGTTCTTCTAGAGGACCGAGGTTCAATTCCCAGCACCCACATGGCAGC

TCACAAGTGCTTGTAACACCTGGGATCCAACAACCTCATACAGACATACA

TGCATGCAAAACACTAATATACATAAAATAAATCCATTAAAAAGTGTTTG

ATGATGCTGGAAGAGGAAAAAAGGCTCAACTTGTGGGTTTGGGAGCAGTT

AGTTAAAGCAACAAACCGACAGTAAAGGAGCTAAGCTTTTATTTCTTCAG

CAGAGGCATAAACAAGGGGCCGAAGTCACTGAGGCACCAGCTGCCTTTAT

TCCATTTCCCTCCCATGGAAGCACATCAGCTCAAGTCAAGCAGAGCAGCC

TGGGATGGGAGGTCATCTCATTGGAGAAGGAGGCAGGAGGCATTGTGAGG

GGAGGGAGGACAAGGCTGGGAATGGGAAGTCCTGAGCTCAGAATCAGAAT

GAGGACAAGATCTTCAGTTTCCTTCTTAATATAAAGAGGTATCACAGAGG

TCTCTATAGAAGTCTACTGGAAGCCTCACACAGGCACAAGGGTACATTTG

AAAAACTGTGACAGCCAGGGAGAGTCCCCTTCTGAAGTGTCCTTCCTCAG

AGACTGCAGCACCTGACTGTGCCCCAGTCTGCAAGAGGTTTGGGGAGAGC

FIG.3D(35)

```
AACTGACCTCCTGAGGACCCCAGATGAATCTTTAAGATGGCCTGCTTTTG

GTTTTGGTTGGTTGGTTTTTAGACAGATCTAGGAGAGTTGGTGATGAGCT

TGAATTCTCTGTCCTCCTGCCTGACCTCCAAATGCCCAGCTTCACATGGG

CTCCCATTAAGTTGTGAGTTTCGGTGTCTGGCTCCTGCTCTCACAGCCAG

TGCAGTACATTGAGCTCCATAGAGATAGCGCCGGGGCAAATGAGAGCTGG

ACGGGCACTGGGTGACTCTGTGCCTTGTGCCGGAAAATCAACTAAACATG

GGCAAAGGAGATCCTAAGAAGCCGAGAGGCAAAATGTCCTCATATGCACT

CTTTGTGAAAACCTGCTGGGAGGAGCACAAGAAGAAGCACCCGGATGCTT

CTGTCAACTTCTCAGAGTTCTCCAAGAAGTGCTCAGAGAGGTGGAAGACC

ATGTCTGCTAAAGAAAAGGGGAAATTTGAAGATATGGCAAAGGCTGACAA

GGCTCGTTATGAAAGAGAAATGAAAACCTACATCCCCTGCCCCCAAACAG

GAGACCAAAACGAAGTACTAGGACCCCAATGCACCCAATGCCTTCTTCGG

CCTTCTTGTTCTGTTCTGAGTACCTCCCCAAAATCAAAGGTGAGCACCCA

GCTTATCCATTGGTGATGTTGCAAAGAAACTAGGAGAGATGTGAACAACG

CTGCAGCAGATGACAAGCAACCCTAGGAGAAGAAGGCTGCCAAGCTGAAG

GAAAAGTACGAGAAGGATATTGCTGCCTACAGAGCTAAAGGAAAACCTGA

TGCAGCAAAAAAAAAAAAAAAGGGGGGTGGCCAAGGCTGAAAAGAGCAAGA

AAAAGAAGGAAGAGGAAGATGGGAGGAGTATGAGGAAGAGGAGGAAGAAG

AAAGATGAAGAAGAATATGATGATGATGAATAAGCTGGTTCTAGTTTTTT

TCTCATCTATAAAGCATTTAACCCCCCTGTATACAATTCACTCCTTTTAA

AGAAAAAAATTGAAATGTAAGCCTGTGTTAGATTTGTTTTTAAACTTTAC
```

FIG.3D(36)

AGTGTCTTTTTTTTGTATAATTAACATACTGCCGAATATGTCTTTAGATA

GCCCTGTTCTGGTGGTATTTTCAATAGCCAGTAACCTTGCCTGGTACAGT

CTGGGGGTTGTAAATTGGCATGGAAATTTAAAGCAGGTTCTTGTTGGTGC

ACAGCATAAATTAGTTATATATGGGGACAGTAGTTTGGTTTTGGTTTTAT

TTTTGGGTTTTTTTTTTTCATCTTCAGTCGCCTCTGATGCAGCTTATATG

AATATGATTGTTGTTCTGTTAACTGAATACCACTCTGTAATTGAAAAAAA

AAAATCGTGGCTGTCTTGACATCCTGAATGTTTCTAAGTAAATACAGTTT

TGTTTTTATTAATATTGTCCTTTCGACAGGTCTGAAAGTTTTCTTCTTGA

GGGAAAGCAGTCTTTTGCTTTTGTCCCTTTTGGGTCACATGGGTTACTGC

AGTGTGTATCTTTTCATATAGTTAGCTGGAAGAAAGCTTTTGTCCACACA

CCCTGCATATTGTGGTAGGGGTAACACTTTCATCCATATTCAAAGAATCT

CCAAAATCGTGATCAGTTGGATAAGAAATATTATATAACCTACTTGGCAA

AGCAAGGTGTGATCAATTCTGTCACACCATGGGATCATTAGAATCAAGCA

ATCTGAAAATCTGTCCTTAAAGGACTGATAGAAAAGTATTTTCTAATCCT

TATACAAAGGCTCTCCTTTAACTGCCACTGCTATGTAATGACAGTTATGT

TTTGCAGTTTCCCTACTAAAGAAGACCTGAGAATGTATCCCCAAAAGCGT

GAGCCTAAACTACACAACTGCAGTACTATTTGTTGACCTTAGTCCCAGCG

AAGGCTATCACGAGAATGCTAGCTATAATATAATGCCTCTGCCCCTCTAT

CTAAATATGGATTGCTCAGGAAACTTGACTGCTTAAAGGTATTTTTTTCA

TATTGTTGTTCCTCCTATAGGGTTGCAGACCCCTTTAGCTCCTTGGGTAC

TCTCTCTATCTATCTATCTATCTATCTATCTATCTATCTATCTATCTATC

FIG.3D(37)

TATCTCTTGTCAGATTTCTTTTTTCTTTTCTCTTTCTTTCTTTCTTTTTT

TAAGATTTATTTATTATTATTTCTAAGTACACTGTAGCTGTCTTCAGATG

CACCAGAAGAGGGTGTCAGATCTCATTACGGATGGTTGTGAGCCACCATG

TGGTTGCTGGGCTTTGAACTCAGGACCTTAGGAAGAGCAGTCGGTGCTCT

TAACCACTGAGCCATCTCTACAACCCTTAAAGGTATTTTTAAGTAGTTGA

GTCAGCTTTTAAAATTATGCCAGAAGTGTCAAAAGTTCAAAAGTTTAGGA

CCATCCTCTATTGAAGTACAGGGTCATCCTGGGCTACATGAGACCCTGCC

TTAAAACCAAAATCAAACAAACAACAGGAAAAACAAGAGTTAAGAAAGAG

AAAAAGAAGCACTTGGAAACAAAGATCTGTGGAGTATGTATAGGCTTCTC

TACAACAGGTGTATGTAGGATCTTGATGGCTTTTGAGTCTATTACCCTCA

AAGAGGTACTGAGAAACCTAAATGTGATCACCGTGGTCTCTGAGGGGCAC

CTGGCAGGATTATGGGAGATAACTAAAGCTTGCTAATCACAGAGTTTAGG

GAGGGAGGACGTCTCTAAGGCAAGTTAACTGTCTGGTTTGAGATGCTTAG

GTGATGTCTGAGGAAGTAATAAGGCCTGTCCATTTTCATACACACTCAGG

CCTTAAGTCTGGGTAATGGCTACTTGAACATAAAATAGTCCTCTATGAAA

GGAATAATATCTCTGTGTCAGCAGCCTTCACGGCTAATGTTAATTGTGCA

GGAACCCTGCTTCTCAGTCAGACAGAAGCTCAATCAGGCAGGGGCAGGAC

TTCTTTGCCTTTCCCATGTCCTTGTAATTTCCCTGGCTTTTCATCTTGGT

TCAAACATACTTACCTGTTAGGTAATTATAAGAACACCAAATATTACTGA

ATAAAATGTGTTTATGACTTTGTGGTGACTGCCATTCAAGAATTAGATGC

CTTAGCCAGCAATGATGGCACACGCCTTTAATCCCAGCACTTGGGAGGCA

FIG.3D(38)

GAGATAGGCAGATTTCTGAGTTCCAGGACAGCCAGGGCTACACAGAGAAA

CCCTGTCTCGAAAAAACAAAACAAACAAACAAAAAGATTTCGATGTCTTT

ATCACCCAAATCAAGTAACTTTCCAAAGTCTCACAGTGAGATGTAGCCTA

GTTGGGAGCCACATCTAATATATGCTGATGATCTTAACAAGTAGCCTGCT

TGTGTCTTCAGGTGACCACCCCGGTGTCCTCAGCTACCTCTAGAAAGATC

ACACTTTCCTCTGTGGTCTCTGCAGGGTCCCTGTATGATTCTGGAACCTT

GCTGTACTTCTCAGAGTCCTGATTCATAAAGCACTGAGTTTTTGCTTGTT

TGTTTGTTTTGATACTATTGGTAAGAATATATATTGAACCTTGACATGCC

TTTTTAAAATAACATTATTTTTACAATAGTACTTTAGCCTTGATTATGTT

AACTGCTTACTGTTTCAGATGACATTCGTACATCTTTTAATCCTCAAACC

AGTCCTATGAGATGGCTAGCATCATTGTCACATCATTTAGGCAAGGAAAC

AGGTCTTGGGTTAAGCTTCATGCTCAGAGCTCCTTGGAACACAGTGGACT

CAAGTGCAAGCAGACTGACGCGACTGGGTTTTACTAATTCAGTAAGCCTG

TACTCTATGGAGGAAGAGTTTCTGACCACTGGATGCAGTCTGATGACCTC

TGACTGTTCTGTTTGAAAGGTTTCTTTCAGTGATTTTATTTTTCTCCATG

TGGACTTTTTTTCCAGCTTTTAAAATATATATATATATCTTATTCGCTTC

ACATCCTGCTCACTGTCCTCCCTCCCCTGTCATCCCCTCCTACAATCCTT

CATATCCCCCCTTACCTTCTGAGCAGCTGGGAGCCCCTCTGGGTATCCCC

ACACTCGGGCACATCAAGTCTGTGAGGCTGGACGCATCTTCCCCCACTGT

GGCCAGACAAGGCAGCCCAACTAGAACATATCCCACAGACAGGCAACAGC

TTTTAGGATAGCCCCTGCTCCAGTTGTTCAGCACCCACATGAAGACCAAG

FIG.3D(39)

CTGCACATCTGCTACATATGTGCAGGGAGGCCTAAGTTCAGCCCATGTAT

GTTCTTTGGTTTGTGGTTCAGTCTCTGAGAACCCCAAGGATACAAGTTAT

CTGACTCTCTTAATCTTCCTATAGAGTTCCTATCTCCTCTGGGGCCCACG

ATTGGTGTCCCTATTGCTTCACTGGGATTCCTGCCTGGCTACACCCACTA

TGACCAAGGCAAGTCTTAGAAAAGACAACATTTAACTGGGGCTGGCTTAC

AGGTTCAGAGGTTCAGTTCAGTATCATCAAGGCAGGAACATGGCATCATC

CAAGCAGGCATAGTATAGAAAGAGCTGAGAGTTCTACAACTTATCTGAAG

GCTGCTAGCAGAATACCGACTTCCAGGCAGCTAGGATGGGGGTCTTCAGA

CCCACACCCACAGTTGGTGTCCCTATTGCTTCACTGGGGTTCCTGCCTGG

CTACAGGAGGTAGCCTCTTCAGGTTCCATATCCCCAATGCTGTGAGCCAC

AGTTAAGGTCACCCACTATTGATTCTAGGGTGTCTCCCTCATCCCAGGTC

TCTTTCATTGTGGAGATGCCCCCCACTTCCCCACCACTGTCAGTTGCAGA

TTTCCATTCTCGGGACCATCTGGCCATGCCTTCTGTTTCTCCTCACACCT

GATCCCGACACCCCCGCCCATTCCTTCTCCTACCTAGTTCCCTCCCTCCA

TATGCTTCCTATGACTATTTTATTCCCCCTTCTAAGTGAGATTCAAGCAT

CCTCACTTGGGCCGGCCTTCTTGTTTTGTTTCTTTGGGACTGTGGAGTGT

AGCTTGGGTATCCCATTTTTTTATGGCTAATATCTGCTTATAAGTGAGTA

CATACCATTCGTGTCCTTTTGGGATTGAGTTACCTCACTCAGGATGGTAT

TCTTAAGTTCTATTCATTTGCCTGCAAAATTCATGATGTTTTTGTTTTTA

GTAACTGAATAGTAGTCCACTGTATAGATGTACCACAGTTTCTTTATCCA

TTCTTCAGTTGAGTGAAATCTAGGTTGTTTCCAGTTTCTGGCTATTACAA

FIG.3D(40)

ATAAAGCTGCTATGAACATAGTGGAGCATGTGTCCTTGTGGGATGGTAGA

GCATCTTTTGGGCATATGCCCAGGAGTGATGATATAGCTGAGTCTTGAAG

TAGAACTATTCTTAGTTTTCTAAAAAACCACGAAATTGATTTCCAAAGTA

GTTGTACAAATTTGCACTCCCTCTAACCAAGCAAGTGAAAGATCTGTATG

ACAAGAACTACAAGTCCCTGAAGAAATAAACTGAAGAAGATATCAAAAGA

TGGAAAGATCTCCCATGATCGTGAATAGGTAGGATTAACAAGGTGAAACT

GGACATCTTACCAAAAGCAATCTAGAGATTCAGTGCAATCCCCATCAAAA

TTCCAACACAATTTTTCTGTAGACCTTGAAAGAGCAATTCTCAGTTTCAT

ATAGGAAAACATAAAGCCCAGGAGAGCCAAAACAGTTCTGAGCCATAAAC

GAACTTGTGGAGGAATCACCATCCCTGACCTTAAAGCCGCACTACAGAGC

AGTCGTGATTAAAACAACAACAAAGGCTGCGCACTTTTGGTACAGAAACA

GACGTGCTGACCAATGGCATCCAATCCAAGATCCAGAAAGAAACCCACAC

ACTATAGTTTTTTTTTAAATATAAAGTTCTTCAGCTTAATGCTTCTCATT

ATTCATGAGAGAAGAAGACTCAACAGCAAAGAAGGTGAAACAAGGGTGAC

AAGTACCACAGGGCTCTCGAGTGTCTCTTGTGATGGACTAGGGAGCCCGT

CAGTTCTGAATGCTCAGGAATGTGGTTCACAGTGTGGCCACAGTACAGAA

GATCCCCGAGATAAGGCAGAAGACAGTCACCACAGGTCATCTCCACAGGG

CAAGGACTCAGTATATGGCATATTACTAATGCTCTTAAATATTTACTGAA

CAAAGGAACAAAATGCTGAGTCTGTCACAGAGATGAAAATAGCCGTTGCT

TCAGGGGACAGCAGAAGATAGCCTTTTTTTCTCCTTGAATGGTAGTTAAT

TTAATGTTGCCTCTATATTATTAGAAATAAATTACAAGCTGAAAAATAAT

FIG.3D(41)

GAGTCATACGCAGTGATTTCTCTTGCTTTAGGCTGTCTTTACTACAAACC

CATTTCAGGCTAAATGATTTTGTCTTAATCACAGTCTATGGTAATCTGTC

AAGCCAGTTGTGACCTGTCTTCCTTTCCTTCTTCCCAGCATGCAAGTGCA

ATGGGCACGCATCACTGTGCAACACCAACACCGGCAAGTGCTTCTGTACC

ACCAAAGGTGTCAAGGGGGACGAGTGCCAGCTGTGAGTACCACACACACT

CTGTGTCTCCAGTGGGGGACTGGGCCTTGCAGCTGCCTGGGCCCTGTCGG

CCACCTGCTTGCCTGGGCATTGTTGCCCTTCACTCCCAGGGTCTTTGAGT

GGACTAGTGTGGAGGTTTACCTTTTTTCCTTCAGACAGGTTATCTCAGTT

ACTTTAATATTGCTCTGATAAAACATATGACCAAGGCAACTTACAAAATA

AAGCCTTTAATTGGGCTTATGACTTAAGAGCATTGGAGTCTACATTGAGT

TCCAGGGCAATAGAGCTACATAGTAAGACTGTATCAATCAATCAATAAAT

AGGACTACATAGTAAGACTGTATCAATCAATCAGTAGATGAAGAGAAAGA

AAGAAAGAAAGAAAGAAAGAAAGAAAGAAAGGAAGGAAGGAAGGAAGGAA

GGAAGGAAGGAAGGAAGGGGAAGAACAAAACAAGCTTAGATAGGAAGAAC

AGGATAGAATGAATGACAAATGCTTGAAAAATGTTTTAGCTGTACTTTTA

GAAGCATACTCAATCCACACAGAAGTAAAAATGTTGTTCCTTATGAGTAG

TACCTAGCATTATTACATATGTACTTGCCTGTGTCCTTGGGCAAGTATTT

GTTTATTTGTTGTTTTTATACTGTTGCTGGTGTAAATTACTGAGCAGTTA

GCAGAAACATTCCTGCAAATGGGATAGTCTCTCTGATCTGAATAATGATA

TAGTTTATGTAAAAGGATTTACTTGGTTTAAAAATAAATATAGAGTCTGT

GCTTTAAATGTCAATAGAAGATAATTTCTTTTTTCCCTAGATGTGAGGTA

FIG.3D(42)

GAAAATCGATACCAGGGAAACCCTCTCAAAGGAACATGCTACTGTAAGTT

TTTGTAATTGTTTCTAGAGAGTAATTGAACAAAACGACATTGCTTTTTTT

TTTTACCATTGTCTGAGAATGATAAATGCTTGGGGGATGAAGCAAATACT

CATAGCCATGCCCCTGACTTGGTGAACACTGTTCTAACTGAGGCATGGTC

TCTGCTGGTCATCCAGAGCAGTTAGCAGGGGTGCTGTCCTGCCTGTCCTT

GTTCAGCTCCCGCGGAGGCGTGCTCATTCACCATTGCCCAGTGTAGCTTA

TCATGTCCAATCTTCAGACAGCCAGGAAGGAGTTTCTAAGATAGAGGTGC

GTTCCACCATTCTCTCTGCAGCTGATTTGTGCTCACAAACAAGTAAATAA

AACACCAAATTAATACCTTGGTGTGAAAGTGAATCTGGTAAGCTTACAGC

TTTATCATAAATATATTTTTTGTCTATGAGAATCTACATAGTAGGTTCTA

GACTATAGAACAATAAAAAAAGGAATTAACATTTGGCATATGCAGCATAA

TGGTATATATAAATTGTAGAAGAAAATGGATGGTTCTAGACCTGAAAAGA

CAAGAAAATTGCTTGTGTGTAATCTGGGCAGGTCTTAAGTTGTGACCTTC

AACATCTGCTTCCCAAGCAGCTGGAACCACCAGGCCTACAGAATTCTTAG

CTATGATTCTAAAGGTCATTCATCAAATATAATGTTAATGTGTATTTTAT

TAAAGTTTCAAACTTCTATCTTTAATAATCTGCAAATGTAGCTCAGTAGA

GGAGAGCTCTCGCTGTAAGGTCCTGTGTTCTATCCCCAGCACAACAAAAC

AAGACATTTAAGAAAAAATTAAAACAAGTTGGCTGTATTGTCTCAGTATC

TCATCCTTGAGATAGTGAGGCAGGAGGACTTTTAGTTTGAGGCCTATGTG

GGTTATGTAGTGTGAAACCTTTCTCAAATAATATTTACACTTTTTTCTTT

AAAAAACAACTTTTTTCTTAATTTATGTGTTTTGCAACATGTAAGTCTGT

FIG.3D(43)

GCAATGTGAACATATCTGTTGCCTTTGAATGCCAGAGAGGGTTTCAGTTT

TCCTGGATCTGGAGTTACCAAGGGTTGTGAGCTGCCATAGTGGGTGCTGG

TAATGAACTGAGTCCTCTGGAAGAGCAGCCAGTGCTCTTAACTGCTGAGC

CATCTCTGCTGCTAGGTACTCCCCCTTCCCCCCTTAAATTTAAGACAAAG

GTCTCACTGTGTAGCCTCAGATGGTCTAGAACTCAATTTGTAGAATGGTT

GACCTTTGAACTCACAAAACTCTGCCTGCTTCTGCCTCCTGAGTGTTGAG

ATTAAAGTTGTATGTCACCACACCTGCCCCTATGATTTCTATATTTAATA

AAGATCATGACTAGGATATAGAGAACACTTTTAGAACTGAAGAAGAAGAC

AGTTACAGTTAAAAGCAAAACAAAAACAAAAACAAAACAAAACCCAGAAA

AAAAAAGAATGAAAACTAGCACTGAAGAAAAAATAAATTTTAAAAATAGG

CAAAGAGTCACTATTATATTGTGATGGATGTGTTATATGTTTAAAACCAC

AAGTGAGATACAGGCCTGAAATGACTTTAATCGAAGCTACACCAGCCTGG

GGTGGTAGTTCAGTTGGTAAAGTTCTTGCTATGCAAGCACAAGAAGCTGG

GTTTGATGCCCAGGACCCATGCTGAAACCCAGGAGTGCTGCTGAGTGCTT

CAGCTCTGGGGTGGCAGGGCTCACTGGCAGGAAGCCTAGGCTAAGAGAGA

CTCTGTCTCGAAAAACAAGGCCGATGGCACCTGATGAACGGCATCTCAGC

ATGACCTTTGCTCGGCATATAATGTGTACACACAAATTCATAGTTTAGTA

GAAGACAAGTATGATCTGCTTTTCATGAAGTCTGTTGTAATACGCCTTCT

TTAGTTAACCATAGTTGCTTAAAAAAAGAAAAAAATCGACCTCACTGGAC

AGAAAATGGATAGAGTGTTCTAATAGCCAATTCAATTCATCATCATTATC

AAAACCTATAACTTAGGGGGCTGGAGAGATGGCTCAGCGGGTAAGAGCAC

FIG.3D(44)

TGACTCCTCTTCTGAAGGTCCTGAGTTCAAATCCCAGCAACCAGATGGTG

GCTCACAACCATCCATAAAGAGATCTGATGCCCTCTTCTGGAGTGTCTGA

AGACAGCTACAGTGTACTTACATAAAATAAATAAATAAATCTTTAAAAAA

AAACACCTATAACTTAAACTTATCAATAACTTTAACTTTCCTACCCCATG

CTTCCTAGTTACCCATTCTGCTTTCTGTTTGTATGATCCTGGGTATGGCA

TCTTAATGGAACCACAGTGTTTGACTTTGTATCTACTTAATATTAGGCAT

GATGCCTCTGACTCTCATCCCTGATATAGCACAGTTCAAAATTGCCTTTC

TTTGGTGCTGTACATATAGCTGAGCGTTTGAGTGCTTCCCTGCATGCACA

GGTTTCTGAATTCAATCCCCAGCACAAAAAATGATAAAAAGAAAGCAAAA

AGGCTTATTTTTACAGCTGGACAGATCATCCTGCATTGTGCCTGTCATGT

TTTGCTTGTTTCTTCTGTCAGTGGACACTGTGTTACTTCTACCTTTTGGT

TGTTGTCAGGAATATTGTAAACATGAGTGAATATACACCCAGAAGTACAA

CTGGATGTGGTAATTCTATGAGTGTTTTGTTTTTTGAGGGATGGTTATTA

TTGTTTCCATACAATAAATTACATTTCCTTACAGTTCATTACATTTCCAA

AAGCCATGCATAGCATTTCTGTTGTTCTACATTCTTATTGACACCAGTTT

TCAATTTACATTTATTTTGTGAGTTTTTTAATTGGTAACCATCATAATGG

ACATAAAAAATAGCTCATTGTAGTTTTGGTATTTGTATTTCAGTAATGCT

TGGTGTGATTATCTTTTTATATTCTTATTAACCATTAGTGTGTATCTTTT

TTTGGAAAAACACCTCTTCAAGGGTTTTACTATGTAGCTCTGGCTGGCCT

GGAACTTGTGCAGACCAGGCTTGCCTCCGGTTCCCACTGTCTTAGGTAGG

TTTCCATTGCTGTGAAGAGGCACCATGACCAGAGCAACTCTTACGAAGGA

FIG.3D(45)

CATTTAATTGGGGCTGGCTTACAGTTTCAGAGGTTTAATCCATTATCATC

ATGGCAGGAAGCATGGCAGCATCCAGGCAGATGTGGTGCTGGAGGAGCCG

AGAGAGTTCTATATCTTGATTCAAAAATAGCCAGGAAAAGACTGTCTACA

GCAGGCAACCAGGAGGAGACTGTCTTCCATATTGGGCAGAACTTGAGCAC

TAGGAGTGTTCCAAAGCCACCTACACAGTGACACAGTACATCCAAAAAGG

CCACACCTATTCCAACAAGGCCACACCTCCTAATAGTTCTACTTCTCATG

GGCCAAGCATACTCAAACCACTACATCCACCTACTTCTGTCTCCCGAATG

CTGGGATTAAAGGCATATGTTGCCATTACCCAATTTTAAACCAGATTATT

ATTGTTTTTTTGTACAACAGACTTTTAAGGTTAAAGTTTGCAGCAATAGG

CATTCTTTGAAGCTGTATCACACTGATATATGTCTGTTGTTTTCTTCCTT

CCTAGATTAAAATAGTACAGTATATTCAAGTTTCAATTGTCCCTTTCCAT

AAGAAGTCCTGGTTTCTGTTCCATTATTAGTTTATATCTTAGTGTTCTTA

AGTAAAAATACTCAGTATTTATAGATGAGTTAGATTAGAGCCAAACCCCA

ATCAGGGTATTGGTAATGAAGGTTTGCTGGATAATTCAAAGGATACTGCA

AAGATCTGGTTTCTAATGGAAAGAACATGTAAGTTGGCCATTAGTGGACC

ACACATCTGTATTTCTTATTCTTTGGAACCTTGGGCAGGATAGACAGATG

AGCTAAGATTCCTTCATAGCTATTGAATTTGTGAGAAAAACAAATTGTGT

TTCCAGAAACCTGCTTTAGTTTGTATCAACACTTACTTTCTTTCTGTGTG

TGGTGTGTGTGATGTGCCTGTACCATTTTCAAGTTTTTCTTCCTTCTTTC

CATAGATACCCTTCTCATTGACTATCAGTTCACCTTTAGCCTGTCCCAGG

AAGACGACCGCTACTACACAGCCATCAACTTTGTGGCTACTCCTGATGAA

FIG.3D(46)

GTAAGCTTTTCTTTTAAGCTGTCTTATTTTGTGTTAAATTTTGTATAGGT

TTTTTTCTTGGTCATCCTGGACAAAAGTACTACATAGAAGCAGACAGTAT

CAGGGTGGGAATATAAAAGGCAACCAGTTTTTAAGTATTTTTTTATTTAC

TTGTTGACAGTTTTATATGATTATATAATGTGCTTGATGATATTCAACCT

GTGACCTTTTGTCTCCCTCATACTTAGTTCCTTCTCTCCCCACCAAGTCA

CCTTCACTCCCTCTCGTGTGTGTGTGTGTGTGTGTGTGTGTGTGTGTGTG

TGTGTGTGAGAGAGAGAGAGAGAGAGAGAGAGAGAGAGAGAGAGAGAGAA

AGACAGACAGACAGATAGACAGAGAGACAGAGATTGATTGATTGATTGAT

TGATTGATTGATTGATTGATTTACCTACCTAGTTTACCAGCTGACTGCAG

GAGCATGCTGGGTGGGAAGTTCTTACTGGAGCATAGACACATTACAGTGA

CTACACCACTGAAGAAAGTGACTCCCTCTCAGGTAGTCTTCACTGCCACT

AGGTCCTCAGGGATCAAGAGAATGTTTGGAGTCTACATTTTATCTTTTTT

CCACTCAGAAGGCAAACATTACTGAATGTTTTTAAGTAGTAGAATAATGT

TCATGATAGTCTGTTTAATATTAAATTAAGAATTTGTTCCTAATTATAAA

ATTTTTAGAAGATAGACAAGAAGACAAAATTTTTGAGTTAACAGTTTGAA

AGGTTTATTTTTATTTTATTTTATATGTATGAATATTTTAGCTTCTTGTA

TCCCTGTGCATCATGTGTGTGCAGTGCCTGTGGAGGCCAGAAATAGATAT

TGGATCCCTGGAACTAGAGTGATAGATCATTGTGAGCCATCATATGGGTG

CTAGAACCAACCCAGGGTCCTCTGCAAGAGCAGTGAGTGCTCTTAACTGC

TAGGCCATTTCTTTAGCCCCTAAATGTGAACAACTCTTTAAATAAATGTA

AGTGATCTTAAATACTCTGGAGAAAAATCTGTAGCTATACCTTACTTTTT

FIG.3D(47)

AAAAATTATTTTGTTTTATATTATGAGTGTTTTGCCTACATATATGTGTG

TCTGATGCCTGCAGAGGTCAGAAGAGGGTGTTGGATCCCCTAGAACTGGG

GTTACAGATGGCTGTGAGCAGCTATGTGGTGCCTGGGAGTTGAACCCTGG

TTCTCTGTTAGGGCAACAACTGCTTTTAACCATCAACCCATCTCTTTGGC

ACATGGGTGCATTGTTGGTTTGGCTGCTTGAGTTGTGTGTGAGGGGTGTG

TGTGCATACATATGTGGGTCCATGCTTATCCAGTGGAGGCCAGAGGTCAG

AGTCATGTATCTCTCTGTTACTTTCTACCTTATGTTTTGGAAGCAAGATT

AGATAGACCCCTGGGACCTTCCTGTCTTCTCCTCAGCACTAGGACTACAA

GTCCACACCTGACTTTTTACATGGGGCTTCAGATCTAACTCAGTCCCAAC

ACTTGTTTCATTTCCTTAGCACCTTGGCTAGATTCTTAGGATTTTAGAAG

GAGCTTATAGCAAAATACCACAAGTGAAATTTACTACTGCCTTAGTCATA

AGCAAATATTGAAGGCTCAGTCTTTAAGGGTATAATTGATAGTGTTCTTT

TTTTTTTTAAGTAAACAAATAGCCTGTCATGGTAACTATCGCTGTAGTCC

CATTACTTGTGAGAGATGTCAGCTCAAGGCCAGCCTCCGCTACATAAGTA

AGGGAAGACCAGCCTGAGCTATATGGGACTCTATCAAAACAAATAAACAT

TGTAGAATTTTTGTAATACTTATTAGAAGGTAGCTGATGATCATGAGAGT

CTTTAGACATTTCTTCATTCCACTGTTTTGTGTGTGTGTGTTTCATGACA

GATTTCTTACTAGATTTATCTCTTTGTGTGTGTGTGTGTGTGTGTGTGTT

TTACAAAATGACAAAGATTTTAGTCCTTCTCGTGGAAAGTAGTTGCTAGT

GGTCAGCAGATACTTGCTAGTATAAATAAATGAGCATAGATCTGCGCTTG

CAAAGGAAGACAAAGGGAAAAAAGGTTTTCTTGAACATAATTCCTACTTT

FIG.3D(48)

GTGAAAGAAACTTCTCATTTGGAAATTACATTTTGAAAATAGGTATTGTG

AATGTTTCCATTGTGGTTTGTGGTATAACTATCAAATAACACTTTTTTAA

AAAGAAAAATCTTAATTTTCTAAGATTTTTAAATACCCTTTTAAAATGAG

CATTTCCAGCATGGTTTGATTAATTTGTAAAATGTAAGAATATAGTATCT

AAGGCTACAGAAATGACTCAGTGGTTAAGAGCACTGGCTGCTTTACAGAG

GACCCAGGTTCCATCCCCAGCACCCTCATGACAGTTCACAGCCATCTGTA

TTTCTAGTTCCAGGGCATCTGATGCCCTTCTCTGATTTTCTCCAGTACTA

GTGACACACAGCATACATTTGAACAAAACCACTGATACACATAAAATAAA

TTGTTTTCAAGAAACAATATAGCATCTAATTAGCTTACAAAACTAATTAT

TTGTTTCTGTACTAATTACGTTTCTATTGGCATGACTAAGGCAACTTATA

AGAGAAAGCATTTAATTTGGGGTTCACACTTCTAGTGCCTTAGATTCTAT

GAGCATCATGGTAGGGAGTGTGGCAGTAGGCAGGCAGGCATGGTGCTGGA

GCAGAGGCTGAGAGCTCACATTTGATTTTCTACTAGAAGACACAGAGAGA

GCTAACTGGAAAAGGCATGGGCTTTTCAAACCTCAAAGCCCCCCTCTAGG

AACACACACCTCCACCAAGGCCATACCTCCTAATCAAACAGTCCTACCAA

CTGAGGACTAACCATTCAGAGATAGATGAGTCTATGGAGGCCATTGTCAT

CCAAACCACCACAGGCCCCAAGAAAGATTTGTTAGTGAAATTTCAGTGAA

AACTAAAACAGCATTAGAATTTACCTGGCATAGCCAGCAATGATCTCTTC

TGTTCAGTGCCACAGATTTCTTTGAGTTAAAACTCAGTTGTTAAAACCAA

AAATCAAAATGTAATTGGCACTTTAAATTGCTATAAGGGGAAACAAGGTT

TTCAAAGCCATGAAACCATATTCAGAATAATTTTAGCGAGAGAAATATTT

FIG.3D(49)

TTTCTTTTTTTTGTCGTTTCTTTTTTTTCTTGGAGAGAAATATTTTTATT

ATTTTATATTATTTTAATTACATATTTAATTATTAACCATTTCTGACAGA

GGGCAAAAGGTGAGGATCTTCATGGAACTAATATCTGATAAAGCACCAAA

TTCTTCCCAACTCTGGGATGCAAATGACAGTTCAACTTCAGTTTATTGCT

TGTATTGAAGAAAATTGACAAGAAATGTCATGTCTTAACATAAGCATGGA

TTTCTTTTAAGATGTAGAATAGTCTATAATTAATGTTTTTGAGACTAGTA

AGACCTGATTATTGTTGTATCTTAAAATCTAGAAGGTACTAACAATTTTC

TAATGTGTATTTTTTTTTTCATCAGCAAAACAGGGATTTGGACATGTTCA

TCAATGCCTCCAAAAACTTCAACCTCAACATCACCTGGGCCACCAGCTTC

CCAGGTACAGACACACCTAGAGAGATGGATTGGCAAGTTTAGTGTAGGAG

TTGGGGAAGGAGGCTCTGAAGGCTGGTGAGTGAGTTCAGAGCCCACCTCT

GCCTCTTAGTAGCCATGGCACCTTGAACAAGCCATGCTTGAACAAGCATG

TACAATTCCCTCTCTACCTTAGGCTACTCAGAGTGAGGAGTCACAGCTCT

TGCCTCCAGCGTTGCTGGTTCAGGTTGGTTGGATGGCTGCTCCCTGCTTT

GCCACCACCTTCCAGCACTATGACTATCTCTATGTTTGTGCTTCACAGGG

GAAAAACTAAAGTGACTCATAGTTTTAAGAAATGAAAACTCTTTAAGGGA

AGGGGGATAACTCTAATATGTAGAGGTATTCATACTTTGGGATAACTCCT

AAAAGTACAGCTTTTCCATTCTTGTTTATCTTATAGTGACTATAAAATTC

TGATGGCCCTAATGTAGCAGTTACTATAAATAACCACTCCATAACTTGAT

AGCCCTGAAGATAGACCTAGGTTTGAATTTACCTGCACGGTGTTGAACAA

GTTACTGAAGCTTTCTTTTCTTTGTTTTTTAAGTTTGTTTTATTTTATGT

FIG.3D(50)

GTGTGTTTGCCTTTGCCTGTATGTGTATAAGTGTACCATGTATGTGCAGT

GCTTGAGAAGGTCAGAAGAGGACATCAGCTCCCCACCCTCAACGAGTTAC

AGACAATTATGAACTACTATATCTGTGCTGGCAACAGAACCCAGGTCTTC

TGAAAGAGCAACCAGTGCTCTTAACTGCTGAGCCATCTCTCTCTAGCCCC

CAAGTTACCTAAACTTTCTGATCCAGTTTCCTTCTTTATAAAATGATACA

GTGAAAATAGCTTTGCTATGTACAGAGATATTCCAACTTTTTAATATTAC

AACATGACATCTACAAATATGTTAGCCCTCATTCATAATCTTGCCTGAAT

TGTAGAGTGTTGCAAGGAATAAATGAAATAAAGGAGGTACTTATTATAGA

GTTTGAGGTTTGCCTTCATGCATAAAGAGAAGCTTTTTTGAGTCTGTACT

ACTCATGTTCTTAGCCAATGGAGTATATAAAATATGGTAGAACCATTTAG

AAATGGAGTCTCACTGGGTACAGGCCTGAATGCAGTGGTAGCAGGTAGCA

GAAAGAAGGCCTGAGTGGCTGCTTGAGCACCTTCTCCATCAAGACTTGAG

GACCTTTCTGCTTAGGAAGTGATGAGCGAGTAAGTGTCCCTGAACAGGAG

CCTTGAGCATATTCTACAGTGTGAAGCAGAAATACAAAGGAGTTGAGGTA

TCATGTGCAAAATGAATGCAGTGTCTGTTTTATATGTATGATTGTTTTAC

ATACATGTATGTCTGTGCATCGCTTATATATCTGGAGCCTCTGAGACAGA

TTACTTAATCTATTGGGACTTGAGTTTTTCCAATCTGTAGATGGAGATAG

GAAGGTGTTGTGTGGGTTAGAGACTGAAGCTCATAAGGCTATATTCTTTT

GACACTGTAAGTGCTCAATAAACTTTTACCCTCATTACTAGTGCGCAAAG

ATTCTTTCTGATTGGCATACCCGCCTCCCAAGTCTTTATTTTTATTCTTG

CTTCTTTCTAGCCGGAACCCAGACTGGAGAAGAGGTGCCTGTTGTTTCAA

FIG.3D(51)

AAACCAACATCAAGGAATACAAAGATAGCTTCTCTAATGAGAAATTTGAT

TTTCGCAACCATCCAAACATCACTTTCTTTGTTTATGTCAGTAATTTCAC

TTGGCCCATCAAAATTCAGGTAAGAACTGCTTTTTAACTTCATTCCCGTA

AAGATGGTGACATCTCTTTAGTGGAGACTAACTTCACTCATTTGGAATCT

GTGGTGACTGAAAGATAGTGTTGCTTTGCCTTTGAGGGATCTTTGCCATA

GACTGAGTAGCAGGTGAGTGCTGTTCTTAGGTTGGAGAGATGTTCAGTGA

GTGGAGTGCTTGCTACACAAGCCTGAGGACATGCAGTTCATCTGCAGCCT

CTCATACAAAGCGGGACACGCAGGGTGTGCCTGTCACCTCAGCACTGGAC

ATGCAGTGTGTGCCTGTCACCCCAGCACAGGACACGCAGGGTGTGCCTGT

CACCTCAGCACTGGACATGCAGTGTGTGCCTGTCACCCCAGCACAGGACA

CGCAGTGTGTGCCTGTCACCCCAGCACTGGACACGCAGTGTGTGCCTGTC

ACCCCAGCACTGGGAAGCAGGGGACAGAAAGATCTTGCTTGCTGGCCAGC

CACTCAAAGCTGGATCTGTGAGTTCTAGATTCAGTTAGAGACCCTGTCTC

AAGTAAAATAAGGTAGAGAGGAATTGAGGAAGACACCTGATTACCTCTGG

CTTCTGTATGCATGTGCACATATATATACCTTCACACATATACACACTCA

GAGAAAAAATTCTGAGAGTGTCATATCACTTGTGAAGAAAGTTTTAAAGC

ACTTTTAAAAGCAAGATGAAAGCTATGCAAGGTATGCAAGGTAGTATACT

TTTGTAATCCCAGGATGTGGAAGACCAATGCAGGAGGATCACCCTGAGTT

TGAGGCCATAGGAAGACCCTGCCTCAAAAGGAGGGAAGGAGGGAGGGAGG

GAGAGAGAGAAAGAGAAAGAGAAAGAGAGAGAGAAAGAGAAAGAGAAAAA

GAAAGAAAGAAAGAAAGAAGGAAGGAAGGAGAAAGAAAATCAAATTGATT

FIG.3D(52)

GGCATATAGTTATGTGTTTATTTTTTGAGTAATTGCTATGTAAAAGCCTT

TAGAAATACACAGTTTTAATTATGGAATTGAGTATAAATAAAACAAGTAC

ATGTTTGTAACCAATAAAGTATAAAAATGACACATAAGATGTCAAAGTGG

TATGATGGCTATAATGTGGAGTCCATAGAGGAAGCAGTAGGCAGTATGAG

GTACTGTGTAAAAACACATAGCTTTACTATTGCACAGACAAGTGTGGATT

CTTGTTCTGTGTGTGGTTCATGGAGGCTCTCCAGTTTGCAGATTCTCTGT

GCATGTGTCCTGAAGGATTGGTCTTCCTGCTATGACCTCTGGTGTTATTA

GCCTGAACTGAGTCCTAAGGAGACAGGTAGTGGAAATGTTTGTATTGCAA

AGACAGTATGGGTAGTTGTTTTTAGAAACAGGAGTTCAACAGAATTGATA

GAACTTGTGATCAAGAAGCTAACAGCTGGACTGGGATGTAGCTCAGTTGA

AAGAACGCTTGTCTAACATTAAGAAGCCCTGGGTACCATCACTACCACAG

CATAAACTGAGAGTAGTGACAGACTCATGTGTCCCAGCACTGGGAAGGTA

GAGGTAGGAGGATCAGAGGCTGCCCAGGGAGGTTGAGAGTGACTTACGCT

AGGAGATAGATCTAAAAATGAAAAGGAAAAAGAACTTGGTAGCTGCTAGA

GCTACCATGAAGAGAGTGGAGCTTAAGGATTCAGCTGAAGAATGTAAACT

GCCTTCTGATGACAACTGAGAGTCGCTGAGTTATTTAAAGTCAGGAAGTG

AACAAAGATCAGTGTTTCAGAAAGACCTCTGTGGCAACAGTATTGACTAG

AAGTAGCCCCTCCTATGTCAGGTACTGGTTTAGACTGTATTTGGAAGTGT

CCTCTTTCTTGATGGCCCTCAGACACCTTTCATGGCCACTCCTCTGCATT

TGTACCCCATAGCCACACACTTGATGGTTCTTTATTACATAAATAGCTCC

TTATAGGCAATGATAGATTTTATATTTTTGATAATTTTAAGATAAACTCT

FIG.3D(53)

ATGTCATTGCATAGAATTTAGTAGTTGTAGGTACTCAGTAAATGTATATA

GGATGAATACAAAAGCTTTAGGGTAACAGTATTTTGTTCTTCTTCCCCCG

CATTTTTAACTATCTCATAGTAGCACAGACTAACCCATAACTGACCATGA

AGCCAAGGATGACCTTGAACTCCTGTACCTTCTACCTCTTCCCCGAAAGT

GCTGAAGTTACTGGCATGTGCTGCTCACCCAACTAATAGCAAGTTTTTCT

TATAAAGGTGCTGATGCCCTTTCCCTGTTTGTGTTAATTGCTGACACTTA

AAAGCTCTTTATCCCAACCCACAGTGTTAAAGAGTTTAGTTAAATTTTGT

GGAAATTTTGTCCCAAATGAAGTGGTTGATGGCAGGCCTGGTGGCTCCTT

CCTATAATTCCAACACTCAGGAGACAGAGTCAGGACGATGGCCAAGAATT

CAAGGCCTTGGGCCTACAGAGTAGAAGAGAGAAGAATGAGGATTCGAACA

CCTGATTAAATAGATACCATTTCCTGCTACCAACCTGTGCCTTAGCTACT

CTTCTATTGCCGTGACAAAACATCATACCCAAGGCAGCTTATAAAAGAAA

GCATTTATTAGGACTCACAGTTTCAAGGGTTATACTCCAAAACCATCATG

GCCGGGAGCAGGCAGCAGGCAGGAACATCTGCTGTGAGGAAGAGCTGAGA

GCTCACTTCTTTATCCACAAATAGGAGGCAGAGAGAAAGCTAACTAGGAA

TAGAATGAGCTTTGCAGACCTCAAAGCCCACCTCCTTCCCAAACATTTCC

ACCAATTGGGAACTAAGTATTCTAATCTGTGAGCCTCTGGAGGCCCATTC

TTATTTAAACTACCACACTTTATAAGTTAATACTACATGTGATGAGGAAA

CTGGTATGGGAATTCTGAAAAGTAGTTCACAGGAGTGGGAGGGGCTGAAC

GTGAGTAGATGCTAGCATGTGTGTCAGGAGTGAAGTGTTCAGAGCATTGC

CTGGTTTGACTTCTCTCCAGAGCTGAGGTGAACATGCTTTGTGCCAATAC

FIG.3D(54)

AAACCCGTATTAAAGCGGTGGTAGTTACTGAAAATCAGTGCAGGGCTGTG

GTCTCAACACAATGTTTGAAAAAGAAAACAGGGCATCCACATCAGGCAGT

GTACAGCTGCTTATAATTCCAGTCCTCTGGCCTCTGCTCACATGCACATA

CCCCCCCATACATACACACATGATTAAACATAATGAAAAATTAAAAATTA

ATGCTATAAAAATGGAAAGAGCCGGGCGTGGTGGTGCATGCCTTTAATCC

CAGCACTTGGGAGGCAGAGGCAGGCGGATTTCTGAGTTCGAGGCCAGCCT

GATCTACAGAGTGAGTTCCAGTACAGCTAGGGCTACACAGAGAAACCCTG

TCTCGAAAAACAAAAACAAAAACAAAAACAAAAAAAAAAGTGGAAAGAAA

GGTTCACTGTTTCACAGGAAAACTCTGAGAGGTGATAATCCAATCCCAGT

TTAAAATATACTCCATAGTGCACACAGCCTCTCCCATCCTTGGCAACTGA

GGCCTGTGAGAAGACTCAGTCCTCTCCTGGCTTCCAACCTTACAGTGTTC

AAAACTCTTCTGCAAGATCCACATGGTCCTACCAAGACCCTGAAGGTCAG

GCATGCTGATTAGGCTGTCTCTGGGCCTGAAGTGAAAGGTAAACACTTCC

GAGATCTCCAAAGCCTTGGGAAGATTCTGAAATGTATGGGTGTTGGTTCA

GGTAGACTCTCAGCCTTGGTGAAGCTGCCCCCGGAGCTGTAGGGTTATCT

GCAGAAAGTCAGCCAGGTGCACTTACCCTGGAATCCTCTCCCATTCACAG

ACACCTCCCTGAGGCTTTGTGGCTTCACCTCACTGTGCAGCTAGCTCCTG

TTTTACATGCTTATATAATGAATGGTCTTGGTAAAGAAGATGATAAAGGC

AAGCTAGAGGCCTTTTTTTTCCCCTCTTCAAATTTTGATTGGCCTTTCCC

TACTGTTACACTGTCTACTCAAGGTTTTGAGCATTTACTTTGTGTACATA

GTAAAAGCAAAGTACATATTTTTAAGTAGAAAAGAAAGCATCTGTGGTCT

FIG.3D(55)

TTGATATAGGTGCTTTTCTTTATTTTAATAGTAATACTTATTCCATGCTT

GTTAAGAAATTCATTCACAGCGTGTTTTCATAGAGACTTTCTCTATAGAG

ATATATAGAAATCTAGACATGAGGACAGCCCACTAACCCACTCTTCAGAC

ACTAGCTGCTTCTCTTAGAGCCCTGGGCTCTCACCCTTTGGAGGACAGCC

ATCCTCACTCATATGTGACAAGCTTAGACACAGAATAATCACAGAGACTC

CAGCCTCCCCCACAAACCCACAATGCCAATATCCCATATTCCCAGGAACT

TTTAATAAGCCATCCACTCTAATACTCCATCTCTTATCTCAGGCATAGGC

CCTGGTTTTGGTTTGCTTCAGAGTACTGCCTTTTCTCTACCACGCCCTTC

CCACTCTTTGCTGACCCTCCAGAGATGTCATTTCCAAATGAAGGGGGTTT

TTGGTTCTGTGGGTGTTTTGTTTTTCAGTGCAGTTCCTTAACTGCTATTC

AGGGGACGGAGCAGGCAAACCAGATCTCTAACTTCTGAGGCCTGTGAAGA

GAAGCATCAGAACCTCCCAGGGGAGCTGTAGGAGCAGGAGTCAGGCCTAG

ATATGACTGTGAGAGAGTGGGGACCATTACCAGTGTCTTACAAATGAGGG

GAAGGACTACCGTGCTGGGCCCTGAAAGATAAGGAGGACCAGGCTTCAGG

AAGGTAGGACACATTCTGCTGACTGTCTGGGATTGAGGACAGTAACACAA

CTACTTAGACATACTTTGAATGAAGGACAGACTTAGTGCTTCAGAACTGT

AAATCCATTATATCTTTCCCAAGTCTTAGGCTAGCCAAGTTTCTCAACAT

TTATCTACCTCATCCCAAAGGGTTCCCAGGACAAATATTTCTTACTCAAA

CATTTGATGGGAGTTGGAATCAGGTTGAGGAAATGCAGGGGTGTAGATTT

TAGATTTCTGGGAATATGTATAGATAGCTACCTTCTGTTGGATAGAAAAT

GAGATTGTAAGTTTTTCAGTGTTTTTTTACACGAGTTTGTGTGCCCATGT

FIG.3D(56)

ATGCACATGTGGAGGCCACGGGTCTACCTTAGGTGTCTTCTTCAGGAACC

AGCCATCTTATTTTTAAGATGATCTCTCTCCAGACCTCAGGGCTATCAAC

ACACCTCAGGGATCCATCCTCCTGACTGTATGTCCCTAGCATTTGGGTTA

CTGTACCACCATGCTCAGGTCTTTGTGTAGGTCCTGGGGATCACAGTTAG

GTTCTCATACTGCAGGGCAAGCACTTTGTAAACAACTATCTCCCCTGCAT

ATGGAAGTATTACCACTAAATTACAACAAGATTTTCTTCTATTAAAATTA

TATTTTAGAAGCTGGATATAGTAATGCGTTGGGGCAAAAGGAGGGAGGGA

AATGAAGAGGATAGGAAGAGGGGGAGGGAGAAGGGAAAGAGTGGAGGCGG

GATCAGAAGTCCAATGTTATTCAAGGGCAGCCTGACCTAGATAAATCCCT

ATTAAAAAGTTTTCAGTATAGAAACTTCTCATCACCTTCATTATCAGAAA

AGCCCCTAAATTCAGAACACTTTTTAATCTTAATTAGTTGACAATTTCAT

AAATGTATTATTTATATATATGAATAACATTTTCCTCCTACCTTTTTTTC

CCTTCCCCTCTGATGATTCCCATCCTCCCAACCAAGCCCCCCTTCTGCAT

TTGTTTGTTGCTTTAATGACCCACTGAGTTCCATTGGGCTCACTTCCATG

AGTGTGACTAGAAGAGCTATTTATCAGAATGTGGGCAACTTACCAGTAGT

GACACTGATGAAGAAAGTGTTTCCCTCTTACCCAGTAACCATTAATGGCC

AGGAGCTCCTGGGAGGGGTGGGCGCCTTATGAGCCCCTTCTCCAAAATGC

TTTCAAACTGTGACCAGCTATATTTAATGTTTTTATTATGCCTGTGTATC

CATGTGGGACAAGAAAGCTTGAGAGTATCATAGCATGCATGTGGAGGTCA

AAGAACAACTGTGTAAAGTCAGATCTCACTTCCCACCTTCACATGGGCTC

TGGCACTGAACTCATGTCAGTGACCTGAGAGGCACTTTATCCTCTAACAC

FIG.3D(57)

GCACCCTGTGCCCAGCCTAAAATTTGACCTTTGCAAGGTTTAGTGTGTGT

TATCTGACTGTCTGAGTAAGGATGACAAAATGAAACCAAACTTATGGGAT

AAAGCTTGGTGGTTGTATCAGTACATTTTTATTGTTGTGATAAAACATTA

TGACCAAGACAGCTTATAGAAGAGTTTATTTGGGTGTATAGTTCCAGAGA

GGTAAGAGTCTGTCCTGACAAGGAAGCTGTGGCAGCAAGTGGCAGGTATG

GCTACAGGAGCAGGAAGCAGAAAGAGCAAACTAGAAACAGTTGAGGTTTT

TTAATAGGAAAGCCCACTCCCCTAATGATGTCCTTCCCCTAGCAGACCAC

AAGTCCTAACCCTCCCTACACAGCACCACCAGCTGGGGAGTTCAAATGTC

TGGGACTGCAGGGGACATCTCATTCAGACCACCTCAGTGGGAGAATGCTT

GCCTTCATAGTATGTGCAAGGCCCTAGGTTCAATTCTAGCCAAGAAAAGA

GAACATGAGGAAAGAAAAGAAGGTGGGAGAGAGTAGAGAAAGAAGAGAAG

AAGAGGAAAAAGGAAGGGAAGGGGGAGACAGAGGAAAGCAGGGAAGCAGA

GGAGAGGAGAAGAGAAAGAAAAGATTAACCAGCCTGGTTTTTAATAGCAC

CCCTCCCACTCTCAGTAGTTCCCAATTTGAGCATTAAGTTCAAGACTGAT

AGATATTTCTGGGTGGGTGACCAGTGTGGTCATAAACATGGTGACTTTTG

CTCTCCGTACAACTTGTGATTATGAACTTGTTAGATGATCAGCTTCAACA

GGAGAGGGCCTCCTTTAGTCTCAGGTGCCCCCTCCAGCCACCCTGGGACT

CGCAGCCTCTCTGTGATGAGACACAGGACATTAACTGGTATGGTTCTGCT

TTGCCAAAACGTCAGTCCATGGTTGAACTCTCCACAATGAGAAAGAAGCT

TTGAGAATCATTACATGGCATCAGGCAAGCCAGGACTGATGGAGCCTGAG

AAAGGGCCAGGAGCATCCGCAGGTTTTGGCACCCAGTACTAACTAGTAAA

FIG.3D(58)

AGCACCTCATAGGTTTCTTTAAAATGCAAACACTAAGGAAAATCTAACTT
TTTTTTATTTATTAAGGCCATTCATTTTATTTTATAAGTATTTTGCCTGT
ATACATATGTACCACATGCATACAAGGTCAAAAGATAGTATTGGGTCTTC
GAACTGGAGGTACAGATGATTGTGAGCTGCCATGTGGATCCTCGAAATTG
AACCTAGGTCGTCTACAAGAGCAGGAAGTGCTCTTAACTTCTGAGCCATC
TCTCCAGCTCCAGAAAAGCTACTCATAAAAGTCAAATCTAAGCCATGTGT
CTGGTGATGTACACCTTTAATTGTAGCACATGGAAGGCGGAAGTAGGCGG
ATTGTTATTCATCCAAGGCCAGTCTTCTCTTAACAGTGACAAAAACAAAA
CCAAACCCGAAACCTGTTACTTTGCACTTTAGAGTATAAGTGATAGAGAA
AAGACACAGAAATTTTAGAATCTATACCTTAAAATACCTTATGGCTTATA
TGATACTGTTGGGACCATATTTACTTATGGAATGCAAAAAAAAAAAAAAA
AAAAAAAGATGGGGGGGGAGCTGAAGGTCTCCTTTCTATTCTGTTGTAAA
TCTAGCTATAAAAAGAGTAAGAGGCATGAGTGTGTCTCAGTGGTAGAGCA
CCTGCTTAGCTTGTGTGGGATTGAATGATCCTCAGCACCACAGAAGAAGG
GTGGGGCAATAAATTTAGGAAAATAAGATGCTAATCATTGACTTTCTTGA
TTTTTTTAAAAAAAGTTATTATTTTATGTTTATTGTATATGTTTATATTT
TCTATGTGTGTTTTTTGATGTGTGCTGGAGGGATGGGGGCCACTTGCTGAA
CTTCCCAATTGTTATCATAACTACCATCTTTAGTGAAACAGTTACCATCT
ACTTAGTAATTGTTTCATTCGAATAGATACTGAACACTCTTAATCTGAAA
CTAATGCTCAGAAAGTTCCACTTTGCCAAGCAAGCAGGATAATGTAAGCC
TATAATTTTAGCACTGGGAGGGTGAGGCAGAATTGTGAGCTCAAGGGCAC

FIG.3D(59)

CCTGAGCTTTTGAGATCCTGTCTCAAATAAAATTAAATTATATAGATATC

AGATTTTCAGAATAGGTGTGTTCAGCTGCTGAATAAATCTAAGCAAATAT

CCCCAAAGAACCCTGAAATCTGAAACGTATTAGTTCTAAGCCCTATGTTG

TGTGTGTGTGTGTGTGTGTGTGTGTGTGTGTGTGTGTGTGTGTGTGTGTG

TAAGATAGATTCTCACTATGTAACCCTAGCTTGCCTGGATCTTGCTATAT

AGAGAGACCAGGCATATGCTATCGTGCCTGGGAGTCCCAAACGTTTTAGA

TGAAAGATTTCAGTTGTACCATTATCTTCCTAATGAGGGCTCTGGTCTAG

TGAGGCAGGTGACATTAGGCCAGTAGTAAGTATTAGGAATTGGTGATGAC

GGTCAATTCTGAGACACACAGTAGATACATCTAATCTACCAATACAACCA

ATGATTTAGAAAGAATTAGGCCATAGTTAAATTTGCAGTGTTTTTCTTCT

CCACAAAATAATGTTACTTCTTTCAGTTCTTAGTTCAAATACAGTAGGAA

TTTTTTATATTCTTGGTGCTAAACACTATTATTTTATAGTAAAGTTAGTA

AGATAGAAATGACGCCCTGTGGGTTGTCTGGTCGTAGTCTGTAGCTGAGG

CCATTTTGCTGAGAAGCAGCGTAGGCTGTCACTGGCTTTGTCACCCATAT

TTTCTGTATTTTTGCTGCAGATTGCCTTCTCCCAGCACAGCAACTTCATG

GACCTGGTACAGTTCTTCGTGACTTTCTTCAGGTAATTTCTCTATGCTAA

TTGTACACATTCCATCGAGACAGTCCCTTAACTGCAGCTTGCTTTGTATA

TCCCTACAAAGCTGCTTTTCACTCACAGTGATGTAAATTTAGTCTGATGT

GATAAAACTCTCCGTTTGTATGATTCGGCTCTTTGCATGGGGAGAGGTTT

GGGCTCAAGCAGTTATTAATAATATAGCTACTGCTGTGAGCTACATGTCT

TAATCTGTCTTAATCAAGATATGACTGTGATTTTCCATAGGGAAAGGTAA

FIG.3D(60)

```
GGTTTACTTGCAAACTCCTGGGGTTCTCCTTTTTTTATAGTTTTCTTATT

AGTAGGGTTTTTTTTTTTTTTGAGAATACTATGCAGAAATGATTGAAAAG

AACAAATTAGTCATTGCATATTGGTAAGAGAAGCAGCAAGAGCCACCTCA

CCTCCCTCTGCTCTCCCCAAATAGAAACTGCTCTGCTGTGCTGCTTCTCT

ACCTTCACACCAATGCTCGGCCTGCCAACTCAGTTATCTTTCCTTTCCTT

TTAAGATAGGGTCTCTCCTTATAGTAGTTATGACTGTCCTGGAATTCTAA

ATAGAAGAGGTTGGCTTTCAAATCACAGATCCTCCTGCCTCTGCCTTCTG

AGTACTGGAAGTATGGTGTATGCCACCGTGCCACAGCTAACTCAGTTATT

TTTTGGTGTTCTATAACTGCCTTACATACATACAGACCAGGTACACACAA

AATTCCTTTCCATTAATTTAATAGTTATATCACAATGCATTGACCAACTA

AAAAATCCTAAATTGACTTATGATTCTACTTGCTCATGTTTTAAAGGAAA

GGTTACTCTTTGCTTATCTTAAATGTAATATTTTTCCTTTGCAGTTGCTG

TTTAAATTTTCCCTATAAGTCGACCCCAAATTTACATCTATAATCTGGCA

AAACAAAAAGACCTCTAGTGATGGTTGTCTCTTAGCTTTAGTCTCTCTTG

GACTCCATTCCCTCCACCCATAATGTTCCATCCTCTGTCCTTAAGTGTAC

TAGTCTCCAAGGCCTGCTATGTGGTTGTCATTGTTGTAGTTACTTTTCTA

TGTTGTGACAAAGCACCCTGACAGTGGCAATTTAGAAAGCATATAATTTG

AGGATCACAGTTCCTGGTTAGAATCCATGACCATCTTAGCAAAGGCAGAC

AGGCAGGCCTGGCACTGAACAAGTAGCTGAGATCGTCCATCTGGTCCACA

AGCATAAGGCAGAGAAGCTAATTGGGAATGGCATGGGCTTTGGAAACCTC

AGAGTCCACTCTTAGTGATACCTCCTTATCCTTCCAAACAGTATTACACA
```

FIG.3D(61)

TTCAAACTTCAAATGTGTGAGCCTCTGGGGACCACTCTCATTTAAACCAC

CACAGTGATCTTGGCAACTTCTTTTGTGTTCGTCCCATGCCACAGTCTTT

CCATGTATTTCTCCTTTTGCTGGAACTTTTTCCCTCGAAGGTTCCTGAGG

AAAGAAACATAGATAACTTTTGTATGTACTTCTACAACTGAAAGTATCTT

AATTTTTGCCCTAACAAATTTTTGTTTGCTTACTTGCTTGCTTACTTGAT

TCTGCGTGCATGCATTTATTTGTTTGTTTGTTTGTTTGTTTGTTTGAGAC

AAGATCTCTCTTTGTAGTTCTGGCTGCCTCAAACTCAGAGAGATTCATCT

GCCTCTGCCTCCAGAATGCTGGGATAAAGGCATGCTCCACCATACCTAAT

CCAACCTCACAATTTTTTAAGTGTGTATTTATATGTGTGTGTGGTATATG

TAAAGGTGTGTGTGTTCATGCACACATGTGCAGAGATCAGAGGAGTCAGG

TTTTCTCATCTATCACTCTCTGCCTTATTATTTTGAGACAGGGTCTCTTG

TTCGATATTACATATACTAGGTGAGATAGCCCAGGAGCTTGTAGGAATTC

TCTCCCATTTCTACCTTCCAAATGTGTGCTACTGCATCTGGCTTTAAGCA

AGTTCTGGGAATCTGAGGTCAGGTCCTTACACCTATGTAGCAACTCTGCC

TACTGAGTCATCTTACTAGTATTCACAAGGTCAAAGGTTGGGACCAACAG

CCAAGGTTGTCCTCAGATCTCCACACAGATGTACCCACAATTATACAAAC

ACTCAACATAAACCTATTTACACACCCACATCACACGCACACACATACAT

GCACATACAAAAAAATGCTTTTTGAAAGAAGTAGAGAATGCTAGATATGG

TATTACACGTATATAATCCAAGCCACTCTGGAAGCTGAGGCAGGAGGATT

TCAAGTTTGAAACCAGCTTGACCACATAATTATACCATGCCTCAAAAATT

GTATAGAGAATAAGAATGAATATGAATGAGACTAAAGTCATATCTCAGTT

FIG.3D(62)

```
ACTTTTCTATTGCTGTGGCAAAACACCATGACAAAGGTAATTTACAGAAG

AGATTATTGGGGCATATAGTTTCAGAGGGTGAGTCCATGACAATTATGAT

ATGGCACTGAAGTAATAGCTGAGAGCTTAAATCTGGTCCACAACATTAGG

CAGACAGAGAGCTAACTGGAAATAGCCATGAGATTTTGAAACCTCAAGCC

CCACTCCTAGTGATGTCCCACACCTCCTAATCCTTCCCAAACAGTTCCAT

CAGCTGGGAACAAGATATTCAACATATAAGCCTATGGGGGTCATTCTCAT

TCAAACCACCAGTAGTAATTATTAGAGCCCAGCAAAGAAGGAAGGGATAG

AAAGAAATGATTGATGGGAACTGGGGTGAAGTCTGATACAGAGAGATCTT

TATGTACTGCAGCGTAGCTCAGGAAGATAACTATGGTTAAGGACAATTAG

CTAAGTGATTAGTAGAGAGGATTTTAATATTTCCAATACAAAGAAATGCT

GCAGGCCTGAAATAGGGTACGTTTCAGTGACCCAGATCTGATTATTACAA

CTCATACACTTGTACCAACCACATAAATATGTACAATAATTGTGTCAGTT

TTATATTAAATAAAAATGTGGAGCAAGTTAAAAAATGCCTGTTTTAAACT

GATCACAGTTATATGCCAGCTTTTCTTTGCTGTGACAAAATACCATAGGG

AGTAGTTTATAAGGAAAGAGATTTCCTCCAGCTCATAATTCCAGAATTTT

CAGTCTAGAGTCAGTTAGTTCTATCATATTGGGCCCACAGCTAGACCAAA

TACAATGATGGGGAGAATGTGGTAAAGAAAAGTATTTACCTCAGAGTGGT

CAGGAGGAACACAAGACAAAATATACATTTCAGTCCCATACCTCCAGTGA

CTTGCTTCATCCAAACAGACGCCACCATCCAATAGCCATTAAAATACAAG

TCAACCAGTTGATTGACATCCATTGATCTTAGTCATATCCCTAAATTCAA

CCTCTAAGCTCTGATGCTCTGGGGGCCAAGCCTCTATTGCATAAATCTCT
```

FIG.3D(63)

GGAGCATATTTCATAATATGAAATATTAAACAGGTCTCTCAGGAGCTGTT

TGGTAGACTTAGTTGTTTTTTTTTTTTTTTTGTTTAAGGTTTTTTTGGTT

GGGTTTTGTTTTGTTTTGTTTTGTTTTGTTTGTTTGTTTGTTTGTTTTTT

TTCGAGACCGGGTTTCTCTGTATAGCCCTGGCGGTCCTGGAACTCACTTG

TAGACCAGGCTGGCCTCGGACTCAGAAATTTACCTGCCTCCTCCTCCCAA

GTGCTGGGATTAAAGGTGTGCGACACCACTGCCTGGCCTAGACTTATTTT

TTTAATCAGATTTGAGTCTTTGCCTCTGGAATCACAGTAGCTTTTCCCAT

TCAACACCTAGTTTACAGAAGAAAGAAAACCCAATTTTTTTTTTTATAAT

CATTAGACAACTAGAAGTTTTCCCTCCTATTAAGAAAACATATTAACGGG

CTGGCGAGATGGCTCAGTGGGTAAGAGCACCCGACTGCTCTTCCCAAGGT

CCAGAGTTCAAATCCCAGCAACCACATGGTGGCTCACAACCATCCGTAAC

GAGATCTGACTCCCTCTTCTGGAGTGTCTGAAGACAGCTACAGTGTACTT

ACATATAATCAATAAATAAATCTTTTTAAAAAAAAAAAAAAAGAAAAAGA

AAAAGAAAACATATTAACAGTATTGAGAAAACTGTTGGCTTAAATTTGAT

GATTTGAATTTTATTTTACTAATAAATGCATGTATTGCTGGGCATGGCAG

CACATCCCAGCACTCAGGATTCCGAGATAAGAGATCATAAGTCCACGCTA

GCTGGAATAGCAAAATAAAATCTTTTTTTAAAAAATATACATACATACAT

ACATACATACATACATACATACATACACACACACACACTTTTCTCAGT

AGTACGGCCAATTAGTTGACTTGTCTAACGGAGGGAGGAAGAGGAGGCAG

AGAGCATGCTGTTCAGATCACGTTCTCTTTTGCATTCAGTCTGGGACCCC

AGCCCATAGTGTGGTGCTGCCCACATTGATTATTGGTATTCAGTTAACCC

FIG.3D(64)

AGTGTAGAAACTCTCTCAGAGACATGCCCAGATGCTTGCCTCATAACCAC
TGTGTATGTATATATGCTTACAGAAAATATACTCATCATTACACATAAAT
TTCATCCACTTACCTCTTATGAAAAGTTGATTATTTACTGAGATTTTTCT
CATTCTGAAAATCCATAAAGTCTACCACATTGATTAAATTACTTGTTTTT
TACCTGTTATTGCTCATGTTAGAATTGCTTTCCTTATTTGGGGTAAGCTG
TCGTTGGCCACTGTGAGGGGCTTATCAAGAAGTCAGAAATGGGAACACCT
TCTAGGAAGTCAGGACTGGAAGCTTAGCTGAGCCAGCAAGTGTTTCTCAC
ACTGCACTTCCTGTGAGCCTACCTGTGCGGCATCAGGAACTGGAGTTGGG
ACCTTGAGGATTGTTCCCTGGAGGCAGGGGTGGAGTCAGGCAGGGGTGAA
GCTGACTCACAAGATGGTCTTGCCTTTCAGTTGTTTCCTCTCGCTGCTTC
TGGTGGCTGCAGTGGTCTGGAAGATCAAGCAGAGCTGTTGGGCATCCAGG
CGGAGAGAGGTAAGCCCAAGTAGACAAACTCCACATAAAACTCATTTTTT
TCCTTCTTTCTAGGCAGATCACTTTTACCTGTTGAGTGATGACTAATATT
CATATGAGAAGCATGCTGTTTAACCTGCATTCTGTGGTTCCACTATGTGC
CATCAGTAGATTTTAATTATTCTTGCATAAAGTGTCATTAGTTTTGCCAC
TGCTTGATTCAAGTCTTCCTAAGAGTCTTTCCTAAGAATATGAGTGTAGA
GACAAGTTCAGCTCAGTGACAGAGCACTTGCCTGGCATAAACTGAGTCCC
TGGATTCTAGTCTCAGCACCCTCTAATAGCACAACACTAGAGACAAAGCT
TCTAACCTGTGGGTCTTGGGCAGCAGGTAGGGGAGGGGGATTTAAAAAAC
AAAAACAAACCTCTAGCTGTAGCCTGTGTCATTTGTTATGACTAAGCACT
AGAGTGGGTACTAGTAGACATGCCATGTGGACATTGAGCACCTCTCCATC

FIG.3D(65)

CCAGGCACTGATCCAGGTGGTTCTGCTTTATCTTCATCTCCACCCTAGGA

TATAAGGGAGGCTACGTAACTACCCATCACCACACAGATGCTGAGGTACA

GAACTGAGGGGTAACTAGTGCCTCTGCCTTCACAGCACAGGTTCCTAAAC

ACGTTTTCTACAAACACTTCATTTGTTCTAGTCTGTTCATTTAAGAATCT

CATGTTCTGACTGAATGAGCTAGACAACTCACCCTAGACTATACATTCTA

AAGAAGGGCAACAAGGCAGTTTTGTTACTGTTGAGAAGAAAACAAAGTTA

TTTCCGTATGAGTTATTGAGATAGAATAGTAGAGATTTGTCTGAATACAA

AATAGAAAGTATATAAAAGTATATAAGTGGATCATAAAGAAAGCAACAAT

CAACTGGAAAATATTTGCAGTATCATGAGAGAGAGAAAACTAGAAGATGA

ACCCCCTCAAAAAAGGATTTTTAAAATATGCTTAGACTGTATTCAGTCAG

CTAATAAACTTTTTTTACCTTTATTTGGAATTTACGAATAGCACTGAACC

TGACCATTGTAAATGCACGAGGTCAGGCATGACTTGTTCCCAGTAGGAAG

TTGTTTTTAGTTCTTGCTGTGGCCTGGGTCCTGATGGAAGTTCTTTACCC

ACCTTATCTCCTGTCCTCTTGGCAGAGGTTCTAGAATAGTGCTGTGATGG

GGTAGCAACTGTCTTCCTGTGACCCTGCACCTAGATTATTACAGAACCCA

GACTGGGTTTGCTGAGTTAATGGAAATTCTTTCTAGGTTCAGTAGAGAGA

TGTGCTGACACATACTAGGCCATCTAGTTTTTCAGTAATGCTCAGAGACC

GCAATAGGATATGTAACAGCAACAAAATTTTTAACATAAAATTTCCCTTC

TAAAACAGAGTGATGATTTATGTAGCTTCAGGATCCTGCCTCCTAGAAGA

TGGTTTGAAGCAAGGCCAGTTTGTCTTCCCTAGCATAACCTCAGAAGACC

TCTCATATTATTGATGGTATAGGAATGAATGCCCACATTCTGTATTTGAG

FIG.3D(66)

ATGTGTGCTATAGTATCTCATCTGACCCAACATGAAAACATTTCAAGCCA

TGTGTGCTTGGGTAAGGTAGGAGTTCAAAGTCATCCAGTGAGTTCAAGGC

CAGCCTGGGCTGCATGAGACACTGTCTCATAAACAGACACTTGAATCTCA

TTTAAAGAAGACATTGAAGACTTGATACTTTGAACACCTATCCTAACGTA

TCCACCCCCAAATCCAGAGTCCTTCATGTTCTTGTCCTCTGCAGTTCCAC

TTTCATTGTGTTCTCAGCAGCAGCTCTCTCCGAGGAGAGTTGTCTCCCAT

CCTATCAGCCATCTTTTTTATTGTTGTTGCTCTGACAATGTCTGGTTCAG

GTTTTAACACAAAGCAAGCTAGAGTGATTTTAATCTAGCAACAAAAATAT

AAAAAGGTAAGTTTTTGCCCTTTTATATATTCAATCAACAGATATCATAG

CATTATATCCTCCACTTTAACTTTTATTTCTTACTGGTAAGGGCTTTTTA

TAAAAATATAATAGTGTTACCACATGTAACAAAATTTGATACCTTGTGCT

ACCTAGCACCTTGTCATGTCCAGTTTTCCTCAGCTGTCACAGAAGCGACA

CTGCATCTGATCAGTTTGAATCAGAGAGAGTGTAGCATGTCTAATATCTA

GTATTCACTAATAAAATCTCAGTACTAAGCATATTAATAATACTATATTA

TTCATTAGCAACTTCTTCGGGAGATGCAACAGATGGCCAGCCGCCCCTTT

GCTTCTGTAAACGTTGCCTTGGAAACAGATGAAGAACCTCCTGATCTCAT

TGGGGGAAGTATAAAGGTGAGAAGTGGCTCAAAGGTCCATATAGCTTTTC

AGAACTCAGGCCTCAGTTTGCTAGGCTACAGACAGCAAGCGCTCTGTGTG

TCACTCCTGTCTCCTCTCTAACAGTTAGTCAGCAGAAGCAACCCCGAGCG

ACCGTAAGGGGCTCTGTGTGTGGCTTTACTTTTCGAGTTGTTGCATGTCA

GATTTTAACATGCAAATTAAGCTTGTTATTCTTACTTTGTGGCATAATAC

FIG.3D(67)

TTTATAGTTTTTATTTGGAAATATCTAATCTGGGCTAGGTGTGATGGTGC

ACATCTTTAATCTCAGTTCAGAGGAGGCAGAGACAGAGGCAGGCAGGATC

TCCTTGAGTTCTAGAACAGCTGGTCTACATAATGAGACCCTATATGTTAG

AAAAAAAGAAAGAGGGGGTGGGGGAAGGCAGCTAACTTTAACCATTAATT

GAACCAACACACACACATTTTGTTCAGAGCCCCAGTACTCAATTAAAAGC

CAGGCAGGCATGGTAACAGTACTTAGGGAGTCAGAAACAGGATTCCCAGA

GTAAGCAGTCTGACTAGGCTAGCAGGAAATGGTGAGTTTCAGGTTCAGCA

AGAGGCCCTGCCTCAGTAAGTAAATTGAAGAACAACTGAGGGAGACTTGC

ATGTGCACTTGTGCATGCACCCACACATGCACTTGCACACATACCATATG

TCACCATGCTTAGACTATAAAATGTAGTCACTACTGGCAGCACATGCCTA

CAATACAGATGCAGGAGAATCACTGCAAATTTGAGATCAGCCTGGGCTAC

TGGACAAGATTTTGTCTCAAGAAAACTAAAACAATACAAAAGTGTACTGG

GGGGGTTATTCTAATGCCAGTGTTTATGACAGCACATTCAGAACTGACAG

TAAAGGCAATCAAGGACTGTCAGTGGTGGGTATATACATAGGCAGAGGAG

CAACTGCTACTAGAAACTGTTTATCCTTTAAAAGACTAATGTATGCTGCA

GCATAGACAAACGTTAAGTTGTGTTAAGTAAAAGATGCTGTATCATTCCA

CTTACCCATCGAGAATAATCAAATACAAGACAGAGTAAAATAGTGACTGC

TAGAGGCTTAAAAGAAAAGACCAGGGGGTGGGGAAAGGGAGGGAAGGAAG

TGGGAGAGGGAGGAAGGGAGAGAGGGAGGGAGGGAGCCAGACTTTGTGGC

TTACAGCATCAAGAGGCTGAGGCAGAAGGGTTACAAATTCAAGGCCCTAC

TGGGCTACATAGTGAGAAGTAGGATTTCCTTGAGCTGTCTTTCTAGGTCA

FIG.3D(68)

TAATCTCTCATTGGGGGAAGTCAGGGCAGGGACTTGAGGCAGAAACCATG

GGGAATGCTATTTGCTGGCTCCTTCCCAGGCTCCTCTCTAGCTTTGTTTT

CTCATTTTGTTTTTACTGTCTATGGGTGTTTTACCTGCTTGTTTTTCTGT

GTACCATATACATGCCTGCTACCCACAGAGGCACTGATGCCTGGAACTGG

AGTTACAGATGGTTGCAGGCTGCCCTGTGAGTGCTGGGAACTAAACTCGG

GTCCTCTACATGAGCAAGTGTTCTTAACCATTGAGCCATCTCTCCAGCCT

ATAAAATTCTTTTTTAAAAATAAAGTCTGCAACAGAAAATGAATATTTTC

TAGAGCTGAAGCATTCAATGAGTGGATAAAGAATCCATTTGATGAGCTAT

CTACCTTTCACAAGCTCTTAACCCCTACAGACTCAGGACTTAGTGGCTGG

AAGATGAATGTAAAACAGGTAGCTCTCTCCATAATATCTGGTCTGTTTGT

GCCAGGTGTGCAGAACTGTGCAACAGGTCACCATACAAACCGGCGTGGGC

CTTTCCTGACACTCACACAGCTCTCGGGACAGTGCCCGTGGGGACCTCTT

ATTGACCTTATAAGCACCTGACTGTGCAGTGTAGCAGGGAGTTAAGGTGC

TTCTGTTTTCTTCCTCCAGACCGTTCCTAAGCCCATTGCCCTGGAGCCCT

GCTTTGGTAACAAAGCCGCAGTCCTCTCTGTATTCGTGAGGCTCCCTCGA

GGACTGGGAGGAATCCCTCCTCCTGGTCAGTCAGGTGAGTAGACAGGAGA

CAATGACAGATATTGGTCTGTGAAGGACTGAGTCTTAGACACTTCTTCTG

GTATAGAACCTGGGTCTGGGCACAGTGCTTAGTGGTACAGAGCTTTGGTG

GAACAATTCTATAGTCCCCAAACTGTGTTCTGAGCACTGACATTCCTGTC

CTGGGGTGGAAGTTCAGGACCTTCCTCACGGTGCACAGCGTCCTCAGACA

TTCATGCTCTGGTCCCCTTGACTCTATTGATCCCTGCTTTCTTTTTTTTT

FIG.3D(69)

TTAACCCCTTGTTCTTATCTCAAATTTAGGCTTTTTCTTCCTTGATACAA

GCTCCTATTCATCTCCATGCCTCTGGCTTCCAGCCATGTCCTCAAAGCTT

GTGTTGCCAAGTACAGAGTTCTAGTCATGCTCCACATCTTCTTAAGGTCT

TGCTATGCAGCCTTAGCTGGACGAGTGCTCGTTATAGGCCAGGCAGTGGT

GGTACACGCCTTATGTCCTAGCACTGAGGAGGCAGAGGCAGGCAGATCTC

TGAGTTCAAGACCACCCTGGTCTACAGAGTAAATTCCAGGACAACCAGAG

CTACATAGGGAAACCCTGTCTCAAAAAAATAAAAACAACAACAGGAACAA

CCCCAAAAACTCATTATATTGCCCAGGCTGGCTTCAAACTCATAGTTATC

CTCCTACTTCAGCCTCCAAAGTGCTGGGATTATGGGTGTGACCCTTCATG

CCCAGATTGTCTTAAATATGAGGCATGAAGAAGTATTATGAAAACATAAA

GGATATTTTGAAAATTATAATTCTACTGGGTTAATGCAGATCCATTTTCA

TTTCATTGAAATAATGATACAGCCTTTGGAGGTTAGGGGAGCCTCTCCTG

TTTTCAAACTGACTTTGAACTTCTGATCATCCCGCCACCACCGCCACCTC

CTCCTCCTCCTCCTCCTCCCCAGTGCTGAGATACATCACTACTCCTGGTT

TATGTGGCACAGAGGCTCAAACCCAGGGCCTCATGCATGCTAGGCAGACA

CTCTACCAGCCAACCTACCCACAGCTCCTAGATGTGCACCGTATTACAAA

CATTTATTCTTCAGCATGTTTTTTTTTTTTTTTCCTAAAAATCATCTCTA

CAGGAAACAAGTACCAGTGGTGTTTTAGGGCAGGAATAGGAAGAAAATAT

TTTTACTATATACTCTTTTTTTTTAATCATTTTTTAGATTTTATTTATTT

TAAAATTTATTTACTATTATTAATAAGTACACTGTAGCTGTCTTCAGACA

ACCCAGCAGAGGGCATCAGATCTCATTACGGATGGTTGTGAGCCACCACG

FIG.3D(70)

TAGTTGCTGGGATTTGAACTCAGGACCTTTGGAAGAGCAGTCAGTGCTCT

TAACTGGTGAGCCATCTCTCCAGCCCCTACTATATACTCTTTTAAATGAC

TTATTTGCTTTTATTTTTATGTGCATTGGTAATCTGCCTGCATGTATGTC

TCTGAGAGAGGATCAGATTCCTTGGAATTTGAGTTACCTTGTGGGTGCTG

GGAATTGAACCCAGGTCCTCTGGAAGAACAGCCAGTGCTCATAACTGCTG

AGCCGTCTCTGCAGCCCCTACTATATACTTTTTTTATAGTTTTGAATTTT

TTTTTCTTTTTGGGTATTGCTAAGGATCAAATATAGATCTACTATTTATT

TTTTATAACATCCATTAGTATTTTTATAACTTACTACATAGTTTGCCAAT

TCTTTTATACATGTCCATCAAACATGTAAGTCATAATTTATATAAACCTT

GTGTTAAAGCTGGAGGCACAGAAGGAAGATTGCTACAGAGTGAAGTCTAG

ACTAGCCAGGGCTATATAGTGGGACCCTGTTGCAAAGAAAAAGTTCTCTC

TTTAAACACAAAGGCAGTATGAAAAGACATACCTTGATTCTGAAGCTGTG

CATAGGAATGCCTCACACAGTGTTCTGCTCAGGACTATACTCAGATGCAG

TGGTCTGAGGGACTTGGTGGTGTCTCAGCCAAAATAACCTGGAGTTTAGT

AGGAAAGTCTCCTTTATCCGTGTCCAGTCCTGAAGGGAAGCCTTATTTAT

GTATGATGAGTCAGGACCCATTGTCTTCATCTTACTTGGCATCCCCCCAG

CACTGAGTCTCTGAGTTAGCCTTACTTGGACAGAGTGACTCTCTGGGCAC

TCTGGACAGCATCTCCTGCTTCAAAAGGGCAAGATCTTTAGAAGACACAG

AGATGGAGCAGGTCTTACATGGAGATATAGCAGCTTTTCCTTCCTGACCC

TTGACCCAATGCTTCTTTGGAAATCCTCATGAAACCCTGCTCCTTTCTGG

AGACCCACCCCACAGCAGGGTTATCCATGCCAAGCTTCCTGTACTTTCTC

FIG.3D(71)

TTTTTGAGGAAGCACATACACACAAAGTTTTAGTAGCTCGCACATCTCAC

TGTGAAGTAGTGATACTTTCATTGCTATCTTCTGGAAACAGGCAGGAGTA

GGCACACGCTCAGAGCATAGCTGCACTCTCATTCACTTGCCACCCTGAGG

CAGAGCACACGACTTTGTGATCTGCTATGGAGGAGAGAGAAATGAGTAGT

TAGGTGTGTATAAATAAGCTAACACCATCACCCCTTTATCTTTCACTAGG

GAAATGTAAAAAGAAATCTGAAATTATTTTGTAAAAAAGTAAGCTGCTTC

ATGACACATGTCCCCTCTTGTGGGTTCTTCCAAGGTCTCGCTGTGGCCAG

TGCCCTGGTGGACATTTCTCAGCAGATGCCAATAGTGTACAAGGAGAAGT

CAGGAGCTGTAAGAAACCGGAAGCAGCAGCCGCCTGCACAGCCTGGAACC

TGCATTTGATACTGGGGCAGGAATTCGCCCTCACAGAGGGCGTGTGGTCC

ACGAAGCTGTCTACAGGGGAGGCTGCAGGCAGGAAGCAGGCGTGGGGCAG

AAGACTGGGGACCCTTGAAGCGTCCAACTCATGTGCATGATCATGCAAGC

TGTTTTCATGGCTCACCCCTCTGTGTCCAGCATCTAACCTTTTACTTCTG

TGTAGGAAATAATTTAATTACAAGTCCAGGAATGGTCTGCTCTACTCATG

GGTGGAGGAGACCAGTGCCGACCCCGTGAGAGCTGAAGGTGATGCTGAGG

TCCCTTGTGGAAGCCTCTCTTGGGAATCTCAACTGCAGAGGAGCTGCCCT

CTGTCAGCAGCTCTCCAGCATGGTCCTCTGACACTCCTCAGATGAACTGT

TCTCATCGGAAGCTTGCTGTCTTTTTACAAGATGAGCTTTTACTCTCTTC

CAGGAAGTAGCTTTTTTTCTAGCTGAGAATTAATAATGGTCTTTCTCTTT

GGAAGTCATATCAAAGTATAATTGATGGGGGCCTTGTTTTGTTTTGTTTT

GGTTTTTGGAGACAGGGTCTCACTGTGTAGTCCTAGCTGGCCTGGAACTC

FIG.3D(72)

ACTATGTAGATCAGGCTGGACTGAACTCACAAAGATCCACCTGCCTCTGC

CTCACAAATGCTGGGATAAAAAGCATGAACCACCAGGCCCAGCAAAGAGG

GCTATTCTAAATGTCAAGGTCAATGGAGTTAGAATATATATAAAAAAATG

CAATTGATAATTCTCTATAGAAACTTGATTAATTTTAATCCATTCTTTCC

TTCTCTTTCTCTCACTCTGTCTTACACACATGCACACATACACACACACT

AAGTGCCTAGACTTTGAATAGATCTAGCAATTGGACATTAGTAAGCCTAA

GTTTTTACATGATTGCATTCCTACATTCTTGTAAACTTTAAGTAACTACC

ATTGCAGTTTGTTCTTTTTTTAAAGTCTAATTTGCAGCCAAGAACGAGTA

ATTCTCACCCCAAGCAACATCTAATAGGGACTGAGTGACCCCAGCCCAGC

CTAGTGTCACTTTAGGCCTGACGTTTGAGCAACCCTCGGCTCTTGCCAAG

GCACCACAGAATGCACTTGCTCATGCCCTGTGCCTCTTGAGCAGAAAAGA

GCACTGACAACTGGGACACCTGGCTCTGTCTTCCTACAGCTGCTCGCACT

GACCTGTGGGAACCTGTGGGTCATCCCCAGGCTGAATGGAGTACACACTA

GAAGAGGGATGATGCCTAGCATTGGGGCAGCATCTGCTCAGCACATGGAA

AGGGACCTGGTTCCATCTCCCCTGGGCAGGAGTTGGTCCAGCCTCCTCCC

AGACCCAGCTGGTGGCTGTGAGGAGGTGGGGAATGCTAATGAGAATGAAA

AGCACATGGGTTGATGGGAAGGGACAAGATTACCACGTTAGGAGGGTGAG

CAGCCCTCTGCTATGTGCCCAGGACCCTGCCTGGACATTGCATTTCCCCA

TTTATGGTGCTCCGTATTCTGGCATTATGCAGCAGCCTCACACACCTGTC

CTCTCCTTCTTCATGTCCTACAGTTCTGCTATCACCTGACTAGAATAGCC

CTCTAGGCAACAGTGCTCAAATGTATGAGTTTGGAGAAGTTAACAATCAG

FIG.3D(73)

AAGAACAAAAACTGTAGTGTTTCACCTTTAAATGCAGTGTTGAAGAGGGA

GCCTTTCTCTAAGCCCTGCACTAACCCACTCCTCCCAAGACTCTTGTGGA

GTGACAGTTCCAAGCTGAACCATAAATCACTGATGCACAAAACACTGCTA

GAAGGCTCACCTCTCAAAACACGACTCTTTGCATCACTATTAAAGAGCAG

AAAGTTCTAGAAATGATCCCAGCCTCATCCCCTATACAGTTAGGAGCTCC

CCACATCTCTACCAAAACCCAGCACATAAGTATCTGCGTGGTCTAGCCTT

TCATCTCCGTAACAAGCCAGGGGACTCTTGGCCAAAAGAAAGAAAGGGAA

GTTGCACTAGGGCTTGTCCGTCCATAAGGAATTCCCCTCTGCTTTGCTCA

AAGGACCAAATTTCTTTGGCCAAAGAAGTTGCTTCTATGTTAGTCCCATA

CCCTGAAGTAATATGTACCATGGCTCCCACCTACCTGTTTATGCTCTCCC

TGCCCCCAGGGAAACTGTTTATTCTTTCAAAAGAAGCAAACAGCGTTCAT

TTCTGCTCCTGTAATGGAGAAACAGCCAGCTCCCCTGCATCCCTTACAGC

CAACAGCTCCCTTCAGGCTTAGAGCAGGGGGAATGGCAGGGATTAAGAGC

TCAGCTCAGAGCCAGTTACCAAGATGGAATGGAGTTGTGACCCAGTAACT

GTGTCACGAGAGACCATGTATATAAAATAGTCATGACGACACTGACCTCT

TGCACTTGTACATAACTATACTGTAGTGTCCAGAATGTTCAGACATTCAG

GGTGTACATAAACAGAAGAGTATCATAATGTATTTTTATTAAACACTAAC

ATCTGAGTTTCACCTAATCTGTTTCTGTGCCATATACTGGGTATCCAAGC

TCTGGGAAGTTATCCTACCAGGCCCTGATCTGTTGATAAGGCACTATACA

CCATGCTGGTGTGTTCTGTAGCCTTGTGCCCATTAGGTAACTGAACAATG

ATTCAGCTCTTAGAATACCTAGGAAGACAGCAAGCAGGGTGACACACGGC

FIG.3D(74)

TGTGATCTAAGCATTCAGAAGACAGAGGCAGGAAGAAAATTCAAAAATGG

GGCTGGAGAGATGGCTCAGTGGTTAAAAGCACTGGCTGCTCTTGGTCAGG

ACACTAGTTCAGTTCCCAGTACCCACATGGTGGCTCACAACCTTCTGTGA

CTACAGTTCCAGATAACCTGACACCCTCCTCTGGCCTCCTCGGGTGCCTG

TGGTGGTCCACCTGGTGCACAGACAAACACCCAATACACACAAAACAAAA

GTAACTCAAGAATAGCCTGGGCTACATAGCAAGAGCCTGTCTCAAAACAA

ACGAACCTATGAAGAGCCAGGCAGTCTATCTATTTACATGGCAGTATACT

AGAGAAACTCAGGAAGCAAGAGTGTTCATCACTGTTGTAATTTCAAATGC

TCCTTGTGATTTCTGGCATCTCTGTGGGGTGAGGTGTTCTGTTACTCTTC

ACATTCAAAGACTGTCACCCATGAACGTCAGACTTTGCAAAGGGGCTCTC

TAAGCTGCACTGTTGTGGCTTTGTCTAAAATTTTAATGACGTTTCTGAGA

ACCATGTTCTTTTTATACTAAAATCTGGGGATGGGAGGGCTCATTTGTTG

ATAAATAGCACTATTTTCCCACACCTCAGCCTCCTGTCCCCGTCCTGGTC

TTCCCTACACAGTCTGGAGAGGGCTCTGAAAGGTCCACAGAGTTTGACAG

ACACGAAAGCAACCCATTGCCCCGTTGACCTGACCTGGAAGAAGACTGTC

AGCAAAAGGAAAATACCAGAATATCTGGAAAGCTTGAAGTGTAAGATGGG

ATCTCGTTGGGGAATTGGATGAAGAAAAGCAGAGCGCCTCTGGTAGGTGA

CTCTGCAGCCTGCCAGCGCCCGCCCTCTTTCTACACAGCAGAGTGTGCAT

GGCAAGGAAATGAGTCACCTCCTTGGGGGATGGTGCTGTTTTTATGAAAA

CCTCTGATCCTTGGTGTCCTTTAATTGATCTGTTCAACAAATATTTACTA

AACACTTCTAAGCTAACATTAGGGCAGTGACTGAGGTGGAAACCCAGCTC

FIG.3D(75)

TTTAGACAGCTGTCATCCTAGGATAGCTTCCTGGAAGCAGAACCAAGAAG

CCAGAAGGTTCTTCCTAGGGTGGCCTTGGCTCCCTGAAGGAATCTGAAAT

GCTGACCCTGTCACAACCTCCCAGCACAGCTTTGGAATGAGACATCAGCC

TGGCCTCCAGCAGAGCAGAGGCTCTGGAGCTCCACATCCTGCCTGCAGGG

AGCCCTCAGGGTGCCCTCCAGAGTACAGGGAGAAACTAAAGGCAATAACA

GAAGCTGCTCTCAGAGCCTGACTGTGCACAAAACACTAGTGAAGCCTGCT

GAACTAATTCTGCCTCTGGAAATCTTTTCTGGTTCTTTACAGTTTGTTGT

TTTGTTTTGATCCAAGCTTAGTTTGTTACTATGTGTGATTTAGCATCTGT

CGCACTTGTGTAAATATGGAGTAAGTATTGTAAACTATTTAATTGCTGCG

ATTGTTGGGTTATACATACATTTAGGACTGCAATTTTTTGGTATTTTTTG

TATTGTAAAATAACAGCTAATTTCATCAGGAACAAGAGAATTAAGGGGGT

CTGCATTTTAAATGCAGATGTGAAGCACTTGTATATAAATAAAAGTAAAT

ACTATAATACAAAGTTCCTTCTGAAATAAAAGTAGATCTGGTAAAAATGT

GCGTGCGTTTCGTTCTGAATGTTCAATGCTAATTTTGTTTTATTTTATAT

TTACATTTTAGTCCTTATTTTAGCAGTGAGGAGACAGGCACAGCAGTGCA

TTCTCACCTTGGCAGCTGAGGAATCCCCTAGAGTAGACTGCAACTCAAGA

CTCTTGGCTTCCACACTGAAAAGAGTTTCAGTTTATGAAGCAGAGTTTAG

GAAGTTTAGTGAGGAATTTAAGGACTTCTTTTAATGTTTGTGTCTACATA

TGTGGGTACATATATGACACAGCATGCATGTGGAAGGCAAACAACACCTT

AATGGAAGTGGCCTGAAGAACAAACTCAGGACTTCAATCTTGGCAGCATA

AACCTTTACCTAATGAGTCATCTCCAGTCTATACGGGGTGTGTGTGTGAA

FIG.3D(76)

CACATGTGCAACAGCACACAGTGGAGGTCAGCACAACTCTTGCGAGTCAA

TTCTCCCTTACCTTGTAAGACCTAGAATTCCACATTGCCCAGGCTCTGAA

AGTTAGGTTGGGTCCACACTGGGCCATGGCTGATGAAATGTTGGAAAAGT

GATAACACCAAACTTTTGCACAGAAAATATTTTCATCTGGGGCCTTCCCT

GGAGTTCACAGGCTAAAGTGTTGGAAGGAACATGGGTCCCTGAGCCACCA

CTTTCACAAAAACTACCTGATCAAGAAGAACTATTCTGGGTTTCTGTTGC

TAAAATTCCTTCCCAGAGAGAAATGTAAGCAATGTCTGCCCCTTCAAGGG

TCCCAGCAAGAAACCAAGGCACAATTCCACCAAAGTTCACTAGAAAACCA

GTGAGTTTATTGGGCTTCCGTGCAGAACATACATGAGGGGTTACTTAGAG

AAGTGTGGATACTCCTCCCCCTAACAATCCACACCCTGAAAAAGCCTTAC

CCAGCAGGGATGAGGGCTTCCCCAGACCCACATTGATGGTGCTCCCATTC

CATTTTTCCCTGGCATGCAAAGAGATAGACAGAAAAATAGATTATATATA

ATATACACATAAATTAGAAAAATAGATTATATAATATACACATAAATTAT

ATATTATATATATAATATATAATACACAGATAGATTATATATGATATATA

AAACACACAGAAATAGGGTATATATAATATATAATACACAAACTACTCAG

CTATTAAAAACAGTGGATTCATGAAATTCTTAGGCAAATGGATGGAACTA

GAAAATATTCTGAGTGAGGTAACCCAATCACAAAAGAACACACATGGTAT

GCACTCACTGATAAGTGGATATTAGCCCAGAAGCTTGGAATACCCAAGAT

ACCATTCACAGACCACATGAAGCTCAAGAAAGGAAGATCAACGTGTGGGT

GCTTCTGTTCTTCTTAGAGGAACACCCTCATAAAGTAGTGGTGGGGGGTG

GGGGGAGACAGAATAGGTGGTTTCCAGGAGAGGAGGAAAACAGGAAAGGG

FIG.3D(77)

AATAAATAACATTTGAAATGTAAATAAAGAAAATACCCAATAATAAAAGA

AAAAGAATTTTGAAACAGAGGGTAAAAAATAATACACAAACCAGGTAGAT

AGATTATATATAATATATATAACACAGAGATAGATAGATAGATAGATAGA

TAGATAGATAGATAGATAGATAGATAGATAGATAGATAGGTCAACTGCTC

GCCCCTCCACTAGGTAACATGCAGTTAAGGCAGAGCTGCATACAACAGAT

GTTAGGGATACTCAGGTGAGAATCTCAGGCTTTGCTCCATCCATCTATGC

TGGGGTGTAAGCTGTCAACAAGTTTAGCTGGGATGATGCTTTGCAAGAGG

GCACAGCTGAATGCCCTAAGATGGTAGATGCTTGGCTCAAAGGAGACACT

ACAGCTCTGCATCAAGGCAAACTAACTGAGATGAGGGCCTTTATTTTCCA

GATCTGTATCCTGGAGCATCATTCACCTGTTACTACACTGAAAACATTTG

GTGTTGGTTTCATGGCAGATGACAGGCAGTGAGAGAAGTACAGCAGCGGA

CTGCTAGAGGTGGGGGTTCTGTCAGGACGTGGGAGGCTGTTTGGTTAGTA

ACTTGGAAAGCAACAAGTTTTTAGCTAGAGGGAGAAAAGCTGGAGATAAC

TGTACTTGCTTGATTTCTTAAATATCAAATTTTATTTTATGCATATGGGT

ATTTTGCTTGCATGTATGGCTATACACTACATGCTTGTGGTGCCCACAGA

GACCAGAGGAAGTAGTGTGAGCCTCTGAAACTGAAGTTACAGACATTACG

ACTTGAGTGCCTGAAACTGAACCTTGGTCCTCTGGAAGAACAGCCAGGGC

TCCTAACCACTGAGCTATCTCTCCAGCCCTGACAGAACATCATGTACTCC

AGGCTGGTCTCAAATTTGCTTTATAGCCAAGAACGGTCTTAAATTCTGAT

CCTCCTGTTCTCTCAAGTAGTGGGGTTACAGGTCTACACTGCCGTTTTCT

TGAGCAAATCATTACAAATTGAGTTCTAAGCCAGGTGTAATAGTTCATGT

FIG.3D(78)

AGTAACAATCTGGAATTTTGGTCTCTTAAAAAAACAAATATTATAAGAAT

GTATTTTCATTTTAATCCCAGGTGTATGGCATATATCGAACTGCTTTGGA

CTGACTACAGCAGCTATGATTTTTTCTTGTTCTAGCAGAGGTATGGTTTT

GCCAGCTACAGATAGTTTCTGTGATTGTGTGACATTTGGAATTCTGGAAA

CTTTTCAGATGGTATATAAATATTAGAGCCCCAATAGGCAGAGTTGATGA

TTGTTGGTCATTCAGGGGTATTGGTTGTGGTTAGTAGTCTTGCTTGAAGA

AGAAACAAGAACAAATTAGATTCAGAGATCTCTATATCTCTCTCTATCTT

CCTTTCTGTCCTATCTAGTAATAGGGGGTAAAACCAGGATGATAAAGGGT

TGGGGGAACCCACAAAGTAACAAAGACTGGCTACAAGTGGCACCCAACTT

GGAACTCAAAATTGCCATAGAGGAAGCAGCAGGGGATGAAGGAATGGATT

GTGGCTGTTGTTGCTGGGATATTCCTCACTTTGCTCCCAGAGGGGATTTT

TCTGAGGTTTTGTTGTTTTGCTTTGCTTTGCTTTGGTTTTCTTCTACATA

TTCTGTTTTTTAAGTAAGTTGAAATAATAGCCGAGAAGCTGGAAAAGTTT

GGTGTGGAAATGGAGCAGCCTGAGAAACAAACAATGTATGAAATGGGAAA

ACTAAAGGGGCCACTCTTCTCTCTTTTCTGAAAGGCTTGCAGACTTGGTG

GTGCACCTGGAGAGTTTATGGATGGAGATGGAAGCTCTTAGGAGACAAGA

AGCATGGAAAAAGAGAACAAAGGCTCAGTCCCAGTGACTGAAGAGAGCAG

GAGTTTTCCAAAGAAGGTGCATGGGAGGGCCACTGGTCAGAAAAAAAAGG

CTGAAAAATACCAAAGGACAATGTGCTGAAATAGCCCATTTCAAGAGAAA

GGGTTCATCTCAAACCAGCATTCTGACAGAGTGGAAGGAGGGGTGGCTCA

GGGTTATGAGATCACCATCAGCTTTTCCAGTTTTCCCATATAGCATATGC

FIG.3D(79)

CTGCTAATGGTATGGAACAAGAGTAAGGCAAAATAGGATGGTGTCCTATA

GAAATGATAGCTCTAAGGTGTTTTTAAAAGGCCTTGATTTCATATGGAAT

GCACTCTCCTTATGTGGAACGGATATTAAATAACCGGGGTACACAAACTA

GAATCCCTTCCCAAGATTGGAAGGGATTGGTAACAGCTGTACTAGAGACT

GTCAGCCGTTGCAATGGTTAACATGCTGGAGGAAAGAAGCTGTGAACATT

GAACAGTAAAACAGAGCAAGGGGTATTAATATAGTGAACGAACAGCTGCT

AGGTGAAGGGCGGTACTCTAGTGTACAAGCACAGACTCGGTGTCATGAAA

CTACTATAGAACAAGGTTGCCTCAGTGGCTATAACACCTTGGGACAAAGG

AGGAGCCAGGAAAAAGTCCAGTTCATTTACAAAGATTATATAAGGCTCTG

GAGAAGCCTTCACTGATTTTTTTTTTTACAAAGATTAGTCTCAGCTATGA

ACAAAGCCATATCAGACCCTGACACAAGGCAGGTGTTGATAGAGACCTTG

GTGTATGACAATGCAAATACCAAATATAAAAATGTCATTAGACTTTTAAA

GGCACAAGTAATGCCTATGGATGAGTGGATAAGGGATAAGACCAATATTA

GTTCTAATGTGTACTGTGCTAATATCATTGATCAAGCTATAGCTAGAGAT

CTCTGATGTCAAAATGCCTTGTGCTTCAGTTGCAGCAAATACAGTAATTT

GCAAGGAGTCATTGTGGCCAAAACTAAAGGTCTCAGATCTCAAAATGCCT

GATGCTTTGTGGGAAATAGGGTCATTTGCAACAAAAATGTGAACAAGACA

TCTTTAAGGGCAATGGTTTTTCTAAATATAAACCAGAAAGACGGCCTAGG

CTTCCAAGGTTGTGCTGGCGATGTGGCCAGGGTTGCCACTGGACCAATGA

GTGTAGGTCCAAAAGAGATATTCAAGGTAACGTATTACCATCATGAAATG

GTCTTGGGGGCCTATCTTGAGGCCCTGCAGCAAAGAGTATGAGCCATTCC

FIG.3D(80)

AACCAGAGAGTGGCATGGAGACTCAAAACCTTCACTGGGCACTGGAGATT

TAATGCACACTAGCTATTGCAGGCAGCATGGCTCTAGACTTGGCCACAGA

TAAACATCTTGCTCTATCCCCCAAAATTCAAAGTTATAACATAGCTACTG

GAGTGTATGGTCTTTTTCCCTCAGGGACAGTAAGGATAATCTTGGGAAGG

AGTGGATTGACTTCCTAAGAATTCACTGTGCATCAGGAAGTATAGATGAA

TATTTCAAAGGAGAAATTAAAATTGTGGCATATGTAAAGGTAGAGCTGCA

ACTTAACACAGGCGATAGGGTTGCTCAGCTGCTGCTGTTTCCCTATATCA

AAGGCAAAGCAACTGCAGCAGAAAGAGGAGAGGCCTGAAAACCTTGGGCA

CTGACACAAAAATTGCTTATTTCATTGAAAATGTCTGTTTATAACTTCCC

ACTATACAGCACAACAGGAGGGGGCTTAAAACATAATGGGGAAAATGTCA

CAATTCTGCAATTTTTTGTTTCCTTAAAAAAAACACACACACAGAATTTTA

ATAATGTGTTCTCATCTTAATCCCGGGTGTGGGAATTAGGGCTGCTTTGG

ACCATTCCCAGCAGCTGACTATGATTTGCCTCATGCTCTAGCAGAAGTAT

GATTTTTGCCACCTGCAGATAGTTTCTGGGATTGTGTGACATTTGGAATT

TTGGGAACTTTTCTGAAGGTATATAAATGCTAAGGCCCTGGTGGGGAGGG

TTGGTGGTTGGTGGTCATTCAGGGGGGTGGTTGTGGTTAGTGGTCTTGCT

CAAAGAACAAACAAGAAAGTCATTTGATTCAGATGTATCTTTCTTCCTTC

CCCCACTCTTTCTCTCCTCCCCCCGGCACCCTGCCCCCTGCCCCGACCTC

TACCCTTCTTTTTCTATCTAGTGACAAGGATGAAACCAGGGGGATAAAGG

GTGGGAAAAAGAAGAGCCCACAAAGTAACTCAGGTTGGCTACAAGTTCAT

GCCAAGAATCCTAGGACCTTGTTGTTTAAAGGCTTGTTTTATTTTGTGAA

FIG.3D(81)

CATGAATGTTAAATGTACATACATGTTAAGTGTATGTATGTACACCATAT

GCATGCATACAGAATCCAGAAGAAAGTACATTATACCCTGGAATGGAACT

TAGAGTTGTGAGACAGCATGAGGATGCTGGGAACTGAACCCAGTTTCTCC

ACAAGAGGAGTAGTTGCTCTTCACTGCTTAACCTTTCCTCCAGCCCCAAT

CCTAGCATTTTGGAGGCTGATGTAGGAAGATTATCCCAAGTGTGAGGTCA

TCTTGGGCTCCATAATAAGTTTAAGACCAATCTCAGCTCCAGAGTAGGAC

CCTGCCTCAAAAACACACAGGTGGAAAGATGGGTCGGCAATGAAGAGCAC

ACACTGTGCCTCCAGGGGACCCAAGCTTGGGTCCAAGCACCCTTGTTGGG

CAGCTCACAACTGCCTGTAACTCCACCTCCAGAGGATCCTAAGCCACCTT

CTGGCTTGGCTTCATGGAGGGAACAGGTATGTGGGTATCTGAGTGTGACG

AATGAGCAGCAAGTGAGTCTCGCTGTGGCTAGCACAAAGTATGGGCTGAA

GAGCAGGAGGACAGCTGAAAAGTGGCCTTTCCTGGTGACTAAGTTGGTCT

GAGCAGCTGAGTCAGTTTCTTCCTGGCTGCTTGGCTGGTCTCAGTGCTTA

TAAGCTGCTCACTTGTAAGTCTTTTCCTAGGAGCCCAGCTTGTCTAGGGG

TTGTCTTTGCAACTGGCCTTGTCTGACAGTGACTTTCAGCAGTCTTAGCT

GCTTATATACACAGTCTTAGGAAAGAAGGCTGGTGAATCTGATCCATTTC

AGGAACTTTCTGAAGCTATTCTGAATTTACTTTACAAGCTTACCTGCAGG

ATAGAGGATCTCAGCTCTTTATAAACATCCTGTCCTAAAACACCCTGTTG

TTCCTCTTCTCTTTTACATCCTGTGTCTTGAGAAGTTTGCCTCCAGGATG

GAAGTTGTTCAATTCAGAGGACACTGTTGCACAAGCTCCCAGCACCCACA

TGTGAGCTCAGTGCTCTCCTTGGCTCTAGCTCTGCCCTATGAGGTTTTTT

FIG.3D(82)

ATTTTGTCATCATAATCTTTTCCTATATCCTTCCTTGTTCTGGGAACTCA

TCTGGTTCATTTTTTTGGCATTTTGAGAAAAGCTCTCACTATACAAATCA

GGCTGCCTCCAAATCATCTTTTTGCCTTAACCTCCTCAGTACCAAGATCA

CGAGTGGATCTTAACACTTGACTGACTCGTTTAAGTGTGAGGAAATGTGG

ACCAATAAGAGAGCCCAGGAAAGCCCAGGAGAATCTGTAGCCCCATGGCT

GTTGTGTCAGAACCCAGAGTTTTGTCAACAGAATTTGGTTCCTAATTTCT

CCACTTTATAAAAACGAGTGAGAGAAACAGGAACCTATTCAGATCTGGCG

TCTGAGCAATCAGTGGGTGAACATCTAGAGATCTGTTCTGCATCTCCTCG

CCAGCTGGCAGAGCATGCGTAAGGCGGGAGGGAACAAGGGCAATCACTCA

CTCTGGGGCTCAGGCTTGCCCCTTGGGTCAGGTGTTTCTGAGAGACGTGA

TGTCTGCTTCTCTTGTTACCATCCCTCATCCTCTCCCCTCCTTCTGTCCC

CTACTTACCAATTTCACTGGCCAGTGTCCATATTTCCTGCAAAAGCGATT

TGGTTTAATGAGCTTGACTATGCCCGACTCCTTTAGGGAGGGTGGGGAAA

GGGCAACGAGGGCAGTAAGTGGTTTCCACAACCACTTTGCACCCGGCTGC

TGGGCCCCAAGCCAGAGGAACGTGCATGAGCCATGAAGTTTCCACTGATA

AATCCACAGATGCTTCTAGCACCTGCCTTTCTGACTCAGCCTCACCGTGC

CGCCTGCCAGCTGTGAAATCAGTGCCAACAACAGGTAACCGAGACCCAGG

CGCAGGGCCAGGACAGCTGTCTGACACTTCCAGACAGGATGTGGAGGCTG

ACAGTTGTGATGGAGAGGAGATGGGGAGGACAGAGACGGGCTCAGCTTTA

AGACACCGAGCCACAGAGCACCAAACAAAAGCCAGGGCCTTCTGAGGTAG

AAGTAACAGAAACCAAACAGGCAATTCTACTAGTTTCCTGGGACTGTTTG

FIG.3D(83)

CTGCATTTGCCAATCTTGGTAGTTTTAAAAAACAAAAACAGTTTGTTCTC

AGCACTGGCAGAGCTTTCCTCCTCTGGAGGCTCCAGGGGTCCAGACTCTC

CTCTGTGGTACACTGGCTTCAGACATATCTCTTGCCTATGGCTGCCTCAC

TCTAAACTCTGCCTGTCCTTGAATTACCTCTCTCTGCACTGGCTTTATAA

AGGAAACATGAGATTGTGTTTAGGGCCTGTTTGGGTGACCTCCTCAGGAT

CTATAACATAATCACATCTCTACCGTATGAAGTGACGCTTCCGTCCCAGT

GTGTAATACATTTGCCGGCGCCTGTCCTTAGGACAGTGACCACCACCAAC

TGTGGAACTTGACTATGTCCACGTCATCTTCCTACTAGCTTTAGAAGGCT

TATACCCACACTTTCTATCCAGAATTGTATTTTTATTTAGAATCATTCCT

ACTTTTAAAAAAGTCTCTGTGGTTAAAAGCATTGCAGAGGGCTTGGGTTT

TGGTCCCCAGGACCCACATCAAGTGGCTCACAGTGTCCTGGAACTCTTGT

TCCAATACCCTCTTCTGGTCTCCATAGGCACTACATACATATGGCACATA

TATGTATACTCAGGCACACGTGTAAATTTTAATGTCTACTTTTTATGCTA

AATATCAAAGTCACTCGAGCAGTGGAGTTGAGCACACTCACATAAGGAAA

TCATCAGACAGACACTTCATCCTGTGTTGGAGCCACTTTGTGGCTGGAGT

AAGCAGGGCAGAGTGATGTTTTCATTACTCTCTGGCCCCAGCACCCCCTG

CCTCTCCCCACCCATTCGTCCATGCAGGTGGGGAAGAGAATTCTCTTTGT

GAAATTGGAAGTTTGGACCCAGCTTCACTCTTACTCTGCCCAGTACCTCC

TGTGAGAAACCCTCCTATCCCAGGTGACCTGCTGGCTGTGACTCTCCTCA

GCAAAAGGCCCGTGACCCACACTGCGCCACTAATGTATCATCCCCAAATG

CTGAAAAGGAAGCGTGTCTTCCTCTCTCTCTCTTTTTCTTTTGGTCTTTT

FIG.3D(84)

TGAGACAGAGTTTCTCTGTATAGCCCTGGCTGTCCTGGAACTCACTTTGT

AGACCAGGCTGGCCTCGAACTCAGAACTCCGCCTGCCTCTGCCTCCCGAG

TGCTGGGATTAAAGGCGTGCATCACCACTGCCCGGCTGCGTGTCTTTCTC

TTAGCGGTCTCTGTGGAGATGCTGAGTATGAAGCTCATCCTACCCACCCT

TCAGTGGGGCCTTTTCTAGCTACTGAGCAGCTGTGTGAGGACTCGTGATC

ACAAGGTCCTTTGAACCCTTGAGACAGATGTGCCTGAGCCCAGTTTGACC

TGACAAAAGCCTAGAGCTCACTGATAATGCCAGCAAACACCATCTTTGAG

TTTGCAAAGGAATCGCAACACATGCATTCAGTTTCCGTTGCTGGCTGCTG

CTCCAGAGATGGCTATATTCATTCTCAGGTACTCAGACTCAAGAGTAGTT

CTGGCCACACAGGTCTCCACATTTCGAGGTCAAATGACAGAAAACCAGGT

TGGTCTCAGTGCACATGGGTTTATTGAGCCACTGCAGGTGCTGGGGAAAC

CATGGCAGGGAGATCCTGGGAAGCCAGTGGGGTGCTGAGCAGGAGGGACC

TCAGTCTCTCCTTAATGTCTACACACTGTGTCATAGGTGACAAGCCACGT

CAGTGCTGTGACACGGGTAAGCTTAATGGTGAGTAATGGCTAACTGGGAG

GGTATTTAGGCAGCCTTGTCTGTCAGCCTGTTCATATGATCTCCTTAGTG

CCTTGTCATCTTGGAAAAGGACAGTTCCAAATTCTAGGAGCGGGGGCTAG

TCTCTGTCCTGCTCTGTAAGCCCAGGGGACCCAATGAGGCCTCATCTATG

GGTGCTCAGCTCTAGGATGGGGAAGAAAATGGACAAGATGCCTACTGACG

GGAACACAGGCTTTTCAGTCAGACCCTAGCCTCCAGCCCCCAATCCAGAG

GACAGCCACACAGGGGTCCAGGCCTGCAAAGGGCAGCAGACCTGAGGGCA

AGGGAGTTTCAGCTCAGTGAGCAGTCATCGGGAGACATGGCAGTCAGCTG

FIG.3D(85)

TGTCGTCCACGGTTCATGTTCCTAATCAGAGCAGGGCCTGGAGAGCCAGG

GCAGTGAGTGCATACAGCCAGGACACCTTGGGCGTTAGGACAAAACAAGG

ACTGTTTCTGCCTCCAGCTCTTCTCAGGCCACTCGTGCCTTGCCTAGGAA

GGGTAAGAGAGCACAGATGGGAAGGATTCGGAAACTGTCAACTCCCTGTC

CTCTCCCCATACCTACCCGCGGGAAACAGCACCCAGCAGTCTGGTCCTGC

AGAACTGATGGCTGCAAGCTGTCAAAGGCTTGTATGGCACCATCTGCGGA

GTGCAGAGATCCAGAGAAGGCTTGGCCAGGAAACCCTAGAAACTACCCCA

CTCCCTTGGGACAAAAAATAAGACACCCTGGAACCTGCAAGGCATGGCCT

GAGATGGAAGGTCACTGTGCTAAGAATGACCCACAAACTGCTAGTGAGGT

TGACAAGGGCTGCCCCCTCTCCCTTTACAGGTGAACACAATCGGGATTAA

TAAGAGTTTAACTCTCAGCTACTAAGTGGCAGAGACAGGCTTCAAACAGA

CCCCCAGAAATCTGGAACTGAGCCATTCCACCCAGAGGCAAGAACAGCAG

AGGTAAGTTGGGCACACATGGAAGAAAGGGCCACCCCATTAGTGTCAAAA

GGGAGGCCAACTTCAGGCCATTGGACACGTTTTAACGCTGACTTCCACCC

ATGTACCATGGCATGTGCACACTGTCCATCGCCCACACCAAACATGATGC

GACGTAAATAAGACCCACGGGCCAGGCAGCTTGGATTGGGCCACAGACAT

FIG.3D(86)

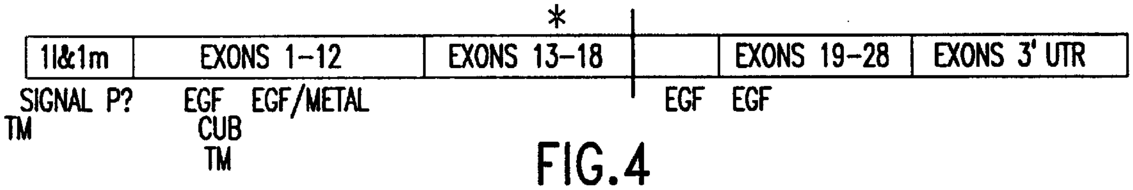

FIG.4

| | | |
|---|---|---|
| Exon 1 | CelegE106 | TCTCCTAGTTGTAGTACATGCTGTTG |
| | CelegE108 | AGGTCCTGTCTCAAGAAATAGCAATAAC |
| Exon2 | CelegE33 | TTTGAAGGCCCCTGAAGTCAGAG |
| | CelegE36 | TTGAGTCCCCATCATAAACATATAAATGG |
| | CelegE37 | TTCTAGGCCAAATAGAATAATGAGACTTC |
| | CelegE40 | AGAACTAATTCCATGAGATGAGTGTG |
| Exon 3 | CelegE41 | TGAAGTTGCTGTAATCTGGTCTGTG |
| | CelegE44 | AAGGAGCCTGACTAGAAGCCTC |
| Exon4 | CelegE69 | TAAACTCCCTACAGTTCACTAACTCAG |
| | CelegE72 | AGCGCTGTTGAGTGTGAATGTTCTG |
| | CelegE73 | AAAGCCACAGTTGTCTGTACAGTGAG |
| | CelegE76 | AGGTCTGCATTAGTTGCAATGTTGC |
| Exon5 | CelegE77 | TATACACCCCCTTATATACACTCAG |
| | CelegE80 | AGAGCCTCTCATAAAGCTGTGGTC |
| | CelegE81 | TTGAACATATATCCGCCAACAACCC |
| | CelegE84 | CTTGGAATACTATAAACTTTCAGGCTGC |
| Exon6 | CelegE101 | TAAAGCAACAGGAAGAGTTGAACTTCTTG |
| | CelegE104 | TGCACCCTGTGTGCACATGG |
| Exon7 | CelegE109 | TTACGGTGTCCTAATAATAAGGGCAG |
| | CelegE111 | AATCATGGGTATTGTTAACTCCGAAAGC |
| | CelegE114 | TGTAACAATGTGTGCCGAGTGTCC |
| | CelegE116 | TCTCTCTCCAGCCCTAGAGTTG |
| Exon8 | CelegE86 | AGAAGAGGAGCCTGCAACATTGAC |
| | CelegE88 | TTTGTTGGCGCTGAAAGCCTTG |
| | CelegE89 | TGGCCACAGTAGTGTTTATGATGAC |
| | CelegE91 | TTAATCAATTGCCTCTGCAGATTCTAG |

FIG.5(1)

| | | |
|---|---|---|
| Exon9 | CelegE93 | TGGCTTACGTATAGGGGGAAATCAAG |
| | CelegE95 | TTGTGTGTGTTCCCTCCAAACACC |
| | CelegE98 | GGACCATTCTTAAGGACAGCCGAT |
| | CelegE100 | ACATAGTGATCTTTCCATCAGCAAAG |
| Exon10 | CelegE117 | TGAATGCACAGAGACCCTCCTG |
| | CelegE120 | CCTCTTACCATTCAGATACTGTTAGG |
| Exon11 | CelegE121 | AGCAACAACTCAAACCAGCCCTAC |
| | CelegE124 | TTCTTCAGTTGCCAACTCCCAGG |
| | CelegE125 | AAGCTGCTTGTGTGGCAGCAG |
| | CelegE128 | AGTAAGGTGAACAGGAAAGTACAGAG |
| Exon12 | CelegE130 | TACATAAGAGAGGCTGCCGCATAG |
| | CelegE132 | CCCTACACTCACACTCATCTAGC |

---

| | | |
|---|---|---|
| Exon13 | CelegE30 | CCCTGTGTTCCAGATCTCCATTG |
| | CelegE32 | TTCCTAGGTCCACCTTGATCTGAG |
| Exon14 | CelegE14 | AGCACCTGAATTCAAATCAGGATGAG |
| | CelegE15 | AAACCAAAGTTCTGAACACATTAACTCAC |
| Exon15 | CelegE17 | CTGGTTGCATTCATAGCTGTGTTTC |
| | CelegE20 | ACAGAAGCCAGCATCACTGGG |
| | CelegE21 | TTACTGGTGCTGGGAGGATATGTC |
| | CelegE24 | ATAAGTACTTCATCACCTCAGCGCTC |
| Exon16 | CelegE1 | TTGATCTTAGCTGACCAGTGTCTC |
| | CelegE4 | TCTGCATGGACTTGAGCAGAAAGTC |
| Exon17 | CelegE6 | CAAATCTTGTGATAGTGAATTACAAGTTGG |
| | CelegE8 | TTTATAGCTGCCCTCAATACATTTTCC |
| | CelegE9 | TGTACCTGCAGCCATTGCTTGG |
| | CelegE12 | GGATCTGGGCTCTAGTTTATGTACG |

FIG.5(2)

| | | |
|---|---|---|
| Exon18 | CelegE25 | TTGAACTATAGGCACAGACAGCTG |
| | CelegE27 | AACTTGACCTGTGTGACTTACGC |
| Exon19 | CelegE193 | TCACAGTCTATGGTAATCTGTCAAGC |
| | CelegE194 | AAGGGCAACAATGCCCTGGCAA |
| Exon20 | CelegE195 | TTCCTGCAAATGGGATAGTCTCTCTG |
| | CelegE196 | ATCCCCCAAGCATTTATCATTCTCAG |
| Exon21 | CelegE197 | TGTGTTTCCAGAAACCTGCTTTAGTTTG |
| | CelegE198 | TAGTACTTTTGTCCAGGATGACCAAG |
| Exon22 | CelegE199 | TGACAAGAAATGTCATGTCTTAACATAAGC |
| | CelegE200 | TTCAGAGCCTCCTTCCCCAACT |
| Exon23 | | |
| Exon24 | CelegE203 | TAGTCTGTAGCTGAGGCCATTTTGC |
| | CelegE204 | AAGCAAGCTGCAGTTAAGGGACTGT |
| Exon25 | CelegE205 | TTGGGACCTTGAGGATTGTTCCC |
| | CelegE206 | CACTCAACAGGTAAAAGTGATCTGCC |
| Exon26 | CelegE207 | TGCATCTGATCAGTTTGAATCAGAGAG |
| | CelegE208 | AAACTGAGGCCTGAGTTCTGAAAAGC |
| Exon27 | CelegE181 | CACCAAAGCTCTGTACCACTAAGC |
| | CelegE182 | TGACTGTGCAGTGATGCAGGG |
| Exon28 | CelegE171 | TTGACCTTGACATTTAGAATAGCCCTC |
| ÕUTR? | CelegE172 | GCTGAGAATTAATAATGGTCTTTCTCTTTG |
| | CelegE173 | TACACAGTGAGACCCTGTCTCC |
| | CelegE174 | TAGCTGAGGTCCCTTGTGGAAG |
| | CelegE175 | AGTGTCAGAGGACCATGCTGG |
| | C.elegE176 | CTTGAAGCGTCCAACTCATGTGC |

FIG.5(3)

| | |
|---|---|
| CelegE161 | AACTCATACATTTGAGCACTGTTGCC |
| CelegE162 | TGAGGAGGTGGGGAATGCTAATG |
| CelegE163 | ACATAGCAGAGGGCTGCTCAC |
| CelegE164 | ACTGACCTGTGGGAACCTGTG |
| CelegE165 | AATGCTAGGCATCATCCCTCTTCTAG |
| CelegE166 | AACATCTAATAGGGACTGAGTGACCC |
| CelegE167 | TTCTGTGGTGCCTTGGCAAGAG |
| CelegE168 | CACACATACACACACACTAAGTGCC |
| CelegE169 | TGGTAGTTACTTAAAGTTTACAAGAATGTAGG |
| CelegE170 | AAATGCTGGGATAAAAAGCATGAACCAC |
| C.elegE145 | TTCAGTTACCTAATGGGCACAAGGC |
| CelegE148 | ACGACACTGACCTCTTGCACTTG |
| CelegE150 | TGTACACCCTGAATGTCTGAACATTC |
| CelegE152 | GCGTTCATTTCTGCTCCTGTAATGG |
| CelegE153 | TGAGCTCTTAATCCCTGCCATTCC |
| CelegE154 | TAGGGCTTGTCCGTCCATAAGG |
| CelegE157 | TGTTACGGAGATGAAAGGCTAGACC |
| CelegE158 | TAAGCCCTGCACTAACCCACTC |
| CelegE159 | TGTTTTGAGAGGTGAGCCTTCTAGC |
| CelegE160 | CATGTCCTACAGTTCTGCTATCACC |
| CelegE141 | CTTTTCTTCATCCAATTCCCCACGAG |
| CelegE144 | TCTCTAAGCTGCACTGTTGTGGCT |
| C.elegE129 | TGGAAGCCAAGAGTCTTGAGTTGC |
| CelegE132 | GTCTGCATTTTAAATGCAGATGTGAAGC |
| CelegE134 | CGAAACGCACGCACATTTTTACCAG |
| CelegE136 | GTGTGATTTAGCATCTGTCGCACTTG |
| CelegE137 | TGTATGTATAACCCAACAATCGCTGC |
| CelegE140 | TCCAGAGTACAGGGAGAAACTAAAGG |

FIG.5(4)

AGCGCTATTCAGCTGTGCCTCCTTTGCTGTCTTGGCTCCTCCTGGAGCACTAT
ATGCACCCATGTCCTTACCAGGCCTTTCACAGACGCTGCCATTGAGAGGGT
TGATGCAGGTTGCAGCCTTTAATCCCCGAGTACTAGGCTCTGACAAGATCCCA
CAGAAGCCAGCATCACTGGGCTCAGATGGCATCCACTGCAGCAAACTATTTG
TGAATGGAGACATATCC

FIG.6

GAATTCCGGGCGAAGGGGAGCCGGCGTGCGGGGTGTGTATGTGTTCGCTGGGCGCCGGCTCAGCCCCAGGAAGATGGTG

GCGGTGGCGGCGGCGGCGGCGACTGAGGCGCGGCTGAGGGGGAGCACGAGGACGACAGCAGCGCCTGCGGGCAGGAAGG

GCAGGCAGCACCGACCCTGCACCGCGACAGGGGCCTGGAGGCCGGGACCGCGCGCCCGGCTGTGTCTCCCGCGGGTGCT

GTCGCGGGCGCTGCCCCCGCCGCCGCTGCTGCCGCTGCTCTTTTCGCTGCTGCTGCTGCCGCTGCCCCGGGAGGCCGAG

GCCGCTGCGGTGGCGGCGGCGGTGTCCGGCTCGGCCGCAGCCGAGGCCAAGGAATGTGACCGGCCGTGTGTCAACGGCG

GCCGCTGCAACCCTGGCACCGGCCAGTGCGTCTGCCCCACGGGCTGGGTGGGCGAGCAATGCCAGCACTGCGGGGGCCG

CTTCAGGACATCTGTCTCACGCCTATAATCACAGCTGTTCGGAAGGTGAGGCTGGAGGAACAGTTCGAGGCAAGCTTCG

GCTACAGAATAAGTTCAAGAGTAACCTGGGGCAACTTGGGCTTGTCTCCAAAACCAAAATGAGCGAAAAGGAGCAAGCT

AGAGTCTTTTGGGAAAATTTTAGCTGACTAATTTTTCACCGAGAACTAACTGGCTCTTCTGGATTTGTAACAGATGGAC

CTGGGAATTATAAATATAAGACGAAGTGCACATGGCTCATTGAAGGACAGCCAAATAGAATAATGAGACTTCGCTTCAA

CCATTTTGCTACAGAATGTAGCTGGGACCATTTATATGTTTATGATGGGGACTCAATCTACGCACCTCTGATTGCTGCC

TTTAGTGGCCTCATTGTTCCTGAAAGAGATGGCAATGAGACGGCTCCTGAGGTCACTGTCACTTCAGGTTATGCACTGC

TGCATTTTTTCAGTGATGCTGCTTATAATCTGACTGGATTTAATATCACTTACAATTTTGACATGTGTCCGAATAATTG

FIG.8A

CTCAGGCCGAGGAGAGTGTAAGAGCAGTAACAGCAGCAGCGCTGTTGAGTGTGAATGTTCTGAAAACTGGAAAGGGGAG

TCGTGTGACATTCCTCACTGTACAGACAACTGTGGCTTTCCTCACCGAGGCATCTGTAATGCAAGCGATACCAGAGGGT

GCTCCTGCTTTCCTCACTGGCAGGGTCCTGGATGTTCAATTCCTGTGCCAGCTAACCAGTCTTTTTGGACTCGAGAAGA

ATATTCTGATTTAAAGCTTCCCAGAGCCTCTCATAAAGCTGTGGTCAATGGAAATATAATGTGGGTTGTTGGCGGATAT

ATGTTCAACCATTCAGATTACAGCATGGTTTTAGCGTATGACCTGACTTCTAGGGAATGGCTTCCACTAAACCATTCTG

TGAACAGTGTGGTTGTAAGATATGGTCATTCTTTGGCATTACATAAGGATAAAATCTACATGTATGGAGGAAAAATTGA

TTCAACAGGGAACGTGACCAATGAGCTGAGAGTATTTCATATTCATAATGAATCATGGGTATTGTTAACTCCGAAAGCT

AAGGATCAGTATGCAGTGGTTGGACACTCAGCACACATTGTTACACTGGCATCTGGCCGTGTGGTCATGTTGGTCATCT

TCGGTCATTGCCCACTCTATGGATATATAAGCGTTGTGCAGGAATATGACTTGGAAAAGAACACATGGAGTATATTACA

TACTCAGGGTGCTCTTGTGCAAGGGGGTTATGGCCACAGTAGTGTTTATGATGACAGGACCAAGGCTCTGTACGTTCAT

GGTGGCTACAAGGCTTTCAGCGCCAACAAATACCGGCTTGCAGATGACCTCTACAGATACGATGTGGATACTCAGATGT

GGACCATTCTTAAGGACAGCCGATTTTTCCGTTACTTGCATACAGCTGTGATAGTGAGTGGAACCATGCTGGTGTTTGG

AGGGAACACACACAATGACACTTCCATGAGCCACGGTGCCAAATGCTTCTCCTCGGACTTCATGGCTTATGACATTGCT

FIG.8B

TGTGACCGATGGTCAGTGCTTCCCAGACCTGAGCTCCATCATGATGTCAACAGATTTGGCCATTCAGCAGTCTTGTACA

ACAGCACCATGTATGTGTTCGGCGGCTTCAACAGCCTCCTCCTCAGTGACGTCTTGGTCTTTACCTCGGAGCAGTGCGA

TGCACACCGCAGTGAAGCTGCTTGTGTGGCAGCAGGACCTGGTATCCGGTGTCTGTGGGACACACAGTCGTCTCGATGT

ACCTCCTGGGAGTTGGCAACTGAAGAACAAGCAGAAAAGTTAAAATCAGAGTGTTTTTCTAAAAGAACCCTTGACCATG

ACAGATGTGACCAGCACACAGATTGTTACAGCTGCACAGCCAATACCAA

FIG.8C

MRLRFNHFATECSWDHLYVYDGDSIYAPLIAAFSGLIVPERDGNETAPEVTVTSGYALLHFFSDAAYNLTGFNITYNFD

MCPNNCSGRGECKSSNSSSAVECECSENWKGESCDIPHCTDNCGFPHRGICNASDTRGCSCFPHWQGPGCSIPVPANQS

FWTREEYSDLKLPRASHKAVVNGNIMWVVGGYMFNHSDYSMVLAYDLTSREWLPLNHSVNSVVVRYGHSLALHKDKIYM

YGGKIDSTGNVTNELRVFHIHNESWVLLTPKAKDQYAVVGHSAHIVTLASGRVVMLVIFGHCPLYGYISVVQEYDLEKN

TWSILHTQGALVQGGYGHSSVYDDRTKALYVHGGYKAFSANKYRLADDLYRYDVDTQMWTILKDSRFFRYLHTAVIVSG

TMLVFGGNTHNDTSMSHGAKCFSSDFMAYDIACDRWSVLPRPELHHDVNRFGHSAVLYNSTMYVFGGFNSLLLSDVLVF

TSEQCDAHRSEAACVAAGPGIRCLWDTQSSRCTSWELATEEQAEKLKSECFSKRTLDHDRCDQHTDCYSCTANTX

FIG.8D

TRANSMEMBRANE SEGMENTS PREDICTED BY MEMSAT

| START | END | ORIENT | SCORE |
|---|---|---|---|
| 22 | 38 | OUT-->INS | 1.7 |
| 50 | 67 | INS-->OUT | 0.5 |
| 183 | 203 | OUT-->INS | 0.3 |
| 386 | 402 | INS-->OUT | 2.8 |
| 458 | 474 | OUT-->INS | 0.1 |

SIGNAL PEPTIDE PREDICTIONS

| METHOD | PREDICT | SCORE | Mat@ |
|---|---|---|---|
| SignalP (eukaryote) | NO | | |

GAATTCCGGAAAAAAAAAAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAAGGAGGGCGAAGGGGAGCCGG

CGTGCGGGGTGTGTATGTGTTCGCTGGGCGCCGGCTCAGCCCCAGGAAGATGGTGGCGGTGGCGGCGGCGGCGGCGACT

GAGGCGCGGCTGAGGGGGAGCACGACGACGACAGCAGCGCCTGCGGGCAGGAAGGGCAGGCAGCACCGACCCTGCACCG

CGACAGGGGCCTGGAGGCCGGGACCGCGCGCCCGGCTGTGTCTCCCGCGGGTGCTGTCGCGGGCGCTGCCCCCGCCGCC

GCTGCTGCCGCTGCTCTTTTCGCTGCTGCTGCTGCCGCTGCCCCGGGAGGCCGAGGCCGCTGCGGTGGCGGCGGCGGTG

TCCGGCTCGGCCGCAGCCGAGGCCAAGGAATGTGACCGGCCGTGTGTCAACGGCGGCCGCTGCAACCCTGGCACCGGCC

AGTGCGTCTGCCCCACGGGCTGGGTGGGCGAGCAATGCCAGCACTGCGGGGGCCGCTTCAGACTAACTGGCTCTTCTGG

ATTTGTAACAGATGGACCTGGGAATTATAAATATAAGACGAAGTGCACATGGCTCATTGAAGGACAGCCAAATAGAATA

ATGAGACTTCGCTTCAACCATTTTGCTACAGAATGTAGCTGGGACCATTTATATGTTTATGATGGGGACTCAATCTACG

CACCTCTGATTGCTGCCTTTAGTGGCCTCATTGTTCCTGAAAGAGATGGCAATGAGACGGCTCCTGAGGTCACTGTCAC

TTCAGGTTATGCACTGCTGCATTTTTTCAGTGATGCTGCTTATAATCTGACTGGATTTAATATCACTTACAATTTTGAC

ATGTGTCCGAATAATTGCTCAGGCCGAGGAGAGTGTAAGAGCAGTAACAGCAGCAGCGCTGTTGAGTGTGAATGTTCTG

AAAACTGGAAAGGGGCCGGAATTC

FIG.9A

EFRKKKKKKKKKKKKKKKKKKKKKKKKKKKKKKKKKKKKKKKKKKKKKKGGRRGAGVRGVYVFAGRRLSPRKMVAVAAAAAT

EARLRGSTTTTAAPAGRKGRQHRPCTATGAWRPGPRARLCLPRVLSRALPPPPLLPLLFSLLLLPLPREAEAAAVAAAV

SGSAAAEAKECDRPCVNGGRCNPGTGQCVCPTGWVGEQCQHCGGRFRLTGSSGFVTDGPGNYKYKTKCTWLIEGQPNRI

MRLRFNHFATECSWDHLYVYDGDSIYAPLIAAFSGLIVPERDGNETAPEVTVTSGYALLHFFSDAAYNLTGFNITYNFD

MCPNNCSGRGECKSSNSSSAVECECSENWKGAGIX

FIG.9B

SIGNAL PEPTIDE PREDICTIONS

| METHOD | PREDICT | SCORE | Mat@ |
|---|---|---|---|
| SignalP (eukaryote) | MAYBE | | 127 |

TRANSMEMBRANE SEGMENTS PREDICTED BY MEMSAT

| START | END | ORIENT | SCORE |
|---|---|---|---|
| 102 | 120 | INS-->OUT | 2.1 |
| 234 | 250 | OUT-->INS | 1.7 |
| 262 | 279 | INS-->OUT | 0.5 |

ATGTACTACTGTAACAAGAAGACCAGCTGCAGGAGCTGTGCCCTGGACCAGAACTGCCAGTGGGAGCCCCGGAATCAGG

AGTGCATTGCCCTGCCCGAAAATATCTGTGGCATTGGCTGGCATTTGGTTGGAAACTCATGTTTGAAAATTACTACTGC

CAAGGAGAATTATGACAATGCTAAATTGTTCTGTAGGAACCACAATGCCCTTTTGGCTTCTCTTACAACCCAGAAGAAG

GTAGAATTTGTCCTTAAGCAGCTGCGAATAATGCAGTCATCTCAGAGCATGTCCAAGCTCACCTTAACCCCATGGGTCG

GGCCTTCGGGAAGGTYCAATGTGTCCTACTKGGTGCTGGGGAAGGATATGKTCCCCATTTTACAAATAGTTTTACTACA

GTGGGATGSCCGTCTTGAGGCCCAGTGTTGCTTGGRATTCTGTGGGAATTTT:ATTCAGGAACCCAGTTACTTCGGGGA

CTGAAGGCTGCAACCTGCATTCAACCCACTYMAATGGTAGTGTCTGTGAAAGGCCTGCAAACCACAGTGCTAAGGCAGT

GCCGGACACCATGTGCCTTGAGGACAGCATGTGGAGATTGCACCAGCGGCAGCTCTGAGTG:CATGTGGTGCAGCAACA

TGAAG:CAGTGTGTGGACTCCAATGCCTATGTGGCCTCCTTCCCTTTTGG:CCAGTGTATGGAATGGTATACGATGAGC

ACCTGCCCCCCTGAAAATTGTTCAGGCTACTGTACCTGTAGTCATTGCTTGGAGCAACCAGGCTGTGGCTGGTGTACTG

ATCCCAGCAATACTGGCAAAGGGAAATGCATAGAGGGTTCCTATAAAGGACCAGTGAAGATGCCTTCGCAAGCCCCTAC

AGGAAATTTCTATCCACAGCCCCTGCTCAATTCCAGCATGTGTCTAGAGGACAGCAGATACAACTGGTCTTTCATTCAC

TGTCCAGCTTGCCAATGCAACGGCCACAGTAAATGCATCAATCAGAGCATCTGTGAGAAGTGTGAGAACCTGACCACAG

FIG.10A(1)

GCAAGCACTGCGAGACCTGCATATCTGGCTTCTACGGTGATCCCACCAATGGAGGGAAATGTCAGCCATGCAAGTGCAA

TGGGCACGCGTCTCTGTGCAACACCAACACGGGCAAGTGCTTCTGCACCACCAAGGGCGTCAAGGGGGACGAGTGCCAG

CTATGTGAGGTAGAAAATCGATACCAAGGAAACCCTCTCAGAGGAACATGTTATTATACTCTTCTTATTGACTATCAGT

TCACCTTTAGTCTATCCCAGGAAGATGATCGCTATTACACAGCTATCAATTTTGTGGCTACTCCTGACGAACAAAACAG

GGATTTGGACATGTTCATCAATGCCTCCAAGAATTTCAACCTCAACATCACCTGGGCTGCCAGTTTCTCAGCTGGAACC

CAGGCTGGAGAAGAGATGCCTGTTGTTTCAAAAACCAACATTAAGGAGTACAAAGATAGTTTCTCTAATGAGAAGTTTG

ATTTTCGCAACCACCCAAATATCACTTTCTTTGTTTATGTCAGTAATTTCACCTGGCCCATCAAAATTCAGATTGCCTT

CTCTCAGCACAGCAATTTTATGGACCTGGTACAGTTCTTCGTGACTTTCTTCAGTTGTTTCCTCTCTTTGCTCCTGGTG

GCTGCTGTGGTTTGGAAGATCAAACAAAGTTGTTGGGCCTCCAGACGTAGAGAGCAACTTCTTCGAGAGATGCAACAGA

TGGCCAGCCGTCCCTTTGCCTCTGTAAATGTCGCCTTGGAAACAGATGAGGAGCCTCCTGATCTTATTGGGGGGAGTAT

AAAGACTGTTCCCAAACCCATTGCACTGGAGCCGTGTTTTGGCAACAAAGCCGCTGTCCTCTCTGTGTTTGTGAGGCTC

CCTCGAGGCCTGGGTGGCATCCCTCCTCCTGGGCAGTCAGGTCTTGCTGTGGCCAGCGCCCTGGTGGACATTTCTCAGC

AGATGCCGATAGTGTACAAGGAGAAGTCAGGAGCCGTGAGAAACCGGAAGCAGCAGCCCCCTGCACAGCCTGGGACCTG

FIG.10A(2)

CATCTGATGCTGGGGCCAGGGACTCTCCCACGCACGAGCTAGTGAGTGGCACACCAGAGCCATCTGCAGGGAAGGGCGT

GGCGGGGAAATGGCTGTGCGGTGCGGGACGGAAGACTGGAAACCCTCAAAGCATCTGACTCACCTGCATGATCACAAGC

TTTCTTTGACGGTTTCTCCCATCCGTGTTCCAGCATCTAACCTTTTACTTTTGCATAGGAAATACTTGATTTAATTACA

GGTCCAGGGATGAGCTGATGGTTGCTGGAGGAGGCCAGTGTAGAGCCAGTGAGAGAACTAGGAATGACACTCAGGTTCA

CTGTGGAAAACTGTTCTTGGGACTGTCTCAACTGTGCAAAAAACAAAAGATGGAGTGTTTACAAGTAGACATTCGTCAT

CAGTTGTTCTTGAACATGGTCTTTTAAAAACTAGTCAGATGAATTAACTTGTTTTCATCTGAAGCCTGCTATCTTTTTT

AAAAGATGTGCTATTTATTCTTGCACGATTTAGGCAATTATCTCTCTTCCAGGGAGTACCTTTTTTTCTAGTTGAGAAT

TAATAATGGTCCATCTCTTTTGATCATATCAAGCTAGGATAGAAGGGGGGCTATTTTAAATGTCAAGGTCAGCAGTGTT

ACTTTGAATGTAAACTGGTATAATAGGTAGTTTTCTATAGTAACTTGATTAATTTAGTCTTAATCCATTTGAAACTCTC

TCTTCCTTTCTCTCTGCCTGTCCCTCTCCTTCTCCATCTCACCCTCCCTCTCTCACACATACACACACAAACACATACA

CACAACACTAAGTGCCTAGACTTTAAATAGATCTAGCAATTGGAAAGTTAGTAAGCCTAAGTTTTTACATAATTGCATT

CCTACATTCTTGTAAAATTTAAATAGCTACCATTGGCAATCTGCTTTTTTTCTAAAATCTGATTTGCAGCCAGGAAAGA

ATTTTCTCACCCAAGGAACATTTGATCTAGCAGCAGGGATGAGAGGAAAGCAGAAATGAATGAACTGTGAAAGCTCCTG

FIG.10A(3)

TTTTTATTATCAAAAAGGACACTGTCAAGAAGGCGCCCCCTGCCCCCACCCCCGTGTCACCCTAGGCCTGATAAGCGAT

CAGAGGAAAGGACTCATTCATGTCACGCTTCCTTGAGCAGAAAAGAGCACTGAGAGCACTTGGGACCCCTGGATCAGAG

AGCATCTGTGTGTCCTGCAGCCTCCTCTGAACTTGTGGTTCATTCTCAGGCTGGGGTGGACTCAGATGCCAGGAAAGGG

ACAGCCTCCCATTGTCAGGCAGAAGCTGCCCAAAGCCTGGAGAAGGACTTGTTTGCCCTCTTTCCCCCAGGAGGGGCTC

GACCCACCCACCCTCCCTCTCAGACCAAGGTGGTGGCTGTGAGGAGGGCAGCAAATGCTGACAAGGATGAAAAGCACAT

GGAAAAAAATGGACGAGGAGGGAAAACTCTGCCAAATGGAAAATGACCAAATTTAAGAGGGTGGGACAGTCCCCTGCTC

CTCTCCCAGAGGGCACTGCTTGGAAATTGTGTTTTCCCCATTTATGGTGCTCTGTATTCTGGCATTATGCAGCAGCCTC

CCAGAAGCTCTCTTCTGCTTCAAAACCTGGGATCTCTGGCATTACCCTATTGGGATGGACCGCTGGACAGCAATGCTCG

AGTTTGTGAATTTGGAGAGATACTCAAAAGAGCTAAAACTGCAGCATTTTACCTTTAAATGCAGTGCCTAGAGAGAGAG

TATTGTCTCTTCCCCAACACTAACCCCACTCCCATGAAGAATTGCCTGGAAAGATGTTTTCAAGGAATTTGAACCATAA

AACACTATCTGATGCACAGAACACCTCTACTTTGAGACTCACCTCTCATAAAGCTTCTTTTTCACATTACTGTTAAAGA

CCAGACGTTCTAGAAAAGACCCCTCCTCTCATGAGCTCCCCCATCCCTGCTACAGAACACAGCACCCATGGCGCCTGCA

GTGGACTGGCCCCTTAATTCCCACAGGCCCCCCAGCAAGGCCAAAGGGAGGCCCCTGGGTATTGTCCTCCTACAAGGA

FIG.10A(4)

AGATCCTCTTTGTTTGTTCAAAGGACCAGTTTTCCTAGGCCAAAGAAGTCTCTTCCCCATGTTAGTCCTATGCCTTGAA

ATATCATGCACCATGACCCACAGCCATCTGGTTATGTCTTATTTTTTTCCTAAAAGATAATGTTTATTTTTAAAAAGGA

AGGAAGAAGCAAGTGAAGTTTCATTCTGCTCCAGCGGTGGGGAAGCCGCTGAATCCACCTGCTTCTCCTTTGCAACCGA

CAGCAAACAGCTTTCTCCGGCCTCAGGGCAGAAAAAGGGAATGGCAGGGAGTAAGAGGCGCTGGGCTCGGAGCCTGTTT

CCAAGAAGGAATTGGTTGTCATCTGGCAGTGTTGCGCGTCACAAGAGAGCCTGTATATAAATTAAAATAGTCAAGACAA

CACTGACCTTGCACTTGTACATAACTATACAGTAGTGTCCAGAATGTTCAGACATTCGGAGTGTACATAAAACAGAAAA

AATCTTCATGTATTTTTATTAAATATAACAATGTCTGAGTTTCACCTAAGATGTTTTTGTGCCATATGCTGGATATCCA

GGTTCTCGCCAGGCCCCGATACATGAATAACAAACCCAAGAAACGCATCCCCATTGTGTGATGTGTTCAGATGCATCTG

GCACCAATTAGGTATTTCTTAAAACAGGACTCATCTGTCAGAGTGCACATGAAAAATCAGGCAGGGAATCGAAACGACA

GCGCTGGAGGAGACTCAGGAAGCAGAGGCGTCCCTGCCGCTGCCCTTGGCCCTGCAAGCACATCATGACCCTTTCTGGC

AGCCTCTTGGTGCTCTGGGTAGTGAGGGATGACCAGTCTTGTCCTGAGAAATGTTTCTCTTAGTCTTTAAGTTCAAAGA

CTAACCTGTAGCAATCAGACTTTCCAAAAGGGGGTTCTCCATTTTTTTGTAGTTTTGTCTAAATTTTTTAATGACCATTTC

CTGGAATCAGTTTATTATACTGAAAACTGGGGGTGGGAGTAGGGAGCTAGTTTGTTGATAAATAGTTCCCATTTCCCCG

FIG.10A(5)

TGGAGAATTTGACATACCCTGGACTCCTGTGTGCCTCCTGCCATCCCTGCACACAGCCTGGGGAGAAGCCTGTGCCTCC

CCGTGTGGAGAGAAGGCAACCCCAGATCCCCTGAGCTAACCCGGAGGAAAGGCAGTCCTGGACAGAAGACTGTCAGCAG

AAGGAAAGTACTGGACTACCCGTGGGTAAGTCCTGCCATTCAAGACTGGAGACACCTGGGAAATAAAAAGAGCAGGGCA

CTGCTGGTGGGAAGAGGCATTTTACCTTCCAGTGCAAATCCTGCTCCTTTGATTTAATGGGGTGTACTGGGGCCAGGGG

CTGATTCACTTCCTTGGGAGATGGTGGTGTTTTCATGAACATCTTTGATCCTTCCATTTCATTTATTCATCCATCCATT

CAACAAGTATTTGCTAAACACTAACTTAAGCTAATGCTAGGGTAGTGACTGAGATGTAAAAATAGATTTTAGAATTAAA

ACAAAATCCAAGTCCTCACACCCCTGTCATCCCAGGAGATCTTTCCTTGTGGTGGTTTCTGTGAGAATTGGCCATCCTG

AGGACACAGCCAGGACGGCAGAGGCCTCCTGGCCTCAGGGCATGCCCTGCCTACCTTCTGAAATGTTTACCCCATTGAC

CAAACTTGGCTCCAGCCATTGCGGTGGTTTCTAGATAGCCAGGCCCACCAAGAGATATTGCCCCTTGATGAGAGTCAAA

CACCCTGCCTACAAGGAGATGTTTTGAAATGGAGAGGAAAATTGGCACCTCATCTTTTAAAGGCAGTAATGGAATTGAT

TTTCAGTAACTGAATTTGTGCACAAAACATTCTAAACACTAGTGAAGCCTGTTTCGTTGAACTAATTCTGGCTCTGGAA

ATGTTTTTGTTTTATAGTTATTTACGATTTCGTTTGTTTGGATTCAAGCTTAGTTTGTTAATATGTATAATTTAGCATC

TATTACACTCATGTAAATATGGAGTAAGTATTGTAAACTATTTCATTGCGGGGATTGTGGGTGTTATACATACATTTAG

FIG.10A(6)

GACTGCAATTTTTTGGTATTTTTTGTATTGTAAAATAACAGCTAATTTAAGCAGGAACAAGAGAACTAAGGGAGGTCTG

TGCATTTTAAACACAAATGTGAAGAACTTGTATATAAACAAAAGTAAATACTATAATACAAACTTCCTTCTGAAATAAA

AGTAGATCTGGTAAAAAAAAAAAAAGAAAAAAAAAAAAAAAAAAGGGCGGCCGC

FIG. 10A(7)

MYYCNKKTSCRSCALDQNCQWEPRNQECIALPENICGIGWHLVGNSCLKITTAKENYDNAKLFCRNHNALLASLTTQKK

VEFVLKQLRIMQSSQSMSKLTLTPWVGPSGRXNVSYXVLGKDMXPILQIVLLQWDXRLEAQCCLXFCGNFXSGTQLLRG

LKAATCIQPTXMVVSVKGLQTTVLRQCRTPCALRTACGDCTSGSSEXHVVQQHEXSVWTPMPMWPPSLLXQCMEWYTMS

TCPPENCSGYCTCSHCLEQPGCGWCTDPSNTGKGKCIEGSYKGPVKMPSQAPTGNFYPQPLLNSSMCLEDSRYNWSFIH

CPACQCNGHSKCINQSICEKCENLTTGKHCETCISGFYGDPTNGGKCQPCKCNGHASLCNTNTGKCFCTTKGVKGDECQ

LCEVENRYQGNPLRGTCYYTLLIDYQFTFSLSQEDDRYYTAINFVATPDEQNRDLDMFINASKNFNLNITWAASFSAGT

QAGEEMPVVSKTNIKEYKDSFSNEKFDFRNHPNITFFVYVSNFTWPIKIQIAFSQHSNFMDLVQFFVTFFSCFLSLLLV

AAVVWKIKQSCWASRRREQLLREMQQMASRPFASVNVALETDEEPPDLIGGSIKTVPKPIALEPCFGNKAAVLSVFVRL

PRGLGGIPPPGQSGLAVASALVDISQQMPIVYKEKSGAVRNRKQQPPAQPGTCI

FIG.10B

FIG.15A
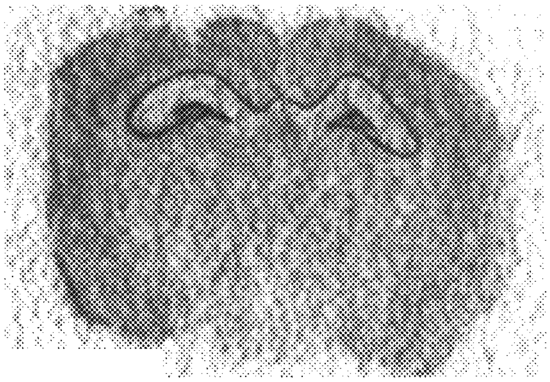
FIG.15B
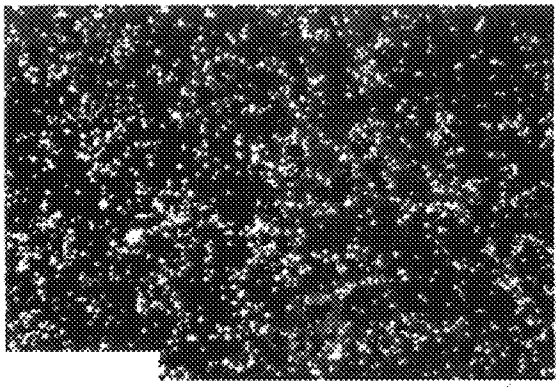
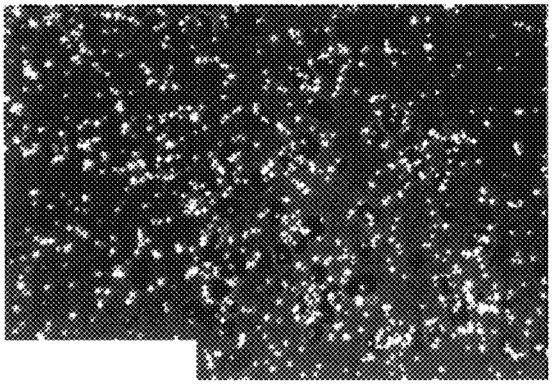
FIG.15C
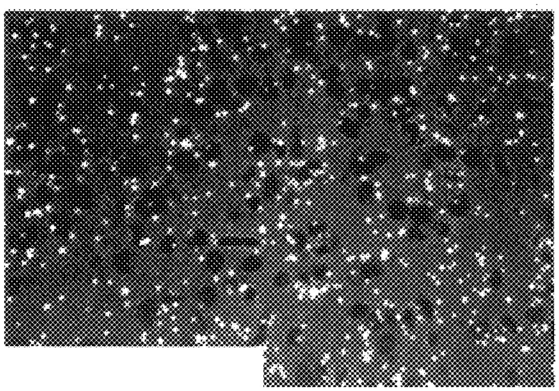
FIG.15D

```
                                                    [     Transmembrane
obe2        FRNHPNITFFVYVSNFTWP-------IKIQIAFSQHSNFMDLVQFFVTFFSCFLSLLLVA
KIAA0534    FRSNPNITFYVYVSNFSWP-------IKIQIAFSQHNTIMDLVQFFVTFFSCFLSLLLVA
YC81_CAEEL  FGPDSNTTFFVRVYNFNTP-------VQIVVSFAQSPPIN-WVLFFVIFAACFIVLLVVA
MEGF8       LKSSRFYLLLLGVGDPSGPGANGSADSQGLLFFRQDQAHIDLFVFFSVFFSCFFLFLSLC
                ]                      Site
obe2        AVVWKIKQSCWASRRREQLLREMQQMASRPFASVETLPWNR------------------
KIAA0534    AVVWKIKQTCWASRRREQLLRERQQMASRPFASVDVALEVGAEQTEFLRGPLEGAPKPIA
YC81_CAEEL  GLLWMIKVRIEAYRRNQRRIDEIEHMASRPFASTKMELSMLSQFSSAG------------
MEGF8       VLLWKAKQALDQRQEQRRHLQEMTKMASRPFAKVTVCFPPDPTAPASAWKP-AGLPPP-A
```

FIG.16A

```
                10        20        30        40        50        60
inputs  MVAVAAAAATEARLRGSTTTTAAPAGRKGRQHRPCTATGAWRPGPRARLCLPRVLSRALP
        :::  ::::::::::  :..::: ::: :                  ::.
        MVA  AAAATEARLRRRTAATAALAGRSG---------------GPH--------------
                 10        20      [     EGF          30

                                                          EGF1
                70        80        90       100       110       120
inputs  PPPLLPLLFSLLLLPLPREAEAAAVAAAVSGSAAAEA[KECDRPCVNGGRCNPGTGQCVCP
                                                  ::::::::::::::::
        ------------------------------------------CVNGGRCNPGTGQCVCP
                                                        40

               130   CUB 140       150  CUB  160       170       180
inputs  TGWVGEQC]Q[HCGGRFRLTGSSGFVTDGPGNYKYKTKCTWLIEGQPNXIMRLRFNHFATEC
        .::::::::::::::::::::::::::::::::::::::::::::::.:::::::::::::
        AGWVGEQCQHCGGRFRLTGSSGFVTDGPGNYKYKTKCTWLIEGQPNRIMRLRFNHFATEC
         50     ] [ 60       70        80  CUB  90       100

               190       200       210       220       230       240
inputs  SWDHLYVVYDGDSIYAPLIAAFSGLIVPERDGNETAPEVTVTSGYALLHFFSDAAYNLTGF
        :::::::::::::::::::.::::::::::::::::::.:::..::::::::::::::::::
        SWDHLYVVYDGDSIYAPLVAAFSGLIVPERDGNETVPEVVATSGYALLHFFSDAAYNLTGF
        110       120       130       140       150       160

                      EGF2                                  EGF3
               250       260       270       280       290       300
inputs  NITY]N[FDMCPNNCSGRGECKSSNSSSXVECECSENWKGXAC]D[IPHCTDNCGFPHRGICNX
        ::::.::::::::::::::::: ::::..::::::::::::::.::::::::::::::::::.
        NITYSFDMCPNNCSGRGECKISNSSDTVECECSENWKGEACDIPHCTDNCGFPHRGICNS
        170   ] [  180  EGF2 190       200      ]210       220

                                          Kelch1               Kelch2
               310       320       330       340       350       360
inputs  SDXRGCSCFSDWQGPG]C[SVPVPANQSFWTREEYSNLKLPRASH]K[AVVNGNIMWVVGGYMF
        ::.:::::::::::::::::::::::::::::::::::::::::::::::::::::::::
        SDVRGCSCFSDWQGPGCSVPVPANQSFWTREEYSNLKLPRASHKAVVNGNIMWVVGGYMF
        230       240       250       260       270       280

                                                      Kelch3
               370       380       390       400       410       420
inputs  NHSDYNMVLAYDLASREWLPLNRSVNNVVVRYG]H[SLALYKDKIYMYGGKIDSTGNVTNEL
        ::::::::::::::::::::::::::::::::::::::::::::::::::::::::::::
        NHSDYNMVLAYDLASREWLPLNRSVNNVVVRYGHSLALYKDKIYMYGGKIDSTGNVTNEL
        290       300       310       320       330       340
```

FIG.17A

```
                                              kelch4
             430         440         450         460         470         480
inputs  RVFHIHNESWVLLTPKAKEQYAVVG]H[SAHIVTLKNGRVVMLVIFGHCPLYGYISNVQEYD
        :::::::::::::::::::::::::::::::::::::::::::::::::::::::::::::
        RVFHIHNESWVLLTPKAKEQYAVVGHSAHIVTLKNGRVVMLVIFGHCPLYGYISNVQEYD
        350         360         370         380         390         400

                                              Kelch5
             490         500         510         520         530         540
inputs  LDKNTWSILHTQGALVQGGYG]H[SSVYDHRTRALYVHGGYKAFSANKYRLADDLYRYDVDT
        :::::::::::::::::::::::::::::::::::::::::::::::::::::::::::::
        LDKNTWSILHTQGALVQGGYGHSSVYDHRTRALYVHGGYKAFSANKYRLADDLYRYDVDT
        410         420         430         440         450         460

                                    Kelch 6nt
             550         560         570         580         590         600
inputs  QMWTILKDSRFFRYL]H[TAVIVSGTMLVFGGNTHNDTSMSHGAKCFSSDFMAYDIACDRWS
        :::::::::::::::::::::::::::::::::::::::::::::::::::::::::::::
        QMWTILKDSRFFRYLHTAVIVSGTMLVFGGNTHNDTSMSHGAKCFSSDFMAYDIACDRWS
        470         480         490         500         510         520

                                   kelch 1ct
             610         620         630         640         650         660
inputs  VLPRPDLHHDVNRFG]H[SAVLHNSTMYVFGGFNSLLLSDILVFTSEQ]CDAHRSEAACLAAG
        ::::::     . ..  ::::::::::::::::::::::::::::::::::::::::::::
        VLPRPDSTMMSTDLAIPAVLHNSTMYVFGGFNSLLLSDILVFTSEQCDAHRSEAACLAAG
        530         540         550         560         570         580

                                              plexin 1
             670         680         690         700         710         720
inputs  PGIRCVWNTGSSQCISWALATDEQEEKLKSECFSKRTLDH[DRCDQHTDCYSCTANTNDCH
        :::::::::::::::::::::::::::::::::::::::::::::::::::::::::::::
        PGIRCVWNTGSSQCISWALATDEQEEKLKSECFSKRTLDHDRCDQHTDCYSCTANTNDCH
        590         600         610         620         630      [640
                                         ligand-binding γ cytokine chain

             730         740         750         760         770         780
inputs  WCNDHCVPRNHSCSEGQISIFRYENCPKDNPMYYCNKKTSCRSCALDQNCQWEPRNQECI
        :::::::::::::::::::::::::::::::::::::::::::::::::::::::::::::
        WCNDHCVPRNHSCSEGQISIFRYENCPKDNPMYYCNKKTSCRSCALDQNCQWEPRNQECI
        650         660         670         680         690         700

                                   c-type lectin
             790         800         810         820         830         840
inputs  AL]PENI[CGIGWHLVGNSCLKITTAKENYDNAKLFCRNHNALLASLTTQKKVEFVLKQLRI
        :::::::::::::::::::::::::::::::::::::::::::::::::::::::::::::
        ALPENICGIGWHLVGNSCLKITTAKENYDNAKLFCRNHNALLASLTTQKKVEFVLKQLRI
        710  [      720         730         740         750         760
```

FIG.17B

```
                850       860       870       880       890       900
inputs  MQSSQSMSKLTLTPWVGLRKINVSYWCWEDMSPFTNSLLQWMPSEPSDAGFCGILSEPST
        ::::::::::::::::::::::::::::::::::::::::::::::::::::::::::::
        MQSSQSMSKLTLTPWVGLRKINVSYWCWEDMSPFTNSLLQWMPSEPSDAGFCGILSEPST
        770       780       790       800       810       820

                                          plexin repeat 2
                910       920       930       940       950       960
inputs  RGLKAATCINPLNGSVC]ERPANHS[AKQCRTPCALRTACGDCTSGSSECMWCSNMKQCVDS
        ::::::::::::::::::::::::::::::::::::::::::::::::::::::::::::
        RGLKAATCINPLNGSVCE]RPANHSAKQCRTPCALRTACGDCTSGSSECMWCSNMKQCVDS
        830       840       850       860       870       880

                970       980       990      1000      1010      1020
inputs  NAYVASFPFGQCMEWYTMSTCPPENCSGYCTCSHCLEQPGCGWCTDPSNTGKGKCIEGSY
        ::::::::::::::::::::::::::::::::::::::::::::::::::::::::::::
        NAYVASFPFGQCMEWYTMSTCPPENCSGYCTCSHCLEQPGCGWCTDPSNTGKGKCIEGSY
        890       900       910       920       930       940

                                                     lamin-like EGF-1
               1030      1040      1050      1060      1070      1080
inputs  KGPVKMPSQAPTGNFYPQPLLNSSMCLEDSRYNWSFIHC]PA[CQCNGHSKCINQSICEKCE
        ::::::::::::::::::::::::::::::::::::::::::::::::::::::::::::
        KGPVKMPSQAPTGNFYPQPLLNSSMCLEDSRYNWSFIHCPACQCNGHSKCINQSICEKCE
        950       960       970       980       990      1000

                                                   lamin-like EGF-2
               1090      1100      1110      1120      1130      1140
inputs  NLTTGKHCETCISGFYGDPTNGGKCQ]P[CKCNGHASLCNTNTGKCFCTTKGVKGDECQLCE
        ::::::::::::::::::::::::::::::::::::::::::::::::::::::::::::
        NLTTGKHCETCISGFYGDPTNGGKCQPCKCNGHASLCNTNTGKCFCTTKGVKGDECQLCE
       1010      1020      1030      1040      1050      1060

               1150      1160      1170      1180      1190      1200
inputs  VENRYQGNPLRGTCYY]TLLIDYQFTFSLSQEDDRYYTAINFVATPDEQNRDLDMFINASK
        ::::::::::::::::::::::::::::::::::::::::::::::::::::::::::::
        VENRYQGNPLRGTCYYTLLIDYQFTFSLSQEDDRYYTAINFVATPDEQNRDLDMFINASK
       1070      1080      1090      1100      1110      1120

               1210      1220      1230      1240      1250      1260
inputs  NFNLNITWAASFSAGTQAGEEMPVVSKTNIKEYKDSFSNEKFDFRNHPNITFFVYVSNFT
        ::::::::::::::::::::::::::::::::::::::::::::::::::::::::::::
        NFNLNITWAASFSAGTQAGEEMPVVSKTNIKEYKDSFSNEKFDFRNHPNITFFVYVSNFT
       1130      1140      1150      1160      1170      1180
```

FIG.17C

```
                                        TM
               1270      1280      1290      1300      1310      1320
inputs  WPIKIQIAFSQHSNFMD[LVQFFVTFFSCFLSLLLVAAVVWKI]KQSCWASRRREQLLREMQ
        :::::::.                                    :.       ::
        WPIKIQV-------------------------------------QT       EQ------
       1190

               1330      1340      1350      1360      1370      1380
inputs  QMASRPFASVNVALETDEEPPDLIGGSIKTVPKPIALEPCFGNKAAVLSVFVRLPRGLGG

        ------------------------------------------------------------

               1390      1400      1410      1420
inputs  IPPPGQSGLAVASALVDISQQMPIVYKEKSGAVRNRKQQPPAQPGTCIN

        -------------------------------------------------
```

FIG.17D

ATGGTGGCGGTGGCCGCAGCGGCGGCAACTGAGGCAAGGCTGAGGAGGAGGACGGCGGCGACGGCAGCGCTCGCGGGCAGGAGCGGCGGGCC

GCACCGACCCTGCACCGCGACAGGGGCCTGGAGGCCGGGACCGCGCGCCCGGCTGTGTCTCCCGCGGGTGCTGTCGCGGGCGCTGCCCCCGC

CGCCGCTGCTGCCGCTGCTCTTTTCGCTGCTGCTGCTGCCGCTGCCCCGGGAGGCCGAGGCCGCTGCGGTGGCGGCGGCGGTGTCCGGCTCG

GCCGCAGCCGAGGCCAAGGAATGTGACCGGCCGTGTGTCAACGGCGGTCGCTGCAACCCTGGCACCGGCCAGTGCGTCTGCCCCGCCGGCTG

GGTGGGCGAGCAATGCCAGCACTGCGGGGGCCGCTTCAGACTAACTGGATCTTCTGGGTTTGTGACAGATGGACCTGGAAATTATAAATACA

AAACGAAGTGCACGTGGCTCATTGAAGGACAGCCAAATAGAATAATGAGACTTCGTTTCAATCATTTTGCTACAGAGTGTAGTTGGGACCAT

TTATATGTTTATGATGGGGACTCAATTTATGCACCGCTAGTTGCTGCATTTAGTGGCCTCATTGTTCCTGAGAGAGATGGCAATGAGACTGT

CCCTGAGGTTGTTGCCACATCAGGTTATGCCTTGCTGCATTTTTTTAGTGATGCTGCTTATAATTTGACTGGATTTAATATTACTTACAGTT

TTGATATGTGTCCAAATAACTGCTCAGGCCGAGGAGAGTGTAAGATCAGTAATAGCAGCGATACTGTTGAATGTGAATGTTCTGAAAACTGG

AAAGGTGAAGCATGTGACATTCCTCACTGTACAGACAACTGTGGTTTTCCTCATCGAGGCATCTGCAATTCAAGTGATGTCAGAGGATGCTC

CTGCTTCTCAGACTGGCAGGGTCCTGGATGTTCAGTTCCTGTACCAGCTAACCAGTCATTTTGGACTCGAGAGGAATATTCTAACTTAAAGC

TCCCCAGAGCATCTCATAAAGCTGTGGTCAATGGAAACATTATGTGGGTTGTTGGAGGATATATGTTCAACCACTCAGATTATAACATGGTT

CTAGCGTATGACCTTGCTTCTAGGGAGTGGCTTCCACTAAACCGTTCTGTGAACAATGTGGTTGTTAGATATGGTCATTCTTTGGCATTATA

FIG. 18A(1)

CAAGGATAAAATTTACATGTATGGAGGAAAAATTGATTCAACTGGGAATGTGACCAATGAGTTGAGAGTTTTTCACATTCATAATGAGTCAT

GGGTGTTGTTGACCCCTAAGGCAAAGGAGCAGTATGCAGTGGTTGGGCACTCTGCACACATTGTTACACTGAAGAATGGCCGAGTGGTCATG

CTGGTCATCTTTGGTCACTGCCCTCTCTATGGATATATAAGCAATGTGCAGGAATATGATTTGGATAAGAACACATGGAGTATATTACACAC

CCAGGGTGCCCTTGTGCAAGGGGGTTACGGCCATAGCAGTGTTTACGACCATAGGACCAGGGCCCTATACGTTCATGGTGGCTACAAGGCTT

TCAGTGCCAATAAGTACCGGCTTGCAGATGATCTCTACCGATATGATGTGGATACCCAGATGTGGACCATTCTTAAGGACAGCCGATTTTTC

CGTTACTTGCACACAGCTGTGATAGTGAGTGGAACCATGCTGGTGTTTGGGGGAAACACACACAATGACACATCTATGAGCCATGGCGCCAA

ATGCTTCTCTTCAGATTTCATGGCCTATGACATTGCCTGTGACCGCTGGTCAGTGCTTCCCAGACCTGATCTCCACCATGATGTCAACAGAT

TTGGCCATTCAGCAGTCTTACACAACAGCACCATGTATGTGTTCGGTGGTTTCAATAGTCTCCTCCTCAGCGACATCCTGGTATTCACCTCG

GAACAGTGTGATGCGCATCGGAGTGAAGCCGCTTGTTTAGCAGCAGGACCTGGTATTCGGTGTGTGTGGAACACAGGGTCGTCTCAGTGTAT

CTCGTGGGCGCTGGCAACTGATGAACAAGAAGAAAAGTTAAAATCAGAATGTTTTTCCAAAAGAACTCTTGACCATGACAGATGTGACCAGC

ACACAGATTGTTACAGCTGCACAGCCAACACCAATGACTGCCACTGGTGCAATGACCATTGTGTCCCCAGGAACCACAGCTGCTCAGAAGGC

CAGATCTCCATTTTTAGGTATGAGAATTGCCCCAAGGATAACCCTATGTACTACTGTAACAAGAAGACCAGCTGCAGGAGCTGTGCCCTGGA

CCAGAACTGCCAGTGGGAGCCCCGGAATCAGGAGTGCATTGCCCTGCCCGAAAATATCTGTGGCATTGGCTGGCATTTGGTTGGAAACTCAT

FIG.18A(2)

GTTTGAAAATTACTACTGCCAAGGAGAATTATGACAATGCTAAATTGTTCTGTAGGAACCACAATGCCCTTTTGGCTTCTCTTACAACCCAG

AAGAAGGTAGAATTTGTCCTTAAGCAGCTGCGAATAATGCAGTCATCTCAGAGCATGTCCAAGCTCACCTTAACCCCATGGGTCGGCCTTCG

GAAGATCAATGTGTCCTACTGGTGCTGGGAAGATATGTCCCCATTTACAAATAGTTTACTACAGTGGATGCCGTCTGAGCCCAGTGATGCTG

GATTCTGTGGAATTTTATCAGAACCCAGTACTCGGGGACTGAAGGCTGCAACCTGCATCAACCCACTCAATGGTAGTGTCTGTGAAAGGCCT

GCAAACCACAGTGCTAAGCAGTGCCGGACACCATGTGCCTTGAGGACAGCATGTGGAGATTGCACCAGCGGCAGCTCTGAGTGCATGTGGTG

CAGCAACATGAAGCAGTGTGTGGACTCCAATGCCTATGTGGCCTCCTTCCCTTTTGGCCAGTGTATGGAATGGTATACGATGAGCACCTGCC

CCCCTGAAAATTGTTCAGGCTACTGTACCTGTAGTCATTGCTTGGAGCAACCAGGCTGTGGCTGGTGTACTGATCCCAGCAATACTGGCAAA

GGGAAATGCATAGAGGGTTCCTATAAAGGACCAGTGAAGATGCCTTCGCAAGCCCCTACAGGAAATTTCTATCCACAGCCCCTGCTCAATTC

CAGCATGTGTCTAGAGGACAGCAGATACAACTGGTCTTTCATTCACTGTCCAGCTTGCCAATGCAACGGCCACAGTAAATGCATCAATCAGA

GCATCTGTGAGAAGTGTGAGAACCTGACCACAGGCAAGCACTGCGAGACCTGCATATCTGGCTTCTACGGTGATCCCACCAATGGAGGGAAA

TGTCAGCCATGCAAGTGCAATGGGCACGCGTCTCTGTGCAACACCAACACGGGCAAGTGCTTCTGCACCACCAAGGGCGTCAAGGGGGACGA

GTGCCAGCTATGTGAGGTAGAAAATCGATACCAAGGAAACCCTCTCAGAGGAACATGTTATTATACTCTTCTTATTGACTATCAGTTCACCT

TTAGTCTATCCCAGGAAGATGATCGCTATTACACAGCTATCAATTTTGTGGCTACTCCTGACGAACAAAACAGGGATTTGGACATGTTCATC

FIG. 18A(3)

AATGCCTCCAAGAATTTCAACCTCAACATCACCTGGGCTGCCAGTTTCTCAGCTGGAACCCAGGCTGGAGAAGAGATGCCTGTTGTTTCAAA

AACCAACATTAAGGAGTACAAAGATAGTTTCTCTAATGAGAAGTTTGATTTTCGCAACCACCCAAATATCACTTTCTTTGTTTATGTCAGTA

ATTTCACCTGGCCCATCAAAATTCAGATTGCCTTCTCTCAGCACAGCAATTTTATGGACCTGGTACAGTTCTTCGTGACTTTCTTCAGTTGT

TTCCTCTCTTTGCTCCTGGTGGCTGCTGTGGTTTGGAAGATCAAACAAAGTTGTTGGGCCTCCAGACGTAGAGAGCAACTTCTTCGAGAGAT

GCAACAGATGGCCAGCCGTCCCTTTGCCTCTGTAAATGTCGCCTTGGAAACAGATGAGGAGCCTCCTGATCTTATTGGGGGGAGTATAAAGA

CTGTTCCCAAACCCATTGCACTGGAGCCGTGTTTTGGCAACAAAGCCGCTGTCCTCTCTGTGTTTGTGAGGCTCCCTCGAGGCCTGGGTGGC

ATCCCTCCTCCTGGGCAGTCAGGTCTTGCTGTGGCCAGCGCCCTGGTGGACATTTCTCAGCAGATGCCGATAGTGTACAAGGAGAAGTCAGG

AGCCGTGAGAAACCGGAAGCAGCAGCCCCCTGCACAGCCTGGGACCTGCATCTGATGCTGGGGCCAGGGACTCTCCCACGCACGAGCTAGTG

AGTGGCACACCAGAGCCATCTGCAGGGAAGGGCGTGGCGGGGAAATGGCTGTGCGGTGCGGGACGGAAGACTGGAAACCCTCAAAGCATCTG

ACTCACCTGCATGATCACAAGCTTTCTTTGACGGTTTCTCCCATCCGTGTTCCAGCATCTAACCTTTTACTTTTGCATAGGAAATACTTGAT

TTAATTACAGGTCCAGGGATGAGCTGATGGTTGCTGGAGGAGGCCAGTGTAGAGCCAGTGAGAGAACTAGGAATGACACTCAGGTTCACTGT

GGAAAACTGTTCTTGGGACTGTCTCAACTGTGCAAAAAACAAAAGATGGAGTGTTTACAAGTAGACATTCGTCATCAGTTGTTCTTGAACAT

GGTCTTTTAAAAACTAGTCAGATGAATTAACTTGTTTTCATCTGAAGCCTGCTATCTTTTTTAAAAGATGTGCTATTTATTCTTGCACGATT

FIG.18A(4)

TAGGCAATTATCTCTCTTCCAGGGAGTACCTTTTTTTCTAGTTGAGAATTAATAATGGTCCATCTCTTTTGATCATATCAAGCTAGGATAGA

AGGGGGGCTATTTTAAATGTCAAGGTCAGCAGTGTTACTTTGAATGTAAACTGGTATAATAGGTAGTTTTCTATAGTAACTTGATTAATTTA

GTCTTAATCCATTTGAAACTCTCTCTTCCTTTCTCTCTGCCTGTCCCTCTCCTTCTCCATCTCACCCTCCCTCTCTCACACATACACACACA

AACACATACACACAACACTAAGTGCCTAGACTTTAAATAGATCTAGCAATTGGAAAGTTAGTAAGCCTAAGTTTTTACATAATTGCATTCCT

ACATTCTTGTAAAATTTAAATAGCTACCATTGGCAATCTGCTTTTTTTCTAAAATCTGATTTGCAGCCAGGAAAGAATTTTCTCACCCAAGG

AACATTTGATCTAGCAGCAGGGATGAGAGGAAAGCAGAAATGAATGAACTGTGAAAGCTCCTGTTTTTATTATCAAAAAGGACACTGTCAAG

AAGGCGCCCCCTGCCCCCACCCCCGTGTCACCCTAGGCCTGATAAGCGATCAGAGGAAAGGACTCATTCATGTCACGCTTCCTTGAGCAGAA

AAGAGCACTGAGAGCACTTGGGACCCCTGGATCAGAGAGCATCTGTGTGTCCTGCAGCCTCCTCTGAACTTGTGGTTCATTCTCAGGCTGGG

GTGGACTCAGATGCCAGGAAAGGGACAGCCTCCCATTGTCAGGCAGAAGCTGCCCAAAGCCTGGAGAAGGACTTGTTTGCCCTCTTTCCCCC

AGGAGGGGCTCGACCCACCCACCCTCCCTCTCAGACCAAGGTGGTGGCTGTGAGGAGGGCAGCAAATGCTGACAAGGATGAAAAGCACATGG

AAAAAAATGGACGAGGAGGGAAAACTCTGCCAAATGGAAAATGACCAAATTTAAGAGGGTGGGACAGTCCCCTGCTCCTCTCCCAGAGGGCA

CTGCTTGGAAATTGTGTTTTCCCCATTTATGGTGCTCTGTATTCTGGCATTATGCAGCAGCCTCCCAGAAGCTCTCTTCTGCTTCAAAACCT

GGGATCTCTGGCATTACCCTATTGGGATGGACCGCTGGACAGCAATGCTCGAGTTTGTGAATTTGGAGAGATACTCAAAAGAGCTAAAACTG

FIG.18A(5)

CAGCATTTTACCTTTAAATGCAGTGCCTAGAGAGAGAGTATTGTCTCTTCCCCAACACTAACCCCACTCCCATGAAGAATTGCCTGGAAAGA

TGTTTTCAAGGAATTTGAACCATAAAACACTATCTGATGCACAGAACACCTCTACTTTGAGACTCACCTCTCATAAAGCTTCTTTTTCACAT

TACTGTTAAAGACCAGACGTTCTAGAAAAGACCCCTCCTCTCATGAGCTCCCCCATCCCTGCTACAGAACACAGCACCCATGGCGCCTGCAG

TGGACTGGCCCCTTAATTCCCACAGGCCCCCCCAGCAAGGCCAAAGGGAGGCCCCTGGGTATTGTCCTCCTACAAGGAAGATCCTCTTTGTT

TGTTCAAAGGACCAGTTTTCCTAGGCCAAAGAAGTCTCTTCCCCATGTTAGTCCTATGCCTTGAAATATCATGCACCATGACCCACAGCCAT

CTGGTTATGTCTTATTTTTTTCCTAAAAGATAATGTTTATTTTTAAAAAGGAAGGAAGAAGCAAGTGAAGTTTCATTCTGCTCCAGCGGTGG

GGAAGCCGCTGAATCCACCTGCTTCTCCTTTGCAACCGACAGCAAACAGCTTTCTCCGGCCTCAGGGCAGAAAAAGGGAATGGCAGGGAGTA

AGAGGCGCTGGGCTCGGAGCCTGTTTCCAAGAAGGAATTGGTTGTCATCTGGCAGTGTTGCGCGTCACAAGAGAGCCTGTATATAAATTAAA

ATAGTCAAGACAACACTGACCTTGCACTTGTACATAACTATACAGTAGTGTCCAGAATGTTCAGACATTCGGAGTGTACATAAAACAGAAAA

AATCTTCATGTATTTTTATTAAATATAACAATGTCTGAGTTTCACCTAAGATGTTTTTGTGCCATATGCTGGATATCCAGGTTCTCGCCAGG

CCCCGATACATGAATAACAAACCCAAGAAACGCATCCCCATTGTGTGATGTGTTCAGATGCATCTGGCACCAATTAGGTATTTCTTAAAACA

GGACTCATCTGTCAGAGTGCACATGAAAAATCAGGCAGGGAATCGAAACGACAGCGCTGGAGGAGACTCAGGAAGCAGAGGCGTCCCTGCCG

CTGCCCTTGGCCCTGCAAGCACATCATGACCCTTTCTGGCAGCCTCTTGGTGCTCTGGGTAGTGAGGGATGACCAGTCTTGTCCTGAGAAAT

FIG.18A(6)

GTTTCTCTTAGTCTTTAAGTTCAAAGACTAACCTGTAGCAATCAGACTTTCCAAAAGGGGGTTCTCCATTTTTTGTAGTTTTGTCTAAATTT

TTAATGACCATTTCCTGGAATCAGTTTATTATACTGAAAACTGGGGGTGGGAGTAGGGAGCTAGTTTGTTGATAAATAGTTCCCATTTCCCC

GTGGAGAATTTGACATACCCTGGACTCCTGTGTGCCTCCTGCCATCCCTGCACACAGCCTGGGGAGAAGCCTGTGCCTCCCCGTGTGGAGAG

AAGGCAACCCCAGATCCCCTGAGCTAACCCGGAGGAAAGGCAGTCCTGGACAGAAGACTGTCAGCAGAAGGAAAGTACTGGACTACCCGTGG

GTAAGTCCTGCCATTCAAGACTGGAGACACCTGGGAAATAAAAAGAGCAGGGCACTGCTGGTGGGAAGAGGCATTTTACCTTCCAGTGCAAA

TCCTGCTCCTTTGATTTAATGGGGTGTACTGGGGCCAGGGGCTGATTCACTTCCTTGGGAGATGGTGGTGTTTTCATGAACATCTTTGATCC

TTCCATTTCATTTATTCATCCATCCATTCAACAAGTATTTGCTAAACACTAACTTAAGCTAATGCTAGGGTAGTGACTGAGATGTAAAAATA

GATTTTAGAATTAAAACAAAATCCAAGTCCTCACACCCCTGTCATCCCAGGAGATCTTTCCTTGTGGTGGTTTCTGTGAGAATTGGCCATCC

TGAGGACACAGCCAGGACGGCAGAGGCCTCCTGGCCTCAGGGCATGCCCTGCCTACCTTCTGAAATGTTTACCCCATTGACCAAACTTGGCT

CCAGCCATTGCGGTGGTTTCTAGATAGCCAGGCCCACCAAGAGATATTGCCCCTTGATGAGAGTCAAACACCCTGCCTACAAGGAGATGTTT

TGAAATGGAGAGGAAAATTGGCACCTCATCTTTTAAAGGCAGTAATGGAATTGATTTTCAGTAACTGAATTTGTGCACAAAACATTCTAAAC

ACTAGTGAAGCCTGTTTCGTTGAACTAATTCTGGCTCTGGAAATGTTTTTGTTTTATAGTTATTTACGATTTCGTTTGTTTGGATTCAAGCT

TAGTTTGTTAATATGTATAATTTAGCATCTATTACACTCATGTAAATATGGAGTAAGTATTGTAAACTATTTCATTGCGGGGATTGTGGGTG

FIG.18A(7)

TTATACATACATTTAGGACTGCAATTTTTTGGTATTTTTTGTATTGTAAAATAACAGCTAATTTAAGCAGGAACAAGAGAACTAAGGGAGGT

CTGTGCATTTTTAAACACAAATGTGAAGAACTTGTATATAAACAAAAGTAAATACTATAATACAAACTTCCTTCTGAAATAAAAGTAGATCTG

GTAAAAAAAAAAAAAGAAAAAAAAAAAAAAAAA

FIG.18A(8)

MVAVAAAAATEARLRRRTAATAALAGRSGGPHRPCTATGAWRPGPRARLCLPRVLSRALPPPPLLPLLFSLLLLPLPREAEAAAVAAAVSGS

AAAEAKECDRPCVNGGRCNPGTGQCVCPAGWVGEQCQHCGGRFRLTGSSGFVTDGPGNYKYKTKCTWLIEGQPNRIMRLRFNHFATECSWDH

LYVYDGDSIYAPLVAAFSGLIVPERDGNETVPEVVATSGYALLHFFSDAAYNLTGFNITYSFDMCPNNCSGRGECKISNSSDTVECECSENW

KGEACDIPHCTDNCGFPHRGICNSSDVRGCSCFSDWQGPGCSVPVPANQSFWTREEYSNLKLPRASHKAVVNGNIMWVVGGYMFNHSDYNMV

LAYDLASREWLPLNRSVNNVVVRYGHSLALYKDKIYMYGGKIDSTGNVTNELRVFHIHNESWVLLTPKAKEQYAVVGHSAHIVTLKNGRVVM

LVIFGHCPLYGYISNVQEYDLDKNTWSILHTQGALVQGGYGHSSVYDHRTRALYVHGGYKAFSANKYRLADDLYRYDVDTQMWTILKDSRFF

RYLHTAVIVSGTMLVFGGNTHNDTSMSHGAKCFSSDFMAYDIACDRWSVLPRPDLHHDVNRFGHSAVLHNSTMYVFGGFNSLLLSDILVFTS

EQCDAHRSEAACLAAGPGIPCVWNTGSSQCISWALATDEQEEKLKSECFSKRTLDHDRCDQHTDCYSCTANTNDCHWCNDHCVPRNHSCSEG

QISIFRYENCPKDNPMYYCNKKTSCRSCALDQNCQWEPRNQECIALPENICGIGWHLVGNSCLKITTAKENTDNAKLFCRNHNALLASLTTQ

KKVEFVLKQLRIMQSSQSMSKLTLTPWVGLRKINVSYWCWEDMSPFTNSLLQWMPSEPSDAGFCGILSEPSTRGLKAATCINPLNGSVCERP

ANHSAKQCRTPCALRTACGDCTSGSSECMWCSNMKQCVDSNAYVASFPFGQCMEWYTMSTCPPENCSGYCTCSHCLEQPGCGWCTDPSNTGK

GKCIEGSYKGPVKMPSQAPTGNFYPQPLLNSSMCLEDSRYNWSFIHCPACQCNGHSKCINQSICEKCENLTTGKHCETCISGFYGDPTNGGK

CQPCKCNGHASLCNTNTGKCFCTTKGVKGDECQLCEVENRYQGNPLRGTCYYTLLIDYQFTFSLSQEDDRYYTAINFVATPDEQNRDLDMFI

FIG.18B

NASKNFNLNITWAASFSAGTQAGEEMPVVSKTNIKEYKDSFSNEKFDFRNHPNITFFVYVSNFTWPIKIQIAFSQHSNFMDLVQFFVTFFSC

FLSLLLVAAVVWKIKQSCWASRRREQLLREMQQMASRPFASVNVALETDEEPPDLIGGSIKTVPKPIALEPCFGNKAAVLSVFVRLPRGLGG

IPPPGQSGLAVASALVDISQQMPIVYKEKSGAVRNRKQQPPAQPGTCICWGQGLSHARASEWHTRAICREGRGGEMAVRCGTEDWKPSKHLT

HLHDHKLSLTVSPIRVPASNLLLLHRKYLILQVQGADGCWRRPVSQENEHSGSLWKTVLGTVSTVQKTKDGVFTSRHSSSVVLEHGLLKTSQ

MNLVFISLLSFLKDVLFILARFRQLSLFQGVPFFLVENWSISFDHIKLGKGGYFKCQGQQCYFECKLVVVFYSNLINLVLIHLKLSLPFSLP

VPLLLHLTLPLSHIHTQTHTHNTKCLDFKIQLESAVFTLHSYILVKFKLPLAICFFSKIFAARKEFSHPRNISSSRDERKAEMNELKLLFLL

SKRTLSRRRPLPPPPCHPRPDKRSEERTHSCHASLSRKEHEHLGPLDQRASVCPAASSELVVHSQAGVDSDARKGTASHCQAEAAQSLEKDL

FALFPPGGARPTHPPSQTKVVAVRRAANADKDEKHMEKNGRGGKTLPNGKPNLRGWDSPLLLSQRALLGNCVFPIYGALYSGIMQQPPRSSL

LLQNLGSLALPYWDGPLDSNARVCEFGEILKRAKTAAFYLMQCLEREYCLFPNTNPTPMKNCLERCFQGITIKHYLMHRTPLLDSPLIKLLF

HITVKDQTFKRPLLSAPPSLLQNTAPMAPAVDWPLNSHRPPQQGQREAPGYCPPTRKILFVCSKDQFSAKEVSSPCSYALKYHAPPTAIWLC

LIFFLKDNVYFKGRKKQVKFHSAPAVGKPLNPPASPLQPTANSFLRPQGRKREWQGVRGAGLGACFQEGIGCHLAVLRVTREPVYKLKSRQH

PCTCTLYSSVQNVQTFGVYIKQKKSSCIFIKYNNVVSPKMFLCHMLDIQVLARPRYMNNKPKKRIPIVCVQMHLAPIRYFLKQDSSVRVHMK

NQAGNRNDSAGGDSGSRGVPAAALGPASTSPFLAASWCSGGMTSLVLRNVSLSLVQRLTCSNQTFQKGVLHFLFCLNFPFPGISLLYKLGVG

FIG.18C

VGSFVDKFPFPRGEFDIPWTPVCLLPSLHTAWGEACASPCGEKATPDPLSPGGKAVLDRRLSAEGKYWTTRGVLPFKTGDTWEIKRAGHCWW

EEAFYLPVQILLLFNGVYWGQGLIHFLGRWWCFHEHLSFHFIYSSIHSTSICTLTANARVVTEMKILELKQNPSPHTPVIPGDLSLWWFLEL

AILRTQPGRQRPPGLRACPAYLLKCLPHPNLAPAIAVVSRPGPPRDIAPESNTLPTRRCFEMERKIGTSSFKGSNGIDFQLNLCTKHSKHSL

FRTNSGSGNVFVLLFTISFVWIQAFVNMYNLASITLMIWSKYCKLFHCGDCGCYTYIDCNFLVFFVLNNSFKQEQENGRSVHFKHKCEELVY

KQKILYKLPSEIKVDLVKKKKEKKKKK

FIG.18D

ATGGTGGCGGTGGCCGCAGCGGCGGCAACTGAGGCAAGGCTGAGGAGGAGGACGGCGGCGACGGCAGCGCTCGCGGGCAGGAGCGGCGGGCCGCACCGACCCTGCACC

GCGACAGGGGCCTGGAGGCCGGGACCGCGCGCCCGGCTGTGTCTCCCGCGGGTGCTGTCGCGGGCGCTGCCCCCGCCGCCGCTGCTGCCGCTGCTCTTTTCGCTGCTG

CTGCTGCCGCTGCCCCGGGAGGCCGAGGCCGCTGCGGTGGCGGCGGCGGTGTCCGGCTCGGCCGCAGCCGAGGCCAAGGAATGTGACCGGCCGTGTGTCAACGGCGGT

CGCTGCAACCCTGGCACCGGCCAGTGCGTCTGCCCCGCCGGCTGGGTGGGCGAGCAATGCCAGCACTGCGGGGGCCGCTTCAGACTAACTGGATCTTCTGGGTTTGTG

ACAGATGGACCTGGAAATTATAAATACAAAACGAAGTGCACGTGGCTCATTGAAGGACAGCCAAATAGAATAATGAGACTTCGTTTCAATCATTTTGCTACAGAGTGT

AGTTGGGACCATTTATATGTTTATGATGGGGACTCAATTTATGCACCGCTAGTTGCTGCATTTAGTGGCCTCATTGTTCCTGAGAGAGATGGCAATGAGACTGTCCCT

GAGGTTGTTGCCACATCAGGTTATGCCTTGCTGCATTTTTTTAGTGATGCTGCTTATAATTTGACTGGATTTAATATTACTTACAGTTTTGATATGTGTCCAAATAAC

TGCTCAGGCCGAGGAGAGTGTAAGATCAGTAATAGCAGCGATACTGTTGAATGTGAATGTTCTGAAAACTGGAAAGGTGAAGCATGTGACATTCCTCACTGTACAGAC

AACTGTGGTTTTTCCTCATCGAGGCATCTGCAATTCAAGTGATGTCAGAGGATGCTCCTGCTTCTCAGACTGGCAGGGTCCTGGATGTTCAGTTCCTGTACCAGCTAAC

CAGTCATTTTGGACTCGAGAGGAATATTCTAACTTAAAGCTCCCCAGAGCATCTCATAAAGCTGTGGTCAATGGAAACATTATGTGGGTTGTTGGAGGATATATGTTC

AACCACTCAGATTATAACATGGTTCTAGCGTATGACCTTGCTTCTAGGGAGTGGCTTCCACTAAACCGTTCTGTGAACAATGTGGTTGTTAGATATGGTCATTCTTTG

GCATTATACAAGGATAAAATTTACATGTATGGAGGAAAAATTGATTCAACTGGGAATGTGACCAATGAGTTGAGAGTTTTTCACATTCATAATGAGTCATGGGTGTTG

TTGACCCCTAAGGCAAAGGAGCAGTATGCAGTGGTTGGGCACTCTGCACACATTGTTACACTGAAGAATGGCCGAGTGGTCATGCTGGTCATCTTTGGTCACTGCCCT

FIG.19A

CTCTATGGATATATAAGCAATGTGCAGGAATATGATTTGGATAAGAACACATGGAGTATATTACACACCCAGGGTGCCCTTGTGCAAGGGGGTTACGGCCATAGCAGT

GTTTACGACCATAGGACCAGGGCCCTATACGTTCATGGTGGCTACAAGGCTTTCAGTGCCAATAAGTACCGGCTTGCAGATGATCTCTACCGATATGATGTGGATACC

CAGATGTGGACCATTCTTAAGGACAGCCGATTTTTCCGTTACTTGCACACAGCTGTGATAGTGAGTGGAACCATGCTGGTGTTTGGGGGAAACACACACAATGACACA

TCTATGAGCCATGGCGCCAAATGCTTCTCTTCAGATTTCATGGCCTATGACATTGCCTGTGACCGCTGGTCAGTGCTTCCCAGACCTGATCTCCACCATGATGTCAAC

AGATTTGGCCATTCAGCAGTCTTACACAACAGCACCATGTATGTGTTCGGTGGTTTCAATAGTCTCCTCCTCAGCGACATCCTGGTATTCACCTCGGAACAGTGTGAT

GCGCATCGGAGTGAAGCCGCTTGTTTAGCAGCAGGACCTGGTATTCGGTGTGTGTGGAACACAGGGTCGTCTCAGTGTATCTCGTGGGCGCTGGCAACTGATGAACAA

GAAGAAAAGTTAAAATCAGAATGTTTTTCCAAAAGAACTCTTGACCATGACAGATGTGACCAGCACACAGATTGTTACAGCTGCACAGCCAACACCAATGACTGCCAC

TGGTGCAATGACCATTGTGTCCCCAGGAACCACAGCTGCTCAGAAGGCCAGATCTCCATTTTTAGGTATGAGAATTGCCCCAAGGATAACCCTATGTACTACTGTAAC

AAGAAGACCAGCTGCAGGAGCTGTGCCCTGGACCAGAACTGCCAGTGGGAGCCCCGGAATCAGGAGTGCATTGCCCTGCCCGAAAATATCTGTGGCATTGGCTGGCAT

TTGGTTGGAAACTCATGTTTGAAAATTACTACTGCCAAGGAGAATTATGACAATGCTAAATTGTTCTGTAGGAACCACAATGCCCTTTTGGCTTCTCTTACAACCCAG

AAGAAGGTAGAATTTGTCCTTAAGCAGCTGCGAATAATGCAGTCATCTCAGAGCATGTCCAAGCTCACCTTAACCCCATGGGTCGGCCTTCGGAAGATCAATGTGTCC

TACTGGTGCTGGGAAGATATGTCCCCATTTACAAATAGTTTACTACAGTGGATGCCGTCTGAGCCCAGTGATGCTGGATTCTGTGGAATTTTATCAGAACCCAGTACT

CGGGGACTGAAGGCTGCAACCTGCATCAACCCACTCAATGGTAGTGTCTGTGAAAGGCCTGCAAACCACAGTGCTAAGCAGTGCCGGACACCATGTGCCTTGAGGACA

FIG. 19B

GCATGTGGAGATTGCACCAGCGGCAGCTCTGAGTGCATGTGGTGCAGCAACATGAAGCAGTGTGTGGACTCCAATGCCTATGTGGCCTCCTTCCCTTTTGGCCAGTGT

ATGGAATGGTATACGATGAGCACCTGCCCCCCTGAAAATTGTTCAGGCTACTGTACCTGTAGTCATTGCTTGGAGCAACCAGGCTGTGGCTGGTGTACTGATCCCAGC

AATACTGGCAAAGGGAAATGCATAGAGGGTTCCTATAAAGGACCAGTGAAGATGCCTTCGCAAGCCCCTACAGGAAATTTCTATCCACAGCCCCTGCTCAATTCCAGC

ATGTGTCTAGAGGACAGCAGATACAACTGGTCTTTCATTCACTGTCCAGCTTGCCAATGCAACGGCCACAGTAAATGCATCAATCAGAGCATCTGTGAGAAGTGTGAG

AACCTGACCACAGGCAAGCACTGCGAGACCTGCATATCTGGCTTCTACGGTGATCCCACCAATGGAGGGAAATGTCAGCCATGCAAGTGCAATGGGCACGCGTCTCTG

TGCAACACCAACACGGGCAAGTGCTTCTGCACCACCAAGGGCGTCAAGGGGGACGAGTGCCAGCTATGTGAGGTAGAAAATCGATACCAAGGAAACCCTCTCAGAGGA

ACATGTTATTATACTCTTCTTATTGACTATCAGTTCACCTTTAGTCTATCCCAGGAAGATGATCGCTATTACACAGCTATCAATTTTGTGGCTACTCCTGACGAACAA

AACAGGGATTTGGACATGTTCATCAATGCCTCCAAGAATTTCAACCTCAACATCACCTGGGCTGCCAGTTTCTCAGCTGGAACCCAGGCTGGAGAAGAGATGCCTGTT

GTTTCAAAAACCAACATTAAGGAGTACAAAGATAGTTTCTCTAATGAGAAGTTTGATTTTCGCAACCACCCAAATATCACTTTCTTTGTTTATGTCAGTAATTTCACC

TGGCCCATCAAAATTCAGGTGCAAACTGAACAATGAGGACGCATGGACACAGGAAGGGGAACATCACACACCAGGGCCTGTTGTGGGGTGGGGGGAAGGGGAAGGGAT

AGCATTAGGGGATATACCTAATGTTAAATGACGAGTTAATGGGTGCAGCACACCAACATGGCATATGTATACATATGTAACAAACCTGCATGTTGTGCACATGTACCC

TAAAACTTAAAGTATAATTAAAAAAAAAAAAAGAAAAAAAAAAAAAAAAAAAAAAAAAAAAAAAAAAAAAAAAAAA

FIG.19C

MVAVAAAAATEARLRRRTAATAALAGRSGGPHRPCTATGAWRPGPRARLCLPRVLSRALPPPPLLPLLFSLLLLPLPREAEAAAVAAAVSGSAAAEAKECDRPCVNGG

RCNPGTGQCVCPAGWVGEQCQHCGGRFRLTGSSGFVTDGPGNYKYKTKCTWLIEGQPNRIMRLRFNHFATECSWDHLYVYDGDSIYAPLVAAFSGLIVPERDGNETVP

EVVATSGYALLHFFSDAAYNLTGFNITYSFDMCPNNCSGRGECKISNSSDTVECECSENWKGEACDIPHCTDNCGFPHRGICNSSDVRGCSCFSDWQGPGCSVPVPAN

QSFWTREEYSNLKLPRASHKAVVNGNIMWVVGGYMFNHSDYNMVLAYDLASREWLPLNRSVNNVVVRYGHSLALYKDKIYMYGGKIDSTGNVTNELRVFHIHNESWVL

LTPKAKEQYAVVGHSAHIVTLKNGRVVMLVIFGHCPLYGYISNVQEYDLDKNTWSILHTQGALVQGGYGHSSVYDHRTRALYVHGGYKAFSANKYRLADDLYRYDVDT

QMWTILKDSRFFRYLHTAVIVSGTMLVFGGNTHNDTSMSHGAKCFSSDFMAYDIACDRWSVLPRPDLHHDVNRFGHSAVLHNSTMYVFGGFNSLLLSDILVFTSEQCD

AHRSEAACLAAGPGIRCVWNTGSSQCISWALATDEQEEKLKSECFSKRTLDHDRCDQHTDCYSCTANTNDCHWCNDHCVPRNHSCSEGQISIFRYENCPKDNPMYYCN

KKTSCRSCALDQNCQWEPRNQECIALPENICGIGWHLVGNSCLKITTAKENYDNAKLFCRNHNALLASLTTQKKVEFVLKQLRIMQSSQSMSKLTLTPWVGLRKINVS

YWCWEDMSPFTNSLLQWMPSEPSDAGFCGILSEPSTRGLKAATCINPLNGSVCERPANHSAKQCRTPCALRTACGDCTSGSSECMWCSNMKQCVDSNAYVASFPFGQC

MEWYTMSTCPPENCSGYCTCSHCLEQPGCGWCTDPSNTGKGKCIEGSYKGPVKMPSQAPTGNFYPQPLLNSSMCLEDSRYNWSFIHCPACQCNGHSKCINQSICEKCE

NLTTGKHCETCISGFYGDPTNGGKCQPCKCNGHASLCNTNTGKCFCTTKGVKGDECQLCEVENRYQGNPLRGTCYYTLLIDYQFTFSLSQEDDRYYTAINFVATPDEQ

NRDLDMFINASKNFNLNITWAASFSAGTQAGEEMPVVSKTNIKEYKDSFSNEKFDFRNHPNITFFVYVSNFTWPIKIQVQTEQGRMDTGRGTSHTRACCGVGGRGRDS

IRGYTCMTSWVQHTNMAYVYICNKPACCAHVPNLKYNKKKKKKKKKKKKKKKKKK

FIG.19D

ATGGTGGCGGTGGCCGCAGCGGCGGCAACTGAGGCAAGGCTGAGGAGGAGGACGGCGGCGACGGCAGCGCTCGCGGGCAGGAGCGGCGGGCCGCACCGACCCTGCACC

GCGACAGGGGCCTGGAGGCCGGGACCGCGCGCCCGGCTGTGTCTCCCGCGGGTGCTGTCGCGGGCGCTGCCCCCGCCGCCGCTGCTGCCGCTGCTCTTTTCGCTGCTG

CTGCTGCCGCTGCCCCGGGAGGCCGAGGCCGCTGCGGTGGCGGCGGCGGTGTCCGGCTCGGCCGCAGCCGAGGCCAAGGAATGTGACCGGCCGTGTGTCAACGGCGGT

CGCTGCAACCCTGGCACCGGCCAGTGCGTCTGCCCCGCCGGCTGGGTGGGCGAGCAATGCCAGCACTGCGGGGGCCGCTTCAGACTAACTGGATCTTCTGGGTTTGTG

ACAGATGGACCTGGAAATTATAAATACAAAACGAAGTGCACGTGGCTCATTGAAGGACAGCCAAATAGAATAATGAGACTTCGTTTCAATCATTTTGCTACAGAGTGT

AGTTGGGACCATTTATATGTTTATGATGGGGACTCAATTTATGCACCGCTAGTTGCTGCATTTAGTGGCCTCATTGTTCCTGAGAGAGATGGCAATGAGACTGTCCCT

GAGGTTGTTGCCACATCAGGTTATGCCTTGCTGCATTTTTTTAGTGATGCTGCTTATAATTTGACTGGATTTAATATTACTTACAGTTTTGATATGTGTCCAAATAAC

TGCTCAGGCCGAGGAGAGTGTAAGATCAGTAATAGCAGCGATACTGTTGAATGTGAATGTTCTGAAAACTGGAAAGGTGAAGCATGTGACATTCCTCACTGTACAGAC

AACTGTGGTTTTCCTCATCGAGGCATCTGCAATTCAAGTGATGTCAGAGGATGCTCCTGCTTCTCAGACTGGCAGGGTCCTGGATGTTCAGTTCCTGTACCAGCTAAC

CAGTCATTTTGGACTCGAGAGGAATATTCTAACTTAAAGCTCCCCAGAGCATCTCATAAAGCTGTGGTCAATGGAAACATTATGTGGGTTGTTGGAGGATATATGTTC

AACCACTCAGATTATAACATGGTTCTAGCGTATGACCTTGCTTCTAGGGAGTGGCTTCCACTAAACCGTTCTGTGAACAATGTGGTTGTTAGATATGGTCATTCTTTG

GCATTATACAAGGATAAAATTTACATGTATGGAGGAAAAATTGATTCAACTGGGAATGTGACCAATGAGTTGAGAGTTTTTCACATTCATAATGAGTCATGGGTGTTG

TTGACCCCTAAGGCAAAGGAGCAGTATGCAGTGGTTGGGCACTCTGCACACATTGTTACACTGAAGAATGGCCGAGTGGTCATGCTGGTCATCTTTGGTCACTGCCCT

FIG.20A

CTCTATGGATATATAAGCAATGTGCAGGAATATGATTTGGATAAGAACACATGGAGTATATTACACACCCAGGGTGCCCTTGTGCAAGGGGGTTACGGCCATAGCAGT

GTTTACGACCATAGGACCAGGGCCCTATACGTTCATGGTGGCTACAAGGCTTTCAGTGCCAATAAGTACCGGCTTGCAGATGATCTCTACCGATATGATGTGGATACC

CAGATGTGGACCATTCTTAAGGACAGCCGATTTTTCCGTTACTTGCACACAGCTGTGATAGTGAGTGGAACCATGCTGGTGTTTGGGGGAAACACACACAATGACACA

TCTATGAGCCATGGCGCCAAATGCTTCTCTTCAGATTTCATGGCCTATGACATTGCCTGTGACCGCTGGTCAGTGCTTCCCAGACCTGATCTCCACCATGATGTCAAC

AGATTTGGCCATTCAGCAGTCTTACACAACAGCACCATGTATGTGTTCGGTGGTTTCAATAGTCTCCTCCTCAGCGACATCCTGGTATTCACCTCGGAACAGTGTGAT

GCGCATCGGAGTGAAGCCGCTTGTTTAGCAGCAGGACCTGGTATTCGGTGTGTGTGGAACACAGGGTCGTCTCAGTGTATCTCGTGGGCGCTGGCAACTGATGAACAA

GAAGAAAAGTTAAAATCAGAATGTTTTTCCAAAAGAACTCTTGACCATGACAGATGTGACCAGCACACAGATTGTTACAGCTGCACAGCCAACACCAATGACTGCCAC

TGGTGCAATGACCATTGTGTCCCCAGGAACCACAGCTGCTCAGAAGGCCAGATCTCCATTTTTAGGTATGAGAATTGCCCCAAGGATAACCCTATGTACTACTGTAAC

AAGAAGACCAGCTGCAGGAGCTGTGCCCTGGACCAGAACTGCCAGTGGGAGCCCCGGAATCAGGAGTGCATTGCCCTGCCCGGTAGGCCTTGCAGGGTCATCTTGGTG

TGTGTGGGTCCATTACTTCAGCCTGCTTCCCCCAACACTGTGCAGCCTAAGTTGAACCTAGCAGAGGGGAAGAGCTAATTCTGTCCATTCATCCCCCACACGAGTATT

ATGGGCTTTTTTGTTTTTAACTAAAATACAGTTCTTAAGTATTTGTTCCTACTGTCCTTTGAAATAAAGTGAAACATCCTTTGCTGCTCTGTAAAAAAAAAAAAAAAA

AAAAAAAAAAAAAAAAAAAAAAAAAAAAAAAA

FIG.20B

MVAVAAAAATEARLRRRTAATAALAGRSGGPHRPCTATGAWRPGPRARLCLPRVLSRALPPPPLLPLLFSLLLLPLPREAEAAAVAAAVSGSAAAEAKECDRPCVNGG

RCNPGTGQCVCPAGWVGEQCQHCGGRFRLTGSSGFVTDGPGNYKYKTKCTWLIEGQPNRIMRLRFNHFATECSWDHLYVYDGDSIYAPLVAAFSGLIVPERDGNETVP

EVVATSGYALLHFFSDAAYNLTGFNITYSFDMCPNNCSGRGECKISNSSDTVECECSENWKGEACDIPHCTDNCGFPHRGICNSSDVRGCSCFSDWQGPGCSVPVPAN

QSFWTREEYSNLKLPRASHKAVVNGNIMWVVGGYMFNHSDYNMVLAYDLASREWLPLNRSVNNVVVRYGHSLALYKDKIYMYGGKIDSTGNVTNELRVFHIHNESWVL

LTPKAKEQYAVVGHSAHIVTLKNGRVVMLVIFGHCPLYGYISNVQEYDLDKNTWSILHTQGALVQGGYGHSSVYDHRTRALYVHGGYKAFSANKYRLADDLYRYDVDT

QMWTILKDSRFFRYLHTAVIVSGTMLVFGGNTHNDTSMSHGAKCFSSDFMAYDIACDRWSVLPRPDLHHDVNRFGHSAVLHNSTMYVFGGFNSLLLSDILVFTSEQCD

AHRSEAACLAAGPGIRCVWNTGSSQCISWALATDEQEEKLKSECFSKRTLDHDRCDQHTDCYSCTANTNDCHWCNDHCVPRNHSCSEGQISIFRYENCPKDNPMYYCN

KKTSCRSCALDQNCQWEPRNQECIALPGRPCRVILVCVGPLLQPASPNTVQPKLNLAEGKSFCPFIPHTSIMGFFVFNNTVLKYLFLLSFEIKNILCCSVKKKKKKKK

KKKKKKKK

FIG.20C

```
                            SEQUENCE LISTING

<160> NUMBER OF SEQ ID NOS: 131

<210> SEQ ID NO: 1
<211> LENGTH: 8827
<212> TYPE: DNA
<213> ORGANISM: Mus musculus

<400> SEQUENCE: 1

gaattccggg cgaaggggag ccggcgtgcg gggtgtgtat gtgttcgctg ggcgccggct      60

cagccccagg aagatggtgg cggtggcggc ggcggcggcg actgaggcgc ggctgagggg     120

gagcacgagg acgacagcag cgcctgcggg caggaagggc aggcagcacc gaccctgcac     180

cgcgacaggg gcctggaggc cgggaccgcg cgcccggctg tgtctcccgc gggtgctgtc     240

gcgggcgctg cccccgccgc cgctgctgcc gctgctcttt tcgctgctgc tgctgccgct     300

gccccgggag gccgaggccg ctgcggtggc ggcggcggtg tccggctcgg ccgcagccga     360

ggccaaggaa tgtgaccggc cgtgtgtcaa cggcggccgc tgcaaccctg gcaccggcca     420

gtgcgtctgc cccacgggct gggtgggcga gcaatgccag cactgcgggg gccgcttcag     480

gacatctgtc tcacgcctat aatcacagct gttcggaagg tgaggctgga ggaacagttc     540

gaggcaagct tcggctacag aataagttca agagtaacct ggggcaactt gggcttgtct     600

ccaaaaccaa aatgagcgaa aaggagcaag ctagagtctt ttgggaaaat tttagctgac     660

taattttca ccgagaacta actggctctt ctggatttgt aacagatgga cctgggaatt     720

ataaatataa gacgaagtgc acatggctca ttgaaggaca gccaaataga ataatgagac     780

ttcgcttcaa ccattttgct acagaatgta gctgggacca tttatatgtt tatgatgggg     840

actcaatcta cgcacctctg attgctgcct ttagtggcct cattgttcct gaaagagatg     900

gcaatgagac ggctcctgag gtcactgtca cttcaggtta tgcactgctg cattttttca     960

gtgatgctgc ttataatctg actggattta atatcactta caattttgac atgtgtccga    1020

ataattgctc aggccgagga gagtgtaaga gcagtaacag cagcagcgct gttgagtgtg    1080

aatgttctga aaactggaaa ggggagtcgt gtgacattcc tcactgtaca gacaactgtg    1140

gctttcctca ccgaggcatc tgtaatgcaa gcgataccag agggtgctcc tgctttcctc    1200

actggcaggg tcctggatgt tcaattcctg tgccagctaa ccagtctttt tggactcgag    1260

aagaatattc tgatttaaag cttcccagag cctctcataa agctgtggtc aatggaaata    1320

taatgtgggt tgttggcgga tatatgttca accattcaga ttacagcatg gttttagcgt    1380

atgacctgac ttctagggaa tggcttccac taaaccattc tgtgaacagt gtggttgtaa    1440

gatatggtca ttctttggca ttacataagg ataaaatcta catgtatgga ggaaaaattg    1500

attcaacagg gaacgtgacc aatgagctga gagtatttca tattcataat gaatcatggg    1560
```

-continued

```
tattgttaac tccgaaagct aaggatcagt atgcagtggt tggacactca gcacacattg   1620
ttacactggc atctggccgt gtggtcatgt tggtcatctt cggtcattgc ccactctatg   1680
gatatataag cgttgtgcag gaatatgact tggaaaagaa cacatggagt atattacata   1740
ctcagggtgc tcttgtgcaa gggggttatg gccacagtag tgtttatgat gacaggacca   1800
aggctctgta cgttcatggt ggctacaagg ctttcagcgc caacaaatac cggcttgcag   1860
atgacctcta cagatacgat gtggatactc agatgtggac cattcttaag gacagccgat   1920
ttttccgtta cttgcataca gctgtgatag tgagtggaac catgctggtg tttggaggga   1980
acacacacaa tgacacttcc atgagccacg gtgccaaatg cttctcctcg gacttcatgg   2040
cttatgacat tgcttgtgac cgatggtcag tgcttcccag acctgagctc catcatgatg   2100
tcaacagatt tggccattca gcagtcttgt acaacagcac catgtatgtg ttcggcggct   2160
tcaacagcct cctcctcagt gacgtcttgg tctttacctc ggagcagtgc gatgcacacc   2220
gcagtgaagc tgcttgtgtg gcagcaggac ctggtatccg gtgtctgtgg gacacacagt   2280
cgtctcgatg tacctcctgg gagttggcaa ctgaagaaca agcagaaaag ttaaaatcag   2340
agtgtttttc taaaagaacc cttgaccatg acagatgtga ccagcacaca gattgttaca   2400
gctgcacagc caataccaat gactgccact ggtgcaatga tcactgtgtc cctgtgaacc   2460
acagctgcac agaaggccag atctccattg ccaagtatga gagttgcccc aaggataacc   2520
ccatgtacta ctgcaataag aaaaccagct gcaggagctg tgccctagac cagaactgcc   2580
agtgggagcc ccggaatcaa gagtgcatcg ccctgccgga aaatatctgt ggcaatggct   2640
ggcatttggt tggaaactcg tgtctgaaaa tcactactgc taaggagaat tatgacaatg   2700
ctaaattgtc ctgtaggaac cacaatgcct tttggcttc cctcacatcc cagaagaagg    2760
tggagtttgt ccttaagcag cttcgattaa tgcaatcatc tcaaagtatg tccaagctca   2820
ctctgactcc atgggttggt cttcggaaga tcaatgtgtc ttactggtgc tgggaggata   2880
tgtctccatt cacaaatagt ttgctgcagt ggatgccatc tgagcccagt gatgctggct   2940
tctgtgggat cttgtcagag cctagtactc ggggattaaa ggctgcaacc tgcatcaacc   3000
ctctcaatgg cagcgtctgt gaaaggcctg caaaccacag tgccaagcag tgccggacac   3060
catgtgccct gcggacagcg tgtggcgagt gcactagcag cagctcggag tgcatgtggt   3120
gcagtaacat gaagcagtgt gtggactcca atgcctacgt ggcctccttc ccttttggcc   3180
agtgtatgga atggtatacg atgagcagct gcccacctga aaattgctct ggctactgta   3240
cctgcagcca ttgcttggag cagccaggct gtggttggtg tactgatcct agcaatactg   3300
ggaaaggaaa atgtattgag ggcagctata aaggacctgt gaagatgccg tcacaggcct   3360
ctgcaggaaa tgtgtatcca cagccccttc tgaactccag catgtgtcta gaggacagca   3420
gatacaactg gtctttcatt cactgtccag cttgccagtg caacggacac agcaaatgca   3480
tcaaccagag tatctgtgag aagtgtgagg acctgaccac gggcaagcac tgcgagacct   3540
gcatatctgg cttctatggt gacccgacta atggaggcaa atgtcagcca tgcaagtgca   3600
atgggcacgc atcactgtgc aacaccaaca ccggcaagtg cttctgtacc accaaaggtg   3660
tcaaggggga cgagtgccag ctatgtgagg tagaaaatcg ataccaagga aaccctctca   3720
aaggaacatg ctactatacc cttctcattg actatcagtt cacctttagc ctgtcccagg   3780
aagacgaccg ctactacaca gccatcaact ttgtggctac tcctgatgaa caaaacaggg   3840
atttggacat gttcatcaat gcctccaaaa acttcaacct caacatcacc tgggccacca   3900
gcttcccagc cggaacccag actggagaag aggtgcctgt tgtttcaaaa accaacatca   3960
```

-continued

```
aggaatacaa agatagcttc tctaatgaga aatttgattt tcgcaaccat ccaaacatca   4020
ctttctttgt ttatgtcagt aatttcactt ggcccatcaa aattcagatt gccttctccc   4080
agcacagcaa cttcatggac ctggtacagt tcttcgtgac tttcttcagt tgtttcctct   4140
cgctgcttct ggtggctgca gtggtctgga agatcaagca gagctgttgg gcatccaggc   4200
ggagagagca acttcttcgg gagatgcaac agatggccag ccgcccottt gcttctgtaa   4260
acgttgcctt ggaaacagat gaggagcctc ctgatcttat tggggggagt ataaagactg   4320
ttcccaaacc cattgcactg gagccgtgtt ttggcaacaa agccgctgtc ctctctgtgt   4380
ttgtgaggct ccctcgaggc ctgggtggca tccctcctcc tgggcagtca ggtcttgctg   4440
tggccagcgc cctggtggac atttctcagc agatgccgat agtgtacaag gagaagtcag   4500
gagccgtgag aaaccggaag cagcagcccc ctgcacagcc tgggacctgc atctgatgct   4560
ggggccaggg actctcccac gcacgagcta gtgagtggca caccagagcc atctgcaggg   4620
aagggcgtgg cggggaaatg gctgtgcggt gcgggacgga agactggaaa ccctcaaagc   4680
atctgactca cctgcatgat cacaagcttt ctttgacggt ttctcccatc cgtgttccag   4740
catctaacct tttacttttg cataggaaat acttgattta attacaggtc cagggatgag   4800
ctgatggttg ctggaggagg ccagtgtaga gccagtgaga gaactaggaa tgacactcag   4860
gttcactgtg gaaaactgtt cttgggactg tctcaactgt gcaaaaaaca aaagatggag   4920
tgtttacaag tagacattcg tcatcagttg ttcttgaaca tggtctttta aaaactagtc   4980
agatgaatta acttgttttc atctgaagcc tgctatcttt tttaaaagat gtgctattta   5040
ttcttgcacg atttaggcaa ttatctctct tccagggagt accttttttt ctagttgaga   5100
attaataatg gtccatctct tttgatcata tcaagctagg atagaagggg ggctatttta   5160
aatgtcaagg tcagcagtgt tactttgaat gtaaactggt ataataggta gttttctata   5220
gtaacttgat taatttagtc ttaatccatt tgaaactctc tcttcctttc tctctgcctg   5280
tccctctcct tctccatctc accctccctc tctcacacat acacacacaa acacatacac   5340
acaacactaa gtgcctagac tttaaataga tctagcaatt ggaaagttag taagcctaag   5400
tttttacata attgcattcc tacattcttg taaaatttaa atagctacca ttggcaatct   5460
gctttttttc taaaatctga tttgcagcca ggaaagaatt ttctcaccca aggaacattt   5520
gatctagcag cagggatgag aggaaagcag aaatgaatga actgtgaaag ctcctgtttt   5580
tattatcaaa aaggacactg tcaagaaggc gccccctgcc cccacccccg tgtcacccta   5640
ggcctgataa gcgatcagag gaaaggactc attcatgtca cgcttccttg agcagaaaag   5700
agcactgaga gcacttggga cccctggatc agagagcatc tgtgtgtcct gcagcctcct   5760
ctgaacttgt ggttcattct caggctgggg tggactcaga tgccaggaaa gggacagcct   5820
cccattgtca ggcagaagct gcccaaagcc tggagaagga cttgtttgcc ctctttcccc   5880
caggaggggc tcgacccacc caccctccct ctcagaccaa ggtggtggct gtgaggaggg   5940
cagcaaatgc tgacaaggat gaaaagcaca tggaaaaaaa tggacgagga gggaaaactc   6000
tgccaaatgg aaaatgacca aatttaagag ggtgggacag tcccctgctc ctctcccaga   6060
gggcactgct tggaaattgt gttttcccca tttatggtgc tctgtattct ggcattatgc   6120
agcagcctcc cagaagctct cttctgcttc aaaacctggg atctctggca ttaccctatt   6180
gggatggacc gctggacagc aatgctcgag tttgtgaatt tggagagata ctcaaaagag   6240
ctaaaactgc agcattttac ctttaaatgc agtgcctaga gagagagtat tgtctcttcc   6300
```

-continued

```
ccaacactaa ccccactccc atgaagaatt gcctggaaag atgttttcaa ggaatttgaa   6360
ccataaaaca ctatctgatg cacagaacac ctctactttg agactcacct ctcataaagc   6420
ttctttttca cattactgtt aaagaccaga cgttctagaa aagacccctc ctctcatgag   6480
ctcccccatc cctgctacag aacacagcac ccatggcgcc tgcagtggac tggcccctta   6540
attcccacag gcccccccag caaggccaaa gggaggcccc tgggtattgt cctcctacaa   6600
ggaagatcct ctttgtttgt tcaaaggacc agttttccta ggccaaagaa gtctcttccc   6660
catgttagtc ctatgccttg aaatatcatg caccatgacc cacagccatc tggttatgtc   6720
ttattttttt cctaaaagat aatgtttatt tttaaaaagg aaggaagaag caagtgaagt   6780
ttcattctgc tccagcggtg gggaagccgc tgaatccacc tgcttctcct ttgcaaccga   6840
cagcaaacag ctttctccgg cctcagggca gaaaaaggga atggcaggga gtaagaggcg   6900
ctgggctcgg agcctgtttc caagaaggaa ttggttgtca tctggcagtg ttgcgcgtca   6960
caagagagcc tgtatataaa ttaaaatagt caagacaaca ctgaccttgc acttgtacat   7020
aactatacag tagtgtccag aatgttcaga cattcggagt gtacataaaa cagaaaaaat   7080
cttcatgtat ttttattaaa tataacaatg tctgagtttc acctaagatg tttttgtgcc   7140
atatgctgga tatccaggtt ctcgccaggc cccgatacat gaataacaaa cccaagaaac   7200
gcatccccat tgtgtgatgt gttcagatgc atctggcacc aattaggtat ttcttaaaac   7260
aggactcatc tgtcagagtg cacatgaaaa atcaggcagg gaatcgaaac gacagcgctg   7320
gaggagactc aggaagcaga ggcgtccctg ccgctgccct tggccctgca agcacatcat   7380
gaccctttct ggcagcctct tggtgctctg ggtagtgagg gatgaccagt cttgtcctga   7440
gaaatgtttc tcttagtctt taagttcaaa gactaacctg tagcaatcag actttccaaa   7500
agggggttct ccattttttg tagttttgtc taaattttta atgaccattt cctggaatca   7560
gtttattata ctgaaaactg ggggtgggag tagggagcta gtttgttgat aaatagttcc   7620
catttccccg tggagaattt gacataccct ggactcctgt gtgcctcctg ccatccctgc   7680
acacagcctg gggagaagcc tgtgcctccc cgtgtggaga gaaggcaacc ccagatcccc   7740
tgagctaacc cggaggaaag gcagtcctgg acagaagact gtcagcagaa ggaaagtact   7800
ggactacccg tgggtaagtc ctgccattca agactggaga cacctgggaa ataaaaagag   7860
cagggcactg ctggtgggaa gaggcatttt accttccagt gcaaatcctg ctcctttgat   7920
ttaatggggt gtactggggc caggggctga ttcacttcct tgggagatgg tggtgttttc   7980
atgaacatct ttgatccttc catttcattt attcatccat ccattcaaca agtatttgct   8040
aaacactaac ttaagctaat gctagggtag tgactgagat gtaaaaatag attttagaat   8100
taaaacaaaa tccaagtcct cacacccctg tcatcccagg agatctttcc ttgtggtggt   8160
ttctgtgaga attggccatc ctgaggacac agccaggacg gcagaggcct cctggcctca   8220
gggcatgccc tgcctacctt ctgaaatgtt taccccattg accaaacttg gctccagcca   8280
ttgcggtggt ttctagatag ccaggcccac caagagatat tgccccttga tgagagtcaa   8340
acaccctgcc tacaaggaga tgttttgaaa tggagaggaa aattggcacc tcatctttta   8400
aaggcagtaa tggaattgat tttcagtaac tgaatttgtg cacaaaacat tctaaacact   8460
agtgaagcct gtttcgttga actaattctg gctctggaaa tgtttttgtt ttatagttat   8520
ttacgatttc gtttgtttgg attcaagctt agtttgttaa tatgtataat ttagcatcta   8580
ttacactcat gtaaatatgg agtaagtatt gtaaactatt tcattgcggg gattgtgggt   8640
gttatacata catttaggac tgcaattttt tggtattttt tgtattgtaa aataacagct   8700
```

-continued

```
aatttaagca ggaacaagag aactaaggga ggtctgtgca ttttaaacac aaatgtgaag   8760

aacttgtata taaacaaaag taaatactat aatacaaact tccttctgaa ataaaagtag   8820

atctggt                                                             8827


<210> SEQ ID NO: 2
<211> LENGTH: 1260
<212> TYPE: PRT
<213> ORGANISM: Mus musculus

<400> SEQUENCE: 2

Met Arg Leu Arg Phe Asn His Phe Ala Thr Glu Cys Ser Trp Asp His
 1               5                  10                  15

Leu Tyr Val Tyr Asp Gly Asp Ser Ile Tyr Ala Pro Leu Ile Ala Ala
            20                  25                  30

Phe Ser Gly Leu Ile Val Pro Glu Arg Asp Gly Asn Glu Thr Ala Pro
        35                  40                  45

Glu Val Thr Val Thr Ser Gly Tyr Ala Leu Leu His Phe Phe Ser Asp
    50                  55                  60

Ala Ala Tyr Asn Leu Thr Gly Phe Asn Ile Thr Tyr Asn Phe Asp Met
65                  70                  75                  80

Cys Pro Asn Asn Cys Ser Gly Arg Gly Glu Cys Lys Ser Ser Asn Ser
                85                  90                  95

Ser Ser Ala Val Glu Cys Glu Cys Ser Glu Asn Trp Lys Gly Glu Ser
            100                 105                 110

Cys Asp Ile Pro His Cys Thr Asp Asn Cys Gly Phe Pro His Arg Gly
        115                 120                 125

Ile Cys Asn Ala Ser Asp Thr Arg Gly Cys Ser Cys Phe Pro His Trp
    130                 135                 140

Gln Gly Pro Gly Cys Ser Ile Pro Val Pro Ala Asn Gln Ser Phe Trp
145                 150                 155                 160

Thr Arg Glu Glu Tyr Ser Asp Leu Lys Leu Pro Arg Ala Ser His Lys
                165                 170                 175

Ala Val Val Asn Gly Asn Ile Met Trp Val Val Gly Gly Tyr Met Phe
            180                 185                 190

Asn His Ser Asp Tyr Ser Met Val Leu Ala Tyr Asp Leu Thr Ser Arg
        195                 200                 205

Glu Trp Leu Pro Leu Asn His Ser Val Asn Ser Val Val Val Arg Tyr
    210                 215                 220

Gly His Ser Leu Ala Leu His Lys Asp Lys Ile Tyr Met Tyr Gly Gly
225                 230                 235                 240

Lys Ile Asp Ser Thr Gly Asn Val Thr Asn Glu Leu Arg Val Phe His
                245                 250                 255

Ile His Asn Glu Ser Trp Val Leu Leu Thr Pro Lys Ala Lys Asp Gln
            260                 265                 270

Tyr Ala Val Val Gly His Ser Ala His Ile Val Thr Leu Ala Ser Gly
        275                 280                 285

Arg Val Val Met Leu Val Ile Phe Gly His Cys Pro Leu Tyr Gly Tyr
    290                 295                 300

Ile Ser Val Val Gln Glu Tyr Asp Leu Glu Lys Asn Thr Trp Ser Ile
305                 310                 315                 320

Leu His Thr Gln Gly Ala Leu Val Gln Gly Gly Tyr Gly His Ser Ser
                325                 330                 335

Val Tyr Asp Asp Arg Thr Lys Ala Leu Tyr Val His Gly Gly Tyr Lys
```

-continued

```
            340                 345                 350

Ala Phe Ser Ala Asn Lys Tyr Arg Leu Ala Asp Asp Leu Tyr Arg Tyr
        355                 360                 365

Asp Val Asp Thr Gln Met Trp Thr Ile Leu Lys Asp Ser Arg Phe Phe
    370                 375                 380

Arg Tyr Leu His Thr Ala Val Ile Val Ser Gly Thr Met Leu Val Phe
385                 390                 395                 400

Gly Gly Asn Thr His Asn Asp Thr Ser Met Ser His Gly Ala Lys Cys
                405                 410                 415

Phe Ser Ser Asp Phe Met Ala Tyr Asp Ile Ala Cys Asp Arg Trp Ser
            420                 425                 430

Val Leu Pro Arg Pro Glu Leu His His Asp Val Asn Arg Phe Gly His
        435                 440                 445

Ser Ala Val Leu Tyr Asn Ser Thr Met Tyr Val Phe Gly Gly Phe Asn
    450                 455                 460

Ser Leu Leu Leu Ser Asp Val Leu Val Phe Thr Ser Glu Gln Cys Asp
465                 470                 475                 480

Ala His Arg Ser Glu Ala Ala Cys Val Ala Ala Gly Pro Gly Ile Arg
                485                 490                 495

Cys Leu Trp Asp Thr Gln Ser Ser Arg Cys Thr Ser Trp Glu Leu Ala
            500                 505                 510

Thr Glu Glu Gln Ala Glu Lys Leu Lys Ser Glu Cys Phe Ser Lys Arg
        515                 520                 525

Thr Leu Asp His Asp Arg Cys Asp Gln His Thr Asp Cys Tyr Ser Cys
    530                 535                 540

Thr Ala Asn Thr Asn Asp Cys His Trp Cys Asn Asp His Cys Val Pro
545                 550                 555                 560

Val Asn His Ser Cys Thr Glu Gly Gln Ile Ser Ile Ala Lys Tyr Glu
                565                 570                 575

Ser Cys Pro Lys Asp Asn Pro Met Tyr Tyr Cys Asn Lys Lys Thr Ser
            580                 585                 590

Cys Arg Ser Cys Ala Leu Asp Gln Asn Cys Gln Trp Glu Pro Arg Asn
        595                 600                 605

Gln Glu Cys Ile Ala Leu Pro Glu Asn Ile Cys Gly Asn Gly Trp His
    610                 615                 620

Leu Val Gly Asn Ser Cys Leu Lys Ile Thr Thr Ala Lys Glu Asn Tyr
625                 630                 635                 640

Asp Asn Ala Lys Leu Ser Cys Arg Asn His Asn Ala Phe Leu Ala Ser
                645                 650                 655

Leu Thr Ser Gln Lys Lys Val Glu Phe Val Leu Lys Gln Leu Arg Leu
            660                 665                 670

Met Gln Ser Ser Gln Ser Met Ser Lys Leu Thr Leu Thr Pro Trp Val
        675                 680                 685

Gly Leu Arg Lys Ile Asn Val Ser Tyr Trp Cys Trp Glu Asp Met Ser
    690                 695                 700

Pro Phe Thr Asn Ser Leu Leu Gln Trp Met Pro Ser Glu Pro Ser Asp
705                 710                 715                 720

Ala Gly Phe Cys Gly Ile Leu Ser Glu Pro Ser Thr Arg Gly Leu Lys
                725                 730                 735

Ala Ala Thr Cys Ile Asn Pro Leu Asn Gly Ser Val Cys Glu Arg Pro
            740                 745                 750

Ala Asn His Ser Ala Lys Gln Cys Arg Thr Pro Cys Ala Leu Arg Thr
        755                 760                 765
```

-continued

```
Ala Cys Gly Glu Cys Thr Ser Ser Ser Ser Glu Cys Met Trp Cys Ser
    770                 775                 780

Asn Met Lys Gln Cys Val Asp Ser Asn Ala Tyr Val Ala Ser Phe Pro
785                 790                 795                 800

Phe Gly Gln Cys Met Glu Trp Tyr Thr Met Ser Ser Cys Pro Pro Glu
                805                 810                 815

Asn Cys Ser Gly Tyr Cys Thr Cys Ser His Cys Leu Glu Gln Pro Gly
            820                 825                 830

Cys Gly Trp Cys Thr Asp Pro Ser Asn Thr Gly Lys Gly Lys Cys Ile
        835                 840                 845

Glu Gly Ser Tyr Lys Gly Pro Val Lys Met Pro Ser Gln Ala Ser Ala
    850                 855                 860

Gly Asn Val Tyr Pro Gln Pro Leu Leu Asn Ser Ser Met Cys Leu Glu
865                 870                 875                 880

Asp Ser Arg Tyr Asn Trp Ser Phe Ile His Cys Pro Ala Cys Gln Cys
                885                 890                 895

Asn Gly His Ser Lys Cys Ile Asn Gln Ser Ile Cys Glu Lys Cys Glu
            900                 905                 910

Asp Leu Thr Thr Gly Lys His Cys Glu Thr Cys Ile Ser Gly Phe Tyr
        915                 920                 925

Gly Asp Pro Thr Asn Gly Gly Lys Cys Gln Pro Cys Lys Cys Asn Gly
    930                 935                 940

His Ala Ser Leu Cys Asn Thr Asn Thr Gly Lys Cys Phe Cys Thr Thr
945                 950                 955                 960

Lys Gly Val Lys Gly Asp Glu Cys Gln Leu Cys Glu Val Glu Asn Arg
                965                 970                 975

Tyr Gln Gly Asn Pro Leu Lys Gly Thr Cys Tyr Tyr Thr Leu Leu Ile
            980                 985                 990

Asp Tyr Gln Phe Thr Phe Ser Leu Ser Gln Glu Asp Asp Arg Tyr Tyr
        995                 1000                1005

Thr Ala Ile Asn Phe Val Ala Thr Pro Asp Glu Gln Asn Arg Asp Leu
    1010                1015                1020

Asp Met Phe Ile Asn Ala Ser Lys Asn Phe Asn Leu Asn Ile Thr Trp
1025                1030                1035                1040

Ala Thr Ser Phe Pro Ala Gly Thr Gln Thr Gly Glu Glu Val Pro Val
                1045                1050                1055

Val Ser Lys Thr Asn Ile Lys Glu Tyr Lys Asp Ser Phe Ser Asn Glu
            1060                1065                1070

Lys Phe Asp Phe Arg Asn His Pro Asn Ile Thr Phe Phe Val Tyr Val
        1075                1080                1085

Ser Asn Phe Thr Trp Pro Ile Lys Ile Gln Ile Ala Phe Ser Gln His
    1090                1095                1100

Ser Asn Phe Met Asp Leu Val Gln Phe Phe Val Thr Phe Phe Ser Cys
1105                1110                1115                1120

Phe Leu Ser Leu Leu Leu Val Ala Ala Val Val Trp Lys Ile Lys Gln
                1125                1130                1135

Ser Cys Trp Ala Ser Arg Arg Arg Glu Gln Leu Leu Arg Glu Met Gln
            1140                1145                1150

Gln Met Ala Ser Arg Pro Phe Ala Ser Val Asn Val Ala Leu Glu Thr
        1155                1160                1165

Asp Glu Glu Pro Pro Asp Leu Ile Gly Gly Ser Ile Lys Thr Val Pro
    1170                1175                1180
```

-continued

```
Lys Pro Ile Ala Leu Glu Pro Cys Phe Gly Asn Lys Ala Ala Val Leu
1185                1190                1195                1200

Ser Val Phe Val Arg Leu Pro Arg Gly Leu Gly Gly Ile Pro Pro Pro
                1205                1210                1215

Gly Gln Ser Gly Leu Ala Val Ala Ser Ala Leu Val Asp Ile Ser Gln
            1220                1225                1230

Gln Met Pro Ile Val Tyr Lys Glu Lys Ser Gly Ala Val Arg Asn Arg
        1235                1240                1245

Lys Gln Gln Pro Pro Ala Gln Pro Gly Thr Cys Ile
    1250                1255                1260


<210> SEQ ID NO: 3
<211> LENGTH: 17056
<212> TYPE: DNA
<213> ORGANISM: Mus musculus

<400> SEQUENCE: 3

agattttatg ccttcgtaca cgcctcccat aagatggaca aggtgtacta attactgcca     60

ttactgttgc tgaccccaga ggtcaatgtc ctcacatggc ctctactggc actgtctggg    120

cagaaactgt atatccaact ggtgaacctg aaagccctat gactacttgg tgtctctggt    180

gctaacccta gtcgttgggg catcttactg tatcctggta aggaaagaca tccaggctcc    240

ccacttaymk wwacyrgywm rgmycakgsy mgrgcyaawk tkctgtrrmr tctggctggc    300

atagagacat tactattgaa agttttgtct ttctaaatcc ttggactaaa gagagcacaa    360

gattttctgg aagatcttgc tttaaatttt ttttttattc ttttgagatg ctacatataa    420

ttagaggccc tgcacatgga ggcgagaacc ccacctctgg gctacatcct acgtcttttc    480

cttagggtat tttttttct ttcttgtacc tatcagtatt actaagttgc aaatgtgctc    540

agcagtaaat ttaacataca taggcaaaaa gaaaagtctc aggacaccct gcctcacact    600

gtttactgtg ctcaggagta ctgagccata ctgttttctt gctgctgctt tttttctctt    660

ggttgtttac acacagtgtt caaggtgtgt taatcatagt tagtatttca atttttttctt    720

aggtcagcaa gaaagctcac agaggaagag tgctttgctg ccagcctgat gacctgggtg    780

acccaagtga tctcacctac agggtgggag cacagcacag cattccaagt ctttttctga    840

ccacacaggc actatggcac acaaacacac aggatacata aatgttaaaa aaaaaaaaag    900

acttttatat ttttctccat ataatttaaa agattcctct ttcaacattc cttttgcaaa    960

gcagtatcat tgtgtttgta tatgtgtgtc cttccacatt ttgtcttcaa ttctaaattt   1020

ttagaattgt tagcctggtc ctctcatttc tactactttc tctagtaaac tgtcctttca   1080

tattacacat cgctctcctg tcacctgttt tagagctgtc atccatttta taaggttact   1140

tcactgttct acactacttt gtgtctttta attactatgc ctggggtgat tcaaaaactg   1200

tctgtgatgg gttggttgag gatggctcca ataggttcaa cacttggtcc tgattggtgg   1260

aactgttttg ggaaggatta ggaggtgtga ccttgtgggg gagtgtgtca ctgggagtga   1320

gtgacctttg aggtttcaaa agcccatgct aggcccagtg tctgtctgcc tgtctgtctg   1380

tctcctccct ttgctctttc ttccctccca cttgcttgca gatcagattc gagctcttag   1440

ctactgctcc cgtgctgtgc cttgctgcta ccatgcttct tgccatgatg ttcatagact   1500

tactctctga aactgtaaat aagcccccta ataaaatgct ttcttttaaa actgccttga   1560

tcatggtgtc tcttcaaaga aatagaacat taacaaaaac actataccaa actgcctaat   1620

agtcctacta attttatgat gagtgctagt gctttataat cactagaaga aaaaatttcc   1680
```

```
aggccataaa attaacatgg ttttaagtat gtataaatct tgtcttgaaa tctgttttct      1740

ataactaact ctaatatgat aatgtatatt ctaccttcaa aaaagcacaa ataagacttc      1800

aaaccctggg aattgttaga caaaggccat ttaatactaa taagctataa actgaaacca      1860

tctgatatat gaaaactatt aataaaatca agataaaata acccctattt ataaacttta      1920

ctatatacct aaagcaaaat atcaaagaaa gtaccttaaa aagataaatt attcttattt      1980

tgacaatgaa ttctttgggg cgttaaattg tagaatatca acacatatca agaaagttta      2040

gaagaaaact accaaagttt aaacagactt cctcggtaa ttactggtga tttcttggct       2100

tttttttttt acactgcagt ttttcagggt ggaaacttaa gctttgtaca gaagcactta     2160

ccaccactct cagagctgga aatggctcaa agggcaaagc attacaagcc tggcaacctg      2220

aaccaaatac ccaaaacact tgcaaaggtg aaaggagaaa actaactcca ggaagttgtc      2280

cttcgagctc ctcttgcaca ccactgtata caccccctta tatacactca gttaccataa      2340

ataaaatgtt tcattataaa gacacttacg ctaaaaccat gctgtaatct gaatggttga      2400

acatatatcc gccaacaacc cacattatat ttccattgac cacagcttta tgagaggctc      2460

tgggaagctt taaatcagaa tattcttctc gagtccaaaa agactggtta gctggcacag      2520

gaattgagca tccaggacct aataaaaaaa aaaaaaacaa caacaacaac aaatagcttc      2580

acaaaatgca gcctgaaagt ttatagtatt ccaagttcca atctaagtgc aaagaatatt      2640

taaagacttg tggggctaga gagatggctc agtggttaag aaaactgact gctcttcttg      2700

gaggtcctga gttcaaatcc cagcaactac atggtggctc acaaccatat gtaatgggga     2760

tctgatgccc tcttctggtg tgtctgaaga cagcaacaat gtactcacat gaaataaata      2820

aattaatttt ttaaaaaaca gaccagaaaa aaaaaaaaaa aaaagacttg tgtttccttt      2880

agcacttaag cgcaaacatc tttaacttgt ggggttttaa aggtttttac atgtacaggt      2940

attttgttta catgtatgcc tatataccac ttgcttgctt ggtacccaat gatgtcagga      3000

aaaggcattg aatcccctgg aactagagtt acagatctta tgagctactt tgtggatgct      3060

aggatcaaac ctgagtcctc tggaagagca accagtactc ttaaccaaga agccatctgc      3120

ttagcaccta acatgagttt ttaacttact caagatacag accaaaacca atcactccct      3180

tataaaattt aatactacac actttctgat aatttggcaa tttctgataa tcaggttaaa      3240

cttttttaga ggtaaaaatc ttgctgaagc aacatttagt agaaagggta gaccaagggg      3300

ttattatatt aactcatgtg gaaaaggcat tagggttgaa atataatgac agatcaaaat      3360

cgatcttctg gcaagtccag gcgctgaata gatgaaagag acaaagggag aattggacaa      3420

actaaaaaca tttacatgaa cacttacttt ctgaggacct aagcatagaa ggaaaatcac      3480

taaaccaacg atgactgctt cctcaatacc ccagggaatt ccctacagta ccttagtacc      3540

cggttgtgtt gggtaatggc actagatgac agcactgaga ctctaaggaa cgcttgtcct      3600

cctctcagct tgagtctctg cttctctatc accagaccat gttccctaat tcccacgaat      3660

gagttgcaaa ggatttgtca aacctttcca caattctaag cacatagata acaaccacat      3720

atatgtaaat tcaaagaatc tgaataaatg gagatgaatg cttaaatgcc acctgataca      3780

tgattaacat aaggcgtatg gctgctaaaa taaactccct acagttcact aactcagaac      3840

tttctgtgag ggaaaggact ttgaagggca gctcctaccc tgccagtgag gaaagcagga      3900

gcaccctctg gtatcgcttg cattacagat ggctcggtga ggaaagccac agttgtctgt      3960

acagtgagga atgtcacacg actccccttt ccagttttca gaacattcac actcaacagc      4020

gctgctgctg ttactgctct tacactctcc tcggcctgag caattattcg gacacatgtc      4080
```

-continued

```
aaaactacaa agacaggaga aaacgaagtc aacaatttca actaagcaac attgcaacta   4140
atgcagacct tcctccttca gtttaagttc agttcatttg caagtgtgac tgcaggactt   4200
accagttagc ccaagtgtgc tcacagagct ctgtgtagct agagccccag gctcaagtaa   4260
tgaaatcaaa tcaaccttgc tgcattcaca tatgaagaag gaagaataaa taactcacaa   4320
agttagagaa attacaaaac aatagacatt tgtgcaaaat cacttagact tagctcaaga   4380
ctggcaacca ggatcctact ctttctggta gctcattagt aaagagttct acaaaagcag   4440
caaggtcatg ctaggaagtg gaggaaggag aggaagccaa tgagctgcca acattcacgg   4500
tatacatttc tctgtaaaga ttctgagaat taacagaatt taagattatt ttccagtgat   4560
gtagttaaag gtctttagta acttttatca gcttagaagg agaagagcag ttaacttcat   4620
gtatgagttt aagtgtctca tgacttaaga taacagtttt gctacaattt gaaatgccat   4680
acttcagact ttttaaaggg gtgcattagt ggactattac aatagcttaa aaatatagat   4740
ttctcctact gatgattatt actgagacac tactagtctt tattaaattc acttagcaaa   4800
actcctgaca ttttcttcca gcagcggaag aatgtctctc tcttctagga gatcctcagt   4860
gacaagatct agaaagacca agaactgtgg tcccaaccag tggggctgat atttgtttaa   4920
ccttttagct cctgtttctt caattatgaa aaaaaaaaaa aagaagaaga agaaaatcca   4980
tgttaaaatt tagcaaggag cctgactagc tagaagcctc cctccaatat attagtgtta   5040
ttaagtcatt tgagtagtat cacaaatatt aaatctaaat atcttacttg taagtgatat   5100
taaatccagt cagattataa gcagcatcac tgaaaaaatg cagcagtgca taacctgaag   5160
tgacagtgac ctcaggagcc gtctcattgc catctctttc aggaacaatg aggccactga   5220
aatgtaaaca cagaccagat tacagcaact tcaacagaaa ctgtctatat gttactattt   5280
gatcctgctg ctcctgttcc aacacacact gtaaatgtga ctctagctgg cctcaaattc   5340
acagacccac ctgcttccac ctcctgggtt ataggcatgc gctactatgc ccaacatcta   5400
aaaggatttg aaatctatga ctttgattga atttttggtt ttttgttttt gctataaact   5460
ttttattata atactctcaa gtctctacaa taacattatt aacaaacttt atgaattgac   5520
aactgtcaaa tatatactgt tgaaagaaaa tactttacat atttttgtaa tatgtatcat   5580
ataatctttt taatgtattt tatagatgtc ttatataagt aaaaatagaa aagtttactg   5640
atttataatc cttatactat tagctttcag acgtattttt gttgttaaac tggtaacaca   5700
ttttatgttt ataattcaca ataagcactg ccactgaagg tgccaaaggc tccctagaat   5760
ctcagtaaga acctagtggg taatatttga agttttggat gccagtaaat tcatgtgtaa   5820
agatttattg agtaagtgac taccagcggg acagtggtgg tgcacgcctt tagtcccagc   5880
acttgggagg cagaggcagg cgaatttctg agttcgaggc cagcctggtc tacagagtga   5940
gttcccagga taaccagggc tacacagaga aaccctgtca ccctgtctca aaaaaaaaaa   6000
aaaaaaaaaa aagaatatac catttttaag gcatttgatc cacaaaatca taccaccttg   6060
ttttacaaaa gatatatatt aacttgaagg ctggaaatgg tggcacatgt ctttagtccc   6120
agtattggga agacagaccc agatggatct ctgagttcaa gaccagcatg gtctacatag   6180
tgaattccat gtaagtttgt ccgtgtgtgt aacttgaaac ctcattatag aatggaagtg   6240
tctaccccac cccacttacc aacagtaagg aatattatgt tggtcccgct catttaatac   6300
atggtgtact cccaaggtaa atcattttca tgtttagtcg ctcctattat tttttccatt   6360
atcaattcac tacaactact accaccaatc acatttagcc actagaaaag ccatgtgatt   6420
```

-continued

```
tgctccacac atacaacttc actcaataaa taaacatctt atcagtacta ctctctcttt   6480
cactcactca atccctagtc ccctaagttt ttggacgatt acaccaggta aattcctact   6540
tcagggttat gaccatctta aaaactacga cctagcaatt ctctttgtat aagaaatact   6600
tccccgtata tacacagaaa aacaaagaac actactacag cactattcag atgacaactg   6660
actaaaagtc acctaattgc ttatttatgg gagttgatta aattagtcat tacaaatctg   6720
taggtctgca agactaacca agagcttcgt gaggacaata ggtagggcta cccagagaaa   6780
ccctgtcacc ctgtctcgaa aaaaaaaaaa aaaaagggag gcacagagaa aaaacaacag   6840
gcccggggta cctgtacatc tatgtaagcg taggtacatg cacataaaag tgactacaag   6900
agaacataaa cagagagcgc cgatgagaag aggatgggat ttttcattta atttgcgtgt   6960
atgagagcac ctatatgtgc atgttatccg caccaaagtg tgtagggtac attatgtgag   7020
tgtgcctgca gacgtcactg tcaggtgtct tcaatcactc ccctcctttt tcttctggag   7080
ataagagttt catgaagtag tactggctgg actagaactc actatgcaaa ccaggctggc   7140
cttgaattct cagagagcct cttgagtgct ggaattatat gcatgtgccg caacacagcc   7200
cacctcattt tggggggtag gatctttcac tgaacctgag ctcactgatt ggttagaccg   7260
gactggccag taagttccag gacctctctt gtctccgcct cttcagcact gtgatcacag   7320
gctcacaacc acacctggac ttttacttga gtcctggaga tctaaactca gctctccatg   7380
cctgtgcaga aggaattaaa ctgagccagc tgtctcagta tcaagagaga acataggaac   7440
tgtaagattc tgacagtact ctagggctta cagaacaccg acacattttc tactatgtat   7500
tcagttaata aaagaataaa tacaaacaaa aaaacatgag aaacatatag aggcagagac   7560
agacagacac acacacacac acacacacac acgcacacac acacacacac acacacgcac   7620
ttagacgggt gtgggggaag aaagagcaag gccacctaga aacaggtacg ttccatgcaa   7680
atgatcacag gaaaggattg gggatttttta accacttgtg ggaaatgctg tactctccta   7740
ttctagcaca gatttgagga aaaagtagac cagagagtct gtccttccac atatcctgga   7800
aagtcactga catgtccaag ttttgatttc ttcataggga caatgagaga aacccagact   7860
atctcacagc agcacagcaa ggaccaacca gcagagcagg agaagtgctt acagcagtgt   7920
gctgctagaa ggtgcaacag tcttcttaca gagggcattt aaatatgcag gatggataag   7980
tttgccaact acaactacag aggctggaca aggtaggaca gcttcttcac tgtcaaagac   8040
gtttgggcag ttgcttctat ttaccttaaa atcaaactgt gacagctgtg gcatatatag   8100
atttctccca gaatgaaaac acattaactc acttatgtca ataatatgga gtaaacacaa   8160
acatagtcta tctagctcag catgcaagac atgtgaggaa gaggagctac tgtgagtccc   8220
tatccctgtc cctaaggaaa ccaatatatg taaatgtagt ctaagctgca ggcagttctt   8280
caactgccta ccccaggctg ctcaccactt cacattctaa gcacagacta gaaagtatga   8340
tcaacctctg aacactgtgc tataatgtta ccatcaatct cacacacaaa tttcataaca   8400
ttttaagtaa gtctatgatg attctatgtt gtgtcccagt tatataagat ccataggtca   8460
cagggtagac attcaaggac accaacattt ggaattttgg gtttttttgg tgtactgtat   8520
atacttgcta gtgcaggtac ccatgctcat gtgtgtagaa gttgggcgtc tttcttctat   8580
cactgtctac tttatatttt ctttattgtt tcatttgata tgtataggtg ttttgcctgc   8640
atatatgtgt atgtttgttg ccagaagagg gtattgaatt ccctgggact agagttacag   8700
gtggttgtga ggcaccatta tgggtactgg gactcaatcc tgggttctct ggaagggcag   8760
ccagtacttt taatcactga gccatctctt tagcttcctt cgttcattcg ttcgttcatt   8820
```

-continued

```
ccttcattcc ttcattcctt cattcagagg attgagatac cttcctcagt taggctggct   8880
agccaatgga ctctgggaat ctatctgttc agctattctc tccttcccca tccaagtgct   8940
ggggatacag gcaggtccta ctgggttcat tttgaaaaat tacagaacta tgtattttct   9000
tcataaatct gaaactcagc ataactgtct caggctaaca tggaatccct aaatatatat   9060
gaggcacaac ctgactttac caactgtact atgtaaattt gctagtatat tagtcaacac   9120
ttaatggaaa aacatctgat aaaaacaact tacaggccaa taggcaagga gacacttggg   9180
gaggtggatt caaggcagtc actggattct tgaatttaag tccagcctag gctacatgag   9240
attctgcttc aaaaaataaa caattaaatt tatgggggaa agaatgatgt attttggttt   9300
cagaaattcc atcctatcat ccaagggaga tattgtataa cagcgaagtt cctcagctca   9360
cagcagtcag tagcatatag acaatcctgg ctccaagcct atgaaaacac agcctgtact   9420
aaaggtgtgt tcctgtgttt tgagtgagat gtgcccccta agtcttgtgt atttgaatac   9480
ttggcactca cttggtggcg atttgggagg aattaggagg tgtggccttg gtggaaaagg   9540
agcatcacta gggtcaaggt ttcaaaatcc tcctgccatc atccccaata tgtcctctct   9600
gcctcctgct tgcagttcaa gctatgagct cttagttact acttccacca cctacccctg   9660
ctatctctgc tccatcatca tggactccta ttctggtgga actgttagtc caaaaaagtc   9720
ctttcttcta caacttgatt tgatgccaga tctagccccc cagcctagct agcaatatac   9780
caaggtatac catcttgaac tctaggtgtc tctcaatcca atcaagctac ataagattaa   9840
ccatcatacc tagtcatccc caaatcagtg tatctctctc ctcccaagac tataagctcc   9900
tcaagggtca aaatatgtag aaaggaagaa agattctcaa aggtcaagga tcagaccttg   9960
gtgaggattg agcactgtct acactttgcc tggtaaagaa gggtccacaa tgtaaaagag  10020
aactgacctg aacagttttc aattaggtgc taacaaatgt ctcatacgta ttgagtttct  10080
tataaataaa taaataaata aataaataaa taagcaagca agcaagcaag cacttaagag  10140
cactagctgc tttcttcctg aagacctggt ttcaattacc cagcacttat acagaggctc  10200
ataccaattg taactccagt ttgatgatat ccaacatctt cttctagcct tcagacacca  10260
agcaccaagc atgtaatggt ataacacatg tataccaaac acccatacaa accaattttt  10320
aaaaaaatat tcgagccggc gtggtggcgc acgcctttaa tcccagcact cgggagacag  10380
aggcaggtgg atttctgagt tcgaggccag cgtggtctac agagtgagtt ccaggacagc  10440
cagggctgca cagagaaacc ctgtctcgaa aaaccaaaaa aaaaaaaaaa aaaaaaaaat  10500
agtcatttta gggctggaga gatggctcag gggttaagag cactgactgt tcttccagag  10560
gtccttagtt caatatccag caaccacatg gtggctcaca gccatttgta atggggatcc  10620
aatatcccat tctggtgtgt ctgaagacag ctatagtgta aataaaataa agaaatcata  10680
taaataaaat aaataaatct ttttaaaaat attaattaac ccaggctgaa cctaaactta  10740
caaacttccc acattaggct ctttaatgcg ggtgttatag gtctgaatac cagcttaaga  10800
ataatattct tctgaagaat gtgccctggt caatcaccat gaccacacct gccaacaggt  10860
ccttcataaa atacttggta tatgttgaat gttccataaa attatggagc tagaaaaggt  10920
agtgagctag aaggatatta aagatataaa ccattgcccc agtggtcctc acatttgtct  10980
agtaatagaa cgttgttaaa ctgtttttat ttagaatttc aatatataaa agacaaatat  11040
gaaatagtcc ggaagcaaat taagctacag cttgcagcaa agccagatag aatgcagatt  11100
aaactaacac agtacctttg tcttatgttt tagatgctaa agtctagtct acaaccccag  11160
```

-continued

```
ctgcccttga actcttagca gtcctcttgc ttcagcctct catgctgcta gggttaaaag  11220
tatgtgcgac cacacacagt tttgaagttt agagcactta aatgatctat tcagcaactc  11280
aggcaggatt tacactgaaa gtaaattatc ttatgaatcc tttttggttt tccttttatt  11340
catttcattc atgcacctta catgaactat ctattgctag gctgtctcta tactggatgc  11400
tcagcacatc accaacatgc cgattcttct actggtacaa tggcaatgct gagaaaacca  11460
cacaacctaa gacagtaggg aggtggtgct ctgattgttg gtgttgttgt tgttgttgtt  11520
ttggtttttc gagacagggt ttctctgtgt agccctggct gtcctagaac tcactctgta  11580
gaccgggctg gcctcaaact cagaaatccg cctgcctctg cctcccaagt gctgggatta  11640
aaggcgtgtg ccaccacgcc gggctctggt gctctgattt ttaaatacaa caattttcag  11700
ctagcaatgt aactcagtag taaaatgcct gcccagcatg cacaaggctc cagactggac  11760
cctgagcacc acaacacttt ttaaaagatg tgtttatttt attttatgtg catgagtgtt  11820
ttgcttacat gaatgtctgc actgtgttta cctggtgcct gtgaaggtta gaaggcaatg  11880
gagctatgga gagttgtaaa ctaccatgtg gaaatggagc tatggagagt tgtaaactac  11940
catgtgggta ctaggaattg aatcagggca ctcctctgca agaacaacaa aggctcttaa  12000
cagctaaaat attactacaa acccacacca caaaatttta aattgataga cattatcacc  12060
ttagttctag atagagaatg tgcttggcat tgtaagtact aaaaaggttt tggggtggat  12120
cttttatatt atctcactat aattttataa aattaatact caaatatgtt ataagttaag  12180
gtttttattt ttgtttttca tttctgtatt ttgtctatgt agctctgcct ggcctgaaac  12240
tcatgggaac ttgactggcc tcaaactcag agagacctga acggccctgc ctccaaagag  12300
ctgggactaa ccatgcccaa cagtaggtag ctttaatacc taaccagtgt attagttcat  12360
gctctcaatt aaccaacatt ctctacatac agaaattttt atgcctattt aatcaaatac  12420
acagtctaag taaactctaa gtacaactgc ttggctcata ttcttacaat ggctatggct  12480
agctaattca aaggccagtc acataaaagg gtctctatga attctgatta acaaatgcag  12540
ttaaatagat gaattcctaa aaagtagtat cataataata tcatatttag tttttgtgct  12600
tccattatag tttgaggtgc ctcctcccat aatgcaaggt atatttcaaa taatagatat  12660
atacatggtt aacacatggc aaatgccatt ttaaatgctt agcacagcct gctctttggc  12720
tccattaagt gaaactctta agttctcagt taaaataatt gttggagagc tataggagca  12780
atgggtggag aactagtctt ctaatttgtc ctttgcctcc ttgcgtacta agtagtccct  12840
ccctcactat gtggcattcc agcagactac caccaagaga agaacagaaa agtgttgatt  12900
tctttctaaa gtaaagaaat aaggggccag tgagatacct cagcaggtca aagccatttg  12960
cctagaaacc aaagttcaat ccttggaagc cctgtaaagg tggaattaga aaacagactc  13020
cacaaaactg tcctctaacc tccactcggg cacacatgtg ccaacccctc cattctccct  13080
cccccacata caaagtaaca ataaactttc agaaaattta agttgctacg catggtgatt  13140
gatgaatgtc tttaattcta gctcttggga agcagaagtg ggtggatctc tgtcagttca  13200
agaccaacct ggtctatata gtgtgttcca ggcatccagg actacacaca cacacacaaa  13260
attacgtgaa ggaagtagaa tgtttgaagg aaagaagtct ggaaatgggg atggagagag  13320
acctcagcaa ttaagaaaag gtcttgcacc ggacgtggtg gtgcatgcct ttaatcccag  13380
cactcgggag gcagaggcag gcggatttct gagttcgagg ccagcctggt ctacaaagtg  13440
agttccagga cagccagggc tacacagaga aacccagtct cgaaaaaacc aaaaccaaaa  13500
acagaaaacc agtatgatag gtcaggcaat tggatcgaga caggacactc aagatagcta  13560
```

-continued

```
gcctgtgcaa tatagaaaga agtctcatgg aagagagagg gaagggaagg agggggggaga  13620
gagagagaga gagagagaga gagagagaga gagagagaga gagaatgaga gcgagagagc  13680
gagcgcacct cagttgatac aagattgggg ccctgagttc catccccagc atcccataaa  13740
ttgggtgtag cagcacacac ctgtatccca gcagagaggc aaaagacaag ttcaaagtcc  13800
tatatggaaa aagtgtgaga tcagcctgga gacctggtgt gtggcagtgg ggtgaggggt  13860
gtcatcaagg agaaggctta gtaagtaaag gacctgcgtt ggttcttgag ttcaagtctc  13920
cagcaatcag agaaagccag aaccattgca caaacttgta agccaagtgt tggactggac  13980
agagacaggc aaatgtttga ggtccaggtt cagtaagaga ccctatctca aaaaatctga  14040
tggagagtaa cactggaaga actcagagtg agtcacacat gcacacacag gtgaatgtgt  14100
atacaaaggg ggcagggagg gagaatgaga ggagactggg agatatctgt agttcatgtc  14160
tgtaattcta gcacttcaga ggcagctgga gctacacagc aagaccccgt ctcaaaaaca  14220
aacccaagcc tgacagtggt gaggtacacc tttaagccca gaggcaggag aatctctgag  14280
ttcaagggca gcctgagtga gttccaggac aaccagggct ccacaaagaa acactgtctt  14340
gaaaaaaacc aaaaccaacc aaacaaaaaa gaatcaaaaa caaccaccac cactacaaca  14400
aagcaaacaa gggagaaggt ataaaatgct taggagagtc ttcctttagt ctccatcctt  14460
tgggtactcc ttccccacag aaagccacta ctaccaattt cttacataag ctgctgtttt  14520
agacacaggt tttttttttt tttaaatata gtaacatatt catgtgtagc tcatttttct  14580
agtgagtggt tggtccttct tttaacagtt taaaggacct ctatgtttaa aggcgattgg  14640
cccttgtctg gagtatgggt tgtattttcc caatttgtga gttttaccca acctattgcc  14700
tattacctat ggccatttat tcttgtcgat aagtagtttc caattgtatg actatggtca  14760
cagtgttcca tggactcttc tgccgctaga cagcccctgg gtctgaattt gagatggtta  14820
caagggtgat tggctctgct ccctgggtgc tgggattaaa ggcgtgcacc tccacaccca  14880
atttgttctg ttttgtaaga aatgaggttt tattgtgttg ctcaggctga tctcagtctc  14940
ctggcctcaa ggtatcctcc catgtcgata cacagcacaa ggcgtaggaa aagtggcaga  15000
tttttttaaa ttaagttttc tttccaaaat atagattcag aaatgtgaga ttttcacaaa  15060
gtgaacctgc tcacttccct ggctctmgaa tctccattgt ggctcccgcc catccctttt  15120
gcccaccagt ggctgttgta ttgacttcta tcccattcct taactatacc tgtccttggt  15180
cttcgctgtg aacttgcttg ggctgagaat caccttgttc cgggcacatc aggtcagtga  15240
gggtgtttcc agagagtttt aacagagacc agaagaccca ctccaaatgt gggtggcaat  15300
acctgatgtt ctgtcatcct ggactgggta ggaagaggaa agtaagaagc aaacggcacc  15360
cccacctctc tgtctgcttc ctcgccgaca caaagtgacc agggcctccc actcctgccc  15420
cctcagctag agacacttgc tgccatcttt ccaaccactc tgagactgtg cctactaacc  15480
gtgacccaaa ataaatgttt ccttccttaa ggttgccttt gttagctcct ttaatagagc  15540
ggtaggacat gtaactgcca caggcagcca tcgctgccag cccctcccac tgaccgtctg  15600
agaaccacac tcagctgtag gcacagctct catagctgtg tgggcgtagc tctgtctact  15660
cggtcattcc cctgctgccg agcatttatt gttttcagtt cctggctgat gggtagcact  15720
gttatgaaca tcctagtaca aatctcaggg tgacacgcgc cttcattttt cctgagaaaa  15780
tgcccaagga taaaatgcta gggccaaggg aagaatattt caccattaag agacactggt  15840
caggactgga aagatggccc agtggttaag agcactgact actcttccag aggtcctgag  15900
```

-continued

```
ttcaattctc agcaaccaca tggtggctca caaccatctg taatgggatc caatgtcctc  15960

ttctggtgtg tctgaagaca gtgacagtgt acctacatac atgaaataaa taaataaata  16020

tctgagagag acagacagac agacactggc tagtcatctc acaatgttct catgtttaaa  16080

atatgatacc atttgtataa agcagaaaca caggaaaaat aaaatctgtg gtattatatt  16140

tgatttttaa attaacttga ttagtgaagt tagcagctac actgggcagg ggttgggagt  16200

ggggtactct gaagtgctgg tatttctggt tttgtttttt gtttgtttgt ttttttatct  16260

tatttatatt acatagaaag ccattttgct aatacactta ccatgtgtat atattgtgct  16320

tgaattacag ctaagtaatt atttctgagg ggctttagac tactgaagat tgggcccaat  16380

gagccccacc ccaagtagtc tccaacatcc ctcttggaag tacttgagag caaagattca  16440

agtcacatgt ccccaaaccc tcagcagcca ccacccttta ggtgtggctt ttgctctcgg  16500

tcatcctgga acatcttgcc atctttggtt tgttctctcc ctgtcttgcc tctggtagag  16560

ctgggtttct gtgcttctat tcaaccatgt acaagaacca tgtgccacct gccatgtgcc  16620

aagcctgtgc cagtccctgt gagcgagcag cccaccccgt gagttatcat gtgaggagct  16680

atgaggagca ggaaggggcc cggatgactt cagcagacag tatgaagcaa gcactgtgcg  16740

atttatgctc cctggccaca tgcccacaga tggtgtctga gacactagcg tttaatattt  16800

gaattctcca cattctagcc tagacatttt ggttgcaaga agaaaattga ctccagttgt  16860

atcctggaat gaaatttatt ggaggaaaat actggacagg ctcccagaga aaatacgata  16920

ttcaggcaca aaaagaaatg gggactgagg atctgaagtt caaggtcatc tgtaatgaga  16980

ttgaagtcag tttgggctac atgggacctg gtctaggggg aatggggaag agaagggaag  17040

ggatcgagat agggat                                                  17056
```

```
<210> SEQ ID NO: 4
<211> LENGTH: 5973
<212> TYPE: DNA
<213> ORGANISM: Mus musculus

<400> SEQUENCE: 4

caatgtgctc tgacgattaa tgggctagaa atgtgtggct gttgattagt gaaaagatgt     60

catggttcag gagattggta gtctctgtgg gaagacaact cactgaaagg gaggaaatag    120

cctggaagag ataaagagac agtgatcagc taggaagctt aaaatttaaa ttttgttgga    180

agtactgtta ggaatactag cagaggccag atgaatgtat ggttaagtta tagcaaagga    240

aaagattgtt aatggtgagg ttaggaatgc agggtgacac caacctgtaa tgtcagcatt    300

agcgagatag aagcaggtgt ttaaggccat tctctgctac ttagcaagtt gaggccaatc    360

tggaccacat gagacctttt ttcaaaaata aatctcctta aacaaaagag gctgggtttt    420

ttgatagatt cttcaagatg ttaatgtaaa taaatggaag accaaggatg gcatgctaat    480

atcctcagtg tctgaagaag gactatgtag tgttggctgc tgactctgaa gtaagtgctc    540

attactgaca gatagtgtat cttagagcct ggcagatggg atggaagtga ggaagcaagt    600

agcacctttg tatattatgt tctaagtagc cagagatact tgacacaaaa caaagttgag    660

aaaatgtatc ttctagaaaa tacagacatg gaaaggtgtc ctttctataa aagaggtatt    720

aaacattaac ctgaaaaaaa agttagcaaa ttgggctttg gcaaatgaat atagtcaagt    780

ttcattttta ttttgttttt tgtatatgac tgtttggctt gttgtaccat gtgtgttcct    840

ggtgcctagg aagtcagctg gagttacaga tggtgtgagt tgccatgtgg gtgctgagag    900

atgaacctag gtcctctgga agagcagtta gtgctcttaa ccactgagcc atctctctag    960
```

-continued

```
ttccttctgt agaattttca ttaatttaca aaggagaaag tataaatgat aaaaccatga   1020
gaagatagac cggcactaga attagtggag tcaaaatgtt aatgatatgt cagatacgcc   1080
ttatatgagg aagttgcaaa attatgaaaa tccaggcact ccactgagtt agaaatctag   1140
gctctgatgc atactgctat ggtaaggtag caagtggcca ttgagtgcag aagtgagtct   1200
ggatgggtct tctggtgttg tggagcacac agactgctgt cttctgcatt gcagtttcac   1260
ctgtatttcc ttggaactac ttagctttgc aactaggcgt taaaaaaaac tttatattta   1320
tggttttaag ttatttattt gttttatttt attttatgag acatagtctc actctctaac   1380
ctaggctggc ctggaactgc ctaggtaact tgagctggtg attctcttgc catagccttc   1440
taaaatttta gattgcaggc ataagccaga ccactcctga cttttgtagc catttttctg   1500
acatgaagtg taactttgct ttcataacta aaatgattta gttgttttgt tattgtttaa   1560
tcccttttgc tttgaatgta tccttttgtg tgggtggcag atatataacc acagactttt   1620
ccacaggcat cctaccctag gtccagaaat gactctgaga cgtcttatat atgaatgaat   1680
gcctaggcca atagctttgg ctgatttcca cgggttcata gctcagttat cccatttaaa   1740
ctagtctaag tcatgccatg aggctacata cccctccttc agtttcaggc gactgtcttc   1800
tcagttgtgt aatgtcctat cctctgttgc tgctccccaa cccccatcct tgcgtcatag   1860
tccgtctgtc ctcgtctccc cccatttact tgcacaacgg actctactct agaagtcctc   1920
tctgtgctgg agcttgcacc tccgctctcc ccgtctaagc taataggcaa cagcattgta   1980
cagacaggtg atgcttccat acatcgcaca ggagattctc cctacacaga tacttattca   2040
tccagcgtga atgcaaccgt ccaggcgtgt tctcctagtt gtagtacatg ctgttgtatc   2100
agtctgatga atttctttgt ctttacaacc aagaaagata atactgtaag aaattttgac   2160
taacattttt tctttattta aattacagac taactggctc ttctggattt gtaacagatg   2220
gacctgggaa ttataaatat aagacgaagt gcacatggct cattgaagga cagtaagtta   2280
taatggctga ctttatttta atttattata agagcacagt atagcacaaa atacttccat   2340
gtgtgttatt gctatttctt gagacaggac ctttctgact gagtaactca ggctgacctt   2400
gaattttgct atgctacctc tgcttcccaa gtgctagggt ggtaggtgtg gaccaccatg   2460
ccctgctgct aaaataccgt tcattgatgc ttttcatttg gatagtgttc ttgcttttta   2520
aaatttactt tttgggggac cagagagatg gctcagtggg taaagtgctt gctgaacaag   2580
tctggttatg tgagttaatc cctggctccc acagtggaag agtgactcct gaaagttgtc   2640
ttctgactcc cacgcttgtg catgcacgca cacacacaaa taataaaata aaaaattaaa   2700
aggaaatttt ctttttttggg tgatagggat tgaacctatg acttcactaa gcaagtgctc   2760
tattgttaaa taattccttt aatttgtggg tttttttttt ttaggttcca agttgactta   2820
atgttataaa tgaaagatac ataccagaaa tttgcatatt tctaatagtt taaaaaactt   2880
agttaaaatc tttttaatag tttgcttaaa tctttatata ataatgctat tatatcattt   2940
ttctaaatat tgattttatt atcagcaaaa cagtaaatga gccatcagaa taaccactgt   3000
agcctgtttc cctggccctc tgtccttcca tctgtctatc ttctcttttt tttccttttt   3060
tgtgcctgtc atttagggca aagcatttta gtctctgaac aaaactttga aatttccaag   3120
taactcttgt ttatttgttg tgtctcatat tcaacccaag aaatattatt tactaactca   3180
tttaaaagca acaattataa cccactacat gttagcagaa aaacctattt gtttttattg   3240
agacgggatc acactagtaa gcactacatg gcatggcgtt cactgtgtag atcaggcagg   3300
```

-continued

```
ctggcttcgt gctcttgaca gtcctcctgt gtttgtctct cacttctgag tgctgggatt   3360
atagacatta ccaacacacc gatttggggg gttggggtac tgggatcagt ccagagttgc   3420
atggatgcta ggcaagcact ccaccaactt agctatatcc ctggtcataa atgtcataag   3480
gaaaaaaatt ccttatattt aaagaaattt taagaattgc attgtttaag atttcacaga   3540
tctctttgct atctggcaat cttttttgat attttgtttt gtttttaaaa atatgtggta   3600
tgtaaacaaa cttaaatatg aatgggacag ttccagatga gagtgaaaag ttaaatattt   3660
gggagaaaaa ttgataggtt tatctattat ggaaaatttc agagatttta gtaaaatttg   3720
aaaatggagc tgggaggtct gaggtagtca tctaaagctg ccagttgtag agcgtgttgg   3780
agtgtggagt cagagggagt tactgataca cttgttgaaa ttgcccaggc ttcatgggaa   3840
gtgatgaggg gctgttactg tgactctggg cagggcttgt tagtttcctt tggatttagt   3900
ctcagtcaga gttgatacat agtttcctga ggacgtggct tttggtaca gtgctgtgaa    3960
aaggcagaga agcaggtaaa cttagaaaat gtgtgttttt aaagtgatgt gttatgaaat   4020
cttacgtaag atgaataaag aaagaagtgg ggacactgag ggctcctgtt tctaaatgtt   4080
aaaagcaagg ctggaaacat tctttgaagg cccctgaagt cagagcccgt gtctcttttg   4140
gttcccagga catttttgat attcccttac acatagcaaa tactaactag atctctgaca   4200
aatgcaggaa agctgtttat atttatatat atttatattg tatatttttc tccttataaa   4260
ttctttaaaa gtctgtttta gtagttaatg ttatgattat tataaattac ttaattattt   4320
ttctaggcca aatagaataa tgagacttcg cttcaaccat tttgctacag aatgtagctg   4380
ggaccattta tatgtttatg atggggactc aatctacgca cctctgattg ctgcctttag   4440
gtaagccctg ctgcatttca tctcaggaag taagtgtgtc tccaggatgg agtccgtgct   4500
gcatttactt tattctgcag tcacactcat ctcatggaat tagttctgtt ctggtgagct   4560
acagttcact tggtttttat gtactgggtc gttttccatg tatactagta tgtagccacg   4620
gttagtcttg aacttctggt tctcctgcct ccaccttcca agtgctagga gtataggctt   4680
gtgccactgt gcctgactca tttcacattc ttgaactgtg aagttttgat aacactatta   4740
aatttacctg ctatttgtga ttttgttaaa gtttgcatta aaaagttttt gactatattg   4800
ataatatttt tgtgacaaat ttaaatcaga aaccatacct ttcttgttct tgtatgtatt   4860
tcattccata ggcccttagg aataactttt ttcaatagta tatagttctc tcagtttgta   4920
tatatgtatt attagggata ggaggagctt tctggaagac tatttataaa ttggacaatg   4980
gctagctgtt gagagtgagg aatttgctag ttttgttttg taaatccctc cccaatgcat   5040
ctgtattagt gatttaataa aataatgcaa ttttgtcagt tatatgggtt gcactgaatt   5100
tttgctattt tattttaaga aagatttttg tgtgtctaca gtgtatatga gtgtatgata   5160
tgtgtgcgtg tgcatgtgtg tgtgtacttc tatgcaggta ctcacatgct atggtgtgca   5220
cgtaaggttg gagtgcagcc tcacatgttg atcattatat tccaccttgt tagagatagg   5280
ttgtctttgt tgtttgctgc ggcctggagc tggagctgga gctaacgagt ctcagccacc   5340
tgacatgggt actgggaacc aagagcagca agacctcttc ttcttcttct tcttttttca   5400
ttttcggttt ttcaagacag ggtttctctg tatagccctg gctgtcctgg aactcactct   5460
gtagaccagg ctggcctcga actcagaaat ctgcctgcct ctgcctccca aatgctggga   5520
ttaaaggtgt gtgccaccac cacccagcct aaaagatttt cttactaaaa tatatttcta   5580
aattaattag ttggaatctg gttcatactt ctttttgaaa caaaaccagc attttttttc   5640
attctacata cagagacatt gacactagac actggttatg agtagttact ataagaatgg   5700
```

-continued gaaattattc caccccttgta aaacttaata caactcctta tcaggctctg aagacttttt 5760
aaaagcaaga attgtatata acacacagaa atgatttaga ctatttagat ctttattgca 5820
tgggatttta aaattattat tgtatttcgt gggcatgttt tgtctatgta gcatatgtgc 5880
ctgtagaggc aaccaccaag taggtcctgg gaatcaaacc tggtacccct gctcttaggt 5940
gttcttaact gctgagccat ctctccagtc ctc 5973

<210> SEQ ID NO: 5
<211> LENGTH: 90050
<212> TYPE: DNA
<213> ORGANISM: Mus musculus

<400> SEQUENCE: 5
aggcaagaaa gagccagcga gcctccagac agaccattag aaattccaca gtcagcacaa 60
tagggagaac agtaaatctt acattaaaag aaggccaggg cctggtagca aaaggtttta 120
atttaagcac ttgagaggga gaggaggcaa atctctctga ttgggggttg gggttaatgg 180
tgaatgccat gacaccctgc tcagagttag ccttctcccc taaaaaaatt ttaaattcat 240
tttcaatgct gacacagtta atcatagaca ttgtatctca gacacctcaa catactccag 300
actgcagcac cagcccactg ctgaggctgt cgttcagttg gtagaaggca tgctcagcat 360
tcgcgaagca ccagacttca tccttagcac tacataaaac tgggtgtggt catgcacact 420
tataacttca gcaccatgga ggcagaggca ggatgatgag aacttgagga tcattctcag 480
ttacataggg agtttgaggt taagcagggg tacaggaggc ctgtctcaaa caaacagaca 540
aacagacaaa caaacaaact tcaaaaaact cttgaagtac taggcctagt acgtgctgag 600
attgtaggta tatgtcatca tgcctgttgt agaatgagtg agagcggact ccataggctt 660
atagatttga atcttggtgt ctgtctatgt catgtcatcc ctgcacaaaa gcccacacta 720
ggcccacaca ttctctctgt ctgctgcatg tgggttagat gtgagctctc agctgctgct 780
ccagtgccat gcctgcctgc tgccaggctc cagccatgac ggtcagggac taactctctg 840
aaactgtaac caagttccca atgaaatgct ttctttcata agttgccttg gtcatggtgt 900
ctgcttcaca gcaataacac ggtgactaag atacctggct cctcccctcc ccaccccacc 960
attatttacc ataaagtaaa caatacacag ttggataaca tgatactgaa gttattttcc 1020
tgtttcctga tgtaacccaa ttttggacaa gattaagcct taaatagcaa gctgtgaggc 1080
aggataaaga aaaagctcgc aggccaatgt ctgctttacc aaattctgtt cagcagtcta 1140
aagctgccgt cacctcgact cctgtgatgg catttccatc actatcttag atattccctg 1200
ggtcacaacc ttttagtaca cagattgcaa ctctgatgga atggctgact gcttggctaa 1260
ttaaagcaag ctagagtttg tctggcttcc ttgtctgaat ggggaggtgg tatttacaaa 1320
attttgtaaa taaactacta tatttgcatg atgtatataa atttgatgtg gctgctttta 1380
aatcatttaa cctaaactgt cccacagaat catctgtttg attggaaaga ttgtagcttc 1440
aagagaattt ctgctgaacc tgaaatgatt cataatgatg tgtctgaaga atgtgtgcta 1500
tcacctacgg tttttgtttt agttgatatt tgtactttaa gatttccttt atgtatgtgt 1560
gtgtgtgtgt atttatgtga atgtatacct catgtatgtg gtgctcaagg acacctgaag 1620
aagggctctg gagctggagt tacagggagt tgtgagtgct aggaaagaaa gctgggtaca 1680
ctgggaaatc aaaaggtgct tctaaccact gagaaatcct gccagcccct tggtttatta 1740
aaaatatcaa acaaaaccaa cactagttac ataagtatct ctctctcttt ctttctctct 1800

-continued

```
ttctttctct ctctctttct ctctctctct ctctgtcaca cacacacaca cacacacaca   1860
cacacacaca cacacaaagg atccataata gttcttctgt atcccggtta aatataagtt   1920
cttaggggct agagagatgg ctcagcagtt aagagtgctt gttgttcttc cagaggaccc   1980
aagttcagat cctagtacac acatcaggca gctcacagct acccatatct ccagctccag   2040
gaagaaccaa tcaatgccta tggcccatgc aagcaccagc acacatatgc tccacaaaca   2100
tccatatata tagctaaaag taataaaaat aaatcttcaa aaaattaatt ctggttgaac   2160
tgaaaaagat cacctaacat ttagaaaaag cagtttacta gtgaatagga cataaatcat   2220
ggtatcaaat attctgttgt taaaggaagc aactagaaaa agcatgtgtt tgaaataacc   2280
aatggataca aaacaaatga ggcaacccca acatctgtca gtaccttgca aaccaacaca   2340
ataaatttga ttttatttaa atcgtagtta tttttcatgc tagtagtttt gaaacacaat   2400
aaatttgatt ttatttaaat cgtagttatt tttcatgcta gtagttttga aaccaagatc   2460
tagattttgt atagccacat aaatacacat tagaattgca aactgatacg agcttcatct   2520
tcatcagtct ctcttcatga aaagcagtta cagggactga gacatgactc agcagttacg   2580
gcatgggctg ttcttccata cgacatggat tcaattctca gtgcccaaat gttggctcac   2640
aaccatttgt aactctggtc ccaggggatc tgacactctt cttggcttct atggccactg   2700
tattcatacg gtacacagac acatatgcag gcaaaactca acaaaaaaaa taaggtttaa   2760
aaaaaagaat tagaacttaa aggcacttca ttccgtcagc actaaatcag cctctctgga   2820
gtcttcccac ttcatgagaa aatcgtcagc tctccactgc tgtctgtggc tgaggagcag   2880
gacctggaca acgttcagag attgtcagtg catctctttt cttctttggt ttgctgtcat   2940
caggttcact gtcacattcc ctttgtacca tccttccttt aacagccttt tgaaaatgca   3000
gaaatgttgg atgctgcctt cagttcacac aggctgtctt tttagctcct catctatcta   3060
tgcttaattt gttagtggtg ctcacccatg tatgtgttta tgtcatgaag ccacaagatg   3120
agccttgatt gagtcttgct gtcagtgtgg atcacagaaa tgacacccta tcatctttgc   3180
ttcctgcttg ttagaagtca ttgattctgc ttatactcaa ggcccacagt attatacttg   3240
ggtgtgaacc ccaggaagca gggaggtggg gggtgtcatg gatactactc agatatctga   3300
ctgttgtgat atttcatcag ttctcattgg tcctatcttt aaaatctgcc ctacatctag   3360
agctggctgt ggtggtgtgt gtggtggcat cagtatcaga acttggatta cagaggcagg   3420
aagattgtga tttttgaggc cagaataggt gcatacaaag atcctgtctg caaaagaaac   3480
aaatgtgcaa ataattataa ctactttact aatagcctaa ctaataacca ctgctagtgc   3540
tgtgtccacg aaaaggtgaa gtaaactgtg aaaatgactt ccccttctgt gtgacacacg   3600
ccgtcatgtg attttacttg tgtctcatca ttgtttttcc ttctgtttgc atgtgtgaat   3660
gttcacatgt ggaagccaga agtcagtgtt gagtgtcttc ataattgatc tctattctct   3720
ttgttttgag acagggtttt gagactaagc ccagtgctca gtgattcatc cagtaaactg   3780
tagggagctt cctgtctctg cctccacagt gttgggatta caagcatgat ccaaattatg   3840
tgacaagcgc tttactaact tagccatgtc ctcagctccc cactcccctt ttcttttctt   3900
cttctttttt ttagacttac ttgtttattt ttatgaatgt cttgcctgca tgcatacaca   3960
cacacacaca cacacacaca cacacacaca ccccacatgc aagcaattcc agaagagggc   4020
attgaatccc tgaaactgga gttccagtta actgtgagcc tgtcatgtgc gtactgggag   4080
ctaaatccgg gttctctgga aggtcagcaa ggtcttacct gggagccgtc tctttagctc   4140
atgtgtttct ctcttgaagc aagaaaccta ggaatcattt tgaaacttcc ttcacagcct   4200
```

-continued

```
ttatcataac ttcacgtcaa tttttaccta ctctttcaac aaatacatgt tatatttact   4260
tatttttatg tttagcctgc tattggtttc tacttagcct cttgcagtag agttctgtca   4320
gatttatgtt tctattgctt ttaatttatt tgtaaaggtg aatgggaaaa tatttaaaaa   4380
ttacagatcc catcatttac tatattctta aaagccatgg ctagccaggc ttggttgtgc   4440
atgcttgtac tcccaggact ctgacaactc agtaaggagg agagtgaatc agaaaatagc   4500
gccagcctgt gctgcttagc aagaaacaga aacaagtaca atcacacaca tagaaaatcc   4560
cccattaata ccatcccatt agatataatg gtcctgtatg accattcaac cactgtttgt   4620
cctctgtact gcagtaacag tcttctgccc ttgcccgtga agcacgtgcg caccccgcct   4680
ccaagtgctt ttgcactggt gtcctccgtc tagatgtcct gttactatat gtaaggactg   4740
gtttctcctc ctctttacag ttcaatctaa ttgtctcatg aaaagatctt tcctgaccat   4800
ctggttcaga caggttctcc ctgttgttgt tttgtttttt gttttatagt tctaaattcc   4860
tttcaggaac ttttgcttat tttaaattcc ctgagtgcat acgtgtgctt gttgttgctc   4920
atgctcgttg tttgggctta ctttactatc agctctggat gtggttcaca gaaggtgctc   4980
aggggagcac tctcagccac tcatctcaca cgggttatag atatatgtat tgatgctacg   5040
tttgcttgtg agccatgttt taaagattag aatatctttt ctatgtgtac tctatcaaaa   5100
cacatgttag ggctttatct attttataca gatattggtg ttcttgcttt actaattttc   5160
atggaatttc ggtgaatatt agtattttag ataggaagac ttgtctcaaa atgtagctca   5220
gctggttgag tgcctgcctg catgtagaaa gccctgtatt cactctccag cacctcagaa   5280
gtgggccatg gtgcatatgc tgtcatctca gcactccgga gggagagaaa agagaatctg   5340
gagttcaagg ttatccttgg ctatataaca agtccaagat cagcctgggc tacatggcat   5400
cctgcctcaa aatcaaacac caaatcaaaa agctcacatc ttgatccaaa agaaggtaga   5460
gagaatacac tgggaaagtc tttgaaacct caaagctaac tccaagtgac agtgacacct   5520
ccttagcagg gccataaatt ctaatccttc cccaaagccc accaactgga gaccaagtat   5580
tcaaagataa gaatctatgc agtccattct ccttcaaact accacagtag gttttcttaa   5640
aaaaagaaaa aagaatattt taattgattg tgattattca gtattattca tgaataatca   5700
tgaactacat ggcaggacta taaactatta ttttttttaa agatttattt atttatttta   5760
tgtatgtgag tacactgtag ctgtcttcag acacaccaga agagagcatc aaatcccatt   5820
acagatggtt gtgagccacc aagtggttgc tgggaattga actcaggacc tctggaagaa   5880
cagtcagttc tcttaaccac taagccatct ctccagcccc tataaactat tattatattt   5940
ataaaatata aatccgtgag tctgtgcacc cctgtgtgca catggatggg acatctttga   6000
actggattat atcatactta gaagaataca agatactctg ttttgtcatt tgggtgaaaa   6060
tatggtctgt ttattttgca ggtatgacct gacttctagg gaatggcttc cactaaacca   6120
ttctgtgaac agtgtggttg taagatatgg tcattctttg gcattacata aggtaaacta   6180
tctcaactct tcaccaagca agaagttcaa ctcttcctgt tgctttatgt cattgaatac   6240
tatcgagctt tggttttagt tggtataagc tttgttttga tgtcatggag gtatataatt   6300
caccaagttg tcaccaagtt gtaattggaa attgaagtta gaacgatttt aatccatggt   6360
gtcttgcatt tggatactct gatcacagtt aacaatgaag attaaatagt gtcagcaagc   6420
ctatgcccat tatcaagtct agcatactgc atgcgtgtga ctgagtagcc attgttatct   6480
ccttgttttg agcgtatatt gtagaatgag gcaactgtat tttccacacc attttcgttc   6540
```

-continued

```
tgtaacacgt ttcatgtaga gaaggtgatt tagagagggg aagaatgtga ttgtattggt   6600
tggttctttc tctatgctat tcctagcaag tcaccgaaga gctcatgtta ctcacacttc   6660
ttaagctggg atcacaatga gattgtgaac cactcattgt tgttttccaa tataattttt   6720
aaaaagatgt atttattttt attttatgtg tgtgggtgtt ttgcctgcat gtatgcctgt   6780
gtatactgtt cctccagagg tcagaagagg atggcatcag aactggtggc tgttagctgc   6840
catgtgggta ctaggaacta aacccgggtc ctctgcaaga gcagcaagtg ttcataaact   6900
ctctctccag ccctagagtt gatttcttaa tggttttaaa aatcctgttt acatctttct   6960
tataggataa aatctacatg tatggaggaa aaattgattc aacagggaac gtgaccaatg   7020
agctgagagt atttcatatt cataatgaat catgggtatt gttaactccg aaagctaagg   7080
atcagtatgc agtggttgga cactcagcac acattgttac actggcatct ggccgtgtgg   7140
tcatgttggt catcttcggt cattgcccac tctatggata tataagcgtt gtgcaggaat   7200
atgacttggg tatgtatttt ttccagtgga ggcatcttga atatcatact gagaacccct   7260
gcccttatta ttaggacacc gtaacaaaat tcagcatgat cttgatccag taccttgtct   7320
tgaaatagta tcagtagata actggtgaga ttgaggttgt tgaagtccct gtgcaacagc   7380
tgtttcttac ttgtcaaggt ctagtcttgg cttgggaggg gttctgagga aaggggtgtc   7440
aaaaaaccca aaaagtccaa ttgtaggtcc aagctggcag ctgtatattg cattaaggaa   7500
agctgaggga aatttgggat atttatttca tctattagtc tacatcaagc aagtcaagcg   7560
ctcacagtca acgtttgcac cctcaaatta gtaacaaaag agggggaact gaggagtcca   7620
gcatggtcct ggttgggaca gaatgacatg gttccagccc tgagacaggg gcagcaggtc   7680
cgggcctcca tggatgtcac actatggaca taaacctgtt tgtataataa tgtacatatt   7740
tcatgctcct cttctgagta atgtccttct gttaatgtga atgacttcat gataatcaga   7800
gccagtgtga gtctgggaag taaatggtgg gaccttcagg acagctctta aggctgtgga   7860
aaagaacatg agttcaaaac catatacttc ctcaactata caaaaataga aggatgcaat   7920
atgaattgta tgaggggctt cacagatcta aaggaacaaa agcagcttcg ctgtgagcca   7980
acttgtcaga aagatattga gtaagcagtt aaagagattt agggagtgct gattgctaga   8040
ggaggccacc cagctaagtt tgtgcttaca aaggcagaca aagtcctgag ttcagggtgg   8100
gcctggaaca gagcaaggtt agttagacct tggtgtggta gaaatggtaa tttccagaca   8160
ggatacccaa ctagtttttg tgcttaacag aggcaggtag atctctgaat tcttttgtaa   8220
tgttaaaagg aaatgtgtgc ttgttgtctc ccaaggggcc tgagtcccag gatgctgatt   8280
tataggaaac ctggagtaac tgggtttatg acctgcagga gacgagctat ccagaatgtt   8340
ttttgcaata gcaagagaga actgcctgga gaactgcctt cagcaaagaa tagcaagaga   8400
aagctgtcta gagagagagc tgtctgtaga gaaagccggt cagagagaaa gtagactgga   8460
aaactgtctc cagcttggac ccacaatttg actttttgtt tttgttgaca agttgccctc   8520
ccccagaaac accttcctca ggacccctcc caagccaagg cagggccttg gcccttcttg   8580
tcagcttgca aggagccaaa gatagcatta aatgctttgg atatcaaaat aagcaaaatg   8640
caaaacagta aacactctaa aataattctg gctagtcctt taaatattag gccagtgcac   8700
tgttatttta ccttaatgta taatcttgtg ttacatttta ttgtttttat tgtataatag   8760
gaatgtcaga attataattt tgtaacattt gtttgacatt cctgtgaaaa tgcatctaaa   8820
gatcattaaa gtgcatctga agatcataag gactcactga ggagcacagg gaattaagtg   8880
tctgcttaag agaactttga atctttaatc tttagaattt gttttaaaaa tttgaatctt   8940
```

-continued

```
gccagtgtgg tggcgcatcc ctttggtccc agcactcaag gggcagaggc aggtgtatct   9000
ccattagtgt gaggccagcc tggtctacag agcaagttcc aggccaggca gggtacacag   9060
agaaacccta gcttaacaaa acaaaacaaa atatgaatct ttaaaaactt gttctgtgaa   9120
aatttcatac atgtatacaa tatagcttgt tcatatccac cgccattcct tccagctcct   9180
ctaggctttc ccagtgcatc tccttcctag ccttatggcc tccctttcag ggtgaaggtt   9240
agcacactga gtccagttag tgctgatccg atgcagtctt gtctagatgg tcttctttat   9300
aataaggtga aagtatatcc taaacttccg tcttttgctc taaggtgttt agactttaaa   9360
ctaatgttta aatcgtttaa ataatttatt atttcataag aagaggagcc tgcaacattg   9420
actttaacta ttgtctctta tccagaaaag aacacatgga gtatattaca tactcagggt   9480
gctcttgtgc aagggggtta tggccacagt agtgtttatg atgacaggac caaggctctg   9540
tacgttcatg gtggctacaa ggctttcagc gccaacaaat accggcttgc agatgacctc   9600
tacagatacg atgtggatac tcagatgtgg tgggtgtttt cctagagctt tcccttggta   9660
gtctagaatc tgcagaggca attgattaaa aatactgtgc tatggtttga cttttgttca   9720
gcattgtatg taacaaagtt aggagatcaa tacagtaata gagttaaggt actaatggtg   9780
ctgttgctgt ctgttagtgc ttagtgcttt agacctgatt cactgaactc tagcaaggtt   9840
tcctctcttc agaattctca gcaataaaag ctgtgctgat tttatccata cttaaaaagc   9900
atatccttcc ttttctcttt ttggtgttgg ggatcaaacc ttgtacatga ataggctata   9960
ccatctttat ccatttacat caccaaacag gatgctctcg tgcctatttg atagggtttt  10020
cactcacttc gaactgaaac ttgggttgta agagtatggt acttttagca aatggaaata  10080
aatttgagtt atgatgcaat tataaagcac tggtctctct gtatttccct cctccttcta  10140
ctccctccct cttcctttct gaccccctct ctcaacatac attagagacc atgctttgac  10200
tgtcaattta tgctgtgctg aagatcaggt ctttagtggc tgtgaaccac ggagcctatg  10260
cagtggaagt tctggtctct ggcttttgcc ttactaataa aacactgagc ataaattttg  10320
atttgtattt cacaattctt acctggaatt cttaagtgga attatggagc catagagaat  10380
gaacatttta gggcttttaa tatagtttcc cgaaatttta acagattttc atgattgtta  10440
aaggaagtgg cttacgtata gggggaaatc aagtattgca catttgaatc taaagttata  10500
aagtaattac atttaaattg gcaaataagt attcttttaa aactaacctt atatttatta  10560
tttctaaata aactcaaaag gaccattctt aaggacagcc gatttttccg ttacttgcat  10620
acagctgtga tagtgagtgg aaccatgctg gtgtttggag ggaacacaca caatgacact  10680
tccatgagcc acggtgccaa atgcttctcc tcagacttca tggcttatga cattggtaag  10740
ctttccaaag atgttttagc ttcaggaata ttttctttgc tgatggaaag atcactatgt  10800
taaaataatt gcaccattta aaagaagtcc aggtggtaga atttgcattt aatttgagta  10860
gggttacaca tctattgaaa agcattattt tggattaaac tacattaaat tctttgtgaa  10920
atcactcttc ttaattgctt taattctttt tttaggttga gttaattggt atcttctttc  10980
ttataagtgc cttacatagt agtggtggta gttgtaacca ccagtgttat gttaagtttg  11040
atgggatatg ctgtttccta gaaacctggt tttacacatg ctgttgatgt caatatacat  11100
gtggccagaa gagggcagtg tctgtttatt cctggaaaat aaacatcagc tgctctgttg  11160
tgtaaatatc acccatgtga tgttctttct gtttatttgt ctttgcattt tgagacagcc  11220
tcactatgta gtctaattgg ctgaagctca gtatatagat caaggtgacc ttgaacttag  11280
```

-continued

```
agaaatcctc ctgcctcttc tgagtgctaa gattaaagat gtgtactacg aatgaaaaaa  11340
aaaaatgtgt actaccacac ctgactagag attcatttta aaaattattc ttattgtgat  11400
aaaatgctca gaataacact caccatctta atgttttaag tagtttagat ttaaatatat  11460
tcctagtgtt attcatgtta taataccatc tgcttgccga cttcttgtaa aactgaaact  11520
ctgcccttaa acaatagttc ctctcttcat ccctcactcc agcctcttga aatcattttc  11580
tatatctcta tgattttgac tagtctaaat taggcatttt ttaaaaaaaa tattttgttt  11640
acttgtatgt gtatgagtgt tttgcatgca tgtatgttaa gcacaccatg tatattcagt  11700
gcccatagaa gccaaaagta ggcatagatt ccccagagct ggaattacag acttttgtga  11760
gccaccatgt gggtgctgga tactgtgccc aaatcctttg gaggaatagt gagtcttctt  11820
agctgttgag ccatcttgtc agccctagat gtttgttttt aacaaacgtg tttttgccag  11880
ccattgagtt tttaaattga gaatgggggg tacactatag ttagtcctta gcttcaagct  11940
tgtggaagca gaaatgagaa gacaatataa tcttaactca ggaggattct tgctggctga  12000
aacaaagatg tgaaattacc tccgagcact cctaagccac tggggtgagc agggtggtct  12060
ggagaggcct tgaagagaag ctgtctgagc ttgttcctgg ggacactggg agtcaaatag  12120
acctcctggg caggggggatt tagtgcagac aagaggcagg aaagtacatg tcaaatattt  12180
aggacttttg aaccgctacc tttcttttgt catggtaaca cagaaggtag caggtgactg  12240
ttagactaga atgttcagat ctgattcaga gtgccaggga tcgttggttg gtcttgtgta  12300
aagtctcaca agtgatagaa tcatatgtgt gtcttagact ttttttgttg taggtatttt  12360
agatttttct tgtttttcct ttttgtaagt ctggccctca cactatggtc caggcaggct  12420
taagacttat ggtaaccatc ctactctgcc tttatgggcc accatgacca atttaagaag  12480
ctctcttggg tggcattgtg ataagtgatc tggaaggggc atattgacag ttagcaggct  12540
gctactgcag aagtcctaat taggtttgta tcaaggccat ggaaggagca gtgacttcta  12600
gtacctggct gttgtgtgtc ttgacaaaaa tataactgcc ctttcttccc aagtgtctac  12660
tatggaccac ctttgccaaa actaaaagca gattcagaga aaaacatatc atgattgcac  12720
atggctataa tccctgaact taggaggatg agaaatatgg caagattgag accagtctga  12780
actatctagt aagaccgtgt ctttaataaa aatagtaaaa attataaaat cagggagtag  12840
gatctgggaa gaagagaatg aagtaagtgt ggggcatatc caattggaga tgtctttagg  12900
acagagctga ttgctgagag gtggttgtag gagaggtgag ttattgtggg gcataaaaga  12960
tgagcaagag tcagagacag ttggagaaca gagtctgaac aagagtagag actaaagaga  13020
gtgtcagaga agcagggaga aaataggtga gattgatgac ctgtgagata tgttaatggc  13080
cagaagagtg gctaaaaatg actggagaat ccttcagact tgtcaacaaa gaaatccttt  13140
agcctaattt agggtgcagg cggctgagga aggacatagg tgaaatatgt gctctgtgtg  13200
ttcattttta ttaaagctta tctgcaaagg cctcagattt gctgtgtact tgtagctgag  13260
gctcttttga actcctggtt ctcctggctc caccttccca agtgctagga ttacagatgt  13320
gtgccctagt taaaatagct gtatacctag cattaaaaat tttaagttag aaaatactgt  13380
ggtgctccgg ggatgcatct cagcagtaga gtgcttgcct gctatacaca aggccctggg  13440
actgatccct agcaccacaa atactaaagc agacattctg gtagggaaaa ctggtagaca  13500
gcagagtggt gaccatcagg agggggggttg tgggtgatga atgactacat taattagaag  13560
ttctgtgcag tatatttatt tcatgccctg aaacattgct gctgctgttg ctgctttcct  13620
ttacacataa taacataact aaaagacaga caagcatgtg gtatgaggct gtggatgagg  13680
```

-continued

```
cattctttgt tttccttttt tttttttttt tgagacaggg tttctctgac ctggctgtct  13740
gaaactcagt aggtagaaca ggctggcctt gaatgcacag agaccctcct gcttctgcct  13800
tctgagtgct gggttcaaaa tttatgtttt tttctataaa gactgagagt tcacatggac  13860
tatatatgac aacctactct gaaatgtgtt tttctccccc ttagcttgtg accgatggtc  13920
agtgcttccc agacctgagc tccatcatga tgtcaacaga tttggccatt cagcagtctt  13980
gtacaacagg taattggaaa gcaaaggctc tattactgtc ttacatctta tattcatttt  14040
taatatcaac ttcctaacag ttgtatctga atggtaagag gtttggggag aaaaaaggag  14100
agaaggcagt tctaagtgca cgataaggta aggggaatag gactgggagg ttatggggtc  14160
aaagagcaag tctgaagtct gcactatatc caggtgtgtg ctcaggaata cttttctgac  14220
cagcagagct ctttttccat ttgctccagg aaccttagtc ctgtaaagga catgcaaagg  14280
actagggttg tgggccagca atagagtgtt tatctagctt gcacaagatc ctgagttctg  14340
acctcagcat tttgccttct gcaaacacag catttgccat aagggacatg cagaatggcc  14400
attttaccta gtcacttgaa agtgtgcttt aagattgaga aacttaacag cctgctgatg  14460
ctgacttttc ttattttgct tctgttactg ctttctgctt ctttctttaa tactctaatg  14520
cttacattat atagtcctac aggtattcaa attttctgtt ggagtttcct aatacaagta  14580
atttaacttg cattaggaaa aggataaaag tgccattctg gagttgtgaa gaatgaccgt  14640
ttagaagcta gatagtgggg aaagatgata tctttaatca tgtgattatt tagtgtttta  14700
caagtatata ggggattgtg gcaagaccat tgtatgatta gagactaaag tggaaagatt  14760
ttttaaatat cttgttaact tgagtgttat cttaaattac aatctgatgc tttccttcag  14820
aaaaagccct aaatgcctct tgaggttttc atctggcaag tatcatgtca cctggccttg  14880
ctggtggaat ctgccccagc tcatgtgtgt tcttagtgtt ctcctagcac agagttaggc  14940
acgtgtgggc atttgcatac taatgtatag taatagtaac aattgaatga attgtctatt  15000
aaaacattct taagttttac ccaaacacag agaggtcgac aatttgtcat aaaatgtagt  15060
ttatccatga atcaaaatca ggaatgactg tctgaacagt gtttttattt tttattttat  15120
tttattttgt gtaatttctg tgatgtgttt gaatatctca gttttaggca ggattggaaa  15180
tgttagaggt tggtaagagg tcatggttgc agtttgatca tgagagaaat cgatggctct  15240
cccttcattg cagtgttgtc agtcagcagt gtgggatcac ctatgtctaa cagttgttct  15300
aattgagaga ggattacagg agggaaagca gtgagattgt gaggtgctag atgaggagat  15360
ggcatttacc tagcagcctt ctctcccgcc ctcccatcat gtgacctgag agattcacaa  15420
tttctgaaga tatcagctgt gcttagttta agcaatagtt ttattaacta aatccaactt  15480
gattcatgtt attcccaggg aaccagtggt aggattaaaa atgaatccta gtgttctttt  15540
tggttattgg aatgtcaagt tttcagacac tgtaacgaat acagagccat acaatcacta  15600
tatttatttg gtcctttgtt gacttagaaa aattgaagcc cagtttaggt gagctaccaa  15660
atttctcatt gtggattagt attaaacttg cgtggagttg tgggatcttg gaagtggggg  15720
ctaagcatcc gtgtttgtca cagcccagaa ggaacagatg aggttccttt tgaggagtct  15780
tatgtcttta tgaacttgga cttagaaata tttgatgtgt ttaattctgc tgtagttttt  15840
taaactctag ctagtgagca tcttttcaca ggagcgcttg agtctgacct acagccattg  15900
tctgtctctg gtgtgcatat tacaaatgca ctgggagcgt ttcttgaccc aaacatataa  15960
ttagattttt cttctaaaaa ggtctagttt gggaaggaat gaaagggatt agagaaatgt  16020
```

-continued

```
tgtgggtttg gtatttattt atttatttat ttatttattt aatgtatatg aatgatctat  16080
cttcatgtat acctgcatgc caaaagagga catcagactc atgatggtga tgaaccatca  16140
tgtggttgct gggaattgaa ctcaagacct ctggaaaaac agctggtgat cttaactgct  16200
gaggcatctc tccagcccaa ttgttctgtt ttagtttgag gatgaacatc taatttagag  16260
atgccctgct tttccaaaag tgagttttaa acactaattt ccattgtcag tggattggtc  16320
ttttaagaat ataggtagtg gtggcacacg cctttaatcc cagcacttgg gaggcagagg  16380
caggtggatt tctgagttcg agaccagcct ggtttacaga gtgagttcca ggacagccag  16440
ggatacacag agaaaccctg tctcgaaaag caaacaaaca aaaacaaaac aaacaaacaa  16500
aaacaaacaa aaagaatata ggttggaata ggttggaagc agccaatgat agtgcatacc  16560
tttaatccca gcacttgaga agcagaggca ggtggaactc tgagtttgag gccagcctag  16620
ttagtctaca gagtattttc ctggagagcc aaggctatat atagaaaccc tatcttgaaa  16680
ggccaaaaaa ggaggaaaaa aaaaaaaaag aaaagaaaaa agaaaaaaag aatgcaggtt  16740
gggcagtcag ggtaagtgtc taaggtaaga ggaattcttc aaggtggaaa gtcatgagtt  16800
ctgcgccagc ctaggctaca gagtactgaa aggggaagag actgtccatg tgtcagaccc  16860
tcatttctcc aaaagtcaca tgactatatt ttttctgtat tgcccactct tccatacatg  16920
cacctaacaa taaatattga agttcactct gtggcactat atctatgtga tagacttcta  16980
gaaaagtgat ttaaagttca aaaggtaaat acgtagtttt gtttcaagtt gccaaaatcc  17040
ctttagtaga ctcctacaat cttacatgcc cagtagcagt atagaagctt gcttgttgcc  17100
ttgaagcctc accaattcaa atattaggta acatttgtta catttttctt tgtcagctgg  17160
ataggtaatg aatgacacaa caatgtgttc ccattttctc tgcattacta attgaagtcc  17220
tatcacccac agcagactga agagttcctt taatatttta tggactttga caaacctagg  17280
attcatagct tccatacaga gaggaatttc acaaatagca aagttgggct gttagaagaa  17340
taaaaagaga attctgagta cagcttctca aagaagagtc ccacgtaggt gtcctctggg  17400
atgtgcctag atgcagggtt attgtacagg agctcttctg tctgctctct gatacttgag  17460
attatagggt tgcagggaaa tgcattagat ggcattacaa actgataaga taaagttagg  17520
agctatcaga gatttaggac atggtttttc tctgtaaatg gggcttctgg tgagattcct  17580
agaaaatgct gtttatagct aggaatgggg ttatagctag gaatggggaa agaccttaag  17640
cagttgtgag ctgtggtgga atgcatgtgt tttcagtttg ctaaggcttc cgggaatact  17700
tttcctgtcg ataattttct ttcactctct ttgtagcctt ctttgtatta aaatcctctc  17760
tgcttgcttt tgtgtgtgaa tgtgtgtatg tgtgtgtttg tgtatgtgtg tgtatgcatg  17820
tgcatgtagg tccctacata ggacagaaca tatttcctgg agttataggt gcttgtgagc  17880
agccttttag ggaaccaaac tctgtcctct ggaagagtag cccctttaac tgctgagtca  17940
tttcagcctc aagaatcttc tcttttccct attagtagaa gatgtcatct tagctctagg  18000
aactacacca cctctggcct cagtggacac ccatttacat atgcacatac agcagacaga  18060
catataacta aagataaaat aaatcttttt aaaatgtcat ttccctgtgt actaattttc  18120
catgtacaca ctcacaggta gatttttaaa ctattctgag tgatcacaaa gcagagcaga  18180
aggtgaaatt tgagagaata gatgatatta gtggattttg agaccttgaa aataatgtct  18240
cagagcatta aattaatcac tcatgtatgt atgtatgtat ataagtatgt atgcatgtat  18300
tatgtggatg ggggtgctgt agcacatgtg tggaagtcag aggacaactt tgtgaagtca  18360
tgtttctcct tccatcttta tatggttcca gtgattgagc tcagattgtc tacctgtgta  18420
```

-continued

```
gcaagtgcct tacctgctga cctgtcgcac tagccctctc agaggacttt taatatttgg  18480
aatatttcta acgattgaca gtcaaaagtt tattgtgagc caggcactta aaatcctagc  18540
acttgtgaga cacaagatgg aggtcagtcc agtctactga gttctagacc agcaagggct  18600
acacagtgaa acctgtctca aaaatttcaa aagcggagct agagaaatta cccaaggagc  18660
taaagggaac tgcaacccta taggtggaac aacaatatga actaaccagt acctgggagc  18720
tcttgtcttt agctgcatat gtatcaaaag atggcctagt cggccatcac tgcaaagaga  18780
ggcccattgg acttgcaaac tttatatgcc ccagtacagg ggaacgccag ggccaaaaag  18840
ggggagtggg tgggtagggg attggggggg tgggtatggg gaacctttgg gatagcattg  18900
aaaatgtaaa cgaggaaaat acctaataat aaaaaaaaga aatgatatca gaaaaaaata  18960
aaaaaataaa aaataaaata aaataaaatt tcaaaagcaa caactcaaac cagccctacg  19020
tcgtgcctct gagttctcag taaattcctt ctctctctcc tctcagcacc atgtatgtgt  19080
tcggcggctt caacagcctc ctcctcagtg acgtcttggt ctttacctcg gagcagtgcg  19140
atgcacaccg cagtgaagct gcttgtgtgg cagcaggacc tggtatccgg tgtctgtggg  19200
acacacagtc gtctcgatgt acctcctggg agttggcaac tgaagaacaa gcagaaaagt  19260
taaaatcaga gtgtttttct aaaagaagta tgttttttct ctacttagaa tttaaaaatc  19320
taattttatc tgaattgtga aggaacctag tctctgtact ttcctgttca ccttactctc  19380
tagttatttc ttaataaaaa aatacacaag atctttggat gggaggaagc atgtggctcc  19440
tggaagctgt tagcaggtaa taagttgtct ttgaattaca caggctttgt gtaccaactc  19500
ctggtctggc tgcaggtgat ctgaagccat agcacaatga aatttgtttt cattttggtt  19560
ttatgagaca gggtcttgct ctatagctca tactggtcaa gctccttgtc agcctcctcc  19620
ttcagcctct tgaatgctgg ggttataggc atgcatcact ggccctactt gggaaatatt  19680
ttgatgacag acatgctata tatttctttg ttcagtttag tagccactag caatctgtta  19740
ttattagata tttgaaatgt ggctatgtaa ctaaggggct aactgttttc ttttctttag  19800
tgtatgtagt gaggcagatg tagtagcaca cgcctgcaat ccagacactc acgaggctga  19860
ggcaagaggc agttctaggc cagcctgggc tgtgtaatga gaccttgtct caagagccaa  19920
aacatcaaca ataaaagaac agtatgtggc tattggctgt tatgttgatg atgaaggtct  19980
agtgttaagg ataagagcct ctaatggtat gatcacatat agcaaattgc tctggtagac  20040
agcagagagc tgctgttctt gaaaagtatt tccagccccc tttagctgta tatagcaagc  20100
agtacagcat aacagacaaa ctatggtccc ttcttctaga gcccctggcg tgctcttgtt  20160
atttttctct cctttgctac ttgcttagtg gttgctctga gcaccacttc accaactcag  20220
cgaagtaacg tgcaaaaatg tttggaaaat aagaatgcct ccaagatatt tgtccatatc  20280
aatctttaaa gtatgaaact acttccttat ctagttgttg cagttacatg agagttatat  20340
taggcagaga ctacttctgt ttttctggta tgtgttaaat aaagttgtgc agggacataa  20400
agctcctgag gctgtgctgt tgattagaat tttggttcat ttatggaaaa cagcttacca  20460
gaacctggta ggattcataa ttctcccgaa acagttagaa ttggtagaat aaccaaaatt  20520
taaagttaag cttaaatata cagtgcattg gaaataatat tatcttctga ggttcagtat  20580
gagcccatta gtttacctca ctttctgggt agacctaatc ctgtcagagt aaacttggca  20640
agaaaagcag cctacatgaa aactgatcag gcagggaagt ttctgtggcc tctcttcctg  20700
cttgtgtatg tcatattcat gaaatgattt atagatggca acatggcttt tagcttcttg  20760
```

-continued

```
tttggggatt taatgagaat tatgttaggt ctacaaagag tggaagttgt gaaatccaca  20820
ggtttggagt cacatgagta tatagagttc gagttagcaa gtgcctcctg tggggttgtg  20880
ggtcactggg tatacctgca cccaggtagg ccttgcattt gtaacaagga caaatgtatt  20940
ggtctctcat attgctttct taggcttctg cacagcttct ggtgttaatt ctgttgctag  21000
ttgatgtttg tcgtgggaag aaaagcatcc attacttctt agaagctata aaattaacag  21060
acctttgctt ttcactttct ggacactatg ggaggacagt tataaaacag tgtttctcgg  21120
attgtctgct tatatctgtt ttattttaac ctaaacatgg cactgctttt ttcctttcag  21180
tttgactata cactttgctt cctgactatt gttaggagct ttcctacctc agattataca  21240
taagagaggc tgccgcatag ttgatgggtt tgtcttctct ctgtagccct tgaccatgac  21300
agatgtgacc agcacacaga ttgttacagc tgcacagcca ataccaatga ctgccactgg  21360
tgcaatgatc actgtgtccc tgtgaaccac agctgcacag aaggccaggt cagatgctgt  21420
ttttcacgga ttttagggaa tagaaaaatg ctagatgagt gtgagtgtag ggcaaataat  21480
gagtagagtt ctttttaaaa tgggatatcg atttgaattc tactgttgct caggttttct  21540
cttaggaagg gatgctatat acatcctgat tccaaggatc gctcctgctg ctgaggtctt  21600
tgtgcagtgt ttccgaaagc atgttttaca gaatgccctt ggcccatatc tgactcagca  21660
tgacatctgg gctaatcatg tatgatttgt tataggtgat aataggctat gagtaaggtg  21720
atccagcttt tgctgtcttt gatggcttat gacatttttt tctcaaagtt taatgcattt  21780
cataagaaat aagacttgag attgctatgg tgggcacggg ctgggaggag ctctggaaaa  21840
gcagcaggtt cagctttcac gttttacaga taagcattgg ctgaggcttg gtggtgccag  21900
tggttccgtt gggctgctag cttgccagct aaaagcatgt tagtgagaat acacactgtg  21960
gtattcacat tgcagtgctg cttcctgttc attctaattc tatcattcat ccatctacct  22020
atctctatct atctatctat ctatctatct atctacctac ctacctacct acctacctac  22080
ctacctacct acctaccact tatctaattc tatctgtctg tctgtctgtc tttctgtcta  22140
tctatcctcc atctaattct atctatctgt ccacctatct atcatctaat tttatacatc  22200
catccatcta tccatctatc tgtctgtcta tcatatatgt aattctaacc attcatctat  22260
ctatccactt atctgtctgt catctaattc catccattta tgtatctatc tatatatcta  22320
attctatcta ttcaattctt ttcttttttt ctatctttct ttctgcagtt accattctca  22380
gttaattctc actgagttat ttgtgtgaat aacaaaacac ttctcccctg tgttccagat  22440
ctccattgcc aagtatgaga gttgccccaa ggataacccc atgtactact gcaataagaa  22500
aaccagctgc aggagctgtg ccctagacca gaactgccag tgggagcccc ggaatcaaga  22560
gtgcatcgcc ctgccgggta ggccttgcac agggatgtcc tctataaggt ccaagcttgg  22620
tcctccctcc tcagatcaag gtggacctag gaacaagatt gcttattctg tctatttagc  22680
cctctcacta ttgggggggg gggggggcga tattttgtat gtttttaact taaatgtggt  22740
ttttatgtat gtatttacta gcctttgaaa gaaagtgaag tgtcagctca tgttctggag  22800
aattgggggg tagcttagat ccatgttaca aactgtgtcc cactgtcctt ccttctgctg  22860
tgaaggagaa cctggcacta gagctctgtg gtctcagcag cagtcaggaa cctgcaggaa  22920
gcacttactg acagttgtgt gagaagagat ttctgtacca gcatcatctc ccatgtgacc  22980
ttccttcccg actatttcag cagaggttgt tcagggtatt aacttaggtc ctgaggccag  23040
ctagccctga ctaaatctct atgatgtatt tgcttgatca ggatatccag gaaggggagc  23100
ttctgtgctc tccaacatcg aggtttgagg ggaagttggt ctgactcttt tgaaagcatt  23160
```

-continued

```
ttatttagtt tgctgaatgg gctttagttt agccagtgtt ctattgctgt gaagagatac  23220
catttccaac gtgtaacttt tatgaaagga aacatttaag tgggggcttg cagtctcaga  23280
agctattatc atcatgacag ggagcataga ggcacaaagg caggcattag agtggtagct  23340
gagagctaca tcctcatctg tgagcagagg cagacaaggt gtgaaaaaga cagaacctgg  23400
cctgggcttt tgagacctca aagtctacca cccccagtga gacacttcct ccaacagctc  23460
ctgcaacaaa gctccatccc ccgatccttc tccagtcctg ccactccctg gtgaatgagc  23520
actcacatat atgagcctat gggggtcatt cttactcaag ccactacagg ctttgttttg  23580
tgtctcagac tttatgtcaa tagaatacct agacaccttg ttacaagaca ggcctggaaa  23640
gcctgcagtg ctgactccct gccagtagca cattctgagg agcaagtccc ttaagtcgct  23700
tacctgctct tacattacgc ctttccctga ccatttagtg agcactgttg gtgtccccaa  23760
cctgaacctg gttctgggga aacacttgct tattcacttc cgtgctaatg gccagggagc  23820
aagcatgctt tcatgcaaca ctgtgagttc agtacaacca caggaggaga ttgcagactt  23880
ccttcgtgta ctgtatcact atgaggtttt ccaaaccagt ctccctttca cctcattttt  23940
tggcatgcct tatgtacttg cttatacttt ctatcttatg acatgaaaac agagtggcat  24000
ttggaggctt aaatttatca cattcccaat tcaattccat tttcagttta ctctttctgt  24060
atatacatca gtgtgcagat aaatatctct ttgtgtgagc attggaggcc agaggttaac  24120
ctctggtata ttcttcctct atcactcttc acagggtcct ttgatgaatg tggagctcac  24180
tgattacata gactagctga ctcaaccctc aggcctcata accctgcctc tagccctcag  24240
atgagattac aagcaagcaa aactacgcct ggccttttat gtgggtgctt ggaatttgaa  24300
ctgggtactt atgcttgaca caagtatttt atccactgaa ccatctccca agcctccatt  24360
tgcagttttt tacctcaccc ttccaatata tatatttatt tgtatgccct ttgttcaaga  24420
ttttagtcac cttttacatt tttcttcaaa aataattgca ccaatttctt aataatggca  24480
cccaaaagta ggaacattag cctagagtat accctgtgag ccaggaaatg tgactggtga  24540
gacttgtaaa agggtctttt tattctggcc ctcagcggag gctcagcagt ggagcatgca  24600
tgctgttcct ctggaggacc cgaggtcccc aggggccagg tcacaaccac ttgtaacttt  24660
aactctgatc taatgccctc tatggctttt gtgctatagt ctcttgcact aacccacact  24720
caaggcacac atacacacat tctttaaaag ataaattatt ttattttcaa aggttttttt  24780
ctgcatatag aagttaataa tttgtctgtt atgctcacca gatcctaaca aagcacctga  24840
aattcaaatc aggatgagtt cagatgttca gtattttgaa ctagtaaacc gaactgcata  24900
attcctaaaa ctttgttttc tttcctcttc ccctttaaaa aagaaaatat ctgtggcaat  24960
ggctggcatt tggttggaaa ctcgtgtctg aaaatcacta ctgctaagga gaattatgac  25020
aatgctaaat tgtcctgtag gaaccacaat gcctttttgg cttccctcac atcccagaag  25080
aaggtggagt ttgtccttaa gcagcttcga ttaatgcaat catctcaaag tatggtgagt  25140
taatgtgttc agaactttgg tttctagggc acaacagcag ctcttatgta gaaggccaca  25200
gttgtatgtt atttgcctgg taagagaaag aattacaata aatgattaat aatatactgt  25260
gggcctctat ttcagaggct cttcttttga tacctttctt cttgtcttaa aaagttcagt  25320
actttgcata ttttattagt tgttattatt aagtaaatta taaggtatga acatatggaa  25380
tgaatggtaa tatgtgtaca tattctggtg acatcagatt attttgtact tgatttatat  25440
ctagattctg cttgggaaaa gggagagtaa aatgttagtt acctaggtgt cattaaagcc  25500
```

-continued

```
atctacagcc cctggaggta ttattatagc acatagtgta atcgtcagta agaaatgtaa  25560
aatctgccca ggttttatag ccttcttcct aaggcttctg aactcagaaa gttctcttac  25620
tctagagcca aactctcaaa tggcttgtag ttactatata gtctcatttg gtatttttct  25680
tggtaagtct aattctaaga cttgtgattt gactgtgatg cttcagtcaa ttagatattc  25740
acagagcagc ttttctgtct atgctggctg tggtacagag agatgtgagg gacatgtttt  25800
tgtctagcca ggagaagaca gaatgcagct cagcatctct catttggcac caccttcatg  25860
tgatgggatg ccggtatggt gtgggtcctg gttgttaaat ctcaggaagt ccatatatcc  25920
agaaatgacc tcaactatag gtggatttct ggcaattagg taaaagtcag cattccttgg  25980
gcacttggga aactggttac catctgcata aaggagtcat ttcccttcta tctggcagaa  26040
gggacatatg gctatctatt gtgcctgtca gcatggaagc acatgctagt ctccaggtcc  26100
ccccaatatc acaagtacct atagcagtga attagttaaa ctgatttggc tcccaatggg  26160
tcaagtacag ctgcacctgc ccaagagctc tttgggtttg caaatgagag acacatagtt  26220
aatttttata tgctttgact agttcagttg ctggacattt ctaatcctcc ctgcagtagc  26280
atacattaac ccctccaact ttcctgagtc aacttactaa ctcaacattt catctctgac  26340
accccagacc taatggcaga gtggccctta gagccacttt cccaattttt tttttatcag  26400
atattttctt tattttcatt tccaatgtcc cctttcctag tttccctgtc ctctccccct  26460
gctccccaac ccacccactc cctcttcctg gccttggcat tcccctatac tggggcatag  26520
agccttcaca ggaccaagga cctctcctcc cattgatgac cgactaggcc atcctctgct  26580
gaatatacag ctagcaccac gagtcccacc atgtgttttc tttgattggt ggtttagtct  26640
cagggagctc tggggtactg gttagttcat attggtgttc actttcccaa attcttacat  26700
ggctggttta gttctttcct gcagctctta ggtctaatcc ctttccttcc tctgtcatgg  26760
tgattgcctt cctctcctat ctcagttcct tgcctgctca atctaaaagt cccacctcca  26820
tctttctgcc cagccactgg ctgtatgcag ttctttatta tcagttgaag ccagctaggg  26880
gcagagacct tcaggtctgt aagtgctttg gggagcagaa ttaagacaaa gcattagaac  26940
caattcccaa caagtacctg ctatacattt caaagtccat attagtctcc tgggtcttcc  27000
cttccccagc tacttgtcct ccttgtaatc caaatgacaa gctttttcac acatctcttt  27060
atctcacatt tccctagccc tggccatgtc cacttgttct tttactctct gctctgctct  27120
ctttccaatg cctctggata ttttctctct cttattcaca ataaaaacca aaccaaacca  27180
aacaaaaaac cttaccctaa taatggagtg gtcacgcctg aggtttcctt actgctcccc  27240
cttgcacacg tcttgtgtct gacacactgg caggctttta ttagcagcag gctctaggag  27300
ctgagagaag cagcaggcac ctctgaggtg gtagttacta gagtgattag aacagacagt  27360
ggagacgtgg ctggaaatat ggactctggt gtttggagcc aagtatggta ggcggcagaa  27420
gccagcagaa gcatgatcca caccttcacc aggttgcttc cattgggaaa ggctggaccc  27480
cttgggaagg ggtccctttg tgccttccta ggtgttcgga gccaggtgtg tgagggatac  27540
agtaaaggga ctgactgcat gactgctcca ttagggtgaa gggttttgtt gtgaatagga  27600
gaaacaaaat gtgcagaggc atctgggaga gagcagagca gagtgaaaag gaagcagtgt  27660
aggcatggtc agggctaggg acagcggaga cagcaagata gcgagtgggt gataaggtga  27720
gagagagtgt gtgtgtgcgg tgcacacatc acgtgcatta taaggaggct gagtagctag  27780
ctgggggggag ggaagggcca gaaaactagc atgcactctg aaacgggtac ttgtgatgct  27840
gagggagctt gggggagaag ggcatgcctc aagaccagaa gagggagttg gagttacagt  27900
```

-continued

```
ttgtaagatg cctaatttga atgctgagat ccaaactctg atcctttggc tgaacatcat  27960
atctgctgag ccatctctcc agcccctaga aaggtggtga tggtggttgt tcttgttttg  28020
ttttattttg tttaaatggg gagccaggta cagtacatca tgcctttaat cccagcagga  28080
gattcaggag atagagacag gtagatctct ttgagttcaa gggcaccttg gtgtgtatag  28140
gaaattccat ccacccaggg ctacagaagg gtaccttgtc tttaaaaaaa aaaaaaagaa  28200
agaaagaaag aaaaagaaaa aaaaaagaga atgaaatttc agagttatgc aagataggag  28260
ctcagtggta gagtgtgtgc ccaggaagtg ctgggtttga ctcctcagaa caacagcagg  28320
ggcagaaact agtctacagg ttcatgagtg gtgttttgtt ttgttttaca taaaatgtgt  28380
tgaattagat aagtagataa aatgtgactc atacacagat aaatagataa aatgtgatac  28440
atgtacctgt acatagaaga ttatgatctc acctttaaaa aggaggaaat agagagtttt  28500
ggtagttaca ccacaggaaa actggaaaag aaaatgtata tatgaggctg tgccccatgg  28560
ctaaaggaac atgtttttaa gtcatttgaa ttcaccaaac agttttaggt aatgatatat  28620
ggttttgcat acaaccagta ttttataaat attagcaagg tcacatcatt tatgaaccaa  28680
catttaaact aaatttgtaa atcatcattt ctttatagca cttgtcatag aacataagta  28740
gtttaaaatg tgattattgc tttgctcttg atgtctgaaa atcttcatgt attctcttct  28800
ttgagccatt tttatgcttt gcagtactgg atgcatattg aagtgatcac ttattttaat  28860
ctaccttgcc tgagtttggg gaatagatgg tttccacatg tctgtgggtt atgcctaagc  28920
tagtggtttt tatgttagag cttgttttgg ggaaggcact ggttgcattc atagctgtgt  28980
ttcttttgcc tgtagtccaa gctcactctg actccatggg ttggtcttcg gaagatcaat  29040
gtgtcttact ggtgctggga ggatatgtct ccattcacaa atagtttgct gcagtggatg  29100
ccatctgagc ccagtgatgc tggcttctgt gggatcttgt cagagcctag tactcgggga  29160
ttaaaggctg caacctgcat caaccctctc aatggcagcg tctgtgaaag gcctggtaag  29220
gacatgggtg catatagtgc tccaggagga gccaagacag caaaggaggc acagctgaat  29280
gagcgctgag gtgatgaagt acttatggca gcagggagag gagcaccaat ttaggcatat  29340
gtatttcaaa cagaacccga ttccagatag tctttcttgg cctctgactg ctttaagcca  29400
tactgaaaac caaaaataaa attgctgaaa gaacccagtt tatattgagc tgcactgttt  29460
cgttggtctc aaagtgttga gaattgttct agaagattat ttccttggtg ttggcagaga  29520
agtgctatgg aggaaacaac aacctgaaac caaagaaaca tttagaaaag cagcaagtca  29580
ggacactatt cagacactgc tggggtgggg ggagaggggc atggccaaag aagccgacag  29640
agccaacacc aggctgtggc aatgtcctgc gctgaggtta aggttagact ccatgaggcc  29700
aggcccagaa cagccataca caaatgagga ctccaaaaca agaggtgcaa gtgtagtgga  29760
gactccatcc ctgcaggtcc tgtttcagga aatgattgta ctttgcctga gtaatacagc  29820
ctaggagcta ctttctgata gggtttttta aatacttaca aagaattatt tatctttaat  29880
catgtggttt tgtatgtgtg tgcttgcaca tgcagtgctt gtgagagaga gtatgtgtga  29940
gagcatgcat gtatgagagt gtgagaatat atgtgagaga gtgtgagtgc atgtgtgcgt  30000
gtgtgcatct gtgtgtacag gtgtgtgtac atgcatgtgt gtataagagt atgtgagagt  30060
gtgggtgtgt gtgtgagagt atgtgagaat atatgtatga gtgtgtgtga gtatgagtgt  30120
atgtgcgtgc ctgcatgtgt gtgtgtgtgt gtgtgtgtgt gtgtgtgtgt gtgtgtgtgt  30180
agaagtggcc ttggaaaaca gagttgtcag atctcttaga gatatagttg cagttggttg  30240
```

-continued

```
tgagccatct catatgagcg ctggaagttg aaattgggtt ctctggaatc ctctgggttc  30300
cttgttgaag cctgaatatt ttgataaata tttatgtcat tatccctcaa aattgtaaat  30360
gtagaattta acaaactcag gtcttgagtc atctttgtcc caaggtttgt ttgtttggtt  30420
ttttgttccc ccaccttttc ttcagtgctt ttaaaaaaga gagtccattt tttcctaaat  30480
gtttaaatac agttgaggaa tagaacatct gactccaatt tcctgggttt ccctccatgt  30540
agtgtagtgc tgacctgatt tcagtgtgca ttgaaaactt tgatcacttg gaaggcagct  30600
atgctcacca ctatactacc aatgtctgca atcctatagg agaaacaaca atatgaacta  30660
actagtaccc cccagagctg tgtctctagt tgcatatgta gcagaggatg gcctagtcag  30720
ccatcattgg gaggagaggc ccttggtatt gcgaagatca tatgccccag tacaggggaa  30780
tgccaggacc aggaagcaag agtgggtggg ttggggagca gtgcgggggg ggggggtata  30840
gggggttttg gggatagcat ttgaaatgta aatgaagaaa ataactaata aaaattgcct  30900
taaaaaaaaa caaaaaagaa aagtttttga tcttagctga ccagtgtctc tttgggtctt  30960
aatttccagc aaaccacagt gccaagcagt gccggacacc atgtgccctg cggacagcgt  31020
gtggcgagtg cactagcagc agctcggagt gcatgtggtg cagtaacatg aagcagtgtg  31080
tggactccaa tgcctacgtg gcctccttcc cttttggcca gtgtatggaa tggtatacga  31140
tgagcagctg cccacgtaag tggaaggagc ttttgaacat ttgcaggcaa gttgggcttg  31200
actttctgct caagtccatg cagaagctgg tcgggccggc ccttccagat taacatgtat  31260
gtatagaatg cagcacagtg ttccatgcag taaatcagtt acatcaagga gaaggcacag  31320
ggtacagaaa taccttttct tcttcagggt aatattataa ttcaatctgt ataatgtttc  31380
tacatcttaa tctaccagta tgtaaagtgc tttctagtag aggcctcccc agctcccttt  31440
ttcatccaac atcctgatat taaaaggttg gaaaagtccc tgttatatat tatgtaaaat  31500
gtggggccct ttaaattatt tcagttcaat aatcactata gggtactatt tttaattcat  31560
ggaagttaaa tcatctgtta aaagaaaagg taataacagt aaattcaaat cttgtgatag  31620
tgaattacaa gttggattgt tttgccttgt tttttaatag ctgaaaattg ctctggctac  31680
tgtacctgca gccattgctt ggagcagcca ggctgtggtt ggtgtactga tcctagcaat  31740
actgggaaag gaaaatgtat tgagggcagc tataaaggac ctgtgaagat gccgtcacag  31800
gcctctgcag gaaatgtgta tccacagccc cttctgaact ccagcatgtg tctagaggac  31860
agcagataca actggtcttt cattcactgt ccaggtaaga tgcctgtgta tcctagttca  31920
aatctcgtac ataaactaga cgcccagatc ccttggctca cttgttttct tgactgtgtt  31980
tgagttcttt ctgtgttctg catcaccttg ttggatcata gctggcaaag gtgctctcct  32040
ttctgtgggc tttttcttta cttgattgat tgtttctttg gttgcacaga agctttttag  32100
ctttctgaag tcccatttgc cagttgtcct taattcctgg gcgagtagaa gcctcataaa  32160
aaaaagttcc ttcctacaca tgtatcatgt agggcactgc ctatgtttta ttccagaagt  32220
ttcagaggtt cgggttatgt ctttgatcca tttagggtta ctttttgtga aaggtaatgg  32280
acacagttct gtttcattca ttattctaca tgtggacatc tacttttccc agcaccagtt  32340
ttgaagatgt tatcttttct gcaggttgtt tgtttgcttg ttttgtctct tcagaaaatc  32400
ccagatggcg gtagctgtga gtgcttaggc ttggcctacc tgtttcatta tgttggcttg  32460
catgtctgtt ttgtgcagtg ccaccatatt gtcttaattg ctatagctct gcaatctatc  32520
ttgacatctg tgttggcaat cctgcagttt cgacccttct gctcagcagt gctttggcca  32580
tctggggtct tttctgggtt cataatgaat tttaggattt ttttttctat ttctgagaaa  32640
```

-continued gtattgttga tattttgatt gcgattgaat tgaatctgta aattgctttt ggtagaatgg 32700
tcattttcac aatattaatt ttactgatcc atgaacatag gatgactcca gtctctcatg 32760
tctccctata gccctgtctt aagagatttg gagtcttcat tgtagaagtc cttcacctcc 32820
ttggttaagt ttatttctag atattgtatt gtctttggta ttataaatgg tagtatgtcc 32880
atgatcttgt tctcagtgtt tttttagttt agttttttt aatttatgtg tatgagtgtt 32940
tgttttatat atgtgtatat gtgcattcat gtcctctggg catcagatcc cctgggactg 33000
gatttacaga cagctttgag ctgcctgtag gtgctgagaa ttgaacccag gtcctctgca 33060
agaacagcca gtgctcctac tccccagccc cagaagtact aatttttaag agctgatttt 33120
ctacctttgc tgacattgtt gattgtttct agaagtttag tgatagagtt tttgagattt 33180
cttatatatc ttatgttatc tgtaaaaagg gataatttga ctccttttcc tatttatatc 33240
cttttatttc tttcatttgc catattgttc tagctagtgc ttcccgctca gtattgaaaa 33300
gagtggtgat tgtgaacagc ttttcttatt tcttatttta atgggattat tcacccattt 33360
aagataatgt tggttatggg tttgtcatac acagcccttc ttatattgag gtatgttcct 33420
tccagtcctg ttctctctag gacttttttt tttttaatca agaaagcata ttgggttttt 33480
tgttgttgtt attttgtttt gtttttctag acaaggtttc tctgtgcagc cctggctgtc 33540
ctggaattca ctctgtagac caggctggcc ttgaactcag aaatccacct gcctctgcct 33600
cccgagtgct gggattaaag gcgtgcacca ccactgcctg gcacatgttg gttattttgc 33660
aagccctttc tacatctact aagatgagca tgtggtttca tctttgtctg tttatattgt 33720
ctgttgtatt tattgactta tgtgtgttga gccaacctga agttctggga taaaacccac 33780
atgctttgga tgatttttgt gctatgtgct tatattgtgt ttgttagtgc tttattgagg 33840
acgtctgcat ccgtgttcat ctggggtact gtctgtagtt tgcttatttt gttgtcttta 33900
cctgctctgc attttagagt aatcctggat ttatagaaag catttgggag tagtccttct 33960
gtttattaaa aaaaaaaatt aagaatgatt ggttgttgtg tggtggaatt ctgctgtgaa 34020
cccatctggt tctggactct attcggaagg ctttttatta ctgtttcagt ctccttgttt 34080
gcagtgatct atttaggttg ctaatctcct tatgattcat ttggatgaat caagaaatta 34140
atccatctct ttagatttcc agcttaatgg aatatgagtg ttaaagtatt tctttatagc 34200
attctgtatt ttttggcatc tgttgtaata tttccctgtt ctttctgtta atctctttct 34260
ttcttgtggt tagttgggct aagaggctct tggttttttt tttttttttt tatcttttta 34320
aaggaccagc tcttagattc attaattctt tgtattattt tccttgtttc tttttcactg 34380
atttcatttt agattttatt atttcttgcc atctactgcg tttgggttgg ttttagttat 34440
ttttccaaga ttttcagttt catcactaag tcattcattt gggctctttt gggtttcttc 34500
acgagaaccc acttgggact gttaccttcc cttttagacc tgcttttaat gtgccccaga 34560
gatttgttac attgtctttt cgatttaact tagtttcagg aatattttga tttcttcttt 34620
gacccattca tcattcggta atgagttgtt taatctctag tgagtttata catttattag 34680
aattttgttt actgatgatt ttaaggtgtt tggctttgtt tgtttgtttg tttgtttgtt 34740
tttcgagaca gggtttctct gttgtagctc tggctttctc tatgtagaac agtctgacct 34800
caaattcaca gagatccacc tgcctctgcc actgaagttc tgggattaaa ggtgtgtgcc 34860
accactacct ggctgatttt aagttttatt acataataga caggtagggt acatagattt 34920
tctacatttg tgaaggtttg cgttgtttgt cagcatgtaa ttctgtgtgc tgctgaggga 34980

-continued

```
atgtatgttg ttttgacagt taggtggaaa agtctgtaga catctgttag atccatttta  35040
catttcaaga agccatttaa ttctgaagtt tctctgctta ttttttccca ggtgacttac  35100
ctattggaga aaatagggtg ctaaaatcat ttactattat tgtttttttt aagaagaaaa  35160
taattaattt aaaaaaccct ggaaagaaag ataccaaatg tgaatcatgt ttcctggata  35220
gtggggttat atttgatcat ttatttttcc tctcaaatac tgtgagtttt tacaatgaat  35280
aacaacataa atatttttat gttgctgtgg actttaactt tgctttgata atatatttgg  35340
ttttttgaga ctaatttctt tttgatattt tattttctca tactagtttt tagtaaactt  35400
tggttttgtt ttgtttgtat tttttagact ggccaccaac ttgctatgtt gtcaagggtg  35460
gccttaaaat ccacacccaa tactttgtcc tctctttctt tctttctttt ttttttttat  35520
tggaacaaaa tttctaggtg ggaatctcac tatgttaccc aggctgacct gaaacttctg  35580
ggcttaagca agatgggtgc acatgatcag agacgctgcg ctgcccgcct cagcccctgc  35640
tagttggaac tataggcaca gacagctgta cttcactcat ttcaatgatt taacatttag  35700
actatatgca aataaatatg aaatgtattc accaagttct cctatgggag aaacagagcc  35760
cttaagattt tttcctttca gcttgccagt gcaacggaca cagcaaatgc atcaaccaga  35820
gtatctgtga gaagtgtgag gacctgacca cgggcaagca ctgcgagacc tgcatatctg  35880
gcttctatgg tgacccgact aatggaggca aatgtcagcg taagtcacac aggtcaagtt  35940
agtcacaagt caggtacaat agtacagtac ctgcagttga cttaaatatc ttaaagggaa  36000
aaggcctctt ggtttgggat attgcctttc ttaattatgt taaattgtta aaagtttaac  36060
tgaggggcta gaaatgtggc tcagttggct aagaacactg actgttcttc tagaggaccg  36120
aggttcaatt cccagcaccc acatggcagc tcacaagtgc ttgtaacacc tgggatccaa  36180
caacctcata cagacataca tgcatgcaaa acactaatat acataaaata aatccattaa  36240
aaagtgtttg atgatgctgg aagaggaaaa aaggctcaac ttgtgggttt gggagcagtt  36300
agttaaagca acaaaccgac agtaaaggag ctaagctttt atttcttcag cagaggcata  36360
aacaaggggc cgaagtcact gaggcaccag ctgcctttat tccatttccc tcccatggaa  36420
gcacatcagc tcaagtcaag cagagcagcc tgggatggga ggtcatctca ttggagaagg  36480
aggcaggagg cattgtgagg ggagggagga caaggctggg aatgggaagt cctgagctca  36540
gaatcagaat gaggacaaga tcttcagttt ccttcttaat ataaagaggt atcacagagg  36600
tctctataga agtctactgg aagcctcaca caggcacaag ggtacatttg aaaaactgtg  36660
acagccaggg agagtcccct tctgaagtgt ccttcctcag agactgcagc acctgactgt  36720
gccccagtct gcaagaggtt tggggagagc aactgacctc ctgaggaccc cagatgaatc  36780
tttaagatgg cctgcttttg gttttggttg gttggttttt agacagatct aggagagttg  36840
gtgatgagct tgaattctct gtcctcctgc ctgacctcca aatgcccagc ttcacatggg  36900
ctcccattaa gttgtgagtt tcggtgtctg gctcctgctc tcacagccag tgcagtacat  36960
tgagctccat agagatagcg ccggggcaaa tgagagctgg acgggcactg ggtgactctg  37020
tgccttgtgc cggaaaatca actaaacatg ggcaaaggag atcctaagaa gccgagaggc  37080
aaaatgtcct catatgcact ctttgtgaaa acctgctggg aggagcacaa gaagaagcac  37140
ccggatgctt ctgtcaactt ctcagagttc tccaagaagt gctcagagag gtggaagacc  37200
atgtctgcta aagaaaaggg gaaatttgaa gatatggcaa aggctgacaa ggctcgttat  37260
gaaagagaaa tgaaaaccta catcccctgc ccccaaacag gagaccaaaa cgaagtacta  37320
ggaccccaat gcacccaatg ccttcttcgg ccttcttgtt ctgttctgag tacctcccca  37380
```

-continued

```
aaatcaaagg tgagcaccca gcttatccat tggtgatgtt gcaaagaaac taggagagat  37440
gtgaacaacg ctgcagcaga tgacaagcaa ccctaggaga agaaggctgc caagctgaag  37500
gaaaagtacg agaaggatat tgctgcctac agagctaaag gaaaacctga tgcagcaaaa  37560
aaaaaaaaaa ggggggtggc caaggctgaa aagagcaaga aaaagaagga agaggaagat  37620
gggaggagta tgaggaagag gaggaagaag aaagatgaag aagaatatga tgatgatgaa  37680
taagctggtt ctagtttttt tctcatctat aaagcattta acccccctgt atacaattca  37740
ctccttttaa agaaaaaaat tgaaatgtaa gcctgtgtta gatttgtttt taaactttac  37800
agtgtctttt ttttgtataa ttaacatact gccgaatatg tctttagata gccctgttct  37860
ggtggtattt tcaatagcca gtaaccttgc ctggtacagt ctgggggttg taaattggca  37920
tggaaattta aagcaggttc ttgttggtgc acagcataaa ttagttatat atggggacag  37980
tagtttggtt ttggttttat ttttgggttt ttttttttca tcttcagtcg cctctgatgc  38040
agcttatatg aatatgattg ttgttctgtt aactgaatac cactctgtaa ttgaaaaaaa  38100
aaaatcgtgg ctgtcttgac atcctgaatg tttctaagta aatacagttt tgtttttatt  38160
aatattgtcc tttcgacagg tctgaaagtt ttcttcttga gggaaagcag tcttttgctt  38220
ttgtcccttt tgggtcacat gggttactgc agtgtgtatc ttttcatata gttagctgga  38280
agaaagcttt tgtccacaca ccctgcatat tgtggtaggg gtaacacttt catccatatt  38340
caaagaatct ccaaaatcgt gatcagttgg ataagaaata ttatataacc tacttggcaa  38400
agcaaggtgt gatcaattct gtcacaccat gggatcatta gaatcaagca atctgaaaat  38460
ctgtccttaa aggactgata gaaaagtatt ttctaatcct tatacaaagg ctctccttta  38520
actgccactg ctatgtaatg acagttatgt tttgcagttt ccctactaaa gaagacctga  38580
gaatgtatcc ccaaaagcgt gagcctaaac tacacaactg cagtactatt tgttgacctt  38640
agtcccagcg aaggctatca cgagaatgct agctataata taatgcctct gcccctctat  38700
ctaaatatgg attgctcagg aaacttgact gcttaaaggt atttttttca tattgttgtt  38760
cctcctatag ggttgcagac ccctttagct ccttgggtac tctctctatc tatctatcta  38820
tctatctatc tatctatcta tctatctatc tatctcttgt cagatttctt ttttcttttc  38880
tctttctttc tttctttttt taagatttat ttattattat ttctaagtac actgtagctg  38940
tcttcagatg caccagaaga gggtgtcaga tctcattacg gatggttgtg agccaccatg  39000
tggttgctgg gctttgaact caggacctta ggaagagcag tcggtgctct taaccactga  39060
gccatctcta caacccttaa aggtattttt aagtagttga gtcagctttt aaaattatgc  39120
cagaagtgtc aaaagttcaa aagtttagga ccatcctcta ttgaagtaca gggtcatcct  39180
gggctacatg agaccctgcc ttaaaaccaa aatcaaacaa acaacaggaa aaacaagagt  39240
taagaaagag aaaaagaagc acttggaaac aaagatctgt ggagtatgta taggcttctc  39300
tacaacaggt gtatgtagga tcttgatggc ttttgagtct attaccctca aagaggtact  39360
gagaaaccta aatgtgatca ccgtggtctc tgaggggcac ctggcaggat tatgggagat  39420
aactaaagct tgctaatcac agagtttagg gagggaggac gtctctaagg caagttaact  39480
gtctggtttg agatgcttag gtgatgtctg aggaagtaat aaggcctgtc cattttcata  39540
cacactcagg ccttaagtct gggtaatggc tacttgaaca taaaatagtc ctctatgaaa  39600
ggaataatat ctctgtgtca gcagccttca cggctaatgt taattgtgca ggaaccctgc  39660
ttctcagtca gacagaagct caatcaggca ggggcaggac ttctttgcct ttcccatgtc  39720
```

-continued

```
cttgtaattt ccctggcttt tcatcttggt tcaaacatac ttacctgtta ggtaattata  39780
agaacaccaa atattactga ataaaatgtg tttatgactt tgtggtgact gccattcaag  39840
aattagatgc cttagccagc aatgatggca cacgccttta atcccagcac ttgggaggca  39900
gagataggca gatttctgag ttccaggaca gccagggcta cacagagaaa ccctgtctcg  39960
aaaaaacaaa acaaacaaac aaaaagattt cgatgtcttt atcacccaaa tcaagtaact  40020
ttccaaagtc tcacagtgag atgtagccta gttgggagcc acatctaata tatgctgatg  40080
atcttaacaa gtagcctgct tgtgtcttca ggtgaccacc ccggtgtcct cagctacctc  40140
tagaaagatc acactttcct ctgtggtctc tgcagggtcc ctgtatgatt ctggaacctt  40200
gctgtacttc tcagagtcct gattcataaa gcactgagtt tttgcttgtt tgtttgtttt  40260
gatactattg gtaagaatat atattgaacc ttgacatgcc tttttaaaat aacattattt  40320
ttacaatagt actttagcct tgattatgtt aactgcttac tgtttcagat gacattcgta  40380
catcttttaa tcctcaaacc agtcctatga gatggctagc atcattgtca catcatttag  40440
gcaaggaaac aggtcttggg ttaagcttca tgctcagagc tccttggaac acagtggact  40500
caagtgcaag cagactgacg cgactgggtt ttactaattc agtaagcctg tactctatgg  40560
aggaagagtt tctgaccact ggatgcagtc tgatgacctc tgactgttct gtttgaaagg  40620
tttctttcag tgattttatt tttctccatg tggacttttt ttccagcttt taaaatatat  40680
atatatatct tattcgcttc acatcctgct cactgtcctc cctcccctgt catcccctcc  40740
tacaatcctt catatccccc cttaccttct gagcagctgg gagcccctct gggtatcccc  40800
acactcgggc acatcaagtc tgtgaggctg gacgcatctt cccccactgt ggccagacaa  40860
ggcagcccaa ctagaacata tcccacagac aggcaacagc ttttaggata gcccctgctc  40920
cagttgttca gcacccacat gaagaccaag ctgcacatct gctacatatg tgcagggagg  40980
cctaagttca gcccatgtat gttctttggt ttgtggttca gtctctgaga accccaagga  41040
tacaagttat ctgactctct taatcttcct atagagttcc tatctcctct ggggcccacg  41100
attggtgtcc ctattgcttc actgggattc ctgcctggct acacccacta tgaccaaggc  41160
aagtcttaga aaagacaaca tttaactggg gctggcttac aggttcagag gttcagttca  41220
gtatcatcaa ggcaggaaca tggcatcatc caagcaggca tagtatagaa agagctgaga  41280
gttctacaac ttatctgaag gctgctagca gaataccgac ttccaggcag ctaggatggg  41340
ggtcttcaga cccacaccca cagttggtgt ccctattgct tcactggggt tcctgcctgg  41400
ctacaggagg tagcctcttc aggttccata tccccaatgc tgtgagccac agttaaggtc  41460
acccactatt gattctaggg tgtctccctc atcccaggtc tctttcattg tggagatgcc  41520
ccccacttcc ccaccactgt cagttgcaga tttccattct cgggaccatc tggccatgcc  41580
ttctgtttct cctcacacct gatcccgaca cccccgccca ttccttctcc tacctagttc  41640
cctccctcca tatgcttcct atgactattt tattccccct tctaagtgag attcaagcat  41700
cctcacttgg gccggccttc ttgttttgtt tctttgggac tgtggagtgt agcttgggta  41760
tcccattttt ttatggctaa tatctgctta taagtgagta cataccattc gtgtcctttt  41820
gggattgagt tacctcactc aggatggtat tcttaagttc tattcatttg cctgcaaaat  41880
tcatgatgtt tttgttttta gtaactgaat agtagtccac tgtatagatg taccacagtt  41940
tctttatcca ttcttcagtt gagtgaaatc taggttgttt ccagtttctg gctattacaa  42000
ataaagctgc tatgaacata gtggagcatg tgtccttgtg ggatggtaga gcatcttttg  42060
ggcatatgcc caggagtgat gatatagctg agtcttgaag tagaactatt cttagttttc  42120
```

-continued taaaaaacca cgaaattgat ttccaaagta gttgtacaaa tttgcactcc ctctaaccaa 42180
gcaagtgaaa gatctgtatg acaagaacta caagtccctg aagaaataaa ctgaagaaga 42240
tatcaaaaga tggaaagatc tcccatgatc gtgaataggt aggattaaca aggtgaaact 42300
ggacatctta ccaaaagcaa tctagagatt cagtgcaatc cccatcaaaa ttccaacaca 42360
atttttctgt agaccttgaa agagcaattc tcagtttcat ataggaaaac ataaagccca 42420
ggagagccaa aacagttctg agccataaac gaacttgtgg aggaatcacc atccctgacc 42480
ttaaagccgc actacagagc agtcgtgatt aaaacaacaa caaaggctgc gcacttttgg 42540
tacagaaaca gacgtgctga ccaatggcat ccaatccaag atccagaaag aaacccacac 42600
actatagttt ttttttaaat ataaagttct tcagcttaat gcttctcatt attcatgaga 42660
gaagaagact caacagcaaa gaaggtgaaa caagggtgac aagtaccaca gggctctcga 42720
gtgtctcttg tgatggacta gggagcccgt cagttctgaa tgctcaggaa tgtggttcac 42780
agtgtggcca cagtacagaa gatccccgag ataaggcaga agacagtcac cacaggtcat 42840
ctccacaggg caaggactca gtatatggca tattactaat gctcttaaat atttactgaa 42900
caaaggaaca aaatgctgag tctgtcacag agatgaaaat agccgttgct tcaggggaca 42960
gcagaagata gccttttttt ctccttgaat ggtagttaat ttaatgttgc ctctatatta 43020
ttagaaataa attacaagct gaaaaataat gagtcatacg cagtgatttc tcttgcttta 43080
ggctgtcttt actacaaacc catttcaggc taaatgattt tgtcttaatc acagtctatg 43140
gtaatctgtc aagccagttg tgacctgtct tcctttcctt cttcccagca tgcaagtgca 43200
atgggcacgc atcactgtgc aacaccaaca ccggcaagtg cttctgtacc accaaaggtg 43260
tcaaggggga cgagtgccag ctgtgagtac cacacacact ctgtgtctcc agtgggggac 43320
tgggccttgc agctgcctgg gccctgtcgg ccacctgctt gcctgggcat tgttgccctt 43380
cactcccagg gtctttgagt ggactagtgt ggaggtttac ctttttttcct tcagacaggt 43440
tatctcagtt actttaatat tgctctgata aaacatatga ccaaggcaac ttacaaaata 43500
aagcctttaa ttgggcttat gacttaagag cattggagtc tacattgagt tccagggcaa 43560
tagagctaca tagtaagact gtatcaatca atcaataaat aggactacat agtaagactg 43620
tatcaatcaa tcagtagatg aagagaaaga aagaaagaaa gaaagaaaga aagaaagaaa 43680
ggaaggaagg aaggaaggaa ggaaggaagg aaggaagggg aagaacaaaa caagcttaga 43740
taggaagaac aggatagaat gaatgacaaa tgcttgaaaa atgttttagc tgtactttta 43800
gaagcatact caatccacac agaagtaaaa atgttgttcc ttatgagtag tacctagcat 43860
tattacatat gtacttgcct gtgtccttgg gcaagtattt gtttatttgt tgtttttata 43920
ctgttgctgg tgtaaattac tgagcagtta gcagaaacat tcctgcaaat gggatagtct 43980
ctctgatctg aataatgata tagtttatgt aaaaggattt acttggttta aaaataaata 44040
tagagtctgt gctttaaatg tcaatagaag ataatttctt ttttccctag atgtgaggta 44100
gaaaatcgat accagggaaa ccctctcaaa ggaacatgct actgtaagtt tttgtaattg 44160
tttctagaga gtaattgaac aaaacgacat tgcttttttt ttttaccatt gtctgagaat 44220
gataaatgct tgggggatga agcaaatact catagccatg cccctgactt ggtgaacact 44280
gttctaactg aggcatggtc tctgctggtc atccagagca gttagcaggg gtgctgtcct 44340
gcctgtcctt gttcagctcc cgcggaggcg tgctcattca ccattgccca gtgtagctta 44400
tcatgtccaa tcttcagaca gccaggaagg agtttctaag atagaggtgc gttccaccat 44460

-continued

```
tctctctgca gctgatttgt gctcacaaac aagtaaataa aacaccaaat taataccttg  44520
gtgtgaaagt gaatctggta agcttacagc tttatcataa atatattttt tgtctatgag  44580
aatctacata gtaggttcta gactatagaa caataaaaaa aggaattaac atttggcata  44640
tgcagcataa tggtatatat aaattgtaga agaaaatgga tggttctaga cctgaaaaga  44700
caagaaaatt gcttgtgtgt aatctgggca ggtcttaagt tgtgaccttc aacatctgct  44760
tcccaagcag ctggaaccac caggcctaca gaattcttag ctatgattct aaaggtcatt  44820
catcaaatat aatgttaatg tgtattttat taaagtttca aacttctatc tttaataatc  44880
tgcaaatgta gctcagtaga ggagagctct cgctgtaagg tcctgtgttc tatccccagc  44940
acaacaaaac aagacattta agaaaaaatt aaaacaagtt ggctgtattg tctcagtatc  45000
tcatccttga gatagtgagg caggaggact tttagtttga ggcctatgtg ggttatgtag  45060
tgtgaaacct ttctcaaata atatttacac tttttttcttt aaaaaacaac ttttttctta  45120
atttatgtgt tttgcaacat gtaagtctgt gcaatgtgaa catatctgtt gcctttgaat  45180
gccagagagg gtttcagttt tcctggatct ggagttacca agggttgtga gctgccatag  45240
tgggtgctgg taatgaactg agtcctctgg aagagcagcc agtgctctta actgctgagc  45300
catctctgct gctaggtact ccccccttccc cccttaaatt taagacaaag gtctcactgt  45360
gtagcctcag atggtctaga actcaatttg tagaatggtt gacctttgaa ctcacaaaac  45420
tctgcctgct tctgcctcct gagtgttgag attaaagttg tatgtcacca cacctgcccc  45480
tatgatttct atatttaata aagatcatga ctaggatata gagaacactt ttagaactga  45540
agaagaagac agttacagtt aaaagcaaaa caaaaacaaa aacaaaacaa aacccagaaa  45600
aaaaaagaat gaaaactagc actgaagaaa aaataaattt taaaaatagg caaagagtca  45660
ctattatatt gtgatggatg tgttatatgt ttaaaaccac aagtgagata caggcctgaa  45720
atgactttaa tcgaagctac accagcctgg ggtggtagtt cagttggtaa agttcttgct  45780
atgcaagcac aagaagctgg gtttgatgcc caggacccat gctgaaaccc aggagtgctg  45840
ctgagtgctt cagctctggg gtggcagggc tcactggcag gaagcctagg ctaagagaga  45900
ctctgtctcg aaaaacaagg ccgatggcac ctgatgaacg gcatctcagc atgacctttg  45960
ctcggcatat aatgtgtaca cacaaattca tagtttagta gaagacaagt atgatctgct  46020
tttcatgaag tctgttgtaa tacgccttct ttagttaacc atagttgctt aaaaaaagaa  46080
aaaaatcgac ctcactggac agaaaatgga tagagtgttc taatagccaa ttcaattcat  46140
catcattatc aaaacctata acttaggggg ctggagagat ggctcagcgg gtaagagcac  46200
tgactcctct tctgaaggtc ctgagttcaa atcccagcaa ccagatggtg gctcacaacc  46260
atccataaag agatctgatg ccctcttctg gagtgtctga agacagctac agtgtactta  46320
cataaaataa ataaataaat ctttaaaaaa aaacacctat aacttaaact tatcaataac  46380
tttaactttc ctaccccatg cttcctagtt acccattctg ctttctgttt gtatgatcct  46440
gggtatggca tcttaatgga accacagtgt ttgactttgt atctacttaa tattaggcat  46500
gatgcctctg actctcatcc ctgatatagc acagttcaaa attgcctttc tttggtgctg  46560
tacatatagc tgagcgtttg agtgcttccc tgcatgcaca ggtttctgaa ttcaatcccc  46620
agcacaaaaa atgataaaaa gaaagcaaaa aggcttattt ttacagctgg acagatcatc  46680
ctgcattgtg cctgtcatgt tttgcttgtt tcttctgtca gtggacactg tgttacttct  46740
accttttggt tgttgtcagg aatattgtaa acatgagtga atatacaccc agaagtacaa  46800
ctggatgtgg taattctatg agtgttttgt tttttgaggg atggttatta ttgtttccat  46860
```

-continued

```
acaataaatt acatttcctt acagttcatt acatttccaa aagccatgca tagcatttct  46920
gttgttctac attcttattg acaccagttt tcaatttaca tttattttgt gagtttttta  46980
attggtaacc atcataatgg acataaaaaa tagctcattg tagttttggt atttgtattt  47040
cagtaatgct tggtgtgatt atctttttat attcttatta accattagtg tgtatctttt  47100
tttggaaaaa cacctcttca agggttttac tatgtagctc tggctggcct ggaacttgtg  47160
cagaccaggc ttgcctccgg ttcccactgt cttaggtagg tttccattgc tgtgaagagg  47220
caccatgacc agagcaactc ttacgaagga catttaattg gggctggctt acagtttcag  47280
aggtttaatc cattatcatc atggcaggaa gcatggcagc atccaggcag atgtggtgct  47340
ggaggagccg agagagttct atatcttgat tcaaaaatag ccaggaaaag actgtctaca  47400
gcaggcaacc aggaggagac tgtcttccat attgggcaga acttgagcac taggagtgtt  47460
ccaaagccac ctacacagtg acacagtaca tccaaaaagg ccacacctat tccaacaagg  47520
ccacacctcc taatagttct acttctcatg ggccaagcat actcaaacca ctacatccac  47580
ctacttctgt ctcccgaatg ctgggattaa aggcatatgt tgccattacc caattttaaa  47640
ccagattatt attgtttttt tgtacaacag acttttaagg ttaaagtttg cagcaatagg  47700
cattctttga agctgtatca cactgatata tgtctgttgt tttcttcctt cctagattaa  47760
aatagtacag tatattcaag tttcaattgt ccctttccat aagaagtcct ggtttctgtt  47820
ccattattag tttatatctt agtgttctta agtaaaaata ctcagtattt atagatgagt  47880
tagattagag ccaaacccca atcagggtat tggtaatgaa ggtttgctgg ataattcaaa  47940
ggatactgca aagatctggt ttctaatgga aagaacatgt aagttggcca ttagtggacc  48000
acacatctgt atttcttatt ctttggaacc ttgggcagga tagacagatg agctaagatt  48060
ccttcatagc tattgaattt gtgagaaaaa caaattgtgt ttccagaaac ctgctttagt  48120
ttgtatcaac acttactttc tttctgtgtg tggtgtgtgt gatgtgcctg taccattttc  48180
aagtttttct tccttctttc catagatacc cttctcattg actatcagtt cacctttagc  48240
ctgtcccagg aagacgaccg ctactacaca gccatcaact ttgtggctac tcctgatgaa  48300
gtaagctttt cttttaagct gtcttatttt gtgttaaatt ttgtataggt ttttttcttg  48360
gtcatcctgg acaaaagtac tacatagaag cagacagtat cagggtggga atataaaagg  48420
caaccagttt ttaagtattt ttttatttac ttgttgacag ttttatatga ttatataatg  48480
tgcttgatga tattcaacct gtgacctttt gtctccctca tacttagttc cttctctccc  48540
caccaagtca ccttcactcc ctctcgtgtg tgtgtgtgtg tgtgtgtgtg tgtgtgtgtg  48600
tgtgtgtgag agagagagag agagagagag agagagagag agagagagaa agacagacag  48660
acagatagac agagagacag agattgattg attgattgat tgattgattg attgattgat  48720
ttacctacct agtttaccag ctgactgcag gagcatgctg ggtgggaagt tcttactgga  48780
gcatagacac attacagtga ctacaccact gaagaaagtg actccctctc aggtagtctt  48840
cactgccact aggtcctcag ggatcaagag aatgtttgga gtctacattt tatctttttt  48900
ccactcagaa ggcaaacatt actgaatgtt tttaagtagt agaataatgt tcatgatagt  48960
ctgtttaata ttaaattaag aatttgttcc taattataaa atttttagaa gatagacaag  49020
aagacaaaat ttttgagtta acagtttgaa aggtttattt ttattttatt ttatatgtat  49080
gaatatttta gcttcttgta tccctgtgca tcatgtgtgt gcagtgcctg tggaggccag  49140
aaatagatat tggatccctg gaactagagt gatagatcat tgtgagccat catatgggtg  49200
```

-continued

```
ctagaaccaa cccagggtcc tctgcaagag cagtgagtgc tcttaactgc taggccattt  49260
ctttagcccc taaatgtgaa caactcttta aataaatgta agtgatctta aatactctgg  49320
agaaaaatct gtagctatac cttacttttt aaaaattatt ttgttttata ttatgagtgt  49380
tttgcctaca tatatgtgtg tctgatgcct gcagaggtca gaagagggtg ttggatcccc  49440
tagaactggg gttacagatg gctgtgagca gctatgtggt gcctgggagt tgaaccctgg  49500
ttctctgtta gggcaacaac tgcttttaac catcaaccca tctctttggc acatgggtgc  49560
attgttggtt tggctgcttg agttgtgtgt gaggggtgtg tgtgcataca tatgtgggtc  49620
catgcttatc cagtggaggc cagaggtcag agtcatgtat ctctctgtta ctttctacct  49680
tatgttttgg aagcaagatt agatagaccc ctgggacctt cctgtcttct cctcagcact  49740
aggactacaa gtccacacct gactttttac atggggcttc agatctaact cagtcccaac  49800
acttgtttca tttccttagc accttggcta gattcttagg attttagaag gagcttatag  49860
caaaatacca caagtgaaat ttactactgc cttagtcata agcaaatatt gaaggctcag  49920
tctttaaggg tataattgat agtgttcttt tttttttaa gtaaacaaat agcctgtcat  49980
ggtaactatc gctgtagtcc cattacttgt gagagatgtc agctcaaggc cagcctccgc  50040
tacataagta agggaagacc agcctgagct atatgggact ctatcaaaac aaataaacat  50100
tgtagaattt ttgtaatact tattagaagg tagctgatga tcatgagagt ctttagacat  50160
ttcttcattc cactgttttg tgtgtgtgtg tttcatgaca gatttcttac tagatttatc  50220
tctttgtgtg tgtgtgtgtg tgtgtgtgtt ttacaaaatg acaaagattt tagtccttct  50280
cgtggaaagt agttgctagt ggtcagcaga tacttgctag tataaataaa tgagcataga  50340
tctgcgcttg caaaggaaga caaagggaaa aaaggttttc ttgaacataa ttcctacttt  50400
gtgaaagaaa cttctcattt ggaaattaca ttttgaaaat aggtattgtg aatgtttcca  50460
ttgtggtttg tggtataact atcaaataac actttttaa aaagaaaaat cttaattttc  50520
taagattttt aaataccctt ttaaaatgag catttccagc atggtttgat taatttgtaa  50580
aatgtaagaa tatagtatct aaggctacag aaatgactca gtggttaaga gcactggctg  50640
ctttacagag gacccaggtt ccatccccag caccctcatg acagttcaca gccatctgta  50700
tttctagttc cagggcatct gatgcccttc tctgattttc tccagtacta gtgacacaca  50760
gcatacattt gaacaaaacc actgatacac ataaaataaa ttgttttcaa gaaacaatat  50820
agcatctaat tagcttacaa aactaattat ttgtttctgt actaattacg tttctattgg  50880
catgactaag gcaacttata agagaaagca tttaatttgg ggttcacact tctagtgcct  50940
tagattctat gagcatcatg gtagggagtg tggcagtagg caggcaggca tggtgctgga  51000
gcagaggctg agagctcaca tttgattttc tactagaaga cacagagaga gctaactgga  51060
aaaggcatgg gcttttcaaa cctcaaagcc cccctctagg aacacacacc tccaccaagg  51120
ccatacctcc taatcaaaca gtcctaccaa ctgaggacta accattcaga gatagatgag  51180
tctatggagg ccattgtcat ccaaaccacc acaggcccca agaaagattt gttagtgaaa  51240
tttcagtgaa aactaaaaca gcattagaat ttacctggca tagccagcaa tgatctcttc  51300
tgttcagtgc cacagatttc tttgagttaa aactcagttg ttaaaaccaa aaatcaaaat  51360
gtaattggca ctttaaattg ctataagggg aaacaaggtt ttcaaagcca tgaaaccata  51420
ttcagaataa ttttagcgag agaaatattt tttcttttt ttgtcgtttc ttttttttct  51480
tggagagaaa tatttttatt attttatatt attttaatta catatttaat tattaaccat  51540
ttctgacaga gggcaaaagg tgaggatctt catggaacta atatctgata aagcaccaaa  51600
```

-continued

```
ttcttcccaa ctctgggatg caaatgacag ttcaacttca gtttattgct tgtattgaag  51660
aaaattgaca agaaatgtca tgtcttaaca taagcatgga tttcttttaa gatgtagaat  51720
agtctataat taatgttttt gagactagta agacctgatt attgttgtat cttaaaatct  51780
agaaggtact aacaattttc taatgtgtat tttttttttc atcagcaaaa cagggatttg  51840
gacatgttca tcaatgcctc caaaaacttc aacctcaaca tcacctgggc caccagcttc  51900
ccaggtacag acacacctag agagatggat tggcaagttt agtgtaggag ttggggaagg  51960
aggctctgaa ggctggtgag tgagttcaga gcccacctct gcctcttagt agccatggca  52020
ccttgaacaa gccatgcttg aacaagcatg tacaattccc tctctacctt aggctactca  52080
gagtgaggag tcacagctct tgcctccagc gttgctggtt caggttggtt ggatggctgc  52140
tccctgcttt gccaccacct tccagcacta tgactatctc tatgtttgtg cttcacaggg  52200
gaaaaactaa agtgactcat agttttaaga aatgaaaact ctttaaggga agggggataa  52260
ctctaatatg tagaggtatt catactttgg gataactcct aaaagtacag cttttccatt  52320
cttgtttatc ttatagtgac tataaaattc tgatggccct aatgtagcag ttactataaa  52380
taaccactcc ataacttgat agccctgaag atagacctag gtttgaattt acctgcacgg  52440
tgttgaacaa gttactgaag ctttcttttc tttgtttttt aagtttgttt tattttatgt  52500
gtgtgtttgc ctttgcctgt atgtgtataa gtgtaccatg tatgtgcagt gcttgagaag  52560
gtcagaagag gacatcagct ccccaccctc aacgagttac agacaattat gaactactat  52620
atctgtgctg gcaacagaac ccaggtcttc tgaaagagca accagtgctc ttaactgctg  52680
agccatctct ctctagcccc caagttacct aaactttctg atccagtttc cttctttata  52740
aaatgataca gtgaaaatag ctttgctatg tacagagata ttccaacttt ttaatattac  52800
aacatgacat ctacaaatat gttagccctc attcataatc ttgcctgaat tgtagagtgt  52860
tgcaaggaat aaatgaaata aaggaggtac ttattataga gtttgaggtt tgccttcatg  52920
cataaagaga agctttttttg agtctgtact actcatgttc ttagccaatg gagtatataa  52980
aatatggtag aaccatttag aaatggagtc tcactgggta caggcctgaa tgcagtggta  53040
gcaggtagca gaaagaaggc ctgagtggct gcttgagcac cttctccatc aagacttgag  53100
gacctttctg cttaggaagt gatgagcgag taagtgtccc tgaacaggag ccttgagcat  53160
attctacagt gtgaagcaga aatacaaagg agttgaggta tcatgtgcaa aatgaatgca  53220
gtgtctgttt tatatgtatg attgttttac atacatgtat gtctgtgcat cgcttatata  53280
tctggagcct ctgagacaga ttacttaatc tattgggact tgagtttttc caatctgtag  53340
atggagatag gaaggtgttg tgtgggttag agactgaagc tcataaggct atattctttt  53400
gacactgtaa gtgctcaata aacttttacc ctcattacta gtgcgcaaag attctttctg  53460
attggcatac ccgcctccca agtctttatt tttattcttg cttctttcta gccggaaccc  53520
agactggaga agaggtgcct gttgtttcaa aaaccaacat caaggaatac aaagatagct  53580
tctctaatga gaaatttgat tttcgcaacc atccaaacat cactttcttt gtttatgtca  53640
gtaatttcac ttggcccatc aaaattcagg taagaactgc tttttaactt cattcccgta  53700
aagatggtga catctcttta gtggagacta acttcactca tttggaatct gtggtgactg  53760
aaagatagtg ttgctttgcc tttgagggat ctttgccata gactgagtag caggtgagtg  53820
ctgttcttag gttggagaga tgttcagtga gtggagtgct tgctacacaa gcctgaggac  53880
atgcagttca tctgcagcct ctcatacaaa gcgggacacg cagggtgtgc ctgtcacctc  53940
```

-continued

```
agcactggac atgcagtgtg tgcctgtcac cccagcacag gacacgcagg gtgtgcctgt  54000
cacctcagca ctggacatgc agtgtgtgcc tgtcacccca gcacaggaca cgcagtgtgt  54060
gcctgtcacc ccagcactgg acacgcagtg tgtgcctgtc accccagcac tgggaagcag  54120
gggacagaaa gatcttgctt gctggccagc cactcaaagc tggatctgtg agttctagat  54180
tcagttagag accctgtctc aagtaaaata aggtagagag gaattgagga agacacctga  54240
ttacctctgg cttctgtatg catgtgcaca tatatatacc ttcacacata tacacactca  54300
gagaaaaaat tctgagagtg tcatatcact tgtgaagaaa gttttaaagc acttttaaaa  54360
gcaagatgaa agctatgcaa ggtatgcaag gtagtatact tttgtaatcc caggatgtgg  54420
aagaccaatg caggaggatc accctgagtt tgaggccata ggaagaccct gcctcaaaag  54480
gagggaagga gggagggagg gagagagaga aagagaaaga gaaagagaga gagaaagaga  54540
aagagaaaaa gaaagaaaga aagaaagaag gaaggaagga gaaagaaaat caaattgatt  54600
ggcatatagt tatgtgttta ttttttgagt aattgctatg taaaagcctt tagaaataca  54660
cagttttaat tatggaattg agtataaata aaacaagtac atgtttgtaa ccaataaagt  54720
ataaaaatga cacataagat gtcaaagtgg tatgatggct ataatgtgga gtccatagag  54780
gaagcagtag gcagtatgag gtactgtgta aaaacacata gctttactat tgcacagaca  54840
agtgtggatt cttgttctgt gtgtggttca tggaggctct ccagtttgca gattctctgt  54900
gcatgtgtcc tgaaggattg gtcttcctgc tatgacctct ggtgttatta gcctgaactg  54960
agtcctaagg agacaggtag tggaaatgtt tgtattgcaa agacagtatg ggtagttgtt  55020
tttagaaaca ggagttcaac agaattgata gaacttgtga tcaagaagct aacagctgga  55080
ctgggatgta gctcagttga aagaacgctt gtctaacatt aagaagccct gggtaccatc  55140
actaccacag cataaactga gagtagtgac agactcatgt gtcccagcac tgggaaggta  55200
gaggtaggag gatcagaggc tgcccaggga ggttgagagt gacttacgct aggagataga  55260
tctaaaaatg aaaaggaaaa agaacttggt agctgctaga gctaccatga agagagtgga  55320
gcttaaggat tcagctgaag aatgtaaact gccttctgat gacaactgag agtcgctgag  55380
ttatttaaag tcaggaagtg aacaaagatc agtgtttcag aaagacctct gtggcaacag  55440
tattgactag aagtagcccc tcctatgtca ggtactggtt tagactgtat ttggaagtgt  55500
cctctttctt gatggccctc agacaccttt catggccact cctctgcatt tgtaccccat  55560
agccacacac ttgatggttc tttattacat aaatagctcc ttataggcaa tgatagattt  55620
tatatttttg ataattttaa gataaactct atgtcattgc atagaattta gtagttgtag  55680
gtactcagta aatgtatata ggatgaatac aaaagcttta gggtaacagt attttgttct  55740
tcttccccg catttttaac tatctcatag tagcacagac taacccataa ctgaccatga  55800
agccaaggat gaccttgaac tcctgtacct tctacctctt ccccgaaagt gctgaagtta  55860
ctggcatgtg ctgctcaccc aactaatagc aagtttttct tataaaggtg ctgatgccct  55920
ttccctgttt gtgttaattg ctgacactta aaagctcttt atcccaaccc acagtgttaa  55980
agagtttagt taaattttgt ggaaattttg tcccaaatga agtggttgat ggcaggcctg  56040
gtggctcctt cctataattc caacactcag gagacagagt caggacgatg gccaagaatt  56100
caaggccttg ggcctacaga gtagaagaga gaagaatgag gattcgaaca cctgattaaa  56160
tagataccat ttcctgctac caacctgtgc cttagctact cttctattgc cgtgacaaaa  56220
catcataccc aaggcagctt ataaaagaaa gcatttatta ggactcacag tttcaagggt  56280
tatactccaa aaccatcatg gccgggagca ggcagcaggc aggaacatct gctgtgagga  56340
```

-continued

```
agagctgaga gctcacttct ttatccacaa ataggaggca gagagaaagc taactaggaa  56400
tagaatgagc tttgcagacc tcaaagccca cctccttccc aaacatttcc accaattggg  56460
aactaagtat tctaatctgt gagcctctgg aggcccattc ttatttaaac taccacactt  56520
tataagttaa tactacatgt gatgaggaaa ctggtatggg aattctgaaa agtagttcac  56580
aggagtggga ggggctgaac gtgagtagat gctagcatgt gtgtcaggag tgaagtgttc  56640
agagcattgc ctggtttgac ttctctccag agctgaggtg aacatgcttt gtgccaatac  56700
aaacccgtat taaagcggtg gtagttactg aaaatcagtg cagggctgtg gtctcaacac  56760
aatgtttgaa aaagaaaaca gggcatccac atcaggcagt gtacagctgc ttataattcc  56820
agtcctctgg cctctgctca catgcacata ccccccccata catacacaca tgattaaaca  56880
taatgaaaaa ttaaaaatta atgctataaa aatggaaaga gccgggcgtg gtggtgcatg  56940
cctttaatcc cagcacttgg gaggcagagg caggcggatt tctgagttcg aggccagcct  57000
gatctacaga gtgagttcca gtacagctag ggctacacag agaaaccctg tctcgaaaaa  57060
caaaaacaaa aacaaaaaca aaaaaaaaag tggaaagaaa ggttcactgt ttcacaggaa  57120
aactctgaga ggtgataatc caatcccagt ttaaaatata ctccatagtg cacacagcct  57180
ctcccatcct tggcaactga ggcctgtgag aagactcagt cctctcctgg cttccaacct  57240
tacagtgttc aaaactcttc tgcaagatcc acatggtcct accaagaccc tgaaggtcag  57300
gcatgctgat taggctgtct ctgggcctga agtgaaaggt aaacacttcc gagatctcca  57360
aagccttggg aagattctga aatgtatggg tgttggttca ggtagactct cagccttggt  57420
gaagctgccc ccggagctgt agggttatct gcagaaagtc agccaggtgc acttaccctg  57480
gaatcctctc ccattcacag acacctccct gaggctttgt ggcttcacct cactgtgcag  57540
ctagctcctg ttttacatgc ttatataatg aatggtcttg gtaaagaaga tgataaaggc  57600
aagctagagg cctttttttt cccctcttca aattttgatt ggcctttccc tactgttaca  57660
ctgtctactc aaggttttga gcatttactt tgtgtacata gtaaaagcaa agtacatatt  57720
tttaagtaga aaagaaagca tctgtggtct ttgatatagg tgcttttctt tattttaata  57780
gtaatactta ttccatgctt gttaagaaat tcattcacag cgtgttttca tagagacttt  57840
ctctatagag atatatagaa atctagacat gaggacagcc cactaaccca ctcttcagac  57900
actagctgct tctcttagag ccctgggctc tcaccctttg gaggacagcc atcctcactc  57960
atatgtgaca agcttagaca cagaataatc acagagactc cagcctcccc cacaaaccca  58020
caatgccaat atcccatatt cccaggaact tttaataagc catccactct aatactccat  58080
ctcttatctc aggcataggc cctggttttg gtttgcttca gagtactgcc ttttctctac  58140
cacgcccttc ccactctttg ctgaccctcc agagatgtca tttccaaatg aaggggggttt  58200
ttggttctgt gggtgttttg tttttcagtg cagttcctta actgctattc aggggacgga  58260
gcaggcaaac cagatctcta acttctgagg cctgtgaaga gaagcatcag aacctcccag  58320
gggagctgta ggagcaggag tcaggcctag atatgactgt gagagagtgg ggaccattac  58380
cagtgtctta caaatgaggg gaaggactac cgtgctgggc cctgaaagat aaggaggacc  58440
aggcttcagg aaggtaggac acattctgct gactgtctgg gattgaggac agtaacacaa  58500
ctacttagac atactttgaa tgaaggacag acttagtgct tcagaactgt aaatccatta  58560
tatctttccc aagtcttagg ctagccaagt ttctcaacat ttatctacct catcccaaag  58620
ggttcccagg acaaatattt cttactcaaa catttgatgg gagttggaat caggttgagg  58680
```

-continued aaatgcaggg gtgtagattt tagatttctg ggaatatgta tagatagcta ccttctgttg 58740
gatagaaaat gagattgtaa gtttttcagt gttttttttac acgagtttgt gtgcccatgt 58800
atgcacatgt ggaggccacg ggtctacctt aggtgtcttc ttcaggaacc agccatctta 58860
tttttaagat gatctctctc cagacctcag ggctatcaac acacctcagg gatccatcct 58920
cctgactgta tgtccctagc atttgggtta ctgtaccacc atgctcaggt ctttgtgtag 58980
gtcctgggga tcacagttag gttctcatac tgcagggcaa gcactttgta aacaactatc 59040
tcccctgcat atggaagtat taccactaaa ttacaacaag attttcttct attaaaatta 59100
tattttagaa gctggatata gtaatgcgtt ggggcaaaag gagggaggga aatgaagagg 59160
ataggaagag ggggagggag aagggaaaga gtggaggcgg gatcagaagt ccaatgttat 59220
tcaagggcag cctgacctag ataaatccct attaaaaagt tttcagtata gaaacttctc 59280
atcaccttca ttatcagaaa agcccctaaa ttcagaacac tttttaatct taattagttg 59340
acaatttcat aaatgtatta tttatatata tgaataacat tttcctccta cctttttttc 59400
ccttcccctc tgatgattcc catcctccca accaagcccc ccttctgcat ttgtttgttg 59460
ctttaatgac ccactgagtt ccattgggct cacttccatg agtgtgacta gaagagctat 59520
ttatcagaat gtgggcaact taccagtagt gacactgatg aagaaagtgt ttccctctta 59580
cccagtaacc attaatggcc aggagctcct gggaggggtg ggcgccttat gagccccttc 59640
tccaaaatgc tttcaaactg tgaccagcta tatttaatgt ttttattatg cctgtgtatc 59700
catgtgggac aagaaagctt gagagtatca tagcatgcat gtggaggtca aagaacaact 59760
gtgtaaagtc agatctcact tcccaccttc acatgggctc tggcactgaa ctcatgtcag 59820
tgacctgaga ggcactttat cctctaacac gcaccctgtg cccagcctaa aatttgacct 59880
ttgcaaggtt tagtgtgtgt tatctgactg tctgagtaag gatgacaaaa tgaaaccaaa 59940
cttatgggat aaagcttggt ggttgtatca gtacattttt attgttgtga taaaacatta 60000
tgaccaagac agcttataga agagtttatt tgggtgtata gttccagaga ggtaagagtc 60060
tgtcctgaca aggaagctgt ggcagcaagt ggcaggtatg gctacaggag caggaagcag 60120
aaagagcaaa ctagaaacag ttgaggtttt ttaataggaa agcccactcc cctaatgatg 60180
tccttcccct agcagaccac aagtcctaac cctccctaca cagcaccacc agctggggag 60240
ttcaaatgtc tgggactgca ggggacatct cattcagacc acctcagtgg gagaatgctt 60300
gccttcatag tatgtgcaag gccctaggtt caattctagc caagaaaaga gaacatgagg 60360
aaagaaaaga aggtgggaga gagtagagaa agaagagaag aagaggaaaa aggaagggaa 60420
gggggagaca gaggaaagca gggaagcaga ggagaggaga agagaaagaa aagattaacc 60480
agcctggttt ttaatagcac ccctcccact ctcagtagtt cccaatttga gcattaagtt 60540
caagactgat agatatttct gggtgggtga ccagtgtggt cataaacatg gtgacttttg 60600
ctctccgtac aacttgtgat tatgaacttg ttagatgatc agcttcaaca ggagagggcc 60660
tcctttagtc tcaggtgccc cctccagcca ccctgggact cgcagcctct ctgtgatgag 60720
acacaggaca ttaactggta tggttctgct ttgccaaaac gtcagtccat ggttgaactc 60780
tccacaatga gaaagaagct ttgagaatca ttacatggca tcaggcaagc caggactgat 60840
ggagcctgag aaagggccag gagcatccgc aggttttggc acccagtact aactagtaaa 60900
agcacctcat aggtttcttt aaaatgcaaa cactaaggaa aatctaactt ttttttattt 60960
attaaggcca ttcattttat tttataagta ttttgcctgt atacatatgt accacatgca 61020
tacaaggtca aaagatagta ttgggtcttc gaactggagg tacagatgat tgtgagctgc 61080

-continued

```
catgtggatc ctcgaaattg aacctaggtc gtctacaaga gcaggaagtg ctcttaactt  61140
ctgagccatc tctccagctc cagaaaagct actcataaaa gtcaaatcta agccatgtgt  61200
ctggtgatgt acacctttaa ttgtagcaca tggaaggcgg aagtaggcgg attgttattc  61260
atccaaggcc agtcttctct taacagtgac aaaaacaaaa ccaaacccga aacctgttac  61320
tttgcacttt agagtataag tgatagagaa aagacacaga aattttagaa tctatacctt  61380
aaaatacctt atggcttata tgatactgtt gggaccatat ttacttatgg aatgcaaaaa  61440
aaaaaaaaaa aaaaaaagat ggggggggag ctgaaggtct cctttctatt ctgttgtaaa  61500
tctagctata aaaagagtaa gaggcatgag tgtgtctcag tggtagagca cctgcttagc  61560
ttgtgtggga ttgaatgatc ctcagcacca cagaagaagg gtggggcaat aaatttagga  61620
aaataagatg ctaatcattg actttcttga tttttttaaa aaaagttatt attttatgtt  61680
tattgtatat gtttatattt tctatgtgtg tttttgatgt gtgctggagg gatgggggcc  61740
acttgctgaa cttcccaatt gttatcataa ctaccatctt tagtgaaaca gttaccatct  61800
acttagtaat tgtttcattc gaatagatac tgaacactct taatctgaaa ctaatgctca  61860
gaaagttcca ctttgccaag caagcaggat aatgtaagcc tataatttta gcactgggag  61920
ggtgaggcag aattgtgagc tcaagggcac cctgagcttt tgagatcctg tctcaaataa  61980
aattaaatta tatagatatc agattttcag aataggtgtg ttcagctgct gaataaatct  62040
aagcaaatat ccccaaagaa ccctgaaatc tgaaacgtat tagttctaag ccctatgttg  62100
tgtgtgtgtg tgtgtgtgtg tgtgtgtgtg tgtgtgtgtg tgtgtgtgtg taagatagat  62160
tctcactatg taaccctagc ttgcctggat cttgctatat agagagacca ggcatatgct  62220
atcgtgcctg ggagtcccaa acgttttaga tgaaagattt cagttgtacc attatcttcc  62280
taatgagggc tctggtctag tgaggcaggt gacattaggc cagtagtaag tattaggaat  62340
tggtgatgac ggtcaattct gagacacaca gtagatacat ctaatctacc aatacaacca  62400
atgatttaga aagaattagg ccatagttaa atttgcagtg tttttcttct ccacaaaata  62460
atgttacttc tttcagttct tagttcaaat acagtaggaa ttttttatat tcttggtgct  62520
aaacactatt attttatagt aaagttagta agatagaaat gacgccctgt gggttgtctg  62580
gtcgtagtct gtagctgagg ccattttgct gagaagcagc gtaggctgtc actggctttg  62640
tcacccatat tttctgtatt tttgctgcag attgccttct cccagcacag caacttcatg  62700
gacctggtac agttcttcgt gactttcttc aggtaatttc tctatgctaa ttgtacacat  62760
tccatcgaga cagtccctta actgcagctt gctttgtata tccctacaaa gctgcttttc  62820
actcacagtg atgtaaattt agtctgatgt gataaaactc tccgtttgta tgattcggct  62880
ctttgcatgg ggagaggttt gggctcaagc agttattaat aatatagcta ctgctgtgag  62940
ctacatgtct taatctgtct taatcaagat atgactgtga ttttccatag ggaaaggtaa  63000
ggtttacttg caaactcctg gggttctcct ttttttatag ttttcttatt agtagggttt  63060
tttttttttt tgagaatact atgcagaaat gattgaaaag aacaaattag tcattgcata  63120
ttggtaagag aagcagcaag agccacctca cctccctctg ctctccccaa atagaaactg  63180
ctctgctgtg ctgcttctct accttcacac caatgctcgg cctgccaact cagttatctt  63240
tcctttcctt ttaagatagg gtctctcctt atagtagtta tgactgtcct ggaattctaa  63300
atagaagagg ttggctttca aatcacagat cctcctgcct ctgccttctg agtactggaa  63360
gtatggtgta tgccaccgtg ccacagctaa ctcagttatt ttttggtgtt ctataactgc  63420
```

-continued

```
cttacataca tacagaccag gtacacacaa aattcctttc cattaattta atagttatat  63480
cacaatgcat tgaccaacta aaaaatccta aattgactta tgattctact tgctcatgtt  63540
ttaaaggaaa ggttactctt tgcttatctt aaatgtaata tttttccttt gcagttgctg  63600
tttaaatttt ccctataagt cgaccccaaa tttacatcta taatctggca aaacaaaaag  63660
acctctagtg atggttgtct cttagcttta gtctctcttg gactccattc cctccaccca  63720
taatgttcca tcctctgtcc ttaagtgtac tagtctccaa ggcctgctat gtggttgtca  63780
ttgttgtagt tacttttcta tgttgtgaca aagcaccctg acagtggcaa tttagaaagc  63840
atataatttg aggatcacag ttcctggtta gaatccatga ccatcttagc aaaggcagac  63900
aggcaggcct ggcactgaac aagtagctga gatcgtccat ctggtccaca agcataaggc  63960
agagaagcta attgggaatg gcatgggctt tggaaacctc agagtccact cttagtgata  64020
cctccttatc cttccaaaca gtattacaca ttcaaacttc aaatgtgtga gcctctgggg  64080
accactctca tttaaaccac cacagtgatc ttggcaactt cttttgtgtt cgtcccatgc  64140
cacagtcttt ccatgtattt ctccttttgc tggaactttt tccctcgaag gttcctgagg  64200
aaagaaacat agataacttt tgtatgtact tctacaactg aaagtatctt aatttttgcc  64260
ctaacaaatt tttgtttgct tacttgcttg cttacttgat tctgcgtgca tgcatttatt  64320
tgtttgtttg tttgtttgtt tgtttgagac aagatctctc tttgtagttc tggctgcctc  64380
aaactcagag agattcatct gcctctgcct ccagaatgct gggataaagg catgctccac  64440
catacctaat ccaacctcac aattttttaa gtgtgtattt atatgtgtgt gtggtatatg  64500
taaaggtgtg tgtgttcatg cacacatgtg cagagatcag aggagtcagg ttttctcatc  64560
tatcactctc tgccttatta ttttgagaca gggtctcttg ttcgatatta catatactag  64620
gtgagatagc ccaggagctt gtaggaattc tctcccattt ctaccttcca aatgtgtgct  64680
actgcatctg gctttaagca agttctggga atctgaggtc aggtccttac acctatgtag  64740
caactctgcc tactgagtca tcttactagt attcacaagg tcaaaggttg ggaccaacag  64800
ccaaggttgt cctcagatct ccacacagat gtacccacaa ttatacaaac actcaacata  64860
aacctattta cacacccaca tcacacgcac acacatacat gcacatacaa aaaaatgctt  64920
tttgaaagaa gtagagaatg ctagatatgg tattacacgt atataatcca agccactctg  64980
gaagctgagg caggaggatt tcaagtttga aaccagcttg accacataat tataccatgc  65040
ctcaaaaatt gtatagagaa taagaatgaa tatgaatgag actaaagtca tatctcagtt  65100
acttttctat tgctgtggca aaacaccatg acaaaggtaa tttacagaag agattattgg  65160
ggcatatagt ttcagagggt gagtccatga caattatgat atggcactga agtaatagct  65220
gagagcttaa atctggtcca caacattagg cagacagaga gctaactgga aatagccatg  65280
agattttgaa acctcaagcc ccactcctag tgatgtccca cacctcctaa tccttcccaa  65340
acagttccat cagctgggaa caagatattc aacatataag cctatggggg tcattctcat  65400
tcaaaccacc agtagtaatt attagagccc agcaaagaag gaagggatag aaagaaatga  65460
ttgatgggaa ctggggtgaa gtctgataca gagagatctt tatgtactgc agcgtagctc  65520
aggaagataa ctatggttaa ggacaattag ctaagtgatt agtagagagg attttaatat  65580
ttccaataca aagaaatgct gcaggcctga aatagggtac gtttcagtga cccagatctg  65640
attattacaa ctcatacact tgtaccaacc acataaatat gtacaataat tgtgtcagtt  65700
ttatattaaa taaaaatgtg gagcaagtta aaaaatgcct gttttaaact gatcacagtt  65760
atatgccagc ttttctttgc tgtgacaaaa taccataggg agtagtttat aaggaaagag  65820
```

-continued

```
atttcctcca gctcataatt ccagaatttt cagtctagag tcagttagtt ctatcatatt  65880
gggcccacag ctagaccaaa tacaatgatg gggagaatgt ggtaaagaaa agtatttacc  65940
tcagagtggt caggaggaac acaagacaaa atatacattt cagtcccata cctccagtga  66000
cttgcttcat ccaaacagac gccaccatcc aatagccatt aaaatacaag tcaaccagtt  66060
gattgacatc cattgatctt agtcatatcc ctaaattcaa cctctaagct ctgatgctct  66120
gggggccaag cctctattgc ataaatctct ggagcatatt tcataaatatg aaatattaaa  66180
caggtctctc aggagctgtt tggtagactt agttgttttt tttttttttt tgtttaaggt  66240
ttttttggtt gggttttgtt ttgttttgtt ttgttttgtt tgtttgtttg tttgtttttt  66300
ttcgagaccg ggtttctctg tatagccctg gcggtcctgg aactcacttg tagaccaggc  66360
tggcctcgga ctcagaaatt tacctgcctc ctcctcccaa gtgctgggat taaaggtgtg  66420
cgacaccact gcctggccta gacttatttt tttaatcaga tttgagtctt tgcctctgga  66480
atcacagtag cttttcccat tcaacaccta gtttacagaa gaaagaaaac ccaatttttt  66540
tttttataat cattagacaa ctagaagttt tccctcctat taagaaaaca tattaacggg  66600
ctggcgagat ggctcagtgg gtaagagcac ccgactgctc ttcccaaggt ccagagttca  66660
aatcccagca accacatggt ggctcacaac catccgtaac gagatctgac tccctcttct  66720
ggagtgtctg aagacagcta cagtgtactt acatataatc aataaataaa tctttttaaa  66780
aaaaaaaaaa aagaaaaaga aaaagaaaac atattaacag tattgagaaa actgttggct  66840
taaatttgat gatttgaatt ttattttact aataaatgca tgtattgctg ggcatggcag  66900
cacatcccag cactcaggat tccgagataa gagatcataa gtccacgcta gctggaatag  66960
caaaataaaa tcttttttta aaaaatatac atacatacat acatacatac atacatacat  67020
acatacacac acacacacac ttttctcagt agtacggcca attagttgac ttgtctaacg  67080
gagggaggaa gaggaggcag agagcatgct gttcagatca cgttctcttt tgcattcagt  67140
ctgggacccc agcccatagt gtggtgctgc ccacattgat tattggtatt cagttaaccc  67200
agtgtagaaa ctctctcaga gacatgccca gatgcttgcc tcataaccac tgtgtatgta  67260
tatatgctta cagaaaatat actcatcatt acacataaat ttcatccact tacctcttat  67320
gaaaagttga ttatttactg agatttttct cattctgaaa atccataaag tctaccacat  67380
tgattaaatt acttgttttt tacctgttat tgctcatgtt agaattgctt tccttatttg  67440
gggtaagctg tcgttggcca ctgtgagggg cttatcaaga agtcagaaat gggaacacct  67500
tctaggaagt caggactgga agcttagctg agccagcaag tgtttctcac actgcacttc  67560
ctgtgagcct acctgtgcgg catcaggaac tggagttggg accttgagga ttgttccctg  67620
gaggcagggg tggagtcagg caggggtgaa gctgactcac aagatggtct tgcctttcag  67680
ttgtttcctc tcgctgcttc tggtggctgc agtggtctgg aagatcaagc agagctgttg  67740
ggcatccagg cggagagagg taagcccaag tagacaaact ccacataaaa ctcatttttt  67800
tccttctttc taggcagatc acttttacct gttgagtgat gactaatatt catatgagaa  67860
gcatgctgtt taacctgcat tctgtggttc cactatgtgc catcagtaga ttttaattat  67920
tcttgcataa agtgtcatta gttttgccac tgcttgattc aagtcttcct aagagtcttt  67980
cctaagaata tgagtgtaga gacaagttca gctcagtgac agagcacttg cctggcataa  68040
actgagtccc tggattctag tctcagcacc ctctaatagc acaacactag agacaaagct  68100
tctaacctgt gggtcttggg cagcaggtag gggaggggga tttaaaaaac aaaaacaaac  68160
```

-continued ctctagctgt agcctgtgtc atttgttatg actaagcact agagtgggta ctagtagaca 68220
tgccatgtgg acattgagca cctctccatc ccaggcactg atccaggtgg ttctgcttta 68280
tcttcatctc caccctagga tataagggag gctacgtaac tacccatcac cacacagatg 68340
ctgaggtaca gaactgaggg gtaactagtg cctctgcctt cacagcacag gttcctaaac 68400
acgttttcta caaacacttc atttgttcta gtctgttcat ttaagaatct catgttctga 68460
ctgaatgagc tagacaactc accctagact atacattcta aagaagggca acaaggcagt 68520
tttgttactg ttgagaagaa aacaaagtta tttccgtatg agttattgag atagaatagt 68580
agagatttgt ctgaatacaa aatagaaagt atataaaagt atataagtgg atcataaaga 68640
aagcaacaat caactggaaa atatttgcag tatcatgaga gagagaaaac tagaagatga 68700
accccctcaa aaaaggattt ttaaaatatg cttagactgt attcagtcag ctaataaact 68760
ttttttacct ttatttggaa tttacgaata gcactgaacc tgaccattgt aaatgcacga 68820
ggtcaggcat gacttgttcc cagtaggaag ttgtttttag ttcttgctgt ggcctgggtc 68880
ctgatggaag ttctttaccc accttatctc ctgtcctctt ggcagaggtt ctagaatagt 68940
gctgtgatgg ggtagcaact gtcttcctgt gaccctgcac ctagattatt acagaaccca 69000
gactgggttt gctgagttaa tggaaattct ttctaggttc agtagagaga tgtgctgaca 69060
catactaggc catctagttt ttcagtaatg ctcagagacc gcaataggat atgtaacagc 69120
aacaaaattt ttaacataaa atttcccttc taaaacagag tgatgattta tgtagcttca 69180
ggatcctgcc tcctagaaga tggtttgaag caaggccagt ttgtcttccc tagcataacc 69240
tcagaagacc tctcatatta ttgatggtat aggaatgaat gcccacattc tgtatttgag 69300
atgtgtgcta tagtatctca tctgacccaa catgaaaaca tttcaagcca tgtgtgcttg 69360
ggtaaggtag gagttcaaag tcatccagtg agttcaaggc cagcctgggc tgcatgagac 69420
actgtctcat aaacagacac ttgaatctca tttaaagaag acattgaaga cttgatactt 69480
tgaacaccta tcctaacgta tccacccccca aatccagagt ccttcatgtt cttgtcctct 69540
gcagttccac tttcattgtg ttctcagcag cagctctctc cgaggagagt tgtctcccat 69600
cctatcagcc atctttttta ttgttgttgc tctgacaatg tctggttcag gttttaacac 69660
aaagcaagct agagtgattt taatctagca acaaaaatat aaaaaggtaa gtttttgccc 69720
ttttatatat tcaatcaaca gatatcatag cattatatcc tccactttaa cttttatttc 69780
ttactggtaa gggcttttta taaaaatata atagtgttac cacatgtaac aaaatttgat 69840
accttgtgct acctagcacc ttgtcatgtc cagttttcct cagctgtcac agaagcgaca 69900
ctgcatctga tcagtttgaa tcagagagag tgtagcatgt ctaatatcta gtattcacta 69960
ataaaatctc agtactaagc atattaataa tactatatta ttcattagca acttcttcgg 70020
gagatgcaac agatggccag ccgccccttt gcttctgtaa acgttgcctt ggaaacagat 70080
gaagaacctc ctgatctcat tgggggaagt ataaaggtga gaagtggctc aaaggtccat 70140
atagcttttc agaactcagg cctcagtttg ctaggctaca gacagcaagc gctctgtgtg 70200
tcactcctgt ctcctctcta acagttagtc agcagaagca accccgagcg accgtaaggg 70260
gctctgtgtg tggctttact tttcgagttg ttgcatgtca gattttaaca tgcaaattaa 70320
gcttgttatt cttactttgt ggcataatac tttatagttt ttatttggaa atatctaatc 70380
tgggctaggt gtgatggtgc acatctttaa tctcagttca gaggaggcag agacagaggc 70440
aggcaggatc tccttgagtt ctagaacagc tggtctacat aatgagaccc tatatgttag 70500
aaaaaaagaa agagggggtg ggggaaggca gctaacttta accattaatt gaaccaacac 70560

-continued

```
acacacattt tgttcagagc cccagtactc aattaaaagc caggcaggca tggtaacagt  70620
acttagggag tcagaaacag gattcccaga gtaagcagtc tgactaggct agcaggaaat  70680
ggtgagtttc aggttcagca agaggccctg cctcagtaag taaattgaag aacaactgag  70740
ggagacttgc atgtgcactt gtgcatgcac ccacacatgc acttgcacac ataccatatg  70800
tcaccatgct tagactataa aatgtagtca ctactggcag cacatgccta caatacagat  70860
gcaggagaat cactgcaaat ttgagatcag cctgggctac tggacaagat tttgtctcaa  70920
gaaaactaaa acaatacaaa agtgtactgg gggggttatt ctaatgccag tgtttatgac  70980
agcacattca gaactgacag taaaggcaat caaggactgt cagtggtggg tatatacata  71040
ggcagaggag caactgctac tagaaactgt ttatccttta aaagactaat gtatgctgca  71100
gcatagacaa acgttaagtt gtgttaagta aaagatgctg tatcattcca cttacccatc  71160
gagaataatc aaatacaaga cagagtaaaa tagtgactgc tagaggctta aaagaaaaga  71220
ccaggggggtg gggaaaggga gggaaggaag tgggagaggg aggaagggag agagggaggg  71280
agggagccag actttgtggc ttacagcatc aagaggctga ggcagaaggg ttacaaattc  71340
aaggccctac tgggctacat agtgagaagt aggatttcct tgagctgtct ttctaggtca  71400
taatctctca ttgggggaag tcagggcagg gacttgaggc agaaaccatg gggaatgcta  71460
tttgctggct ccttcccagg ctcctctcta gctttgtttt ctcattttgt ttttactgtc  71520
tatgggtgtt ttacctgctt gtttttctgt gtaccatata catgcctgct acccacagag  71580
gcactgatgc ctggaactgg agttacagat ggttgcaggc tgccctgtga gtgctgggaa  71640
ctaaactcgg gtcctctaca tgagcaagtg ttcttaacca ttgagccatc tctccagcct  71700
ataaaattct tttttaaaaa taaagtctgc aacagaaaat gaatattttc tagagctgaa  71760
gcattcaatg agtggataaa gaatccattt gatgagctat ctacctttca caagctctta  71820
acccctacag actcaggact tagtggctgg aagatgaatg taaaacaggt agctctctcc  71880
ataatatctg gtctgtttgt gccaggtgtg cagaactgtg caacaggtca ccatacaaac  71940
cggcgtgggc ctttcctgac actcacacag ctctcgggac agtgcccgtg gggacctctt  72000
attgacctta taagcacctg actgtgcagt gtagcaggga gttaaggtgc ttctgttttc  72060
ttcctccaga ccgttcctaa gcccattgcc ctggagccct gctttggtaa caaagccgca  72120
gtcctctctg tattcgtgag gctccctcga ggactgggag gaatccctcc tcctggtcag  72180
tcaggtgagt agacaggaga caatgacaga tattggtctg tgaaggactg agtcttagac  72240
acttcttctg gtatagaacc tgggtctggg cacagtgctt agtggtacag agctttggtg  72300
gaacaattct atagtcccca aactgtgttc tgagcactga cattcctgtc ctggggtgga  72360
agttcaggac cttcctcacg gtgcacagcg tcctcagaca ttcatgctct ggtccccttg  72420
actctattga tccctgcttt cttttttttt ttaacccctt gttcttatct caaatttagg  72480
ctttttcttc cttgatacaa gctcctattc atctccatgc ctctggcttc cagccatgtc  72540
ctcaaagctt gtgttgccaa gtacagagtt ctagtcatgc tccacatctt cttaaggtct  72600
tgctatgcag ccttagctgg acgagtgctc gttataggcc aggcagtggt ggtacacgcc  72660
ttatgtccta gcactgagga ggcagaggca ggcagatctc tgagttcaag accaccctgg  72720
tctacagagt aaattccagg acaaccagag ctacataggg aaaccctgtc tcaaaaaaat  72780
aaaaacaaca acaggaacaa ccccaaaaac tcattatatt gcccaggctg gcttcaaact  72840
catagttatc ctcctacttc agcctccaaa gtgctgggat tatgggtgtg acccttcatg  72900
```

-continued

```
cccagattgt cttaaatatg aggcatgaag aagtattatg aaaacataaa ggatattttg  72960
aaaattataa ttctactggg ttaatgcaga tccattttca tttcattgaa ataatgatac  73020
agcctttgga ggttagggga gcctctcctg ttttcaaact gactttgaac ttctgatcat  73080
cccgccacca ccgccacctc ctcctcctcc tcctcctccc cagtgctgag atacatcact  73140
actcctggtt tatgtggcac agaggctcaa acccagggcc tcatgcatgc taggcagaca  73200
ctctaccagc caacctaccc acagctccta gatgtgcacc gtattacaaa catttattct  73260
tcagcatgtt tttttttttt tttcctaaaa atcatctcta caggaaacaa gtaccagtgg  73320
tgttttaggg caggaatagg aagaaaatat ttttactata tactcttttt ttttaatcat  73380
tttttagatt ttatttattt taaaatttat ttactattat taataagtac actgtagctg  73440
tcttcagaca acccagcaga gggcatcaga tctcattacg gatggttgtg agccaccacg  73500
tagttgctgg gatttgaact caggaccttt ggaagagcag tcagtgctct taactggtga  73560
gccatctctc cagcccctac tatatactct tttaaatgac ttatttgctt ttattttat  73620
gtgcattggt aatctgcctg catgtatgtc tctgagagag gatcagattc cttggaattt  73680
gagttacctt gtgggtgctg ggaattgaac ccaggtcctc tggaagaaca gccagtgctc  73740
ataactgctg agccgtctct gcagccccta ctatatactt tttttatagt tttgaatttt  73800
tttttctttt tgggtattgc taaggatcaa atatagatct actatttatt ttttataaca  73860
tccattagta tttttataac ttactacata gtttgccaat tcttttatac atgtccatca  73920
aacatgtaag tcataattta tataaacctt gtgttaaagc tggaggcaca gaaggaagat  73980
tgctacagag tgaagtctag actagccagg gctatatagt gggaccctgt tgcaaagaaa  74040
aagttctctc tttaaacaca aaggcagtat gaaaagacat accttgattc tgaagctgtg  74100
cataggaatg cctcacacag tgttctgctc aggactatac tcagatgcag tggtctgagg  74160
gacttggtgg tgtctcagcc aaaataacct ggagtttagt aggaaagtct cctttatccg  74220
tgtccagtcc tgaagggaag ccttatttat gtatgatgag tcaggaccca ttgtcttcat  74280
cttacttggc atccccccag cactgagtct ctgagttagc cttacttgga cagagtgact  74340
ctctgggcac tctggacagc atctcctgct tcaaaagggc aagatcttta gaagacacag  74400
agatggagca ggtcttacat ggagatatag cagcttttcc ttcctgaccc ttgacccaat  74460
gcttctttgg aaatcctcat gaaaccctgc tcctttctgg agacccaccc cacagcaggg  74520
ttatccatgc caagcttcct gtactttctc tttttgagga agcacataca cacaaagttt  74580
tagtagctcg cacatctcac tgtgaagtag tgatactttc attgctatct tctggaaaca  74640
ggcaggagta ggcacacgct cagagcatag ctgcactctc attcacttgc caccctgagg  74700
cagagcacac gactttgtga tctgctatgg aggagagaga aatgagtagt taggtgtgta  74760
taaataagct aacaccatca cccctttatc tttcactagg gaaatgtaaa aagaaatctg  74820
aaattatttt gtaaaaaagt aagctgcttc atgacacatg tcccctcttg tgggttcttc  74880
caaggtctcg ctgtggccag tgccctggtg gacatttctc agcagatgcc aatagtgtac  74940
aaggagaagt caggagctgt aagaaaccgg aagcagcagc cgcctgcaca gcctggaacc  75000
tgcatttgat actggggcag gaattcgccc tcacagaggg cgtgtggtcc acgaagctgt  75060
ctacagggga ggctgcaggc aggaagcagg cgtggggcag aagactgggg acccttgaag  75120
cgtccaactc atgtgcatga tcatgcaagc tgttttcatg gctcacccct ctgtgtccag  75180
catctaacct tttacttctg tgtaggaaat aatttaatta caagtccagg aatggtctgc  75240
tctactcatg ggtggaggag accagtgccg accccgtgag agctgaaggt gatgctgagg  75300
```

-continued

```
tcccttgtgg aagcctctct tgggaatctc aactgcagag gagctgccct ctgtcagcag  75360
ctctccagca tggtcctctg acactcctca gatgaactgt tctcatcgga agcttgctgt  75420
ctttttacaa gatgagcttt tactctcttc caggaagtag cttttttttct agctgagaat  75480
taataatggt ctttctcttt ggaagtcata tcaaagtata attgatgggg gccttgtttt  75540
gttttgtttt ggtttttgga gacagggtct cactgtgtag tcctagctgg cctggaactc  75600
actatgtaga tcaggctgga ctgaactcac aaagatccac ctgcctctgc ctcacaaatg  75660
ctgggataaa aagcatgaac caccaggccc agcaaagagg gctattctaa atgtcaaggt  75720
caatggagtt agaatatata taaaaaaatg caattgataa ttctctatag aaacttgatt  75780
aattttaatc cattctttcc ttctctttct ctcactctgt cttacacaca tgcacacata  75840
cacacacact aagtgcctag actttgaata gatctagcaa ttggacatta gtaagcctaa  75900
gtttttacat gattgcattc ctacattctt gtaaacttta agtaactacc attgcagttt  75960
gttctttttt taaagtctaa tttgcagcca agaacgagta attctcaccc caagcaacat  76020
ctaataggga ctgagtgacc ccagcccagc ctagtgtcac tttaggcctg acgtttgagc  76080
aaccctcggc tcttgccaag gcaccacaga atgcacttgc tcatgccctg tgcctcttga  76140
gcagaaaaga gcactgacaa ctgggacacc tggctctgtc ttcctacagc tgctcgcact  76200
gacctgtggg aacctgtggg tcatccccag gctgaatgga gtacacacta gaagagggat  76260
gatgcctagc attggggcag catctgctca gcacatggaa agggacctgg ttccatctcc  76320
cctgggcagg agttggtcca gcctcctccc agacccagct ggtggctgtg aggaggtggg  76380
gaatgctaat gagaatgaaa agcacatggg ttgatgggaa gggacaagat taccacgtta  76440
ggagggtgag cagccctctg ctatgtgccc aggaccctgc ctggacattg catttcccca  76500
tttatggtgc tccgtattct ggcattatgc agcagcctca cacacctgtc ctctccttct  76560
tcatgtccta cagttctgct atcacctgac tagaatagcc ctctaggcaa cagtgctcaa  76620
atgtatgagt ttggagaagt taacaatcag aagaacaaaa actgtagtgt ttcaccttta  76680
aatgcagtgt tgaagaggga gcctttctct aagccctgca ctaacccact cctcccaaga  76740
ctcttgtgga gtgacagttc caagctgaac cataaatcac tgatgcacaa aacactgcta  76800
gaaggctcac ctctcaaaac acgactcttt gcatcactat taaagagcag aaagttctag  76860
aaatgatccc agcctcatcc cctatacagt taggagctcc ccacatctct accaaaaccc  76920
agcacataag tatctgcgtg gtctagcctt tcatctccgt aacaagccag gggactcttg  76980
gccaaaagaa agaaagggaa gttgcactag ggcttgtccg tccataagga attcccctct  77040
gctttgctca aaggaccaaa tttctttggc caaagaagtt gcttctatgt tagtcccata  77100
ccctgaagta atatgtacca tggctcccac ctacctgttt atgctctccc tgcccccagg  77160
gaaactgttt attctttcaa aagaagcaaa cagcgttcat ttctgctcct gtaatggaga  77220
aacagccagc tcccctgcat cccttacagc caacagctcc cttcaggctt agagcagggg  77280
gaatggcagg gattaagagc tcagctcaga gccagttacc aagatggaat ggagttgtga  77340
cccagtaact gtgtcacgag agaccatgta tataaaatag tcatgacgac actgacctct  77400
tgcacttgta cataactata ctgtagtgtc cagaatgttc agacattcag ggtgtacata  77460
aacagaagag tatcataatg tatttttatt aaacactaac atctgagttt cacctaatct  77520
gtttctgtgc catatactgg gtatccaagc tctgggaagt tatcctacca ggccctgatc  77580
tgttgataag gcactataca ccatgctggt gtgttctgta gccttgtgcc cattaggtaa  77640
```

-continued

```
ctgaacaatg attcagctct tagaatacct aggaagacag caagcagggt gacacacggc  77700
tgtgatctaa gcattcagaa gacagaggca ggaagaaaat tcaaaaatgg ggctggagag  77760
atggctcagt ggttaaaagc actggctgct cttggtcagg acactagttc agttcccagt  77820
acccacatgg tggctcacaa ccttctgtga ctacagttcc agataacctg acaccctcct  77880
ctggcctcct cgggtgcctg tggtggtcca cctggtgcac agacaaacac ccaatacaca  77940
caaaacaaaa gtaactcaag aatagcctgg gctacatagc aagagcctgt ctcaaaacaa  78000
acgaacctat gaagagccag gcagtctatc tatttacatg gcagtatact agagaaactc  78060
aggaagcaag agtgttcatc actgttgtaa tttcaaatgc tccttgtgat ttctggcatc  78120
tctgtggggt gaggtgttct gttactcttc acattcaaag actgtcaccc atgaacgtca  78180
gactttgcaa aggggctctc taagctgcac tgttgtggct ttgtctaaaa ttttaatgac  78240
gtttctgaga accatgttct ttttatacta aaatctgggg atgggagggc tcatttgttg  78300
ataaatagca ctattttccc acacctcagc ctcctgtccc cgtcctggtc ttccctacac  78360
agtctggaga gggctctgaa aggtccacag agtttgacag acacgaaagc aacccattgc  78420
cccgttgacc tgacctggaa gaagactgtc agcaaaagga aaataccaga atatctggaa  78480
agcttgaagt gtaagatggg atctcgttgg ggaattggat gaagaaaagc agagcgcctc  78540
tggtaggtga ctctgcagcc tgccagcgcc cgccctcttt ctacacagca gagtgtgcat  78600
ggcaaggaaa tgagtcacct ccttgggggga tggtgctgtt tttatgaaaa cctctgatcc  78660
ttggtgtcct ttaattgatc tgttcaacaa atatttacta aacacttcta agctaacatt  78720
agggcagtga ctgaggtgga aacccagctc tttagacagc tgtcatccta ggatagcttc  78780
ctggaagcag aaccaagaag ccagaaggtt cttcctaggg tggccttggc tccctgaagg  78840
aatctgaaat gctgaccctg tcacaacctc ccagcacagc tttggaatga gacatcagcc  78900
tggcctccag cagagcagag gctctggagc tccacatcct gcctgcaggg agccctcagg  78960
gtgccctcca gagtacaggg agaaactaaa ggcaataaca gaagctgctc tcagagcctg  79020
actgtgcaca aaacactagt gaagcctgct gaactaattc tgcctctgga aatcttttct  79080
ggttctttac agtttgttgt tttgttttga tccaagctta gtttgttact atgtgtgatt  79140
tagcatctgt cgcacttgtg taaatatgga gtaagtattg taaactattt aattgctgcg  79200
attgttgggt tatacataca tttaggactg caattttttg gtattttttg tattgtaaaa  79260
taacagctaa tttcatcagg aacaagagaa ttaagggggt ctgcatttta aatgcagatg  79320
tgaagcactt gtatataaat aaaagtaaat actataatac aaagttcctt ctgaaataaa  79380
agtagatctg gtaaaaatgt gcgtgcgttt cgttctgaat gttcaatgct aattttgttt  79440
tattttatat ttacatttta gtccttattt tagcagtgag gagacaggca cagcagtgca  79500
ttctcacctt ggcagctgag gaatccccta gagtagactg caactcaaga ctcttggctt  79560
ccacactgaa aagagtttca gtttatgaag cagagtttag gaagtttagt gaggaattta  79620
aggacttctt ttaatgtttg tgtctacata tgtgggtaca tatatgacac agcatgcatg  79680
tggaaggcaa acaacacctt aatggaagtg gcctgaagaa caaactcagg acttcaatct  79740
tggcagcata aacctttacc taatgagtca tctccagtct atacggggtg tgtgtgtgaa  79800
cacatgtgca acagcacaca gtggaggtca gcacaactct tgcgagtcaa ttctccctta  79860
ccttgtaaga cctagaattc cacattgccc aggctctgaa agttaggttg ggtccacact  79920
gggccatggc tgatgaaatg ttggaaaagt gataacacca aacttttgca cagaaaatat  79980
tttcatctgg ggccttccct ggagttcaca ggctaaagtg ttggaaggaa catgggtccc  80040
```

-continued

```
tgagccacca ctttcacaaa aactacctga tcaagaagaa ctattctggg tttctgttgc  80100
taaaattcct tcccagagag aaatgtaagc aatgtctgcc ccttcaaggg tcccagcaag  80160
aaaccaaggc acaattccac caaagttcac tagaaaacca gtgagtttat tgggcttccg  80220
tgcagaacat acatgagggg ttacttagag aagtgtggat actcctcccc ctaacaatcc  80280
acaccctgaa aaagccttac ccagcaggga tgagggcttc cccagaccca cattgatggt  80340
gctcccattc catttttccc tggcatgcaa agagatagac agaaaaatag attatatata  80400
atatacacat aaattagaaa aatagattat ataatataca cataaattat atattatata  80460
tataatatat aatacacaga tagattatat atgatatata aaacacacag aaatagggta  80520
tatataatat ataatacaca aactactcag ctattaaaaa cagtggattc atgaaattct  80580
taggcaaatg gatggaacta gaaaatattc tgagtgaggt aacccaatca caaaagaaca  80640
cacatggtat gcactcactg ataagtggat attagcccag aagcttggaa tacccaagat  80700
accattcaca gaccacatga agctcaagaa aggaagatca acgtgtgggt gcttctgttc  80760
ttcttagagg aacaccctca taaagtagtg gtggggggtg gggggagaca gaataggtgg  80820
tttccaggag aggaggaaaa caggaaaggg aataaataac atttgaaatg taaataaaga  80880
aaatacccaa taataaaaga aaaagaattt tgaaacagag ggtaaaaaat aatacacaaa  80940
ccaggtagat agattatata taatatatat aacacagaga tagatagata gatagataga  81000
tagatagata gatagataga tagatagata gatagatagg tcaactgctc gcccctccac  81060
taggtaacat gcagttaagg cagagctgca tacaacagat gttagggata ctcaggtgag  81120
aatctcaggc tttgctccat ccatctatgc tggggtgtaa gctgtcaaca agtttagctg  81180
ggatgatgct ttgcaagagg gcacagctga atgccctaag atggtagatg cttggctcaa  81240
aggagacact acagctctgc atcaaggcaa actaactgag atgagggcct ttattttcca  81300
gatctgtatc ctggagcatc attcacctgt tactacactg aaaacatttg gtgttggttt  81360
catggcagat gacaggcagt gagagaagta cagcagcgga ctgctagagg tgggggttct  81420
gtcaggacgt gggaggctgt ttggttagta acttggaaag caacaagttt ttagctagag  81480
ggagaaaagc tggagataac tgtacttgct tgatttctta aatatcaaat tttattttat  81540
gcatatgggt attttgcttg catgtatggc tatacactac atgcttgtgg tgcccacaga  81600
gaccagagga agtagtgtga gcctctgaaa ctgaagttac agacattacg acttgagtgc  81660
ctgaaactga accttggtcc tctggaagaa cagccagggc tcctaaccac tgagctatct  81720
ctccagccct gacagaacat catgtactcc aggctggtct caaatttgct ttatagccaa  81780
gaacggtctt aaattctgat cctcctgttc tctcaagtag tggggttaca ggtctacact  81840
gccgttttct tgagcaaatc attacaaatt gagttctaag ccaggtgtaa tagttcatgt  81900
agtaacaatc tggaattttg gtctcttaaa aaaacaaata ttataagaat gtattttcat  81960
tttaatccca ggtgtatggc atatatcgaa ctgctttgga ctgactacag cagctatgat  82020
tttttcttgt tctagcagag gtatggtttt gccagctaca gatagtttct gtgattgtgt  82080
gacatttgga attctggaaa cttttcagat ggtatataaa tattagagcc ccaataggca  82140
gagttgatga ttgttggtca ttcaggggta ttggttgtgg ttagtagtct tgcttgaaga  82200
agaaacaaga acaaattaga ttcagagatc tctatatctc tctctatctt cctttctgtc  82260
ctatctagta ataggggggta aaaccaggat gataaagggt tgggggaacc cacaaagtaa  82320
caaagactgg ctacaagtgg cacccaactt ggaactcaaa attgccatag aggaagcagc  82380
```

-continued

```
aggggatgaa ggaatggatt gtggctgttg ttgctgggat attcctcact ttgctcccag  82440
aggggatttt tctgaggttt tgttgttttg ctttgctttg ctttggtttt cttctacata  82500
ttctgttttt taagtaagtt gaaataatag ccgagaagct ggaaaagttt ggtgtggaaa  82560
tggagcagcc tgagaaacaa acaatgtatg aaatgggaaa actaaagggg ccactcttct  82620
ctcttttctg aaaggcttgc agacttggtg gtgcacctgg agagtttatg gatggagatg  82680
gaagctctta ggagacaaga agcatggaaa aagagaacaa aggctcagtc ccagtgactg  82740
aagagagcag gagttttcca aagaaggtgc atgggagggc cactggtcag aaaaaaaagg  82800
ctgaaaaata ccaaaggaca atgtgctgaa atagcccatt tcaagagaaa gggttcatct  82860
caaaccagca ttctgacaga gtggaaggag gggtggctca gggttatgag atcaccatca  82920
gcttttccag ttttcccata tagcatatgc ctgctaatgg tatggaacaa gagtaaggca  82980
aaataggatg gtgtcctata gaaatgatag ctctaaggtg tttttaaaag gccttgattt  83040
catatggaat gcactctcct tatgtggaac ggatattaaa taaccggggt acacaaacta  83100
gaatcccttc ccaagattgg aagggattgg taacagctgt actagagact gtcagccgtt  83160
gcaatggtta acatgctgga ggaaagaagc tgtgaacatt gaacagtaaa acagagcaag  83220
gggtattaat atagtgaacg aacagctgct aggtgaaggg cggtactcta gtgtacaagc  83280
acagactcgg tgtcatgaaa ctactataga acaaggttgc ctcagtggct ataacacctt  83340
gggacaaagg aggagccagg aaaaagtcca gttcatttac aaagattata taaggctctg  83400
gagaagcctt cactgatttt tttttttaca aagattagtc tcagctatga acaaagccat  83460
atcagaccct gacacaaggc aggtgttgat agagaccttg gtgtatgaca atgcaaatac  83520
caaatataaa aatgtcatta gacttttaaa ggcacaagta atgcctatgg atgagtggat  83580
aagggataag accaatatta gttctaatgt gtactgtgct aatatcattg atcaagctat  83640
agctagagat ctctgatgtc aaaatgcctt gtgcttcagt tgcagcaaat acagtaattt  83700
gcaaggagtc attgtggcca aaactaaagg tctcagatct caaaatgcct gatgctttgt  83760
gggaaatagg gtcatttgca acaaaaatgt gaacaagaca tctttaaggg caatggtttt  83820
tctaaatata aaccagaaag acggcctagg cttccaaggt tgtgctggcg atgtggccag  83880
ggttgccact ggaccaatga gtgtaggtcc aaaagagata ttcaaggtaa cgtattacca  83940
tcatgaaatg gtcttggggg cctatcttga ggccctgcag caaagagtat gagccattcc  84000
aaccagagag tggcatggag actcaaaacc ttcactgggc actggagatt taatgcacac  84060
tagctattgc aggcagcatg gctctagact tggccacaga taaacatctt gctctatccc  84120
ccaaaattca aagttataac atagctactg gagtgtatgg tctttttccc tcagggacag  84180
taaggataat cttgggaagg agtggattga cttcctaaga attcactgtg catcaggaag  84240
tatagatgaa tatttcaaag gagaaattaa aattgtggca tatgtaaagg tagagctgca  84300
acttaacaca ggcgataggg ttgctcagct gctgctgttt ccctatatca aaggcaaagc  84360
aactgcagca gaaagaggag aggcctgaaa accttgggca ctgacacaaa aattgcttat  84420
ttcattgaaa atgtctgttt ataacttccc actatacagc acaacaggag ggggcttaaa  84480
acataatggg gaaaatgtca caattctgca atttttgttt ccttaaaaaa aacacacaca  84540
cagaatttta ataatgtgtt ctcatcttaa tcccgggtgt gggaattagg gctgctttgg  84600
accattccca gcagctgact atgatttgcc tcatgctcta gcagaagtat gatttttgcc  84660
acctgcagat agtttctggg attgtgtgac atttggaatt ttgggaactt ttctgaaggt  84720
atataaatgc taaggccctg gtggggaggg ttggtggttg gtggtcattc agggggggtgg  84780
```

-continued ttgtggttag tggtcttgct caaagaacaa acaagaaagt catttgattc agatgtatct 84840
ttcttccttc ccccactctt tctctcctcc ccccggcacc ctgccccctg ccccgacctc 84900
tacccttctt tttctatcta gtgacaagga tgaaaccagg gggataaagg gtgggaaaaa 84960
gaagagccca caaagtaact caggttggct acaagttcat gccaagaatc ctaggacctt 85020
gttgtttaaa ggcttgtttt attttgtgaa catgaatgtt aaatgtacat acatgttaag 85080
tgtatgtatg tacaccatat gcatgcatac agaatccaga agaaagtaca ttataccctg 85140
gaatggaact tagagttgtg agacagcatg aggatgctgg gaactgaacc cagtttctcc 85200
acaagaggag tagttgctct tcactgctta acctttcctc cagccccaat cctagcattt 85260
tggaggctga tgtaggaaga ttatcccaag tgtgaggtca tcttgggctc cataataagt 85320
ttaagaccaa tctcagctcc agagtaggac cctgcctcaa aaacacacag gtggaaagat 85380
gggtcggcaa tgaagagcac acactgtgcc tccaggggac ccaagcttgg gtccaagcac 85440
ccttgttggg cagctcacaa ctgcctgtaa ctccacctcc agaggatcct aagccacctt 85500
ctggcttggc ttcatggagg gaacaggtat gtgggtatct gagtgtgacg aatgagcagc 85560
aagtgagtct cgctgtggct agcacaaagt atgggctgaa gagcaggagg acagctgaaa 85620
agtggccttt cctggtgact aagttggtct gagcagctga gtcagtttct tcctggctgc 85680
ttggctggtc tcagtgctta taagctgctc acttgtaagt cttttcctag gagcccagct 85740
tgtctagggg ttgtctttgc aactggcctt gtctgacagt gactttcagc agtcttagct 85800
gcttatatac acagtcttag gaaagaaggc tggtgaatct gatccatttc aggaactttc 85860
tgaagctatt ctgaatttac tttacaagct tacctgcagg atagaggatc tcagctcttt 85920
ataaacatcc tgtcctaaaa caccctgttg ttcctcttct cttttacatc ctgtgtcttg 85980
agaagtttgc ctccaggatg gaagttgttc aattcagagg acactgttgc acaagctccc 86040
agcacccaca tgtgagctca gtgctctcct tggctctagc tctgccctat gaggtttttt 86100
attttgtcat cataatcttt tcctatatcc ttccttgttc tgggaactca tctggttcat 86160
ttttttggca ttttgagaaa agctctcact atacaaatca ggctgcctcc aaatcatctt 86220
tttgccttaa cctcctcagt accaagatca cgagtggatc ttaacacttg actgactcgt 86280
ttaagtgtga ggaaatgtgg accaataaga gagcccagga aagcccagga gaatctgtag 86340
ccccatggct gttgtgtcag aacccagagt tttgtcaaca gaatttggtt cctaatttct 86400
ccactttata aaaacgagtg agagaaacag gaacctattc agatctggcg tctgagcaat 86460
cagtgggtga acatctagag atctgttctg catctcctcg ccagctggca gagcatgcgt 86520
aaggcgggag ggaacaaggg caatcactca ctctggggct caggcttgcc ccttgggtca 86580
ggtgtttctg agagacgtga tgtctgcttc tcttgttacc atccctcatc ctctcccctc 86640
cttctgtccc ctacttacca atttcactgg ccagtgtcca tatttcctgc aaaagcgatt 86700
tggtttaatg agcttgacta tgcccgactc ctttagggag ggtggggaaa gggcaacgag 86760
ggcagtaagt ggtttccaca accactttgc acccggctgc tgggccccaa gccagaggaa 86820
cgtgcatgag ccatgaagtt tccactgata aatccacaga tgcttctagc acctgccttt 86880
ctgactcagc ctcaccgtgc cgcctgccag ctgtgaaatc agtgccaaca acaggtaacc 86940
gagacccagg cgcagggcca ggacagctgt ctgacacttc cagacaggat gtggaggctg 87000
acagttgtga tggagaggag atggggagga cagagacggg ctcagcttta agacaccgag 87060
ccacagagca ccaaacaaaa gccagggcct tctgaggtag aagtaacaga aaccaaacag 87120

-continued

```
gcaattctac tagtttcctg ggactgtttg ctgcatttgc caatcttggt agttttaaaa  87180
aacaaaaaca gtttgttctc agcactggca gagctttcct cctctggagg ctccaggggt  87240
ccagactctc ctctgtggta cactggcttc agacatatct cttgcctatg gctgcctcac  87300
tctaaactct gcctgtcctt gaattacctc tctctgcact ggctttataa aggaaacatg  87360
agattgtgtt tagggcctgt ttgggtgacc tcctcaggat ctataacata atcacatctc  87420
taccgtatga agtgacgctt ccgtcccagt gtgtaataca tttgccggcg cctgtcctta  87480
ggacagtgac caccaccaac tgtggaactt gactatgtcc acgtcatctt cctactagct  87540
ttagaaggct tatacccaca ctttctatcc agaattgtat ttttatttag aatcattcct  87600
acttttaaaa aagtctctgt ggttaaaagc attgcagagg gcttgggttt tggtccccag  87660
gacccacatc aagtggctca cagtgtcctg gaactcttgt tccaataccc tcttctggtc  87720
tccataggca ctacatacat atggcacata tatgtatact caggcacacg tgtaaatttt  87780
aatgtctact ttttatgcta aatatcaaag tcactcgagc agtggagttg agcacactca  87840
cataaggaaa tcatcagaca gacacttcat cctgtgttgg agccactttg tggctggagt  87900
aagcagggca gagtgatgtt ttcattactc tctggcccca gcacccccctg cctctcccca  87960
cccattcgtc catgcaggtg gggaagagaa ttctctttgt gaaattggaa gtttggaccc  88020
agcttcactc ttactctgcc cagtacctcc tgtgagaaac cctcctatcc caggtgacct  88080
gctggctgtg actctcctca gcaaaaggcc cgtgacccac actgcgccac taatgtatca  88140
tccccaaatg ctgaaaagga agcgtgtctt cctctctctc tctttttctt ttggtctttt  88200
tgagacagag tttctctgta tagccctggc tgtcctggaa ctcactttgt agaccaggct  88260
ggcctcgaac tcagaactcc gcctgcctct gcctcccgag tgctgggatt aaaggcgtgc  88320
atcaccactg cccggctgcg tgtctttctc ttagcggtct ctgtggagat gctgagtatg  88380
aagctcatcc tacccaccct tcagtggggc cttttctagc tactgagcag ctgtgtgagg  88440
actcgtgatc acaaggtcct ttgaaccctt gagacagatg tgcctgagcc cagtttgacc  88500
tgacaaaagc ctagagctca ctgataatgc cagcaaacac catctttgag tttgcaaagg  88560
aatcgcaaca catgcattca gtttccgttg ctggctgctg ctccagagat ggctatattc  88620
attctcaggt actcagactc aagagtagtt ctggccacac aggtctccac atttcgaggt  88680
caaatgacag aaaaccaggt tggtctcagt gcacatgggt ttattgagcc actgcaggtg  88740
ctggggaaac catggcaggg agatcctggg aagccagtgg ggtgctgagc aggagggacc  88800
tcagtctctc cttaatgtct acacactgtg tcataggtga caagccacgt cagtgctgtg  88860
acacgggtaa gcttaatggt gagtaatggc taactgggag ggtatttagg cagccttgtc  88920
tgtcagcctg ttcatatgat ctccttagtg ccttgtcatc ttggaaaagg acagttccaa  88980
attctaggag cgggggctag tctctgtcct gctctgtaag cccaggggac ccaatgaggc  89040
ctcatctatg ggtgctcagc tctaggatgg ggaagaaaat ggacaagatg cctactgacg  89100
ggaacacagg cttttcagtc agaccctagc ctccagcccc caatccagag gacagccaca  89160
caggggtcca ggcctgcaaa gggcagcaga cctgagggca agggagtttc agctcagtga  89220
gcagtcatcg ggagacatgg cagtcagctg tgtcgtccac ggttcatgtt cctaatcaga  89280
gcagggcctg gagagccagg gcagtgagtg catacagcca ggacaccttg ggcgttagga  89340
caaaacaagg actgtttctg cctccagctc ttctcaggcc actcgtgcct tgcctaggaa  89400
gggtaagaga gcacagatgg gaaggattcg gaaactgtca actccctgtc ctctccccat  89460
acctacccgc gggaaacagc acccagcagt ctggtcctgc agaactgatg gctgcaagct  89520
```

-continued gtcaaaggct tgtatggcac catctgcgga gtgcagagat ccagagaagg cttggccagg 89580
aaaccctaga aactacccca ctcccttggg acaaaaaata agacaccctg gaacctgcaa 89640
ggcatggcct gagatggaag gtcactgtgc taagaatgac ccacaaactg ctagtgaggt 89700
tgacaagggc tgccccctct ccctttacag gtgaacacaa tcgggattaa taagagttta 89760
actctcagct actaagtggc agagacaggc ttcaaacaga cccccagaaa tctggaactg 89820
agccattcca cccagaggca agaacagcag aggtaagttg ggcacacatg gaagaaaggg 89880
ccaccccatt agtgtcaaaa gggaggccaa cttcaggcca ttggacacgt tttaacgctg 89940
acttccaccc atgtaccatg gcatgtgcac actgtccatc gcccacacca aacatgatgc 90000
gacgtaaata agacccacgg gccaggcagc ttggattggg ccacagacat 90050

<210> SEQ ID NO: 6
<211> LENGTH: 226
<212> TYPE: DNA
<213> ORGANISM: Mus musculus

<400> SEQUENCE: 6
agcgctattc agctgtgcct cctttgctgt cttggctcct cctggagcac tatatgcacc 60
catgtcctta ccaggccttt cacagacgct gccattgaga gggttgatgc aggttgcagc 120
ctttaatccc cgagtactag gctctgacaa gatcccacag aagccagcat cactgggctc 180
agatggcatc cactgcagca aactatttgt gaatggagac atatcc 226

<210> SEQ ID NO: 7
<211> LENGTH: 221
<212> TYPE: DNA
<213> ORGANISM: Mus musculus

<400> SEQUENCE: 7
agcgctattc agctgtgcct cctttgctgt cttggctcct cctggagcac tatatgcacc 60
catgtcctta ccaggccttt cacagaccat tgagagggtt gatgcaggtt gcagccttta 120
atccccgagt actaggctct gacaagatcc cacagaagcc agcatcactg ggctcagatg 180
gcatccactg cagcaaacta tttgtgaatg gagacatatc c 221

<210> SEQ ID NO: 8
<211> LENGTH: 2419
<212> TYPE: DNA
<213> ORGANISM: Mus musculus

<400> SEQUENCE: 8
gaattccggg cgaaggggag ccggcgtgcg gggtgtgtat gtgttcgctg ggcgccggct 60
cagccccagg aagatggtgg cggtggcggc ggcggcggcg actgaggcgc ggctgagggg 120
gagcacgagg acgacagcag cgcctgcggg caggaagggc aggcagcacc gaccctgcac 180
cgcgacaggg gcctggaggc cgggaccgcg cgcccggctg tgtctcccgc gggtgctgtc 240
gcgggcgctg cccccgccgc cgctgctgcc gctgctcttt tcgctgctgc tgctgccgct 300
gccccgggag gccgaggccg ctgcggtggc ggcggcggtg tccggctcgg ccgcagccga 360
ggccaaggaa tgtgaccggc cgtgtgtcaa cggcggccgc tgcaaccctg gcaccggcca 420
gtgcgtctgc ccccacgggct gggtgggcga gcaatgccag cactgcgggg gccgcttcag 480
gacatctgtc tcacgcctat aatcacagct gttcggaagg tgaggctgga ggaacagttc 540
gaggcaagct tcggctacag aataagttca agagtaacct ggggcaactt gggcttgtct 600

-continued

```
ccaaaaccaa aatgagcgaa aaggagcaag ctagagtctt ttgggaaaat tttagctgac    660

taatttttca ccgagaacta actggctctt ctggatttgt aacagatgga cctgggaatt    720

ataaatataa gacgaagtgc acatggctca ttgaaggaca gccaaataga ataatgagac    780

ttcgcttcaa ccattttgct acagaatgta gctgggacca tttatatgtt tatgatgggg    840

actcaatcta cgcacctctg attgctgcct ttagtggcct cattgttcct gaaagagatg    900

gcaatgagac ggctcctgag gtcactgtca cttcaggtta tgcactgctg catttttttca   960

gtgatgctgc ttataatctg actggattta atatcactta caattttgac atgtgtccga   1020

ataattgctc aggccgagga gagtgtaaga gcagtaacag cagcagcgct gttgagtgtg   1080

aatgttctga aaactggaaa ggggagtcgt gtgacattcc tcactgtaca gacaactgtg   1140

gctttcctca ccgaggcatc tgtaatgcaa gcgataccag agggtgctcc tgctttcctc   1200

actggcaggg tcctggatgt tcaattcctg tgccagctaa ccagtctttt tggactcgag   1260

aagaatattc tgatttaaag cttcccagag cctctcataa agctgtggtc aatggaaata   1320

taatgtgggt tgttggcgga tatatgttca accattcaga ttacagcatg gttttagcgt   1380

atgacctgac ttctagggaa tggcttccac taaaccattc tgtgaacagt gtggttgtaa   1440

gatatggtca ttctttggca ttacataagg ataaaatcta catgtatgga ggaaaaattg   1500

attcaacagg gaacgtgacc aatgagctga gagtatttca tattcataat gaatcatggg   1560

tattgttaac tccgaaagct aaggatcagt atgcagtggt tggacactca gcacacattg   1620

ttacactggc atctggccgt gtggtcatgt tggtcatctt cggtcattgc ccactctatg   1680

gatatataag cgttgtgcag gaatatgact tggaaaagaa cacatggagt atattacata   1740

ctcagggtgc tcttgtgcaa gggggttatg gccacagtag tgtttatgat gacaggacca   1800

aggctctgta cgttcatggt ggctacaagg ctttcagcgc caacaaatac cggcttgcag   1860

atgacctcta cagatacgat gtggatactc agatgtggac cattcttaag gacagccgat   1920

ttttccgtta cttgcataca gctgtgatag tgagtggaac catgctggtg tttggaggga   1980

acacacacaa tgacacttcc atgagccacg gtgccaaatg cttctcctcg gacttcatgg   2040

cttatgacat tgcttgtgac cgatggtcag tgcttcccag acctgagctc catcatgatg   2100

tcaacagatt tggccattca gcagtcttgt acaacagcac catgtatgtg ttcggcggct   2160

tcaacagcct cctcctcagt gacgtcttgg tctttacctc ggagcagtgc gatgcacacc   2220

gcagtgaagc tgcttgtgtg gcagcaggac ctggtatccg gtgtctgtgg gacacacagt   2280

cgtctcgatg tacctcctgg gagttggcaa ctgaagaaca agcagaaaag ttaaaatcag   2340

agtgtttttc taaaagaacc cttgaccatg acagatgtga ccagcacaca gattgttaca   2400

gctgcacagc caataccaa                                                2419
```

<210> SEQ ID NO: 9
<211> LENGTH: 549
<212> TYPE: PRT
<213> ORGANISM: Mus musculus
<220> FEATURE:
<221> NAME/KEY: SITE
<222> LOCATION: all Xaa positions
<223> OTHER INFORMATION: Xaa=unknown amino acid

<400> SEQUENCE: 9

```
Met Arg Leu Arg Phe Asn His Phe Ala Thr Glu Cys Ser Trp Asp His
 1               5                  10                  15

Leu Tyr Val Tyr Asp Gly Asp Ser Ile Tyr Ala Pro Leu Ile Ala Ala
            20                  25                  30
```

-continued

```
Phe Ser Gly Leu Ile Val Pro Glu Arg Asp Gly Asn Glu Thr Ala Pro
        35                  40                  45

Glu Val Thr Val Thr Ser Gly Tyr Ala Leu Leu His Phe Phe Ser Asp
    50                  55                  60

Ala Ala Tyr Asn Leu Thr Gly Phe Asn Ile Thr Tyr Asn Phe Asp Met
65                  70                  75                  80

Cys Pro Asn Asn Cys Ser Gly Arg Gly Glu Cys Lys Ser Ser Asn Ser
                85                  90                  95

Ser Ser Ala Val Glu Cys Glu Cys Ser Glu Asn Trp Lys Gly Glu Ser
            100                 105                 110

Cys Asp Ile Pro His Cys Thr Asp Asn Cys Gly Phe Pro His Arg Gly
        115                 120                 125

Ile Cys Asn Ala Ser Asp Thr Arg Gly Cys Ser Cys Phe Pro His Trp
    130                 135                 140

Gln Gly Pro Gly Cys Ser Ile Pro Val Pro Ala Asn Gln Ser Phe Trp
145                 150                 155                 160

Thr Arg Glu Glu Tyr Ser Asp Leu Lys Leu Pro Arg Ala Ser His Lys
                165                 170                 175

Ala Val Val Asn Gly Asn Ile Met Trp Val Val Gly Gly Tyr Met Phe
            180                 185                 190

Asn His Ser Asp Tyr Ser Met Val Leu Ala Tyr Asp Leu Thr Ser Arg
        195                 200                 205

Glu Trp Leu Pro Leu Asn His Ser Val Asn Ser Val Val Val Arg Tyr
    210                 215                 220

Gly His Ser Leu Ala Leu His Lys Asp Lys Ile Tyr Met Tyr Gly Gly
225                 230                 235                 240

Lys Ile Asp Ser Thr Gly Asn Val Thr Asn Glu Leu Arg Val Phe His
                245                 250                 255

Ile His Asn Glu Ser Trp Val Leu Leu Thr Pro Lys Ala Lys Asp Gln
            260                 265                 270

Tyr Ala Val Val Gly His Ser Ala His Ile Val Thr Leu Ala Ser Gly
        275                 280                 285

Arg Val Val Met Leu Val Ile Phe Gly His Cys Pro Leu Tyr Gly Tyr
    290                 295                 300

Ile Ser Val Val Gln Glu Tyr Asp Leu Glu Lys Asn Thr Trp Ser Ile
305                 310                 315                 320

Leu His Thr Gln Gly Ala Leu Val Gln Gly Gly Tyr Gly His Ser Ser
                325                 330                 335

Val Tyr Asp Asp Arg Thr Lys Ala Leu Tyr Val His Gly Gly Tyr Lys
            340                 345                 350

Ala Phe Ser Ala Asn Lys Tyr Arg Leu Ala Asp Asp Leu Tyr Arg Tyr
        355                 360                 365

Asp Val Asp Thr Gln Met Trp Thr Ile Leu Lys Asp Ser Arg Phe Phe
    370                 375                 380

Arg Tyr Leu His Thr Ala Val Ile Val Ser Gly Thr Met Leu Val Phe
385                 390                 395                 400

Gly Gly Asn Thr His Asn Asp Thr Ser Met Ser His Gly Ala Lys Cys
                405                 410                 415

Phe Ser Ser Asp Phe Met Ala Tyr Asp Ile Ala Cys Asp Arg Trp Ser
            420                 425                 430

Val Leu Pro Arg Pro Glu Leu His His Asp Val Asn Arg Phe Gly His
        435                 440                 445
```

-continued

```
Ser Ala Val Leu Tyr Asn Ser Thr Met Tyr Val Phe Gly Gly Phe Asn
    450                 455                 460

Ser Leu Leu Leu Ser Asp Val Leu Val Phe Thr Ser Glu Gln Cys Asp
465                 470                 475                 480

Ala His Arg Ser Glu Ala Ala Cys Val Ala Ala Gly Pro Gly Ile Arg
                485                 490                 495

Cys Leu Trp Asp Thr Gln Ser Ser Arg Cys Thr Ser Trp Glu Leu Ala
            500                 505                 510

Thr Glu Glu Gln Ala Glu Lys Leu Lys Ser Glu Cys Phe Ser Lys Arg
        515                 520                 525

Thr Leu Asp His Asp Arg Cys Asp Gln His Thr Asp Cys Tyr Ser Cys
    530                 535                 540

Thr Ala Asn Thr Xaa
545


<210> SEQ ID NO: 10
<211> LENGTH: 1051
<212> TYPE: DNA
<213> ORGANISM: Mus musculus

<400> SEQUENCE: 10

gaattccgga aaaaaaaaaa aaaaaaaaaa aaaaaaaaaa aaaaaaaaaa aaaaaaaaaa      60

aaaaaaaaaa aaaaaaaaaa aaaaaaaaaa aaaaaaaaaa aaaaaaaaaa aaaaaaaaaa     120

aaaaaaaaaa aaaaaaaagg agggcgaagg ggagccggcg tgcggggtgt gtatgtgttc     180

gctgggcgcc ggctcagccc caggaagatg gtggcggtgg cggcggcggc ggcgactgag     240

gcgcggctga gggggagcac gacgacgaca gcagcgcctg cgggcaggaa gggcaggcag     300

caccgaccct gcaccgcgac aggggcctgg aggccgggac cgcgcgcccg gctgtgtctc     360

ccgcgggtgc tgtcgcgggc gctgccccg ccgccgctgc tgccgctgct cttttcgctg     420

ctgctgctgc cgctgccccg ggaggccgag gccgctgcgg tggcggcggc ggtgtccggc     480

tcggccgcag ccgaggccaa ggaatgtgac cggccgtgtg tcaacggcgg ccgctgcaac     540

cctggcaccg gccagtgcgt ctgccccacg ggctgggtgg gcgagcaatg ccagcactgc     600

gggggccgct tcagactaac tggctcttct ggatttgtaa cagatggacc tgggaattat     660

aaatataaga cgaagtgcac atggctcatt gaaggacagc caaatagaat aatgagactt     720

cgcttcaacc attttgctac agaatgtagc tgggaccatt tatatgttta tgatggggac     780

tcaatctacg cacctctgat tgctgccttt agtggcctca ttgttcctga aagagatggc     840

aatgagacgg ctcctgaggt cactgtcact tcaggttatg cactgctgca ttttttcagt     900

gatgctgctt ataatctgac tggatttaat atcacttaca attttgacat gtgtccgaat     960

aattgctcag gccgaggaga gtgtaagagc agtaacagca gcagcgctgt tgagtgtgaa    1020

tgttctgaaa actggaaagg ggccggaatt c                                   1051


<210> SEQ ID NO: 11
<211> LENGTH: 351
<212> TYPE: PRT
<213> ORGANISM: Mus musculus
<220> FEATURE:
<221> NAME/KEY: SITE
<222> LOCATION: all Xaa positions
<223> OTHER INFORMATION: Xaa=unknown amino acid

<400> SEQUENCE: 11

Glu Phe Arg Lys Lys Lys Lys Lys Lys Lys Lys Lys Lys Lys Lys Lys
 1               5                  10                  15
```

-continued

```
Lys Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Gly Gly
        35                  40                  45

Arg Arg Gly Ala Gly Val Arg Gly Val Tyr Val Phe Ala Gly Arg Arg
    50                  55                  60

Leu Ser Pro Arg Lys Met Val Ala Val Ala Ala Ala Ala Ala Thr Glu
65                  70                  75                  80

Ala Arg Leu Arg Gly Ser Thr Thr Thr Thr Ala Ala Pro Ala Gly Arg
                85                  90                  95

Lys Gly Arg Gln His Arg Pro Cys Thr Ala Thr Gly Ala Trp Arg Pro
            100                 105                 110

Gly Pro Arg Ala Arg Leu Cys Leu Pro Arg Val Leu Ser Arg Ala Leu
        115                 120                 125

Pro Pro Pro Pro Leu Leu Pro Leu Leu Phe Ser Leu Leu Leu Leu Pro
    130                 135                 140

Leu Pro Arg Glu Ala Glu Ala Ala Ala Val Ala Ala Ala Val Ser Gly
145                 150                 155                 160

Ser Ala Ala Ala Glu Ala Lys Glu Cys Asp Arg Pro Cys Val Asn Gly
                165                 170                 175

Gly Arg Cys Asn Pro Gly Thr Gly Gln Cys Val Cys Pro Thr Gly Trp
            180                 185                 190

Val Gly Glu Gln Cys Gln His Cys Gly Gly Arg Phe Arg Leu Thr Gly
        195                 200                 205

Ser Ser Gly Phe Val Thr Asp Gly Pro Gly Asn Tyr Lys Tyr Lys Thr
    210                 215                 220

Lys Cys Thr Trp Leu Ile Glu Gly Gln Pro Asn Arg Ile Met Arg Leu
225                 230                 235                 240

Arg Phe Asn His Phe Ala Thr Glu Cys Ser Trp Asp His Leu Tyr Val
                245                 250                 255

Tyr Asp Gly Asp Ser Ile Tyr Ala Pro Leu Ile Ala Ala Phe Ser Gly
            260                 265                 270

Leu Ile Val Pro Glu Arg Asp Gly Asn Glu Thr Ala Pro Glu Val Thr
        275                 280                 285

Val Thr Ser Gly Tyr Ala Leu Leu His Phe Phe Ser Asp Ala Ala Tyr
    290                 295                 300

Asn Leu Thr Gly Phe Asn Ile Thr Tyr Asn Phe Asp Met Cys Pro Asn
305                 310                 315                 320

Asn Cys Ser Gly Arg Gly Glu Cys Lys Ser Ser Asn Ser Ser Ser Ala
                325                 330                 335

Val Glu Cys Glu Cys Ser Glu Asn Trp Lys Gly Ala Gly Ile Xaa
            340                 345                 350
```

<210> SEQ ID NO: 12
<211> LENGTH: 6370
<212> TYPE: DNA
<213> ORGANISM: Homo sapiens

<400> SEQUENCE: 12

```
atgtactact gtaacaagaa gaccagctgc aggagctgtg ccctggacca gaactgccag      60

tgggagcccc ggaatcagga gtgcattgcc ctgcccgaaa atatctgtgg cattggctgg     120

catttggttg gaaactcatg tttgaaaatt actactgcca aggagaatta tgacaatgct     180

aaattgttct gtaggaacca caatgccctt ttggcttctc ttacaaccca gaagaaggta     240
```

-continued

```
gaatttgtcc ttaagcagct gcgaataatg cagtcatctc agagcatgtc caagctcacc    300
ttaaccccat gggtcgggcc ttcgggaagg tycaatgtgt cctactkggt gctggggaag    360
gatatgktcc ccattttaca aatagtttta ctacagtggg atgsccgtct tgaggcccag    420
tgttgcttgg rattctgtgg gaatttttatt caggaaccca gttacttcgg ggactgaagg    480
ctgcaacctg cattcaaccc actymaatgg tagtgtctgt gaaaggcctg caaaccacag    540
tgctaaggca gtgccggaca ccatgtgcct tgaggacagc atgtggagat tgcaccagcg    600
gcagctctga gtgcatgtgg tgcagcaaca tgaagcagtg tgtggactcc aatgcctatg    660
tggcctcctt ccctttggc cagtgtatgg aatggtatac gatgagcacc tgcccccctg    720
aaaattgttc aggctactgt acctgtagtc attgcttgga gcaaccaggc tgtggctggt    780
gtactgatcc cagcaatact ggcaaaggga aatgcataga gggttcctat aaaggaccag    840
tgaagatgcc ttcgcaagcc cctacaggaa atttctatcc acagcccctg ctcaattcca    900
gcatgtgtct agaggacagc agatacaact ggtctttcat tcactgtcca gcttgccaat    960
gcaacggcca cagtaaatgc atcaatcaga gcatctgtga gaagtgtgag aacctgacca   1020
caggcaagca ctgcgagacc tgcatatctg gcttctacgg tgatcccacc aatggaggga   1080
aatgtcagcc atgcaagtgc aatgggcacg cgtctctgtg caacaccaac acgggcaagt   1140
gcttctgcac caccaagggc gtcaaggggg acgagtgcca gctatgtgag gtagaaaatc   1200
gataccaagg aaaccctctc agaggaacat gttattatac tcttcttatt gactatcagt   1260
tcacctttag tctatcccag gaagatgatc gctattacac agctatcaat tttgtggcta   1320
ctcctgacga acaaaacagg gatttggaca tgttcatcaa tgcctccaag aatttcaacc   1380
tcaacatcac ctgggctgcc agtttctcag ctggaaccca ggctggagaa gagatgcctg   1440
ttgtttcaaa aaccaacatt aaggagtaca aagatagttt ctctaatgag aagtttgatt   1500
ttcgcaacca cccaaatatc actttctttg tttatgtcag taatttcacc tggcccatca   1560
aaattcagat tgccttctct cagcacagca attttatgga cctggtacag ttcttcgtga   1620
ctttcttcag ttgtttcctc tctttgctcc tggtggctgc tgtggtttgg aagatcaaac   1680
aaagttgttg ggcctccaga cgtagagagc aacttcttcg agagatgcaa cagatggcca   1740
gccgtccctt tgcctctgta aatgtcgcct tggaaacaga tgaggagcct cctgatctta   1800
ttggggggag tataaagact gttcccaaac ccattgcact ggagccgtgt tttggcaaca   1860
aagccgctgt cctctctgtg tttgtgaggc tccctcgagg cctgggtggc atccctcctc   1920
ctgggcagtc aggtcttgct gtggccagcg ccctggtgga catttctcag cagatgccga   1980
tagtgtacaa ggagaagtca ggagccgtga gaaaccggaa gcagcagccc cctgcacagc   2040
ctgggacctg catctgatgc tggggccagg gactctccca cgcacgagct agtgagtggc   2100
acaccagagc catctgcagg gaagggcgtg gcggggaaat ggctgtgcgg tgcgggacgg   2160
aagactggaa accctcaaag catctgactc acctgcatga tcacaagctt tctttgacgg   2220
tttctcccat ccgtgttcca gcatctaacc ttttactttt gcataggaaa tacttgattt   2280
aattacaggt ccagggatga gctgatggtt gctggaggag gccagtgtag agccagtgag   2340
agaactagga atgacactca ggttcactgt ggaaaactgt tcttgggact gtctcaactg   2400
tgcaaaaaac aaaagatgga gtgtttacaa gtagacattc gtcatcagtt gttcttgaac   2460
atggtctttt aaaaactagt cagatgaatt aacttgtttt catctgaagc ctgctatctt   2520
ttttaaaaga tgtgctattt attcttgcac gatttaggca attatctctc ttccagggag   2580
```

-continued

```
taccttttttt tctagttgag aattaataat ggtccatctc ttttgatcat atcaagctag   2640
gatagaaggg gggctatttt aaatgtcaag gtcagcagtg ttactttgaa tgtaaactgg   2700
tataataggt agttttctat agtaacttga ttaatttagt cttaatccat ttgaaactct   2760
ctcttccttt ctctctgcct gtccctctcc ttctccatct caccctccct ctctcacaca   2820
tacacacaca aacacataca cacaacacta agtgcctaga ctttaaatag atctagcaat   2880
tggaaagtta gtaagcctaa gtttttacat aattgcattc ctacattctt gtaaaattta   2940
aatagctacc attggcaatc tgcttttttt ctaaaatctg atttgcagcc aggaaagaat   3000
tttctcaccc aaggaacatt tgatctagca gcagggatga gaggaaagca gaaatgaatg   3060
aactgtgaaa gctcctgttt ttattatcaa aaaggacact gtcaagaagg cgccccctgc   3120
ccccaccccc gtgtcaccct aggcctgata agcgatcaga ggaaaggact cattcatgtc   3180
acgcttcctt gagcagaaaa gagcactgag agcacttggg acccctggat cagagagcat   3240
ctgtgtgtcc tgcagcctcc tctgaacttg tggttcattc tcaggctggg gtggactcag   3300
atgccaggaa agggacagcc tcccattgtc aggcagaagc tgcccaaagc ctggagaagg   3360
acttgtttgc cctctttccc ccaggagggg ctcgacccac ccaccctccc tctcagacca   3420
aggtggtggc tgtgaggagg gcagcaaatg ctgacaagga tgaaaagcac atggaaaaaa   3480
atggacgagg agggaaaact ctgccaaatg gaaaatgacc aaatttaaga gggtgggaca   3540
gtcccctgct cctctcccag agggcactgc ttggaaattg tgttttcccc atttatggtg   3600
ctctgtattc tggcattatg cagcagcctc ccagaagctc tcttctgctt caaaacctgg   3660
gatctctggc attaccctat tgggatggac cgctggacag caatgctcga gtttgtgaat   3720
ttggagagat actcaaaaga gctaaaactg cagcatttta cctttaaatg cagtgcctag   3780
agagagagta ttgtctcttc cccaacacta accccactcc catgaagaat tgcctggaaa   3840
gatgttttca aggaatttga accataaaac actatctgat gcacagaaca cctctacttt   3900
gagactcacc tctcataaag cttctttttc acattactgt taaagaccag acgttctaga   3960
aaagacccct cctctcatga gctcccccat ccctgctaca gaacacagca cccatggcgc   4020
ctgcagtgga ctggcccctt aattcccaca ggccccccca gcaaggccaa agggaggccc   4080
ctgggtattg tcctcctaca aggaagatcc tctttgtttg ttcaaaggac cagttttcct   4140
aggccaaaga agtctcttcc ccatgttagt cctatgcctt gaaatatcat gcaccatgac   4200
ccacagccat ctggttatgt cttatttttt tcctaaaaga taatgtttat ttttaaaaag   4260
gaaggaagaa gcaagtgaag tttcattctg ctccagcggt ggggaagccg ctgaatccac   4320
ctgcttctcc tttgcaaccg acagcaaaca gctttctccg gcctcagggc agaaaaaggg   4380
aatggcaggg agtaagaggc gctgggctcg gagcctgttt ccaagaagga attggttgtc   4440
atctggcagt gttgcgcgtc acaagagagc ctgtatataa attaaaatag tcaagacaac   4500
actgaccttg cacttgtaca taactataca gtagtgtcca gaatgttcag acattcggag   4560
tgtacataaa acagaaaaaa tcttcatgta tttttattaa atataacaat gtctgagttt   4620
cacctaagat gtttttgtgc catatgctgg atatccaggt tctcgccagg ccccgataca   4680
tgaataacaa acccaagaaa cgcatcccca ttgtgtgatg tgttcagatg catctggcac   4740
caattaggta tttcttaaaa caggactcat ctgtcagagt gcacatgaaa aatcaggcag   4800
ggaatcgaaa cgacagcgct ggaggagact caggaagcag aggcgtccct gccgctgccc   4860
ttggccctgc aagcacatca tgaccctttc tggcagcctc ttggtgctct gggtagtgag   4920
ggatgaccag tcttgtcctg agaaatgttt ctcttagtct ttaagttcaa agactaacct   4980
```

-continued

```
gtagcaatca gactttccaa aagggggttc tccatttttt gtagttttgt ctaaattttt   5040
aatgaccatt tcctggaatc agtttattat actgaaaact gggggtggga gtagggagct   5100
agtttgttga taaatagttc ccatttcccc gtggagaatt tgacataccc tggactcctg   5160
tgtgcctcct gccatccctg cacacagcct ggggagaagc ctgtgcctcc ccgtgtggag   5220
agaaggcaac cccagatccc ctgagctaac ccggaggaaa ggcagtcctg gacagaagac   5280
tgtcagcaga aggaaagtac tggactaccc gtgggtaagt cctgccattc aagactggag   5340
acacctggga aataaaaaga gcagggcact gctggtggga agaggcattt taccttccag   5400
tgcaaatcct gctcctttga tttaatgggg tgtactgggg ccaggggctg attcacttcc   5460
ttgggagatg gtggtgtttt catgaacatc tttgatcctt ccatttcatt tattcatcca   5520
tccattcaac aagtatttgc taaacactaa cttaagctaa tgctagggta gtgactgaga   5580
tgtaaaaata gattttagaa ttaaaacaaa atccaagtcc tcacacccct gtcatcccag   5640
gagatctttc cttgtggtgg tttctgtgag aattggccat cctgaggaca cagccaggac   5700
ggcagaggcc tcctggcctc agggcatgcc ctgcctacct tctgaaatgt ttaccccatt   5760
gaccaaactt ggctccagcc attgcggtgg tttctagata gccaggccca ccaagagata   5820
ttgccccttg atgagagtca aacaccctgc ctacaaggag atgttttgaa atggagagga   5880
aaattggcac ctcatctttt aaaggcagta atggaattga ttttcagtaa ctgaatttgt   5940
gcacaaaaca ttctaaacac tagtgaagcc tgtttcgttg aactaattct ggctctggaa   6000
atgtttttgt tttatagtta tttacgattt cgtttgtttg gattcaagct tagtttgtta   6060
atatgtataa tttagcatct attacactca tgtaaatatg gagtaagtat tgtaaactat   6120
ttcattgcgg ggattgtggg tgttatacat acatttagga ctgcaatttt ttggtatttt   6180
ttgtattgta aaataacagc taatttaagc aggaacaaga gaactaaggg aggtctgtgc   6240
attttaaaca caaatgtgaa gaacttgtat ataaacaaaa gtaaatacta taatacaaac   6300
ttccttctga aataaaagta gatctggtaa aaaaaaaaaa agaaaaaaaa aaaaaaaaaa   6360
gggcggccgc                                                          6370
```

<210> SEQ ID NO: 13
<211> LENGTH: 686
<212> TYPE: PRT
<213> ORGANISM: Homo sapiens
<220> FEATURE:
<221> NAME/KEY: SITE
<222> LOCATION: all Xaa positions
<223> OTHER INFORMATION: Xaa=unknown amino acid

<400> SEQUENCE: 13

```
Met Tyr Tyr Cys Asn Lys Lys Thr Ser Cys Arg Ser Cys Ala Leu Asp
 1               5                  10                  15

Gln Asn Cys Gln Trp Glu Pro Arg Asn Gln Glu Cys Ile Ala Leu Pro
            20                  25                  30

Glu Asn Ile Cys Gly Ile Gly Trp His Leu Val Gly Asn Ser Cys Leu
        35                  40                  45

Lys Ile Thr Thr Ala Lys Glu Asn Tyr Asp Asn Ala Lys Leu Phe Cys
    50                  55                  60

Arg Asn His Asn Ala Leu Leu Ala Ser Leu Thr Thr Gln Lys Lys Val
65                  70                  75                  80

Glu Phe Val Leu Lys Gln Leu Arg Ile Met Gln Ser Ser Gln Ser Met
                85                  90                  95
```

-continued

```
Ser Lys Leu Thr Leu Thr Pro Trp Val Gly Pro Ser Gly Arg Xaa Asn
            100                 105                 110

Val Ser Tyr Xaa Val Leu Gly Lys Asp Met Xaa Pro Ile Leu Gln Ile
        115                 120                 125

Val Leu Leu Gln Trp Asp Xaa Arg Leu Glu Ala Gln Cys Cys Leu Xaa
    130                 135                 140

Phe Cys Gly Asn Phe Xaa Ser Gly Thr Gln Leu Leu Arg Gly Leu Lys
145                 150                 155                 160

Ala Ala Thr Cys Ile Gln Pro Thr Xaa Met Val Val Ser Val Lys Gly
                165                 170                 175

Leu Gln Thr Thr Val Leu Arg Gln Cys Arg Thr Pro Cys Ala Leu Arg
            180                 185                 190

Thr Ala Cys Gly Asp Cys Thr Ser Gly Ser Ser Glu Xaa His Val Val
        195                 200                 205

Gln Gln His Glu Xaa Ser Val Trp Thr Pro Met Pro Met Trp Pro Pro
    210                 215                 220

Ser Leu Leu Xaa Gln Cys Met Glu Trp Tyr Thr Met Ser Thr Cys Pro
225                 230                 235                 240

Pro Glu Asn Cys Ser Gly Tyr Cys Thr Cys Ser His Cys Leu Glu Gln
                245                 250                 255

Pro Gly Cys Gly Trp Cys Thr Asp Pro Ser Asn Thr Gly Lys Gly Lys
            260                 265                 270

Cys Ile Glu Gly Ser Tyr Lys Gly Pro Val Lys Met Pro Ser Gln Ala
        275                 280                 285

Pro Thr Gly Asn Phe Tyr Pro Gln Pro Leu Leu Asn Ser Ser Met Cys
    290                 295                 300

Leu Glu Asp Ser Arg Tyr Asn Trp Ser Phe Ile His Cys Pro Ala Cys
305                 310                 315                 320

Gln Cys Asn Gly His Ser Lys Cys Ile Asn Gln Ser Ile Cys Glu Lys
                325                 330                 335

Cys Glu Asn Leu Thr Thr Gly Lys His Cys Glu Thr Cys Ile Ser Gly
            340                 345                 350

Phe Tyr Gly Asp Pro Thr Asn Gly Gly Lys Cys Gln Pro Cys Lys Cys
        355                 360                 365

Asn Gly His Ala Ser Leu Cys Asn Thr Asn Thr Gly Lys Cys Phe Cys
    370                 375                 380

Thr Thr Lys Gly Val Lys Gly Asp Glu Cys Gln Leu Cys Glu Val Glu
385                 390                 395                 400

Asn Arg Tyr Gln Gly Asn Pro Leu Arg Gly Thr Cys Tyr Tyr Thr Leu
                405                 410                 415

Leu Ile Asp Tyr Gln Phe Thr Phe Ser Leu Ser Gln Glu Asp Asp Arg
            420                 425                 430

Tyr Tyr Thr Ala Ile Asn Phe Val Ala Thr Pro Asp Glu Gln Asn Arg
        435                 440                 445

Asp Leu Asp Met Phe Ile Asn Ala Ser Lys Asn Phe Asn Leu Asn Ile
    450                 455                 460

Thr Trp Ala Ala Ser Phe Ser Ala Gly Thr Gln Ala Gly Glu Glu Met
465                 470                 475                 480

Pro Val Val Ser Lys Thr Asn Ile Lys Glu Tyr Lys Asp Ser Phe Ser
                485                 490                 495

Asn Glu Lys Phe Asp Phe Arg Asn His Pro Asn Ile Thr Phe Phe Val
            500                 505                 510

Tyr Val Ser Asn Phe Thr Trp Pro Ile Lys Ile Gln Ile Ala Phe Ser
```

-continued

```
        515                 520                 525

Gln His Ser Asn Phe Met Asp Leu Val Gln Phe Phe Val Thr Phe Phe
    530                 535                 540

Ser Cys Phe Leu Ser Leu Leu Leu Val Ala Ala Val Val Trp Lys Ile
545                 550                 555                 560

Lys Gln Ser Cys Trp Ala Ser Arg Arg Arg Glu Gln Leu Leu Arg Glu
                565                 570                 575

Met Gln Gln Met Ala Ser Arg Pro Phe Ala Ser Val Asn Val Ala Leu
            580                 585                 590

Glu Thr Asp Glu Glu Pro Pro Asp Leu Ile Gly Gly Ser Ile Lys Thr
        595                 600                 605

Val Pro Lys Pro Ile Ala Leu Glu Pro Cys Phe Gly Asn Lys Ala Ala
    610                 615                 620

Val Leu Ser Val Phe Val Arg Leu Pro Arg Gly Leu Gly Gly Ile Pro
625                 630                 635                 640

Pro Pro Gly Gln Ser Gly Leu Ala Val Ala Ser Ala Leu Val Asp Ile
                645                 650                 655

Ser Gln Gln Met Pro Ile Val Tyr Lys Glu Lys Ser Gly Ala Val Arg
            660                 665                 670

Asn Arg Lys Gln Gln Pro Pro Ala Gln Pro Gly Thr Cys Ile
        675                 680                 685


<210> SEQ ID NO: 14
<211> LENGTH: 8589
<212> TYPE: DNA
<213> ORGANISM: Homo sapiens

<400> SEQUENCE: 14

atggtggcgg tggccgcagc ggcggcaact gaggcaaggc tgaggaggag gacggcggcg     60

acggcagcgc tcgcgggcag gagcggcggg ccgcaccgac cctgcaccgc gacaggggcc    120

tggaggccgg gaccgcgcgc ccggctgtgt ctcccgcggg tgctgtcgcg ggcgctgccc    180

ccgccgccgc tgctgccgct gctcttttcg ctgctgctgc tgccgctgcc ccgggaggcc    240

gaggccgctg cggtggcggc ggcggtgtcc ggctcggccg cagccgaggc caaggaatgt    300

gaccggccgt gtgtcaacgg cggtcgctgc aaccctggca ccggccagtg cgtctgcccc    360

gccggctggg tgggcgagca atgccagcac tgcgggggcc gcttcagact aactggatct    420

tctgggtttg tgacagatgg acctggaaat tataaataca aaacgaagtg cacgtggctc    480

attgaaggac agccaaatag aataatgaga cttcgtttca atcattttgc tacagagtgt    540

agttgggacc atttatatgt ttatgatggg gactcaattt atgcaccgct agttgctgca    600

tttagtggcc tcattgttcc tgagagagat ggcaatgaga ctgtccctga ggttgttgcc    660

acatcaggtt atgccttgct gcattttttt agtgatgctg cttataattt gactggattt    720

aatattactt acagttttga tatgtgtcca aataactgct caggccgagg agagtgtaag    780

atcagtaata gcagcgatac tgttgaatgt gaatgttctg aaaactggaa aggtgaagca    840

tgtgacattc ctcactgtac agacaactgt ggttttcctc atcgaggcat ctgcaattca    900

agtgatgtca gaggatgctc ctgcttctca gactggcagg gtcctggatg ttcagttcct    960

gtaccagcta accagtcatt ttggactcga gaggaatatt ctaacttaaa gctccccaga   1020

gcatctcata aagctgtggt caatggaaac attatgtggg ttgttggagg atatatgttc   1080

aaccactcag attataacat ggttctagcg tatgaccttg cttctaggga gtggcttcca   1140

ctaaaccgtt ctgtgaacaa tgtggttgtt agatatggtc attctttggc attatacaag   1200
```

-continued

```
gataaaattt acatgtatgg aggaaaaatt gattcaactg ggaatgtgac caatgagttg   1260
agagtttttc acattcataa tgagtcatgg gtgttgttga cccctaaggc aaaggagcag   1320
tatgcagtgg ttgggcactc tgcacacatt gttacactga agaatggccg agtggtcatg   1380
ctggtcatct ttggtcactg ccctctctat ggatatataa gcaatgtgca ggaatatgat   1440
ttggataaga acacatggag tatattacac acccagggtg cccttgtgca aggggggttac  1500
ggccatagca gtgtttacga ccataggacc agggccctat acgttcatgg tggctacaag   1560
gctttcagtg ccaataagta ccggcttgca gatgatctct accgatatga tgtggatacc   1620
cagatgtgga ccattcttaa ggacagccga tttttccgtt acttgcacac agctgtgata   1680
gtgagtggaa ccatgctggt gtttgggggga aacacacaca atgacacatc tatgagccat  1740
ggcgccaaat gcttctcttc agatttcatg gcctatgaca ttgcctgtga ccgctggtca   1800
gtgcttccca gacctgatct ccaccatgat gtcaacagat ttggccattc agcagtctta   1860
cacaacagca ccatgtatgt gttcggtggt ttcaatagtc tcctcctcag cgacatcctg   1920
gtattcacct cggaacagtg tgatgcgcat cggagtgaag ccgcttgttt agcagcagga   1980
cctggtattc ggtgtgtgtg gaacacaggg tcgtctcagt gtatctcgtg ggcgctggca   2040
actgatgaac aagaagaaaa gttaaaatca gaatgttttt ccaaaagaac tcttgaccat   2100
gacagatgtg accagcacac agattgttac agctgcacag ccaacaccaa tgactgccac   2160
tggtgcaatg accattgtgt ccccaggaac cacagctgct cagaaggcca gatctccatt   2220
tttaggtatg agaattgccc caaggataac cctatgtact actgtaacaa gaagaccagc   2280
tgcaggagct gtgccctgga ccagaactgc cagtgggagc cccggaatca ggagtgcatt   2340
gccctgcccg aaaatatctg tggcattggc tggcatttgg ttggaaactc atgtttgaaa   2400
attactactg ccaaggagaa ttatgacaat gctaaattgt tctgtaggaa ccacaatgcc   2460
cttttggctt ctcttacaac ccagaagaag gtagaatttg tccttaagca gctgcgaata   2520
atgcagtcat ctcagagcat gtccaagctc accttaaccc catgggtcgg ccttcggaag   2580
atcaatgtgt cctactggtg ctgggaagat atgtccccat ttacaaatag tttactacag   2640
tggatgccgt ctgagcccag tgatgctgga ttctgtggaa ttttatcaga acccagtact   2700
cggggactga aggctgcaac ctgcatcaac ccactcaatg gtagtgtctg tgaaaggcct   2760
gcaaaccaca gtgctaagca gtgccggaca ccatgtgcct tgaggacagc atgtggagat   2820
tgcaccagcg gcagctctga gtgcatgtgg tgcagcaaca tgaagcagtg tgtggactcc   2880
aatgcctatg tggcctcctt cccttttggc cagtgtatgg aatggtatac gatgagcacc   2940
tgccccccctg aaaattgttc aggctactgt acctgtagtc attgcttgga gcaaccaggc  3000
tgtggctggt gtactgatcc cagcaatact ggcaaaggga aatgcataga gggttcctat   3060
aaaggaccag tgaagatgcc ttcgcaagcc cctacaggaa atttctatcc acagcccctg   3120
ctcaattcca gcatgtgtct agaggacagc agatacaact ggtctttcat tcactgtcca   3180
gcttgccaat gcaacggcca cagtaaatgc atcaatcaga gcatctgtga gaagtgtgag   3240
aacctgacca caggcaagca ctgcgagacc tgcatatctg gcttctacgg tgatcccacc   3300
aatggaggga aatgtcagcc atgcaagtgc aatgggcacg cgtctctgtg caacaccaac   3360
acgggcaagt gcttctgcac caccaagggc gtcaaggggg acgagtgcca gctatgtgag   3420
gtagaaaatc gataccaagg aaaccctctc agaggaacat gttattatac tcttcttatt   3480
gactatcagt tcacctttag tctatcccag gaagatgatc gctattacac agctatcaat   3540
```

-continued

```
tttgtggcta ctcctgacga acaaaacagg gatttggaca tgttcatcaa tgcctccaag   3600
aatttcaacc tcaacatcac ctgggctgcc agtttctcag ctggaaccca ggctggagaa   3660
gagatgcctg ttgtttcaaa aaccaacatt aaggagtaca aagatagttt ctctaatgag   3720
aagtttgatt ttcgcaacca cccaaatatc actttctttg tttatgtcag taatttcacc   3780
tggcccatca aaattcagat tgccttctct cagcacagca attttatgga cctggtacag   3840
ttcttcgtga ctttcttcag ttgtttcctc tctttgctcc tggtggctgc tgtggtttgg   3900
aagatcaaac aaagttgttg ggcctccaga cgtagagagc aacttcttcg agagatgcaa   3960
cagatggcca gccgtccctt tgcctctgta aatgtcgcct tggaaacaga tgaggagcct   4020
cctgatctta ttggggggag tataaagact gttcccaaac ccattgcact ggagccgtgt   4080
tttggcaaca aagccgctgt cctctctgtg tttgtgaggc tccctcgagg cctgggtggc   4140
atccctcctc ctgggcagtc aggtcttgct gtggccagcg ccctggtgga catttctcag   4200
cagatgccga tagtgtacaa ggagaagtca ggagccgtga gaaaccggaa gcagcagccc   4260
cctgcacagc ctgggacctg catctgatgc tggggccagg gactctccca cgcacgagct   4320
agtgagtggc acaccagagc catctgcagg gaagggcgtg gcggggaaat ggctgtgcgg   4380
tgcgggacgg aagactggaa accctcaaag catctgactc acctgcatga tcacaagctt   4440
tctttgacgg tttctcccat ccgtgttcca gcatctaacc ttttactttt gcataggaaa   4500
tacttgattt aattacaggt ccagggatga gctgatggtt gctggaggag gccagtgtag   4560
agccagtgag agaactagga atgacactca ggttcactgt ggaaaactgt tcttgggact   4620
gtctcaactg tgcaaaaaac aaaagatgga gtgtttacaa gtagacattc gtcatcagtt   4680
gttcttgaac atggtctttt aaaaactagt cagatgaatt aacttgtttt catctgaagc   4740
ctgctatctt ttttaaaaga tgtgctattt attcttgcac gatttaggca attatctctc   4800
ttccagggag tacctttttt tctagttgag aattaataat ggtccatctc ttttgatcat   4860
atcaagctag gatagaaggg gggctatttt aaatgtcaag gtcagcagtg ttactttgaa   4920
tgtaaactgg tataataggt agttttctat agtaacttga ttaatttagt cttaatccat   4980
ttgaaactct ctcttccttt ctctctgcct gtccctctcc ttctccatct caccctccct   5040
ctctcacaca tacacacaca aacacataca cacaacacta agtgcctaga ctttaaatag   5100
atctagcaat tggaaagtta gtaagcctaa gtttttacat aattgcattc ctacattctt   5160
gtaaaattta aatagctacc attggcaatc tgcttttttt ctaaaatctg atttgcagcc   5220
aggaaagaat tttctcaccc aaggaacatt tgatctagca gcagggatga gaggaaagca   5280
gaaatgaatg aactgtgaaa gctcctgttt ttattatcaa aaaggacact gtcaagaagg   5340
cgccccctgc ccccaccccc gtgtcaccct aggcctgata agcgatcaga ggaaaggact   5400
cattcatgtc acgcttcctt gagcagaaaa gagcactgag agcacttggg acccctggat   5460
cagagagcat ctgtgtgtcc tgcagcctcc tctgaacttg tggttcattc tcaggctggg   5520
gtggactcag atgccaggaa agggacagcc tcccattgtc aggcagaagc tgcccaaagc   5580
ctggagaagg acttgtttgc cctctttccc ccaggagggg ctcgacccac ccaccctccc   5640
tctcagacca aggtggtggc tgtgaggagg gcagcaaatg ctgacaagga tgaaaagcac   5700
atggaaaaaa atggacgagg agggaaaact ctgccaaatg gaaaatgacc aaatttaaga   5760
gggtgggaca gtcccctgct cctctcccag agggcactgc ttggaaattg tgttttcccc   5820
atttatggtg ctctgtattc tggcattatg cagcagcctc ccagaagctc tcttctgctt   5880
caaaacctgg gatctctggc attaccctat tgggatggac cgctggacag caatgctcga   5940
```

-continued

```
gtttgtgaat ttggagagat actcaaaaga gctaaaactg cagcatttta cctttaaatg   6000
cagtgcctag agagagagta ttgtctcttc cccaacacta accccactcc catgaagaat   6060
tgcctggaaa gatgttttca aggaatttga accataaaac actatctgat gcacagaaca   6120
cctctacttt gagactcacc tctcataaag cttctttttc acattactgt taaagaccag   6180
acgttctaga aaagacccct cctctcatga gctcccccat ccctgctaca gaacacagca   6240
cccatggcgc ctgcagtgga ctggcccctt aattcccaca ggccccccca gcaaggccaa   6300
agggaggccc ctgggtattg tcctcctaca aggaagatcc tctttgtttg ttcaaaggac   6360
cagttttcct aggccaaaga agtctcttcc ccatgttagt cctatgcctt gaaatatcat   6420
gcaccatgac ccacagccat ctggttatgt cttatttttt tcctaaaaga taatgtttat   6480
ttttaaaaag gaaggaagaa gcaagtgaag tttcattctg ctccagcggt ggggaagccg   6540
ctgaatccac ctgcttctcc tttgcaaccg acagcaaaca gctttctccg gcctcagggc   6600
agaaaaaggg aatggcaggg agtaagaggc gctgggctcg gagcctgttt ccaagaagga   6660
attggttgtc atctggcagt gttgcgcgtc acaagagagc ctgtatataa attaaaatag   6720
tcaagacaac actgaccttg cacttgtaca taactataca gtagtgtcca gaatgttcag   6780
acattcggag tgtacataaa acagaaaaaa tcttcatgta tttttattaa atataacaat   6840
gtctgagttt cacctaagat gtttttgtgc catatgctgg atatccaggt tctcgccagg   6900
ccccgataca tgaataacaa acccaagaaa cgcatcccca ttgtgtgatg tgttcagatg   6960
catctggcac caattaggta tttcttaaaa caggactcat ctgtcagagt gcacatgaaa   7020
aatcaggcag ggaatcgaaa cgacagcgct ggaggagact caggaagcag aggcgtccct   7080
gccgctgccc ttggccctgc aagcacatca tgaccctttc tggcagcctc ttggtgctct   7140
gggtagtgag ggatgaccag tcttgtcctg agaaatgttt ctcttagtct ttaagttcaa   7200
agactaacct gtagcaatca gactttccaa aaggggggttc tccatttttt gtagttttgt   7260
ctaaattttt aatgaccatt tcctggaatc agtttattat actgaaaact gggggtggga   7320
gtagggagct agtttgttga taaatagttc ccatttcccc gtggagaatt tgacataccc   7380
tggactcctg tgtgcctcct gccatccctg cacacagcct ggggagaagc ctgtgcctcc   7440
ccgtgtggag agaaggcaac cccagatccc ctgagctaac ccggaggaaa ggcagtcctg   7500
gacagaagac tgtcagcaga aggaaagtac tggactaccc gtgggtaagt cctgccattc   7560
aagactggag acacctggga aataaaaaga gcagggcact gctggtggga agaggcattt   7620
taccttccag tgcaaatcct gctcctttga tttaatgggg tgtactgggg ccaggggctg   7680
attcacttcc ttgggagatg gtggtgtttt catgaacatc tttgatcctt ccatttcatt   7740
tattcatcca tccattcaac aagtatttgc taaacactaa cttaagctaa tgctagggta   7800
gtgactgaga tgtaaaaata gattttagaa ttaaaacaaa atccaagtcc tcacacccct   7860
gtcatcccag gagatctttc cttgtggtgg tttctgtgag aattggccat cctgaggaca   7920
cagccaggac ggcagaggcc tcctggcctc agggcatgcc ctgcctacct tctgaaatgt   7980
ttaccccatt gaccaaactt ggctccagcc attgcggtgg tttctagata gccaggccca   8040
ccaagagata ttgccccttg atgagagtca aacaccctgc ctacaaggag atgttttgaa   8100
atggagagga aaattggcac ctcatctttt aaaggcagta atggaattga ttttcagtaa   8160
ctgaatttgt gcacaaaaca ttctaaacac tagtgaagcc tgtttcgttg aactaattct   8220
ggctctggaa atgtttttgt tttatagtta tttacgattt cgtttgtttg gattcaagct   8280
```

-continued

```
tagtttgtta atatgtataa tttagcatct attacactca tgtaaatatg gagtaagtat   8340

tgtaaactat ttcattgcgg ggattgtggg tgttatacat acatttagga ctgcaatttt   8400

ttggtatttt ttgtattgta aaataacagc taatttaagc aggaacaaga gaactaaggg   8460

aggtctgtgc attttaaaca caaatgtgaa gaacttgtat ataaacaaaa gtaaatacta   8520

taatacaaac ttccttctga aataaaagta gatctggtaa aaaaaaaaaa agaaaaaaaa   8580

aaaaaaaaa                                                           8589
```

```
<210> SEQ ID NO: 15
<211> LENGTH: 2787
<212> TYPE: PRT
<213> ORGANISM: Homo sapiens

<400> SEQUENCE: 15

Met Val Ala Val Ala Ala Ala Ala Ala Thr Glu Ala Arg Leu Arg Arg
 1               5                  10                  15

Arg Thr Ala Ala Thr Ala Ala Leu Ala Gly Arg Ser Gly Gly Pro His
            20                  25                  30

Arg Pro Cys Thr Ala Thr Gly Ala Trp Arg Pro Gly Pro Arg Ala Arg
        35                  40                  45

Leu Cys Leu Pro Arg Val Leu Ser Arg Ala Leu Pro Pro Pro Pro Leu
    50                  55                  60

Leu Pro Leu Leu Phe Ser Leu Leu Leu Leu Pro Leu Pro Arg Glu Ala
65                  70                  75                  80

Glu Ala Ala Ala Val Ala Ala Ala Val Ser Gly Ser Ala Ala Ala Glu
                85                  90                  95

Ala Lys Glu Cys Asp Arg Pro Cys Val Asn Gly Gly Arg Cys Asn Pro
            100                 105                 110

Gly Thr Gly Gln Cys Val Cys Pro Ala Gly Trp Val Gly Glu Gln Cys
        115                 120                 125

Gln His Cys Gly Gly Arg Phe Arg Leu Thr Gly Ser Ser Gly Phe Val
    130                 135                 140

Thr Asp Gly Pro Gly Asn Tyr Lys Tyr Lys Thr Lys Cys Thr Trp Leu
145                 150                 155                 160

Ile Glu Gly Gln Pro Asn Arg Ile Met Arg Leu Arg Phe Asn His Phe
                165                 170                 175

Ala Thr Glu Cys Ser Trp Asp His Leu Tyr Val Tyr Asp Gly Asp Ser
            180                 185                 190

Ile Tyr Ala Pro Leu Val Ala Ala Phe Ser Gly Leu Ile Val Pro Glu
        195                 200                 205

Arg Asp Gly Asn Glu Thr Val Pro Glu Val Val Ala Thr Ser Gly Tyr
    210                 215                 220

Ala Leu Leu His Phe Phe Ser Asp Ala Ala Tyr Asn Leu Thr Gly Phe
225                 230                 235                 240

Asn Ile Thr Tyr Ser Phe Asp Met Cys Pro Asn Asn Cys Ser Gly Arg
                245                 250                 255

Gly Glu Cys Lys Ile Ser Asn Ser Ser Asp Thr Val Glu Cys Glu Cys
            260                 265                 270

Ser Glu Asn Trp Lys Gly Glu Ala Cys Asp Ile Pro His Cys Thr Asp
        275                 280                 285

Asn Cys Gly Phe Pro His Arg Gly Ile Cys Asn Ser Ser Asp Val Arg
    290                 295                 300

Gly Cys Ser Cys Phe Ser Asp Trp Gln Gly Pro Gly Cys Ser Val Pro
305                 310                 315                 320
```

-continued

```
Val Pro Ala Asn Gln Ser Phe Trp Thr Arg Glu Glu Tyr Ser Asn Leu
                325                 330                 335

Lys Leu Pro Arg Ala Ser His Lys Ala Val Val Asn Gly Asn Ile Met
            340                 345                 350

Trp Val Val Gly Gly Tyr Met Phe Asn His Ser Asp Tyr Asn Met Val
        355                 360                 365

Leu Ala Tyr Asp Leu Ala Ser Arg Glu Trp Leu Pro Leu Asn Arg Ser
    370                 375                 380

Val Asn Asn Val Val Val Arg Tyr Gly His Ser Leu Ala Leu Tyr Lys
385                 390                 395                 400

Asp Lys Ile Tyr Met Tyr Gly Gly Lys Ile Asp Ser Thr Gly Asn Val
                405                 410                 415

Thr Asn Glu Leu Arg Val Phe His Ile His Asn Glu Ser Trp Val Leu
            420                 425                 430

Leu Thr Pro Lys Ala Lys Glu Gln Tyr Ala Val Val Gly His Ser Ala
        435                 440                 445

His Ile Val Thr Leu Lys Asn Gly Arg Val Val Met Leu Val Ile Phe
    450                 455                 460

Gly His Cys Pro Leu Tyr Gly Tyr Ile Ser Asn Val Gln Glu Tyr Asp
465                 470                 475                 480

Leu Asp Lys Asn Thr Trp Ser Ile Leu His Thr Gln Gly Ala Leu Val
                485                 490                 495

Gln Gly Gly Tyr Gly His Ser Ser Val Tyr Asp His Arg Thr Arg Ala
            500                 505                 510

Leu Tyr Val His Gly Gly Tyr Lys Ala Phe Ser Ala Asn Lys Tyr Arg
        515                 520                 525

Leu Ala Asp Asp Leu Tyr Arg Tyr Asp Val Asp Thr Gln Met Trp Thr
    530                 535                 540

Ile Leu Lys Asp Ser Arg Phe Phe Arg Tyr Leu His Thr Ala Val Ile
545                 550                 555                 560

Val Ser Gly Thr Met Leu Val Phe Gly Gly Asn Thr His Asn Asp Thr
                565                 570                 575

Ser Met Ser His Gly Ala Lys Cys Phe Ser Ser Asp Phe Met Ala Tyr
            580                 585                 590

Asp Ile Ala Cys Asp Arg Trp Ser Val Leu Pro Arg Pro Asp Leu His
        595                 600                 605

His Asp Val Asn Arg Phe Gly His Ser Ala Val Leu His Asn Ser Thr
    610                 615                 620

Met Tyr Val Phe Gly Gly Phe Asn Ser Leu Leu Leu Ser Asp Ile Leu
625                 630                 635                 640

Val Phe Thr Ser Glu Gln Cys Asp Ala His Arg Ser Glu Ala Ala Cys
                645                 650                 655

Leu Ala Ala Gly Pro Gly Ile Arg Cys Val Trp Asn Thr Gly Ser Ser
            660                 665                 670

Gln Cys Ile Ser Trp Ala Leu Ala Thr Asp Glu Gln Glu Glu Lys Leu
        675                 680                 685

Lys Ser Glu Cys Phe Ser Lys Arg Thr Leu Asp His Asp Arg Cys Asp
    690                 695                 700

Gln His Thr Asp Cys Tyr Ser Cys Thr Ala Asn Thr Asn Asp Cys His
705                 710                 715                 720

Trp Cys Asn Asp His Cys Val Pro Arg Asn His Ser Cys Ser Glu Gly
                725                 730                 735
```

-continued

```
Gln Ile Ser Ile Phe Arg Tyr Glu Asn Cys Pro Lys Asp Asn Pro Met
            740                 745                 750

Tyr Tyr Cys Asn Lys Lys Thr Ser Cys Arg Ser Cys Ala Leu Asp Gln
        755                 760                 765

Asn Cys Gln Trp Glu Pro Arg Asn Gln Glu Cys Ile Ala Leu Pro Glu
    770                 775                 780

Asn Ile Cys Gly Ile Gly Trp His Leu Val Gly Asn Ser Cys Leu Lys
785                 790                 795                 800

Ile Thr Thr Ala Lys Glu Asn Tyr Asp Asn Ala Lys Leu Phe Cys Arg
                805                 810                 815

Asn His Asn Ala Leu Leu Ala Ser Leu Thr Thr Gln Lys Lys Val Glu
            820                 825                 830

Phe Val Leu Lys Gln Leu Arg Ile Met Gln Ser Ser Gln Ser Met Ser
        835                 840                 845

Lys Leu Thr Leu Thr Pro Trp Val Gly Leu Arg Lys Ile Asn Val Ser
    850                 855                 860

Tyr Trp Cys Trp Glu Asp Met Ser Pro Phe Thr Asn Ser Leu Leu Gln
865                 870                 875                 880

Trp Met Pro Ser Glu Pro Ser Asp Ala Gly Phe Cys Gly Ile Leu Ser
                885                 890                 895

Glu Pro Ser Thr Arg Gly Leu Lys Ala Ala Thr Cys Ile Asn Pro Leu
            900                 905                 910

Asn Gly Ser Val Cys Glu Arg Pro Ala Asn His Ser Ala Lys Gln Cys
        915                 920                 925

Arg Thr Pro Cys Ala Leu Arg Thr Ala Cys Gly Asp Cys Thr Ser Gly
    930                 935                 940

Ser Ser Glu Cys Met Trp Cys Ser Asn Met Lys Gln Cys Val Asp Ser
945                 950                 955                 960

Asn Ala Tyr Val Ala Ser Phe Pro Phe Gly Gln Cys Met Glu Trp Tyr
                965                 970                 975

Thr Met Ser Thr Cys Pro Pro Glu Asn Cys Ser Gly Tyr Cys Thr Cys
            980                 985                 990

Ser His Cys Leu Glu Gln Pro Gly Cys Gly Trp Cys Thr Asp Pro Ser
        995                 1000                1005

Asn Thr Gly Lys Gly Lys Cys Ile Glu Gly Ser Tyr Lys Gly Pro Val
    1010                1015                1020

Lys Met Pro Ser Gln Ala Pro Thr Gly Asn Phe Tyr Pro Gln Pro Leu
1025                1030                1035                1040

Leu Asn Ser Ser Met Cys Leu Glu Asp Ser Arg Tyr Asn Trp Ser Phe
                1045                1050                1055

Ile His Cys Pro Ala Cys Gln Cys Asn Gly His Ser Lys Cys Ile Asn
            1060                1065                1070

Gln Ser Ile Cys Glu Lys Cys Glu Asn Leu Thr Thr Gly Lys His Cys
        1075                1080                1085

Glu Thr Cys Ile Ser Gly Phe Tyr Gly Asp Pro Thr Asn Gly Gly Lys
    1090                1095                1100

Cys Gln Pro Cys Lys Cys Asn Gly His Ala Ser Leu Cys Asn Thr Asn
1105                1110                1115                1120

Thr Gly Lys Cys Phe Cys Thr Thr Lys Gly Val Lys Gly Asp Glu Cys
                1125                1130                1135

Gln Leu Cys Glu Val Glu Asn Arg Tyr Gln Gly Asn Pro Leu Arg Gly
            1140                1145                1150

Thr Cys Tyr Tyr Thr Leu Leu Ile Asp Tyr Gln Phe Thr Phe Ser Leu
```

-continued

```
        1155                1160                1165

Ser Gln Glu Asp Asp Arg Tyr Tyr Thr Ala Ile Asn Phe Val Ala Thr
    1170                1175                1180

Pro Asp Glu Gln Asn Arg Asp Leu Asp Met Phe Ile Asn Ala Ser Lys
1185                1190                1195                1200

Asn Phe Asn Leu Asn Ile Thr Trp Ala Ala Ser Phe Ser Ala Gly Thr
                1205                1210                1215

Gln Ala Gly Glu Glu Met Pro Val Val Ser Lys Thr Asn Ile Lys Glu
            1220                1225                1230

Tyr Lys Asp Ser Phe Ser Asn Glu Lys Phe Asp Phe Arg Asn His Pro
        1235                1240                1245

Asn Ile Thr Phe Phe Val Tyr Val Ser Asn Phe Thr Trp Pro Ile Lys
    1250                1255                1260

Ile Gln Ile Ala Phe Ser Gln His Ser Asn Phe Met Asp Leu Val Gln
1265                1270                1275                1280

Phe Phe Val Thr Phe Phe Ser Cys Phe Leu Ser Leu Leu Leu Val Ala
                1285                1290                1295

Ala Val Val Trp Lys Ile Lys Gln Ser Cys Trp Ala Ser Arg Arg Arg
            1300                1305                1310

Glu Gln Leu Leu Arg Glu Met Gln Gln Met Ala Ser Arg Pro Phe Ala
        1315                1320                1325

Ser Val Asn Val Ala Leu Glu Thr Asp Glu Glu Pro Pro Asp Leu Ile
    1330                1335                1340

Gly Gly Ser Ile Lys Thr Val Pro Lys Pro Ile Ala Leu Glu Pro Cys
1345                1350                1355                1360

Phe Gly Asn Lys Ala Ala Val Leu Ser Val Phe Val Arg Leu Pro Arg
                1365                1370                1375

Gly Leu Gly Gly Ile Pro Pro Pro Gly Gln Ser Gly Leu Ala Val Ala
            1380                1385                1390

Ser Ala Leu Val Asp Ile Ser Gln Gln Met Pro Ile Val Tyr Lys Glu
        1395                1400                1405

Lys Ser Gly Ala Val Arg Asn Arg Lys Gln Gln Pro Pro Ala Gln Pro
    1410                1415                1420

Gly Thr Cys Ile Cys Trp Gly Gln Gly Leu Ser His Ala Arg Ala Ser
1425                1430                1435                1440

Glu Trp His Thr Arg Ala Ile Cys Arg Glu Gly Arg Gly Gly Glu Met
                1445                1450                1455

Ala Val Arg Cys Gly Thr Glu Asp Trp Lys Pro Ser Lys His Leu Thr
            1460                1465                1470

His Leu His Asp His Lys Leu Ser Leu Thr Val Ser Pro Ile Arg Val
        1475                1480                1485

Pro Ala Ser Asn Leu Leu Leu Leu His Arg Lys Tyr Leu Ile Leu Gln
    1490                1495                1500

Val Gln Gly Ala Asp Gly Cys Trp Arg Arg Pro Val Ser Gln Glu Asn
1505                1510                1515                1520

Glu His Ser Gly Ser Leu Trp Lys Thr Val Leu Gly Thr Val Ser Thr
                1525                1530                1535

Val Gln Lys Thr Lys Asp Gly Val Phe Thr Ser Arg His Ser Ser Ser
            1540                1545                1550

Val Val Leu Glu His Gly Leu Leu Lys Thr Ser Gln Met Asn Leu Val
        1555                1560                1565

Phe Ile Ser Leu Leu Ser Phe Leu Lys Asp Val Leu Phe Ile Leu Ala
    1570                1575                1580
```

-continued

```
Arg Phe Arg Gln Leu Ser Leu Phe Gln Gly Val Pro Phe Phe Leu Val
1585                1590                1595                1600

Glu Asn Trp Ser Ile Ser Phe Asp His Ile Lys Leu Gly Lys Gly Gly
                1605                1610                1615

Tyr Phe Lys Cys Gln Gly Gln Gln Cys Tyr Phe Glu Cys Lys Leu Val
            1620                1625                1630

Val Val Phe Tyr Ser Asn Leu Ile Asn Leu Val Leu Ile His Leu Lys
        1635                1640                1645

Leu Ser Leu Pro Phe Ser Leu Pro Val Pro Leu Leu Leu His Leu Thr
    1650                1655                1660

Leu Pro Leu Ser His Ile His Thr Gln Thr His Thr His Asn Thr Lys
1665                1670                1675                1680

Cys Leu Asp Phe Lys Ile Gln Leu Glu Ser Ala Val Phe Thr Leu His
                1685                1690                1695

Ser Tyr Ile Leu Val Lys Phe Lys Leu Pro Leu Ala Ile Cys Phe Phe
            1700                1705                1710

Ser Lys Ile Phe Ala Ala Arg Lys Glu Phe Ser His Pro Arg Asn Ile
        1715                1720                1725

Ser Ser Ser Arg Asp Glu Arg Lys Ala Glu Met Asn Glu Leu Lys Leu
    1730                1735                1740

Leu Phe Leu Leu Ser Lys Arg Thr Leu Ser Arg Arg Arg Pro Leu Pro
1745                1750                1755                1760

Pro Pro Pro Cys His Pro Arg Pro Asp Lys Arg Ser Glu Glu Arg Thr
                1765                1770                1775

His Ser Cys His Ala Ser Leu Ser Arg Lys Glu His Glu His Leu Gly
            1780                1785                1790

Pro Leu Asp Gln Arg Ala Ser Val Cys Pro Ala Ala Ser Ser Glu Leu
        1795                1800                1805

Val Val His Ser Gln Ala Gly Val Asp Ser Asp Ala Arg Lys Gly Thr
    1810                1815                1820

Ala Ser His Cys Gln Ala Glu Ala Ala Gln Ser Leu Glu Lys Asp Leu
1825                1830                1835                1840

Phe Ala Leu Phe Pro Pro Gly Gly Ala Arg Pro Thr His Pro Pro Ser
                1845                1850                1855

Gln Thr Lys Val Val Ala Val Arg Arg Ala Ala Asn Ala Asp Lys Asp
            1860                1865                1870

Glu Lys His Met Glu Lys Asn Gly Arg Gly Gly Lys Thr Leu Pro Asn
        1875                1880                1885

Gly Lys Pro Asn Leu Arg Gly Trp Asp Ser Pro Leu Leu Leu Ser Gln
    1890                1895                1900

Arg Ala Leu Leu Gly Asn Cys Val Phe Pro Ile Tyr Gly Ala Leu Tyr
1905                1910                1915                1920

Ser Gly Ile Met Gln Gln Pro Pro Arg Ser Ser Leu Leu Leu Gln Asn
                1925                1930                1935

Leu Gly Ser Leu Ala Leu Pro Tyr Trp Asp Gly Pro Leu Asp Ser Asn
            1940                1945                1950

Ala Arg Val Cys Glu Phe Gly Glu Ile Leu Lys Arg Ala Lys Thr Ala
        1955                1960                1965

Ala Phe Tyr Leu Met Gln Cys Leu Glu Arg Glu Tyr Cys Leu Phe Pro
    1970                1975                1980

Asn Thr Asn Pro Thr Pro Met Lys Asn Cys Leu Glu Arg Cys Phe Gln
1985                1990                1995                2000
```

-continued

```
Gly Ile Thr Ile Lys His Tyr Leu Met His Arg Thr Pro Leu Leu Asp
                2005                2010                2015

Ser Pro Leu Ile Lys Leu Leu Phe His Ile Thr Val Lys Asp Gln Thr
            2020                2025                2030

Phe Lys Arg Pro Leu Leu Ser Ala Pro Pro Ser Leu Leu Gln Asn Thr
        2035                2040                2045

Ala Pro Met Ala Pro Ala Val Asp Trp Pro Leu Asn Ser His Arg Pro
    2050                2055                2060

Pro Gln Gln Gly Gln Arg Glu Ala Pro Gly Tyr Cys Pro Pro Thr Arg
2065                2070                2075                2080

Lys Ile Leu Phe Val Cys Ser Lys Asp Gln Phe Ser Ala Lys Glu Val
                2085                2090                2095

Ser Ser Pro Cys Ser Tyr Ala Leu Lys Tyr His Ala Pro Pro Thr Ala
            2100                2105                2110

Ile Trp Leu Cys Leu Ile Phe Phe Leu Lys Asp Asn Val Tyr Phe Lys
        2115                2120                2125

Gly Arg Lys Lys Gln Val Lys Phe His Ser Ala Pro Ala Val Gly Lys
    2130                2135                2140

Pro Leu Asn Pro Pro Ala Ser Pro Leu Gln Pro Thr Ala Asn Ser Phe
2145                2150                2155                2160

Leu Arg Pro Gln Gly Arg Lys Arg Glu Trp Gln Gly Val Arg Gly Ala
                2165                2170                2175

Gly Leu Gly Ala Cys Phe Gln Glu Gly Ile Gly Cys His Leu Ala Val
            2180                2185                2190

Leu Arg Val Thr Arg Glu Pro Val Tyr Lys Leu Lys Ser Arg Gln His
        2195                2200                2205

Pro Cys Thr Cys Thr Leu Tyr Ser Ser Val Gln Asn Val Gln Thr Phe
    2210                2215                2220

Gly Val Tyr Ile Lys Gln Lys Lys Ser Ser Cys Ile Phe Ile Lys Tyr
2225                2230                2235                2240

Asn Asn Val Val Ser Pro Lys Met Phe Leu Cys His Met Leu Asp Ile
                2245                2250                2255

Gln Val Leu Ala Arg Pro Arg Tyr Met Asn Asn Lys Pro Lys Lys Arg
            2260                2265                2270

Ile Pro Ile Val Cys Val Gln Met His Leu Ala Pro Ile Arg Tyr Phe
        2275                2280                2285

Leu Lys Gln Asp Ser Ser Val Arg Val His Met Lys Asn Gln Ala Gly
    2290                2295                2300

Asn Arg Asn Asp Ser Ala Gly Gly Asp Ser Gly Ser Arg Gly Val Pro
2305                2310                2315                2320

Ala Ala Ala Leu Gly Pro Ala Ser Thr Ser Pro Phe Leu Ala Ala Ser
                2325                2330                2335

Trp Cys Ser Gly Gly Met Thr Ser Leu Val Leu Arg Asn Val Ser Leu
            2340                2345                2350

Ser Leu Val Gln Arg Leu Thr Cys Ser Asn Gln Thr Phe Gln Lys Gly
        2355                2360                2365

Val Leu His Phe Leu Phe Cys Leu Asn Phe Pro Phe Pro Gly Ile Ser
    2370                2375                2380

Leu Leu Tyr Lys Leu Gly Val Gly Val Gly Ser Phe Val Asp Lys Phe
2385                2390                2395                2400

Pro Phe Pro Arg Gly Glu Phe Asp Ile Pro Trp Thr Pro Val Cys Leu
                2405                2410                2415

Leu Pro Ser Leu His Thr Ala Trp Gly Glu Ala Cys Ala Ser Pro Cys
```

-continued

```
            2420                2425                2430

Gly Glu Lys Ala Thr Pro Asp Pro Leu Ser Pro Gly Gly Lys Ala Val
        2435                2440                2445

Leu Asp Arg Arg Leu Ser Ala Glu Gly Lys Tyr Trp Thr Thr Arg Gly
    2450                2455                2460

Val Leu Pro Phe Lys Thr Gly Asp Thr Trp Glu Ile Lys Arg Ala Gly
2465                2470                2475                2480

His Cys Trp Trp Glu Glu Ala Phe Tyr Leu Pro Val Gln Ile Leu Leu
                2485                2490                2495

Leu Phe Asn Gly Val Tyr Trp Gly Gln Gly Leu Ile His Phe Leu Gly
            2500                2505                2510

Arg Trp Trp Cys Phe His Glu His Leu Ser Phe His Phe Ile Tyr Ser
        2515                2520                2525

Ser Ile His Ser Thr Ser Ile Cys Thr Leu Thr Ala Asn Ala Arg Val
    2530                2535                2540

Val Thr Glu Met Lys Ile Leu Glu Leu Lys Gln Asn Pro Ser Pro His
2545                2550                2555                2560

Thr Pro Val Ile Pro Gly Asp Leu Ser Leu Trp Trp Phe Leu Glu Leu
                2565                2570                2575

Ala Ile Leu Arg Thr Gln Pro Gly Arg Gln Arg Pro Pro Gly Leu Arg
            2580                2585                2590

Ala Cys Pro Ala Tyr Leu Leu Lys Cys Leu Pro His Pro Asn Leu Ala
        2595                2600                2605

Pro Ala Ile Ala Val Val Ser Arg Pro Gly Pro Pro Arg Asp Ile Ala
    2610                2615                2620

Pro Glu Ser Asn Thr Leu Pro Thr Arg Arg Cys Phe Glu Met Glu Arg
2625                2630                2635                2640

Lys Ile Gly Thr Ser Ser Phe Lys Gly Ser Asn Gly Ile Asp Phe Gln
                2645                2650                2655

Leu Asn Leu Cys Thr Lys His Ser Lys His Ser Leu Phe Arg Thr Asn
            2660                2665                2670

Ser Gly Ser Gly Asn Val Phe Val Leu Leu Phe Thr Ile Ser Phe Val
        2675                2680                2685

Trp Ile Gln Ala Phe Val Asn Met Tyr Asn Leu Ala Ser Ile Thr Leu
    2690                2695                2700

Met Ile Trp Ser Lys Tyr Cys Lys Leu Phe His Cys Gly Asp Cys Gly
2705                2710                2715                2720

Cys Tyr Thr Tyr Ile Asp Cys Asn Phe Leu Val Phe Phe Val Leu Asn
                2725                2730                2735

Asn Ser Phe Lys Gln Glu Gln Glu Asn Gly Arg Ser Val His Phe Lys
            2740                2745                2750

His Lys Cys Glu Glu Leu Val Tyr Lys Gln Lys Ile Leu Tyr Lys Leu
        2755                2760                2765

Pro Ser Glu Ile Lys Val Asp Leu Val Lys Lys Lys Lys Glu Lys Lys
    2770                2775                2780

Lys Lys Lys
2785
```

<210> SEQ ID NO: 16
<211> LENGTH: 4072
<212> TYPE: DNA
<213> ORGANISM: Homo sapiens

<400> SEQUENCE: 16

-continued

```
atggtggcgg tggccgcagc ggcggcaact gaggcaaggc tgaggaggag gacggcggcg      60
acggcagcgc tcgcgggcag gagcggcggg ccgcaccgac cctgcaccgc gacaggggcc     120
tggaggccgg gaccgcgcgc ccggctgtgt ctcccgcggg tgctgtcgcg ggcgctgccc     180
ccgccgccgc tgctgccgct gctcttttcg ctgctgctgc tgccgctgcc ccgggaggcc     240
gaggccgctg cggtggcggc ggcggtgtcc ggctcggccg cagccgaggc caaggaatgt     300
gaccggccgt gtgtcaacgg cggtcgctgc aaccctggca ccggccagtg cgtctgcccc     360
gccggctggg tgggcgagca atgccagcac tgcgggggcc gcttcagact aactggatct     420
tctgggtttg tgacagatgg acctggaaat tataaataca aaacgaagtg cacgtggctc     480
attgaaggac agccaaatag aataatgaga cttcgtttca atcattttgc tacagagtgt     540
agttgggacc atttatatgt ttatgatggg gactcaattt atgcaccgct agttgctgca     600
tttagtggcc tcattgttcc tgagagagat ggcaatgaga ctgtccctga ggttgttgcc     660
acatcaggtt atgccttgct gcattttttt agtgatgctg cttataattt gactggattt     720
aatattactt acagttttga tatgtgtcca aataactgct caggccgagg agagtgtaag     780
atcagtaata gcagcgatac tgttgaatgt gaatgttctg aaaactggaa aggtgaagca     840
tgtgacattc ctcactgtac agacaactgt ggttttcctc atcgaggcat ctgcaattca     900
agtgatgtca gaggatgctc ctgcttctca gactggcagg gtcctggatg ttcagttcct     960
gtaccagcta accagtcatt ttggactcga gaggaatatt ctaacttaaa gctccccaga    1020
gcatctcata aagctgtggt caatggaaac attatgtggg ttgttggagg atatatgttc    1080
aaccactcag attataacat ggttctagcg tatgaccttg cttctaggga gtggcttcca    1140
ctaaaccgtt ctgtgaacaa tgtggttgtt agatatggtc attctttggc attatacaag    1200
gataaaattt acatgtatgg aggaaaaatt gattcaactg ggaatgtgac caatgagttg    1260
agagtttttc acattcataa tgagtcatgg gtgttgttga cccctaaggc aaaggagcag    1320
tatgcagtgg ttgggcactc tgcacacatt gttacactga agaatggccg agtggtcatg    1380
ctggtcatct ttggtcactg ccctctctat ggatatataa gcaatgtgca ggaatatgat    1440
ttggataaga acacatggag tatattacac acccagggtg cccttgtgca agggggttac    1500
ggccatagca gtgtttacga ccataggacc agggccctat acgttcatgg tggctacaag    1560
gctttcagtg ccaataagta ccggcttgca gatgatctct accgatatga tgtggatacc    1620
cagatgtgga ccattcttaa ggacagccga tttttccgtt acttgcacac agctgtgata    1680
gtgagtggaa ccatgctggt gtttggggga aacacacaca atgacacatc tatgagccat    1740
ggcgccaaat gcttctcttc agatttcatg gcctatgaca ttgcctgtga ccgctggtca    1800
gtgcttccca gacctgatct ccaccatgat gtcaacagat ttggccattc agcagtctta    1860
cacaacagca ccatgtatgt gttcggtggt ttcaatagtc tcctcctcag cgacatcctg    1920
gtattcacct cggaacagtg tgatgcgcat cggagtgaag ccgcttgttt agcagcagga    1980
cctggtattc ggtgtgtgtg gaacacaggg tcgtctcagt gtatctcgtg ggcgctggca    2040
actgatgaac aagaagaaaa gttaaaatca gaatgttttt ccaaaagaac tcttgaccat    2100
gacagatgtg accagcacac agattgttac agctgcacag ccaacaccaa tgactgccac    2160
tggtgcaatg accattgtgt ccccaggaac cacagctgct cagaaggcca gatctccatt    2220
tttaggtatg agaattgccc caaggataac cctatgtact actgtaacaa gaagaccagc    2280
tgcaggagct gtgccctgga ccagaactgc cagtgggagc cccggaatca ggagtgcatt    2340
gccctgcccg aaaatatctg tggcattggc tggcatttgg ttggaaactc atgtttgaaa    2400
```

-continued

```
attactactg ccaaggagaa ttatgacaat gctaaattgt tctgtaggaa ccacaatgcc   2460

cttttggctt ctcttacaac ccagaagaag gtagaatttg tccttaagca gctgcgaata   2520

atgcagtcat ctcagagcat gtccaagctc accttaaccc catgggtcgg ccttcggaag   2580

atcaatgtgt cctactggtg ctgggaagat atgtccccat ttacaaatag tttactacag   2640

tggatgccgt ctgagcccag tgatgctgga ttctgtggaa ttttatcaga acccagtact   2700

cggggactga aggctgcaac ctgcatcaac ccactcaatg gtagtgtctg tgaaaggcct   2760

gcaaaccaca gtgctaagca gtgccggaca ccatgtgcct tgaggacagc atgtggagat   2820

tgcaccagcg gcagctctga gtgcatgtgg tgcagcaaca tgaagcagtg tgtggactcc   2880

aatgcctatg tggcctcctt ccctttttggc cagtgtatgg aatggtatac gatgagcacc   2940

tgcccccctg aaaattgttc aggctactgt acctgtagtc attgcttgga gcaaccaggc   3000

tgtggctggt gtactgatcc cagcaatact ggcaaaggga aatgcataga gggttcctat   3060

aaaggaccag tgaagatgcc ttcgcaagcc cctacaggaa atttctatcc acagcccctg   3120

ctcaattcca gcatgtgtct agaggacagc agatacaact ggtctttcat tcactgtcca   3180

gcttgccaat gcaacggcca cagtaaatgc atcaatcaga gcatctgtga gaagtgtgag   3240

aacctgacca caggcaagca ctgcgagacc tgcatatctg gcttctacgg tgatcccacc   3300

aatggaggga aatgtcagcc atgcaagtgc aatgggcacg cgtctctgtg caacaccaac   3360

acgggcaagt gcttctgcac caccaagggc gtcaaggggg acgagtgcca gctatgtgag   3420

gtagaaaatc gataccaagg aaaccctctc agaggaacat gttattatac tcttcttatt   3480

gactatcagt tcacctttag tctatcccag gaagatgatc gctattacac agctatcaat   3540

tttgtggcta ctcctgacga acaaaacagg gatttggaca tgttcatcaa tgcctccaag   3600

aatttcaacc tcaacatcac ctgggctgcc agtttctcag ctggaaccca ggctggagaa   3660

gagatgcctg ttgtttcaaa aaccaacatt aaggagtaca aagatagttt ctctaatgag   3720

aagtttgatt ttcgcaacca cccaaatatc actttctttg tttatgtcag taatttcacc   3780

tggcccatca aaattcaggt gcaaactgaa caatgaggac gcatggacac aggaagggga   3840

acatcacaca ccagggcctg ttgtggggtg gggggaaggg gaagggatag cattagggga   3900

tatacctaat gttaaatgac gagttaatgg gtgcagcaca ccaacatggc atatgtatac   3960

atatgtaaca aacctgcatg ttgtgcacat gtaccctaaa acttaaagta taattaaaaa   4020

aaaaaaaaga aaaaaaaaaa aaaaaaaaaa aaaaaaaaaa aaaaaaaaaa aa           4072
```

<210> SEQ ID NO: 17
<211> LENGTH: 1350
<212> TYPE: PRT
<213> ORGANISM: Homo sapiens

<400> SEQUENCE: 17

```
Met Val Ala Ala Ala Ala Ala Thr Glu Ala Arg Leu Arg Arg Arg Thr
 1               5                  10                  15

Ala Ala Thr Ala Ala Leu Ala Gly Arg Ser Gly Gly Pro His Trp Asp
            20                  25                  30

Trp Asp Val Thr Arg Ala Gly Arg Pro Gly Leu Gly Ala Gly Leu Arg
        35                  40                  45

Leu Pro Arg Leu Leu Ser Pro Pro Leu Arg Pro Arg Leu Leu Leu Leu
    50                  55                  60

Leu Leu Leu Leu Pro Pro Pro Leu Leu Leu Leu Leu Leu Pro Cys Glu
65                  70                  75                  80
```

-continued

```
Ala Glu Ala Ala Ala Ala Ala Ala Ala Val Ser Gly Ser Ala Ala Ala
                85                  90                  95

Glu Ala Lys Glu Cys Asp Arg Pro Cys Val Asn Gly Gly Arg Cys Asn
            100                 105                 110

Pro Gly Thr Gly Gln Cys Val Cys Pro Ala Gly Trp Val Gly Glu Gln
        115                 120                 125

Cys Gln His Cys Gly Gly Arg Phe Arg Leu Thr Gly Ser Ser Gly Phe
    130                 135                 140

Val Thr Asp Gly Pro Gly Asn Tyr Lys Tyr Lys Thr Lys Cys Thr Trp
145                 150                 155                 160

Leu Ile Glu Gly Gln Pro Asn Arg Ile Met Arg Leu Arg Phe Asn His
                165                 170                 175

Phe Ala Thr Glu Cys Ser Trp Asp His Leu Tyr Val Tyr Asp Gly Asp
            180                 185                 190

Ser Ile Tyr Ala Pro Leu Val Ala Ala Phe Ser Gly Leu Ile Val Pro
        195                 200                 205

Glu Arg Asp Gly Asn Glu Thr Val Pro Glu Val Val Ala Thr Ser Gly
    210                 215                 220

Tyr Ala Leu Leu His Phe Phe Ser Asp Ala Ala Tyr Asn Leu Thr Gly
225                 230                 235                 240

Phe Asn Ile Thr Tyr Ser Phe Asp Met Cys Pro Asn Asn Cys Ser Gly
                245                 250                 255

Arg Gly Glu Cys Lys Ile Ser Asn Ser Ser Thr Val Glu Cys Glu Cys
            260                 265                 270

Ser Glu Asn Trp Lys Gly Glu Ala Cys Asp Ile Pro His Cys Thr Asp
        275                 280                 285

Asn Cys Gly Phe Pro His Arg Gly Ile Cys Asn Ser Ser Asp Val Arg
    290                 295                 300

Gly Cys Ser Cys Phe Ser Asp Trp Gln Gly Pro Gly Cys Ser Val Pro
305                 310                 315                 320

Val Pro Ala Asn Gln Ser Phe Trp Thr Arg Glu Glu Tyr Ser Asn Leu
                325                 330                 335

Lys Leu Pro Arg Ala Ser His Lys Ala Val Val Asn Gly Asn Ile Met
            340                 345                 350

Trp Val Val Gly Gly Tyr Met Phe Asn His Ser Asp Tyr Asn Met Val
        355                 360                 365

Leu Ala Tyr Asp Leu Ala Ser Arg Glu Trp Leu Pro Leu Asn Arg Ser
    370                 375                 380

Val Asn Asn Val Val Val Arg Tyr Gly His Ser Leu Ala Leu Tyr Lys
385                 390                 395                 400

Asp Lys Ile Tyr Met Tyr Gly Gly Lys Ile Asp Thr Gly Asn Val Thr
                405                 410                 415

Asn Glu Leu Arg Val Phe His Ile His Asn Glu Ser Trp Val Leu Leu
            420                 425                 430

Thr Pro Lys Ala Lys Glu Gln Tyr Ala Val Val Gly His Ser Ala His
        435                 440                 445

Ile Val Thr Leu Lys Asn Gly Arg Val Val Met Leu Val Ile Phe Gly
    450                 455                 460

His Cys Pro Leu Tyr Gly Tyr Ile Ser Asn Val Gln Glu Tyr Asp Leu
465                 470                 475                 480

Asp Lys Asn Thr Trp Ser Ile Leu His Thr Gln Gly Ala Leu Val Gln
                485                 490                 495
```

-continued

```
Gly Gly Tyr Gly His Ser Ser Val Tyr Asp His Arg Thr Arg Ala Leu
            500                 505                 510

Tyr Val His Gly Gly Tyr Lys Ala Phe Ser Ala Asn Lys Tyr Arg Leu
        515                 520                 525

Ala Asp Asp Leu Tyr Arg Tyr Asp Val Asp Thr Gln Met Trp Thr Ile
    530                 535                 540

Leu Lys Asp Ser Arg Phe Phe Arg Tyr Leu His Thr Ala Val Ile Val
545                 550                 555                 560

Ser Gly Thr Met Leu Val Phe Gly Gly Asn Thr His Asn Asp Thr Ser
                565                 570                 575

Met Ser His Gly Ala Lys Cys Phe Ser Ser Asp Phe Met Ala Tyr Asp
            580                 585                 590

Ile Ala Cys Asp Arg Trp Ser Val Leu Pro Arg Pro Asp Leu His His
        595                 600                 605

Asp Val Asn Arg Phe Gly His Ser Ala Val Leu His Asn Ser Thr Met
    610                 615                 620

Tyr Val Phe Gly Gly Phe Asn Ser Leu Leu Leu Ser Asp Ile Leu Val
625                 630                 635                 640

Phe Thr Ser Glu Gln Cys Asp Ala His Arg Ser Glu Ala Ala Cys Leu
                645                 650                 655

Ala Ala Gly Pro Gly Ile Arg Cys Val Trp Asn Thr Gly Ser Ser Gln
            660                 665                 670

Cys Ile Ser Trp Ala Leu Ala Thr Asp Glu Gln Glu Glu Lys Leu Lys
        675                 680                 685

Ser Glu Cys Phe Ser Lys Arg Thr Leu Asp His Asp Arg Cys Asp Gln
    690                 695                 700

His Thr Asp Cys Tyr Ser Cys Thr Ala Asn Thr Asn Asp Cys His Trp
705                 710                 715                 720

Cys Asn Asp His Cys Val Pro Arg Asn His Ser Cys Ser Glu Gly Gln
                725                 730                 735

Ile Ser Ile Phe Arg Tyr Glu Asn Cys Pro Lys Asp Asn Pro Met Tyr
            740                 745                 750

Tyr Cys Asn Lys Lys Thr Ser Cys Arg Ser Cys Ala Leu Asp Gln Asn
        755                 760                 765

Cys Gln Trp Glu Pro Arg Asn Gln Glu Cys Ile Ala Leu Pro Glu Asn
    770                 775                 780

Ile Cys Gly Ile Gly Trp His Leu Val Gly Asn Ser Cys Leu Lys Ile
785                 790                 795                 800

Thr Thr Ala Lys Glu Asn Tyr Asp Asn Ala Lys Leu Phe Cys Arg Asn
                805                 810                 815

His Asn Ala Leu Leu Ala Ser Leu Thr Thr Gln Lys Lys Val Glu Phe
            820                 825                 830

Val Leu Lys Gln Leu Arg Ile Met Gln Ser Ser Gln Ser Met Ser Lys
        835                 840                 845

Leu Thr Leu Thr Pro Trp Val Gly Leu Arg Lys Ile Asn Val Ser Tyr
    850                 855                 860

Trp Cys Trp Glu Asp Met Ser Pro Phe Thr Asn Ser Leu Leu Gln Trp
865                 870                 875                 880

Met Pro Ser Glu Pro Ser Asp Ala Gly Phe Cys Gly Ile Leu Ser Glu
                885                 890                 895

Pro Ser Thr Arg Gly Leu Lys Ala Ala Thr Cys Ile Asn Pro Leu Asn
            900                 905                 910

Gly Ser Val Cys Glu Arg Pro Ala Asn His Ser Ala Lys Gln Cys Arg
```

-continued

```
        915                 920                 925

Thr Pro Cys Ala Leu Arg Thr Ala Cys Gly Asp Cys Thr Ser Gly Ser
    930                 935                 940

Ser Glu Cys Met Trp Cys Ser Asn Met Lys Gln Cys Val Asp Ser Asn
945                 950                 955                 960

Ala Tyr Val Ala Ser Phe Pro Phe Gly Gln Cys Met Glu Trp Tyr Thr
                965                 970                 975

Met Ser Thr Cys Pro Pro Glu Asn Cys Ser Gly Tyr Cys Thr Cys Ser
            980                 985                 990

His Cys Leu Glu Gln Pro Gly Cys Gly Trp Cys Thr Asp Pro Ser Asn
        995                 1000                1005

Thr Gly Lys Gly Lys Cys Ile Glu Gly Ser Tyr Lys Gly Pro Val Lys
    1010                1015                1020

Met Pro Ser Gln Ala Pro Thr Gly Asn Phe Tyr Pro Gln Pro Leu Leu
1025                1030                1035                1040

Asn Ser Ser Met Cys Leu Glu Asp Ser Arg Tyr Asn Trp Ser Phe Ile
                1045                1050                1055

His Cys Pro Ala Cys Gln Cys Asn Gly His Ser Lys Cys Ile Asn Gln
            1060                1065                1070

Ser Ile Cys Glu Lys Cys Glu Asn Leu Thr Thr Gly Lys His Cys Glu
        1075                1080                1085

Thr Cys Ile Ser Gly Phe Tyr Gly Asp Pro Thr Asn Gly Gly Lys Cys
    1090                1095                1100

Gln Pro Cys Lys Cys Asn Gly His Ala Ser Leu Cys Asn Thr Asn Thr
1105                1110                1115                1120

Gly Lys Cys Phe Cys Thr Thr Lys Gly Val Lys Gly Asp Glu Cys Gln
                1125                1130                1135

Leu Cys Glu Val Glu Asn Arg Tyr Gln Gly Asn Pro Leu Arg Gly Thr
            1140                1145                1150

Cys Tyr Tyr Thr Leu Leu Ile Asp Tyr Gln Phe Thr Phe Ser Leu Ser
        1155                1160                1165

Gln Glu Asp Asp Arg Tyr Tyr Thr Ala Ile Asn Phe Val Ala Thr Pro
    1170                1175                1180

Asp Glu Gln Asn Arg Asp Leu Asp Met Phe Ile Asn Ala Ser Lys Asn
1185                1190                1195                1200

Phe Asn Leu Asn Ile Thr Trp Ala Ala Ser Phe Ser Ala Gly Thr Gln
                1205                1210                1215

Ala Gly Glu Glu Met Pro Val Val Ser Lys Thr Asn Ile Lys Glu Tyr
            1220                1225                1230

Lys Asp Ser Phe Ser Asn Glu Lys Phe Asp Phe Arg Asn His Pro Asn
        1235                1240                1245

Ile Thr Phe Phe Val Tyr Val Ser Asn Phe Thr Trp Pro Ile Lys Ile
    1250                1255                1260

Gln Val Gln Thr Glu Gln Gly Arg Met Asp Thr Gly Arg Gly Thr Ser
1265                1270                1275                1280

His Thr Arg Ala Cys Cys Gly Val Gly Gly Arg Gly Arg Asp Ser Ile
                1285                1290                1295

Arg Gly Tyr Thr Cys Met Thr Ser Trp Val Gln His Thr Asn Met Ala
            1300                1305                1310

Tyr Val Tyr Ile Cys Asn Lys Pro Ala Cys Cys Ala His Val Pro Asn
        1315                1320                1325

Leu Lys Tyr Asn Lys Lys Lys Lys Lys Lys Lys Lys Lys Lys Lys Lys
    1330                1335                1340
```

-continued

```
Lys Lys Lys Lys Lys Lys
1345                1350

<210> SEQ ID NO: 18
<211> LENGTH: 2625
<212> TYPE: DNA
<213> ORGANISM: Homo sapiens

<400> SEQUENCE: 18

atggtggcgg tggccgcagc ggcggcaact gaggcaaggc tgaggaggag gacggcggcg     60

acggcagcgc tcgcgggcag gagcggcggg ccgcaccgac cctgcaccgc gacaggggcc    120

tggaggccgg gaccgcgcgc ccggctgtgt ctcccgcggg tgctgtcgcg ggcgctgccc    180

ccgccgccgc tgctgccgct gctcttttcg ctgctgctgc tgccgctgcc ccgggaggcc    240

gaggccgctg cggtggcggc ggcggtgtcc ggctcggccg cagccgaggc caaggaatgt    300

gaccggccgt gtgtcaacgg cggtcgctgc aaccctggca ccggccagtg cgtctgcccc    360

gccggctggg tgggcgagca atgccagcac tgcgggggcc gcttcagact aactggatct    420

tctgggtttg tgacagatgg acctggaaat tataaataca aaacgaagtg cacgtggctc    480

attgaaggac agccaaatag aataatgaga cttcgtttca atcattttgc tacagagtgt    540

agttgggacc atttatatgt ttatgatggg gactcaattt atgcaccgct agttgctgca    600

tttagtggcc tcattgttcc tgagagagat ggcaatgaga ctgtccctga ggttgttgcc    660

acatcaggtt atgccttgct gcattttttt agtgatgctg cttataattt gactggattt    720

aatattactt acagttttga tatgtgtcca aataactgct caggccgagg agagtgtaag    780

atcagtaata gcagcgatac tgttgaatgt gaatgttctg aaaactggaa aggtgaagca    840

tgtgacattc ctcactgtac agacaactgt ggttttcctc atcgaggcat ctgcaattca    900

agtgatgtca gaggatgctc ctgcttctca gactggcagg gtcctggatg ttcagttcct    960

gtaccagcta accagtcatt ttggactcga gaggaatatt ctaacttaaa gctccccaga   1020

gcatctcata aagctgtggt caatggaaac attatgtggg ttgttggagg atatatgttc   1080

aaccactcag attataacat ggttctagcg tatgaccttg cttctaggga gtggcttcca   1140

ctaaaccgtt ctgtgaacaa tgtggttgtt agatatggtc attctttggc attatacaag   1200

gataaaattt acatgtatgg aggaaaaatt gattcaactg ggaatgtgac caatgagttg   1260

agagtttttc acattcataa tgagtcatgg gtgttgttga cccctaaggc aaaggagcag   1320

tatgcagtgg ttgggcactc tgcacacatt gttacactga agaatggccg agtggtcatg   1380

ctggtcatct ttggtcactg ccctctctat ggatatataa gcaatgtgca ggaatatgat   1440

ttggataaga acacatggag tatattacac acccagggtg cccttgtgca aggggggttac  1500

ggccatagca gtgtttacga ccataggacc agggccctat acgttcatgg tggctacaag   1560

gctttcagtg ccaataagta ccggcttgca gatgatctct accgatatga tgtggatacc   1620

cagatgtgga ccattcttaa ggacagccga tttttccgtt acttgcacac agctgtgata   1680

gtgagtggaa ccatgctggt gtttgggggga aacacacaca atgacacatc tatgagccat  1740

ggcgccaaat gcttctcttc agatttcatg gcctatgaca ttgcctgtga ccgctggtca   1800

gtgcttccca gacctgatct ccaccatgat gtcaacagat ttggccattc agcagtctta   1860

cacaacagca ccatgtatgt gttcggtggt ttcaatagtc tcctcctcag cgacatcctg   1920

gtattcacct cggaacagtg tgatgcgcat cggagtgaag ccgcttgttt agcagcagga   1980

cctggtattc ggtgtgtgtg gaacacaggg tcgtctcagt gtatctcgtg ggcgctggca   2040
```

-continued

```
actgatgaac aagaagaaaa gttaaaatca gaatgttttt ccaaaagaac tcttgaccat   2100

gacagatgtg accagcacac agattgttac agctgcacag ccaacaccaa tgactgccac   2160

tggtgcaatg accattgtgt ccccaggaac cacagctgct cagaaggcca gatctccatt   2220

tttaggtatg agaattgccc caaggataac cctatgtact actgtaacaa gaagaccagc   2280

tgcaggagct gtgccctgga ccagaactgc cagtgggagc cccggaatca ggagtgcatt   2340

gccctgcccg gtaggccttg cagggtcatc ttggtgtgtg tgggtccatt acttcagcct   2400

gcttccccca acactgtgca gcctaagttg aacctagcag aggggaagag ctaattctgt   2460

ccattcatcc cccacacgag tattatgggc ttttttgttt ttaactaaaa tacagttctt   2520

aagtatttgt tcctactgtc ctttgaaata aagtgaaaca tcctttgctg ctctgtaaaa   2580

aaaaaaaaaa aaaaaaaaaa aaaaaaaaaa aaaaaaaaaa aaaaa                   2625


<210> SEQ ID NO: 19
<211> LENGTH: 871
<212> TYPE: PRT
<213> ORGANISM: Homo sapiens

<400> SEQUENCE: 19

Met Val Ala Ala Ala Ala Ala Thr Glu Ala Arg Leu Arg Arg Arg Thr
 1               5                  10                  15

Ala Ala Thr Ala Ala Leu Ala Gly Arg Ser Gly Gly Pro His Trp Asp
            20                  25                  30

Trp Asp Val Thr Arg Ala Gly Arg Pro Gly Leu Gly Ala Gly Leu Arg
        35                  40                  45

Leu Pro Arg Leu Leu Ser Pro Pro Leu Arg Pro Arg Leu Leu Leu Leu
    50                  55                  60

Leu Leu Leu Leu Pro Pro Pro Leu Leu Leu Leu Leu Leu Pro Cys Glu
65                  70                  75                  80

Ala Glu Ala Ala Ala Ala Ala Ala Ala Val Ser Gly Ser Ala Ala Ala
                85                  90                  95

Glu Ala Lys Glu Cys Asp Arg Pro Cys Val Asn Gly Gly Arg Cys Asn
            100                 105                 110

Pro Gly Thr Gly Gln Cys Val Cys Pro Ala Gly Trp Val Gly Glu Gln
        115                 120                 125

Cys Gln His Cys Gly Gly Arg Phe Arg Leu Thr Gly Ser Ser Gly Phe
    130                 135                 140

Val Thr Asp Gly Pro Gly Asn Tyr Lys Tyr Lys Thr Lys Cys Thr Trp
145                 150                 155                 160

Leu Ile Glu Gly Gln Pro Asn Arg Ile Met Arg Leu Arg Phe Asn His
                165                 170                 175

Phe Ala Thr Glu Cys Ser Trp Asp His Leu Tyr Val Tyr Asp Gly Asp
            180                 185                 190

Ser Ile Tyr Ala Pro Leu Val Ala Ala Phe Ser Gly Leu Ile Val Pro
        195                 200                 205

Glu Arg Asp Gly Asn Glu Thr Val Pro Glu Val Val Ala Thr Ser Gly
    210                 215                 220

Tyr Ala Leu Leu His Phe Phe Ser Asp Ala Ala Tyr Asn Leu Thr Gly
225                 230                 235                 240

Phe Asn Ile Thr Tyr Ser Phe Asp Met Cys Pro Asn Asn Cys Ser Gly
                245                 250                 255

Arg Gly Glu Cys Lys Ile Ser Asn Ser Ser Thr Val Glu Cys Glu Cys
            260                 265                 270
```

-continued

```
Ser Glu Asn Trp Lys Gly Glu Ala Cys Asp Ile Pro His Cys Thr Asp
        275                 280                 285

Asn Cys Gly Phe Pro His Arg Gly Ile Cys Asn Ser Ser Asp Val Arg
    290                 295                 300

Gly Cys Ser Cys Phe Ser Asp Trp Gln Gly Pro Gly Cys Ser Val Pro
305                 310                 315                 320

Val Pro Ala Asn Gln Ser Phe Trp Thr Arg Glu Glu Tyr Ser Asn Leu
                325                 330                 335

Lys Leu Pro Arg Ala Ser His Lys Ala Val Val Asn Gly Asn Ile Met
            340                 345                 350

Trp Val Val Gly Gly Tyr Met Phe Asn His Ser Asp Tyr Asn Met Val
        355                 360                 365

Leu Ala Tyr Asp Leu Ala Ser Arg Glu Trp Leu Pro Leu Asn Arg Ser
    370                 375                 380

Val Asn Asn Val Val Val Arg Tyr Gly His Ser Leu Ala Leu Tyr Lys
385                 390                 395                 400

Asp Lys Ile Tyr Met Tyr Gly Gly Lys Ile Asp Thr Gly Asn Val Thr
                405                 410                 415

Asn Glu Leu Arg Val Phe His Ile His Asn Glu Ser Trp Val Leu Leu
            420                 425                 430

Thr Pro Lys Ala Lys Glu Gln Tyr Ala Val Val Gly His Ser Ala His
        435                 440                 445

Ile Val Thr Leu Lys Asn Gly Arg Val Val Met Leu Val Ile Phe Gly
    450                 455                 460

His Cys Pro Leu Tyr Gly Tyr Ile Ser Asn Val Gln Glu Tyr Asp Leu
465                 470                 475                 480

Asp Lys Asn Thr Trp Ser Ile Leu His Thr Gln Gly Ala Leu Val Gln
                485                 490                 495

Gly Gly Tyr Gly His Ser Ser Val Tyr Asp His Arg Thr Arg Ala Leu
            500                 505                 510

Tyr Val His Gly Gly Tyr Lys Ala Phe Ser Ala Asn Lys Tyr Arg Leu
        515                 520                 525

Ala Asp Asp Leu Tyr Arg Tyr Asp Val Asp Thr Gln Met Trp Thr Ile
    530                 535                 540

Leu Lys Asp Ser Arg Phe Phe Arg Tyr Leu His Thr Ala Val Ile Val
545                 550                 555                 560

Ser Gly Thr Met Leu Val Phe Gly Gly Asn Thr His Asn Asp Thr Ser
                565                 570                 575

Met Ser His Gly Ala Lys Cys Phe Ser Ser Asp Phe Met Ala Tyr Asp
            580                 585                 590

Ile Ala Cys Asp Arg Trp Ser Val Leu Pro Arg Pro Asp Leu His His
        595                 600                 605

Asp Val Asn Arg Phe Gly His Ser Ala Val Leu His Asn Ser Thr Met
    610                 615                 620

Tyr Val Phe Gly Gly Phe Asn Ser Leu Leu Leu Ser Asp Ile Leu Val
625                 630                 635                 640

Phe Thr Ser Glu Gln Cys Asp Ala His Arg Ser Glu Ala Ala Cys Leu
                645                 650                 655

Ala Ala Gly Pro Gly Ile Arg Cys Val Trp Asn Thr Gly Ser Ser Gln
            660                 665                 670

Cys Ile Ser Trp Ala Leu Ala Thr Asp Glu Gln Glu Glu Lys Leu Lys
        675                 680                 685
```

-continued

```
Ser Glu Cys Phe Ser Lys Arg Thr Leu Asp His Asp Arg Cys Asp Gln
    690                 695                 700

His Thr Asp Cys Tyr Ser Cys Thr Ala Asn Thr Asn Asp Cys His Trp
705                 710                 715                 720

Cys Asn Asp His Cys Val Pro Arg Asn His Ser Cys Ser Glu Gly Gln
                725                 730                 735

Ile Ser Ile Phe Arg Tyr Glu Asn Cys Pro Lys Asp Asn Pro Met Tyr
            740                 745                 750

Tyr Cys Asn Lys Lys Thr Ser Cys Arg Ser Cys Ala Leu Asp Gln Asn
        755                 760                 765

Cys Gln Trp Glu Pro Arg Asn Gln Glu Cys Ile Ala Leu Pro Gly Arg
    770                 775                 780

Pro Cys Arg Val Ile Leu Val Cys Val Gly Pro Leu Leu Gln Pro Ala
785                 790                 795                 800

Ser Pro Asn Thr Val Gln Pro Lys Leu Asn Leu Ala Glu Gly Lys Ser
                805                 810                 815

Phe Cys Pro Phe Ile Pro His Thr Ser Ile Met Gly Phe Phe Val Phe
            820                 825                 830

Asn Asn Thr Val Leu Lys Tyr Leu Phe Leu Leu Ser Phe Glu Ile Lys
        835                 840                 845

Asn Ile Leu Cys Cys Ser Val Lys Lys Lys Lys Lys Lys Lys Lys Lys
    850                 855                 860

Lys Lys Lys Lys Lys Lys Lys
865                 870


<210> SEQ ID NO: 20
<211> LENGTH: 26
<212> TYPE: DNA
<213> ORGANISM: Artificial Sequence
<220> FEATURE:
<223> OTHER INFORMATION: Primer

<400> SEQUENCE: 20

tctcctagtt gtagtacatg ctgttg                                            26


<210> SEQ ID NO: 21
<211> LENGTH: 28
<212> TYPE: DNA
<213> ORGANISM: Artificial Sequence

<400> SEQUENCE: 21

aggtcctgtc tcaagaaata gcaataac                                          28


<210> SEQ ID NO: 22
<211> LENGTH: 23
<212> TYPE: DNA
<213> ORGANISM: Artificial Sequence

<400> SEQUENCE: 22

tttgaaggcc cctgaagtca gag                                               23


<210> SEQ ID NO: 23
<211> LENGTH: 29
<212> TYPE: DNA
<213> ORGANISM: Artificial Sequence

<400> SEQUENCE: 23

ttgagtcccc atcataaaca tataaatgg                                         29
```

-continued

<210> SEQ ID NO: 24
<211> LENGTH: 29
<212> TYPE: DNA
<213> ORGANISM: Artificial Sequence

<400> SEQUENCE: 24
ttctaggcca aatagaataa tgagacttc 29

<210> SEQ ID NO: 25
<211> LENGTH: 26
<212> TYPE: DNA
<213> ORGANISM: Artificial Sequence

<400> SEQUENCE: 25
agaactaatt ccatgagatg agtgtg 26

<210> SEQ ID NO: 26
<211> LENGTH: 25
<212> TYPE: DNA
<213> ORGANISM: Artificial Sequence

<400> SEQUENCE: 26
tgaagttgct gtaatctggt ctgtg 25

<210> SEQ ID NO: 27
<211> LENGTH: 22
<212> TYPE: DNA
<213> ORGANISM: Artificial Sequence

<400> SEQUENCE: 27
aaggagcctg actagaagcc tc 22

<210> SEQ ID NO: 28
<211> LENGTH: 27
<212> TYPE: DNA
<213> ORGANISM: Artificial Sequence

<400> SEQUENCE: 28
taaactccct acagttcact aactcag 27

<210> SEQ ID NO: 29
<211> LENGTH: 25
<212> TYPE: DNA
<213> ORGANISM: Artificial Sequence

<400> SEQUENCE: 29
agcgctgttg agtgtgaatg ttctg 25

<210> SEQ ID NO: 30
<211> LENGTH: 26
<212> TYPE: DNA
<213> ORGANISM: Artificial Sequence

<400> SEQUENCE: 30
aaagccacag ttgtctgtac agtgag 26

<210> SEQ ID NO: 31
<211> LENGTH: 25
<212> TYPE: DNA
<213> ORGANISM: Artificial Sequence

<400> SEQUENCE: 31
aggtctgcat tagttgcaat gttgc 25

-continued

<210> SEQ ID NO: 32
<211> LENGTH: 25
<212> TYPE: DNA
<213> ORGANISM: Artificial Sequence

<400> SEQUENCE: 32
tatacacccc cttatataca ctcag 25

<210> SEQ ID NO: 33
<211> LENGTH: 24
<212> TYPE: DNA
<213> ORGANISM: Artificial Sequence

<400> SEQUENCE: 33
agagcctctc ataaagctgt ggtc 24

<210> SEQ ID NO: 34
<211> LENGTH: 25
<212> TYPE: DNA
<213> ORGANISM: Artificial Sequence

<400> SEQUENCE: 34
ttgaacatat atccgccaac aaccc 25

<210> SEQ ID NO: 35
<211> LENGTH: 28
<212> TYPE: DNA
<213> ORGANISM: Artificial Sequence

<400> SEQUENCE: 35
cttggaatac tataaacttt caggctgc 28

<210> SEQ ID NO: 36
<211> LENGTH: 29
<212> TYPE: DNA
<213> ORGANISM: Artificial Sequence

<400> SEQUENCE: 36
taaagcaaca ggaagagttg aacttcttg 29

<210> SEQ ID NO: 37
<211> LENGTH: 20
<212> TYPE: DNA
<213> ORGANISM: Artificial Sequence

<400> SEQUENCE: 37
tgcaccctgt gtgcacatgg 20

<210> SEQ ID NO: 38
<211> LENGTH: 26
<212> TYPE: DNA
<213> ORGANISM: Artificial Sequence

<400> SEQUENCE: 38
ttacggtgtc ctaataataa gggcag 26

<210> SEQ ID NO: 39
<211> LENGTH: 28
<212> TYPE: DNA
<213> ORGANISM: Artificial Sequence

<400> SEQUENCE: 39
aatcatgggt attgttaact ccgaaagc 28

-continued

<210> SEQ ID NO: 40
<211> LENGTH: 24
<212> TYPE: DNA
<213> ORGANISM: Artificial Sequence

<400> SEQUENCE: 40
tgtaacaatg tgtgccgagt gtcc 24

<210> SEQ ID NO: 41
<211> LENGTH: 22
<212> TYPE: DNA
<213> ORGANISM: Artificial Sequence

<400> SEQUENCE: 41
tctctctcca gccctagagt tg 22

<210> SEQ ID NO: 42
<211> LENGTH: 24
<212> TYPE: DNA
<213> ORGANISM: Artificial Sequence

<400> SEQUENCE: 42
agaagaggag cctgcaacat tgac 24

<210> SEQ ID NO: 43
<211> LENGTH: 22
<212> TYPE: DNA
<213> ORGANISM: Artificial Sequence

<400> SEQUENCE: 43
tttgttggcg ctgaaagcct tg 22

<210> SEQ ID NO: 44
<211> LENGTH: 25
<212> TYPE: DNA
<213> ORGANISM: Artificial Sequence

<400> SEQUENCE: 44
tggccacagt agtgtttatg atgac 25

<210> SEQ ID NO: 45
<211> LENGTH: 27
<212> TYPE: DNA
<213> ORGANISM: Artificial Sequence

<400> SEQUENCE: 45
ttaatcaatt gcctctgcag attctag 27

<210> SEQ ID NO: 46
<211> LENGTH: 26
<212> TYPE: DNA
<213> ORGANISM: Artificial Sequence

<400> SEQUENCE: 46
tggcttacgt atagggggaa atcaag 26

<210> SEQ ID NO: 47
<211> LENGTH: 24
<212> TYPE: DNA
<213> ORGANISM: Artificial Sequence

<400> SEQUENCE: 47

-continued ttgtgtgtgt tccctccaaa cacc 24

<210> SEQ ID NO: 48
<211> LENGTH: 24
<212> TYPE: DNA
<213> ORGANISM: Artificial Sequence

<400> SEQUENCE: 48
ggaccattct taaggacagc cgat 24

<210> SEQ ID NO: 49
<211> LENGTH: 26
<212> TYPE: DNA
<213> ORGANISM: Artificial Sequence

<400> SEQUENCE: 49
acatagtgat ctttccatca gcaaag 26

<210> SEQ ID NO: 50
<211> LENGTH: 22
<212> TYPE: DNA
<213> ORGANISM: Artificial Sequence

<400> SEQUENCE: 50
tgaatgcaca gagaccctcc tg 22

<210> SEQ ID NO: 51
<211> LENGTH: 26
<212> TYPE: DNA
<213> ORGANISM: Artificial Sequence

<400> SEQUENCE: 51
cctcttacca ttcagatact gttagg 26

<210> SEQ ID NO: 52
<211> LENGTH: 24
<212> TYPE: DNA
<213> ORGANISM: Artificial Sequence

<400> SEQUENCE: 52
agcaacaact caaaccagcc ctac 24

<210> SEQ ID NO: 53
<211> LENGTH: 23
<212> TYPE: DNA
<213> ORGANISM: Artificial Sequence

<400> SEQUENCE: 53
ttcttcagtt gccaactccc agg 23

<210> SEQ ID NO: 54
<211> LENGTH: 21
<212> TYPE: DNA
<213> ORGANISM: Artificial Sequence

<400> SEQUENCE: 54
aagctgcttg tgtggcagca g 21

<210> SEQ ID NO: 55
<211> LENGTH: 26
<212> TYPE: DNA
<213> ORGANISM: Artificial Sequence

<400> SEQUENCE: 55

-continued agtaaggtga acaggaaagt acagag 26

<210> SEQ ID NO: 56
<211> LENGTH: 24
<212> TYPE: DNA
<213> ORGANISM: Artificial Sequence

<400> SEQUENCE: 56
tacataagag aggctgccgc atag 24

<210> SEQ ID NO: 57
<211> LENGTH: 23
<212> TYPE: DNA
<213> ORGANISM: Artificial Sequence

<400> SEQUENCE: 57
ccctacactc acactcatct agc 23

<210> SEQ ID NO: 58
<211> LENGTH: 23
<212> TYPE: DNA
<213> ORGANISM: Artificial Sequence

<400> SEQUENCE: 58
ccctgtgttc cagatctcca ttg 23

<210> SEQ ID NO: 59
<211> LENGTH: 24
<212> TYPE: DNA
<213> ORGANISM: Artificial Sequence

<400> SEQUENCE: 59
ttcctaggtc caccttgatc tgag 24

<210> SEQ ID NO: 60
<211> LENGTH: 26
<212> TYPE: DNA
<213> ORGANISM: Artificial Sequence

<400> SEQUENCE: 60
agcacctgaa ttcaaatcag gatgag 26

<210> SEQ ID NO: 61
<211> LENGTH: 29
<212> TYPE: DNA
<213> ORGANISM: Artificial Sequence

<400> SEQUENCE: 61
aaaccaaagt tctgaacaca ttaactcac 29

<210> SEQ ID NO: 62
<211> LENGTH: 25
<212> TYPE: DNA
<213> ORGANISM: Artificial Sequence

<400> SEQUENCE: 62
ctggttgcat tcatagctgt gtttc 25

<210> SEQ ID NO: 63
<211> LENGTH: 21
<212> TYPE: DNA
<213> ORGANISM: Artificial Sequence -continued

<400> SEQUENCE: 63
acagaagcca gcatcactgg g 21

<210> SEQ ID NO: 64
<211> LENGTH: 24
<212> TYPE: DNA
<213> ORGANISM: Artificial Sequence

<400> SEQUENCE: 64
ttactggtgc tgggaggata tgtc 24

<210> SEQ ID NO: 65
<211> LENGTH: 26
<212> TYPE: DNA
<213> ORGANISM: Artificial Sequence

<400> SEQUENCE: 65
ataagtactt catcacctca gcgctc 26

<210> SEQ ID NO: 66
<211> LENGTH: 24
<212> TYPE: DNA
<213> ORGANISM: Artificial Sequence

<400> SEQUENCE: 66
ttgatcttag ctgaccagtg tctc 24

<210> SEQ ID NO: 67
<211> LENGTH: 25
<212> TYPE: DNA
<213> ORGANISM: Artificial Sequence

<400> SEQUENCE: 67
tctgcatgga cttgagcaga aagtc 25

<210> SEQ ID NO: 68
<211> LENGTH: 30
<212> TYPE: DNA
<213> ORGANISM: Artificial Sequence

<400> SEQUENCE: 68
caaatcttgt gatagtgaat tacaagttgg 30

<210> SEQ ID NO: 69
<211> LENGTH: 27
<212> TYPE: DNA
<213> ORGANISM: Artificial Sequence

<400> SEQUENCE: 69
tttatagctg ccctcaatac attttcc 27

<210> SEQ ID NO: 70
<211> LENGTH: 22
<212> TYPE: DNA
<213> ORGANISM: Artificial Sequence

<400> SEQUENCE: 70
tgtacctgca gccattgctt gg 22

<210> SEQ ID NO: 71
<211> LENGTH: 25
<212> TYPE: DNA
<213> ORGANISM: Artificial Sequence -continued

<400> SEQUENCE: 71
ggatctgggc tctagtttat gtacg 25

<210> SEQ ID NO: 72
<211> LENGTH: 24
<212> TYPE: DNA
<213> ORGANISM: Artificial Sequence

<400> SEQUENCE: 72
ttgaactata ggcacagaca gctg 24

<210> SEQ ID NO: 73
<211> LENGTH: 23
<212> TYPE: DNA
<213> ORGANISM: Artificial Sequence

<400> SEQUENCE: 73
aacttgacct gtgtgactta cgc 23

<210> SEQ ID NO: 74
<211> LENGTH: 26
<212> TYPE: DNA
<213> ORGANISM: Artificial Sequence

<400> SEQUENCE: 74
tcacagtcta tggtaatctg tcaagc 26

<210> SEQ ID NO: 75
<211> LENGTH: 22
<212> TYPE: DNA
<213> ORGANISM: Artificial Sequence

<400> SEQUENCE: 75
aagggcaaca atgccctggc aa 22

<210> SEQ ID NO: 76
<211> LENGTH: 26
<212> TYPE: DNA
<213> ORGANISM: Artificial Sequence

<400> SEQUENCE: 76
ttcctgcaaa tgggatagtc tctctg 26

<210> SEQ ID NO: 77
<211> LENGTH: 26
<212> TYPE: DNA
<213> ORGANISM: Artificial Sequence

<400> SEQUENCE: 77
atcccccaag catttatcat tctcag 26

<210> SEQ ID NO: 78
<211> LENGTH: 28
<212> TYPE: DNA
<213> ORGANISM: Artificial Sequence

<400> SEQUENCE: 78
tgtgtttcca gaaacctgct ttagtttg 28

<210> SEQ ID NO: 79
<211> LENGTH: 26
<212> TYPE: DNA

-continued

<213> ORGANISM: Artificial Sequence

<400> SEQUENCE: 79
tagtactttt gtccaggatg accaag 26

<210> SEQ ID NO: 80
<211> LENGTH: 30
<212> TYPE: DNA
<213> ORGANISM: Artificial Sequence

<400> SEQUENCE: 80
tgacaagaaa tgtcatgtct taacataagc 30

<210> SEQ ID NO: 81
<211> LENGTH: 22
<212> TYPE: DNA
<213> ORGANISM: Artificial Sequence

<400> SEQUENCE: 81
ttcagagcct ccttccccaa ct 22

<210> SEQ ID NO: 82
<211> LENGTH: 25
<212> TYPE: DNA
<213> ORGANISM: Artificial Sequence

<400> SEQUENCE: 82
tagtctgtag ctgaggccat tttgc 25

<210> SEQ ID NO: 83
<211> LENGTH: 25
<212> TYPE: DNA
<213> ORGANISM: Artificial Sequence

<400> SEQUENCE: 83
aagcaagctg cagttaaggg actgt 25

<210> SEQ ID NO: 84
<211> LENGTH: 23
<212> TYPE: DNA
<213> ORGANISM: Artificial Sequence

<400> SEQUENCE: 84
ttgggacctt gaggattgtt ccc 23

<210> SEQ ID NO: 85
<211> LENGTH: 26
<212> TYPE: DNA
<213> ORGANISM: Artificial Sequence

<400> SEQUENCE: 85
cactcaacag gtaaaagtga tctgcc 26

<210> SEQ ID NO: 86
<211> LENGTH: 27
<212> TYPE: DNA
<213> ORGANISM: Artificial Sequence

<400> SEQUENCE: 86
tgcatctgat cagtttgaat cagagag 27

<210> SEQ ID NO: 87
<211> LENGTH: 26

-continued

<212> TYPE: DNA
<213> ORGANISM: Artificial Sequence

<400> SEQUENCE: 87
aaactgaggc ctgagttctg aaaagc 26

<210> SEQ ID NO: 88
<211> LENGTH: 24
<212> TYPE: DNA
<213> ORGANISM: Artificial Sequence

<400> SEQUENCE: 88
caccaaagct ctgtaccact aagc 24

<210> SEQ ID NO: 89
<211> LENGTH: 21
<212> TYPE: DNA
<213> ORGANISM: Artificial Sequence

<400> SEQUENCE: 89
tgactgtgca gtgatgcagg g 21

<210> SEQ ID NO: 90
<211> LENGTH: 27
<212> TYPE: DNA
<213> ORGANISM: Artificial Sequence

<400> SEQUENCE: 90
ttgaccttga catttagaat agccctc 27

<210> SEQ ID NO: 91
<211> LENGTH: 30
<212> TYPE: DNA
<213> ORGANISM: Artificial Sequence

<400> SEQUENCE: 91
gctgagaatt aataatggtc tttctctttg 30

<210> SEQ ID NO: 92
<211> LENGTH: 22
<212> TYPE: DNA
<213> ORGANISM: Artificial Sequence

<400> SEQUENCE: 92
tacacagtga gaccctgtct cc 22

<210> SEQ ID NO: 93
<211> LENGTH: 22
<212> TYPE: DNA
<213> ORGANISM: Artificial Sequence

<400> SEQUENCE: 93
tagctgaggt cccttgtgga ag 22

<210> SEQ ID NO: 94
<211> LENGTH: 21
<212> TYPE: DNA
<213> ORGANISM: Artificial Sequence

<400> SEQUENCE: 94
agtgtcagag gaccatgctg g 21

<210> SEQ ID NO: 95

-continued

<211> LENGTH: 23
<212> TYPE: DNA
<213> ORGANISM: Artificial Sequence

<400> SEQUENCE: 95
cttgaagcgt ccaactcatg tgc 23

<210> SEQ ID NO: 96
<211> LENGTH: 26
<212> TYPE: DNA
<213> ORGANISM: Artificial Sequence

<400> SEQUENCE: 96
aactcataca tttgagcact gttgcc 26

<210> SEQ ID NO: 97
<211> LENGTH: 23
<212> TYPE: DNA
<213> ORGANISM: Artificial Sequence

<400> SEQUENCE: 97
tgaggaggtg gggaatgcta atg 23

<210> SEQ ID NO: 98
<211> LENGTH: 21
<212> TYPE: DNA
<213> ORGANISM: Artificial Sequence

<400> SEQUENCE: 98
acatagcaga gggctgctca c 21

<210> SEQ ID NO: 99
<211> LENGTH: 21
<212> TYPE: DNA
<213> ORGANISM: Artificial Sequence

<400> SEQUENCE: 99
actgacctgt gggaacctgt g 21

<210> SEQ ID NO: 100
<211> LENGTH: 26
<212> TYPE: DNA
<213> ORGANISM: Artificial Sequence

<400> SEQUENCE: 100
aatgctaggc atcatccctc ttctag 26

<210> SEQ ID NO: 101
<211> LENGTH: 26
<212> TYPE: DNA
<213> ORGANISM: Artificial Sequence

<400> SEQUENCE: 101
aacatctaat agggactgag tgaccc 26

<210> SEQ ID NO: 102
<211> LENGTH: 22
<212> TYPE: DNA
<213> ORGANISM: Artificial Sequence

<400> SEQUENCE: 102
ttctgtggtg ccttggcaag ag 22

-continued

<210> SEQ ID NO: 103
<211> LENGTH: 25
<212> TYPE: DNA
<213> ORGANISM: Artificial Sequence

<400> SEQUENCE: 103
cacacataca cacacactaa gtgcc 25

<210> SEQ ID NO: 104
<211> LENGTH: 32
<212> TYPE: DNA
<213> ORGANISM: Artificial Sequence

<400> SEQUENCE: 104
tggtagttac ttaaagttta caagaatgta gg 32

<210> SEQ ID NO: 105
<211> LENGTH: 28
<212> TYPE: DNA
<213> ORGANISM: Artificial Sequence

<400> SEQUENCE: 105
aaatgctggg ataaaaagca tgaaccac 28

<210> SEQ ID NO: 106
<211> LENGTH: 25
<212> TYPE: DNA
<213> ORGANISM: Artificial Sequence

<400> SEQUENCE: 106
ttcagttacc taatgggcac aaggc 25

<210> SEQ ID NO: 107
<211> LENGTH: 23
<212> TYPE: DNA
<213> ORGANISM: Artificial Sequence

<400> SEQUENCE: 107
acgacactga cctcttgcac ttg 23

<210> SEQ ID NO: 108
<211> LENGTH: 26
<212> TYPE: DNA
<213> ORGANISM: Artificial Sequence

<400> SEQUENCE: 108
tgtacaccct gaatgtctga acattc 26

<210> SEQ ID NO: 109
<211> LENGTH: 25
<212> TYPE: DNA
<213> ORGANISM: Artificial Sequence

<400> SEQUENCE: 109
gcgttcattt ctgctcctgt aatgg 25

<210> SEQ ID NO: 110
<211> LENGTH: 24
<212> TYPE: DNA
<213> ORGANISM: Artificial Sequence

<400> SEQUENCE: 110
tgagctctta atccctgcca ttcc 24

-continued

<210> SEQ ID NO: 111
<211> LENGTH: 22
<212> TYPE: DNA
<213> ORGANISM: Artificial Sequence

<400> SEQUENCE: 111
tagggcttgt ccgtccataa gg 22

<210> SEQ ID NO: 112
<211> LENGTH: 25
<212> TYPE: DNA
<213> ORGANISM: Artificial Sequence

<400> SEQUENCE: 112
tgttacggag atgaaaggct agacc 25

<210> SEQ ID NO: 113
<211> LENGTH: 22
<212> TYPE: DNA
<213> ORGANISM: Artificial Sequence

<400> SEQUENCE: 113
taagccctgc actaacccac tc 22

<210> SEQ ID NO: 114
<211> LENGTH: 25
<212> TYPE: DNA
<213> ORGANISM: Artificial Sequence

<400> SEQUENCE: 114
tgttttgaga ggtgagcctt ctagc 25

<210> SEQ ID NO: 115
<211> LENGTH: 25
<212> TYPE: DNA
<213> ORGANISM: Artificial Sequence

<400> SEQUENCE: 115
catgtcctac agttctgcta tcacc 25

<210> SEQ ID NO: 116
<211> LENGTH: 26
<212> TYPE: DNA
<213> ORGANISM: Artificial Sequence

<400> SEQUENCE: 116
cttttcttca tccaattccc cacgag 26

<210> SEQ ID NO: 117
<211> LENGTH: 24
<212> TYPE: DNA
<213> ORGANISM: Artificial Sequence

<400> SEQUENCE: 117
tctctaagct gcactgttgt ggct 24

<210> SEQ ID NO: 118
<211> LENGTH: 24
<212> TYPE: DNA
<213> ORGANISM: Artificial Sequence

<400> SEQUENCE: 118
tggaagccaa gagtcttgag ttgc 24

<210> SEQ ID NO: 119
<211> LENGTH: 28
<212> TYPE: DNA
<213> ORGANISM: Artificial Sequence

<400> SEQUENCE: 119
gtctgcattt taaatgcaga tgtgaagc 28

<210> SEQ ID NO: 120
<211> LENGTH: 25
<212> TYPE: DNA
<213> ORGANISM: Artificial Sequence

<400> SEQUENCE: 120
cgaaacgcac gcacattttt accag 25

<210> SEQ ID NO: 121
<211> LENGTH: 26
<212> TYPE: DNA
<213> ORGANISM: Artificial Sequence

<400> SEQUENCE: 121
gtgtgattta gcatctgtcg cacttg 26

<210> SEQ ID NO: 122
<211> LENGTH: 26
<212> TYPE: DNA
<213> ORGANISM: Artificial Sequence

<400> SEQUENCE: 122
tgtatgtata acccaacaat cgctgc 26

<210> SEQ ID NO: 123
<211> LENGTH: 26
<212> TYPE: DNA
<213> ORGANISM: Artificial Sequence

<400> SEQUENCE: 123
tccagagtac agggagaaac taaagg 26

<210> SEQ ID NO: 124
<211> LENGTH: 94
<212> TYPE: PRT
<213> ORGANISM: Homo sapiens

<400> SEQUENCE: 124

```
Phe Arg Asn His Pro Asn Ile Thr Phe Phe Val Tyr Val Ser Asn Phe
 1               5                  10                  15

Thr Trp Pro Ile Lys Ile Gln Ile Ala Phe Ser Gln His Ser Asn Phe
            20                  25                  30

Met Asp Leu Val Gln Phe Phe Val Thr Phe Phe Ser Cys Phe Leu Ser
        35                  40                  45

Leu Leu Leu Val Ala Ala Val Val Trp Lys Ile Lys Gln Ser Cys Trp
    50                  55                  60

Ala Ser Arg Arg Arg Glu Gln Leu Leu Arg Glu Met Gln Gln Met Ala
65                  70                  75                  80

Ser Arg Pro Phe Ala Ser Val Glu Thr Leu Pro Trp Asn Arg
                85                  90
```

<210> SEQ ID NO: 125

-continued

<211> LENGTH: 113
<212> TYPE: PRT
<213> ORGANISM: Homo sapiens

<400> SEQUENCE: 125

Phe Arg Ser Asn Pro Asn Ile Thr Phe Tyr Val Tyr Val Ser Asn Phe
1 5 10 15

Ser Trp Pro Ile Lys Ile Gln Ile Ala Phe Ser Gln His Asn Thr Ile
20 25 30

Met Asp Leu Val Gln Phe Phe Val Thr Phe Phe Ser Cys Phe Leu Ser
35 40 45

Leu Leu Leu Val Ala Ala Val Val Trp Lys Ile Lys Gln Thr Cys Trp
50 55 60

Ala Ser Arg Arg Arg Glu Gln Leu Leu Arg Glu Arg Gln Gln Met Ala
65 70 75 80

Ser Arg Pro Phe Ala Ser Val Asp Val Ala Leu Glu Val Gly Ala Glu
85 90 95

Gln Thr Glu Phe Leu Arg Gly Pro Leu Glu Gly Ala Pro Lys Pro Ile
100 105 110

Ala

<210> SEQ ID NO: 126
<211> LENGTH: 100
<212> TYPE: PRT
<213> ORGANISM: Homo sapiens

<400> SEQUENCE: 126

Phe Gly Pro Asp Ser Asn Thr Thr Phe Phe Val Arg Val Tyr Asn Phe
1 5 10 15

Asn Thr Pro Val Gln Ile Val Val Ser Phe Ala Gln Ser Pro Pro Ile
20 25 30

Asn Trp Val Leu Phe Phe Val Ile Phe Ala Ala Cys Phe Ile Val Leu
35 40 45

Leu Val Val Ala Gly Leu Leu Trp Met Ile Lys Val Arg Ile Glu Ala
50 55 60

Tyr Arg Arg Asn Gln Arg Arg Ile Asp Glu Ile Glu His Met Ala Ser
65 70 75 80

Arg Pro Phe Ala Ser Thr Lys Met Glu Leu Ser Met Leu Ser Gln Phe
85 90 95

Ser Ser Ala Gly
100

<210> SEQ ID NO: 127
<211> LENGTH: 118
<212> TYPE: PRT
<213> ORGANISM: Homo sapiens

<400> SEQUENCE: 127

Leu Lys Ser Ser Arg Phe Tyr Leu Leu Leu Leu Gly Val Gly Asp Pro
1 5 10 15

Ser Gly Pro Gly Ala Asn Gly Ser Ala Asp Ser Gln Gly Leu Leu Phe
20 25 30

Phe Arg Gln Asp Gln Ala His Ile Asp Leu Phe Val Phe Phe Ser Val
35 40 45

Phe Phe Ser Cys Phe Phe Leu Phe Leu Ser Leu Cys Val Leu Leu Trp
50 55 60

Lys Ala Lys Gln Ala Leu Asp Gln Arg Gln Glu Gln Arg Arg His Leu

-continued

```
65                  70                  75                  80

Gln Glu Met Thr Lys Met Ala Ser Arg Pro Phe Ala Lys Val Thr Val
                85                  90                  95

Cys Phe Pro Pro Asp Pro Thr Ala Pro Ala Ser Ala Trp Lys Pro Ala
            100                 105                 110

Gly Leu Pro Pro Pro Ala
        115


<210> SEQ ID NO: 128
<211> LENGTH: 11
<212> TYPE: DNA
<213> ORGANISM: Artificial Sequence
<220> FEATURE:
<223> OTHER INFORMATION: Primer

<400> SEQUENCE: 128

ttcctcactg g                                                            11


<210> SEQ ID NO: 129
<211> LENGTH: 10
<212> TYPE: DNA
<213> ORGANISM: Artificial Sequence
<220> FEATURE:
<223> OTHER INFORMATION: Primer

<400> SEQUENCE: 129

ggacacacag                                                              10


<210> SEQ ID NO: 130
<211> LENGTH: 1429
<212> TYPE: PRT
<213> ORGANISM: Homo sapiens
<220> FEATURE:
<221> NAME/KEY: SITE
<222> LOCATION: all Xaa positions
<223> OTHER INFORMATION: Xaa=unknown amino acid

<400> SEQUENCE: 130

Met Val Ala Val Ala Ala Ala Ala Ala Thr Glu Ala Arg Leu Arg Gly
 1               5                  10                  15

Ser Thr Thr Thr Thr Ala Ala Pro Ala Gly Arg Lys Gly Arg Gln His
            20                  25                  30

Arg Pro Cys Thr Ala Thr Gly Ala Trp Arg Pro Gly Pro Arg Ala Arg
        35                  40                  45

Leu Cys Leu Pro Arg Val Leu Ser Arg Ala Leu Pro Pro Pro Pro Leu
    50                  55                  60

Leu Pro Leu Leu Phe Ser Leu Leu Leu Leu Pro Leu Pro Arg Glu Ala
65                  70                  75                  80

Glu Ala Ala Ala Val Ala Ala Ala Val Ser Gly Ser Ala Ala Ala Glu
                85                  90                  95

Ala Lys Glu Cys Asp Arg Pro Cys Val Asn Gly Gly Arg Cys Asn Pro
            100                 105                 110

Gly Thr Gly Gln Cys Val Cys Pro Thr Gly Trp Val Gly Glu Gln Cys
        115                 120                 125

Gln His Cys Gly Gly Arg Phe Arg Leu Thr Gly Ser Ser Gly Phe Val
    130                 135                 140

Thr Asp Gly Pro Gly Asn Tyr Lys Tyr Lys Thr Lys Cys Thr Trp Leu
145                 150                 155                 160

Ile Glu Gly Gln Pro Asn Xaa Ile Met Arg Leu Arg Phe Asn His Phe
                165                 170                 175
```

-continued

```
Ala Thr Glu Cys Ser Trp Asp His Leu Tyr Val Tyr Asp Gly Asp Ser
            180                 185                 190

Ile Tyr Ala Pro Leu Ile Ala Ala Phe Ser Gly Leu Ile Val Pro Glu
        195                 200                 205

Arg Asp Gly Asn Glu Thr Ala Pro Glu Val Thr Ala Thr Ser Gly Tyr
    210                 215                 220

Ala Leu Leu His Phe Phe Ser Asp Ala Ala Tyr Asn Leu Thr Gly Phe
225                 230                 235                 240

Asn Ile Thr Tyr Asn Phe Asp Met Cys Pro Asn Asn Cys Ser Gly Arg
                245                 250                 255

Gly Glu Cys Lys Ser Ser Asn Ser Ser Ser Xaa Val Glu Cys Glu Cys
            260                 265                 270

Ser Glu Asn Trp Lys Gly Xaa Ala Cys Asp Ile Pro His Cys Thr Asp
        275                 280                 285

Asn Cys Gly Phe Pro His Arg Gly Ile Cys Asn Xaa Ser Asp Xaa Arg
    290                 295                 300

Gly Cys Ser Cys Phe Ser Asp Trp Gln Gly Pro Gly Cys Ser Val Pro
305                 310                 315                 320

Val Pro Ala Asn Gln Ser Phe Trp Thr Arg Glu Glu Tyr Ser Asn Leu
                325                 330                 335

Lys Leu Pro Arg Ala Ser His Lys Ala Val Val Asn Gly Asn Ile Met
            340                 345                 350

Trp Val Val Gly Gly Tyr Met Phe Asn His Ser Asp Tyr Asn Met Val
        355                 360                 365

Leu Ala Tyr Asp Leu Ala Ser Arg Glu Trp Leu Pro Leu Asn Arg Ser
    370                 375                 380

Val Asn Asn Val Val Val Arg Tyr Gly His Ser Leu Ala Leu Tyr Lys
385                 390                 395                 400

Asp Lys Ile Tyr Met Tyr Gly Gly Lys Ile Asp Ser Thr Gly Asn Val
                405                 410                 415

Thr Asn Glu Leu Arg Val Phe His Ile His Asn Glu Ser Trp Val Leu
            420                 425                 430

Leu Thr Pro Lys Ala Lys Glu Gln Tyr Ala Val Val Gly His Ser Ala
        435                 440                 445

His Ile Val Thr Leu Lys Asn Gly Arg Val Val Met Leu Val Ile Phe
    450                 455                 460

Gly His Cys Pro Leu Tyr Gly Tyr Ile Ser Asn Val Gln Glu Tyr Asp
465                 470                 475                 480

Leu Asp Lys Asn Thr Trp Ser Ile Leu His Thr Gln Gly Ala Leu Val
                485                 490                 495

Gln Gly Gly Tyr Gly His Ser Ser Val Tyr Asp His Arg Thr Arg Ala
            500                 505                 510

Leu Tyr Val His Gly Gly Tyr Lys Ala Phe Ser Ala Asn Lys Tyr Arg
        515                 520                 525

Leu Ala Asp Asp Leu Tyr Arg Tyr Asp Val Asp Thr Gln Met Trp Thr
    530                 535                 540

Ile Leu Lys Asp Ser Arg Phe Phe Arg Tyr Leu His Thr Ala Val Ile
545                 550                 555                 560

Val Ser Gly Thr Met Leu Val Phe Gly Gly Asn Thr His Asn Asp Thr
                565                 570                 575

Ser Met Ser His Gly Ala Lys Cys Phe Ser Ser Asp Phe Met Ala Tyr
            580                 585                 590
```

-continued

```
Asp Ile Ala Cys Asp Arg Trp Ser Val Leu Pro Arg Pro Asp Leu His
        595                 600                 605

His Asp Val Asn Arg Phe Gly His Ser Ala Val Leu His Asn Ser Thr
    610                 615                 620

Met Tyr Val Phe Gly Gly Phe Asn Ser Leu Leu Leu Ser Asp Ile Leu
625                 630                 635                 640

Val Phe Thr Ser Glu Gln Cys Asp Ala His Arg Ser Glu Ala Ala Cys
                645                 650                 655

Leu Ala Ala Gly Pro Gly Ile Arg Cys Val Trp Asn Thr Gly Ser Ser
            660                 665                 670

Gln Cys Ile Ser Trp Ala Leu Ala Thr Asp Glu Gln Glu Glu Lys Leu
        675                 680                 685

Lys Ser Glu Cys Phe Ser Lys Arg Thr Leu Asp His Asp Arg Cys Asp
    690                 695                 700

Gln His Thr Asp Cys Tyr Ser Cys Thr Ala Asn Thr Asn Asp Cys His
705                 710                 715                 720

Trp Cys Asn Asp His Cys Val Pro Arg Asn His Ser Cys Ser Glu Gly
                725                 730                 735

Gln Ile Ser Ile Phe Arg Tyr Glu Asn Cys Pro Lys Asp Asn Pro Met
            740                 745                 750

Tyr Tyr Cys Asn Lys Lys Thr Ser Cys Arg Ser Cys Ala Leu Asp Gln
        755                 760                 765

Asn Cys Gln Trp Glu Pro Arg Asn Gln Glu Cys Ile Ala Leu Pro Glu
    770                 775                 780

Asn Ile Cys Gly Ile Gly Trp His Leu Val Gly Asn Ser Cys Leu Lys
785                 790                 795                 800

Ile Thr Thr Ala Lys Glu Asn Tyr Asp Asn Ala Lys Leu Phe Cys Arg
                805                 810                 815

Asn His Asn Ala Leu Leu Ala Ser Leu Thr Thr Gln Lys Lys Val Glu
            820                 825                 830

Phe Val Leu Lys Gln Leu Arg Ile Met Gln Ser Ser Gln Ser Met Ser
        835                 840                 845

Lys Leu Thr Leu Thr Pro Trp Val Gly Leu Arg Lys Ile Asn Val Ser
    850                 855                 860

Tyr Trp Cys Trp Glu Asp Met Ser Pro Phe Thr Asn Ser Leu Leu Gln
865                 870                 875                 880

Trp Met Pro Ser Glu Pro Ser Asp Ala Gly Phe Cys Gly Ile Leu Ser
                885                 890                 895

Glu Pro Ser Thr Arg Gly Leu Lys Ala Ala Thr Cys Ile Asn Pro Leu
            900                 905                 910

Asn Gly Ser Val Cys Glu Arg Pro Ala Asn His Ser Ala Lys Gln Cys
        915                 920                 925

Arg Thr Pro Cys Ala Leu Arg Thr Ala Cys Gly Asp Cys Thr Ser Gly
    930                 935                 940

Ser Ser Glu Cys Met Trp Cys Ser Asn Met Lys Gln Cys Val Asp Ser
945                 950                 955                 960

Asn Ala Tyr Val Ala Ser Phe Pro Phe Gly Gln Cys Met Glu Trp Tyr
                965                 970                 975

Thr Met Ser Thr Cys Pro Pro Glu Asn Cys Ser Gly Tyr Cys Thr Cys
            980                 985                 990

Ser His Cys Leu Glu Gln Pro Gly Cys Gly Trp Cys Thr Asp Pro Ser
        995                 1000                1005

Asn Thr Gly Lys Gly Lys Cys Ile Glu Gly Ser Tyr Lys Gly Pro Val
```

-continued

```
    1010                1015                1020

Lys Met Pro Ser Gln Ala Pro Thr Gly Asn Phe Tyr Pro Gln Pro Leu
1025                1030                1035                1040

Leu Asn Ser Ser Met Cys Leu Glu Asp Ser Arg Tyr Asn Trp Ser Phe
                1045                1050                1055

Ile His Cys Pro Ala Cys Gln Cys Asn Gly His Ser Lys Cys Ile Asn
            1060                1065                1070

Gln Ser Ile Cys Glu Lys Cys Glu Asn Leu Thr Thr Gly Lys His Cys
        1075                1080                1085

Glu Thr Cys Ile Ser Gly Phe Tyr Gly Asp Pro Thr Asn Gly Gly Lys
    1090                1095                1100

Cys Gln Pro Cys Lys Cys Asn Gly His Ala Ser Leu Cys Asn Thr Asn
1105                1110                1115                1120

Thr Gly Lys Cys Phe Cys Thr Thr Lys Gly Val Lys Gly Asp Glu Cys
                1125                1130                1135

Gln Leu Cys Glu Val Glu Asn Arg Tyr Gln Gly Asn Pro Leu Arg Gly
            1140                1145                1150

Thr Cys Tyr Tyr Thr Leu Leu Ile Asp Tyr Gln Phe Thr Phe Ser Leu
        1155                1160                1165

Ser Gln Glu Asp Asp Arg Tyr Tyr Thr Ala Ile Asn Phe Val Ala Thr
    1170                1175                1180

Pro Asp Glu Gln Asn Arg Asp Leu Asp Met Phe Ile Asn Ala Ser Lys
1185                1190                1195                1200

Asn Phe Asn Leu Asn Ile Thr Trp Ala Ala Ser Phe Ser Ala Gly Thr
                1205                1210                1215

Gln Ala Gly Glu Glu Met Pro Val Val Ser Lys Thr Asn Ile Lys Glu
            1220                1225                1230

Tyr Lys Asp Ser Phe Ser Asn Glu Lys Phe Asp Phe Arg Asn His Pro
        1235                1240                1245

Asn Ile Thr Phe Phe Val Tyr Val Ser Asn Phe Thr Trp Pro Ile Lys
    1250                1255                1260

Ile Gln Ile Ala Phe Ser Gln His Ser Asn Phe Met Asp Leu Val Gln
1265                1270                1275                1280

Phe Phe Val Thr Phe Phe Ser Cys Phe Leu Ser Leu Leu Leu Val Ala
                1285                1290                1295

Ala Val Val Trp Lys Ile Lys Gln Ser Cys Trp Ala Ser Arg Arg Arg
            1300                1305                1310

Glu Gln Leu Leu Arg Glu Met Gln Gln Met Ala Ser Arg Pro Phe Ala
        1315                1320                1325

Ser Val Asn Val Ala Leu Glu Thr Asp Glu Glu Pro Pro Asp Leu Ile
    1330                1335                1340

Gly Gly Ser Ile Lys Thr Val Pro Lys Pro Ile Ala Leu Glu Pro Cys
1345                1350                1355                1360

Phe Gly Asn Lys Ala Ala Val Leu Ser Val Phe Val Arg Leu Pro Arg
                1365                1370                1375

Gly Leu Gly Gly Ile Pro Pro Pro Gly Gln Ser Gly Leu Ala Val Ala
            1380                1385                1390

Ser Ala Leu Val Asp Ile Ser Gln Gln Met Pro Ile Val Tyr Lys Glu
        1395                1400                1405

Lys Ser Gly Ala Val Arg Asn Arg Lys Gln Gln Pro Pro Ala Gln Pro
    1410                1415                1420

Gly Thr Cys Ile Asn
1425
```

-continued

<210> SEQ ID NO: 131
<211> LENGTH: 1198
<212> TYPE: PRT
<213> ORGANISM: Homo sapiens

<400> SEQUENCE: 131

```
Met Val Ala Ala Ala Ala Ala Thr Glu Ala Arg Leu Arg Arg Arg Thr
 1               5                  10                  15

Ala Ala Thr Ala Ala Leu Ala Gly Arg Ser Gly Gly Pro His Cys Val
            20                  25                  30

Asn Gly Gly Arg Cys Asn Pro Gly Thr Gly Gln Cys Val Cys Pro Ala
        35                  40                  45

Gly Trp Val Gly Glu Gln Cys Gln His Cys Gly Gly Arg Phe Arg Leu
    50                  55                  60

Thr Gly Ser Ser Gly Phe Val Thr Asp Gly Pro Gly Asn Tyr Lys Tyr
65                  70                  75                  80

Lys Thr Lys Cys Thr Trp Leu Ile Glu Gly Gln Pro Asn Arg Ile Met
                85                  90                  95

Arg Leu Arg Phe Asn His Phe Ala Thr Glu Cys Ser Trp Asp His Leu
            100                 105                 110

Tyr Val Tyr Asp Gly Asp Ser Ile Tyr Ala Pro Leu Val Ala Ala Phe
        115                 120                 125

Ser Gly Leu Ile Val Pro Glu Arg Asp Gly Asn Glu Thr Val Pro Glu
    130                 135                 140

Val Val Ala Thr Ser Gly Tyr Ala Leu Leu His Phe Phe Ser Asp Ala
145                 150                 155                 160

Ala Tyr Asn Leu Thr Gly Phe Asn Ile Thr Tyr Ser Phe Asp Met Cys
                165                 170                 175

Pro Asn Asn Cys Ser Gly Arg Gly Glu Cys Lys Ile Ser Asn Ser Ser
            180                 185                 190

Asp Thr Val Glu Cys Glu Cys Ser Glu Asn Trp Lys Gly Glu Ala Cys
        195                 200                 205

Asp Ile Pro His Cys Thr Asp Asn Cys Gly Phe Pro His Arg Gly Ile
    210                 215                 220

Cys Asn Ser Ser Asp Val Arg Gly Cys Ser Cys Phe Ser Asp Trp Gln
225                 230                 235                 240

Gly Pro Gly Cys Ser Val Pro Val Pro Ala Asn Gln Ser Phe Trp Thr
                245                 250                 255

Arg Glu Glu Tyr Ser Asn Leu Lys Leu Pro Arg Ala Ser His Lys Ala
            260                 265                 270

Val Val Asn Gly Asn Ile Met Trp Val Val Gly Gly Tyr Met Phe Asn
        275                 280                 285

His Ser Asp Tyr Asn Met Val Leu Ala Tyr Asp Leu Ala Ser Arg Glu
    290                 295                 300

Trp Leu Pro Leu Asn Arg Ser Val Asn Asn Val Val Val Arg Tyr Gly
305                 310                 315                 320

His Ser Leu Ala Leu Tyr Lys Asp Lys Ile Tyr Met Tyr Gly Gly Lys
                325                 330                 335

Ile Asp Ser Thr Gly Asn Val Thr Asn Glu Leu Arg Val Phe His Ile
            340                 345                 350

His Asn Glu Ser Trp Val Leu Leu Thr Pro Lys Ala Lys Glu Gln Tyr
        355                 360                 365

Ala Val Val Gly His Ser Ala His Ile Val Thr Leu Lys Asn Gly Arg
```

-continued

```
    370                 375                 380

Val Val Met Leu Val Ile Phe Gly His Cys Pro Leu Tyr Gly Tyr Ile
385                 390                 395                 400

Ser Asn Val Gln Glu Tyr Asp Leu Asp Lys Asn Thr Trp Ser Ile Leu
                405                 410                 415

His Thr Gln Gly Ala Leu Val Gln Gly Gly Tyr Gly His Ser Ser Val
            420                 425                 430

Tyr Asp His Arg Thr Arg Ala Leu Tyr Val His Gly Gly Tyr Lys Ala
        435                 440                 445

Phe Ser Ala Asn Lys Tyr Arg Leu Ala Asp Asp Leu Tyr Arg Tyr Asp
    450                 455                 460

Val Asp Thr Gln Met Trp Thr Ile Leu Lys Asp Ser Arg Phe Phe Arg
465                 470                 475                 480

Tyr Leu His Thr Ala Val Ile Val Ser Gly Thr Met Leu Val Phe Gly
                485                 490                 495

Gly Asn Thr His Asn Asp Thr Ser Met Ser His Gly Ala Lys Cys Phe
            500                 505                 510

Ser Ser Asp Phe Met Ala Tyr Asp Ile Ala Cys Asp Arg Trp Ser Val
        515                 520                 525

Leu Pro Arg Pro Asp Ser Thr Met Met Ser Thr Asp Leu Ala Ile Pro
    530                 535                 540

Ala Val Leu His Asn Ser Thr Met Tyr Val Phe Gly Gly Phe Asn Ser
545                 550                 555                 560

Leu Leu Leu Ser Asp Ile Leu Val Phe Thr Ser Glu Gln Cys Asp Ala
                565                 570                 575

His Arg Ser Glu Ala Ala Cys Leu Ala Ala Gly Pro Gly Ile Arg Cys
            580                 585                 590

Val Trp Asn Thr Gly Ser Ser Gln Cys Ile Ser Trp Ala Leu Ala Thr
        595                 600                 605

Asp Glu Gln Glu Glu Lys Leu Lys Ser Glu Cys Phe Ser Lys Arg Thr
    610                 615                 620

Leu Asp His Asp Arg Cys Asp Gln His Thr Asp Cys Tyr Ser Cys Thr
625                 630                 635                 640

Ala Asn Thr Asn Asp Cys His Trp Cys Asn Asp His Cys Val Pro Arg
                645                 650                 655

Asn His Ser Cys Ser Glu Gly Gln Ile Ser Ile Phe Arg Tyr Glu Asn
            660                 665                 670

Cys Pro Lys Asp Asn Pro Met Tyr Tyr Cys Asn Lys Lys Thr Ser Cys
        675                 680                 685

Arg Ser Cys Ala Leu Asp Gln Asn Cys Gln Trp Glu Pro Arg Asn Gln
    690                 695                 700

Glu Cys Ile Ala Leu Pro Glu Asn Ile Cys Gly Ile Gly Trp His Leu
705                 710                 715                 720

Val Gly Asn Ser Cys Leu Lys Ile Thr Thr Ala Lys Glu Asn Tyr Asp
                725                 730                 735

Asn Ala Lys Leu Phe Cys Arg Asn His Asn Ala Leu Leu Ala Ser Leu
            740                 745                 750

Thr Thr Gln Lys Lys Val Glu Phe Val Leu Lys Gln Leu Arg Ile Met
        755                 760                 765

Gln Ser Ser Gln Ser Met Ser Lys Leu Thr Leu Thr Pro Trp Val Gly
    770                 775                 780

Leu Arg Lys Ile Asn Val Ser Tyr Trp Cys Trp Glu Asp Met Ser Pro
785                 790                 795                 800
```

-continued

```
Phe Thr Asn Ser Leu Leu Gln Trp Met Pro Ser Glu Pro Ser Asp Ala
                805                 810                 815

Gly Phe Cys Gly Ile Leu Ser Glu Pro Ser Thr Arg Gly Leu Lys Ala
            820                 825                 830

Ala Thr Cys Ile Asn Pro Leu Asn Gly Ser Val Cys Glu Arg Pro Ala
        835                 840                 845

Asn His Ser Ala Lys Gln Cys Arg Thr Pro Cys Ala Leu Arg Thr Ala
    850                 855                 860

Cys Gly Asp Cys Thr Ser Gly Ser Ser Glu Cys Met Trp Cys Ser Asn
865                 870                 875                 880

Met Lys Gln Cys Val Asp Ser Asn Ala Tyr Val Ala Ser Phe Pro Phe
                885                 890                 895

Gly Gln Cys Met Glu Trp Tyr Thr Met Ser Thr Cys Pro Pro Glu Asn
            900                 905                 910

Cys Ser Gly Tyr Cys Thr Cys Ser His Cys Leu Glu Gln Pro Gly Cys
        915                 920                 925

Gly Trp Cys Thr Asp Pro Ser Asn Thr Gly Lys Gly Lys Cys Ile Glu
    930                 935                 940

Gly Ser Tyr Lys Gly Pro Val Lys Met Pro Ser Gln Ala Pro Thr Gly
945                 950                 955                 960

Asn Phe Tyr Pro Gln Pro Leu Leu Asn Ser Ser Met Cys Leu Glu Asp
                965                 970                 975

Ser Arg Tyr Asn Trp Ser Phe Ile His Cys Pro Ala Cys Gln Cys Asn
            980                 985                 990

Gly His Ser Lys Cys Ile Asn Gln Ser Ile Cys Glu Lys Cys Glu Asn
        995                 1000                1005

Leu Thr Thr Gly Lys His Cys Glu Thr Cys Ile Ser Gly Phe Tyr Gly
    1010                1015                1020

Asp Pro Thr Asn Gly Gly Lys Cys Gln Pro Cys Lys Cys Asn Gly His
1025                1030                1035                1040

Ala Ser Leu Cys Asn Thr Asn Thr Gly Lys Cys Phe Cys Thr Thr Lys
                1045                1050                1055

Gly Val Lys Gly Asp Glu Cys Gln Leu Cys Glu Val Glu Asn Arg Tyr
            1060                1065                1070

Gln Gly Asn Pro Leu Arg Gly Thr Cys Tyr Tyr Thr Leu Leu Ile Asp
        1075                1080                1085

Tyr Gln Phe Thr Phe Ser Leu Ser Gln Glu Asp Asp Arg Tyr Tyr Thr
    1090                1095                1100

Ala Ile Asn Phe Val Ala Thr Pro Asp Glu Gln Asn Arg Asp Leu Asp
1105                1110                1115                1120

Met Phe Ile Asn Ala Ser Lys Asn Phe Asn Leu Asn Ile Thr Trp Ala
                1125                1130                1135

Ala Ser Phe Ser Ala Gly Thr Gln Ala Gly Glu Glu Met Pro Val Val
            1140                1145                1150

Ser Lys Thr Asn Ile Lys Glu Tyr Lys Asp Ser Phe Ser Asn Glu Lys
        1155                1160                1165

Phe Asp Phe Arg Asn His Pro Asn Ile Thr Phe Phe Val Tyr Val Ser
    1170                1175                1180

Asn Phe Thr Trp Pro Ile Lys Ile Gln Val Gln Thr Glu Gln
1185                1190                1195
```

METHODS AND COMPOSITIONS FOR THE DIAGNOSIS AND TREATMENT OF BODY WEIGHT DISORDERS, INCLUDING OBESITY

1. INTRODUCTION

The present invention relates to mammalian mahogany genes, including the human mahogany gene, which are novel genes involved in the control of mammalian body weight. The invention encompasses nucleotide sequences of the mahogany gene, host cell expression systems of the mahogany gene, and hosts which have been transformed by these expression systems, including transgenic animals. The invention also encompasses novel mahogany gene products, including mahogany proteins, polypeptides and peptides containing amino acid sequences mahogany proteins, fusion proteins of mahogany proteins polypeptides and peptides, and antibodies directed against such mahogany gene products.

The present invention also relates to methods and compositions for the diagnosis and treatment of mammalian body weight disorders, including obesity, cachexia, and anorexia, and for the identification of subjects susceptible to such disorders. Further, the invention relates to methods of using the mahogany gene and gene products of the invention for the identification of compounds which modulate the expression of the mahogany gene and/or the activity of the mahogany gene product. Such compounds can be useful as therapeutic agents in the treatment of mammalian body weight disorders, including obesity, cachexia, and anorexia.

2. BACKGROUND OF THE INVENTION

Obesity represents the most prevalent of body weight disorders, and it is the most important nutritional disorder in the western world, with estimates of its prevalence ranging from 30% to 50% within the middle-aged population. Other body weight disorders, such as anorexia nervosa and bulimia nervosa, which together affect approximately 0.2% of the female population of the western world, also pose serious health threats. Further, such disorders as anorexia and cachexia (wasting) are also prominent features of other diseases such as cancer, cystic fibrosis, and AIDS.

Obesity, defined as an excess of body fat relative to lean body mass, also contributes to other diseases. For example, this disorder is responsible for increased incidence of diseases such as coronary artery disease, hypertension, stroke, diabetes, hyperlipidemia, and some cancers (See, e.g., Nishina, P. M. et al., 1994, Metab. 43: 554–558; Grundy, S. M. & Barnett, J. P., 1990, Dis. Mon. 36: 641–731). Obesity is not merely a behavioral problem, i.e., the result of voluntary hyperphagia. Rather, the differential body composition observed between obese and normal subjects results from differences in both metabolism and neurologic/metabolic interactions. These differences seem to be, to some extent, due to differences in gene expression, and/or level of gene products or activity (Friedman, J. M. et al., 1991, Mammalian Gene 1: 130–144).

The epidemiology of obesity strongly shows that the disorder exhibits inherited characteristics (Stunkard, 1990, N. Eng. J. Med. 322: 1438). Moll et al. have reported that, in many populations, obesity seems to be controlled by a few genetic loci (Moll et al., 1991, Am. J. Hum. Gen. 49: 1243). In addition, human twin studies strongly suggest a substantial genetic basis in the control of body weight, with estimates of heritability of 80–90% (Simopoulos, A. P. & Childs, B., eds., 1989, in "Genetic Variation and Nutrition in Obesity", World Review of Nutrition and Diabetes 63, S. Karger, Basel, Switzerland; Borjeson, M., 1976, Acta. Paediatr. Scand. 65: 279–287).

In other studies, non-obese persons who deliberately attempted to gain weight by systematically over-eating were found to be more resistant to such weight gain and able to maintain an elevated weight only by very high caloric intake. In contrast, spontaneously obese individuals are able to maintain their status with normal or only moderately elevated caloric intake. In addition, it is a commonplace experience in animal husbandry that different strains of swine, cattle, etc., have different predispositions to obesity. Studies of the genetics of human obesity, and of animal models of obesity demonstrate that obesity results from complex defective regulation of both food intake, food induced energy expenditure, and of the balance between lipid and lean body anabolism.

There are a number of genetic diseases in man and other species which feature obesity among their more prominent symptoms, along with, frequently, dysmorphic features and mental retardation. For example, Prader-Willi syndrome (PWS; reviewed in Knoll, J. H. et al., 1993, Am. J. Med. Genet. 46: 2–6) affects approximately 1 in 20,000 live births, and involves poor neonatal muscle tone, facial and genital deformities, and generally obesity.

In addition to PWS, many other pleiotropic syndromes have been characterized which include obesity as a symptom. These syndromes are genetically straightforward, and appear to involve autosomal recessive alleles. Such diseases include, among others, Ahlstroem, Carpenter, Bardet-Biedl, Cohen, and Morgagni-Stewart-Monel Syndromes.

A number of models exists for the study of obesity (see, e.g., Bray, G. A., 1992, Prog. Brain Res. 93: 333–341; and Bray, G. A., 1989, Amer. J. Clin. Nutr. 5: 891–902). For example, animals having mutations which lead to syndromes that include obesity symptoms have also been identified. Attempts have been made to utilize such animals as models for the study of obesity, and the best studied animal models to date for genetic obesity are mice. For reviews, see, e.g., Friedman, J. M. et al., 1991, Mamm. Gen. 1: 130–144; Friedman, J. M. and Liebel, R. L., 1992, Cell 69: 217–220.

Studies utilizing mice have confirmed that obesity is a very complex trait with a high degree of heritability. Mutations at a number of loci have been identified which lead to obese phenotypes. These include the autosomal recessive mutations obese (ob), diabetes (db), fat (fat), and tubby (tub).

The dominant Yellow mutation (Ay) at the agouti locus causes a pleiotropic syndrome which causes moderate adult onset obesity, a yellow coat color, and a high incidence of tumor formation (Herberg, L. and Coleman, D. L., 1977, Metabolism 26:59), and an abnormal anatomic distribution of body fat (Coleman, D. L., 1978, Diabetologia 14:141–148). The mutation causes the widespread expression of a protein which is normally seen only in neonatal skin (Michaud, E. J. et al., 1994, Genes Devel. 8:1463–1472). The agouti protein has been reported to be a competitive antagonist of α-MSH binding to the melanocortin receptors MC1-R and MC4-R in vitro (Lu et al., 1996, Nature 371:799–802), and the authors speculated that de-regulated ubiquitous expression of agouti may lead to obesity by antagonism of melanocortin receptors expressed outside the hair follicles.

Mahogany (mg) and mahoganoid (md) are mutations that suppress the phenotypic effects of agouti protein in vivo (Lane and Green, 1960, J. Hered. 51: 228–230). The mahogany and mahoganoid mutation have been mapped to mouse chromosomes 2 and 16, respectively (Green, 1989, "Catalog of mutant genes and polymorphic loci", pp. 12–403 in *Genetic Variants and Strains of the Laboratory Mouse*, Lyon, M. F. and Searle, A.G., eds., Oxford University Press, Oxford). Mutations of both mg and md have been shown to suppress the effects of agouti on obesity as well as on coat color (Miller et al., 1997, Genetics 146: 1407–1415).

In summary, therefore, obesity, which poses a major, worldwide health problem, represents a complex, highly heritable trait. Given the severity, prevalence, and potential heterogeneity of such disorders, there exists a great need for the identification of those genes that participate in the control of body weight.

3. SUMMARY OF THE INVENTION

The present invention relates to the identification of novel nucleic acid molecules and proteins encoded by such nucleic acid molecules that are involved in the control of mammalian body weight, and which, further, are associated with mammalian body weight disorders such as obesity, cachexia, and anorexia. The nucleic acid molecules of the present invention represent the genes corresponding to the mammalian mahogany gene, including the human mahogany gene.

Figure 3A:
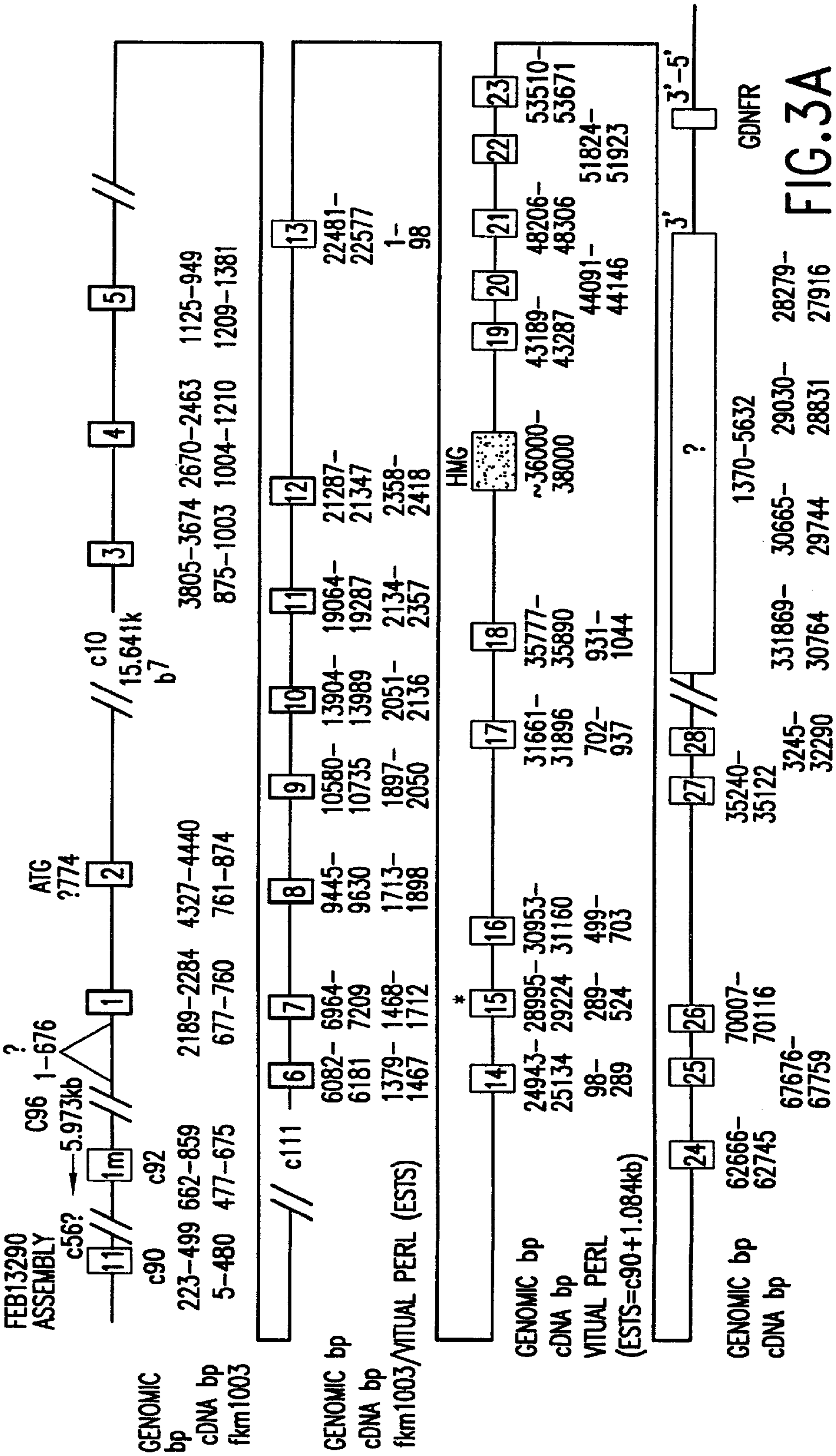

In particular, the compositions of the present invention include nucleic acid molecules which comprise the following sequences: (a) nucleotide sequences of the murine mahogany gene (SEQ ID NO.: 1) shown in FIG. 2A, as well as allelic variants and homologs thereof, as shown, e.g., in FIGS. 8A–8C and 9A; (b) nucleotide sequences that encode the mahogany gene product amino acid sequence (SEQ ID NO.: 2) shown in FIG. 2B; (c) nucleotide sequences that encode portions of the mahogany gene product corresponding to its functional domains and individual exons; (d) nucleotide sequences comprising the novel mahogany gene sequences disclosed herein that encode mutants of the mahogany gene product in which all or a part of one or more of the domains is deleted or altered, as shown, e.g., in FIG. 6; (e) nucleotide sequences that encode fusion proteins comprising the mahogany gene product (SEQ ID NO.: 2), or one or more of its domains fused to a heterologous polypeptide; (f) nucleotide sequences within the mahogany gene, as well as chromosome sequences flanking the mahogany gene, see, e.g., FIG. 3, which can be utilized as part of the methods of the present invention for the diagnosis of mammalian body weight disorders, including obesity, cachexia, and anorexia, which are mediated by the mahogany gene, as well as for the identification of subjects susceptible to such disorders; (g) nucleic acid sequences that hybridize to the above described sequences under stringent or moderately stringent conditions, particularly human mg homologues, as shown, e.g., FIG. 10. The nucleic acid molecules of the invention include, but are not limited to, cDNA and genomic DNA sequences of the mahogany gene.

The present invention also encompasses expression products of the nucleic acid molecules listed above; i.e., proteins and/or polypeptides that are encoded by the above mahogany nucleic acid molecules.

Agonists and antagonists of the mahogany gene and/or gene product are also included in the present invention. Such agonists and antagonists will include, for example, small molecules, large molecules, and antibodies directed against the mahogany gene product. Agonists and antagonists of the invention also include nucleotide sequences, such as antisense and ribozyme molecules, and gene or regulatory sequence replacement constructs, that can be used to inhibit or enhance expression of the mahogany gene.

The present invention further encompasses cloning vectors, including expression vectors, that contain the nucleic acid molecules of the invention and can be used to express those nucleic acid molecules in host organisms. Further, host organisms which have been transformed with these nucleic acid molecules are also encompassed in the present invention. Host organisms of the invention include organisms transformed with the cloning vectors described above, e.g., transgenic animals, particularly non-human transgenic animals, and particularly transgenic non-human mammals.

The transgenic animals of the invention include animals that express a mutant variant or polymorphism of a mahogany gene, particularly a mutant variant or polymorphism of a mahogany gene that is associated with a weight disorder such as obesity, cachexia, or anorexia. The transgenic animals of the invention further include those that express a mahogany transgene at higher or lower levels than normal. The transgenic animals of the invention further include those which express the mahogany gene in all their cells, "mosaic" animals which express the mahogany gene in only some of their cells, and those in which the mahogany gene is selectively introduced into and expressed in a specific cell type(s). The transgenic animals of the invention also include "knock-out" animals. Knock-out animals comprise animals which have been engineered to no longer express the mahogany gene.

The present invention also relates to methods and compositions for the diagnosis of mammalian body weight disorders, including obesity, cachexia, and anorexia, as well as for the identification of subjects susceptible to such disorders. Such methods comprise, for example, measuring expression of the mahogany gene in a patient sample, or detecting a mutation in the mahogany gene in the genome of a mammal, including a human, suspected of exhibiting such a weight disorder. The nucleic acid molecules of the invention can also be used as diagnostic hybridization probes, or as primers for diagnostic PCR analysis to identify of mahogany gene mutations, allelic variations, or regulatory defects, such as defects in the expression of the mahogany gene. Such diagnostic PCR analyses can be used to diagnose individuals with a body weight disorder associated with a particular mahogany gene mutation, allelic variation, or regulatory defect. Such diagnostic PCR analyses can also be used to identify individuals susceptible to such body weight disorders and hyperphagia.

Methods and compositions, including pharmaceutical compositions, for the treatment of body weight disorders such as obesity, cachexia, and anorexia are also included in the invention. Such methods and compositions are capable of modulating the level of mahogany gene expression and/or the level of activity of the mahogany gene product. Such methods include, for example, modulating the expression of the mahogany gene and/or the activity of the mahogany gene product for the treatment of a body weight disorder which is mediated by some other gene, for example by the agouti gene.

The invention still further relates to methods for identifying compounds which modulate the expression of the mammalian mahogany gene and/or the synthesis or activity of mammalian mahogany gene products. Such compounds include therapeutic compounds which can be used as pharmaceutical compositions to reduce or eliminate the symptoms of mammalian body weight disorders such as obesity, cachexia, and anorexia. Cellular and non-cellular assays are described that can be used to identify compounds that interact with the mahogany gene and/or gene product, e.g., modulate the activity of the mahogany gene and/or bind to the mahogany gene product. Such cell-based assays of the invention utilize cells, cell lines, or engineered cells or cell lines that express the mahogany gene product.

In one embodiment, such methods comprise contacting a compound to a cell that expresses a mahogany gene, measuring the level of mahogany gene expression, gene product expression, or gene product activity, and comparing this level to the level of mahogany gene expression, gene product expression, or gene product activity produced by the cell in the absence of the compound, such that if the level obtained in the presence of the compound differs from that obtained in its absence, a compound that modulates the expression of the mammalian mahogany gene and/or the synthesis or activity of mammalian mahogany gene products has been identified.

In an alternative embodiment, such methods comprise administering a compound to a host, e.g., a transgenic animal that expresses a mahogany transgene or a mutant mahogany transgene, and measuring the level of mahogany gene expression, gene product expression, or gene product activity. The measured level is compared to the level of mahogany gene expression, gene product expression, or gene product activity in a host that is not exposed to the compound, such that if the level obtained when the host is exposed to the compound differs from that obtained when the host is not exposed to the compound, a compound that modulates the expression of the mammalian mahogany gene and/or the synthesis or activity of mammalian mahogany gene products, and/or the symptoms of a mammalian body weight disorder, such as obesity, cachexia, or anorexia, has been identified.

The Example presented in Section 6, below, describes the genetic and physical mapping of the mahogany gene to a specific 700 kb interval of mouse chromosome 2. The example presented in Section 7, below, describes the identification of a transcription unit within this chromosome interval, referred to herein as the MG gene, which represents the mahogany gene. The expression and sequence analysis of this candidate mahogany gene is described in the example presented in Section 8, below. These experiments prove that the candidate gene MG is indeed the mahogany gene.

Definitions

As used herein, the following terms shall have the abbreviations indicated.

BAC, bacterial artificial chromosomes bp, base pair(s)

EST, expressed sequence tag mg, mahogany gene

RFLP, restriction fragment length polymorphism

RT-PCR, reverse transcriptase PCR

SSCP, single-stranded conformational polymorphism

SSLP, simple sequence length polymorphisms

STS, short tag sequence

YAC, yeast artificial chromosome

4. BRIEF DESCRIPTION OF THE FIGURES

FIG. 1. Physical map of the mahogany interval of mouse chromosome 2.

FIG. 2. Panel A(1)–A(9), cDNA nucleotide sequence of the wild-type (C57BL/6J) murine mahogany gene (SEQ ID NO: 1), including the 5' and 3' untranslated regions, and Panel B: the derived amino acid sequence (SEQ ID NO: 2) of the mahogany gene product.

FIGS. 3A–D. Genomic structure and nucleotide sequences derived from the wild-type (C57BL/6J) mouse genomic regions containing the mg gene. Panel A, genomic structure; Panel B(1)–B(17), genomic sequence c56 (SEQ ID NO: 3); Panel C(1)–C(6), genomic sequence c96 (SEQ ID NO: 4); Panel D(1)–D(86), genomic sequence of c110/111 (SEQ ID NO: 5).

FIG. 4. Structural depiction of MG cDNA without introns. CUB=CUB domain, metal=metallothionin domain; T-transmembrane domain.

FIGS. Panel 5(1)–5(4), Nucleotide sequence of primers used to amplify each of the exons in the mg gene.

FIG. 6. Nucleotide sequence of the wild-type (SEQ ID NO: 6) and mahogany mutant (SEQ ID NO: 7) sequences in exon 15 of the MG gene. Bases shown in bold are deleted in Mg3J mutant mg.

Figure 7:
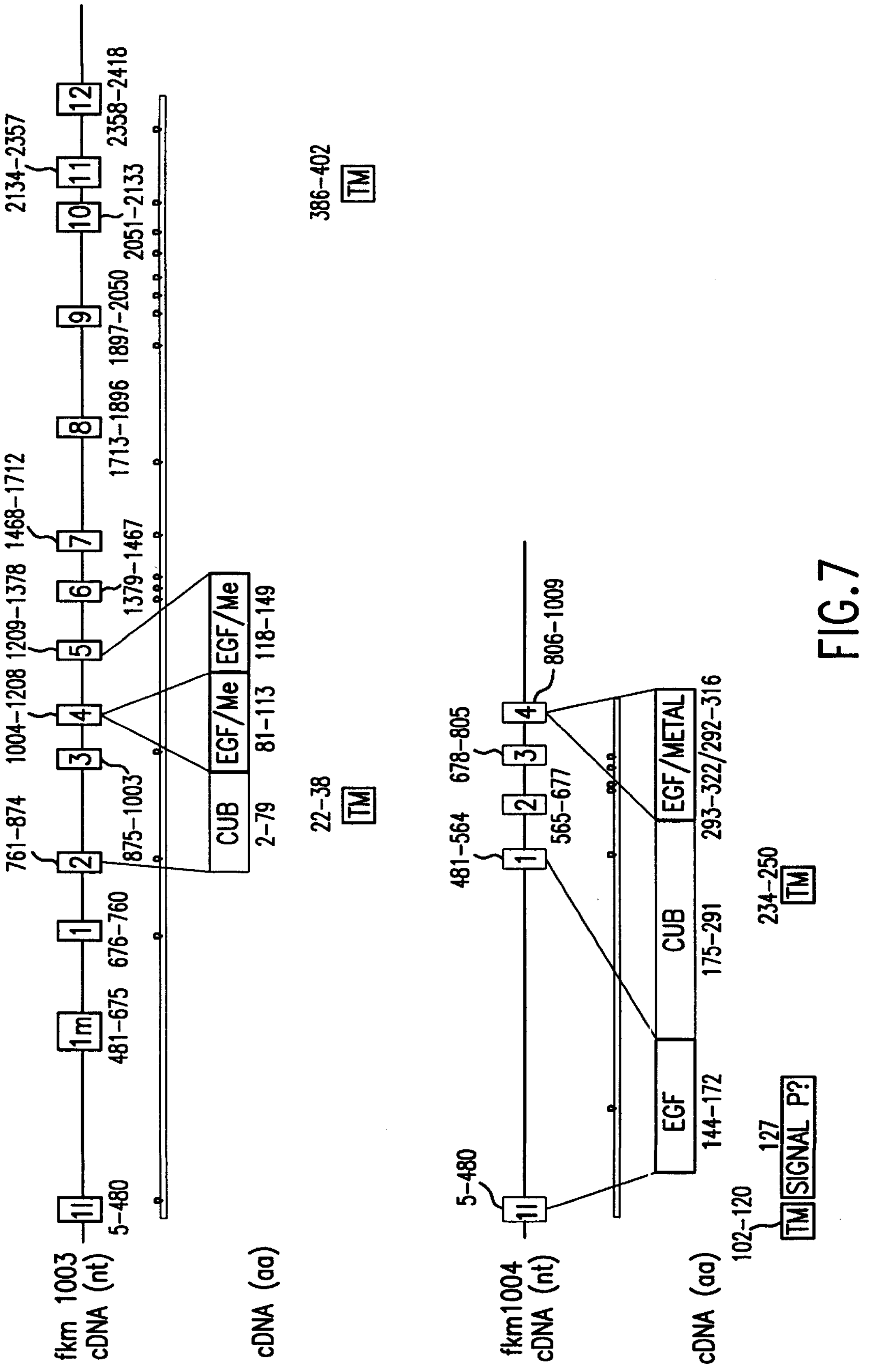
Figure 8E:
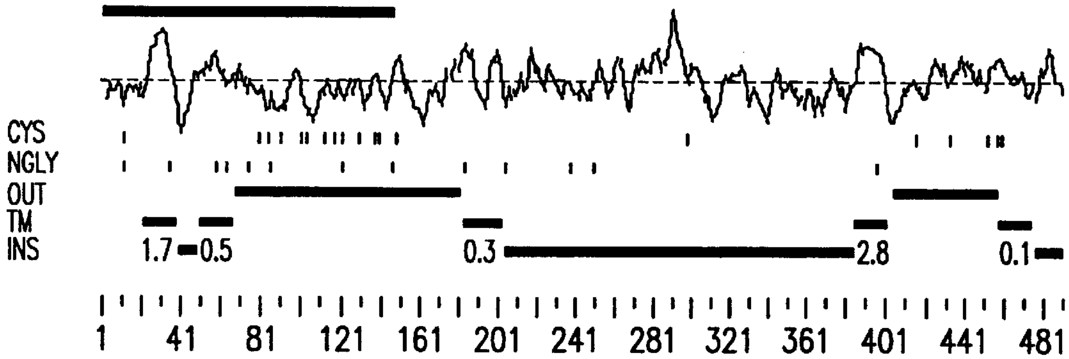

FIG. 7. Differential 5' start sequences in the murine mahogany gene showing splice forms akm1003 and akm1004.

FIGS. 8A–E. Panel A–C, cDNA sequence (SEQ ID NO: 8) from one form of the differential 5' start site found in the murine (akm1003), Panel D, amino acid sequence (SEQ ID NO: 9) encoded by the cDNA of Panel A; Panel E, hydropathy plot of the akm1003 amino acid sequence.

Figure 9C:
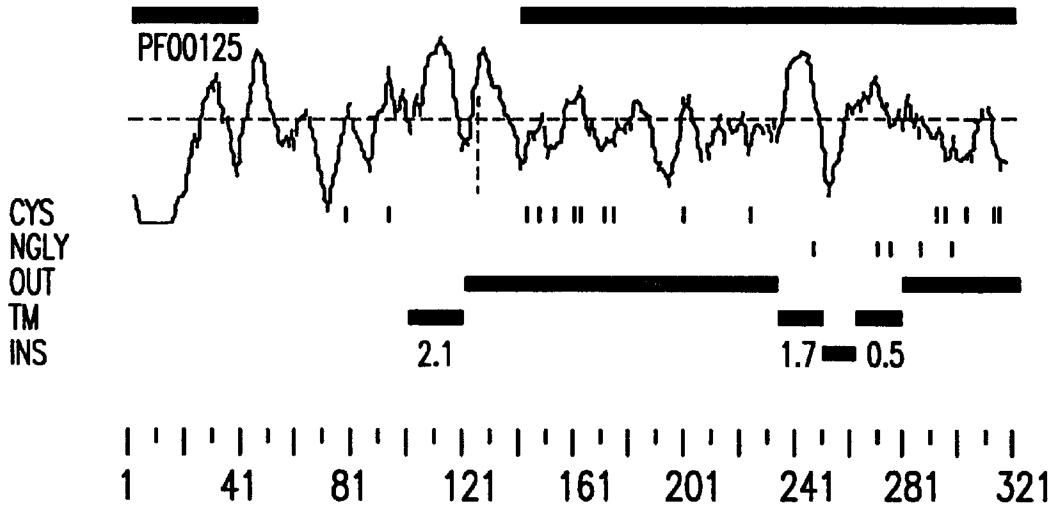

FIG. 9. Panel A, cDNA sequence (SEQ ID NO: 10) from one form of the differential 5' start site found in the murine (akm1004); Panel B, amino acid sequence (SEQ ID NO: 11) encoded by the cDNA of Panel A; Panel C, hydropathy plot of the akm1004 amino acid sequence.

FIGS. 10A–B. Panel A(1)–A(7), Nucleotide sequence of a contig containing a portion of the human MG cDNA (SEQ ID NO: 12), and panel B, the translated amino acid sequence (SEQ ID NO: 13).

Figure 11A:
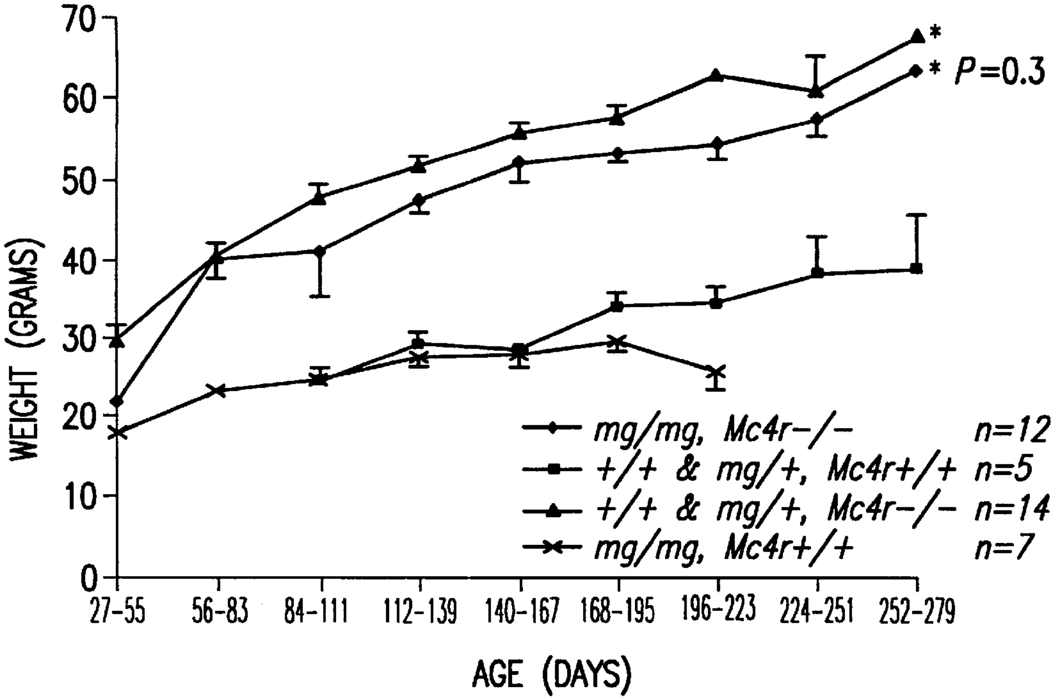
Figure 11B:
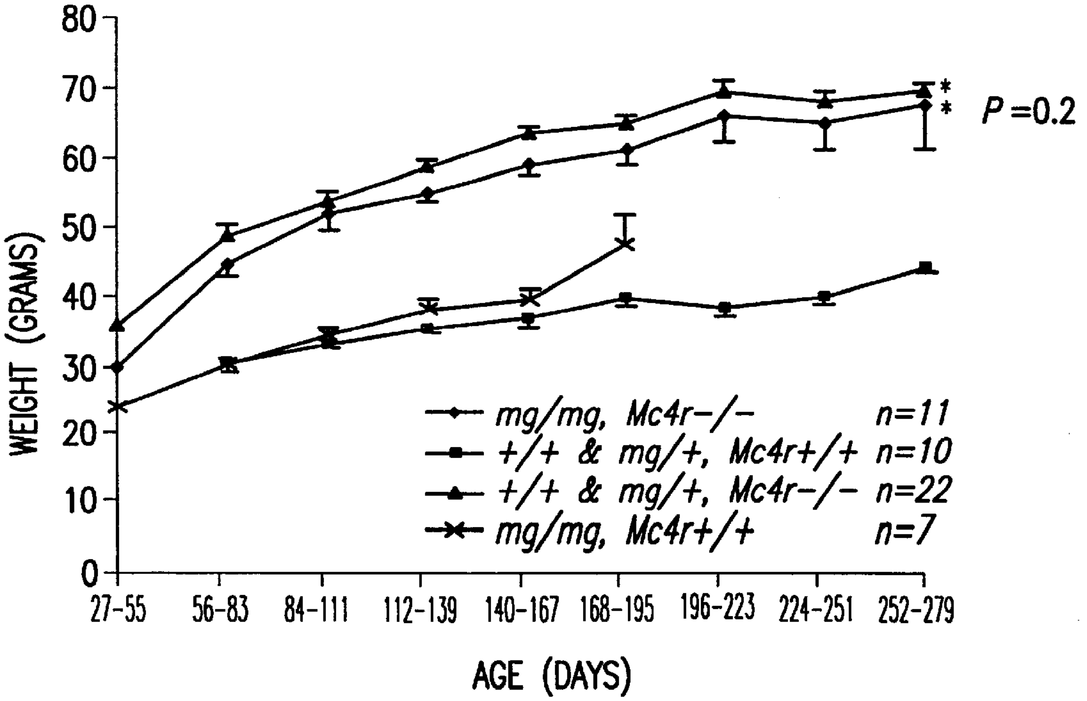

FIG. 11. Effect of mg on MC4r −/− induced weight gain in females (FIG. 11A) and males (FIG. 11B); values depicted are the mean ± SD within a designated time interval.

FIG. 12. Effect of mg on monogenic obese mutants $Lepr^{db}$ (FIG. 12A), tub (FIG. 12B), $Cpe^{fat}$ (FIG. 12C), and on high fat diet induced obesity (FIG. 12D); the values indicated are the mean ± SD of the weight length ratio for each animal.

FIGS. 13A–D. Genetic and physical map of the region surrounding the mg locus; all MIT markers are presented with shortened names, e.g., D2MIT77 is indicated as D2M77; locations of loci which also mapped on the human cytogenetic map are indicated in parentheses after the gene symbol.

A. The genetic map of the mg gene region on the Millennium BSB mapping panel (Misumi, D. J. et al., 1997, *Science* 278:135–138);

B. The genetic map obtained from crosses segregating mg mutant alleles;

C. The ~1 Mb BAC contig across the mg gene region of mouse Chromosome 2;

D. The transcriptional units identified in the mg region; the filled box indicates the mg gene, whereas the hatched box is a member of the High Mobility Group (HMG) gene family which sits between coding exons 21 and 22 of the mg gene.

Figure 14:
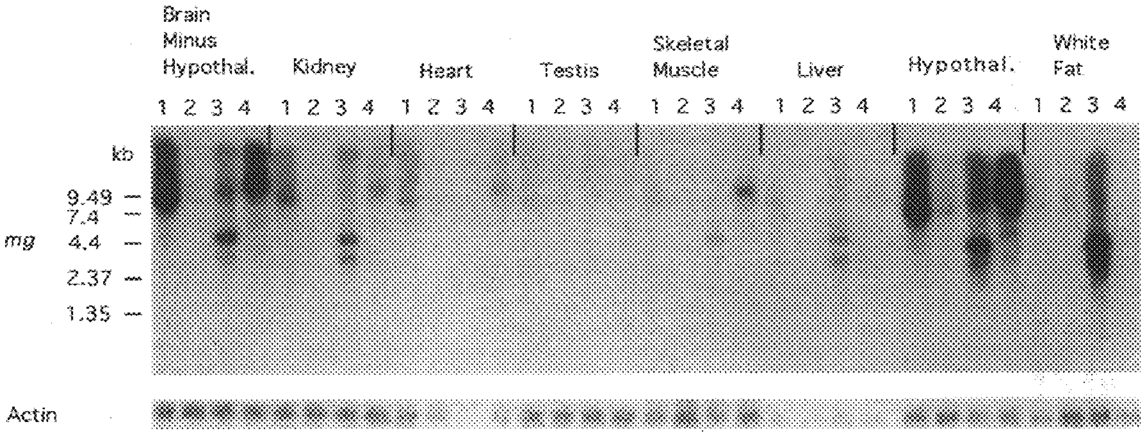

FIG. 14. Northern blot analysis with C3H/HeJ (lane 1), and three mutant alleles of mg: C3HeB/FeJ-$mg^{3J}$ (Lane 2), LDJ/Le-mg (Lane 3), and C3H/HeJ-$m^{J}$ (Lane 4); the size marker is shown on the left, and hybridization with actin is shown below for loading comparisons.

FIG. 15. In situ hybridization data: FIG. 15A demonstrates widespread expression of mg throughout the mouse brain is seen in an antisense autoradiographic image of a C3H/HeJ brain at the level of the 3rd ventricle; decreased expression in mg mutants is documented in selected antisense darkfield images of 10 μm whole mount cross sections of the ventromedial hypothalamic nucleic (VMH) of C3H/HeJ (FIG. 15B), LDJ/Le-mg (FIG. 15C), and C3HeB/FeJ-$m^{3J}$ (FIG. 15D).

Figure 16B:
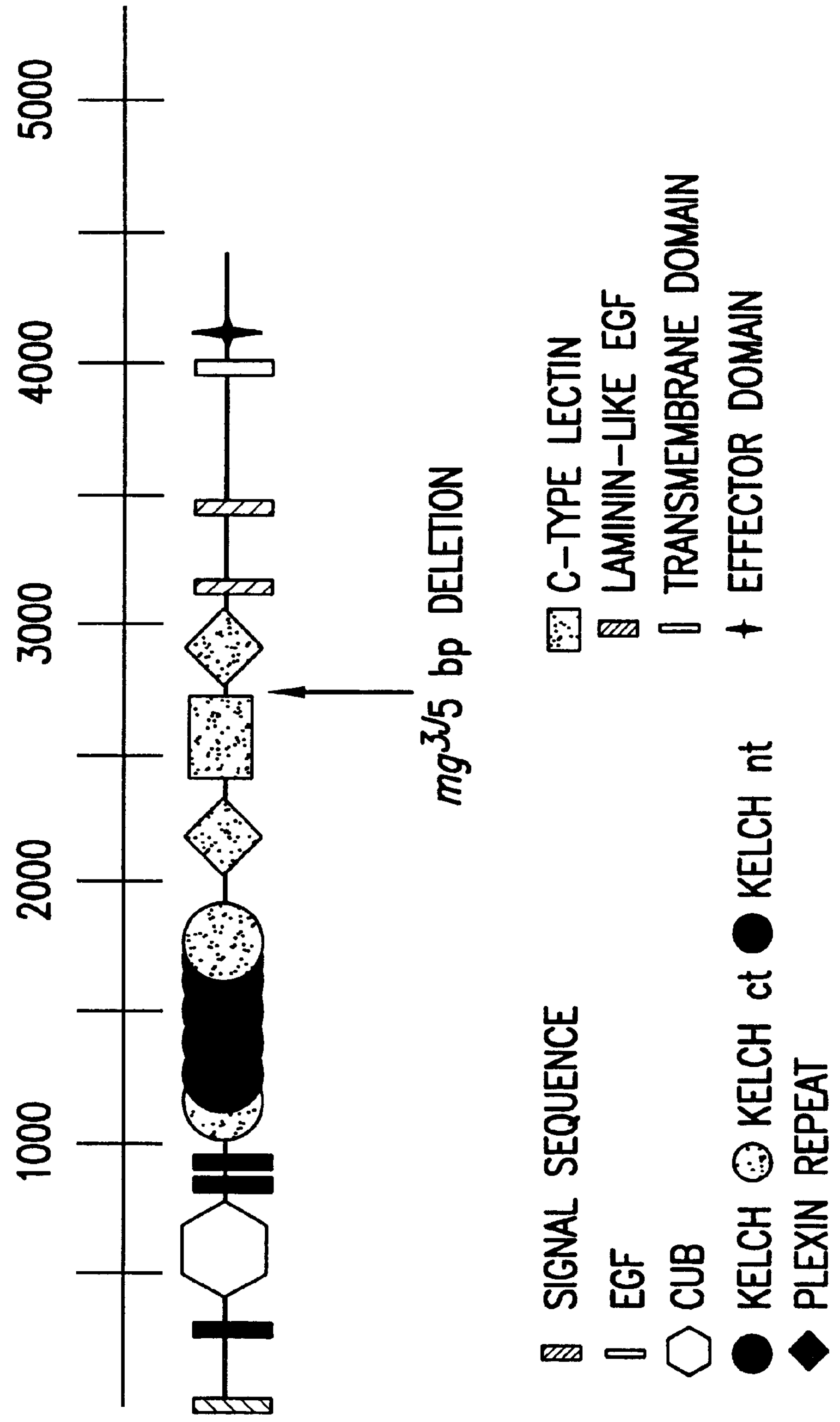

FIG. 16. Alignment of the MG protein sequence with its family members showing the transmembrane region (indicated in brackets) and cytoplasmic tail (FIG. 16A); and a schematic of the molecular modular architecture of MG (FIG. 16B).

FIGS. 17A–D. Sequence alignment of the predicted MG protein sequence (top) with the Attractin protein sequence. Characteristic MG domains are as indicated. See Section 10.2 for details.

FIGS. 18A–D. Panel A, cDNA nucleotide sequence (SEQ ID NO: 14) of the long splice variant of the human ortholog of the mahogany gene, and Panel B, the derived amino acid sequence (SEQ ID NO: 15) of the mahogany gene product which it encodes.

FIGS. 19A–D. Panel A–C, cDNA nucleotide sequence (SEQ ID NO: 16) of a shorter splice variant of the human ortholog of the mahogany gene, and Panel D, the derived amino acid sequence (SEQ ID NO: 17) of the mahogany gene product which it encodes.

FIGS. 20A–C. Panel A–B, cDNA nucleotide sequence (SEQ ID NO: 18) of a second shorter splice variant of the human ortholog of the mahogany gene, and Panel C, the derived amino acid sequence (SEQ ID NO: 19) of the mahogany gene product which it encodes.

5. DETAILED DESCRIPTION OF THE INVENTION

Described herein is the identification of the novel mammalian mahogany (mg) gene, including the human mahogany gene, which is involved in the control of mammalian body weight. Also described are recombinant mammalian, including human mahogany DNA molecules, cloned genes, and degenerate variants thereof. The compositions of the present invention further include mg gene products (e.g., proteins) that are encoded by the mg DNA molecules of the invention, and the modulation of mg gene expression and/or mg gene product activity in the treatment of mammalian body weight disorders, including obesity, cachexia, and anorexia. Also described herein are antibodies against mg gene products (e.g., proteins), or conserved variants or fragments thereof, and nucleic acid probes useful for the identification of mg gene mutations, and the use of such nucleic acid probes in diagnosing mammalian body weight disorders, including obesity, cachexia, and anorexia. Further described are methods for the use of the mg gene and/or mg gene products in the identification of compounds which modulate the activity of the mg gene product.

5.1. The Mahogany Gene

The mahogany genes are novel mammalian genes involved in the control of body weight. The nucleic acid sequences of the mahogany genes, including the murine mahogany gene (SEQ ID NO: 1) shown in FIG. 2A (with splice variants shown in FIGS. 8A–C and 9A) are described herein. The genomic sequence and structure, i.e., the intron/exon structure, of the mahogany genes have also been elucidated, FIG. 3.

The mahogany gene nucleic acid molecules of the present invention comprise: (a) the DNA sequence shown in FIG. 2 (SEQ ID NO: 1), or any DNA sequence that encodes the amino acid sequence of the mahogany gene product shown in FIG. 2, (SEQ ID NO: 2); (b) nucleotide sequences comprising the novel mahogany sequences disclosed herein that encode mutants of the mahogany gene product in which all or a part of one or more of the domains is deleted or altered, FIG. 6; (c) nucleotide sequences that encode fusion proteins comprising a mahogany gene product, or one of its domains fused to a heterologous polypeptide; and (d) nucleotide sequences within a mahogany gene, nucleotide sequences on the chromosome flanking the mahogany gene, FIG. 3, which can be utilized as part of the methods of the invention for identifying and diagnosing individuals who exhibit or are susceptible to weight disorders, including obesity, cachexia, and anorexia.

The mahogany nucleotide sequences of the invention further comprise: (a) any nucleotide sequence that hybridizes to the complement of a nucleic acid molecule that encodes a mahogany gene product under highly stringent conditions , e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & Sons, Inc., New York, at p. 2.10.3) particularly human mg sequences, FIG. 10; and (b) any nucleotide sequence that hybridizes to the complement of a nucleic acid molecule that encodes a mahogany gene product under less stringent conditions, such as moderately stringent conditions, e.g.,washing in 0.2×SSC/0.1% SDS at 42° C. (Ausubel et al., 1989, supra), yet which still encodes a functionally equivalent mahogany gene product.

"Functionally equivalent", as utilized herein, refers to a gene product (e.g., a protein) capable of exhibiting a substantially similar in vivo activity as the endogenous mg gene products encoded by the mg gene sequences described above. The in vivo activity of the mg gene product, as used herein, refers to the ability of the mg gene product, when present in an appropriate cell type, to ameliorate, prevent, or delay the appearance of the mahogany phenotype relative to its appearance when that cell type lacks a functional mahogany gene product.

The invention also includes nucleic acid molecules, preferably DNA molecules, that are the complements of the nucleotide sequences described above. Among the nucleic acid molecules of the invention are deoxyoligonucleotides ("oligos") which hybridize under highly stringent or moderately stringent conditions to the mahogany nucleic acid molecules described above. Exemplary highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as antisense molecules, useful, for example, in mahogany gene regulation, and/or as antisense primers in amplification reactions of mahogany gene nucleic acid sequences. With respect to mahogany gene regulation, such techniques can be used to regulate, for example, weight disorders such as obesity, cachexia, or anorexia. Such sequences may also be used as part of ribozyme and/or triple helix sequences, which are also useful for mahogany gene regulation. Still further, such molecules may be used as components of diagnostic methods whereby, for example, the presence of a particular mahogany allele associated with a weight disorder, such as obesity, cachexia, or anorexia, may be detected. Among the molecules which can be used for diagnostic methods, such as those which involve amplification of genomic mahogany sequences, are primers or probes that can routinely be obtained using the genomic and cDNA sequences disclosed herein.

The nucleotide sequences of the present invention also include (a) DNA vectors that contain any of the foregoing mahogany coding sequences and/or their complements; (b) DNA expression vectors that contain any of the foregoing mahogany coding sequences operatively associated with a regulatory element that directs the expression of the coding sequences; and (c) genetically engineered host cells and organisms that contain any of the foregoing mahogany coding sequences operatively associated with a regulatory element that directs the expression of the coding sequence in the host cell. As used herein, regulatory elements include, but are not limited to inducible and non-inducible promoters, enhancers, operators, and other elements known to those skilled in the art that drive and regulate gene expression. Such regulatory elements include, but are not limited to, the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3'-phosphoglycerate kinase, the promoters of acid phosphatase, and the promoters of the yeast alpha-mating factors.

In addition to the mahogany gene sequences described above, homologs of such sequences, exhibiting extensive homology to one or more domains of the mahogany gene product can be present in other species. In a preferred embodiment, the mahogany gene homologue maps to a chromosomal region that is syntenic to the chromosomal region of the mahogany gene. In a particularly preferred embodiment, a human mahogany gene homologue sequence maps to a human chromosome region that is syntenic to the region of mouse chromosome 2 to which the murine mahogany gene maps, namely 20p15, and comprises the contiged human MG cDNA provided herein. Further, there can also exist homologue genes at other genetic loci within the genome of the same species which encode proteins having extensive homology to one or more domains of the mahogany gene product. Such mahogany homologs can include, for example, secreted forms of the mahogany sequences, see, e.g., Duke-Cohan, J. S. et al. (1998*, Proc. Natl. Acad. Sci. U.S.A.* 95:11336–11341). Such sequences, can be used, for example, in the screening assays, described in Section 5.4.2 below, for compounds that interact with the mahogany gene and/or its gene product and that may therefore be useful in treating and ameliorating body weight disorders.

Other mahogany homologs can be identified and readily isolated, without undue experimentation, by molecular biological techniques well known in the art, and are therefore within the scope of the present invention. As an example, in order to clone a human mahogany gene homologue using isolated murine mahogany gene sequences, such murine mahogany gene sequences may be labeled and used to screen a cDNA library constructed from mRNA obtained from appropriate cells or tissues derived from the organism (in this case, human) of interest. With respect to the cloning of such a human mahogany homologue, a human cDNA library may, for example be used for screening, such as a cDNA library obtained from mRNA isolated from brain tissues, particularly containing hypothalamic regions.

The hybridization washing conditions used should be of a lower stringency when the cDNA library is derived from an organism different from the type of organism from which the labeled sequence was derived. With respect to the cloning of a human mahogany homologue, for example, hybridization can be performed for 4 hours at 65° C. using Amersham Rapid Hyb™ buffer (Cat. #RPN1639) according to manufacturer's protocol, followed by washing, with a final washing stringency of 1.0×SSC/0.1% SDS at 50° C. for 20 minutes being preferred.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

Alternatively, the labeled fragment may be used to screen a genomic library derived from the organism of interest, again, using appropriately stringent conditions.

Further, a mahogany gene homologue may be isolated from nucleic acid of the organism of interest by performing PCR using two degenerate oligonucleotide primer pools designed on the basis of amino acid sequences within the mahogany gene product disclosed herein. The template for the reaction may be cDNA obtained by reverse transcription of mRNA prepared from, for example, human or non-human cell lines or tissue known or suspected to express a mahogany gene allele.

The PCR product may be subcloned and sequenced to ensure that the amplified sequences represent the sequences of a mahogany gene nucleic acid sequence. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library. This method has been used to isolate sequences encoding each of the murine MG gene exons as well as to isolate contigs containing the human MG sequences provided herein, FIG. 10.

PCR technology may also be utilized to isolate full length cDNA sequences. For example, RNA may be isolated, following standard procedures, from an appropriate cellular or tissue source (i.e., one known, or suspected, to express the mahogany gene). A reverse transcription reaction may be performed on the RNA using an oligonucleotide primer specific for the most 5' end of the amplified fragment for the priming of the first strand synthesis. The resulting RNA/DNA hybrid may then be "tailed" with guanines using a standard terminal transferase reaction, they hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989 supra.

Mahogany gene sequences may additionally be used to isolate mutant mahogany alleles. Such mutant alleles may be isolated from individuals either known or proposed to have a phenotype which contributes to the symptoms of body weight disorders such as obesity, cachexia, or anorexia or disorders associated with hyperphagia. Mutant alleles and mutant allele products may then be utilized in the therapeutic and diagnostic systems described below. Additionally, such mahogany gene sequences can be used to detect mahogany gene regulatory (e.g. promoter) defects which can affect body weight.

A cDNA of a mutant mahogany gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in an individual putatively carrying the mutant mahogany allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant mahogany allele to that of the normal mahogany allele, the mutation(s) responsible for the loss of alteration of activity of the mutant mahogany gene product can be ascertained.

Alternatively, a genomic library can be constructed using DNA obtained from an individual suspected of or known to carry the mutant mahogany allele, or a cDNA library can be constructed using RNA from a tissue known, or suspected to express the mutant mahogany allele. The normal mahogany gene or any suitable fragment thereof may then be labeled and used as a probe to identify the corresponding mutant mahogany allele in such libraries. Clones containing the mutant mahogany gene sequences may then be purified and subjected to sequence analysis according to methods well known to those of skill in the art.

Additionally, an expression library can be constructed utilizing cDNA synthesized from, for example, RNA isolated from a tissue known, or suspected to express a mutant mahogany allele in an individual suspected of or known to carry such a mutant allele. In this manner, gene products made by the putatively mutant tissue may be expressed and screened using standard antibody screening techniques in conjunction with antibodies raised against the normal mahogany gene product as described, below, in Section 5.3. For screening techniques, see, for example, Harlow, E. and Lane, eds., 1988, "Antibodies: A Laboratory Manual", Cold Spring Harbor Press, Cold Spring Harbor. In cases where a mahogany mutation results in an expressed gene product with altered function (e.g., as a result of a missense or a frameshift mutation) a polyclonal set of anti-mahogany gene product antibodies are likely to cross-react with the mutant mahogany gene product. Library clones detected via their reaction with such labeled antibodies can be purified and subjected to sequence analysis according to methods well known to those of skill in the art.

5.2. Protein Products of the Mahogany Gene

Mahogany gene products (e.g., proteins), polypeptides and peptide fragments, mutant, truncated, or deleted forms of the mahogany gene product, and/or fusion proteins of the mahogany gene product can be prepared for a variety of uses. For example, such gene products, or peptide fragments thereof, can be used for the generation of antibodies in diagnostic assays, or for the identification of other cellular or extracellular products involved in the regulation of mammalian body weight.

FIG. 2 shows the amino acid sequence (SEQ ID NO: 2) of the murine form of a mahogany gene product. Mahogany gene products, also referred to herein as mahogany proteins, of the present invention additionally include those gene products encoded by the mahogany gene sequences described in Section 5.1, above, particularly the human homologue of the murine mg gene, a fragment of which is shown in FIG. 10.

In addition, mahogany gene products may include proteins that represent functionally equivalent gene products. Such an equivalent mahogany gene product may contain deletions, including internal deletions, additions, including additions yielding fusion proteins, or substitutions of amino acid residues within and/or adjacent to the amino acid sequence encoded by the mahogany gene sequences described, in Section 5.1, above, but that result in a "silent" change, in that the change produces a functionally equivalent mahogany gene product. Such amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

"Functionally equivalent", as utilized herein, refers to a gene product (e.g., a protein) capable of exhibiting a substantially similar in vivo activity as the endogenous mg gene products encoded by the mg gene sequences described in Section 5.1, above. The in vivo activity of the mg gene product, as used herein, refers to the ability of the mg gene product, when present in an appropriate cell type, to ameliorate, prevent, or delay the appearance of the mahogany phenotype relative to its appearance when that cell type lacks a functional mahogany gene product.

Alternatively, where alteration of function is desired, deletion or non-conservative alterations can produce altered, including reduced-activity, mahogany gene products. Such alterations can, for example, alter one or more of the biological functions of the mahogany gene product. Further, such alterations can be selected so as to generate mahogany gene products that are better suited for expression, scale up, etc. in the host cells chosen. For example, cysteine residues can be deleted or substituted with another amino acid residue in order to eliminate disulfide bridges.

As another example, altered mahogany gene products can be engineered that correspond to mutants or variants of the mahogany gene product associated with mammalian weight disorders, such as obesity, cachexia, or anorexia. Altered mahogany gene products can also be engineered that correspond to mutants or variants of the mahogany gene product known to neutralize or ameliorate the symptoms of body weight disorders, such as obesity, cachexia, or anorexia, which are mediated by some other gene, including, but not limited to, body weight disorders mediated by the agouti gene.

Also within the scope of the present invention are peptides and/or proteins corresponding to one or more domains of the mahogany protein or any one of the individual exon encoded regions of the MG protein, as well as fusion proteins in which the full length mahogany protein, a mahogany peptide, or a truncated mahogany protein or peptide is fused to an unrelated heterologous protein. Such proteins and peptides can be designed on the basis of the mahogany nucleotide sequence disclosed in Section 5.1, above, and/or on the basis of the mahogany amino acid sequence disclosed in the Section.

Fusion proteins of the invention include, but are not limited to, IgFc fusions which stabilize the mahogany protein or peptide and prolong half life in vivo; or fusions to any amino acid sequence that allows the fusion protein to be anchored to the cell membrane; or fusions to an enzyme, fluorescent protein, or luminescent protein which provides a marker function.

The mahogany gene products, peptide fragments thereof and fusion proteins thereof, may be produced by recombinant DNA technology using techniques well known in the art. Thus, methods for preparing the mahogany gene products, polypeptides, peptides, fusion peptide and fusion polypeptides of the invention by expressing nucleic acid containing mahogany gene sequences are described herein. Methods that are well known to those skilled in the art can be used to construct expression vectors containing mahogany gene product coding sequences and appropriate transcriptional and translational control signals. These methods include, for example, in vitro recombinant DNA techniques, synthetic techniques, and in vivo genetic recombination. See, for example, the techniques described in Sambrook, et al., 1989, supra, and Ausubel, et al., 1989, supra. Alternatively, RNA capable of encoding mahogany gene product sequences may be chemically synthesized using, for example, synthesizers. See, for example, the techniques described in "Oligonucleotide Synthesis", 1984, Gait, ed., IRL Press, Oxford.

A variety of host-expression vector systems may be utilized to express the mahogany gene product coding sequences of the invention. Such host-expression systems represent vehicles by which the coding sequences of interest may be produced and subsequently purified, but also represent cells that may, when transformed or transfected with the appropriate nucleotide coding sequences, exhibit the mahogany gene product of the invention in situ. These include but are not limited to microorganisms such as bacteria (e.g., *E. coli, B. subtilis*) transformed with recombinant bacteriophage DNA, plasmid DNA or cosmid DNA expression vectors containing mahogany gene product coding sequences; yeast (e.g., Saccharomyces, Pichia) transformed with recombinant yeast expression vectors containing the mahogany gene product coding sequences; insect cell systems infected with recombinant virus expression vectors (e.g., baculovirus) containing the mahogany gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing mahogany gene product coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the mahogany gene product being expressed. For example, when a large quantity of such a protein is to be produced, for the generation of pharmaceutical compositions of mahogany gene product or for raising antibodies to mahogany gene product, for example, vectors that direct the expression of high levels of fusion protein products that are readily purified may be desirable. Such vectors include, but are not limited, to the *E. coli* expression vector pUR278 (Ruther et al., 1983, EMBO J. 2, 1791), in which the mahogany gene product coding sequence may be ligated individually into the vector in frame with the lac Z coding region so that a fusion protein is produced; pIN vectors (Inouye and Inouye, 1985, Nucleic Acids Res. 13, 3101–3109; Van Heeke and Schuster, 1989, J. Biol. Chem. 264, 5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica*, nuclear polyhidrosis virus (AcNPV) is used as a vector to express foreign genes. The virus grows in *Spodoptera frugiperda* cells. The mahogany gene product coding sequence may be cloned individually into non-essential regions (for example the polyhedrin gene) of the virus and placed under control of an AcNPV promoter (for example the polyhedrin promoter). Successful insertion of mahogany gene product coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith, et al., 1983, J. Virol. 46, 584; Smith, U.S. Pat. No. 4,215,051).

In mammalian host cells, a number of viral-based expression systems may be utilized. In cases where an adenovirus is used as an expression vector, the mahogany gene product coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing mahogany gene product in infected hosts. (e.g., See Logan and Shenk, 1984, Proc. Natl. Acad. Sci. USA 81, 3655–3659). Specific initiation signals may also be required for efficient translation of inserted mahogany gene product coding sequences. These signals include the ATG initiation codon and adjacent sequences. In cases where an entire mahogany gene, including its own initiation codon and adjacent sequences, is inserted into the appropriate expression vector, no additional translational control signals may be needed. However, in cases where only a portion of the mahogany gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner, et al., 1987, Methods in Enzymol. 153, 516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, and WI38.

For long-term, high-yield production of recombinant proteins, stable expression is preferred. For example, cell lines that stably express the mahogany gene product may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express the mahogany gene product. Such engineered cell lines may be particularly useful in screening and evaluation of compounds that affect the endogenous activity of the mahogany gene product.

A number of selection systems may be used, including but not limited to the herpes simplex virus thymidine kinase (Wigler, et al., 1977, Cell 11, 223), hypoxanthine-guanine phosphoribosyltransferase (Szybalska and Szybalski, 1962, Proc. Natl. Acad. Sci. USA 48, 2026), and adenine phosphoribosyltransferase (Lowy, et al., 1980, Cell 22, 817) genes can be employed in $tk^-$, $hgprt^-$ or $aprt^-$ cells, respectively. Also, antimetabolite resistance can be used as the basis of selection for the following genes: dhfr, which confers resistance to methotrexate (Wigler, et al., 1980, Natl. Acad. Sci. USA 77, 3567; O'Hare, et al., 1981, Proc. Natl. Acad. Sci. USA 78, 1527); gpt, which confers resistance to mycophenolic acid (Mulligan and Berg, 1981, Proc. Natl. Acad. Sci. USA 78, 2072); neo, which confers resistance to the aminoglycoside G-418 (Colberre-Garapin, et al., 1981, J. Mol. Biol. 150, 1); and hygro, which confers resistance to hygromycin (Santerre, et al., 1984, Gene 30, 147).

Alternatively, the expression characteristic of an endogenous mahogany gene within a cell line or microorganism my be modified by inserting a heterologous DNA regulatory element into the genome of a stable cell line or cloned microorganism such that the inserted regulatory element is operatively linked with the endogenous mahogany gene. For example, an endogenous mahogany gene which is normally "transcriptionally silent", i.e., a mahogany gene which is normally not expressed, or is expressed only a very low levels in a cell line or microorganism, may be activated by inserting a regulatory element which is capable of promoting the expression of a normally expressed gene product in that cell line or microorganism. Alternatively, a transcriptionally silent, endogenous mahogany gene may be activated by insertion of a promiscuous regulatory element that works across cell types.

A heterologous regulatory element may be inserted into a stable cell line or cloned microorganism, such it is operatively linked with an endogenous mahogany gene, using techniques, such as targeted homologous recombination, which are well known to those of skill in the art, and described e.g., in Chappel, U.S. Pat. Nos. 4,215,051; 5,578,461 to Sherwin et al.; International Application No. PCT/US92/09627 (WO93/09222) by Selden et al.; and International Application No. PCT/US90/06436 (WO91/06667) by Skoultchi et al., each of which is incorporated by reference herein in its entirety.

Alternatively, any fusion protein may be readily purified by utilizing an antibody specific for the fusion protein being expressed. For example, a system described by Janknecht, et al. allows for the ready purification of non-denatured fusion proteins expressed in human cell lines (Janknecht, et al., 1991, Proc. Natl. Acad. Sci. USA 88, 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$.nitriloacetic acid-agarose columns and histidine-tagged proteins are selectively eluted with imidazole-containing buffers.

The mahogany gene products can also be expressed in transgenic animals. Animals of any species, including, but not limited to, mice, rats, rabbits, guinea pigs, pigs, micro-pigs, goats, sheep, and non-human primates, e.g., baboons, monkeys, and chimpanzees may be used to generate mahogany transgenic animals. The term "transgenic," as used herein, refers to animals expressing mahogany gene sequences from a different species (e.g., mice expressing human mahogany gene sequences), as well as animals that have been genetically engineered to over express endogenous (i.e., same species) mahogany sequences or animals that have been genetically engineered to no longer express endogenous mahogany gene sequences (i.e., "knock-out" animals), and their progeny.

Any technique known in the art may be used to introduce a mahogany gene transgene into animals to produce the founder lines of transgenic animals. Such techniques include, but are not limited to pronuclear microinjection (Hoppe and Wagner, 1989, U.S. Pat. No. 4,873,191); retrovirus mediated gene transfer into germ lines (Van der Putten, et al., 1985, Proc. Natl. Acad. Sci., USA 82, 6148–6152); gene targeting in embryonic stem cells (Thompson, et al., 1989, Cell 56, 313–321); electroporation of embryos (Lo, 1983, Mol. Cell. Biol. 3, 1803–1814); and sperm-mediated gene transfer (Lavitrano et al., 1989, Cell 57, 717–723) (For a review of such techniques, see Gordon, 1989, Transgenic Animals, Intl. Rev. Cytol. 115, 171–229).

Any technique known in the art may be used to produce transgenic animal clones containing a mahogany transgene, for example, nuclear transfer into enucleated oocytes of nuclei from cultured embryonic, fetal or adult cells induced to quiescence (Campbell, et al., 1996, Nature 380, 64–66; Wilmut, et al., Nature 385, 810–813).

The present invention provides for transgenic animals that carry a mahogany transgene in all their cells, as well as animals that carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, et al., 1992, Proc. Natl. Acad. Sci. USA 89, 6232–6236). The regulatory sequences required for such a cell-type specific activation will depend upon the particular cell type of interest, and will be apparent to those of skill in the art. When it is desired that the mahogany transgene be integrated into the chromosomal site of the endogenous mahogany gene, gene targeting is preferred. Briefly, when such a technique is to be utilized, vectors containing some nucleotide sequences homologous to the endogenous mahogany gene are designed for the purpose of integrating, via homologous recombination with chromosomal sequences, into and disrupting the function of the nucleotide sequence of the endogenous mahogany gene. The transgene may also be selectively introduced into a particular cell type, thus inactivating the endogenous mahogany gene in only that cell type, by following, for example, the teaching of Gu, et al. (Gu, et al., 1994, Science 265, 103–106). The regulatory sequences required for such a cell-type specific inactivation will depend upon the particular cell type of interest, and will be apparent to those of skill in the art.

Once transgenic animals have been generated, the expression of the recombinant mahogany gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include but are not limited to Northern blot analysis of tissue samples obtained from the animal, in situ hybridization analysis, and RT-PCR (reverse transcriptase PCR). Samples of mahogany gene-expressing tissue, may also be evaluated immunocytochemically using antibodies specific for the mahogany transgene product.

5 5.3. Antibodies to Mahogany Gene Products

Described herein are methods for the production of antibodies capable of specifically recognizing one or more mg gene product epitopes, or epitopes of conserved variants, or peptide fragments of the mg gene products. Further, antibodies that specifically recognize mutant forms of mg gene products, are encompassed by the invention.

Such antibodies may include, but are not limited to, polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above. Such antibodies may be used, for example, in the detection of a mg gene product in an biological sample and may, therefore, be utilized as part of a diagnostic or prognostic technique whereby patients may be tested for abnormal levels of mg gene products, and/or for the presence of abnormal forms of such gene products. Such antibodies may also be utilized in conjunction with, for example, compound screening schemes, as described, below, in Section 5.4.2, for the evaluation of the effect of test compounds on mg gene product levels and/or activity. Additionally, such antibodies can be used in conjunction with the gene therapy techniques described, below, in Section 5.4.3.2, to, for example, evaluate the normal and/or engineered mahogany-expressing cells prior to their introduction into the patient.

Anti-mg gene product antibodies may additionally be used in methods for inhibiting abnormal mg gene product activity. Thus, such antibodies may, therefore, be utilized as part of weight disorder treatment methods.

For the production of antibodies against a mg gene product, various host animals may be immunized by injection with a mg gene product, or a portion thereof. Such host animals may include, but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacteri um parvum.*

Polyclonal antibodies are heterogeneous populations of antibody molecules derived from the sera of animals immunized with an antigen, such as a mg gene product, or an antigenic functional derivative thereof. For the production of polyclonal antibodies, host animals such as those described above, may be immunized by injection with mg gene product supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to, the hybridoma technique of Kohler and Milstein, (1975, Nature 256, 495–497; and U.S. Pat. No. 4,376,110), the human B-cell hybridoma technique (Kosbor et al., 1983, Immunology Today 4, 72; Cole et al., 1983, Proc. Natl. Acad. Sci. USA 80, 2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison, et al., 1984, Proc. Natl. Acad. Sci., 81, 6851–6855; Neuberger, et al., 1984, Nature 312, 604–608; Takeda, et al., 1985, Nature, 314, 452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816397, which are incorporated herein by reference in their entirety.)

In addition, techniques have been developed for the production of humanized antibodies. (See, e.g., Queen, U.S. Pat. No. 5,585,089, which is incorporated herein by reference in its entirety.) An immunoglobulin light or heavy chain variable region consists of a "framework" region interrupted by three hypervariable regions, referred to as complementarily determining regions (CDRs). The extent of the framework region and CDRs have been precisely defined (see, "Sequences of Proteins of Immunological Interest", Kabat, E. et al., U.S. Department of Health and Human Services (1983). Briefly, humanized antibodies are antibody molecules from non-human species having one or more CDRs from the non-human species and a framework region from a human immunoglobulin molecule.

Alternatively, techniques described for the production of single chain antibodies (U.S. Pat. No. 4,946,778; Bird, 1988, Science 242, 423–426; Huston, et al., 1988, Proc. Natl. Acad. Sci. USA 85, 5879–5883; and Ward, et al., 1989, Nature 334, 544–546) can be adapted to produce single chain antibodies against mahogany gene products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the $F(ab')_2$ fragments, which can be produced by pepsin digestion of the antibody molecule and the Fab fragments, which can be generated by reducing the disulfide bridges of the $F(ab')_2$ fragments. Alternatively, Fab expression libraries may be constructed (Huse, et al., 1989, Science, 246, 1275–1281) to allow rapid and easy identification of monoclonal Fab fragments with the desired specificity.

5.4. Uses of the Mahognay Genes, Gene Products, and Antibodies

Described herein are various applications of the mahogany genes, of the mahogany gene products, including peptide fragments thereof, and of antibodies directed against mahogany gene products and peptide fragments thereof. Such applications include, for example, prognostic and diagnostic evaluation of body weight disorders and the identification of subjects with a predisposition to such disorders, as described below, in Section 5.4.1. Additionally, such applications include methods for the treatment of body weight and body weight disorders, as described, below, in Section 5.4.2, and for the identification of compounds which modulate the expression of the mahogany gene and/or the activity of the mahogany gene product, as described in Section 5.4.3, below. Such compounds can include, for example, other cellular products which are involved in body weight regulation. These compounds can be used, for example, in the amelioration of body weight disorders, including obesity, cachexia, and anorexia.

While, for clarity, the uses described in this section are primarily uses related to body weight disorder abnormalities, it is to be noted that each of the diagnostic and therapeutic treatments described herein can additionally be utilized in connection with other defects associated with the mahogany gene, such as hyperpigmentation, hyperphagia and other disorders resulting in increased metabolic rates.

5.4.1. Diagnosis of Body Weight Disorder Abnormalities

A variety of methods can be employed for the diagnostic and prognostic evaluation of body weight disorders, including obesity, cachexia, and anorexia, and for the identification of subjects having a predisposition to such disorders.

Such methods may, for example, utilize reagents such as the mahogany gene nucleotide sequences described in Section 5.1, and antibodies directed against mahogany gene products, including peptide fragments thereof, as described, above, in Section 5.3. Specifically, such reagents may be used, for example, for:

(1) the detection of the presence of mahogany gene mutations, or the detection of either over- or under-expression of mahogany gene relative to levels of mahogany expression in a wild-type, non-body weight disorder state which correlates with certain body weight disorders or susceptibility toward such body weight disorders;

(2) the detection of over- or under-abundance of mahogany gene product relative to the abundance of mahogany gene product in a wild-type non-body weight disorder state which correlates with certain body weight disorders or susceptibility toward such body weight disorders; and (3) the detection of an aberrant level of mahogany gene product activity relative to mahogany gene product activity levels in a wild-type, non-body weight disorder state which correlates with certain body weight disorders or susceptibility toward such body weight disorders.

Mahogany gene nucleotide sequences can, for example, be used to diagnose a body weight disorder using, for example, the techniques for detecting mutations in the mahogany gene described above in Section 5.1, above.

The methods described herein may be performed, for example, by utilizing pre-packaged diagnostic kits comprising at least one specific mahogany gene nucleic acid or anti-mahogany gene product antibody reagent described herein, which may be conveniently used, e.g., in clinical settings, to screen and diagnose patients exhibiting body weight disorder abnormalities, and to screen those individuals exhibiting a predisposition to developing a body weight disorder abnormality.

For the detection of mahogany gene mutations, any nucleated cell can be used as a starting source for genomic nucleic acid. For the detection of mahogany gene expression or mahogany gene products, any cell type or tissue in which the mahogany gene is expressed may be utilized, such as, for example, tissues or cells shown herein to express the MG gene.

Nucleic acid-based detection techniques are described, below, in Section 5.4.1.1. Peptide detection techniques are described, below, in Section 5.4.1.2.

5.4.1.1. Detection of Mahogany Gene Nucleic Acid Molecules

Mutations or polymorphisms within the mahogany gene can be detected by utilizing a number of techniques. Nucleic acid from any nucleated cell can be used as the starting point for such assay techniques, and may be isolated according to standard nucleic acid preparation procedures which are well known to those of skill in the art.

Genomic DNA may be used in hybridization or amplification assays of biological samples to detect abnormalities involving mahogany gene structure, including point mutations, insertions, deletions and chromosomal rearrangements. Such assays may include, but are not limited to, Southern analyses, single stranded conformation polymorphism analyses (SSCP), and PCR analyses.

Diagnostic methods for the detection of mahogany gene-specific mutations can involve for example, contacting and incubating nucleic acids obtained from a sample, e.g., derived from a patient sample or other appropriate cellular source with one or more labeled nucleic acid reagents including recombinant DNA molecules, cloned genes or degenerate variants thereof, such as described in Section 5.1, above, under conditions favorable for the specific annealing of these reagents to their complementary sequences within or flanking the mahogany gene. Preferably, the lengths of these nucleic acid reagents are at least 15 to nucleotides.

After incubation, all non-annealed nucleic acids are removed from the nucleic acid:mahogany molecule hybrid. The presence of nucleic acids that have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described in Section 5.1 are easily removed. Detection of the remaining, annealed, labeled mahogany nucleic acid reagents is accomplished using standard techniques well-known to those in the art. The mahogany gene sequences to which the nucleic acid reagents have annealed can be compared to the annealing pattern expected from a normal mahogany gene sequence in order to determine whether a mahogany gene mutation is present.

In a preferred embodiment, mahogany gene mutations or polymorphisms can be detected by using a microassay of mahogany nucleic acid sequences immobilized to a substrate or "gene chip" (see, e.g. Cronin, et al., 1996, Human Mutation 7:244–255).

Alternative diagnostic methods for the detection of mahogany gene specific nucleic acid molecules, in patient samples or other appropriate cell sources, may involve their amplification, e.g., by PCR (the experimental embodiment set forth in Mullis, 1987, U.S. Pat. No. 4,683,202), followed by the analysis of the amplified molecules using techniques well known to those of skill in the art, such as, for example, those listed above. The resulting amplified sequences can be compared to those that would be expected if the nucleic acid being amplified contained only normal copies of the mahogany gene in order to determine whether a mahogany gene mutation exists.

Among those mahogany nucleic acid sequences which are preferred for such amplification-related diagnostic screening analyses are oligonucleotide primers which amplify mahogany exon sequences. The sequences of such oligonucleotide primers are, therefore, preferably derived from mahogany intron sequences so that the entire exon, or coding region, can be analyzed as discussed below. Primer pairs useful for amplification of mahogany exons are preferably derived from adjacent introns. Appropriate primer pairs can be chosen such that each of the 25 mahogany exons are amplified. Primers for the amplification of mahogany exons can be routinely designed by one of ordinary skill in the art by utilizing the exon and intron sequences of mahogany shown in Figures, particularly FIGS. 3 and 5.

Additional mahogany nucleic acid sequences which are preferred for such amplification-related analyses are those which will detect the presence of a mahogany polymorphism which differs from the consensus mahogany sequence depicted in Figures, particularly those that detect the polymorphism identified in exon 15 (FIG. 7). Such polymorphisms include ones which represent mutations associated with body weight disorders such as obesity, cachexia, or anorexia.

Further, well-known genotyping techniques can be performed to type polymorphisms that are in close proximity to mutations in the mahogany gene itself, including mutations associated with weight disorders such as obesity, cachexia, or anorexia. Such polymorphisms can be used to identify individuals in families likely to carry mutations in the mahogany gene. If a polymorphism exhibits linkage isequilibrium with mutations in the mahogany gene, the polymorphism can also be used to identify individuals in the general population who are likely to carry such mutations. polymorphisms that can be used in this way include restriction fragment length polymorphisms (RFLPs), which involve sequence variations in restriction enzyme target sequences, single-base polymorphisms, and simple sequence length polymorphisms (SSLPs).

For example, Weber (U.S. Pat. No. 5,075,217) describes a DNA marker based on length polymorphisms in blocks of (dC-A)n-(dG-dT)n short tandem repeats. The average separation of (dC-dA)n-(dG-dT)n blocks is estimated to be 30,000–60,000 bp. Markers that are so closely spaced exhibit a high frequency co-inheritance, and are extremely useful in the identification of genetic mutations, such as, for example, mutations within the mahogany gene, and the diagnosis of diseases and disorders related to mutations in the mahogany gene.

Also, Caskey et al. (U.S. Pat. No. 5,364,759) describe a DNA profiling assay for detecting short tri and tetra nucleotide repeat sequences. The process includes extracting the DNA of interest, such as the mahogany gene, amplifying the extracted DNA, and labelling the repeat sequences to form a genotypic map of the individual's DNA.

A mahogany probe could additionally be used to directly identify RFLPs. Further, a mahogany probe or primers derived from the mahogany sequence could be used to isolate genomic clones such as YACs, BACs, PACs, cosmids, phage, or plasmids. The DNA contained in these clones can be screened for single-base polymorphisms or SSLPs using standard hybridization or sequencing procedures.

The level of mahogany gene expression can also be assayed. For example, RNA from a cell type or tissue known, or suspected, to express the mahogany gene, such as muscle, brain, kidney, testes, heart, liver, lung, skin, hypothalamus, spleen, and adipose tissue may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the mahogany gene. Such analyses may reveal both quantitative and qualitative aspects of the expression pattern of the mahogany gene, including activation or inactivation of mahogany gene expression.

In one embodiment of such a detection scheme, a cDNA molecule is synthesized from an RNA molecule of interest (e.g., by reverse transcription of the RNA molecule into cDNA). All or part of the resulting cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the mahogany gene nucleic acid reagents described in Section 5.1. The preferred lengths of such nucleic acid reagents are at least 9–30 nucleotides.

For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

As an alternative to amplification techniques, standard Northern analyses can be performed to determine the level of mRNA expression of the mahogany gene, if a sufficient quantity of the appropriate cells can be obtained.

Additionally, it is possible to perform such mahogany gene expression assays "in situ", i.e., directly upon tissue sections (fixed and/or frozen) of patient tissue obtained from biopsies or resections, such that no nucleic acid purification is necessary. Nucleic acid reagents such as those described in Section 5.1 may be used as probes and/or primers for such in situ procedures (see, for example, Nuovo, G. J., 1992, "PCR In Situ Hybridization: Protocols And Applications", Raven Press, New York).

5.4.1.2.Detection of Mahogany Gene Products

Mahogany gene products, including both wild-type and mutant mahogany gene products, conserved variants, and polypeptide fragments thereof, which are discussed, above, in Section 5.2, may be detected using antibodies which are directed against such mahogany gene products. Such antibodies, which are discussed in Section 5.3, below, may thereby be used as diagnostics and prognostics for a body weight disorder. Such methods may be used to detect abnormalities in the level of mahogany gene expression or of mahogany gene product synthesis, or abnormalities in the structure, temporal expression, and/or physical location of mahogany gene product. The antibodies and immunoassay methods described herein have, for example, important in vitro applications in assessing the efficacy of treatments for body weight disorders such as obesity, cachexia, and anorexia. Antibodies, or fragments of antibodies, such as those described below, may be used to screen potentially therapeutic compounds in vitro to determine their effects on mahogany gene expression and mahogany gene product production. The compounds that have beneficial effects on body weight disorders, such as obesity, cachexia, and anorexia, can thereby be identified, and a therapeutically effective dose determined.

In vitro immunoassays may also be used, for example, to assess the efficacy of cell-based gene therapy for a body weight disorders, including obesity, cachexia, and anorexia. Antibodies directed against mahogany gene products may be used in vitro to determine, for example, the level of mahogany gene expression achieved in cells genetically engineered to produce mahogany gene product. In the case of intracellular mahogany gene products, such an assessment is done, preferably, using cell lysates or extracts. Such analysis will allow for a determination of the number of transformed cells necessary to achieve therapeutic efficacy in vivo, as well as optimization of the gene replacement protocol.

The tissue or cell type to be analyzed will generally include those that are known, or suspected, to express the mahogany gene. The protein isolation methods employed herein may, for example, be such as those described in Harlow and Lane (1988, "Antibodies: A Laboratory Manual", Cold Spring Harbor Laboratory Press, Cold Spring Harbor, N.Y.). The isolated cells can be derived from cell culture or from a patient. The analysis of cells taken from culture may be a necessary step in the assessment of cells to be used as part of a cell-based gene therapy technique or, alternatively, to test the effect of compounds on the expression of the mahogany gene.

Preferred diagnostic methods for the detection of mahogany gene products, conserved variants or peptide fragments thereof, may involve, for example, immunoassays wherein the mahogany gene products or conserved variants or peptide fragments are detected by their interaction with an anti-mahogany gene product-specific antibody.

For example, antibodies, or fragments of antibodies, such as those described, above, in Section 5.3, may be used to quantitatively or qualitatively detect the presence of mahogany gene products or conserved variants or peptide fragments thereof. This can be accomplished, for example, by immunofluorescence techniques employing a fluorescently labeled antibody (see below, this Section) coupled with light microscopic, flow cytometric, or fluorimetric detection. Such techniques are especially preferred for mahogany gene products that are expressed on the cell surface.

The antibodies (or fragments thereof) useful in the present invention may, additionally, be employed histologically, as in immunofluorescence or immunoelectron microscopy, for in situ detection of mahogany gene products, conserved variants or peptide fragments thereof. In situ detection may be accomplished by removing a histological specimen from a patient, and applying thereto a labeled antibody that binds to a mahogany polypeptide. The antibody (or fragment) is preferably applied by overlaying the labeled antibody (or fragment) onto a biological sample. Through the use of such a procedure, it is possible to determine not only the presence of the mahogany gene product, conserved variants or peptide fragments, but also its distribution in the examined tissue. Using the present invention, those of ordinary skill will readily recognize that any of a wide variety of histological methods (such as staining procedures) can be modified in order to achieve in situ detection of a mahogany gene product.

Immunoassays for mahogany gene products, conserved variants, or peptide fragments thereof will typically comprise: (1) incubating a sample, such as a biological fluid, a tissue extract, freshly harvested cells, or lysates of cells in the presence of a detectably labeled antibody capable of identifying mahogany gene products, conserved variants or peptide fragments thereof; and (2) detecting the bound antibody by any of a number of techniques well-known in the art.

The biological sample may be brought in contact with and immobilized onto a solid phase support or carrier, such as nitrocellulose, that is capable of immobilizing cells, cell particles or soluble proteins. The support may then be washed with suitable buffers followed by treatment with the detectably labeled mahogany gene product specific antibody. The solid phase support may then be washed with the buffer a second time to remove unbound antibody. The amount of bound label on the solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One of the ways in which the mahogany gene product-specific antibody can be detectably labeled is by linking the same to an enzyme, such as for use in an enzyme immunoassay (EIA) (Voller, A., "The Enzyme Linked Immunosorbent Assay (ELISA)", 1978, Diagnostic Horizons 2, 1–7, Microbiological Associates Quarterly Publication, Walkersville, Md.); Voller, A. et al., 1978, J. Clin. Pathol. 31, 507–520; Butler, J. E., 1981, Meth. Enzymol. 73, 482–523; Maggio, E. (ed.), 1980, Enzyme Immunoassay, CRC Press, Boca Raton, Fla.; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, α-glycerophosphate, dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect mahogany gene products through the use of a radioimmunoassay (RIA) (see, for example, Weintraub, B., Principles of Radioimmunoassays, Seventh Training Course on Radioligand Assay Techniques, The Endocrine Society, March, 1986). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}Eu$, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.4.2. Screening Assays for Compounds that Interact with the Mahogany Gene or Gene Product The following assays are designed to identify compounds that bind to a mahogany gene product, compounds that bind to proteins, or portions of proteins that interact with a mahogany gene product, compounds that interfere with the interaction of a mahogany gene product with proteins and compounds that modulate the activity of the mahogany gene (i.e., modulate the level of mahogany gene expression and/or modulate the level of mahogany gene product activity). Assays may additionally be utilized that identify compounds that bind to mahogany gene regulatory sequences (e.g., promoter sequences; see e.g., Platt, 1994, J. Biol. Chem. 269, 28558–28562), which is incorporated herein by reference in its entirety, and that can modulate the level of mahogany gene expression. Such compounds may include, but are not limited to, small organic molecules, such as ones that are able to cross the blood-brain barrier, gain to and/or entry into an appropriate cell and affect expression of the mahogany gene or some other gene involved in the body weight regulatory pathway, or intracellular proteins.

Methods for the identification of such proteins are described, below, in Section 5.4.2.2. Such proteins may be involved in the control and/or regulation of body weight. Further, among these compounds are compounds that affect the level of mahogany gene expression and/or mahogany gene product activity and that can be used in the therapeutic treatment of body weight disorders, including obesity, cachexia, and anorexia, as described, below, in Section 5.9.

Compounds may include, but are not limited to, peptides such as, for example, soluble peptides, including but not limited to, Ig-tailed fusion peptides, and members of random peptide libraries; (see, e.g., Lam, et al., 1991, Nature 354, 82–84; Houghten, et al., 1991, Nature 354, 84–86), and combinatorial chemistry-derived molecular library made of D- and/or L- configuration amino acids, phosphopeptides (including, but not limited to members of random or partially degenerate, directed phosphopeptide libraries; see, e.g., Songyang, et al., 1993, Cell 72, 767–778), antibodies (including, but not limited to, polyclonal, monoclonal, humanized, anti-idiotypic, chimeric or single chain antibodies, and FAb, $F(ab')_2$ and FAb expression library fragments, and epitope-binding fragments thereof), and small organic or inorganic molecules.

Compounds identified via assays such as those described herein may be useful, for example, in elaborating the biological function of the mahogany gene product and for ameliorating body weight disorders, such as obesity, cachexia, or anorexia. Assays for testing the effectiveness of compounds identified by, for example, techniques such as those described in Sections 5.4.2.1–5.4.2.3, are discussed, below, in Section 5.4.2.4.

5.4.2.1. In Vitro Screening Assays for Compounds that Bind to the Mahogany Gene Product In vitro systems may be designed to identify compounds capable of binding the mahogany gene products of the invention. Compounds identified may be useful, for example, in modulating the activity of unimpaired and/or mutant mahogany gene products, may be useful in elaborating the biological function of the mahogany gene product, may be utilized in screens for identifying compounds that disrupt normal mahogany gene product interactions, or may in themselves disrupt such interactions.

The principle of the assays used to identify compounds that bind to the mahogany gene product involves preparing a reaction mixture of the mahogany gene product and the test compound under conditions and for a time sufficient to allow the two components to interact and bind, thus forming a complex that can be removed and/or detected in the reaction mixture. These assays can be conducted in a variety of ways. For example, one method to conduct such an assay involves anchoring a mahogany gene product or a test substance onto a solid support and detecting mahogany gene product/test compound complexes formed on the solid support at the end of the reaction. In one embodiment of such a method, the mahogany gene product may be anchored onto a solid support, and the test compound, which is not anchored, may be labeled, either directly or indirectly.

In practice, microtiter plates are conveniently utilized as the solid support. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for mahogany gene product or the test compound to anchor any complexes formed in solution, and a labeled antibody specific for the other component of the possible complex to detect anchored complexes.

5.4.2.2. Assays for Proteins that Interact with the Mahogany Gene Product

Any method suitable for detecting protein-protein interactions may be employed for identifying mahogany gene product-protein interactions.

Among the traditional methods that may be employed are co-immunoprecipitation, cross-linking and co-purification through gradients or chromatographic columns. Utilizing procedures such as these allows for the identification of proteins that interact with mahogany gene products. Such proteins can include, but are not limited, the mahoganoid gene product.

Once isolated, such a protein can be identified and can be used in conjunction with standard techniques, to identify proteins it interacts with. For example, at least a portion of the amino acid sequence of a protein that interacts with the mahogany gene product can be ascertained using techniques well known to those of skill in the art, such as via the Edman degradation technique (see, e.g., Creighton, 1983, "Proteins: Structures and Molecular Principles," W. H. Freeman & Co., N.Y., pp.34–49). The amino acid sequence obtained may be used as a guide for the generation of oligonucleotide mixtures that can be used to screen for gene sequences encoding such proteins. Screening may be accomplished, for example, by standard hybridization or PCR techniques. Techniques for the generation of oligonucleotide mixtures and the screening are well-known. (See, e.g., Ausubel, supra, and 1990, "PCR Protocols: A Guide to Methods and Applications," Innis, et al., eds. Academic Press, Inc., New York).

Additionally, methods may be employed that result in the simultaneous identification of genes that encode a protein which interacts with a mahogany gene product. These methods include, for example, probing expression libraries with labeled mahogany gene product, using mahogany gene product in a manner similar to the well known technique of antibody probing of λgt11 libraries.

One method that detects protein interactions in vivo, the two-hybrid system, is described in detail for illustration only and not by way of limitation. One version of this system has been described (Chien, et al., 1991, Proc. Natl. Acad. Sci. USA, 88, 9578–9582) and is commercially available from Clontech (Palo Alto, Calif.).

Briefly, utilizing such a system, plasmids are constructed that encode two hybrid proteins: one consists of the DNA-binding domain of a transcription activator protein fused to the mahogany gene product and the other consists of the transcription activator protein's activation domain fused to an unknown protein that is encoded by a cDNA that has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodologies may be used to screen activation domain libraries for proteins that interact with the "bait" gene product. By way of example, and not by way of limitation, mahogany gene products may be used as the bait gene product. Total genomic or cDNA sequences are fused to the DNA encoding an activation domain. This library and a plasmid encoding a hybrid of a bait mahogany gene product fused to the DNA-binding domain are co-transformed into a yeast reporter strain, and the resulting transformants are screened for those that express the reporter gene. For example, a bait mahogany gene sequence, such as the open reading frame of the mahogany gene, can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait mahogany gene product are to be detected can be made using methods routinely practiced in the art. According to the particular system described herein, for example, the cDNA fragments can be inserted into a vector such that they are translationally fused to the transcriptional activation domain of GAL4. Such a library can be co-transformed along with the bait mahogany gene-GAL4 fusion plasmid into a yeast strain that contains a lacZ gene driven by a promoter that contains GAL4 activation sequence. A cDNA encoded protein, fused to a GAL4 transcriptional activation domain that interacts with bait mahogany gene product will reconstitute an active GAL4 protein and thereby drive expression of the HIS3 gene. Colonies that express HIS3 can be detected by their growth on petri dishes containing semi-solid agar based media lacking histidine. The cDNA can then be purified from these strains, and used to produce and isolate the bait mahogany gene product-interacting protein using techniques routinely practiced in the art.

5.4.2.3. Assays for Compounds that Interfere with Mahogany Gene Product Macromolecule Interaction The mahogany gene products may, in vivo, interact with one or more macromolecules, such as proteins. For example, the mahogany gene products may, in vivo, interact with the mahoganoid gene products. Other macromolecules which interact with the mahogany gene products may include, but are not limited to, nucleic acid molecules and those proteins identified via methods such as those described, above, in Sections 5.4.2.1–5.4.2.2. For purposes of this discussion, the macromolecules are referred to herein as "binding partners". Compounds that disrupt mahogany gene product binding to a binding partner may be useful in regulating the activity of the mahogany gene product, especially mutant mahogany gene products. Such compounds may include, but are not limited to molecules such as peptides, and the like, as described, for example, in Section 5.4.2.1 above.

The basic principle of an assay system used to identify compounds that interfere with the interaction between the mahogany gene product and a binding partner or partners involves preparing a reaction mixture containing the mahogany gene product and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of mahogany gene product and its binding partner. Control reaction mixtures are incubated without the test compound or with a compound which is known not to block complex formation. The formation of any complexes between the mahogany gene product and the binding partner is then detected. The formation of a complex in the control reaction, but not in the reaction mixture containing the test compound, indicates that the compound interferes with the interaction of the mahogany gene product and the binding partner. Additionally, complex formation within reaction mixtures containing the test compound and normal mahogany gene product may also be compared to complex formation within reaction mixtures containing the test compound and a mutant mahogany gene product. This comparison may be important in those cases wherein it is desirable to identify compounds that disrupt interactions of mutant but not normal mahogany gene product.

The assay for compounds that interfere with the interaction of the mahogany gene products and binding partners can be conducted in a heterogeneous or homogeneous format. Heterogeneous assays involve anchoring either the mahogany gene product or the binding partner onto a solid support and detecting complexes formed on the solid support at the end of the reaction. In homogeneous assays, the entire reaction is carried out in a liquid phase. In either approach, the order of addition of reactants can be varied to obtain different information about the compounds being tested. For example, test compounds that interfere with the interaction between the mahogany gene products and the binding partners, e.g., by competition, can be identified by conducting the reaction in the presence of the test substance; i.e., by adding the test substance to the reaction mixture prior to or simultaneously with the mahogany gene product and interactive intracellular binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the mahogany gene product or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the mahogany gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex formation or that disrupt preformed complexes can be identified.

In an alternate embodiment of the invention, a homogeneous assay can be used. In this approach, a preformed complex of the mahogany gene product and the interactive binding partner is prepared in which either the mahogany gene product or its binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances that disrupt mahogany gene product/binding partner interaction can be identified.

In another embodiment of the invention, these same techniques can be employed using peptide fragments that correspond to the binding domains of the mahogany gene product and/or the binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the segments is engineered to express peptide fragments of the protein, it can then be tested for binding activity and purified or synthesized.

For example, and not by way of limitation, a mahogany gene product can be anchored to a solid material as described, above, in this Section by making a GST-1 fusion protein and allowing it to bind to glutathione agarose beads. The binding partner can be labeled with a radioactive isotope, such as $^{35}S$, and cleaved with a proteolytic enzyme such as trypsin. Cleavage products can then be added to the anchored GST-1 fusion protein and allowed to bind. After washing away unbound peptides, labeled bound material, representing the binding partner binding domain, can be eluted, purified, and analyzed for amino acid sequence by well-known methods. Peptides so identified can be produced synthetically or produced using recombinant DNA technology.

5.4.2.4. Assays for the Identification of Compounds that Ameliorate Body Weight Disorders Compounds, including but not limited to binding compounds identified via assay techniques such as those described, above, in Sections 5.4.2.1–5.4.2.3, can be tested for the ability to ameliorate body weight disorder symptoms, including obesity, cachexia, and anorexia. It should be noted that the assays described herein can identify compounds that affect mahogany activity by either affecting mahogany gene expression or by affecting the level of mahogany gene product activity. For example, compounds may be identified that are involved in another step in the pathway in which the mahogany gene and/or mahogany gene product is involved, such as, for example, a step which is either "upfield" or "downfield" of the step in the pathway mediated by the mahogany gene. Such compounds may, by affecting this same pathway, modulate the effect of mahogany on the development of body weight disorders. Such compounds can be used as part of a therapeutic method for the treatment of the disorder.

Described below are cell-based and animal model-based assays for the identification of compounds exhibiting such an ability to ameliorate body weight disorder symptoms.

First, cell-based systems can be used to identify compounds that may act to ameliorate body weight disorder symptoms. Such cell systems can include, for example, recombinant or non-recombinant cell, such as cell lines, that express the mahogany gene.

In utilizing such cell systems, cells that express mahogany may be exposed to a compound suspected of exhibiting an ability to ameliorate body weight disorder symptoms, at a sufficient concentration and for a sufficient time to elicit such an amelioration of such symptoms in the exposed cells. After exposure, the cells can be assayed to measure alterations in the expression of the mahogany gene, e.g., by assaying cell lysates for mahogany mRNA transcripts (e.g., by Northern analysis) or for mahogany gene products expressed by the cell; compounds that modulate expression of the mahogany gene are good candidates as therapeutics.

In addition, animal-based systems or models for a mammalian body weight disorder, for example, transgenic mice containing a human or altered form of mahogany gene, may be used to identify compounds capable of ameliorating symptoms of the disorder. Such animal models may be used as test substrates for the identification of drugs, pharmaceuticals, therapies and interventions. For example, animal models may be exposed to a compound suspected of exhibiting an ability to ameliorate symptoms, at a sufficient concentration and for a sufficient time to elicit such an amelioration of body weight disorder symptoms. The response of the animals to the exposure may be monitored by assessing the reversal of the symptoms of the disorder.

With regard to intervention, any treatments that reverse any aspect of body weight disorder-like symptoms should be considered as candidates for human therapeutic intervention in such a disorder. Dosages of test agents may be determined by deriving dose-response curves, as discussed in Section 5.5.1, below.

5.4.3. Compounds and Methods for the Treatment of Body Weight Disorders

Described below are methods and compositions whereby body weight disorders, including obesity, cachexia, and anorexia, may be treated. Such methods can comprise, for example administering compounds which modulate the expression of a mammalian mahogany gene and/or the synthesis or activity of a mammalian mahogany gene product, so that symptoms of the body weight disorder are ameliorated. Alternatively, in those instances whereby the mammalian body weight disorder results from mahogany gene mutations, such methods can comprise supplying the mammal with a nucleic acid molecule encoding an unimpaired mahogany gene product such that an unimpaired mahogany gene product is expressed and symptoms of the disorder are ameliorated.

In another embodiment of methods for the treatment of mammalian body weight disorders resulting from mahogany gene mutations, such methods can comprise supplying the mammal with a cell comprising a nucleic acid molecule that encodes an unimpaired mahogany gene product such that the cell expresses the unimpaired mahogany gene product, and symptoms of the disorder are ameliorated.

Because a loss of normal mahogany gene function results in the restoration of a non-obese phenotype in individuals exhibiting an agouti mutation (e.g. individuals that ectopically express the agouti gene in all tissues) a decrease or elimination of normal mahogany gene product would facilitate progress towards a normal body weight state in such individuals. Methods for inhibiting or reducing the level of mahogany gene product synthesis or expression can include, for example, methods such as those described in Section 5.4.3.1.

Alternatively, symptoms of certain body weight disorders such as, for example, cachexia and anorexia, which involve a lower than normal body weight phenotype, may be ameliorated by increasing the level of mahogany gene expression and/or mahogany gene product activity. Methods for enhancing the expression or synthesis of mahogany can include, for example, methods such as those described below, in Section 5.4.3.2.

5.4.3.1. Inhibitory Antisense, Ribozyme and Triple Helix Approaches

In another embodiment, symptoms of body weight disorders may be ameliorated by decreasing the level of mahogany gene expression and/or mahogany gene product activity by using mahogany gene sequences in conjunction with well-known antisense, gene "knock-out," ribozyme and/or triple helix methods to decrease the level of mahogany gene expression. Among the compounds that may exhibit the ability to modulate the activity, expression or synthesis of the mahogany gene, including the ability to ameliorate the symptoms of a mammalian body weight disorder, are antisense, ribozyme, and triple helix molecules. Such molecules may be designed to reduce or inhibit either unimpaired, or if appropriate, mutant target gene activity. Techniques for the production and use of such molecules are well known to those of skill in the art.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarily, although preferred, is not required.

A sequence "complementary" to a portion of an RNA, as referred to herein, means a sequence having sufficient complementarily to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In one embodiment, oligonucleotides complementary to non-coding regions of the mahogany gene could be used in an antisense approach to inhibit translation of endogenous mahogany mRNA. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger, et al., 1989, Proc. Natl. Acad. Sci. U.S.A. 86, 6553–6556; Lemaitre, et al., 1987, Proc. Natl. Acad. Sci. U.S.A. 84, 648–652; PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., 1988, BioTechniques 6, 958–976) or intercalating agents (see, e.g., Zon, 1988, Pharm. Res. 5, 539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanlne, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier, et al., 1987, Nucl. Acids Res. 15, 6625–6641). The oligonucleotide is a 2'-0-methylribonucleotide (Inoue, et al., 1987, Nucl. Acids Res. 15, 6131–6148), or a chimeric RNA-DNA analogue (Inoue, et al., 1987, FEBS Lett. 215, 327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein, et al. (1988, Nucl. Acids Res. 16, 3209), methylphosphonate oligonucleotides can be prepared by use of controlled pore glass polymer supports (Sarin, et al., 1988, Proc. Natl. Acad. Sci. U.S.A. 85, 7448–7451), etc.

While antisense nucleotides complementary to the target gene coding region sequence could be used, those complementary to the transcribed, untranslated region are most preferred.

Antisense molecules should be delivered to cells that express the target gene in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290, 304–310), the promoter contained in the 3' long terminal repeat of *Rous sarcoma* virus (Yamamoto, et al., 1980, Cell 22, 787–797), the herpes thymidine kinase promoter (Wagner, et al., 1981, Proc. Natl. Acad. Sci. U.S.A. 78, 1441–1445), the regulatory sequences of the metallothionein gene (Brinster, et al., 1982, Nature 296, 39–42), etc. Any type of plasmid, cosmid, YAC or viral vector can be used to prepare the recombinant DNA construct which can be introduced directly into the tissue site. Alternatively, viral vectors can be used that selectively infect the desired tissue, in which case administration may be accomplished by another route (e.g., systemically).

Ribozyme molecules designed to catalytically cleave target gene mRNA transcripts can also be used to prevent translation of target gene mRNA and, therefore, expression of target gene product. (See, e.g., PCT International Publication WO90/11364, published Oct. 4, 1990; Sarver, et al., 1990, Science 247, 1222–1225).

Ribozymes are enzymatic RNA molecules capable of catalyzing the specific cleavage of RNA. (For a review, see Rossi, 1994, Current Biology 4, 469–471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers, 1995, Molecular Biology and Biotechnology: *A Comprehensive Desk Reference*, VCH Publishers, New York, (see especially FIG. 4, page 833) and in Haseloff and Gerlach, 1988, Nature, 334, 585–591, which is incorporated herein by reference in its entirety.

Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in *Tetrahymena thermophila* (known as the IVS, or L-19 IVS RNA) and that has been extensively described by Thomas Cech and collaborators (Zaug, et al., 1984, Science, 224, 574–578; Zaug and Cech, 1986, Science, 231, 470–475; Zaug, et al., 1986, Nature, 324, 429–433; published International patent application No. WO 88/04300 by University Patents Inc.; Been and Cech, 1986, Cell, 47, 207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes unlike antisense molecules, are catalytic, a lower intracellular concentration is required for efficiency.

Endogenous target gene expression can also be reduced by inactivating or "knocking out" the target gene or its promoter using targeted homologous recombination (e.g., see Smithies, et al., 1985, Nature 317, 230–234; Thomas and Capecchi, 1987, Cell 51, 503–512; Thompson, et al., 1989, Cell 5, 313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas and Capecchi, 1987 and Thompson, 1989, supra). However this approach can be adapted for use in humans provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body. (See generally, Helene, 1991, Anticancer Drug Des., 6(6), 569–584; Helene, et al., 1992, Ann. N.Y. Acad. Sci., 660, 27–36; and Maher, 1992, Bioassays 14(12), 807–815).

Nucleic acid molecules to be used in triple helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and $CGC^+$ triplets across the three associated strands of the resulting triple helix. The pyrimidine-rich molecules provide base complementarily to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may, be introduced into cells via gene therapy methods such as those described, below, in Section 5.9.2 that do not contain sequences susceptible to whatever antisense, ribozyme, or triple helix treatments are being utilized. Alternatively, in instances whereby the target gene encodes an extracellular protein, it may be preferable to co-administer normal target gene protein in order to maintain the requisite level of target gene activity.

Anti-sense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

5.4.3.2. Gene Replacement Therapy

Mahogany gene nucleic acid sequences, described above in Section 5.1, can be utilized for the treatment of a mammalian body weight disorders, including obesity, cachexia, and anorexia. Such treatment can be in the form of gene replacement therapy. Specifically, one or more copies of a normal mahogany gene or a portion of the mahogany gene that directs the production of a mahogany gene product exhibiting normal mahogany gene function, may be inserted into the appropriate cells within a patient, using vectors that include, but are not limited to adenovirus, adeno-associated virus, and retrovirus vectors, in addition to other particles that introduce DNA into cells, such as liposomes.

Because the mahogany gene is expressed in the brain, such gene replacement therapy techniques should be capable delivering mahogany gene sequences to these cell types within patients. Thus, in one embodiment, techniques that are well known to those of skill in the art (see, e.g., PCT Publication No. WO89/10134, published Apr. 25, 1988) can be used to enable mahogany gene sequences to cross the blood-brain barrier readily and to deliver the sequences to cells in the brain. With respect to delivery that is capable of crossing the blood-brain barrier, viral vectors such as, for example, those described above, are preferable.

In another embodiment, techniques for delivery involve direct administration of such mahogany gene sequences to the site of the cells in which the mahogany gene sequences are to be expressed.

Additional methods that may be utilized to increase the overall level of mahogany gene expression and/or mahogany gene product activity include using target homologous recombination methods, discussed in Section 5.2, above, to modify the expression characteristic of an endogenous mahogany gene in a cell or microorganism by inserting a heterologous DNA regulatory element such that the inserted regulatory element is operatively linked with the endogenous mahogany gene in question. Targeted homologous recombination can be thus used to activated transcription of an endogenous mahogany gene that is "transcriptionally silent", i.e., is not normally expressed, or to enhance the expression of an endogenous mahogany gene that is normally expressed.

Further, the overall level of mahogany gene expression and/or mahogany gene product activity may be increased by the introduction of appropriate mahogany-expressing cells, preferably autologous cells, into a patient at positions and in numbers that are sufficient to ameliorate body weight disorder symptoms. Such cells may be either recombinant or non-recombinant.

Among the cells that can be administered to increase the overall level of mahogany gene expression in a patient are normal cells, preferably brain cells, that express the mahogany gene. Alternatively, cells, preferably autologous cells, can be engineered to express mahogany gene sequences, and may then be introduced into a patient in positions appropriate for the amelioration of the body weight disorder symptoms. Alternately, cells that express an unimpaired mahogany gene and that are from a MHC matched individual can be utilized, and may include, for example, brain cells. The expression of the mahogany gene sequences is controlled by the appropriate gene regulatory sequences to allow such expression in the necessary cell types. Such gene regulatory sequences are well known to the skilled artisan. Such cell-based gene therapy techniques are well known to those skilled in the art, see, e.g., Anderson, U.S. Pat. No. 5,399,349.

When the cells to be administered are non-autologous cells, they can be administered using well known techniques that prevent a host immune response against the introduced cells from developing. For example, the cells may be introduced in an encapsulated form which, while allowing for an exchange of components with the immediate extracellular environment, does not allow the introduced cells to be recognized by the host immune system.

Additionally, compounds, such as those identified via techniques such as those described, above, in Section 5.4.2, that are capable of modulating mahogany gene product activity can be administered using standard techniques that are well known to those of skill in the art. In instances in which the compounds to be administered are to involve an interaction with brain cells, the administration techniques should include well known ones that allow for a crossing of the blood-brain barrier.

5.5. Pharmaceutical Preparations and Methods of Administration

The compounds that are determined to affect mahogany gene expression or gene product activity can be administered to a patient at therapeutically effective doses to treat or ameliorate body weight disorders, such as obesity, anorexia, or cachexia. A therapeutically effective dose refers to that amount of the compound sufficient to result in amelioration of symptoms of such a disorder.

5.5.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

5.5.2. Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

6. EXAMPLE

Genetic and Physical Mapping of the Mahogany Locus

In the Example presented herein, studies are described which, first, define the genetic interval on mouse chromosome 2 within which the mahogany gene lies, and second, successfully narrow the interval to approximately 0.29 cM. Further, the physical mapping of this interval is described.

Mouse crosses were performed to obtain homozygous mg/mg mice. First, LDJ-Le-mg mice were crossed with CAST/Ei mice. The F1s were back-crossed with LDJ-Le-mg mice and the resulting litters scored for coat color. Mice showing coat color of mg/mg homozygotes were genotyped to using D2/NDS3 and D2/MIT19 markers to identify meiotic events. Mice showing recocombiant events were fine structure mapped using various markers shown in FIG. 1. All genotyping was performed using PCR-SSLP and then analyzed using PAGE.

After 2300 meiosesis, the mahogany gene was mapped to a 0.99 cM interval FIG. 1. This corresponded to an interval width of 700 kb.

Physical Mapping of the Genetic Interval: The 700 kb mahogany region on mouse chromosome 2 is shown in FIG. 1. Genetic markers, clones spanning the region and open reading frames in the interval are shown in the figure.

7. EXAMPLE

Identification of a Candidate Mahogany Gene

In the Example presented here in, a gene is identified within the cloned DNA described in the Example in Section 6, above, which corresponds to a candidate mahogany gene.

Clones spanning the 700 kb region were sequenced and open reading frames were identified and analyzed through this interval. Nucleic acid sequencing was performed using ABI sequencers and the manufactures recommended procedures. Many novel sequences encoding proteins are located in this interual, see the bottom of FIG. 1. With each open reading frame identified, mutational analysis, primarily via SSCP analysis, was used with the three alleles of the mahogany phenotype mice to identify which of the open reading frames within this interval contain a mutation in an mg mouse.

A mutation was found in one of the genomic/cDNA sequences found in the integral in mg3J mice. FIGS. 3 and 2 provide the genomic and cDNA sequences surrounding the mutation, FIG. 6 shows the mutation in mg3J, and FIGS. 8 and 9 show splice variants in the 5' end of the murine mg gene. The mutation in mg3J mice is a deletion of a GCTGC sequence which results in the creation of a frameshift. Based on the chromosomal location and mutation identification, the cDNA provided in FIG. 2 and the corresponding genomic DNA which contains the contigs provided in FIG. 3 represent the mg gene/locus.

Further analysis of cDNA clones identified two distinct splice variants in the 5' end of the mg gene. FIG. 7 provides an analysis of the structure of the two splice variants, denoted akm1003 and akm1004. FIGS. 8 and 9 provide the nucleic acid and amino acid sequence of the 5' ends of these splice variants and structural analysis of the protein encoded by the 5' regions.

Analysis of libraries of human cDNA sequences led to the identification of three forms of the human ortholog of the mg gene: a long form (FIG. 18) and two shorter splice forms, each of which is shown in FIGS. 19 and 20.

8. EXAMPLE

Characterization of the Mahogany Gene

In the example presented herein, the nucleic acid sequence of the mahogany gene transcript identified in the example presented in Section 7, above, is used to generate Northern analysis data which characterize the expression of the mahogany transcript in a number of tissues both of wild type mice, and of mice exhibiting the mahogany phenotype. The results presented in this example are consistent with the mg gene being the mahogany gene.

For Northern analysis, polyA RNA was isolated from wild-type and the original mg mutant, mg3J and mg-Lester mice and utilized from the Northern analysis following standard protocols. Northern blots prepared from this mRNA were hybridized with a probe obtained from sequences common to the akm1003 and akm1004 sequences. Specifically PCR primers TTCCTCACTGG (SEQ ID NO: 128) and GGACACACAG (SEQ ID NO: 129) were used to amplify cDNA from the akm1003 sequence which had been radiolabelled by random priming using a Gibco-BRL kit according to the manufacturer's recommended protocol.

An mg transcript was found in all mice examined in mRNA isolated from brain (minus the hypothalamus), kidney, heart, testes, liver, skin, and hypothalamus. No expression was seen in muscle.

In a Northern blot run on RNA samples from mahogany mice, the mg transcript was found to be expressed at a reduced level in all tissues in MRNA isolated from mg3J mice, as a varied size fragment in mg-Lester derived mRNA, and at different levels and sizes in original mg mutant mice derived mRNA.

These results are consistent with the mg gene disclosed herein as being the mahogany gene.

9. EXAMPLE

Effects of the Mahogany Gene on Genetic and Dietary Obesity

This section describes experiments which examine whether the mg gene acts specifically within the agouti pathway. Specifically, these experiments test whether mg can suppress the obesity of other monogenic obese mutants as well as whether it can suppress diet-induced obesity. The results show that mg does not suppress obesity in any of the monogenic obese mutants. However, mg can suppress diet-induced obesity. Thus, the mg gene and its corresponding gene product and compounds that modulate mg expression and/or activity have implications in the treatment of diet-induced obesity disorders, as well as in the treatment of disorders related directly to the mg or agouti gene.

9.1. Materials and Methods

Figure 13:
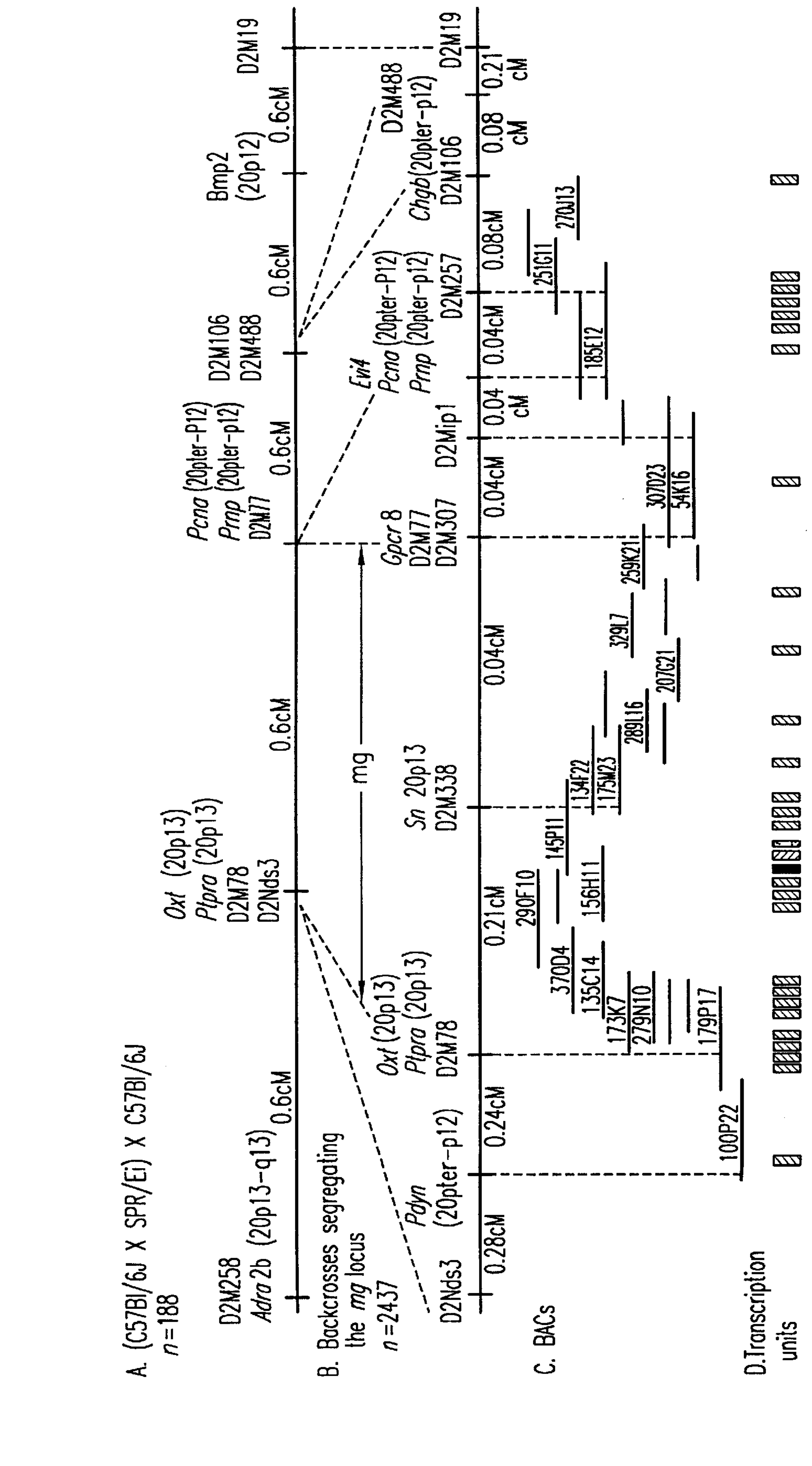

Genetic crosses: The crosses, and the number of animals for each (n) were (LDJ/Le-mg/mg×CAST/Ei)×LDJ/Le-mg/mg (n=1588), (C3HeB/FeJ-$mg^{3J}$/$mg^{3J}$×CAST/Ei)×C3HeB/FeJ-$mg^{3J}$/$mg^{3J}$ (n=324), (C3HeB/FeJ-$mg^{3J}$/$mg^{3J}$×MOLF/Ei)×C3HeB/FeJ-$mg^{3J}$/$mg^{3J}$ (n=216) and (C3HeB/FeJ-$mg^{3J}$/$mg^{3J}$×C57BL6/J)×C3HeB/FeJ-$mg^{3J}$/$mg^{3J}$ (n=309). The 2437 $N_2$ mice were analysed by coat colour to determine their genotype at the mg locus. As mice change color slightly at each hair molt and because the phenotype of mg/mg vs. mg/+ can be subtle, all mice were phenotyped at the same age by a single person. Genomic DNA was made from a tail biopsy of each mouse and analysed for multiple simple sequence length repeat polymorphism (SSLP) markers. The first ~100 mice were typed for a series of polymorphic Mit genetic markers (Deitrich, W. F. et al., 1996, *Nature* 380:149–152) from distal mouse chromosome 2 in order to accurately delimit the position of mg. With the first ~100 mice it was determined that mg mapped approximately 15 cM proximal of Agouti between markers D2Mit19 and D2Nds3 (FIG. 13). All remaining animals were genotyped for D2Mit19 and D2Nds3. Animals recombinant in that interval were typed with all available Mit markers between and for the ever growing number of markers developed during the project which, finally totaled 265 markers.

9.2. Result

The murine mahogany (mg) gene is known to act in a dosage dependent manner within the agouti pathway, to compensate for the agouti overexpression and for lack of signaling from the nul allele McIr (Miller, K. A. et al., 1997, *Genetics* 146:1407–1415; Dinulescu, D. M. et al., *Proc.*

*Natl. Acad. Sci.,* in press; Robbins, L. S. et al., 1993, Cell 72:827–834). The phenotype of mice homozygous for both mg and a null allele of McIr (recessive yellow, $McIr^e$) is yellow, the same as the phenotype of $McIr^e/McIr^e$ mice, indicating that mg is not acting downstream of McIr. ¯A similar experiment was performed with obese Mcr4 knock out mice (FIG. 11). For both sexes, all the animals homozygous for Mc4r−/− were approximately equally obese and were heavier than the mice wild-type at Mc4r independent of the genotype for mg. This data strengthens and confirms the McIr data previously published, strongly suggesting that mg acts at or upstream of both melanocortin receptors.

Figure 12A:
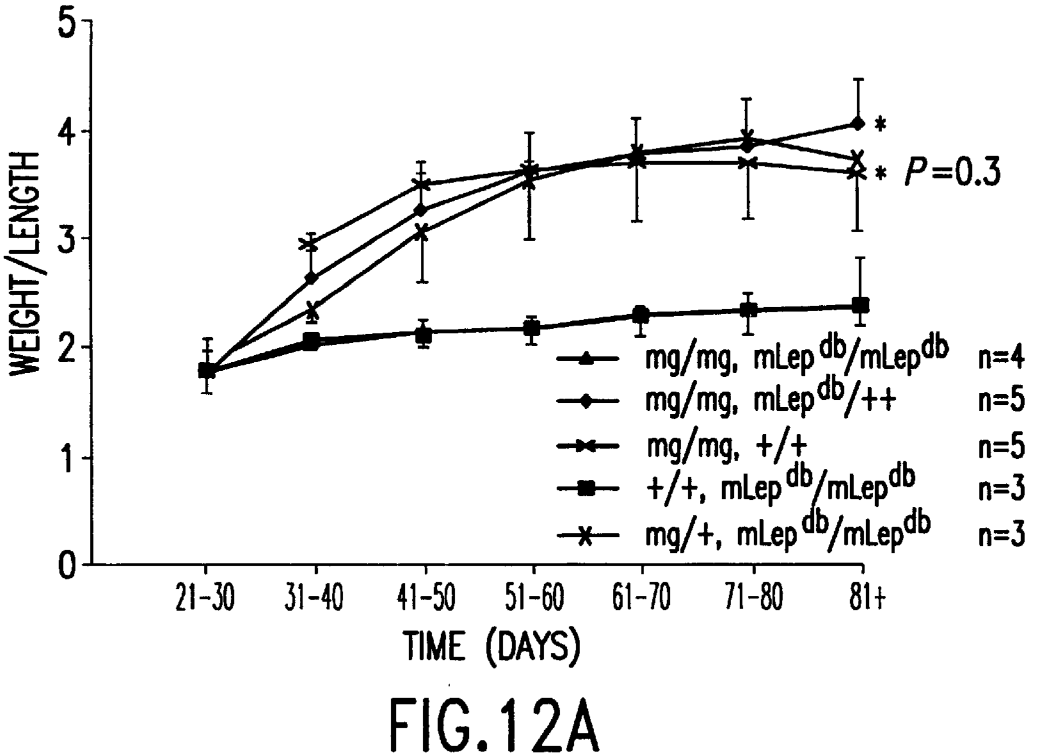
Figure 12B:
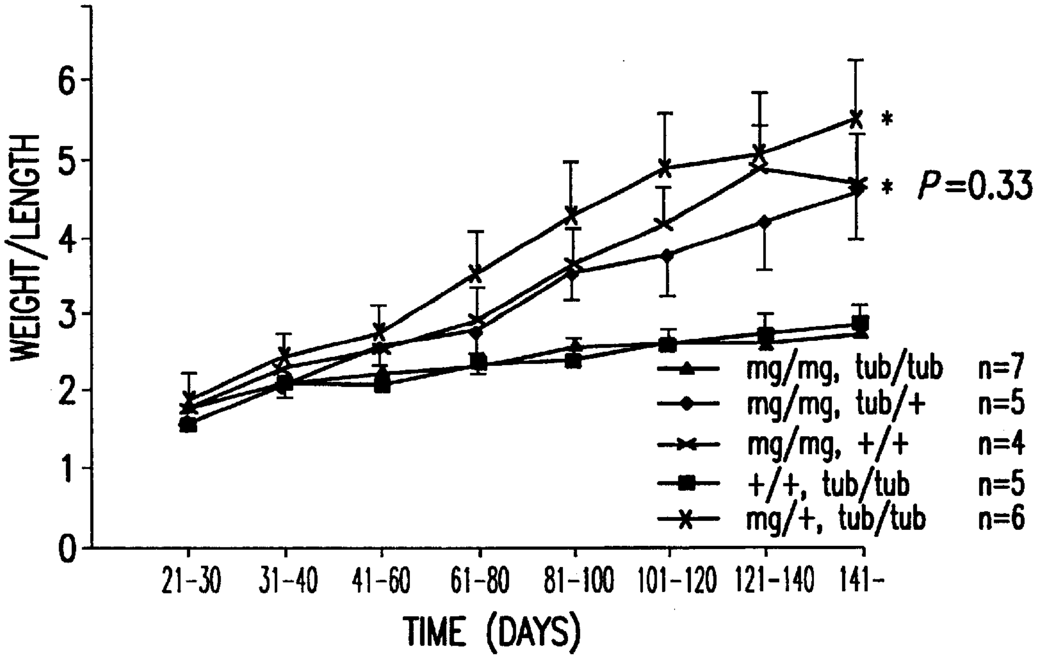
Figure 12C:
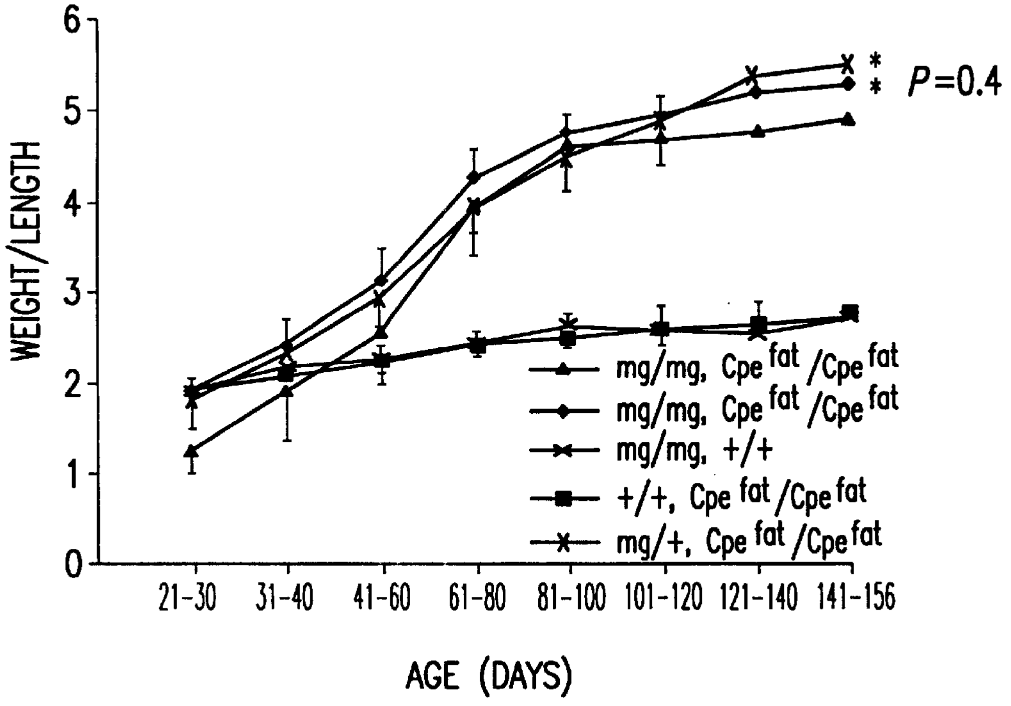
Figure 12D:
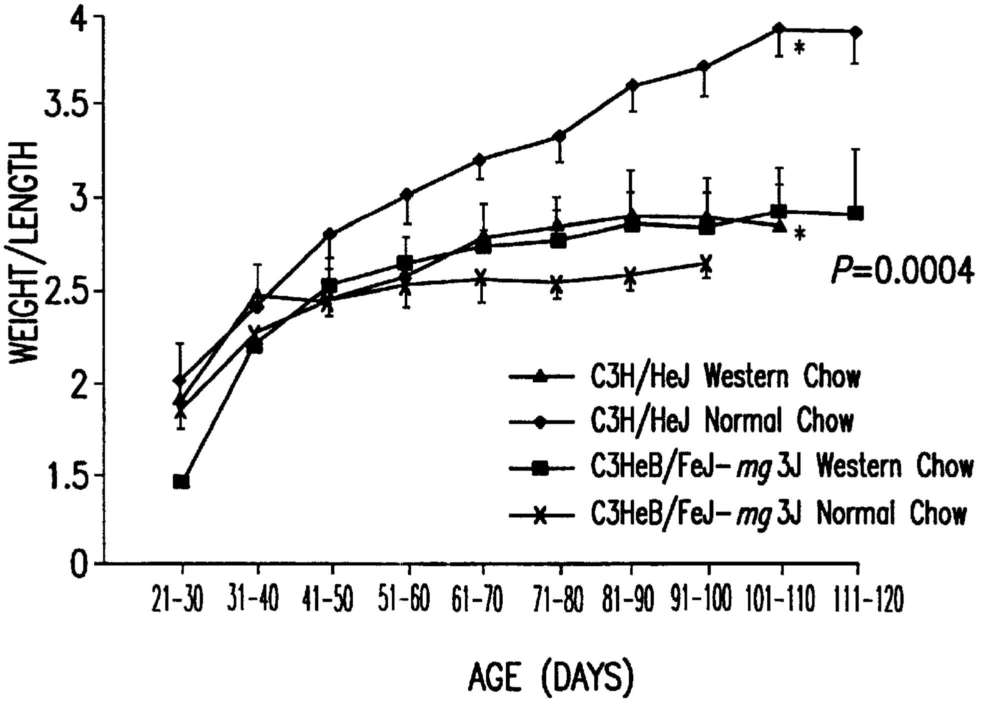

To test whether mg acts specifically within the agouti pathway, experiments were performed to determine whether mg can suppress the obesity of other monogenic obese mutants of the mouse and whether it could suppress diet-induced obesity. Appropriate genetic crosses were set up to produce mice segregating mg and one of the mouse obesity mutations $Cpe^{fat}$, tub, or $Lepr^{db}$ such that all combinations of homozygous and heterozygous animals were on the same mix of genetic background. No suppression of obesity was seen for any of the monogenic obese mutants (FIG. 12) lending credence to the assumed specificity of action within the agouti pathway. To ask whether mg can suppress diet induced obesity C3HeB/FeJ-$mg^{3J}$ and C3H/HeJ mice were placed, at weaning, either on normal chow having a physiological fuel value (PFV) of 3.63 kcal/gm with 9% fat, or onto a high fat diet having a PFV of 4.53 kcal/gm with 42.2% fat. Food consumption and body weight were measured weekly. Converting the grams of food consumed to calories indicated that C3H/HeJ mice on normal chow and high fat diet consumed ~97 kCal/week and ~96 kCal/week, respectively. C3HeB/FeJ-$m^{3J}$ mice on normal chow and high fat diet consumed ~83 kCal/week and ~81 kCal/week, respectively. Despite the equal calorie intake, the C3H/HeJ mice on the high fat diet readily gained more weight than the C3H/HeJ mice on normal chow (p=0.0004). In stark contrast, the C3HeB/FeJ-$mg^{3J}$ mice on either diet showed no statistically significant difference in weight (FIG. 12D). Female data showed the same trends, although there was no statistical significance between any of the mice on either diet.

10. EXPERIMENT

Mapping and Sequencing of the Mahogany Gene

This section describes experiments wherein the murine mahogany gene was genetically and physically mapped to an approximately 0.6 cM interval, and then sequenced. The murine mg sequence obtained was then used to isolate and sequence the human mg gene. Northern and in situ analyses of mg expression in mouse tissue are also described, and sequence motifs of the predicted MG polypeptide are discussed.

10.1. Materials and Methods

Physical Mapping: More than 36,000 individual sequences from the region were compared by BLAST (Altschul, S. F. et al., 1990, *J. Mol. Biol.* 215:403–410) to publicly available sequence databases and analyzed using GRAIL (Guan, X. et al., 1992, *Proc. Eighth IEEE Conference on AI Applications:* 9–13) to identify potential coding sequence. In addition, sequences from overlapping BACs were assembled using phrap (Sing, C. F. et al., 1998, *Genome Res.* 8:175–185; Ewing B. and Green, P., 1998, *Genome Res.* 8:186–194; Gordon, D. et al., 1998, *Genome Res.* 8:195–202), and the resulting contigs were also analyzed using BLAST and GRAIL to aid in gene prediction. This data was displayed in ACEdb (Durbin, Richard and Mieg, Jean Thierry, 1991, A *C. elegans* Database, Documentation, code, and data available from anonymous FTP servers at lirmm.lirmm.fr, cele, mrc-lmb.cam.ac.uk, and ncbi.nlm.nih.gov) to further visualize predicted exons and their relationships to each other.

Northern Blot Analysis: PolyA+ RNA was extracted from the tissues indicated from wild-type, C3H/HeJ and the three mutant alleles of mg, C3HeB/FeJ-$m^{3J}$, LDJ/Le-mg, and C3H/HeJ-$mg^L$, according to the manufacturer's instructions. RNA STAT-60 (Tel-Test, Inc., 1511 Sounty Rd. 129, Friendswood, Tex. 77546) was used to isolate total RNA. PolyA+ was isolated using Poly(A)Pure™ mRNA purification kit (Ambion, Inc., 2130 Woodward St. #200, Austin, Tex. 78744). 2 μg of each mRNA was separated on a 1% agarose-formaldehyde gel, transferred to nylon, and hybridized with a probe for mg corresponding to nt 990–1406 of the murine cDNA sequence with Rapid-hyb Buffer (Amersham LIFE SCIENCE, Gaithersberg, Md.). Filters were washed with 0.11×SSC, 0.1% SDS and exposed to KODAK X-omat film overnight.

10.2. Results

A positional cloning strategy was undertaken to identify the mg gene. Multiple genetic crosses were set up to produce second generation mice (n-2437) segregating mg which were used to genetically localise the mg locus (FIG. 13B). When the genetic map critical interval for mg was resolved to ~0.6 cM physical mapping was initiated. Approximately 1 Mb was contiged with 30 BACs (FIG. 13C), most of which were made into random sheared libraries for shot gun sequencing. At completion of the project it was estimated that 85% sequence coverage across the interval had been achieved and that all genes within the region had been found. Twenty-nine genes were identified, 15 of which are novel genes. Within the final minimal interval for mg, indicated by the arrows in FIG. 13, there were eleven genes of which nine were unknown. All of these genes were tested as candidates for mg by examining the three mutant alleles of the mahogany locus, the original allele, mg, that arose in a stock of Swiss×C3H mice, and two alleles that have independently arisen on the C3H background, C3HeB/FeJ-$mg^{3J}/mg^{3J}$ and C3H/He-$mg^L/mg^L$. Each gene was examined by Northern blot analysis and RT-PCR analysis of RNA from tissues from wild-type and mg mutant mice, by Southern blot analysis of DNA from wild-type and mg mutant mice, and by SSCP analysis of genomic PCR products designed to cover the intron-exon boundaries of much of each of the genes. In all, 20 genes were analyzed in this manner, one of which showed a northern blot difference between the wild type and mutant alleles (FIG. 14).

The wild type expression pattern of this gene gives three bands of size ~9 kb, 4.5 kb, and 3.8 kb, of which the larges message is the most prominent (FIG. 14). The smaller two bands can be seen in all tissues but, depending upon tissue, may require extended exposure. Each of the different mg alleles gave a different expression pattern. C3HeB/FeJ-$mg^{3J}/mg^{3J}$ has extremely low expression, the 9 kb message only being very faint in brain, hypothalamus, and fat on northerns. C3H/He-$mg^L/mg^L$ expresses a single aberrant band of approximately 9.5–10 kb in kidney, heart, muscle, fat, and, most prominently, brain and hypothalamus. The LDJ/Le-mg/mg shows an altered ratio of the three wild type messages: the 9 kb message is reduced, while the two smaller messages are more highly expressed, in particular being very abundant in fat and hypothalamus. In situ analysis was used to look more closely at mg expression in the brain and specifically the hypothalamus. Overall hybridization in LDJ/Le-mg/mg looks equivalent to that of wild type, and the C3HeB/FeJ-$mg^{3J}/mg^{3J}$ shows an overall reduction of expression. Close examination of the hypothalamic region in both wild type and mutant alleles revealed differences in the ventromedial hypothalamic nucleus (VMH). Both C3HeB/FeJ-$mg^{3J}/mg^{3J}$ and the LDJ/Le-mg/mg have reduced VMH expression (FIG. 15) which is particularly interesting as many neuropeptides and receptors known to be involved in body weight regulation are expressed in the VMH, including Mc4r.

Initially, two overlapping mouse cDNAs of 1051 bps and 2419 bps were identified. Using these cDNAs as a starting point it was possible to build over 7990 bps of human sequences, using both the public EST database and an in house database, as well as identifying one cDNA clone from a human liver library. The 23 ESTs used in the contiging are listed in Table I below. Using the derived human sequence, it was then possible to estimate the intron-exon boundaries within the mouse genomic sequence. These were verified by PCR amplification and sequencing. In total, 4079 bps of mouse sequence was obtained, of which 4011 bp are coding sequence. The mouse genomic locus spans over 160 kb, and has 31 identified exons, at least one of which is differentially spliced.

TABLE I

| Gene Bank Accession # | Clone ID # | Clone Source |
|---|---|---|
| NA | NA | Human Endothelial Cell (MPI) |
| AA062169 | 482948 | Soares mouse P3NMF19.5 |
| NA | NA | Human Liver (MPI) |
| AA350292 | 151062 | Infant Brain |
| R87660 | 194640 | Soares Fetal Liver Spleen 1 NFLS |
| T69367 | 82898 | Stratagene Liver |
| T92696 | 118881 | Stratagene Lung |
| H11351 | 47626 | Soares Infant Brain 1 NIB |
| AA350293 | 151062 | Infant Brain |
| AA297697 | 149184 | Fetal Heart II |
| AB011120 | NA | Human Male Brain |
| AA297214 | 129808 | Embryo, 12 week I |
| AA298732 | 184690 | T-Lymphocyte |
| AI076479 | 1676623 | Soares Total Fetus Nb2HF8 9W |
| AA771958 | 1359202 | Soares parathyroid tumor NbHPA |
| R84298 | 194640 | Soares Fetal Liver Spleen 1NFLS |
| D81046 | 1178923 | Human Fetal Brain (Tfujiwara) |
| AA378603 | 183010 | Synovial Sarcoma |
| D60710 | 962349 | Clontech Human Fetal Brain (#6535) |
| D20236 | pm1235 | Human Promyelocyte |
| AA345684 | 147210 | Gall Bladder I |
| H45413 | 182870 | Soares Breast 3NbHBst |
| AA044305 | 486349 | Soares Pregnant Uterus NbHPu |

The mutant mahogany alleles were also sequenced, checking all intron-exon boundaries. A 5 bp deletion at 2809 nt was found in the coding sequence of the mg gene from C3HeB/FeJ-$mg^{3J}/mg^{3J}$ which introduces a stop codon a position 937, two codons 3' of the deletion. This mutation will result in a seriously truncated protein lacking many interesting domains, as discussed below. The $mg^{3J}$ allele is the same allele that showed extremely low expression levels. The combined Northern blot analysis, in situ hybridization analysis, and sequence analysis of the mutant $mg^{3J}$ allele strongly suggest that this gene is the mouse mahogany gene.

The 4011 bp of open reading frame (ORF) of mouse MG predicts a 1336 amino acid polypeptide with molecular mass of 148,706 D (FIG. 17, top sequence). BLAST searches of the NCBI and SwissProt protein databases identified two human paralogues with a similar modular architecture (KIAA0534, Genbank accession no. 3043592; and MEGF8, Genbank accession no. AB011541), as well as a *C. elegans* homologue (YC81_CAEEL, Genbank accession no. Q19981).

Another human protein, Attractin or DPPT-L (Duke-Cohen, J. S. et al., 1998*, Proc. Natl. Acad. Sci. U.S.A.* 95:11336–11341), appears to be a 1198 amino acid residue, approximately 134,000 D, secreted splice variant of the MG polypeptide. An alignment of the predicted MG (top) and Attractin (bottom) amino acid sequences is shown in FIG. 17. Attractin has not identified as being involved in the regulation of body weight. Rather, the protein is reported to mediate an interaction between T lymphocytes and monocytes that leads to the adherence and spreading of monocytes that become foci for T lymphocyte clustering (see Duke-Cohen et al., supra).

Searching the MG polypeptide with the SMART domain tool (Schultz, J. et al., 1998*, Proc. Natl. Acad. Sci. U.S.A.* 95:5857–5864) revealed sequence motifs that may provide further clues to its biological function (FIG. 16B, FIG. 17). The single transmembrane spanning MG protein has a large extracellular sequence of 1289 amino acids containing three EGF domains (Nakayama, M. et al., 1998*, Genomics* 51:27–34), two laminin-like EGF repeats, a CUB domain (Bork, P. and Beckmann, G., 1993*, Mol. Biol.* 231:539–545), a C-type lectin domain (Drickamer, K., 1995*, Nat. Struct. Biol.* 6:437–439; Weis W. I., and Drickamer, K., 1996*, Ann. Rev. Biochem.* 65:441–473), two plexin-like repeats (Maestrini, E. et al., 1996*, Proc. Natl. Acad. Sci. U.S.A.* 93:674–678), and six consecutive kelch repeats (Bork, P. and Doolittle, R. F., 1994*, J. Mol. Biol.* 236:1277–1282). Multiple EGF domains are commonly found in Type-1 membrane proteins involved in cell adhesion and receptor-ligand interactions (Schultz, J. et al, 1998*, Proc. Natl. Acad. Sci. USA* 95:5857–5864). Laminin-EGF-like modules are found in a variety of proteoglycans such as perlecan and heparin sulphate proteoglycan. As CUB domains also frequently occur in glycosylated proteins and c-type lectins are known to be carbohydrate binders, it is likely that MG is heavily glycosylated and that carbohydrate interactions are essential for its function. Many kelch motif containing proteins have been found that, like MG, have multiple consecutive domains. Such consecutive four-stranded β-sheet Kelch motifs form a bladed beta "propeller fold" that is common in many sialidases and other enzymes (Maestrini, E. et al., supra). Unlike the other well recognized domains, the "plexin" repeat is less well defined. It was first recognized as a triple repeat in the Xenopus gene plexin that has similarity to MET (Bork, P. and Beckmann, G., 1993, *Mol. Biol.* 231:539–545). Since then, this cysteine rich repeat has been found in 6 MET gene family members, three of which signal via tyrosine kinase and three of which are hypothesized to have putative signaling function via a novel conserved cytoplasmic domain. However, it is fascinating that there is an eight amino acid stretch that is 100% conserved in the four proteins shown in FIG. 16A from human, mouse, and *C. elegans.* The conservation of sequence across such widely evolutionary divergent species strongly indicates a functional domain, possible a putative signaling motif.

The multi-domain structure of MG is complex, but draws many similarities from receptor and receptor-like proteins.

The full-length MG polypeptide is predicted to be a large membrane-spanning protein with multiple extracellular domains that may have a binding or gathering function as well as a highly conserved putative signaling motif in the cytoplasmic tail.

11. REFERENCE CITED

The present invention is not to be limited in scope by the specific embodiments described herein, which are intended as single illustrations of individual aspects of the invention. Functionally equivalent methods and components are within the scope of the present invention. Indeed, various modifications of the invention, in addition to those shown and described herein, will become apparent to those skilled in the art from the foregoing description and accompanying drawings.

All publications and patent applications mentioned in the specification are herein incorporated by reference to the same extent as if each individual publication or patent application was specifically and individually indicated to be incorporated by reference.

What is claimed is:

1. An isolated nucleic acid molecule comprising the nucleotide sequence of SEQ ID NO: 1, SEQ ID NO: 8, SEQ ID NO: 10, SEQ ID NO: 12, SEQ ID NO: 14 (FIG. 18A), SEQ ID NO: 16 (FIG. 19A), or SEQ ID NO: 18 (FIG. 20A).

2. The isolated nucleic acid molecule of claim 1, wherein the nucleic acid molecule comprises the nucleotide sequence of SEQ ID NO: 14 (FIG. 18A).

3. The isolated nucleic acid molecule of claim 1, wherein the nucleic acid molecule comprises the nucleotide sequence of SEQ ID NO: 16 (FIG. 19A).

4. The isolated nucleic acid molecule of claim 1, wherein the nucleic acid molecule comprises the nucleotide sequence of SEQ ID NO: 18 (FIG. 20A).

5. An isolated nucleic acid molecule comprising a nucleotide sequence that hybridizes to the complement of the open reading frame of: SEQ ID NO: 1; SEQ ID NO: 8; SEQ ID NO: 10; SEQ ID NO: 12; SEQ ID NO: 14; SEQ ID NO: 16; or SEQ ID NO: 18, wherein said hybridization occurs across the full length of said nucleic acid molecule and across the full length of said complement, under stringent conditions comprising hybridization in 0.5 M $NaHPO_4$, 7% SDS, 1 mM EDTA at 68° C., and washing in 0.1×SSC/0.1% SDS at 68° C.

6. The isolated nucleic acid molecule of claim 5, wherein the nucleic acid molecule comprises a nucleotide sequence that hybridizes to said complement of SEQ ID NO: 14 (FIG. 18A) under said stringent hybridization and wash conditions.

7. The isolated nucleic acid molecule of claim 5, wherein the nucleic acid molecule comprises a nucleotide sequence that hybridizes to said complement of SEQ ID NO: 16 (FIG. 19A) under said stringent hybridization and wash conditions.

8. The isolated nucleic acid molecule of claim 5, wherein the nucleic acid molecule comprises a nucleotide sequence that hybridizes to said complement of SEQ ID NO: 18 (FIG. 20A) under said stringent hybridization and wash conditions.

9. The nucleic acid molecule of claim 5, further comprising a heterologous sequence.

10. The nucleic acid molecule of claim 5, wherein the nucleic acid is cDNA.

11. An isolated nucleic acid molecule comprising a nucleotide sequence which encodes a polypeptide comprising the amino acid sequence of SEQ ID NO: 2, SEQ ID NO: 9, SEQ ID NO: 11, SEQ ID NO: 13, SEQ ID NO: 15, SEQ ID NO: 17, or SEQ ID NO: 19.

12. A nucleic acid molecule comprising a nucleotide sequence which encodes a fusion protein comprising the amino acid sequence of SEQ ID NO: 2, SEQ ID NO: 9, SEQ ID NO: 11, SEQ ID NO: 13, SEQ ID NO: 15, SEQ ID NO: 17, or SEQ ID NO: 19.

13. A vector comprising the isolated nucleic acid molecule of any one of claims 2, 3, 4, 5, 11, or 9.

14. A vector comprising the isolated nucleic acid molecule of any one of claims 6–8.

15. An isolated host cell genetically engineered to express the nucleic acid of any one of claims 2, 3, 4, 5, 11, or 9.

16. An isolated host cell genetically engineered to express the nucleic acid of any one of claims 6–8.

17. An isolated host cell genetically engineered to contain the nucleic acid of any one of claims 2, 3, 4, 5, 11, or 9.

18. A method of producing a polypeptide comprising culturing the genetically engineered host cell of claim 15 so that the polypeptide is expressed in cell culture, and recovering the polypeptide from the cell culture.

19. A method of producing a polypeptide comprising culturing the genetically engineered host cell of claim 16 so that the polypeptide is expressed in cell culture, and recovering the polypeptide from the cell culture.

* * * * *